United States Patent
Lee et al.

(10) Patent No.: US 10,644,244 B2
(45) Date of Patent: May 5, 2020

(54) HETEROCYCLIC COMPOUND AND ORGANIC LIGHT EMITTING DEVICE USING SAME

(71) Applicant: LT MATERIALS CO., LTD., Yongin, Gyeonggi-do (KR)

(72) Inventors: Jung-Hyun Lee, Osan (KR); Young-Seok No, Osan (KR); Geon-Yu Park, Osan (KR); Dong-Jun Kim, Yongin (KR); Kee-Yong Kim, Suwon (KR); Jin-Seok Choi, Suwon (KR); Dae-Hyuk Choi, Yongin (KR); Sung-Jin Eum, Yongin (KR); Joo-Dong Lee, Seongnam (KR)

(73) Assignee: LT MATERIALS CO., LTD., Yongin-si (KR)

( * ) Notice: Subject to any disclaimer, the term of this patent is extended or adjusted under 35 U.S.C. 154(b) by 0 days.

(21) Appl. No.: 15/318,794

(22) PCT Filed: Jun. 26, 2015

(86) PCT No.: PCT/KR2015/006560
§ 371 (c)(1),
(2) Date: Dec. 14, 2016

(87) PCT Pub. No.: WO2015/199489
PCT Pub. Date: Dec. 30, 2015

(65) Prior Publication Data
US 2017/0141325 A1    May 18, 2017

(30) Foreign Application Priority Data
Jun. 27, 2014   (KR) ........................ 10-2014-0080226

(51) Int. Cl.
*H01L 51/00* (2006.01)
*C09K 11/02* (2006.01)
(Continued)

(52) U.S. Cl.
CPC ...... *H01L 51/0067* (2013.01); *C07D 491/048* (2013.01); *C07D 495/04* (2013.01);
(Continued)

(58) Field of Classification Search
None
See application file for complete search history.

(56) References Cited

U.S. PATENT DOCUMENTS 4,356,429 A    10/1982  Tang
2011/0168992 A1    7/2011  Bae et al.
(Continued)

FOREIGN PATENT DOCUMENTS

JP    2011-29220 A    2/2011
JP    2012-503027 A    2/2012
(Continued)

OTHER PUBLICATIONS

Beres et al. (Tetrahedron Lett. 2002, 43, p. 6035).*
(Continued)

*Primary Examiner* — Jay Yang
(74) *Attorney, Agent, or Firm* — Birch, Stewart, Kolasch & Birch, LLP

(57) ABSTRACT

The present application provides a hetero-cyclic compound which may significantly improve the service life, efficiency, electrochemical stability, and thermal stability of an organic light emitting device, and an organic light emitting device in which the hetero-cyclic compound is contained in an organic compound layer.

11 Claims, 34 Drawing Sheets

(51) Int. Cl.
  *C07F 7/08* (2006.01)
  *C07D 519/00* (2006.01)
  *C07D 491/048* (2006.01)
  *C07D 495/04* (2006.01)
  *C07F 9/6561* (2006.01)
  *H01L 51/50* (2006.01)

(52) U.S. Cl.
  CPC .......... *C07D 519/00* (2013.01); *C07F 7/0812* (2013.01); *C07F 9/6561* (2013.01); *C09K 11/025* (2013.01); *H01L 51/0052* (2013.01); *H01L 51/0054* (2013.01); *H01L 51/0058* (2013.01); *H01L 51/0061* (2013.01); *H01L 51/0071* (2013.01); *H01L 51/0072* (2013.01); *H01L 51/0073* (2013.01); *H01L 51/0074* (2013.01); *H01L 51/0094* (2013.01); *H01L 51/5012* (2013.01); *H01L 51/5056* (2013.01); *H01L 51/5072* (2013.01); *H01L 51/5092* (2013.01); *H01L 51/5096* (2013.01)

(56) References Cited

U.S. PATENT DOCUMENTS

| | | |
|---|---|---|
| 2011/0266526 A1 | 11/2011 | Ma et al. |
| 2012/0126205 A1 | 5/2012 | Kawamura et al. |
| 2012/0165556 A1 | 6/2012 | Suzuki et al. |
| 2013/0306958 A1 | 11/2013 | Ito et al. |
| 2015/0263297 A1 | 9/2015 | Stoessel et al. |
| 2015/0270502 A1 | 9/2015 | Fuchiwaki et al. |
| 2016/0141515 A1* | 5/2016 | Hayama ................ C09K 11/06 257/40 |

FOREIGN PATENT DOCUMENTS

| | | |
|---|---|---|
| JP | 2012-149045 A | 8/2012 |
| JP | 2013-525446 A | 6/2013 |
| JP | 2013-539750 A | 10/2013 |
| JP | 2013-543250 A | 11/2013 |
| WO | WO 2007/117289 A2 | 10/2007 |
| WO | WO 2012/036482 A1 | 3/2012 |
| WO | WO 2012/070226 A1 | 5/2012 |
| WO | WO 2013/002217 A1 | 1/2013 |
| WO | WO 2014/008982 A1 | 1/2014 |
| WO | WO 2014/088047 A1 | 6/2014 |
| WO | WO -2014/199637 A1 * | 12/2014 |

OTHER PUBLICATIONS

Béres et al., "Straightforward synthesis of 11H-indolo[3,2-c]isoquinoline and benzofuro[3,2-c]isoquinoline by ring transformation", Tetrahedron Letters 2002, vol. 43, No. 34, pp.6035-6038, See abstract; diagram 1, compound 4.

Chemical Abstract Compound, STN express. RN 937639-61-7 (Entered STN: Jun. 17, 2007), RN 937636-15-2 (Entered STN: Jun. 17, 2007), RN 666700-59-0 (Entered STN: Mar. 23, 2004).

Chemical Abstract Compound, STN express. RN 937644-42-3 (Entered STN: Jun. 17, 2007), RN 937639-55-9 (Entered STN: Jun. 17, 2007).

David et al, "Synthesis of fluorescent rhodamine dyes using an extension of the Heck reaction", Tetrahedron Letters, 2008, vol. 49, pp. 1860-1864.

International Search Report, issued in PCT/KR2015/006560 (PCT/ISA/210), dated Jul. 12, 2016.

Jiang et al., "Synthesis of 6-aminophenanthridines via palladium-catalyzed insertion of isocyanides into N-sulfonyl-2-aminobiaryls", RSC Advances, 2014, vol. 4, pp. 17222-17225.

Koltai et al., "A Novel Rearrangement Reaction of 2,5,5-Triaryl-2-Thiazolin-4-Ones During Thiation", Tetrahedron, vol. 29, pp. 2783-2794.

McBurney et al., "Interplay of Ortho- with Spiro Cyclisation during Iminyl Radical Closures onto Arenes and Heteroarenes", Beilstein Journal of Organic Chemistry, 2013, vol. 9, pp. 1083-1092, See abstract; diagram 2, compounds 14a, 14b.

Pakray et al., "The Synthesis of Dimethoxy[1]benzothieno[2,3-c]quinalines", Journal of Heterocyclic Chemistry, 1986, vol. 23, No. 5, pp. 1571-1577.

Taiwanese Office Action for application No. 104120765, dated Feb. 3, 2016.

Yamaguchi et al., "The Synthesis of Benzofuroquinolines. VI. A New Synthesis of Benzofuro[2,3-c]quinoline Derivatives", The Chemical Society of Japan, 1990, vol. 63, No. 3, pp. 952-954.

Yamaguchi et al., "The Synthesis of Benzofuroquinolines. X. Some Benzofuro[3,2-c]isoquinoline Derivatives", Journal of Heterocyclic Chemistry, 1995, vol. 32, No. 5, pp. 1517-1519. See p. 1517, left column.

Kalugin et al., "A convenient synthesis of benzofuro[3,2-c]isoquinolines and naphtho[1',2':4,5]furo[3,2-c]isoquinolines," Tetrahedron Letters, vol. 52, No. 14, 2011 (Available online Dec. 24, 2010), pp. 1557-1560.

Partial Supplementary European Search Report for European Application No. 15810940.5, dated Dec. 19, 2017.

Deprets et al., "New Synthesis of Substituted 6-methylbenzo[b]furo-, -thieno-, and -seleno[2,3-c]quinolines, and Heterocyclic Analogues," Arkivoc, vol. i, 2002 (published on web May 10, 2002), pp. 40-48.

Ock et al., "Synergistic Effect of Pd(II) and Acid Catalysts on Tandem Annulation Reaction for the Regioselective Synthesis of Ring-Fused Quinolines," Bull. Korean Chem. Soc., vol. 31, No. 3, 2010, pp. 704-707.

Yamaguchi et al., "The Synthesis of Benzofuroquinolines. VIII. Some Halobenzofuro[2,3-c]quinoline Derivatives," J. Heterocylic Chem., vol. 27, May-Jun. 1990, pp. 1003-1005.

Gerfaud et al., "Palladium-Catalyzed Annulation of Acyloximes with Arynes (or Alkynes): Synthesis of Phenanthridines and Isoquinolines," Agnew. Chem. Int. Ed., vol. 48, 2009 (Published online Dec. 9, 2008), pp. 572-577.

* cited by examiner

[Figure 1]
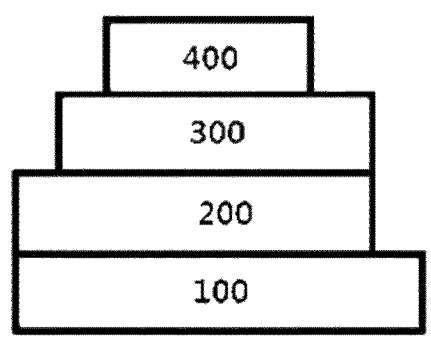
[Figure 2]
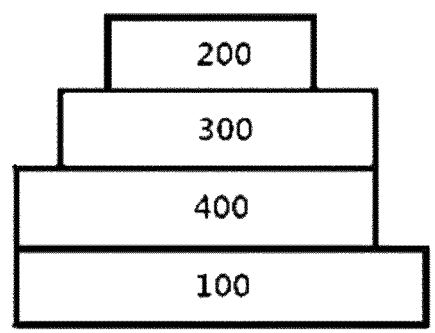

[Figure 3]
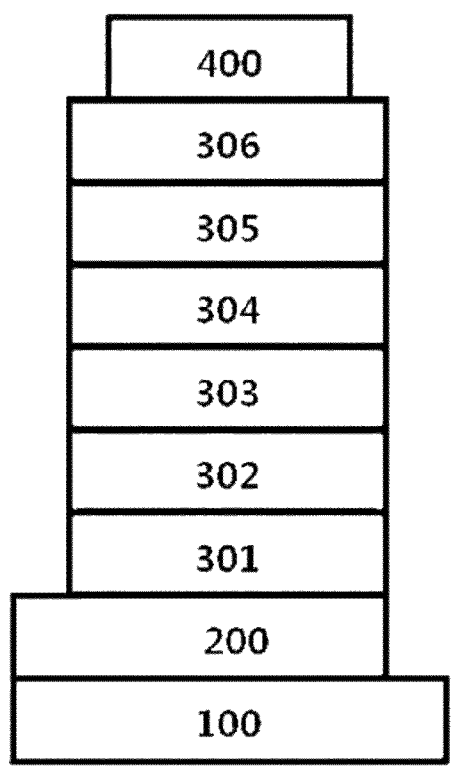

[Figure 4]
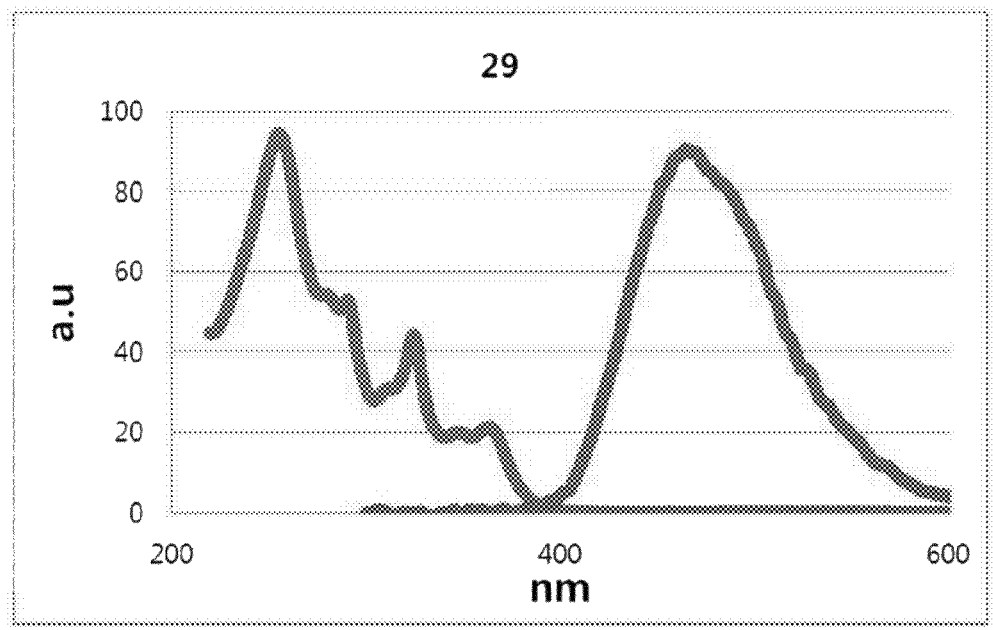
[Figure 5]
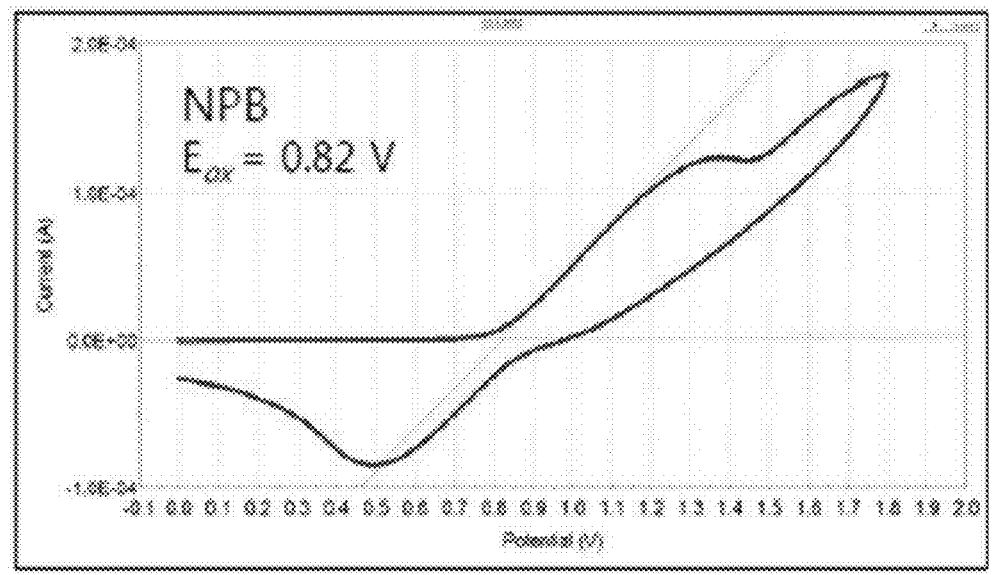

[Figure 6]
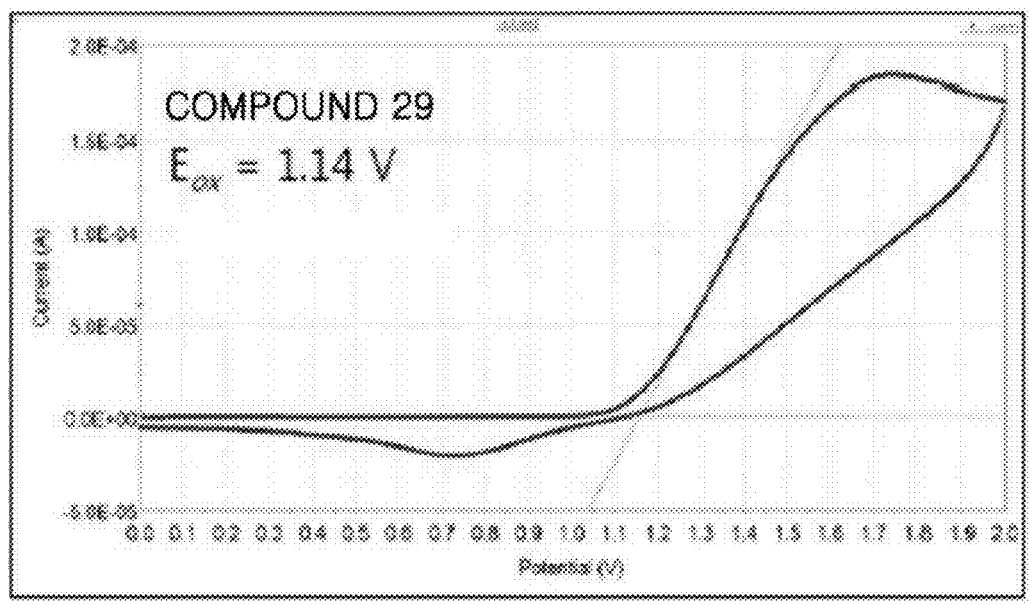
[Figure 7]
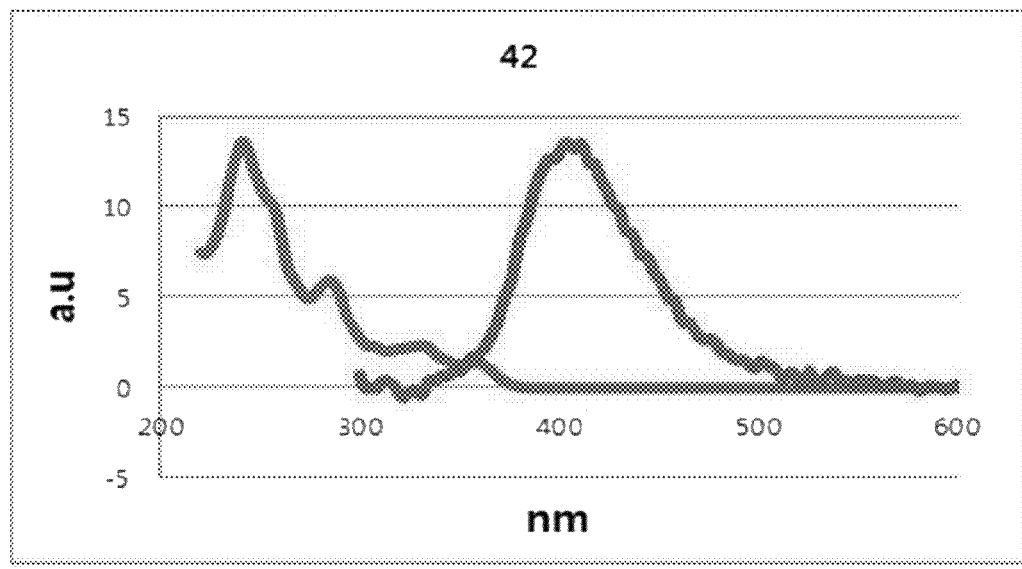

[Figure 8]
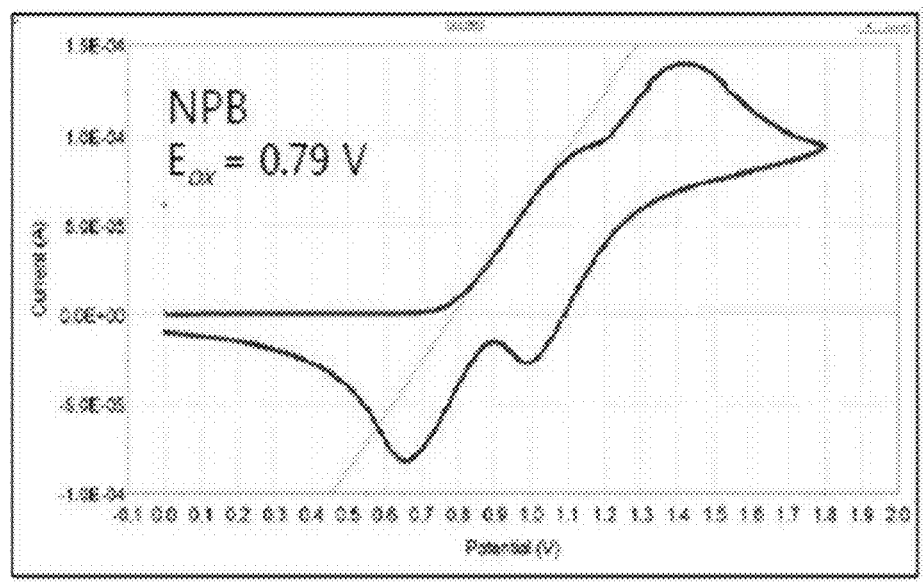
[Figure 9]
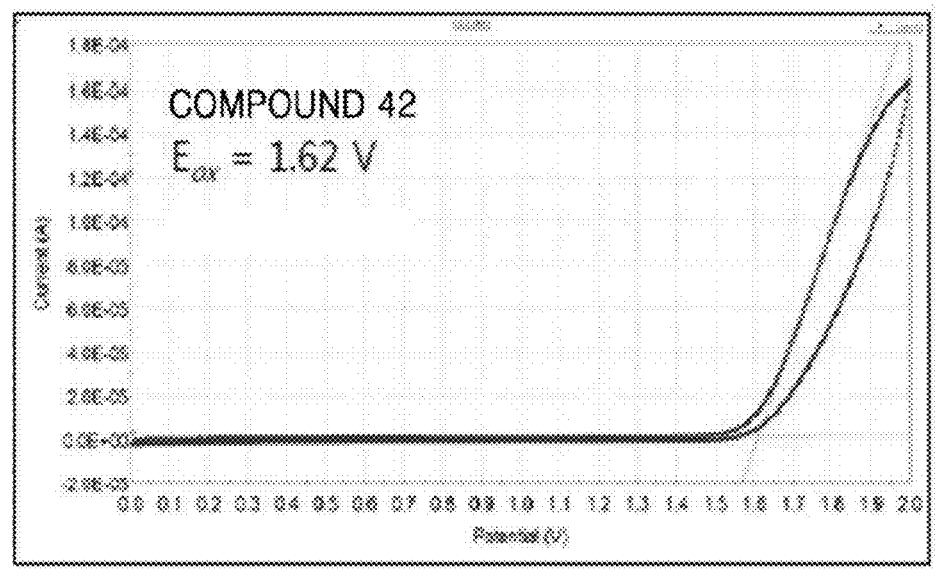

[Figure 10]
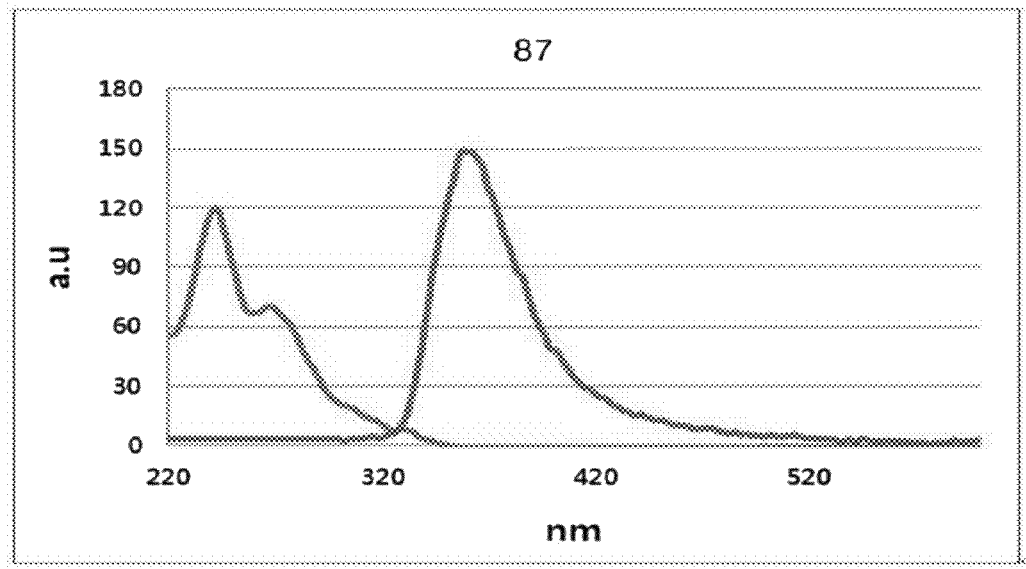
[Figure 11]
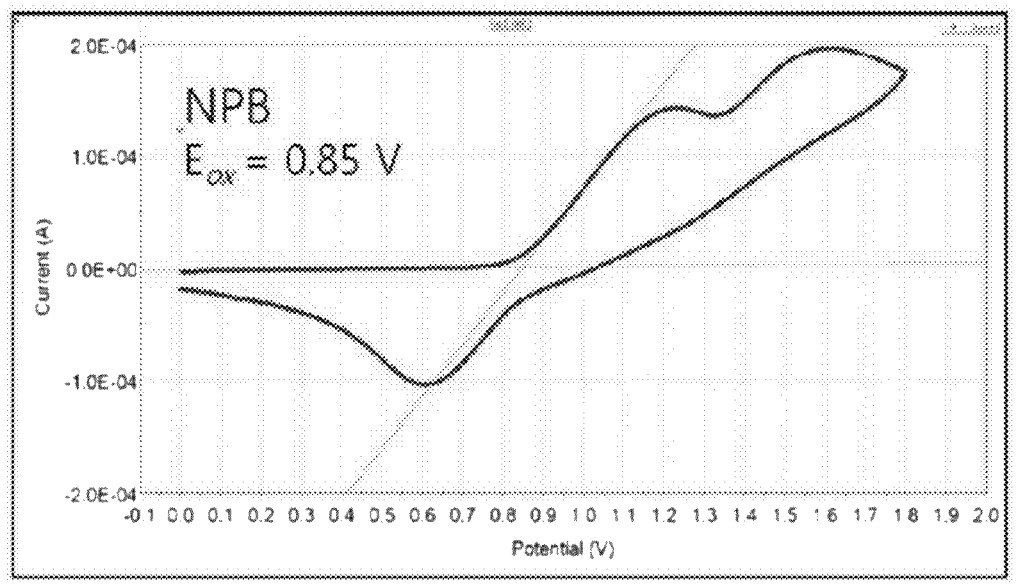

[Figure 12]
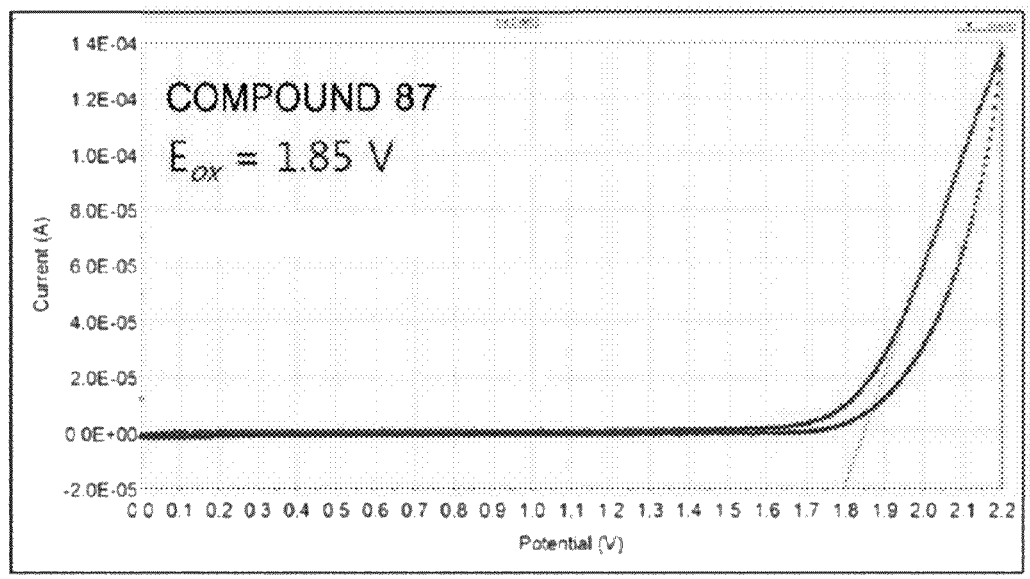
[Figure 13]
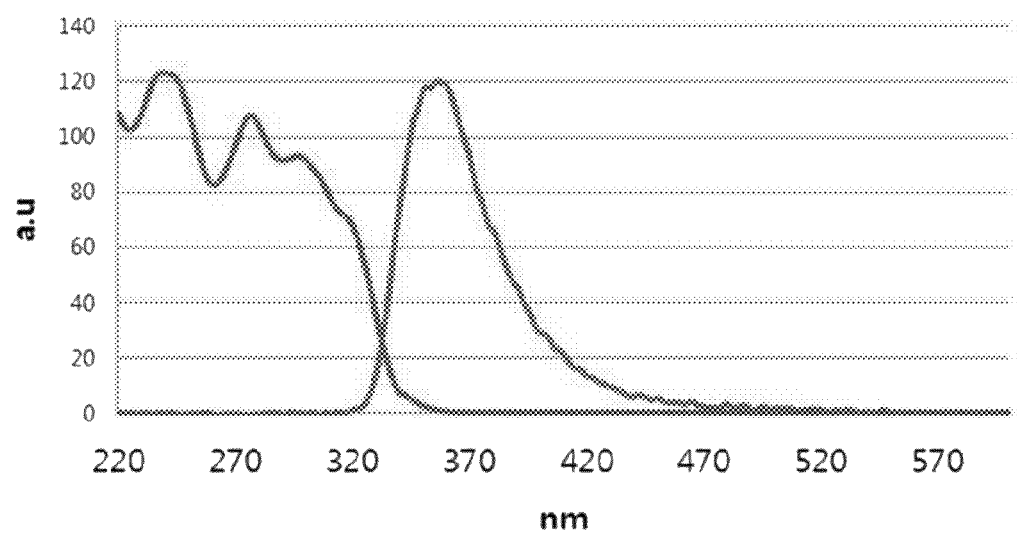

[Figure 14]
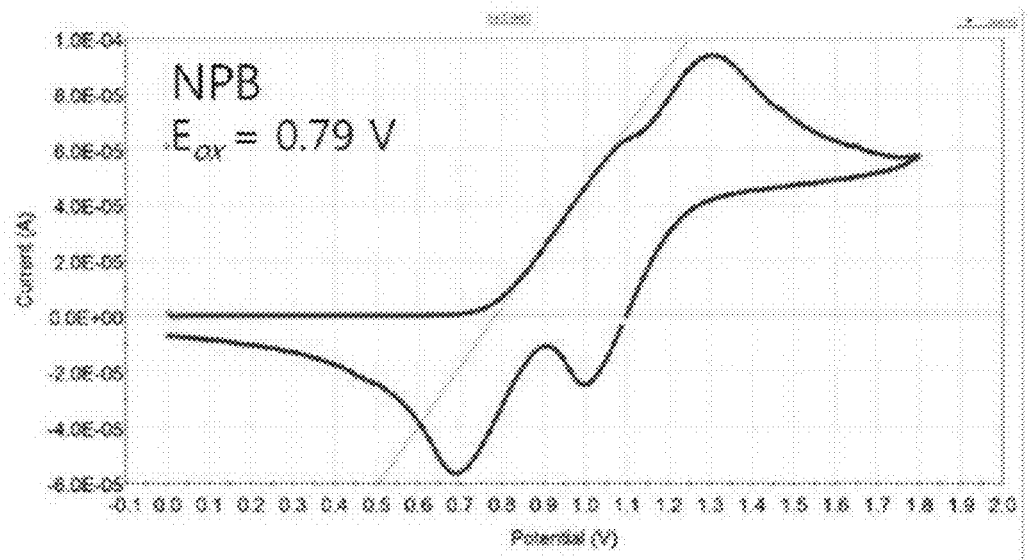
[Figure 15]
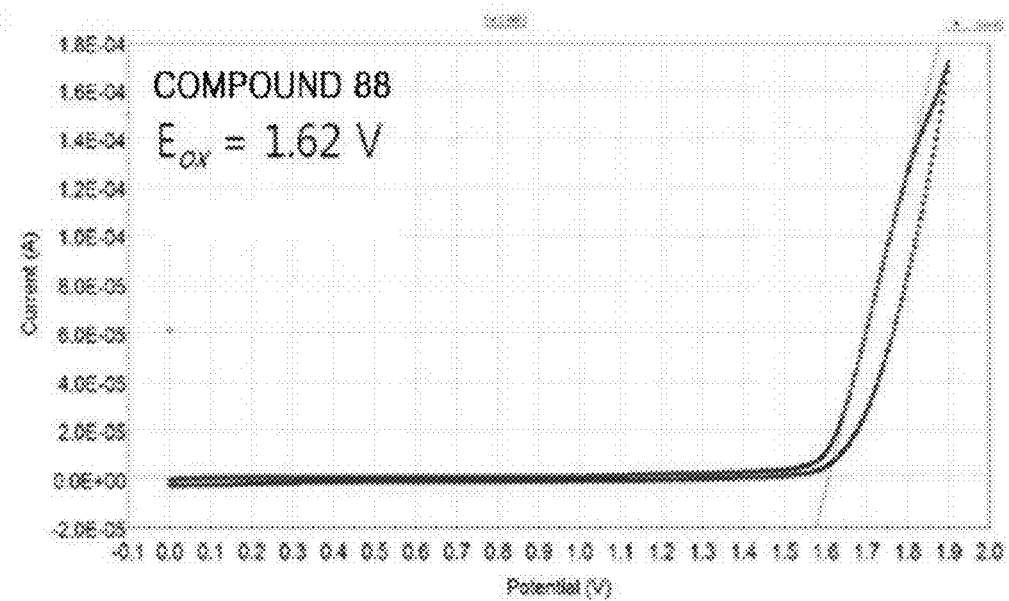

[Figure 16]
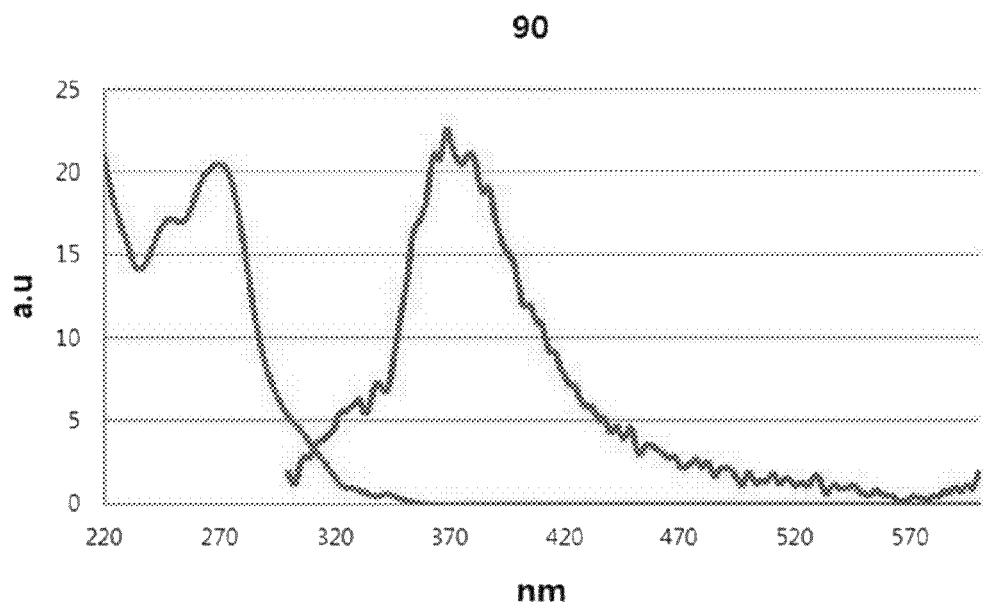
[Figure 17]
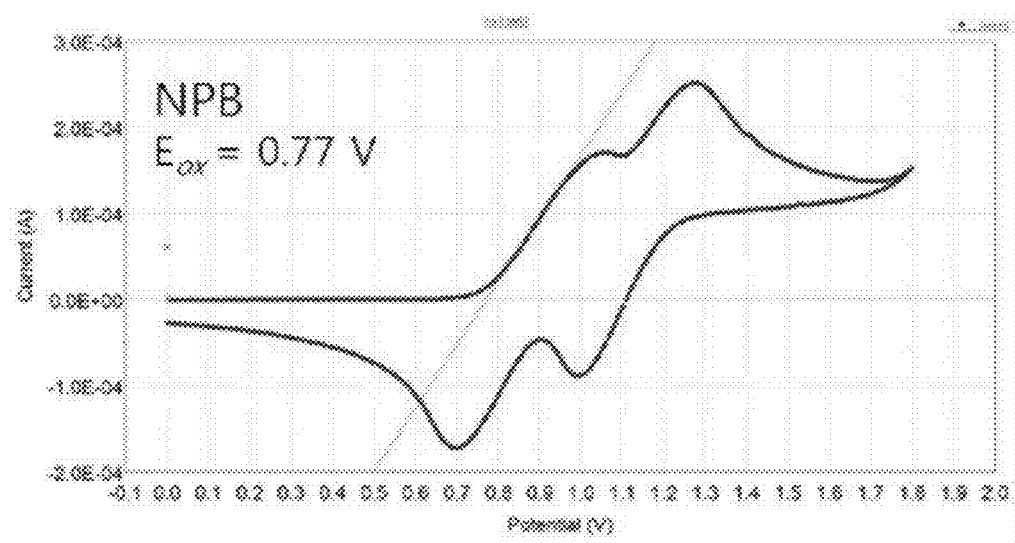

[Figure 18]
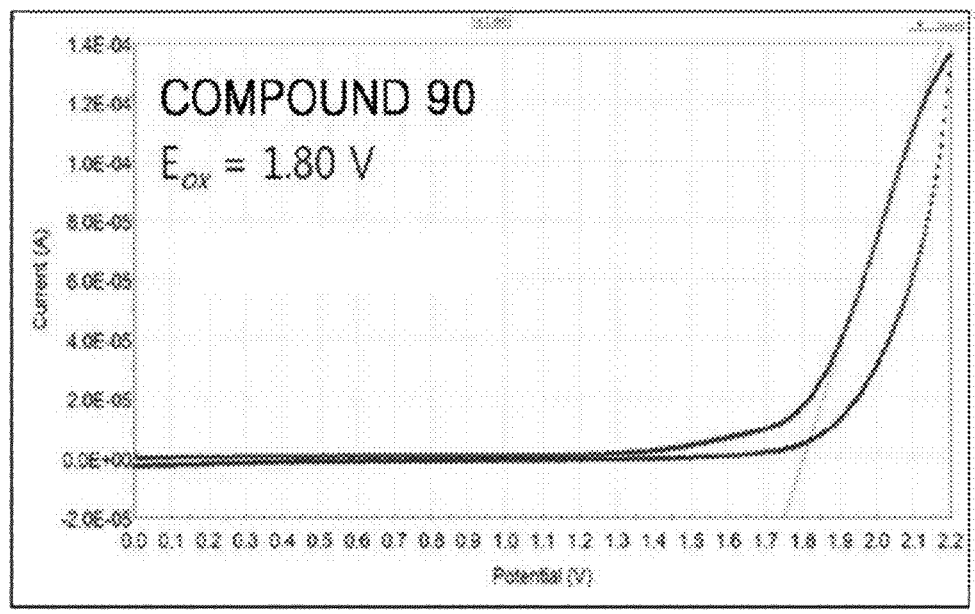
[Figure 19]
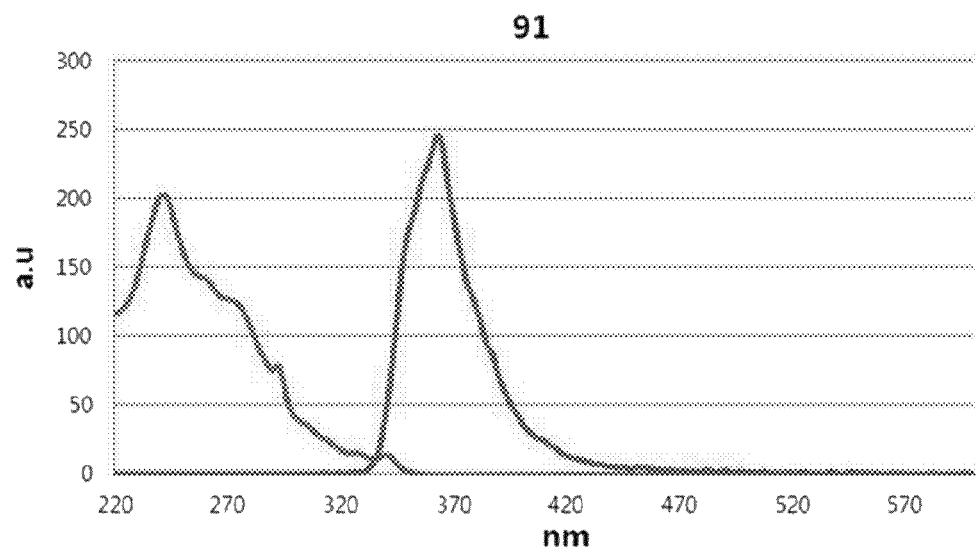

[Figure 20]
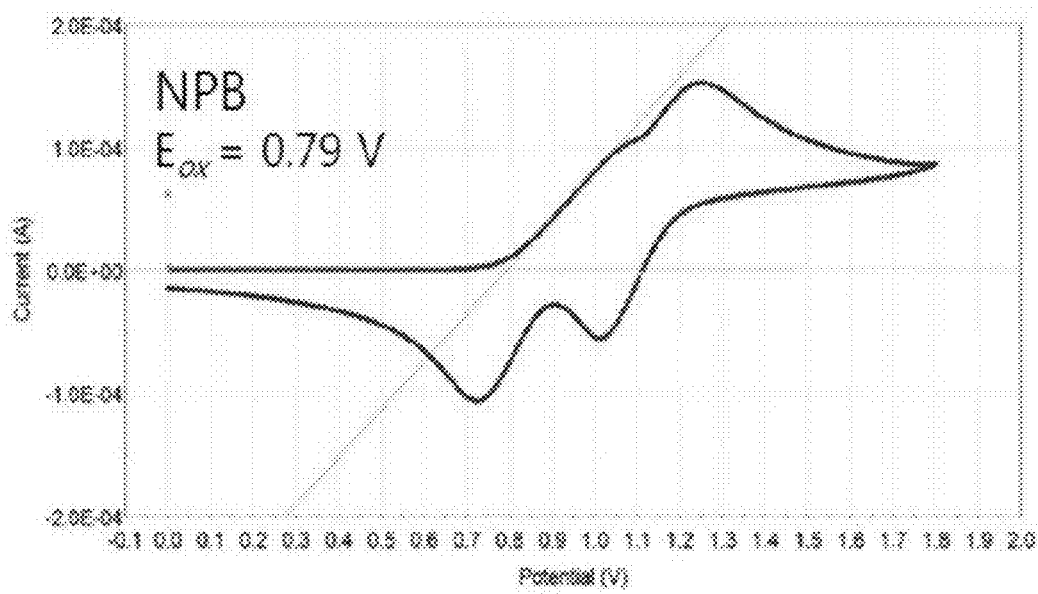
[Figure 21]
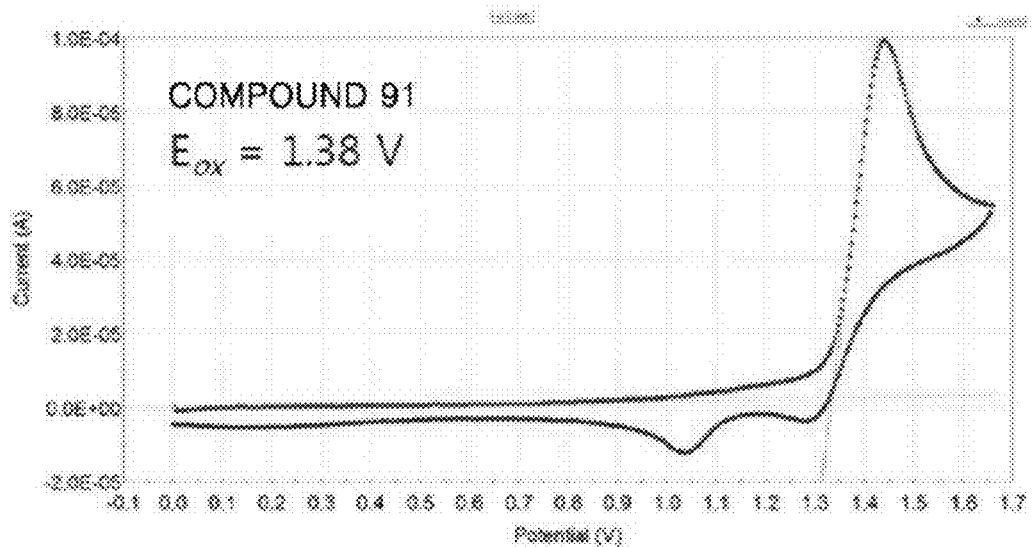

[Figure 22]
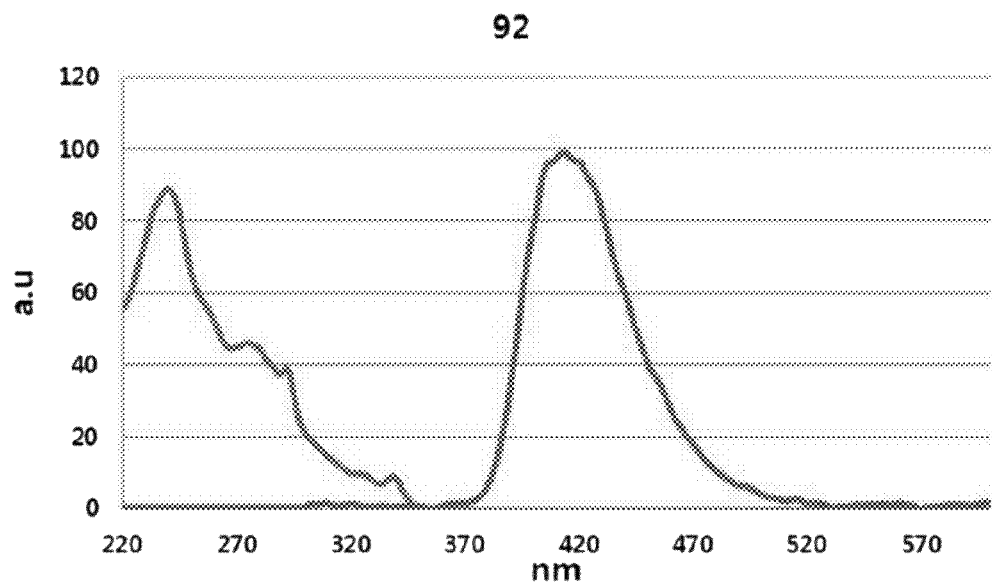
[Figure 23]
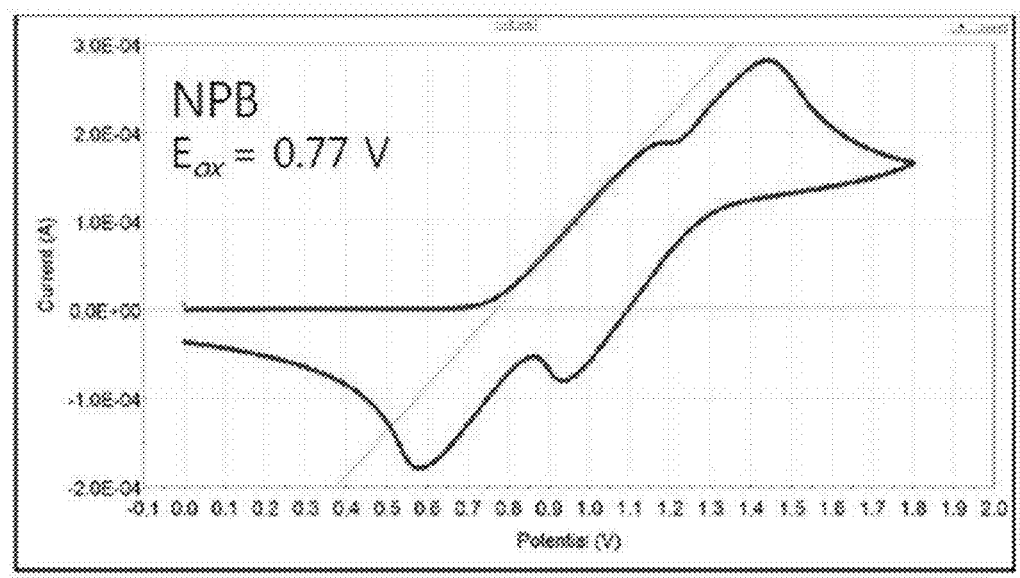

[Figure 24]
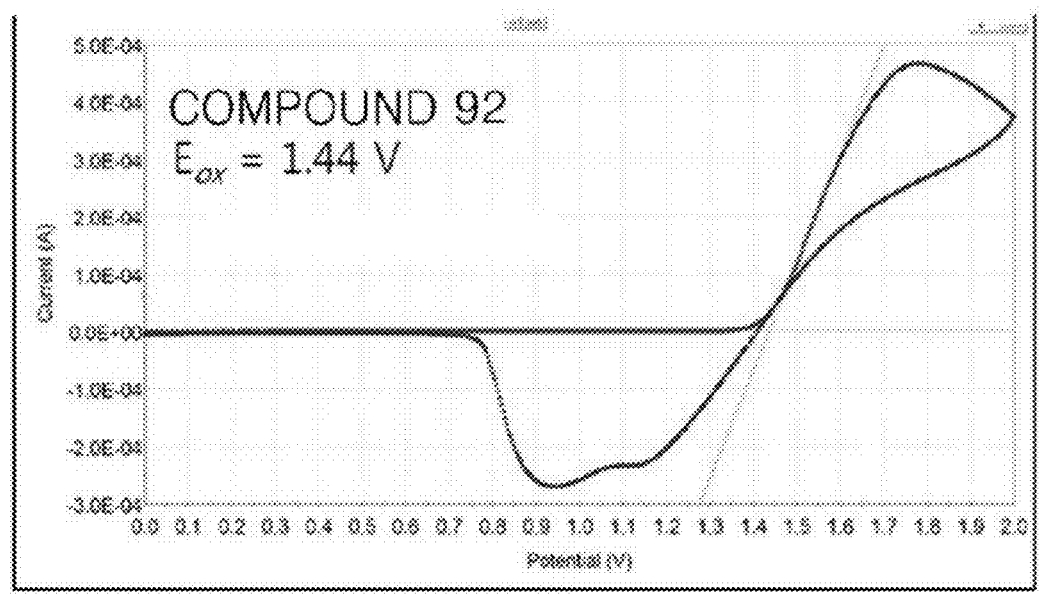
[Figure 25]
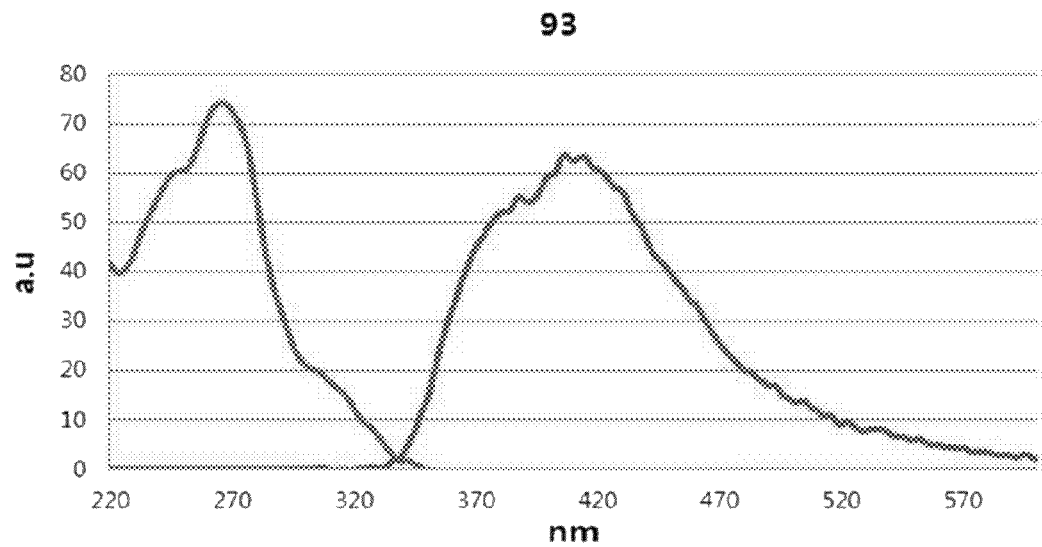

[Figure 26]
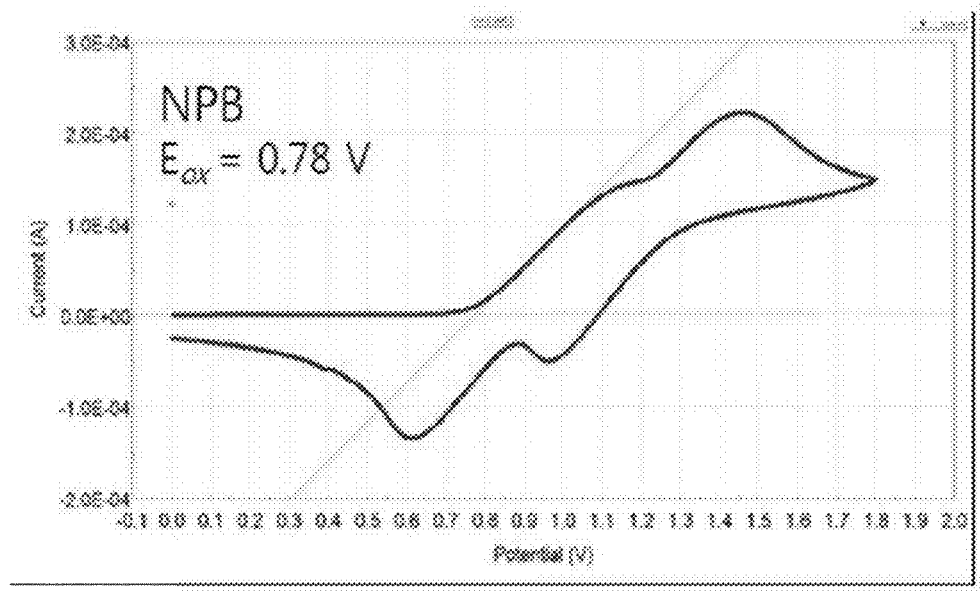
[Figure 27]
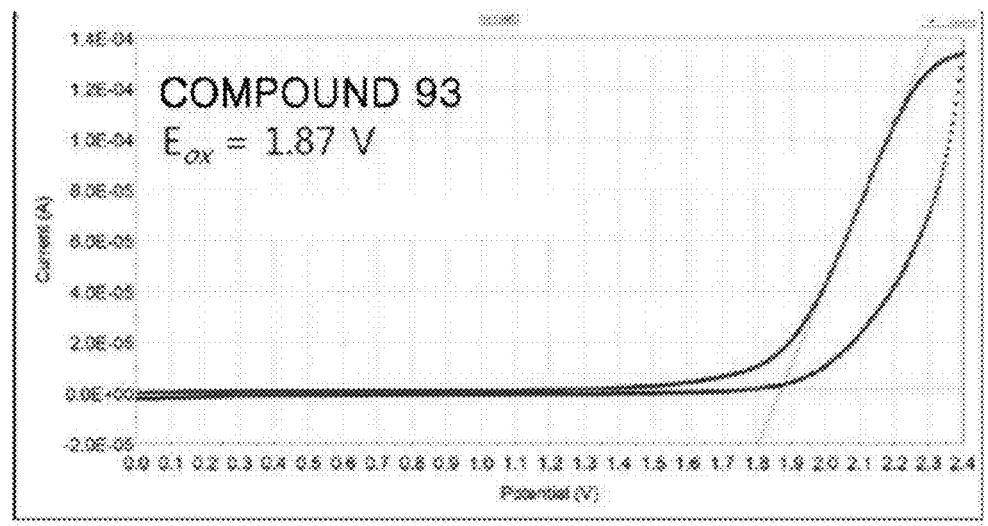

[Figure 28]
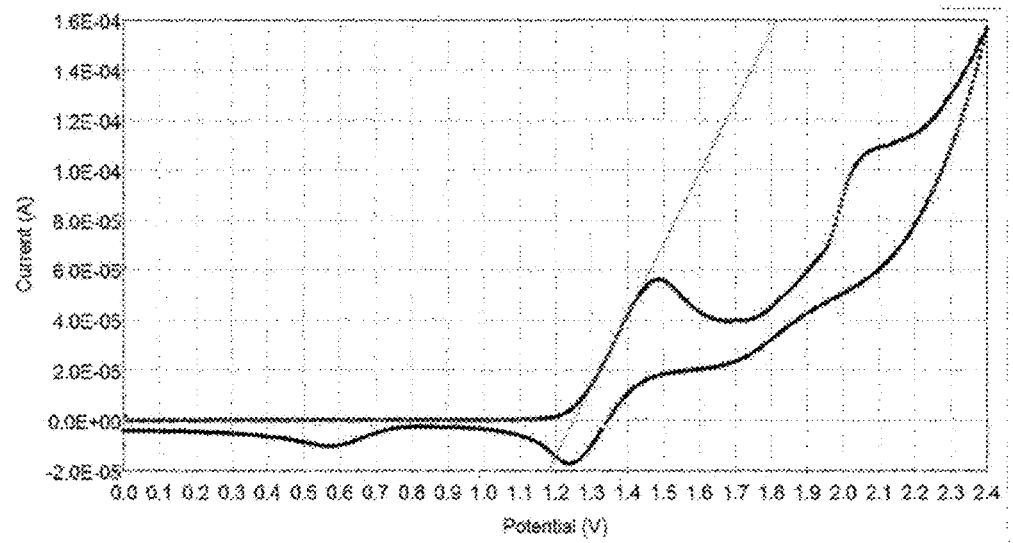
[Figure 29]
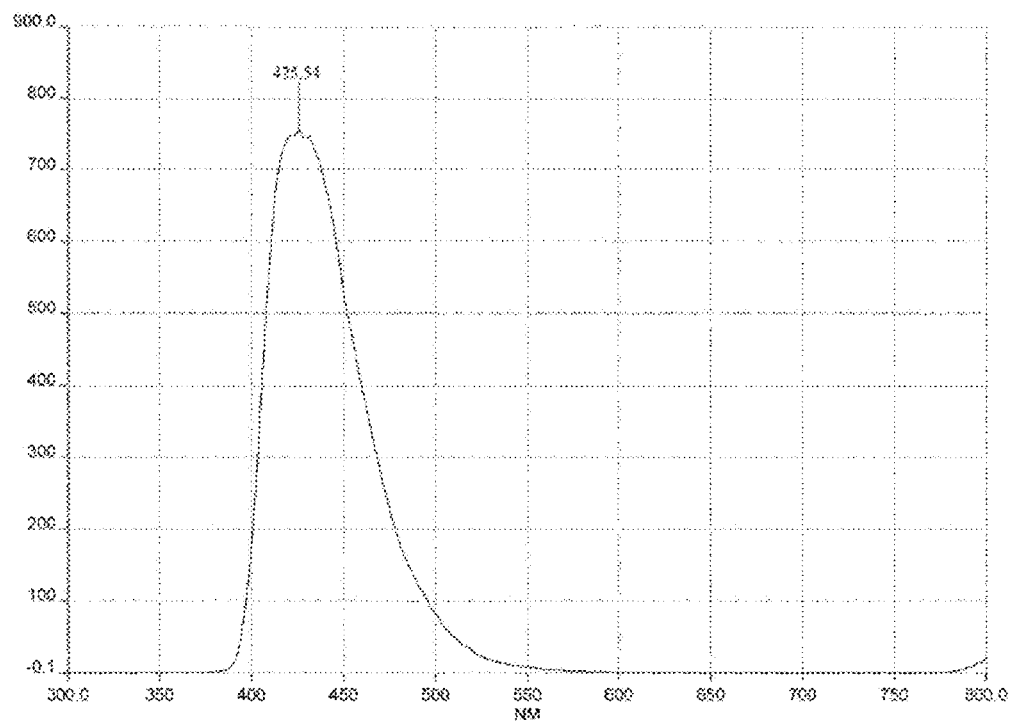

[Figure 30]
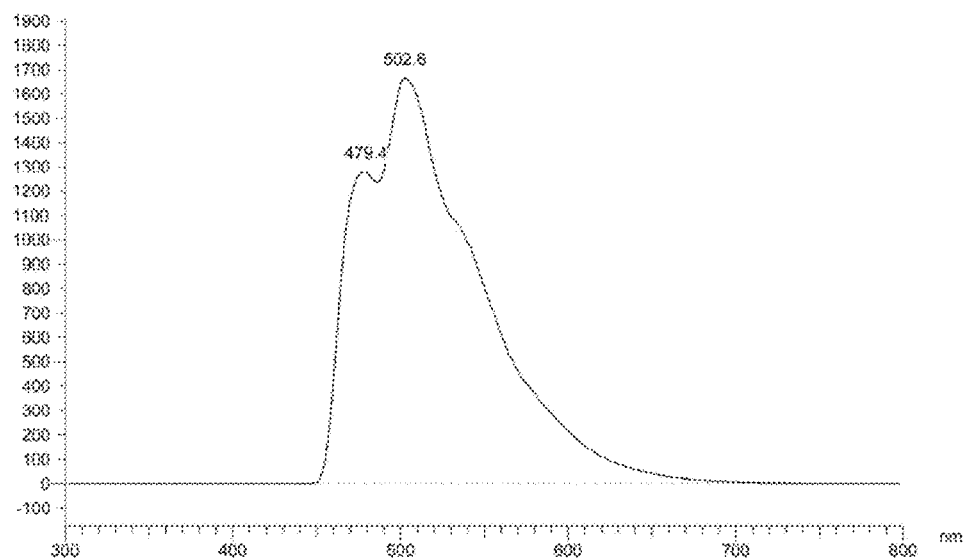
[Figure 31]
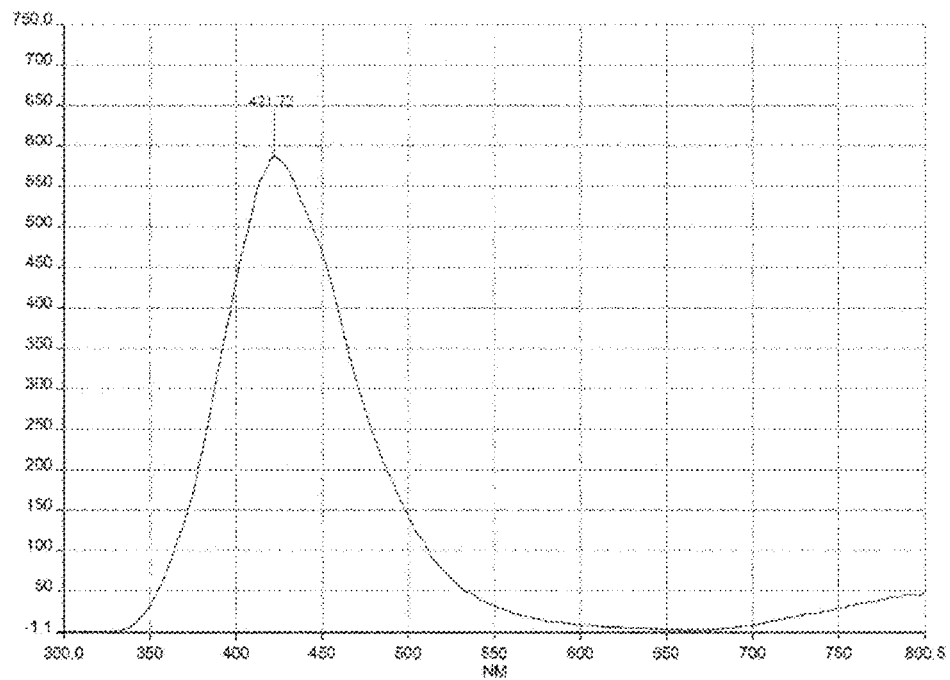

[Figure 32]
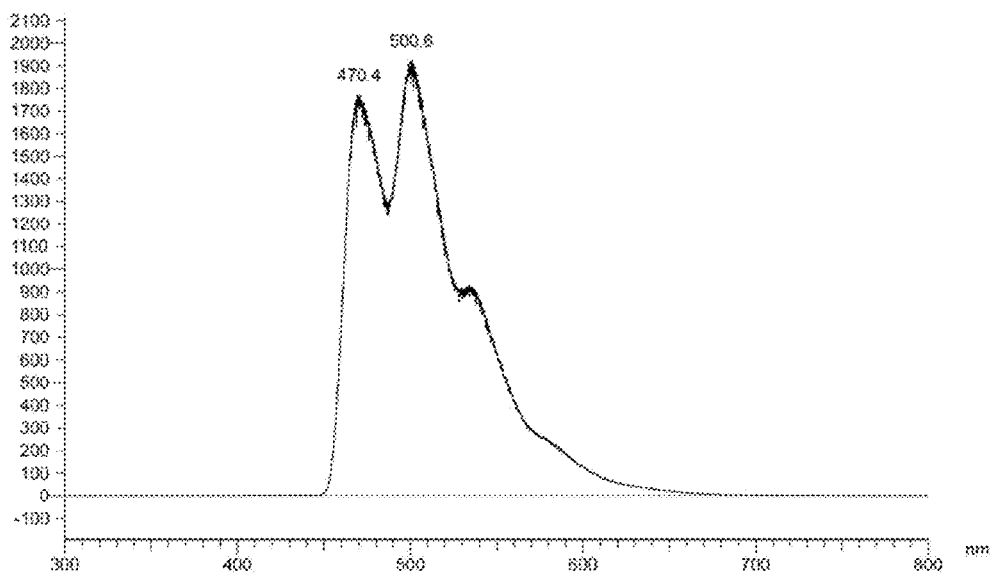
[Figure 33]
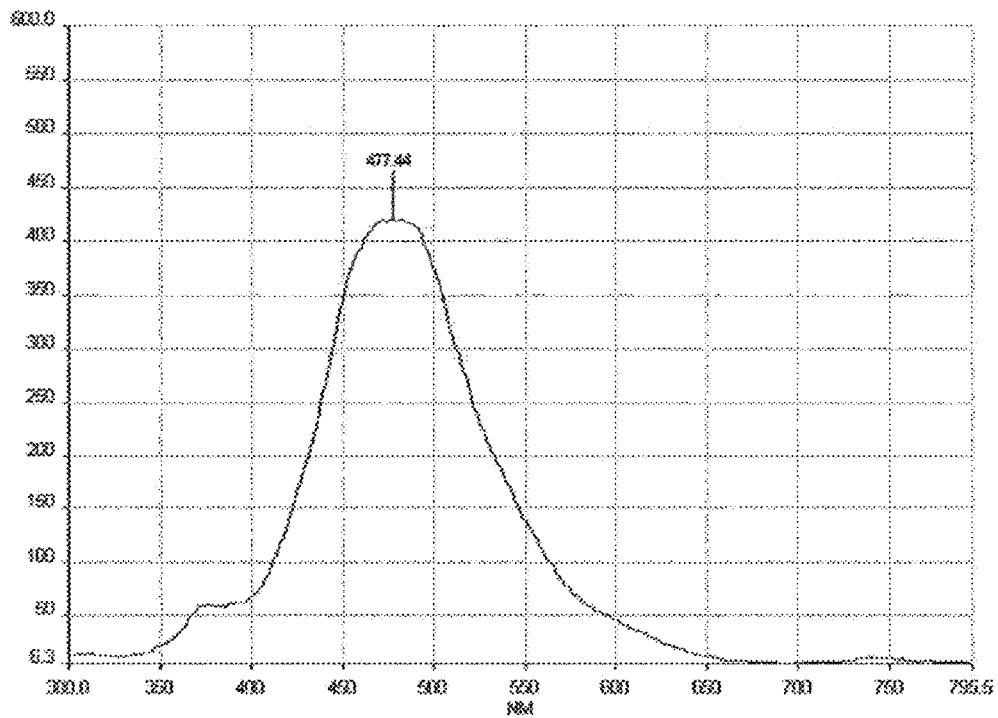

[Figure 34]
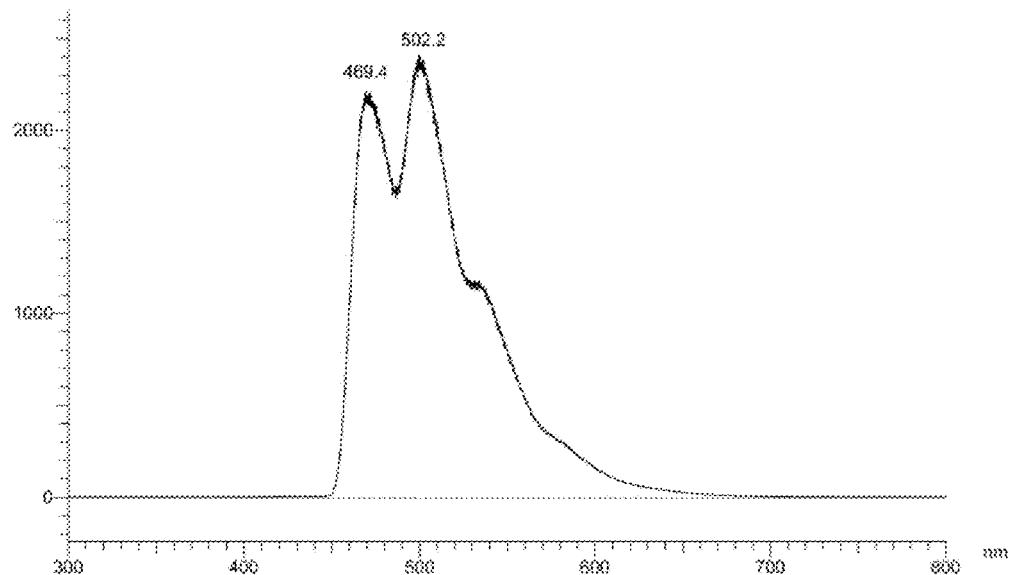
[Figure 35]
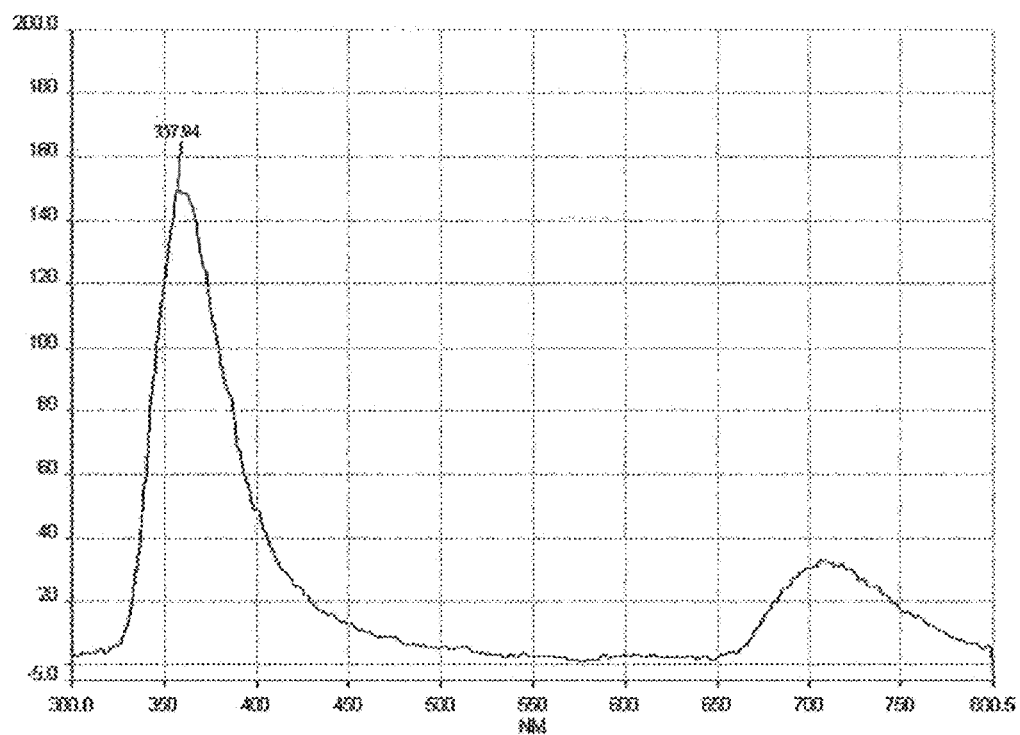

[Figure 36]
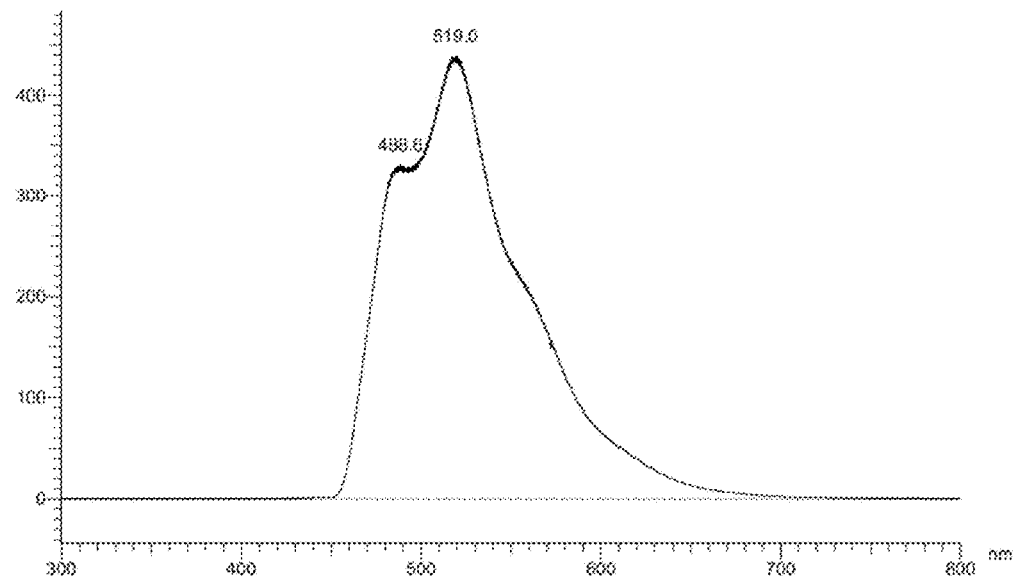
[Figure 37]
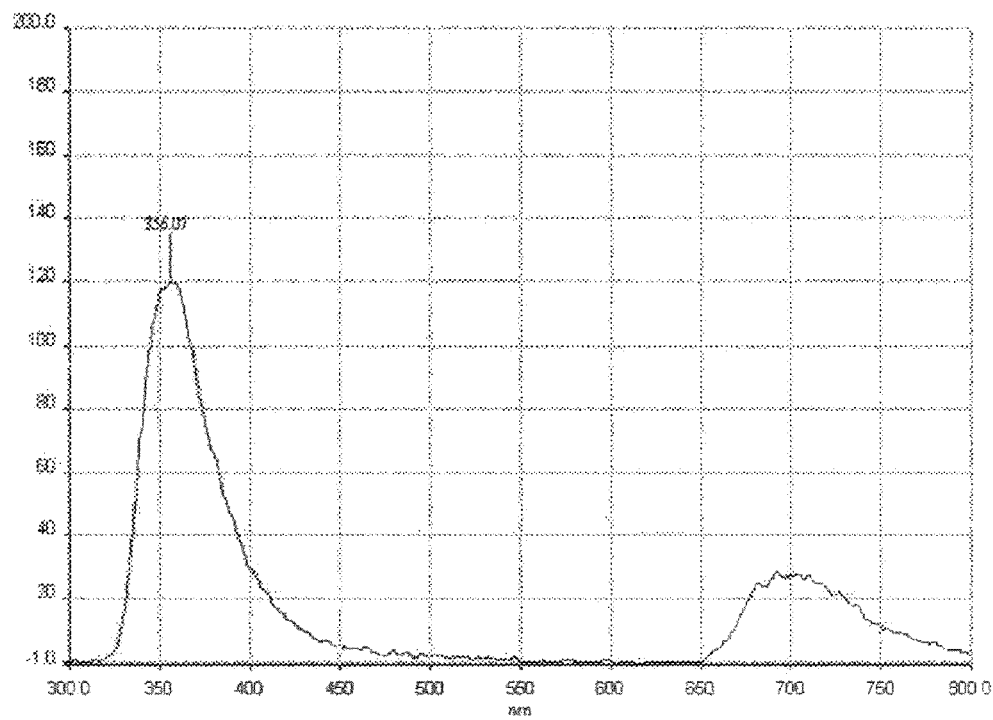

[Figure 38]
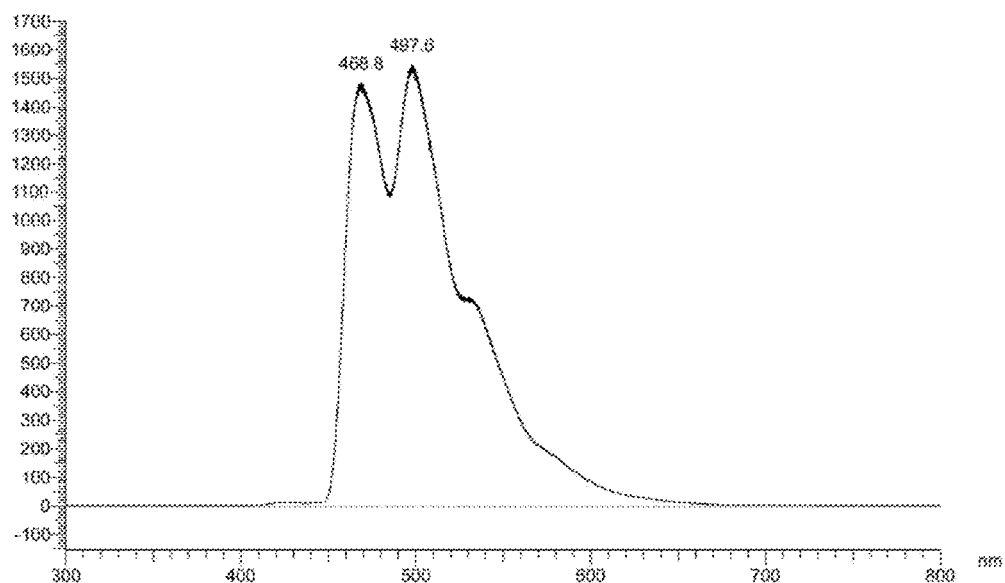
[Figure 39]
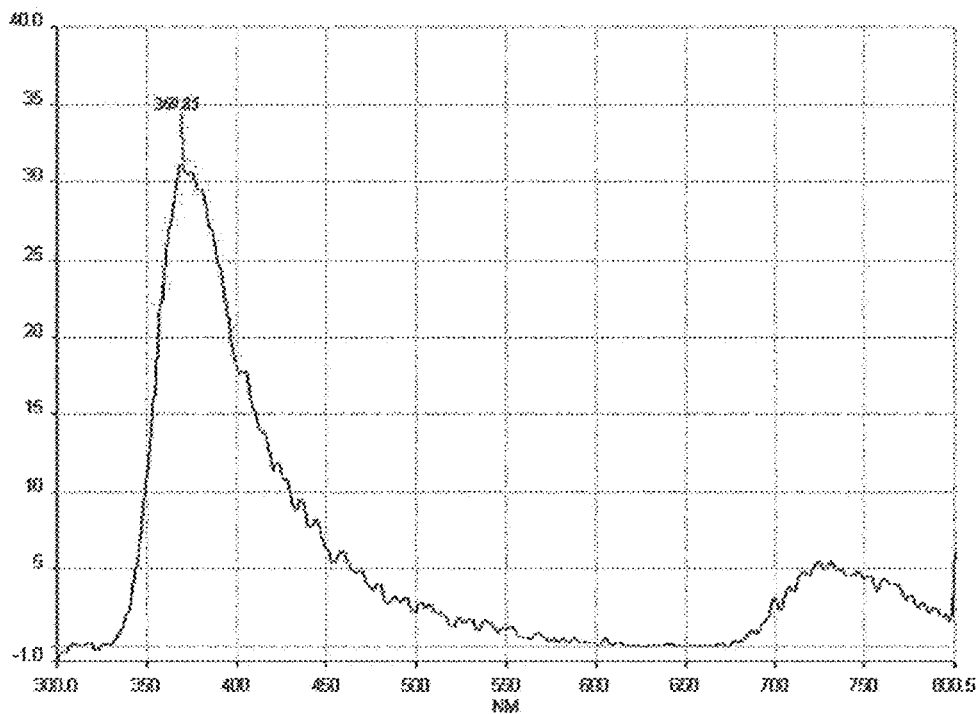

[Figure 40]
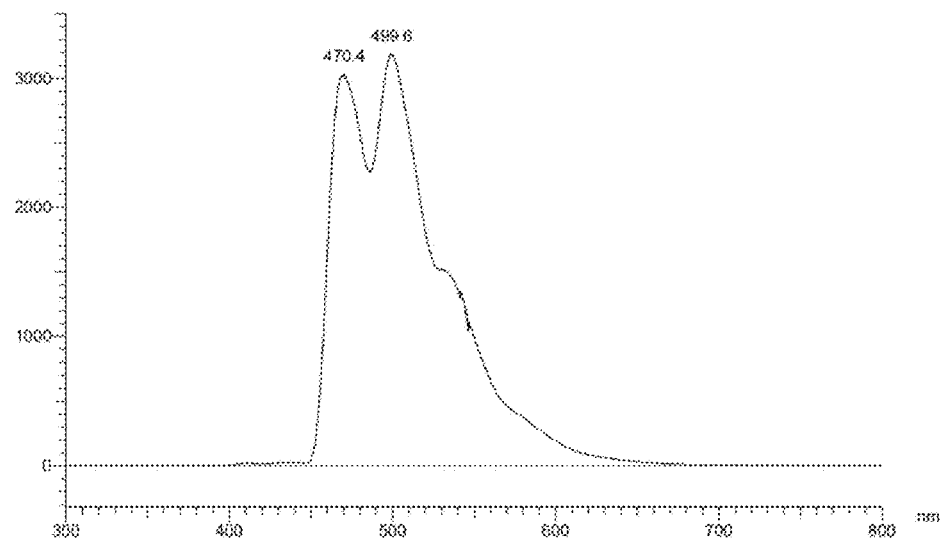
[Figure 41]
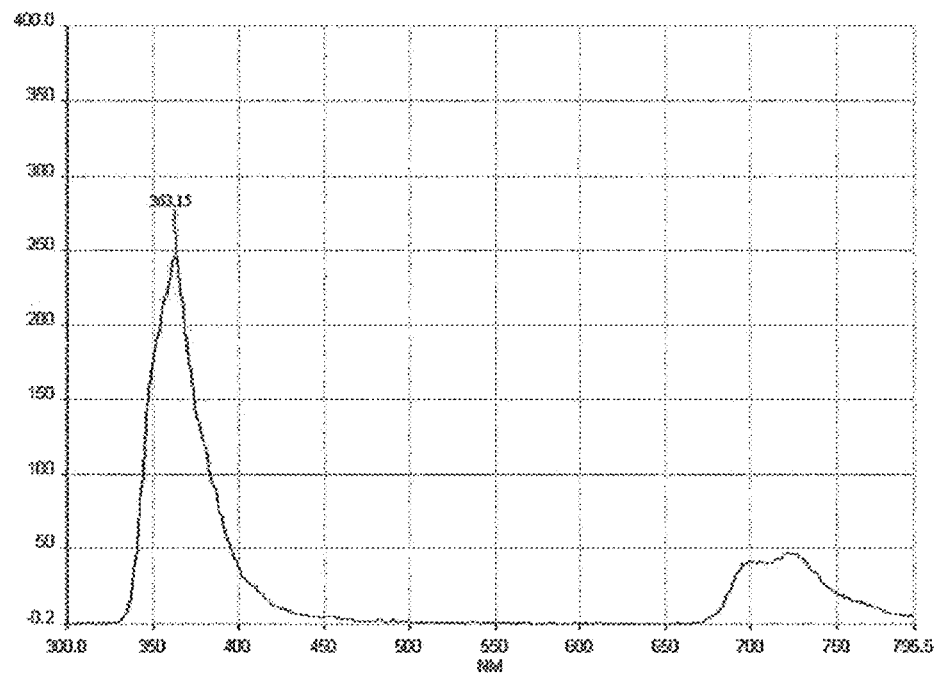

[Figure 42]
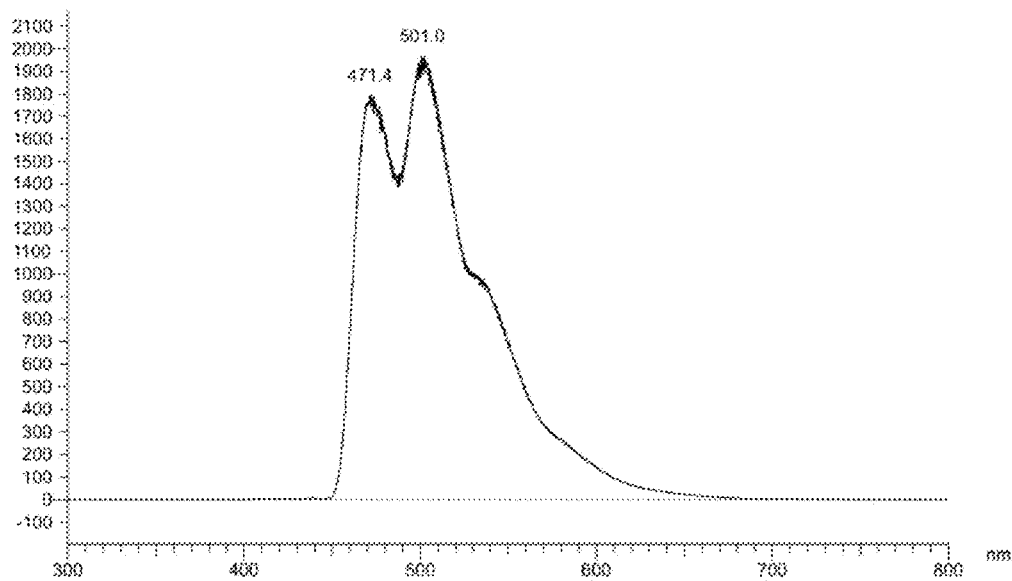
[Figure 43]
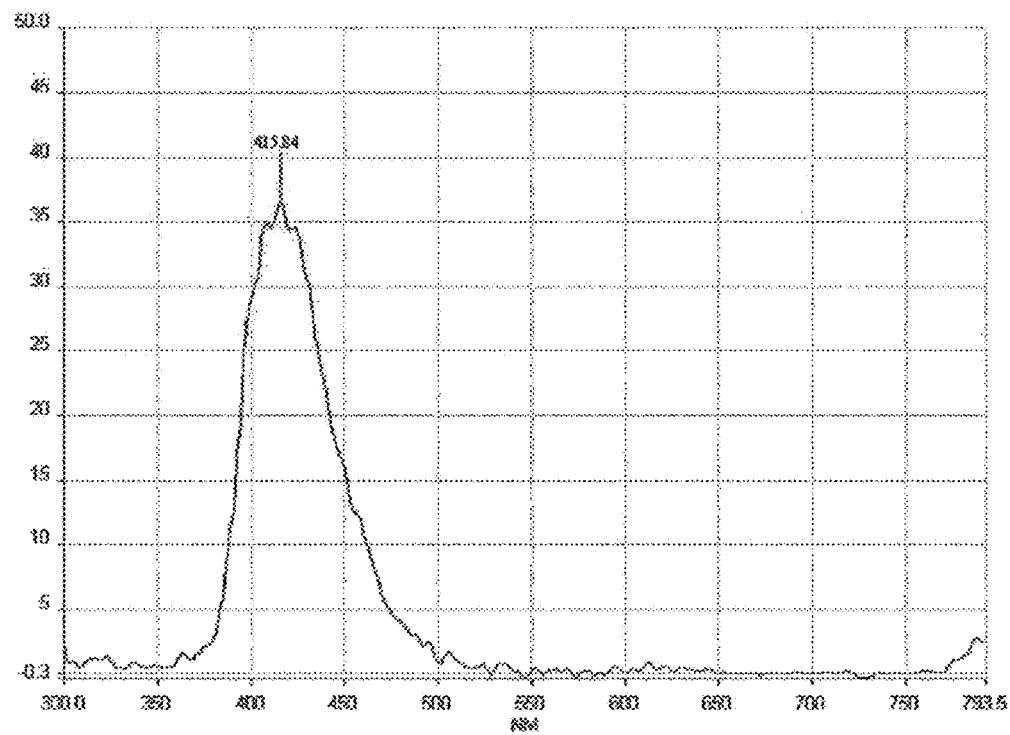

[Figure 44]
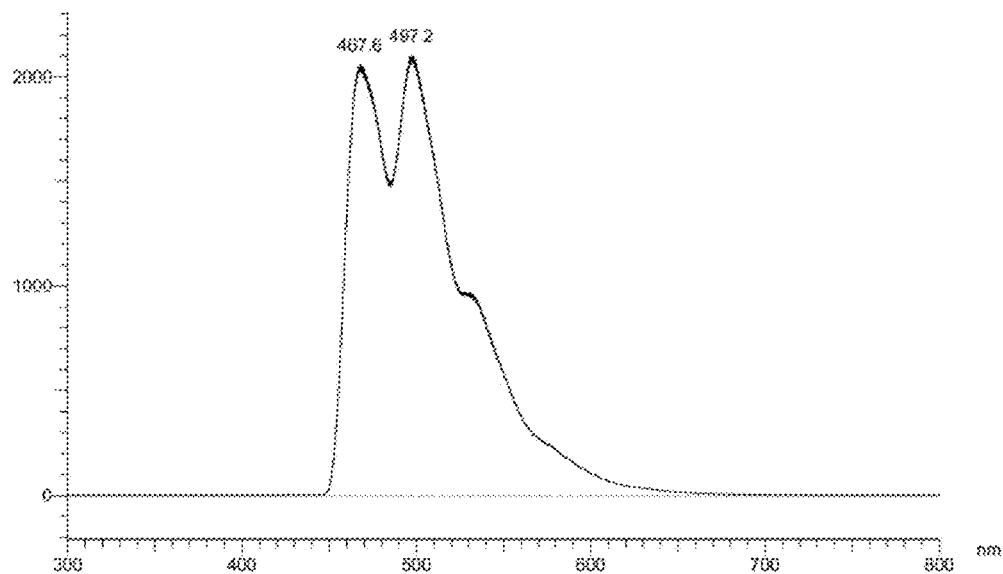
[Figure 45]
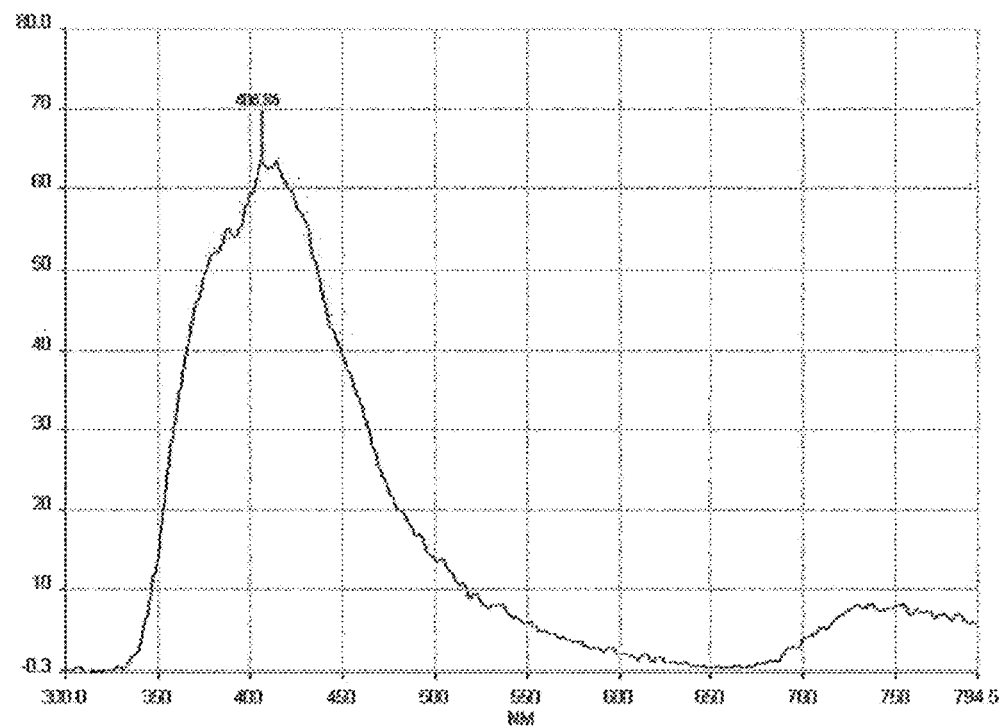

[Figure 46]
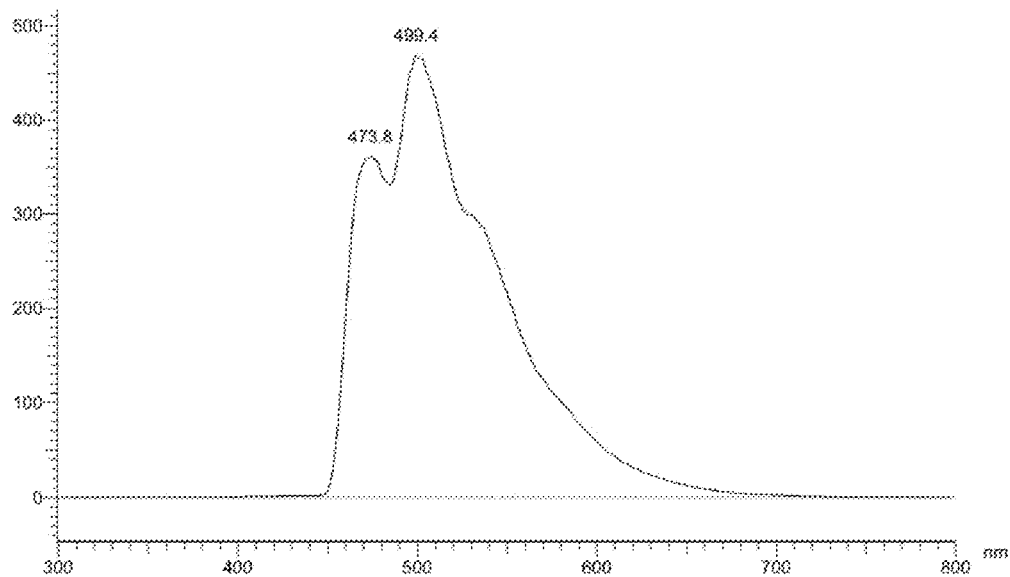
[Figure 47]
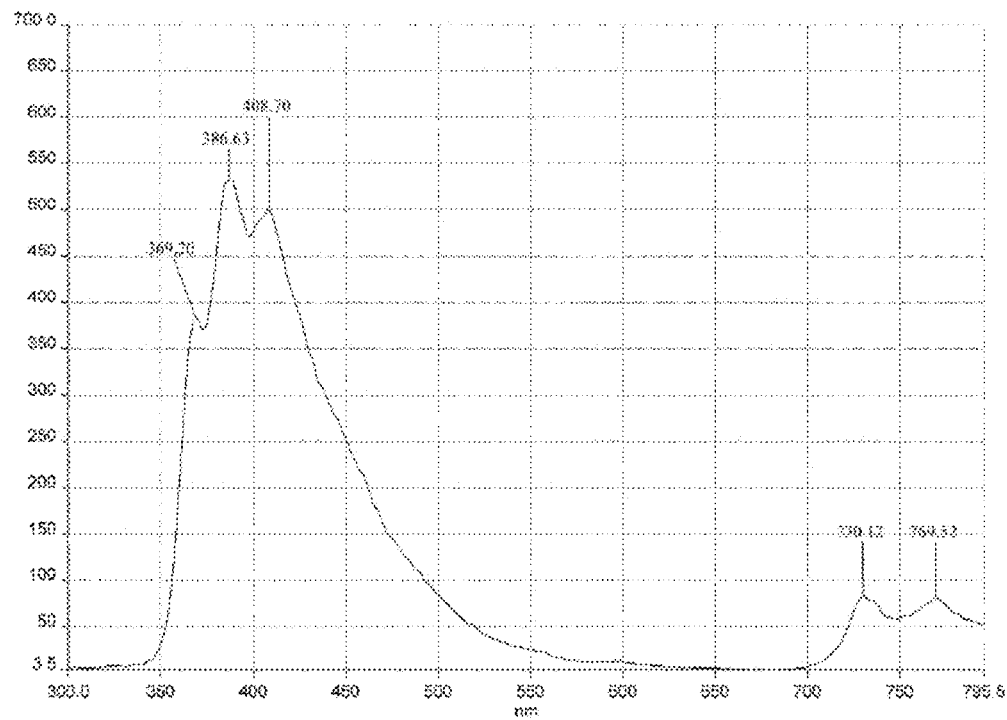

[Figure 48]
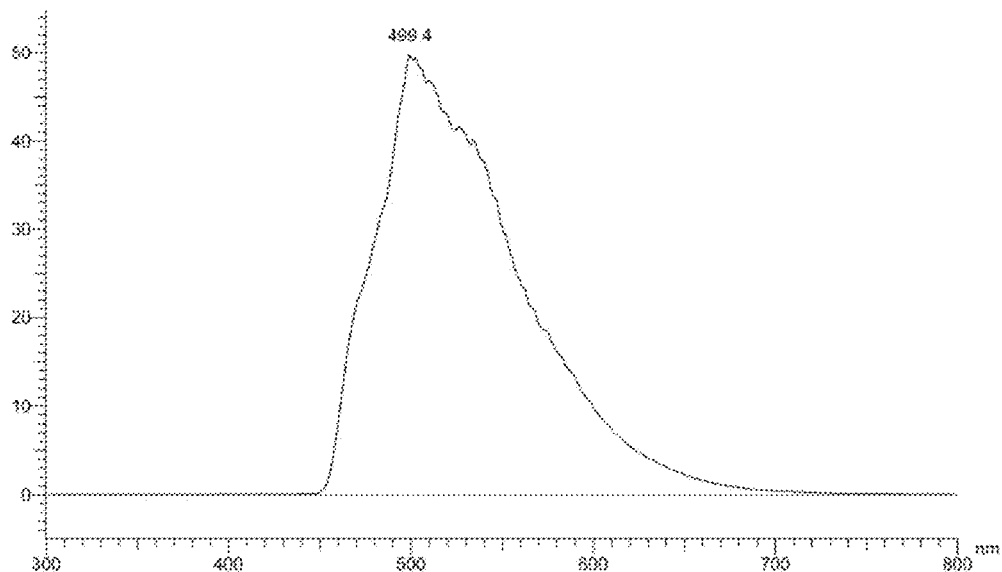
[Figure 49]
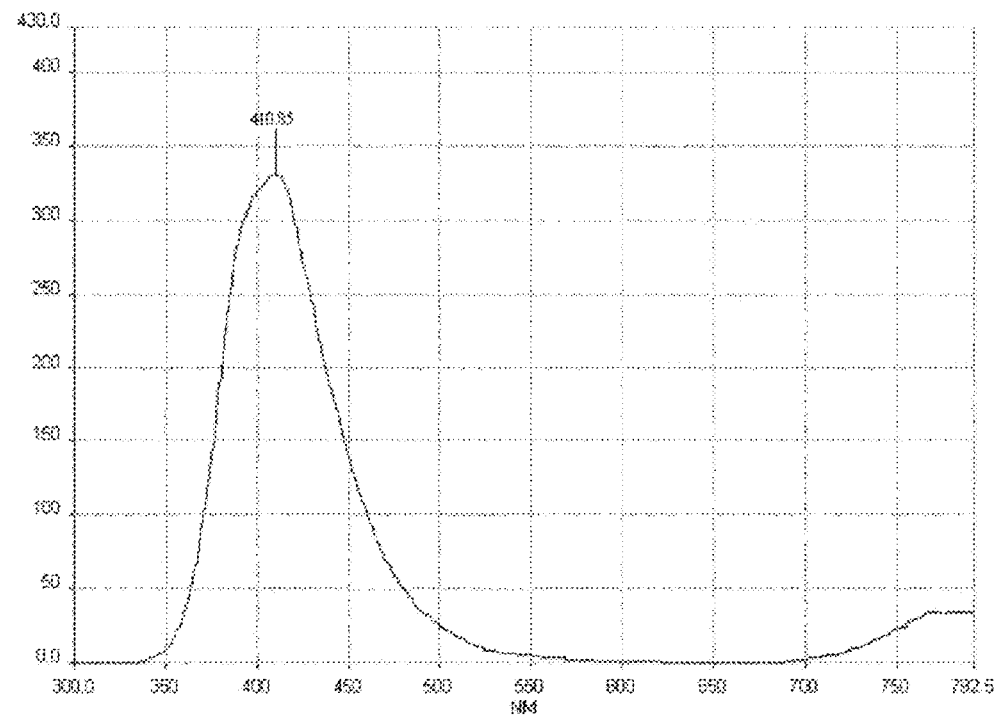

[Figure 50]
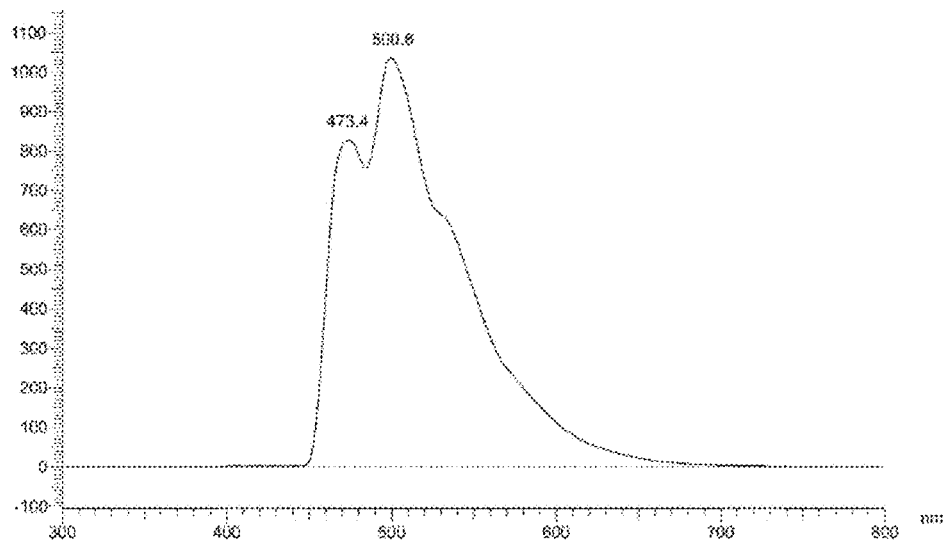
[Figure 51]
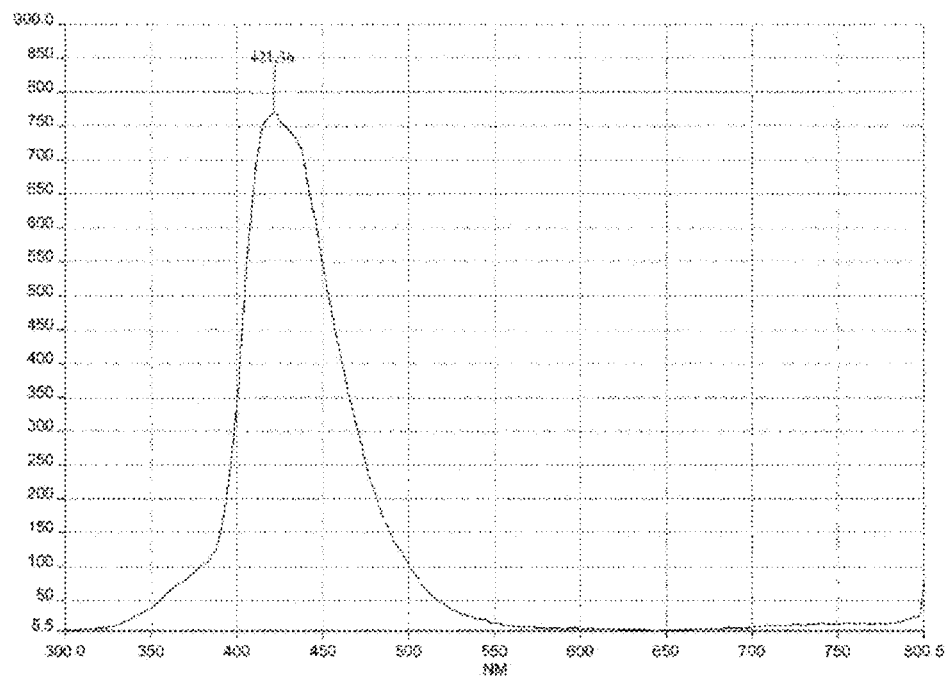

[Figure 52]
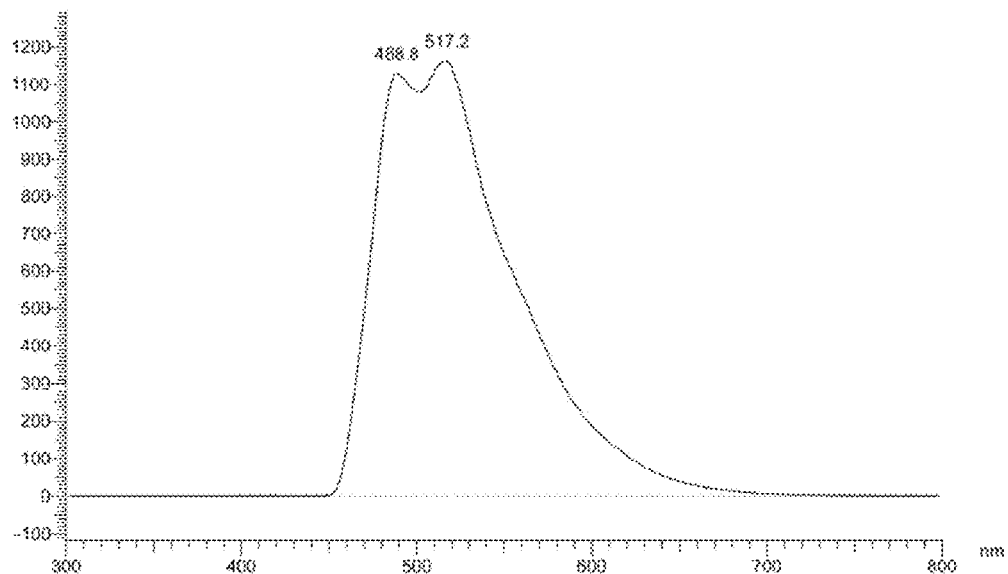
[Figure 53]
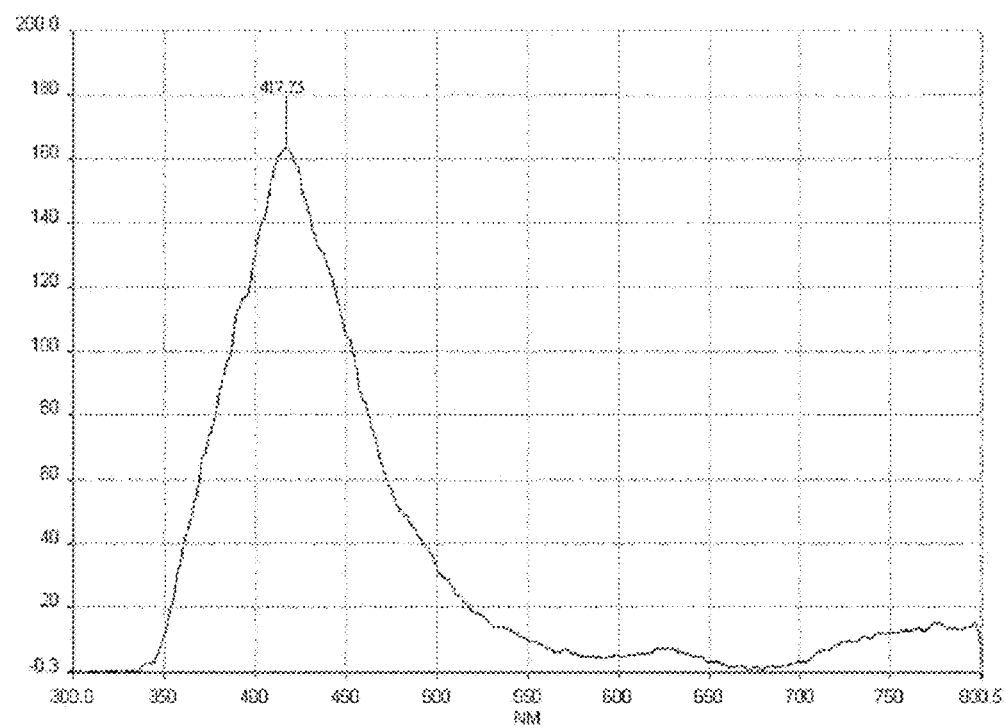

[Figure 54]
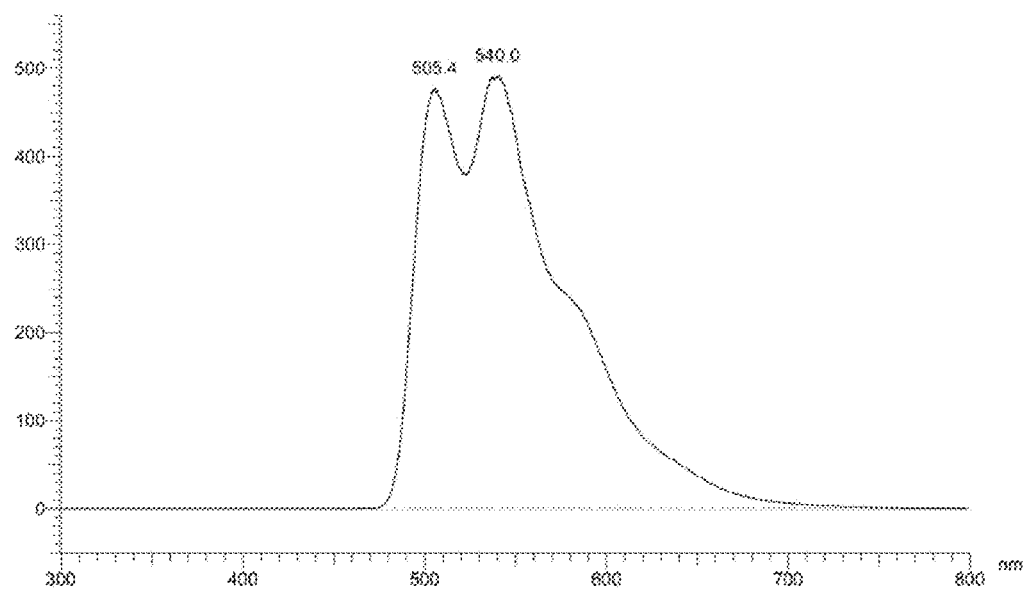
[Figure 55]
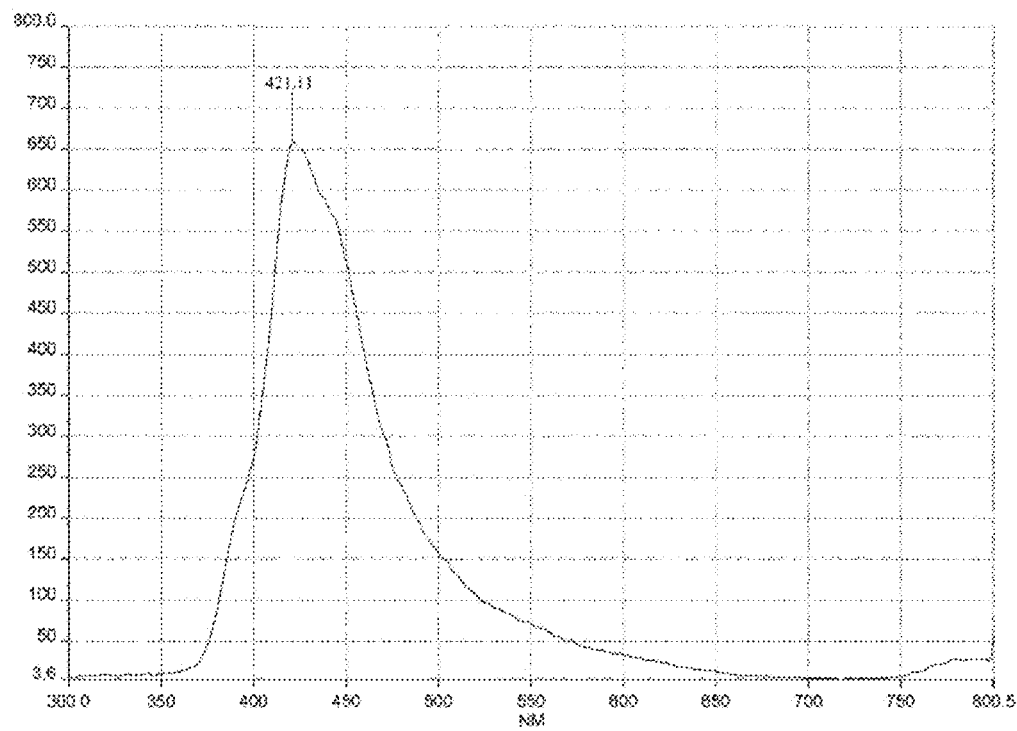

[Figure 56]
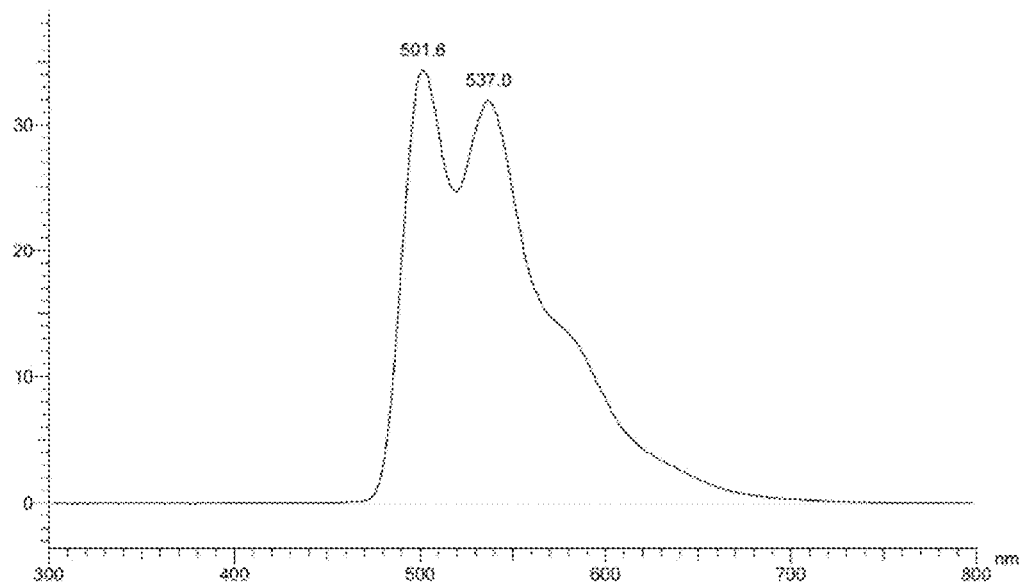
[Figure 57]
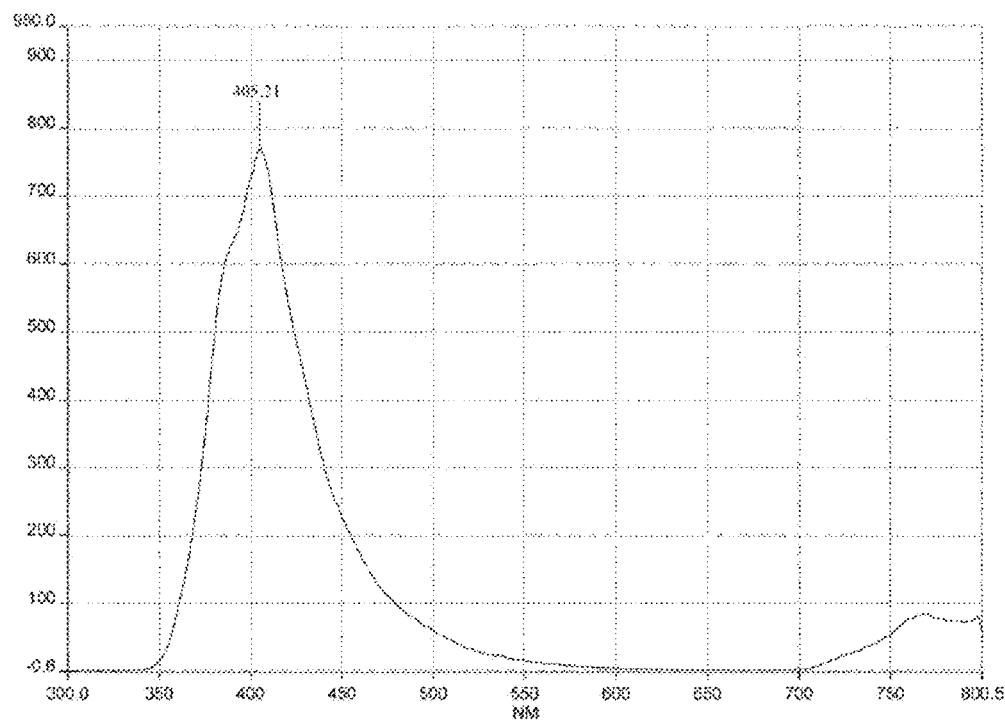

[Figure 58]
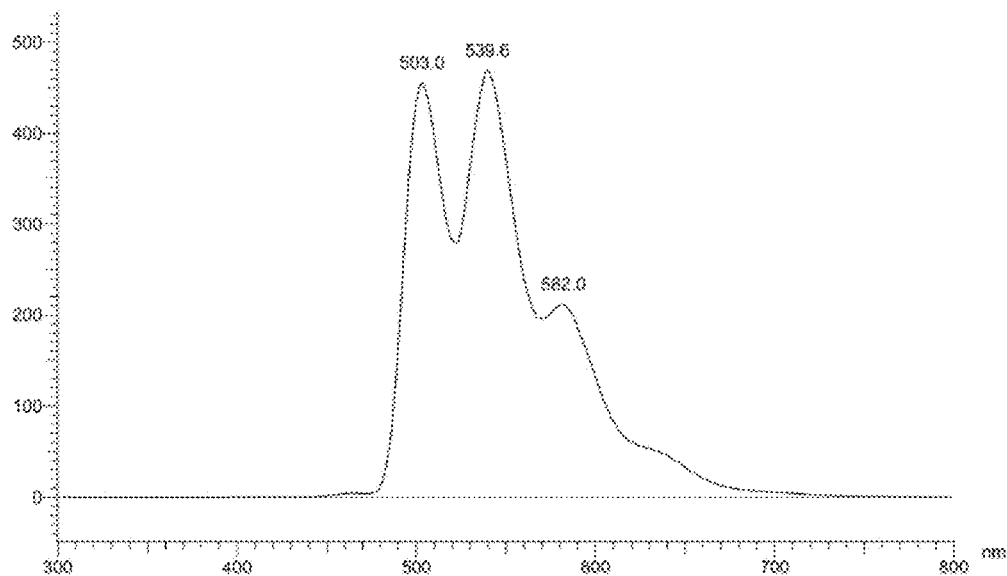
[Figure 59]
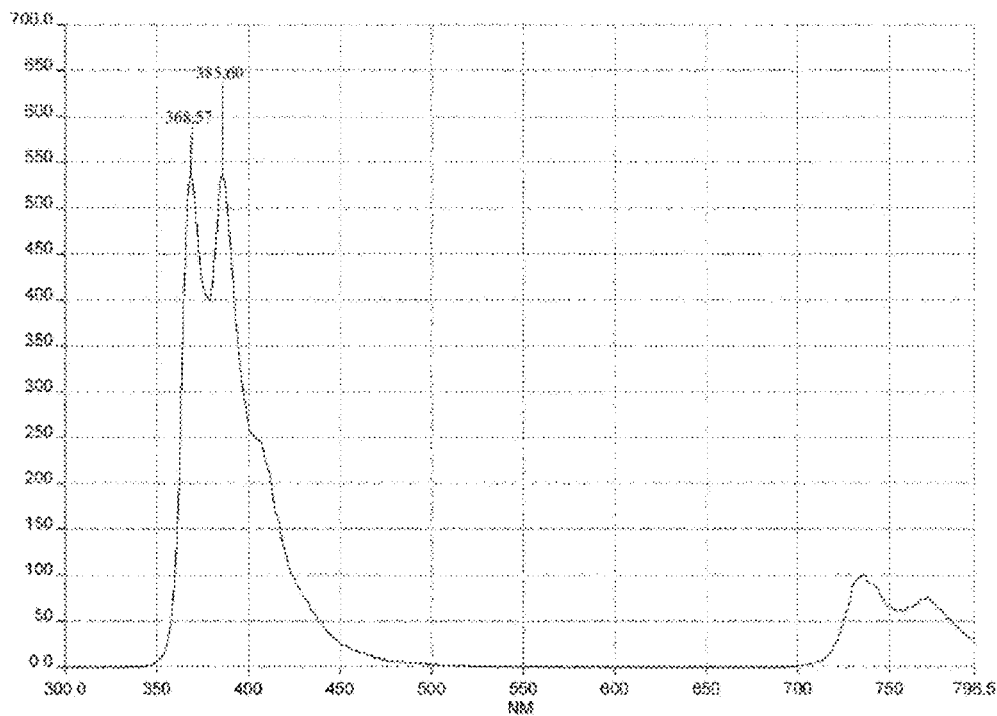

[Figure 60]
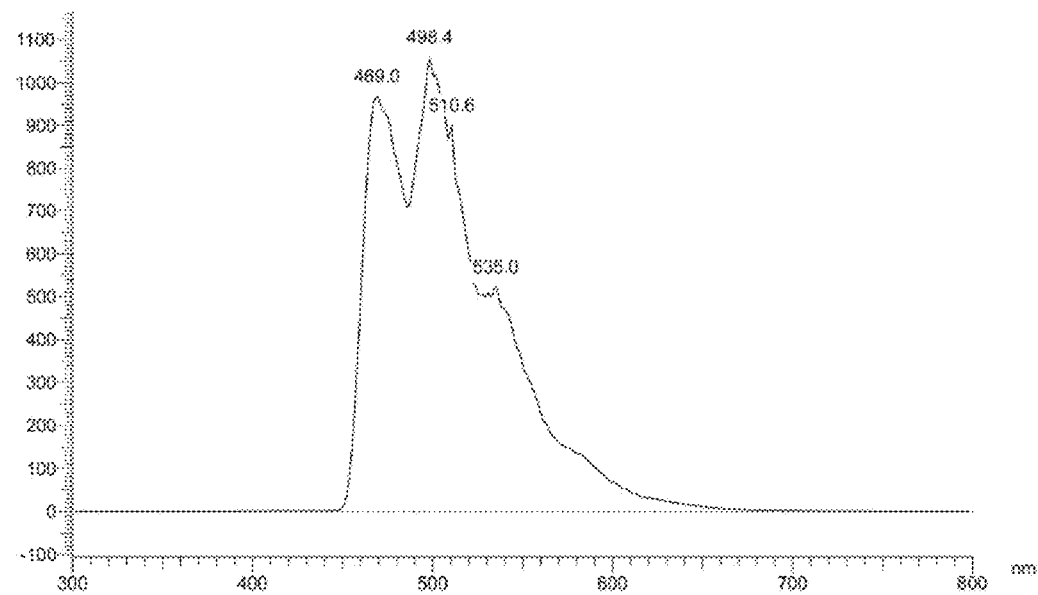
[Figure 61]
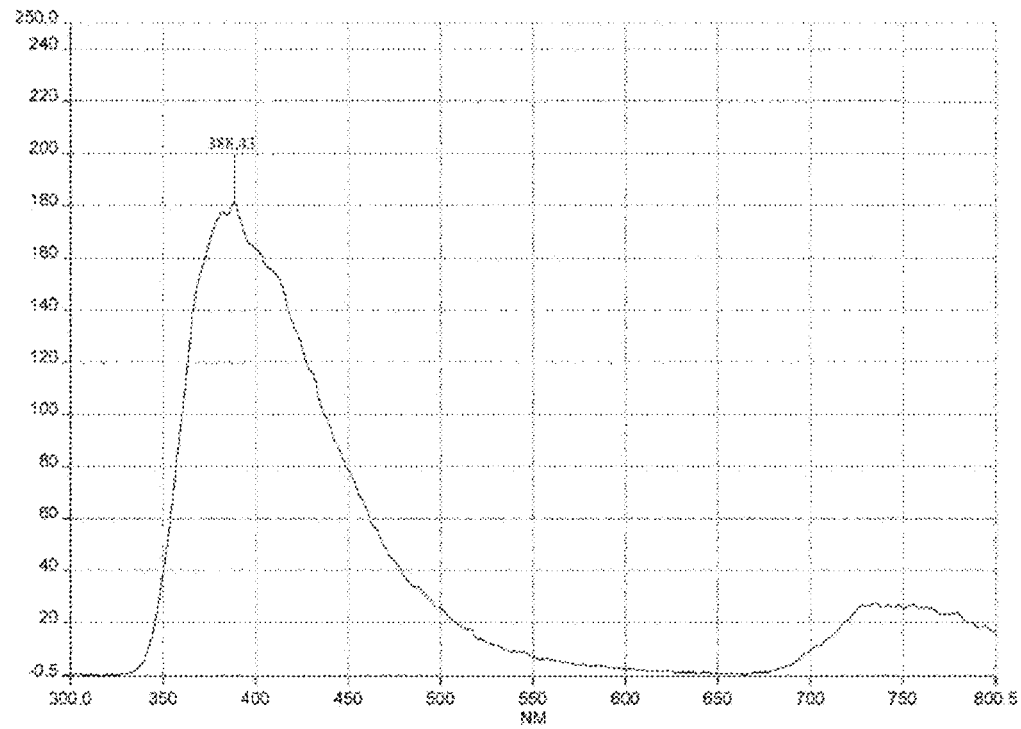

[Figure 62]
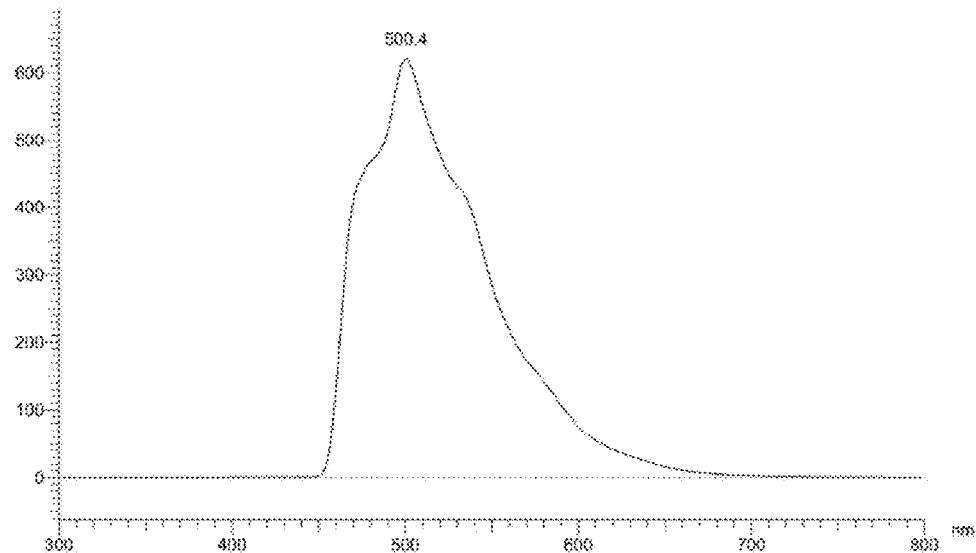
[Figure 63]
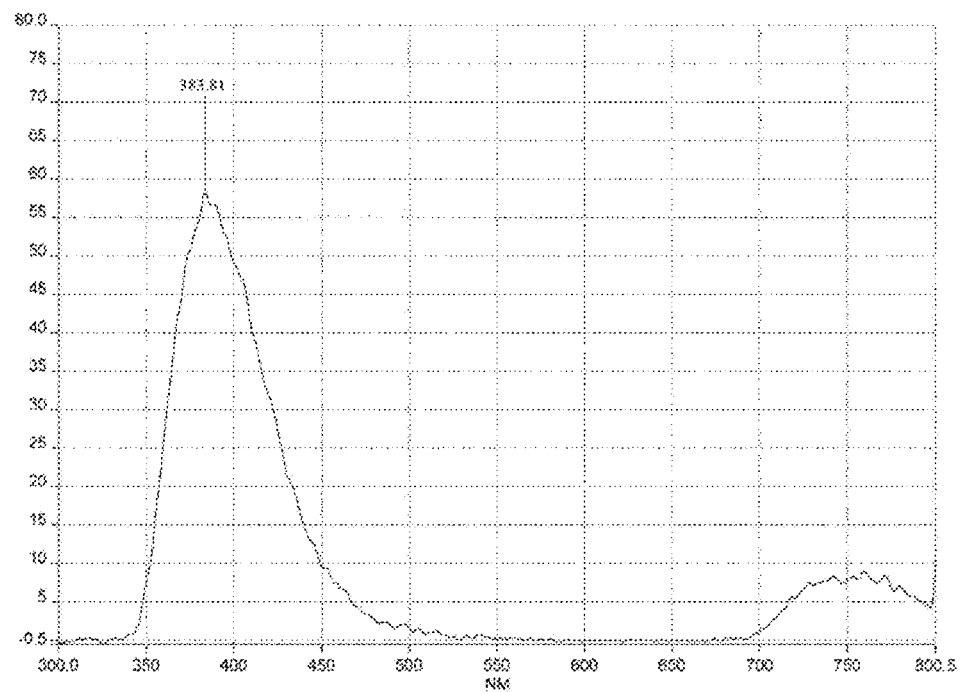

[Figure 64]
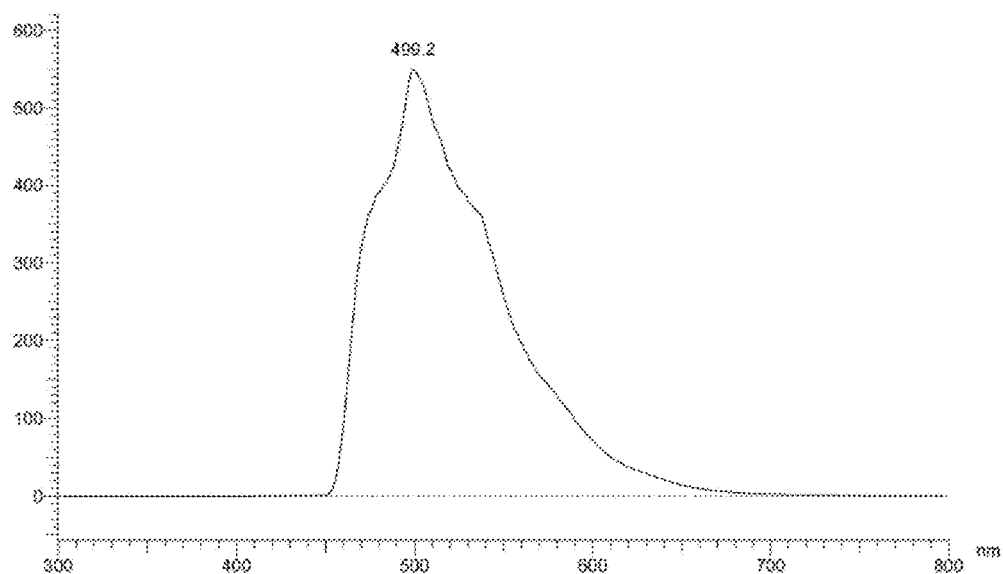
[Figure 65]
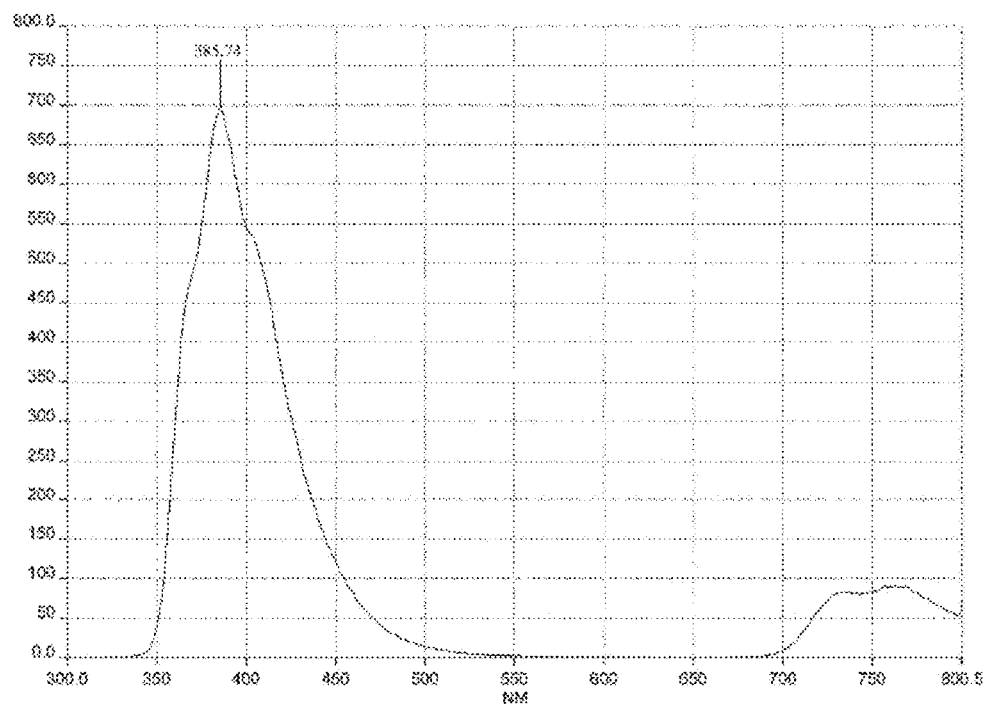

[Figure 66]
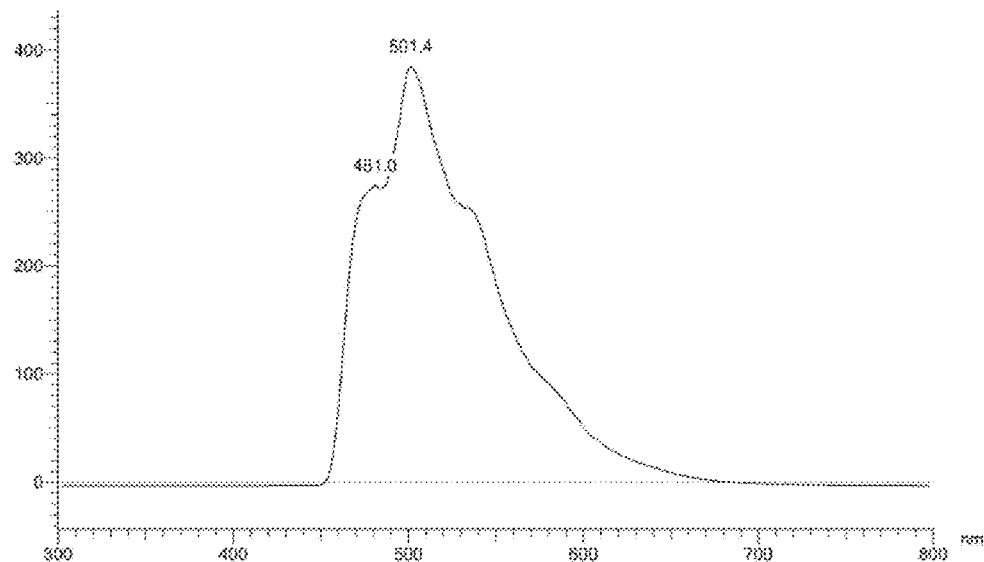
[Figure 67]
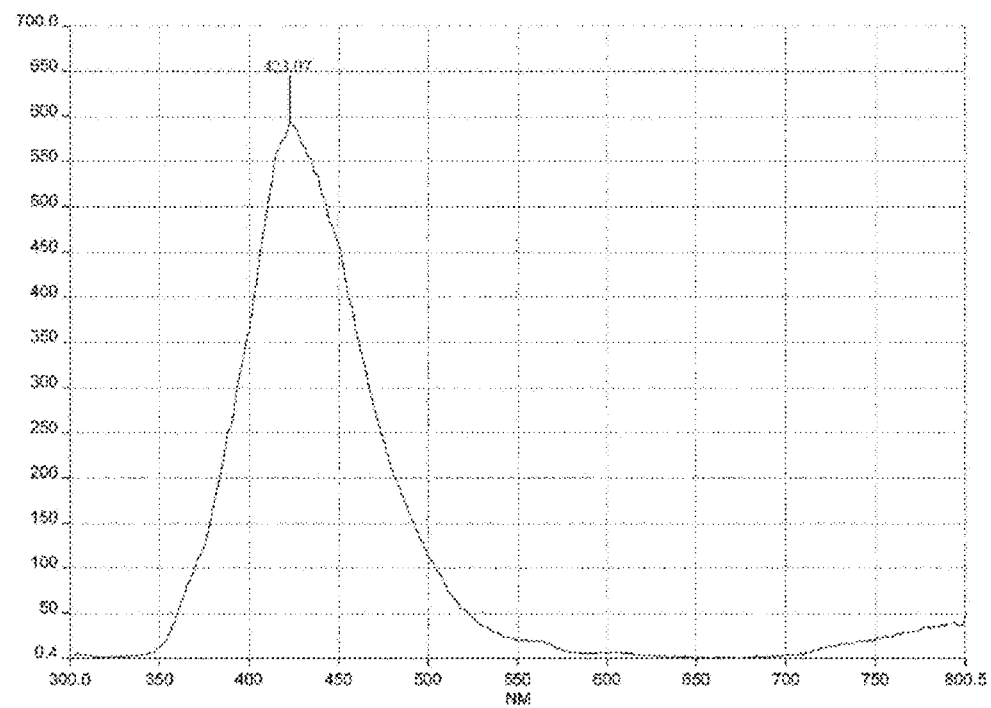

HETEROCYCLIC COMPOUND AND ORGANIC LIGHT EMITTING DEVICE USING SAME

TECHNICAL FIELD

This application claims priority to and the benefit of Korean Patent Application No. 10-2014-0080226 filed in the Korean Intellectual Property Office on Jun. 27, 2014, the entire contents of which are incorporated herein by reference.

The present application relates to a novel hetero-cyclic compound and an organic light emitting device using the same.

BACKGROUND ART

An electroluminescence device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, service life, or efficiency of the organic light emitting device, there is a continuous need for developing a material for an organic thin film.

DETAILED DESCRIPTION OF THE INVENTION

Technical Problem

The present application relates to a novel hetero-cyclic compound and an organic light emitting device using the same.

Technical Solution

The present application provides a compound of the following Formula 1.

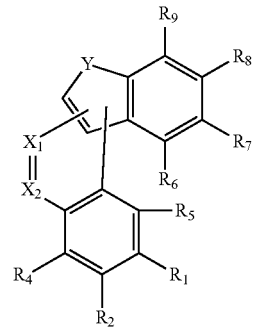

[Formula 1]

In Formula 1,

Y is S or O, $X_1$ and $X_2$ are the same as or different from each other, and are each independently N or $R_{10}$, and $R_1$, $R_2$, and $R_4$ to $R_{10}$ are the same as or different from each other, and are each independently selected from the group consisting of hydrogen; deuterium; halogen; straight-chained or branched substituted or unsubstituted $C_1$ to $C_{60}$ alkyl; straight-chained or branched substituted or unsubstituted $C_2$ to $C_{60}$ alkenyl; straight-chained or branched substituted or unsubstituted $C_2$ to $C_{60}$ alkynyl; straight-chained or branched substituted or unsubstituted $C_1$ to $C_{60}$ alkoxy; monocyclic or polycyclic substituted or unsubstituted $C_3$ to $C_{60}$ cycloalkyl; monocyclic or polycyclic substituted or unsubstituted $C_2$ to $C_{60}$ heterocycloalkyl; monocyclic or polycyclic substituted or unsubstituted $C_6$ to $C_{60}$ aryl; monocyclic or polycyclic substituted or unsubstituted $C_2$ to $C_{60}$ heteroaryl; and amine which is unsubstituted or substituted with $C_1$ to $C_{20}$ alkyl, monocyclic or polycyclic substituted or unsubstituted $C_6$ to $C_{60}$ aryl, or monocyclic or polycyclic substituted or unsubstituted $C_2$ to $C_{60}$ heteroaryl.

Further, the present application provides an organic light emitting device including a positive electrode, a negative electrode, and one or more organic material layers provided between the positive electrode and the negative electrode, in which one or more layers of the organic material layers include the compound of Formula 1.

Advantageous Effects

The compound described in the present specification may be used as a material for the organic material layer of the organic light emitting device. The compound may serve as a hole injection material, a hole transport material, a light emitting material, an electron transport material, an electron injection material, and the like in the organic light emitting device. In particular, the compound of Formula 1 may be used as a material for the light emitting layer of the organic light emitting device, specifically, a phosphorescent host.

BRIEF DESCRIPTION OF DRAWINGS

FIGS. 1 to 3 illustrate a stacking sequence of electrodes and organic material layers of an organic light emitting device according to exemplary embodiments of the present application.

FIG. 4 illustrates a measurement graph of UV and PL of Compound 29.

FIGS. 5 and 6 illustrate $E_{ox}$ values derived from the result of measuring CV of Compound 29.

FIG. 7 illustrates a measurement graph of UV and PL of Compound 42.

FIGS. 8 and 9 illustrate $E_{ox}$ values derived from the result of measuring CV of Compound 42.

FIG. 10 illustrates a measurement graph of UV and PL of Compound 87.

FIGS. 11 and 12 illustrate $E_{ox}$ values derived from the result of measuring CV of Compound 87.

FIG. 13 illustrates a measurement graph of UV and PL of Compound 88.

FIGS. 14 and 15 illustrate $E_{ox}$ values derived from the result of measuring CV of Compound 88.

FIG. 16 illustrates a measurement graph of UV and PL of Compound 90.

FIGS. 17 and 18 illustrate $E_{ox}$ values derived from the result of measuring CV of Compound 90.

FIG. 19 illustrates a measurement graph of UV and PL of Compound 91.

FIGS. 20 and 21 illustrate $E_{ox}$ values derived from the result of measuring CV of Compound 91.

FIG. 22 illustrates a measurement graph of UV and PL of Compound 92.

FIGS. 23 and 24 illustrate $E_{ox}$ values derived from the result of measuring CV of Compound 92.

FIG. 25 illustrates a measurement graph of UV and PL of Compound 93.

FIGS. 26 and 27 illustrate $E_{ox}$ values derived from the result of measuring CV of Compound 93.

FIG. 28 illustrates $E_{ox}$ values derived from the result of measuring CV of Compound 73.

FIG. 29 illustrates a measurement graph of UVPL of Compound 73.

FIG. 30 illustrates a measurement graph of LTPL of Compound 85.

FIG. 31 illustrates a measurement graph of UVPL of Compound 85.

FIG. 32 illustrates a measurement graph of LTPL of Compound 86.

FIG. 33 illustrates a measurement graph of UVPL of Compound 86.

FIG. 34 illustrates a measurement graph of LTPL of Compound 87.

FIG. 35 illustrates a measurement graph of UVPL of Compound 87.

FIG. 36 illustrates a measurement graph of LTPL of Compound 88.

FIG. 37 illustrates a measurement graph of UVPL of Compound 88.

FIG. 38 illustrates a measurement graph of LTPL of Compound 90.

FIG. 39 illustrates a measurement graph of UVPL of Compound 90.

FIG. 40 illustrates a measurement graph of LTPL of Compound 91.

FIG. 41 illustrates a measurement graph of UVPL of Compound 91.

FIG. 42 illustrates a measurement graph of LTPL of Compound 92.

FIG. 43 illustrates a measurement graph of UVPL of Compound 92.

FIG. 44 illustrates a measurement graph of LTPL of Compound 93.

FIG. 45 illustrates a measurement graph of UVPL of Compound 93.

FIG. 46 illustrates a measurement graph of LTPL of Compound 245.

FIG. 47 illustrates a measurement graph of UVPL of Compound 245.

FIG. 48 illustrates a measurement graph of LTPL of Compound 246.

FIG. 49 illustrates a measurement graph of UVPL of Compound 246.

FIG. 50 illustrates a measurement graph of LTPL of Compound 250.

FIG. 51 illustrates a measurement graph of UVPL of Compound 250.

FIG. 52 illustrates a measurement graph of LTPL of Compound 253.

FIG. 53 illustrates a measurement graph of UVPL of Compound 253.

FIG. 54 illustrates a measurement graph of LTPL of Compound 259.

FIG. 55 illustrates a measurement graph of UVPL of Compound 259.

FIG. 56 illustrates a measurement graph of LTPL of Compound 260.

FIG. 57 illustrates a measurement graph of UVPL of Compound 260.

FIG. 58 illustrates a measurement graph of LTPL of Compound 409.

FIG. 59 illustrates a measurement graph of UVPL of Compound 409.

FIG. 60 illustrates a measurement graph of LTPL of Compound 420.

FIG. 61 illustrates a measurement graph of UVPL of Compound 420.

FIG. 62 illustrates a measurement graph of LTPL of Compound 425.

FIG. 63 illustrates a measurement graph of UVPL of Compound 425.

FIG. 64 illustrates a measurement graph of LTPL of Compound 427.

FIG. 65 illustrates a measurement graph of UVPL of Compound 427.

FIG. 66 illustrates a measurement graph of LTPL of Compound 434.

FIG. 67 illustrates a measurement graph of UVPL of Compound 434.

EXPLANATION OF REFERENCE NUMERALS AND SYMBOLS

100: Substrate
200: Positive electrode
300: Organic material layer
301: Hole injection layer
302: Hole transport layer
303: Light emitting layer
304: Hole blocking layer
305: Electron transport layer
306: Electron injection layer
400: Negative electrode

BEST MODE

Hereinafter, the present application will be described in detail.

The compound described in the present specification may be represented by Formula 1. Specifically, the compound of Formula 1 may be used as a material for an organic material layer of an organic light emitting device by the structural characteristics of the core structure and the substituent as described above.

In the present specification, "substituted or unsubstituted" means to be unsubstituted or substituted with one or more substituents selected from the group consisting of deuterium; —CN; straight-chained or branched $C_1$ to $C_{60}$ alkyl; straight-chained or branched $C_2$ to $C_{60}$ alkenyl; straight-chained or branched $C_2$ to $C_{60}$ alkynyl; monocyclic or polycyclic $C_3$ to $C_{60}$ cycloalkyl; monocyclic or polycyclic $C_2$ to $C_{60}$ heterocycloalkyl; monocyclic or polycyclic $C_6$ to $C_{60}$ aryl; monocyclic or polycyclic $C_2$ to $C_{60}$ heteroaryl; —SiRR'R"; —P(=O)RR'; and —NRR', or to be unsubstituted or substituted with a substituent to which two or more substituents among the substituents are linked. For example, "the substituent to which two or more substituents are linked" may be a biphenyl group. That is, the biphenyl group may also be an aryl group, and may be interpreted as a substituent to which two phenyl groups are linked. R, R', and R" are the same as or different from each other, and are each independently straight-chained or branched $C_1$ to $C_{60}$ alkyl; monocyclic or polycyclic $C_6$ to $C_{60}$ aryl; or monocyclic or polycyclic $C_2$ to $C_{60}$ heteroaryl.

In the present specification, the alkyl includes a straight-chain or branch having 1 to 60 carbon atoms, and may be additionally substituted with another substituent. The number of carbon atoms of the alkyl may be 1 to 60, specifically 1 to 40, and more specifically 1 to 20.

In the present specification, the alkenyl includes a straight-chain or branch having 2 to 60 carbon atoms, and may be additionally substituted with another substituent. The number of carbon atoms of the alkenyl may be 2 to 60, specifically 2 to 40, and more specifically 2 to 20.

In the present specification, the alkynyl includes a straight-chain or branch having 2 to 60 carbon atoms, and may be additionally substituted with another substituent. The number of carbon atoms of the alkynyl may be 2 to 60, specifically 2 to 40, and more specifically 2 to 20.

In the present specification, the cycloalkyl includes a monocycle or polycycle having 3 to 60 carbon atoms, and may be additionally substituted with another substituent. Here, the polycycle means a group in which cycloalkyl is directly linked to or fused with another cyclic group. Here, another cyclic group may also be cycloalkyl, but may also be another kind of cyclic group, for example, heterocycloalkyl, aryl, heteroaryl, and the like. The number of carbon atoms of the cycloalkyl may be 3 to 60, specifically 3 to 40, and more specifically 5 to 20.

In the present specification, the heterocyclcoalkyl includes one or more of O, S, Se, N, and Si as a heteroatom, includes a monocycle or polycycle having 2 to 60 carbon atoms, and may be additionally substituted with another substituent. Here, the polycycle means a group in which heterocycloalkyl is directly linked to or fused with another cyclic group. Here, another cyclic group may also be heterocycloalkyl, but may also be another kind of cyclic group, for example, cycloalkyl, aryl, heteroaryl, and the like. The number of carbon atoms of the heterocycloalkyl may be 2 to 60, specifically 2 to 40, and more specifically 3 to 20.

In the present specification, the aryl includes a monocycle or polycycle having 6 to 60 carbon atoms, and may be additionally substituted with another substituent. Here, the polycycle means a group in which aryl is directly linked to or fused with another cyclic group. Here, another cyclic group may also be aryl, but may also be another kind of cyclic group, for example, cycloalkyl, heterocycloalkyl, heteroaryl, and the like. The aryl includes a Spiro group. The number of carbon atoms of the aryl may be 6 to 60, specifically 6 to 40, and more specifically 6 to 25. Specific examples of the aryl include phenyl, biphenyl, triphenyl, naphthyl, anthryl, chrysenyl, phenanthrenyl, perylenyl, fluoranthenyl, triphenylenyl, phenalenyl, pyrenyl, tetracenyl, pentacenyl, fluorenyl, indenyl, acenaphthylenyl, fluorenyl, benzofluorenyl, spirobifluorenyl and the like, or fused rings thereof, but are not limited thereto.

In the present specification, the Spiro group is a group including a spiro structure, and may have 15 to 60 carbon atoms. For example, the spiro group may include a structure in which a 2,3-dihydro-1H-indene group or a cyclohexane group is spiro-bonded to a fluorene group. Specifically, the Spiro group includes a group of the following structural formula.

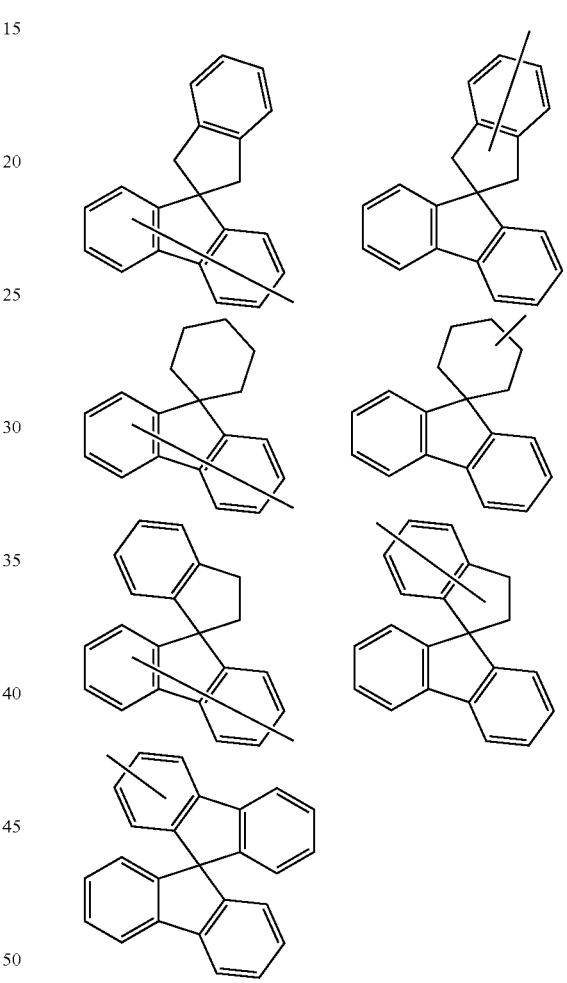

In the present specification, the heteroaryl includes one or more of S, O, Se, N, and Si as a heteroatom, includes a monocycle or polycycle having 2 to 60 carbon atoms, and may be additionally substituted with another substituent. Here, the polycycle means a group in which heteroaryl is directly linked to or fused with another cyclic group. Here, another cyclic group may also be heteroaryl, but may also be another kind of cyclic group, for example, cycloalkyl, heterocycloalkyl, aryl, and the like. The number of carbon atoms of the heteroaryl may be 2 to 60, specifically 2 to 40, and more specifically 3 to 25. Specific examples of the heteroaryl include pyridyl, pyrrolyl, pyrimidyl, pyridazinyl, furanyl, a thiophene group, imidazolyl, pyrazolyl, oxazolyl, isoxazolyl, thiazolyl, isothiazolyl, triazolyl, furazanyl, oxadiazolyl, thiadiazolyl, dithiazolyl, tetrazolyl, pyranyl, thiopyranyl, diazinyl, oxazinyl, thiazinyl, dioxynyl, triazinyl, tetrazinyl, quinolyl, isoquinolyl, quinazolinyl, isoquinazolinyl, naphthyridyl, acridinyl, phenanthridinyl, imidazopyridinyl, diazanaphtalenyl, triazaindene, indolyl, indolyzinyl, benzothiazolyl, benzoxazolyl, benzoimidazolyl, a benzothiophene group, a benzofuran group, a dibenzothiophene group, a dibenzofuran group, carbazolyl, benzocarbazolyl, dibenzocarbazolyl, phenazinyl, dibenzosilole, spirobi(dibenzosilole), dihydrophenazinyl, phenoxazinyl, phenanthridyl and the like, or fused rings thereof, but are not limited thereto.

According to an exemplary embodiment of the present application, Y in Formula 1 is S.

According to an exemplary embodiment of the present application, Y in Formula 1 is O.

According to an exemplary embodiment of the present application, one of $X_1$ and $X_2$ in Formula 1 is N and the other is $CR_{10}$.

According to an exemplary embodiment of the present application, one of $X_1$ and $X_2$ in Formula 1 is N and the other is $CR_{10}$, and at least one of $R_1$, $R_2$, and $R_{10}$ is -(L)m-(Z)n, L is straight-chained or branched substituted or unsubstituted $C_2$ to $C_{60}$ alkylene; monocyclic or polycyclic substituted or unsubstituted $C_2$ to $C_{60}$ arylene; or monocyclic or polycyclic substituted or unsubstituted $C_2$ to $C_{60}$ heteroarylene, m is an integer of 0 to 3, n is an integer of 1 or 2, and Z is selected from the group consisting of monocyclic or polycyclic substituted or unsubstituted $C_6$ to $C_{60}$ aryl; monocyclic or polycyclic substituted or unsubstituted $C_2$ to $C_{60}$ heteroaryl; $—SiR_{11}R_{12}R_{13}$; $—P(=O)R_{14}R_{15}$; and amine which is unsubstituted or substituted with $C_1$ to $C_{20}$ alkyl, monocyclic or polycyclic substituted or unsubstituted $C_6$ to $C_{60}$ aryl, or monocyclic or polycyclic substituted or unsubstituted $C_2$ to $C_{60}$ heteroaryl, and R11 to R15 are the same as or different from each other, and are each independently straight-chained or branched substituted or unsubstituted C1 to C60 alkyl; monocyclic or polycyclic $C_6$ to $C_{60}$ aryl; or monocyclic or polycyclic $C_2$ to $C_{60}$ heteroaryl.

According to an exemplary embodiment of the present application, m may be 0, or an integer of 1, 2, or 3. When m is an integer of 2 or more, L's may be the same as or different from each other.

According to an exemplary embodiment of the present application, when m is an integer of 2, Z's may be the same as or different from each other.

According to an exemplary embodiment of the present application, L is $C_2$ to $C_{60}$ alkylene; or $C_6$ to $C_{60}$ arylene.

According to an exemplary embodiment of the present application, L is phenylene; naphthylene; or anthracenylene.

According to an exemplary embodiment of the present application, Z is substituted or unsubstituted phenyl, substituted or unsubstituted biphenyl, substituted or unsubstituted triphenyl, substituted or unsubstituted naphthyl, substituted or unsubstituted anthracenyl, substituted or unsubstituted phenanthrenyl, substituted or unsubstituted indenyl, substituted or unsubstituted perylenyl, substituted or unsubstituted pyrenyl, substituted or unsubstituted acenaphthalenyl, substituted or unsubstituted fluorenyl, substituted or unsubstituted fluoranthenyl, substituted or unsubstituted triphenylenyl, substituted or unsubstituted phenalenyl, substituted or unsubstituted pyrrole, substituted or unsubstituted pyridyl, substituted or unsubstituted pyrimidyl, substituted or unsubstituted pyridazinyl, substituted or unsubstituted triazinyl, substituted or unsubstituted thienyl, substituted or unsubstituted furanyl, substituted or unsubstituted benzofuranyl, substituted or unsubstituted dibenzofuranyl, substituted or unsubstituted benzothiazole, substituted or unsubstituted benzoxazole, substituted or unsubstituted indolyl, substituted or unsubstituted carbazolyl, substituted or unsubstituted benzocarbazolyl, substituted or unsubstituted dibenzocarbazolyl, substituted or unsubstituted indolo[2,3-a]carbazolyl, substituted or unsubstituted indolo[2,3-b]carbazolyl, substituted or unsubstituted quinolyl, substituted or unsubstituted isoquinolyl, substituted or unsubstituted thiophenyl, substituted or unsubstituted benzothiophenyl, substituted or unsubstituted dibenzothiophenyl, substituted or unsubstituted fluorenyl, substituted or unsubstituted indolinyl, a substituted or unsubstituted 10,11-dihydrodibenzo[b,f]azepine group, a substituted or unsubstituted 9,10-dihydroacridine group, a substituted or unsubstituted spiro group in which 2,3-dihydro-1H-indene or cyclohexane is spiro-bonded to fluorene, substituted or unsubstituted dialkylamine, substituted or unsubstituted diarylamine, substituted or unsubstituted alkylarylamine, a substituted or unsubstituted acetophenone group, a substituted or unsubstituted benzophenone group, $—SiR_{11}R_{12}R_{13}$ or $—P(=O)R_{14}R_{15}$, and $R_{11}$ to $R_{15}$ are the same as or different from each other, and are each independently straight-chained or branched $C_1$ to $C_{60}$ alkyl; monocyclic or polycyclic $C_6$ to $C_{60}$ aryl; or monocyclic or polycyclic $C_2$ to $C_{60}$ heteroaryl.

According to an exemplary embodiment of the present application, Z is selected from substituted or unsubstituted phenyl, substituted or unsubstituted biphenyl, substituted or unsubstituted triphenyl, substituted or unsubstituted naphthyl, substituted or unsubstituted anthracenyl, substituted or unsubstituted carbazolyl, substituted or unsubstituted benzocarbazolyl, substituted or unsubstituted dibenzocarbazolyl, substituted or unsubstituted indolo[2,3-a]carbazolyl, substituted or unsubstituted indolo[2,3-b]carbazolyl, substituted or unsubstituted fluorenyl, substituted or unsubstituted benzofuranyl, substituted or unsubstituted dibenzofuranyl, substituted or unsubstituted thiophenyl, substituted or unsubstituted benzothiophenyl, substituted or unsubstituted dibenzothiophenyl, substituted or unsubstituted triphenylenyl, substituted or unsubstituted triazinyl, substituted or unsubstituted pyrenyl, $—Si(Ph)_3$, $—P(=O)(Ph)_2$, and substituted or unsubstituted diphenylamine, "substituted or unsubstituted" means to be unsubstituted or substituted with at least one selected from methyl, straight-chained or branched propyl, straight-chained or branched butyl, straight-chained or branched pentyl, phenyl, biphenyl, triphenyl, naphthyl, anthracenyl, carbazolyl, benzocarbazolyl, dibenzocarbazolyl, indolo[2,3-a]carbazolyl, indolo[2,3-b]carbazolyl, fluorenyl, benzofuranyl, dibenzofuranyl, thiophenyl, benzothiophenyl, dibenzothiophenyl, triphenylenyl, triazinyl, pyrenyl, $—Si(Ph)_3$, $—P(=O)(Ph)_2$, and diphenylamine, and the substituent may be additionally further substituted.

According to an exemplary embodiment of the present application, $R_{11}$ to $R_{15}$ are the same as or different from each other, and are monocyclic or polycyclic $C_6$ to $C_{60}$ aryl.

According to an exemplary embodiment of the present application, $R_{11}$ to $R_{15}$ are the same as or different from each other, and are phenyl, biphenyl, triphenyl, naphthyl, or anthracenyl.

According to an exemplary embodiment of the present application, $R_4$ to $R_9$ are hydrogen or deuterium.

According to an exemplary embodiment of the present application, Formula 1 is represented by the following Formula 2 or 3.

[Formula 2]

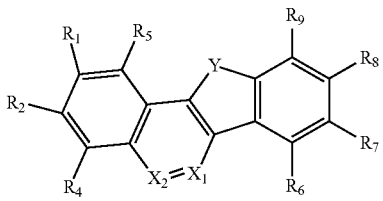

[Formula 3]

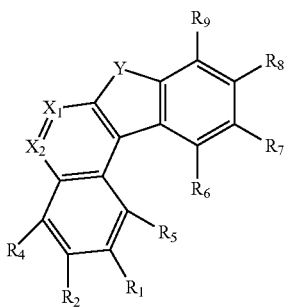

In Formulae 2 and 3, the definitions of Y, $X_1$, $X_2$, $R_1$, $R_2$, and $R_4$ to $R_9$ are the same as those defined in Formula 1.

In an exemplary embodiment of the present application, Formula 1 is represented by any one of the following Formulae 4 to 7.

[Formula 4]

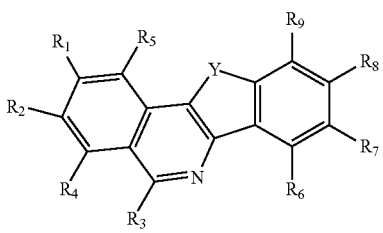

[Formula 5]

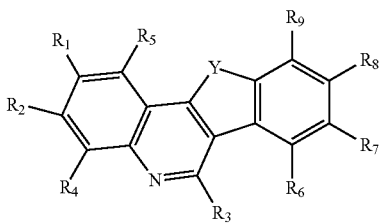

[Formula 6]

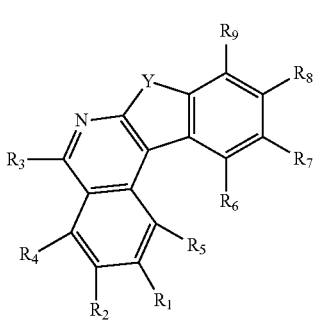

[Formula 7]

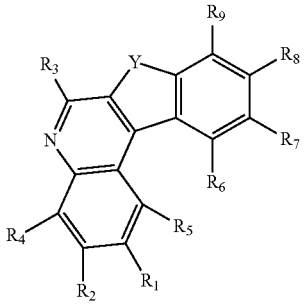

In Formulae 4 to 7, Y, $R_1$, $R_2$, and $R_4$ to $R_9$ are the same as those defined in Formula 1, and $R_3$ is the same as the definition of $R_{10}$ of Formula 1.

According to an exemplary embodiment of the present application, in Formulae 4 to 7, at least one of $R_1$ to $R_3$ is -(L)m-(Z)n, and the others are the same as those defined in Formula 1, and the definitions of Y, $R_4$ to $R_9$, L, m, and Z are the same as those defined in Formula 1.

According to an exemplary embodiment of the present application, in Formulae 4 to 7, $R_1$ is -(L)m-(Z)n, $R_2$ and $R_3$ are hydrogen, deuterium, or phenyl, and L, m, n, and Z are the same as those described above.

According to an exemplary embodiment of the present application, in Formulae 4 to 7, $R_2$ is -(L)m-(Z)n, R1 and $R_3$ are hydrogen, deuterium, or phenyl, and L, m, n, and Z are the same as those described above.

According to an exemplary embodiment of the present application, in Formulae 4 to 7, $R_3$ is -(L)m-(Z)n, R1 and $R_3$ are hydrogen, deuterium, or phenyl, and L, m, n, and Z are the same as those described above.

According to an exemplary embodiment of the present application, in Formulae 4 to 7, m is 0 or 1.

According to an exemplary embodiment of the present application, Formula 1 is represented by any one of the following Formulae 8 to 11.

[Formula 8]

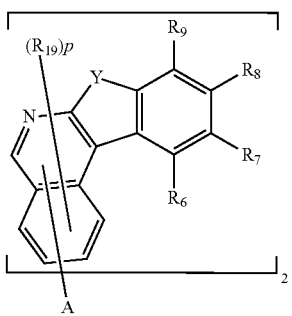

-continued

[Formula 9]

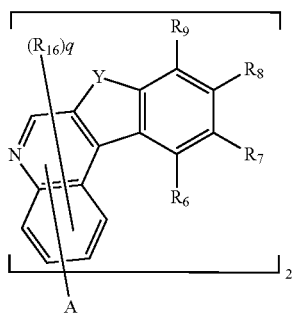

[Formula 10]

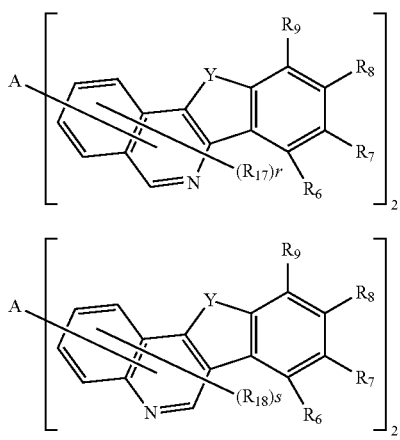

[Formula 11]

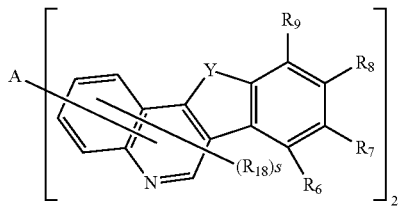

In Formulae 8 to 11,

A is selected from the group consisting of a direct bond; straight-chained or branched substituted or unsubstituted $C_2$ to $C_{60}$ alkylene; straight-chained or branched substituted or unsubstituted $C_2$ to $C_{60}$ alkenylene; straight-chained or branched substituted or unsubstituted $C_2$ to $C_{60}$ alkynylene; monocyclic or polycyclic substituted or unsubstituted $C_3$ to $C_{60}$ cycloalkylene; monocyclic or polycyclic substituted or unsubstituted $C_2$ to $C_{60}$ heterocycloalkylene; monocyclic or polycyclic substituted or unsubstituted $C_6$ to $C_{60}$ arylene; monocyclic or polycyclic substituted or unsubstituted $C_2$ to $C_{60}$ heteroarylene; and amine which is unsubstituted or substituted with $C_1$ to $C_{20}$ alkyl, monocyclic or polycyclic substituted or unsubstituted $C_6$ to $C_{60}$ aryl, or monocyclic or polycyclic substituted or unsubstituted $C_2$ to $C_{60}$ heteroaryl, $R_{16}$ to $R_{19}$ are the same as or different from each other, and are each independently selected from the group consisting of hydrogen; deuterium; halogen; straight-chained or branched substituted or unsubstituted $C_1$ to $C_{60}$ alkyl; straight-chained or branched substituted or unsubstituted $C_2$ to $C_{60}$ alkenyl; straight-chained or branched substituted or unsubstituted $C_2$ to $C_{60}$ alkynyl; straight-chained or branched substituted or unsubstituted $C_1$ to $C_{60}$ alkoxy; monocyclic or polycyclic substituted or unsubstituted $C_3$ to $C_{60}$ cycloalkyl; monocyclic or polycyclic substituted or unsubstituted $C_2$ to $C_{60}$ heterocycloalkyl; monocyclic or polycyclic substituted or unsubstituted $C_6$ to $C_{60}$ aryl; monocyclic or polycyclic substituted or unsubstituted $C_2$ to $C_{60}$ heteroaryl; and amine which is unsubstituted or substituted with $C_1$ to $C_{20}$ alkyl, monocyclic or polycyclic substituted or unsubstituted $C_6$ to $C_{60}$ aryl, or monocyclic or polycyclic substituted or unsubstituted $C_2$ to $C_{60}$ heteroaryl, p, q, r, and s are an integer of 0 to 4, and
the definitions of Y and $R_6$ to $R_9$ are the same as those defined in Formula 1.

Formulae 8 to 11 mean a dimer structure, and A means a linking group of the dimer.

According to an exemplary embodiment of the present application, in Formulae 8 to 11, A is selected from the group consisting of monocyclic or polycyclic substituted or unsubstituted $C_6$ to $C_{60}$ arylene; and monocyclic or polycyclic substituted or unsubstituted $C_2$ to $C_{60}$ heteroarylene.

According to an exemplary embodiment of the present application, in Formulae 8 to 11, A is $C_6$ to $C_{60}$ arylene which is unsubstituted or substituted with alkyl or aryl; or $C_2$ to $C_{60}$ heteroarylene which is unsubstituted or substituted with alkyl or aryl.

According to an exemplary embodiment of the present application, in Formulae 8 to 11, A is a carbazole group which is unsubstituted or substituted with alkyl or aryl; or a fluorene group which is unsubstituted or substituted with alkyl or aryl.

According to an exemplary embodiment of the present application, in Formulae 8 to 11, A is a carbazole group which is unsubstituted or substituted with alkyl or aryl; or a fluorene group which is unsubstituted or substituted with alkyl or aryl, the alkyl is a $C_1$ to $C_{10}$ straight-chain or branch, and the aryl is a $C_6$ to $C_{20}$ aryl.

According to an exemplary embodiment of the present application, Y of Formulae 1 to 7 is

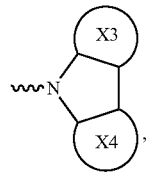

and X3 and X4 may be a monocyclic or polycyclic substituted or unsubstituted $C_6$ to $C_{60}$ aromatic hydrocarbon ring; or a monocyclic or polycyclic substituted or unsubstituted $C_2$ to $C_{60}$ aromatic heterocyclic ring.

The

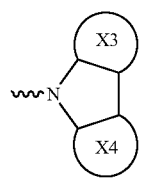

may be represented by any one of the following structural formulae, but is not limited thereto.

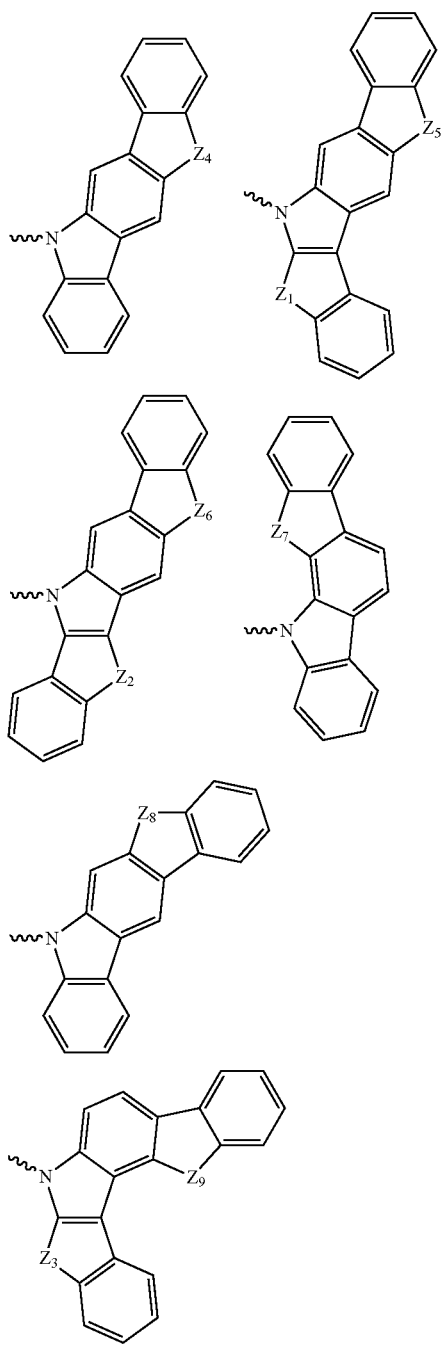

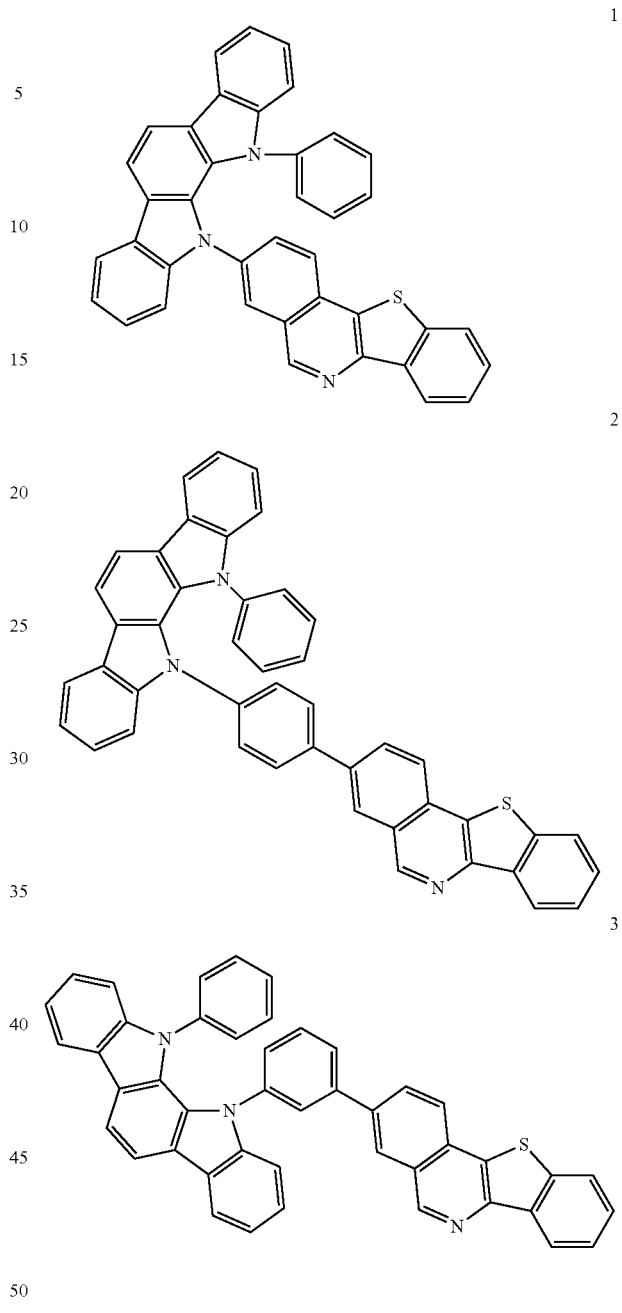

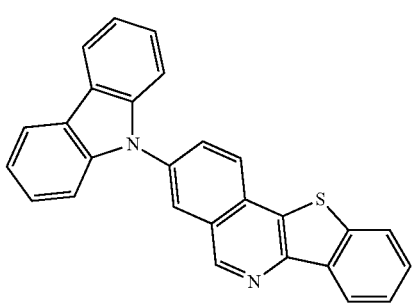

In the structural formulae, $Z_1$ to $Z_3$ are the same as or different from each other, and are each independently S or O, $Z_4$ to $Z_9$ are the same as or different from each other, and are each independently CR'R", NR', S, or O, and R' and R" are the same as or different from each other, and are each independently hydrogen; straight-chained or branched substituted or unsubstituted $C_1$ to $C_{60}$ alkyl; or monocyclic or polycyclic substituted or unsubstituted $C_6$ to $C_{60}$ aryl.

According to an exemplary embodiment of the present application, Formula 1 may be selected from the following compounds.

5
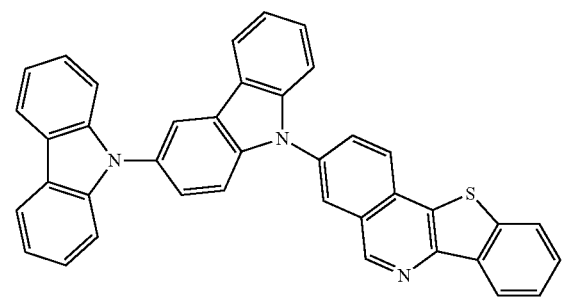
6
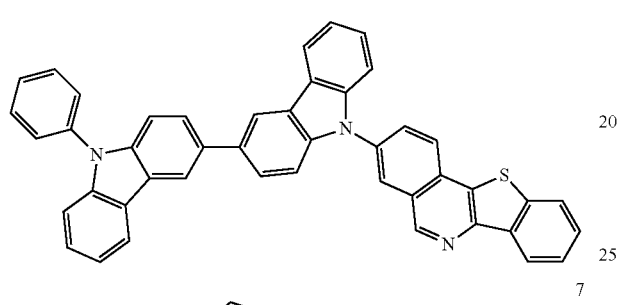
7
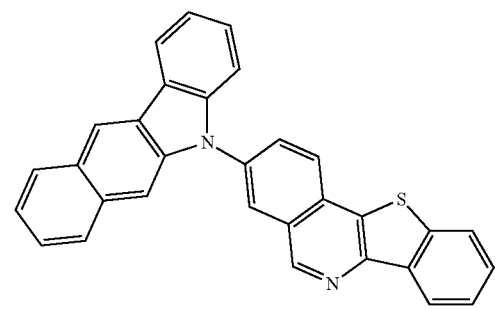
8
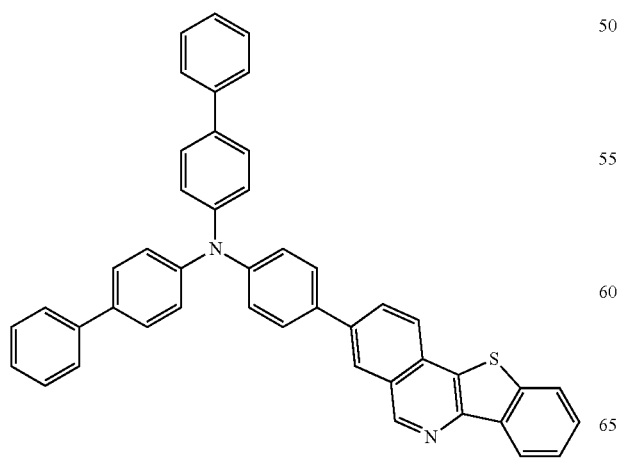
9
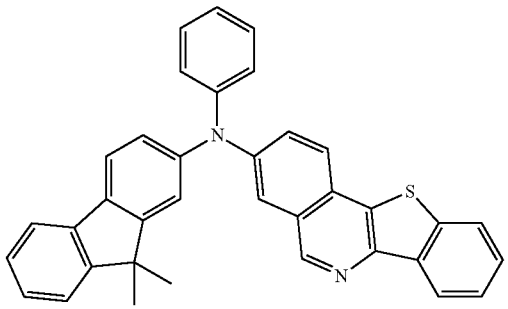
10
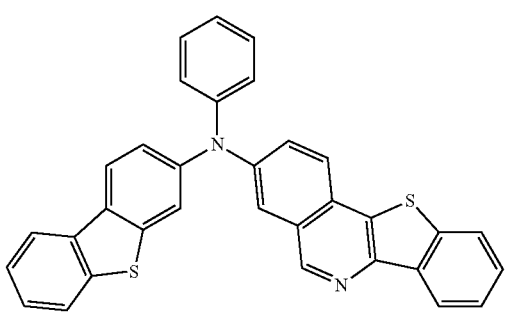
11
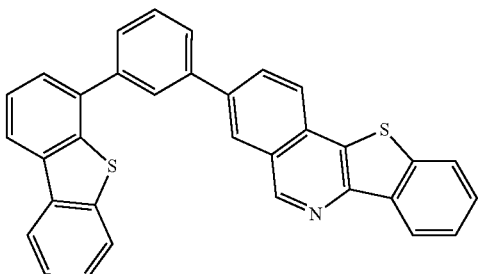
12
13
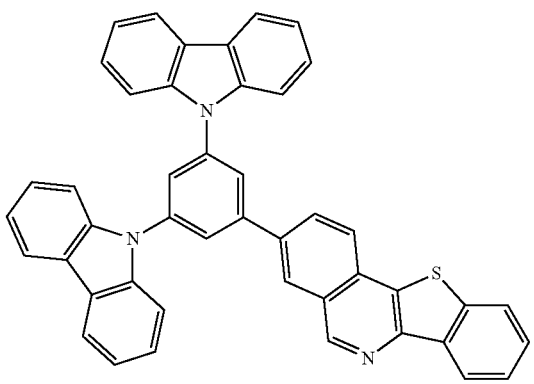

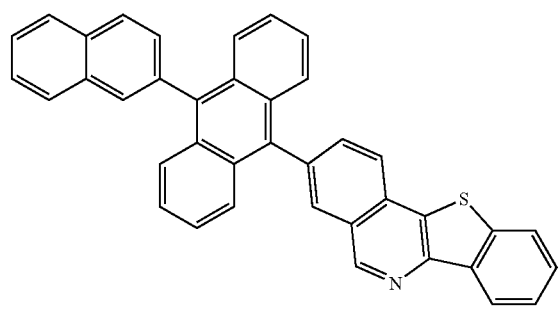
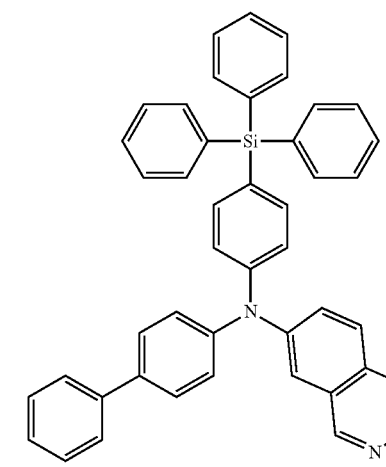
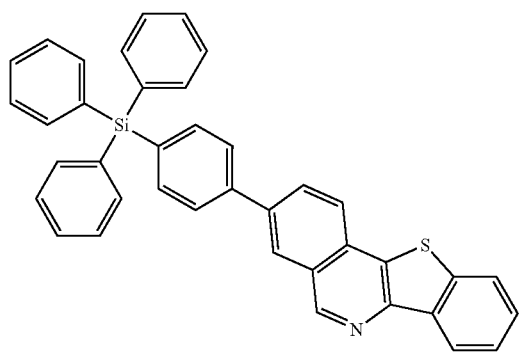
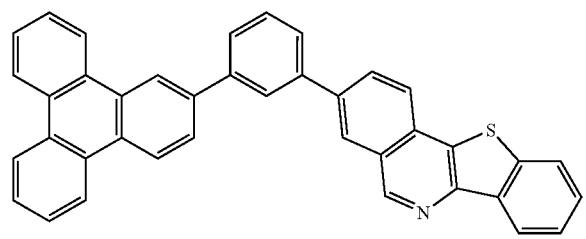
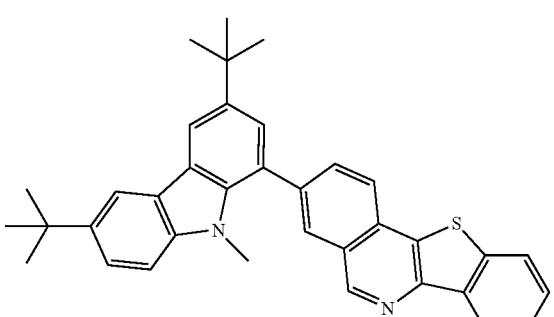
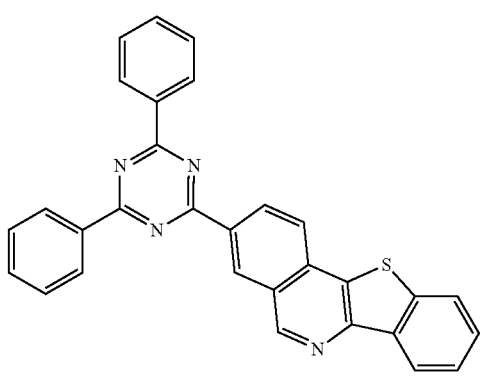
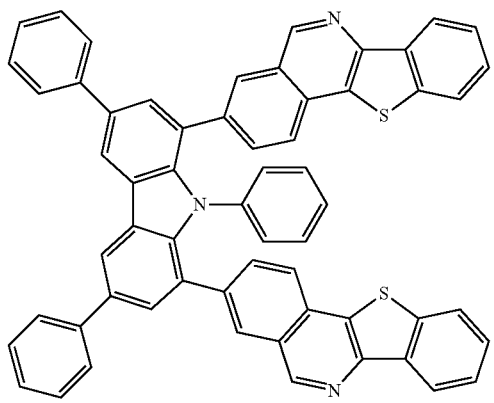

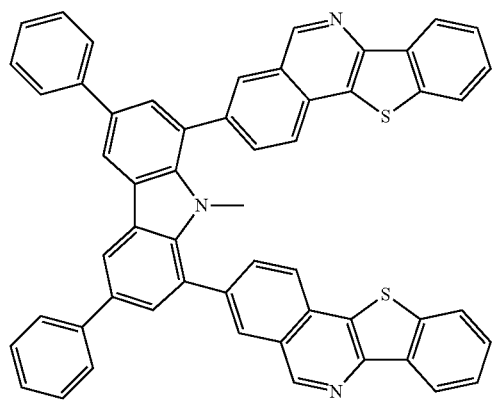
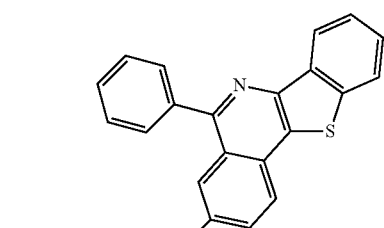

27
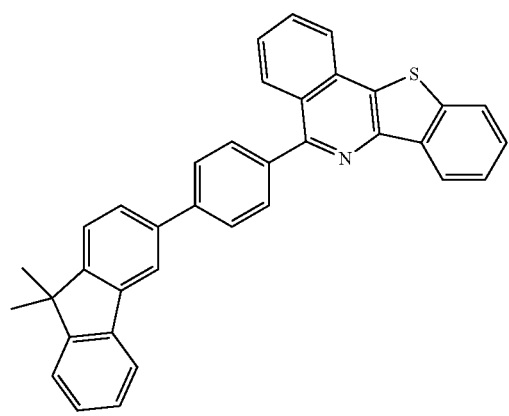
28
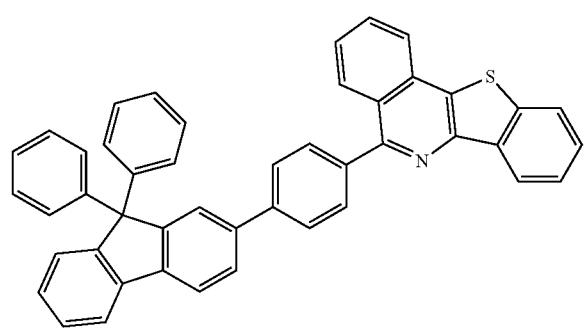
29
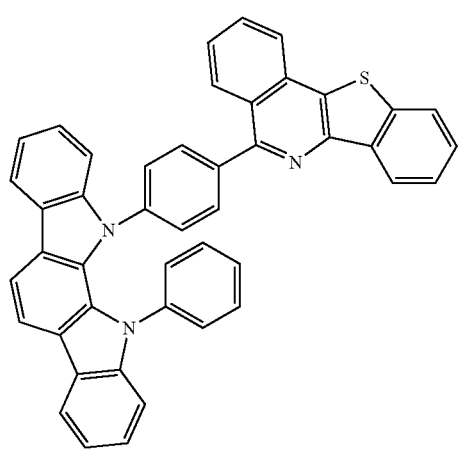
30
31
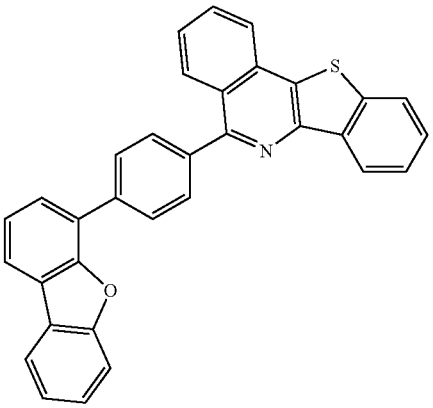
32
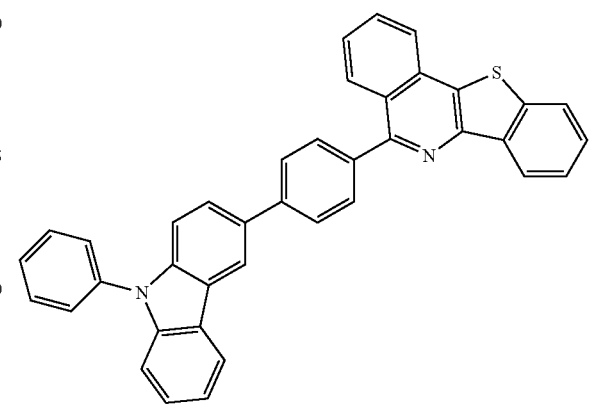
33
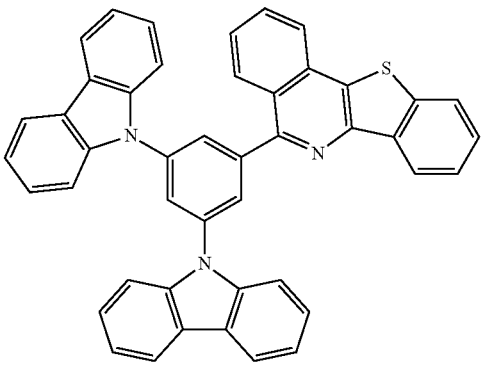
34
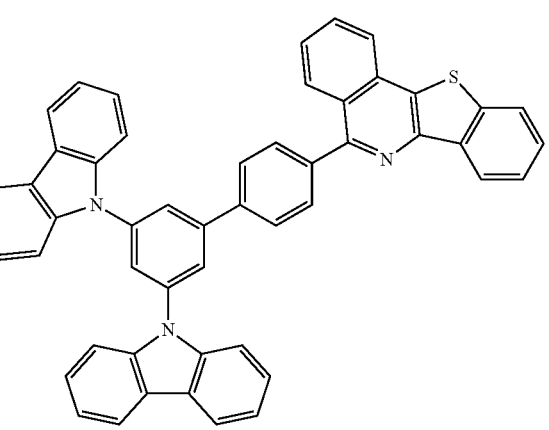

35
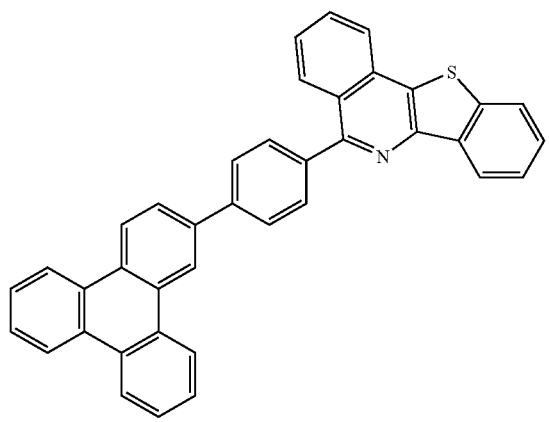
36
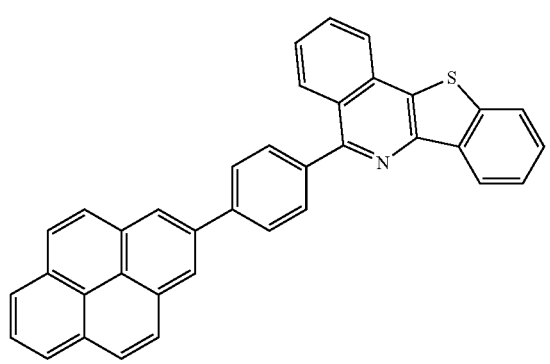
37
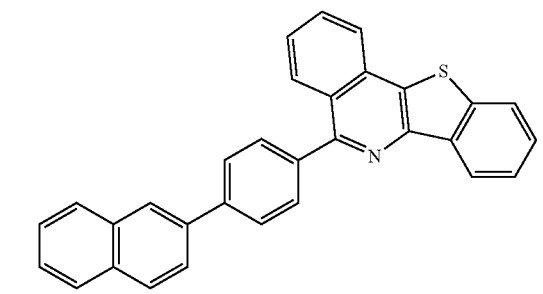
38
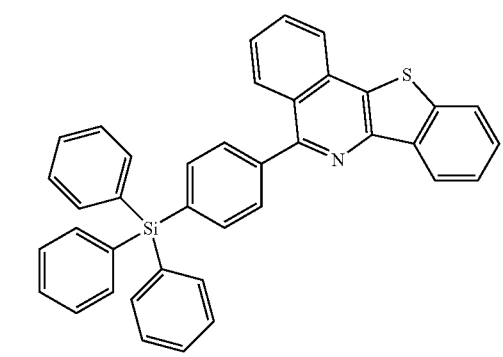
39
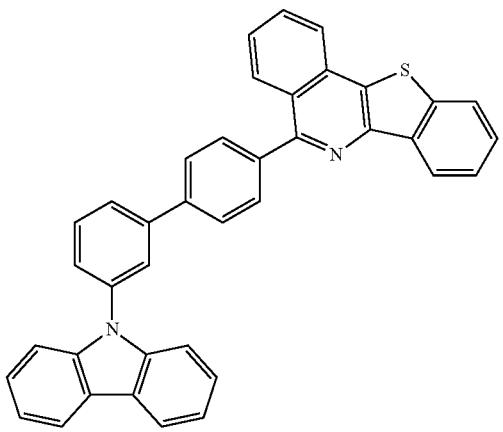
40
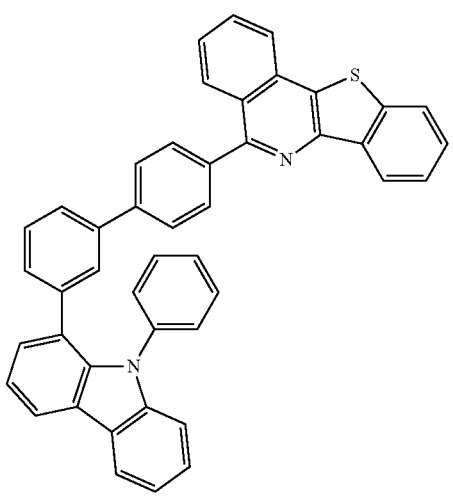
41
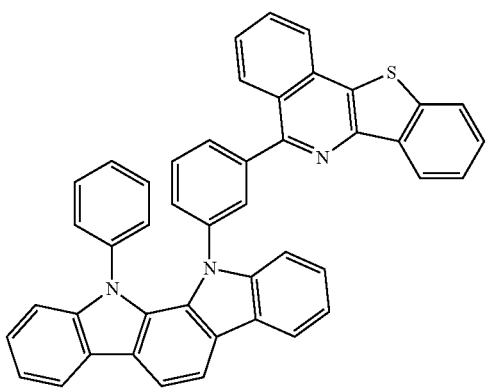

42
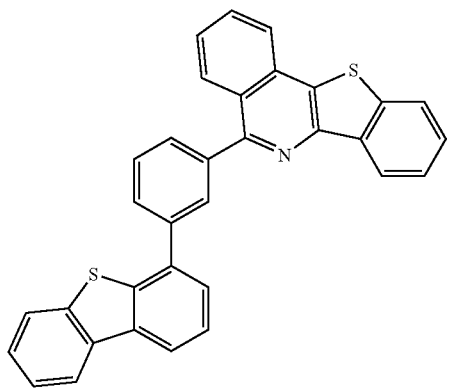
43
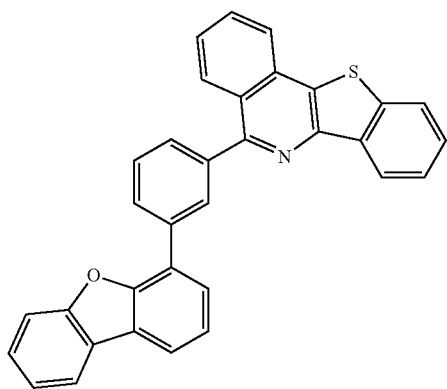
44
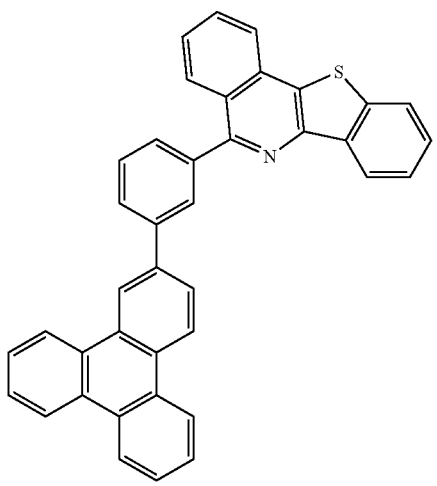
45
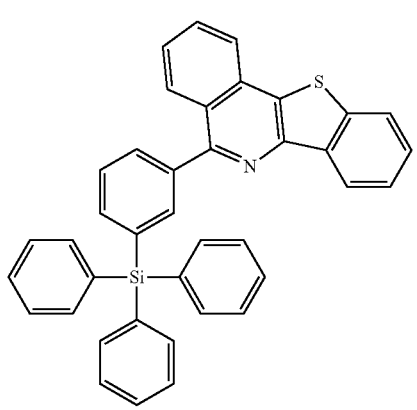
46
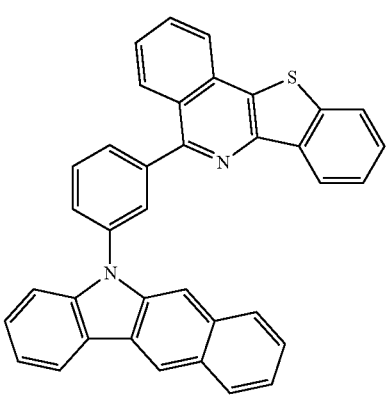
47
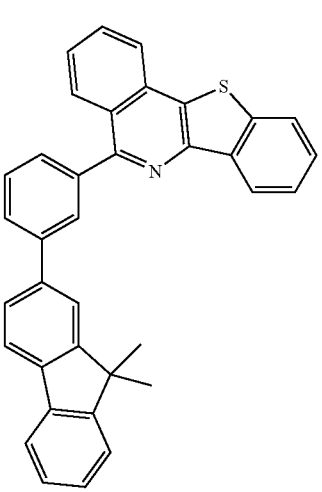
48
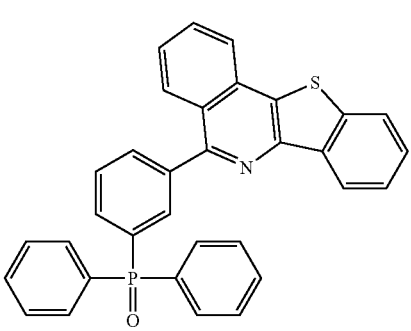
49
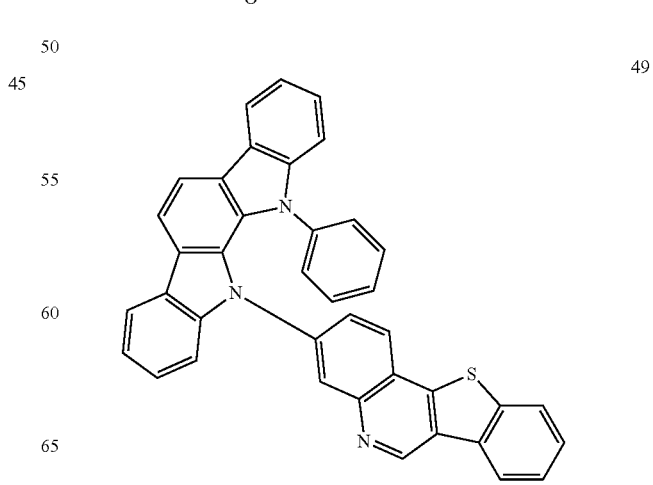

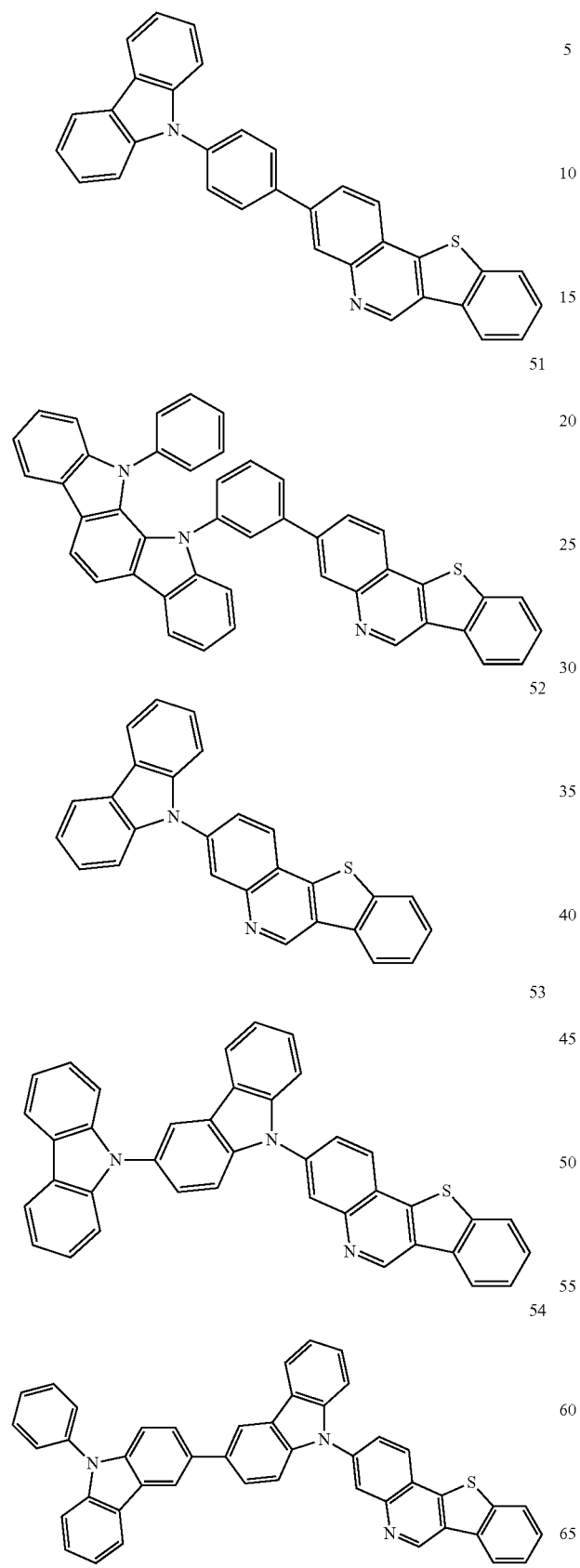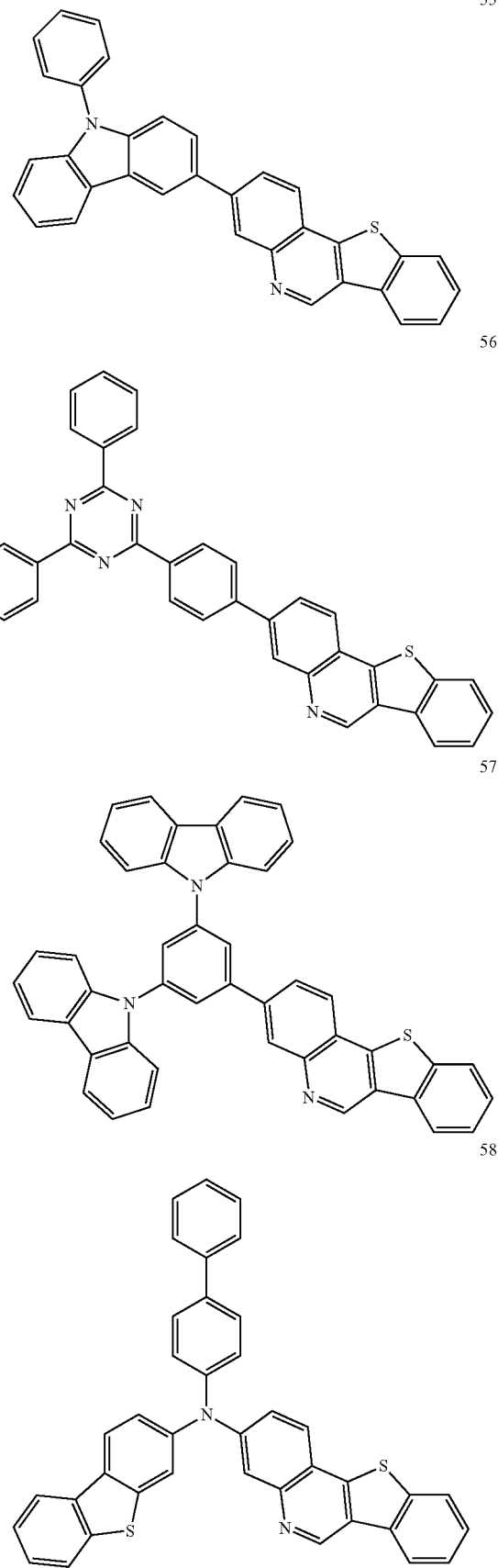

59
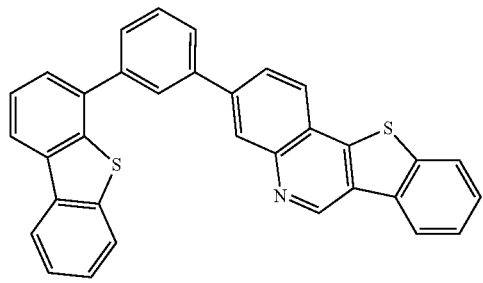
60
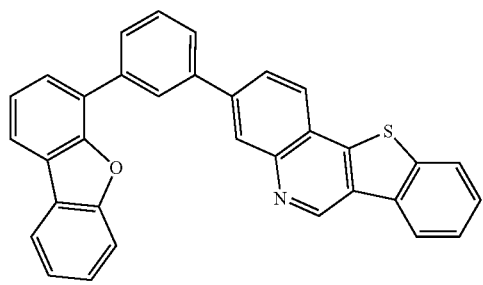
61
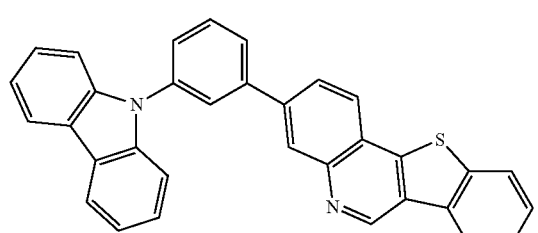
62
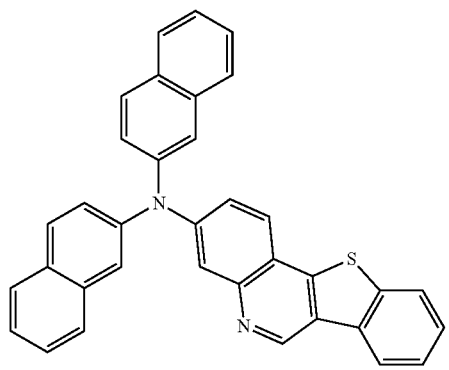
63
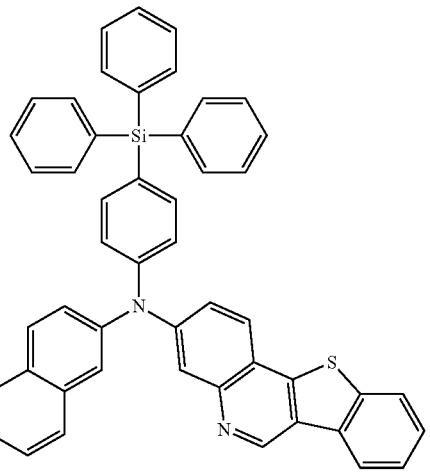
64
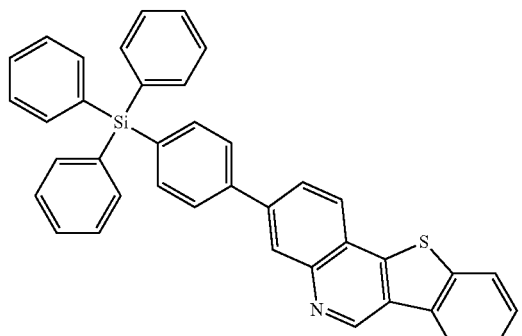
65
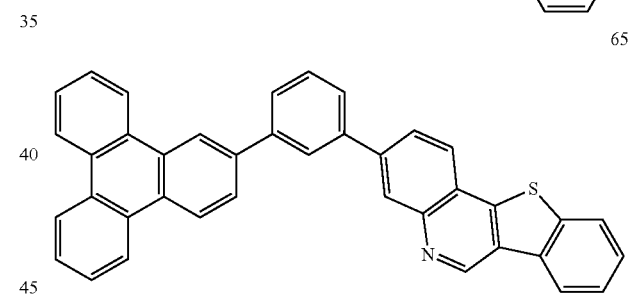
66
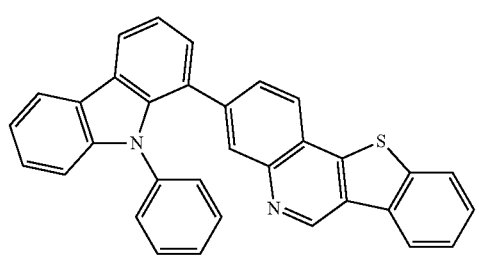

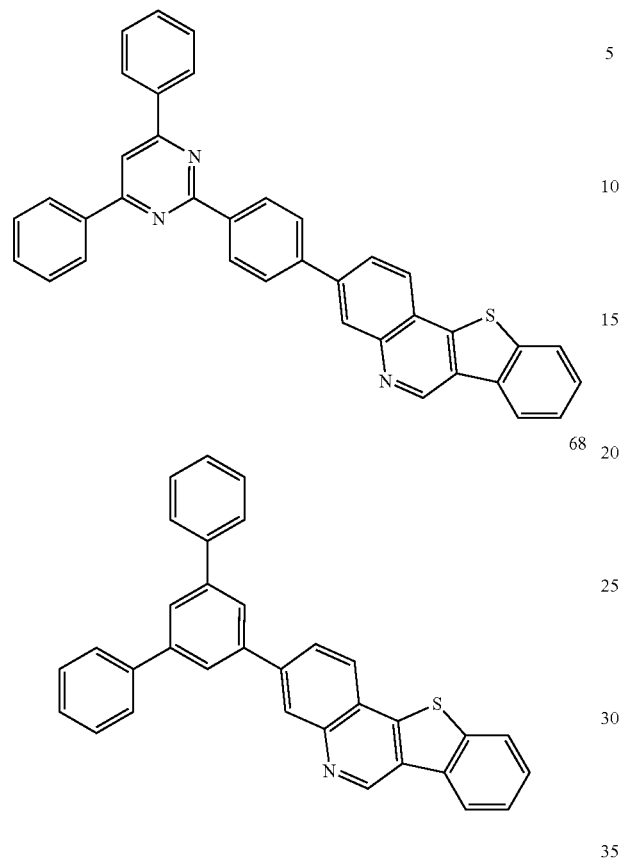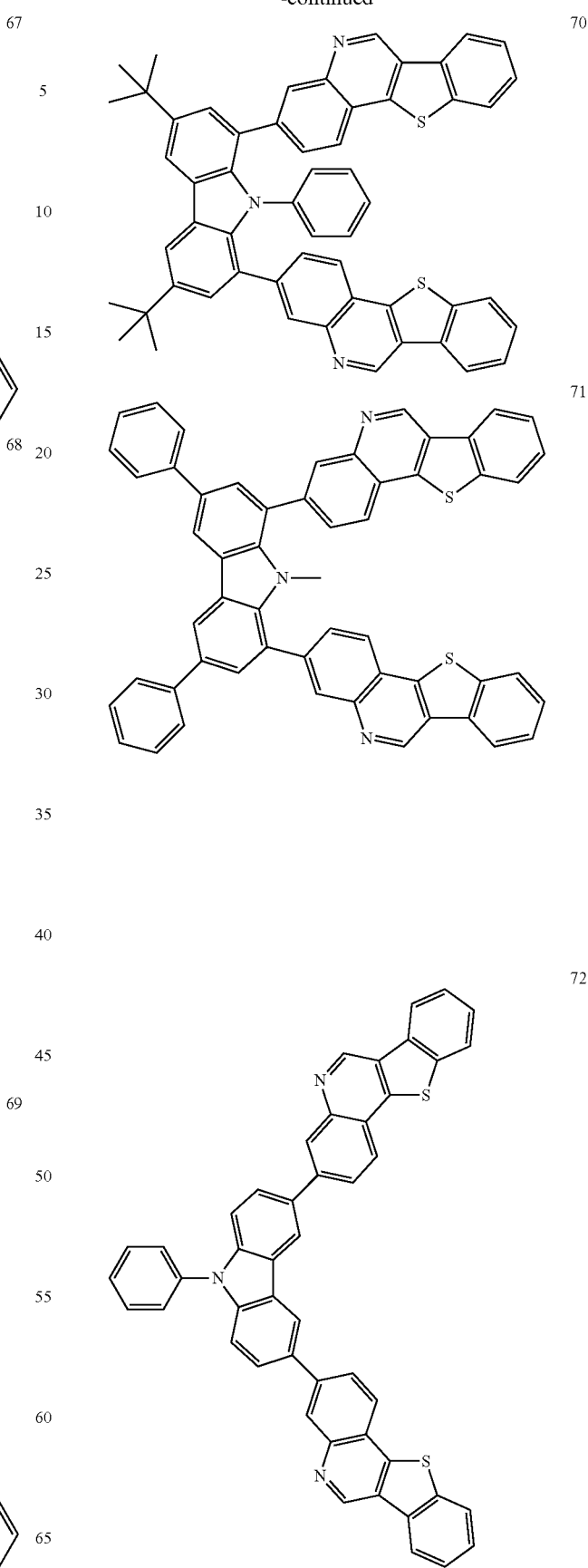

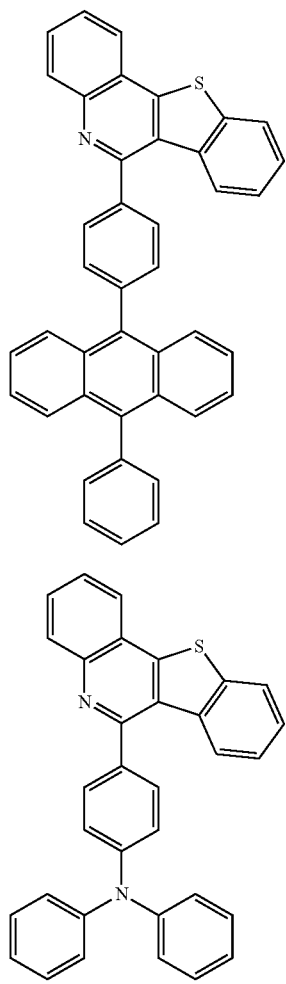
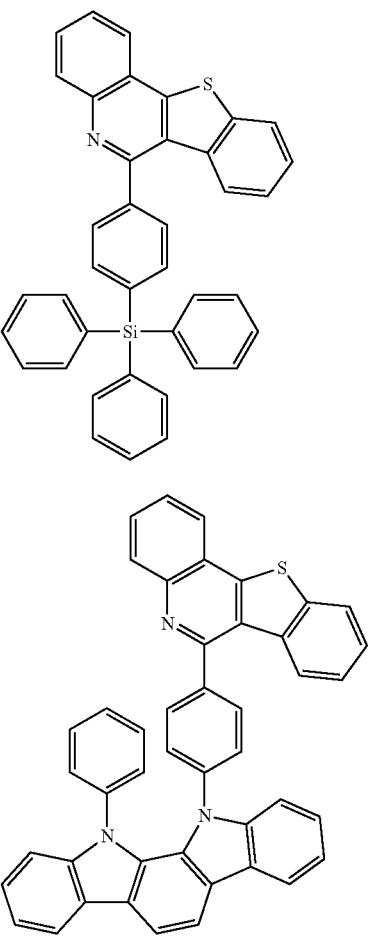
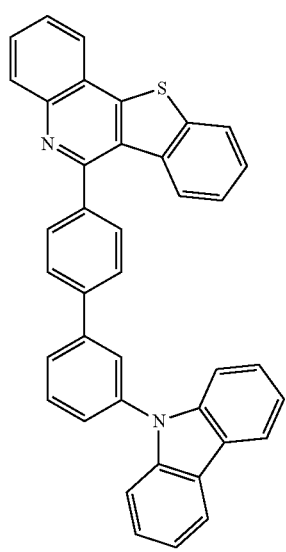
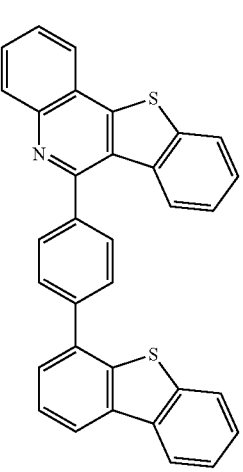

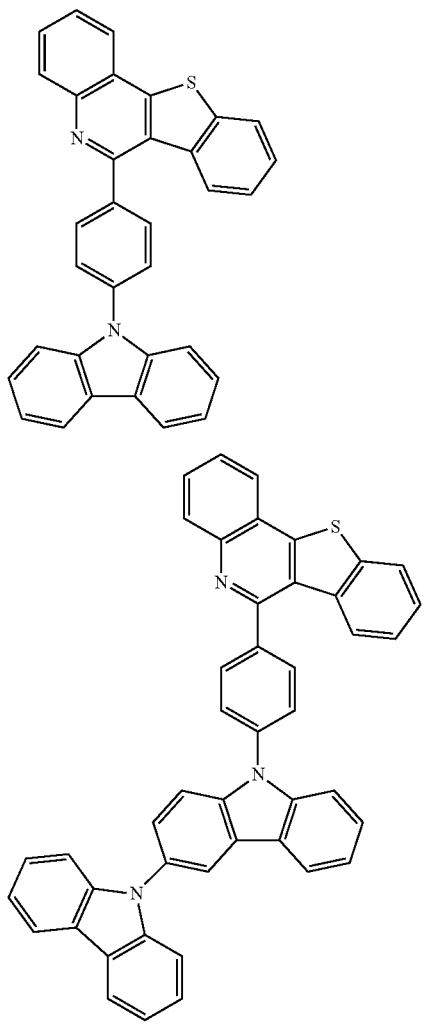
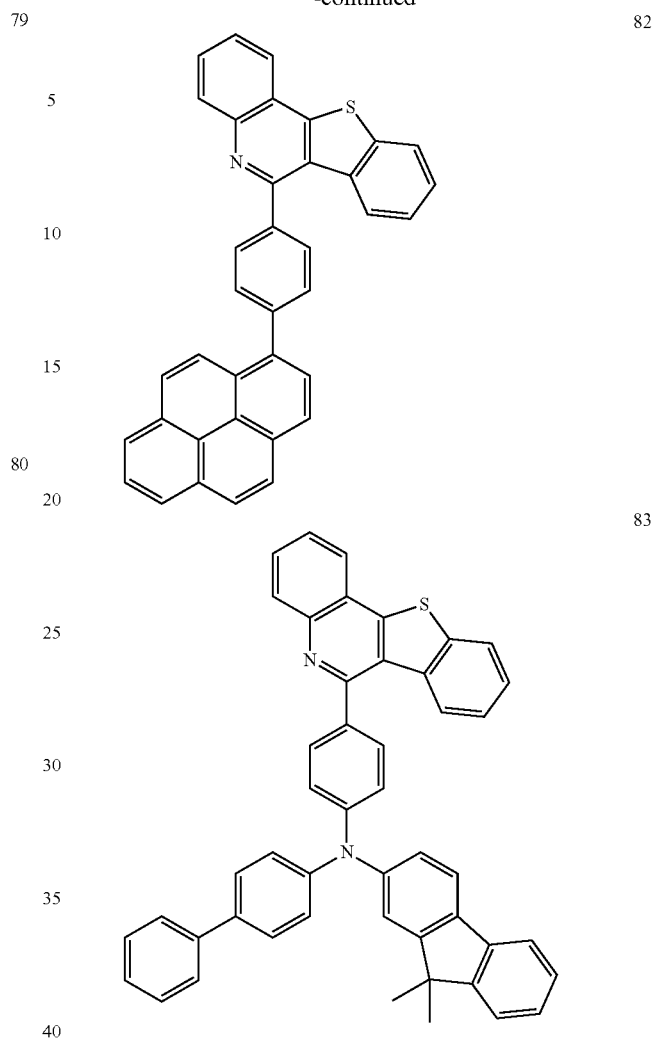
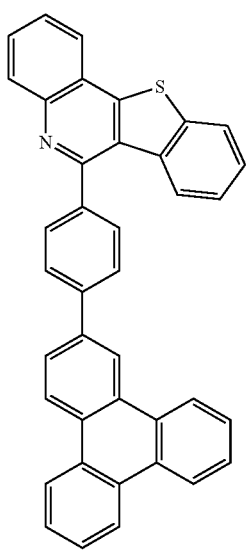
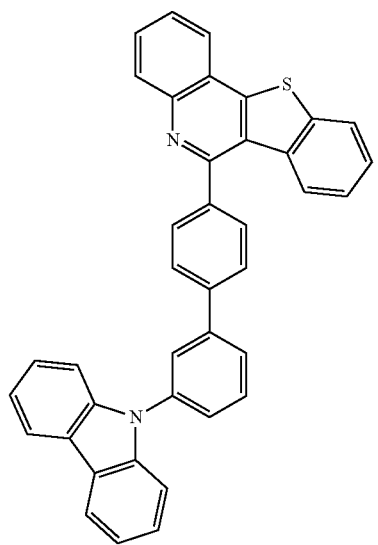

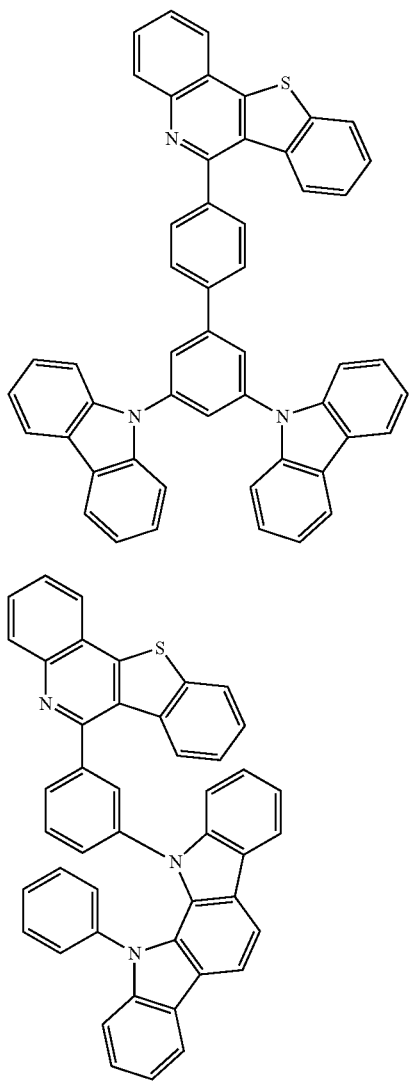
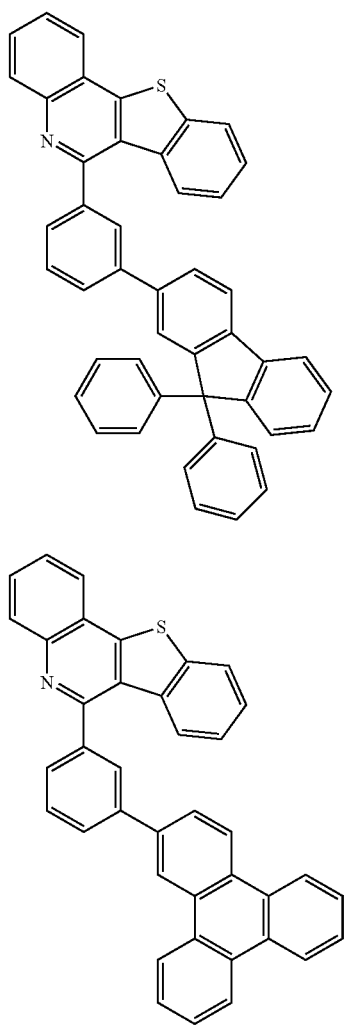
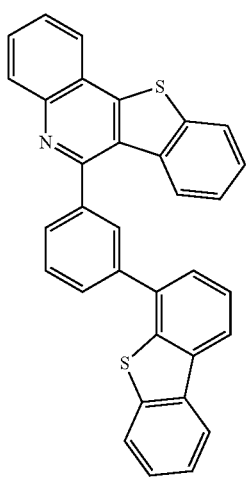
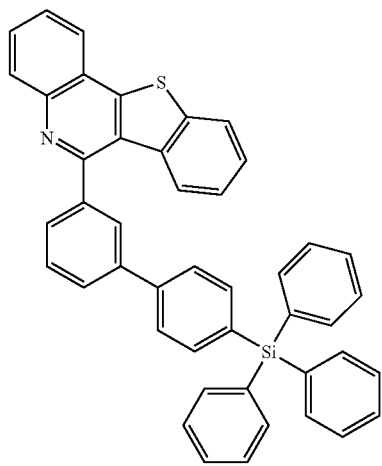

91
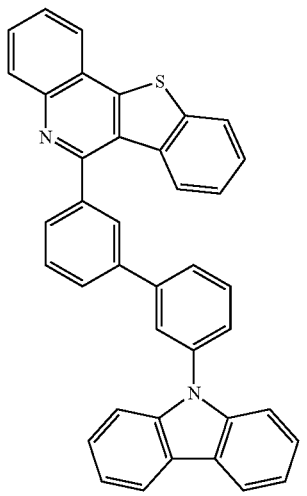
92
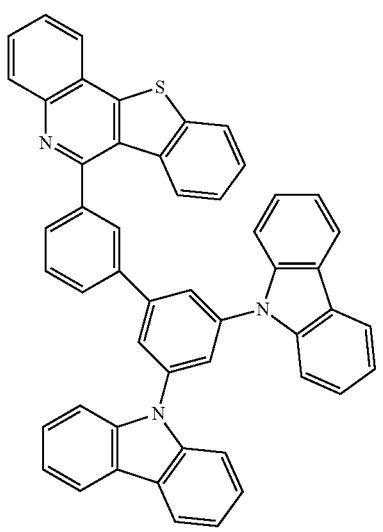
93
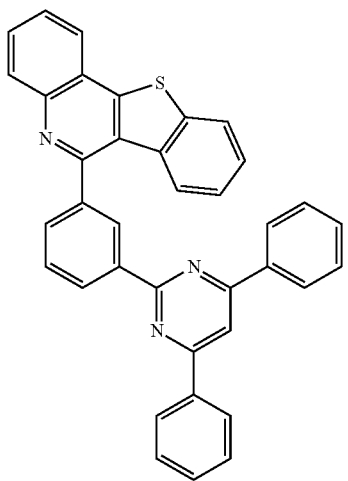
94
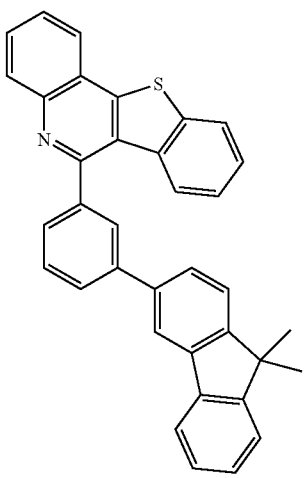
95
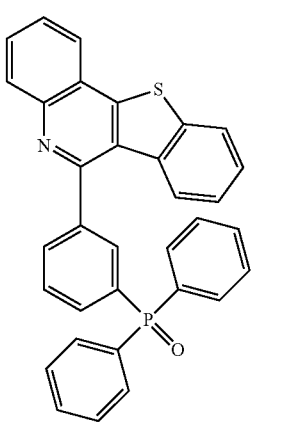
96
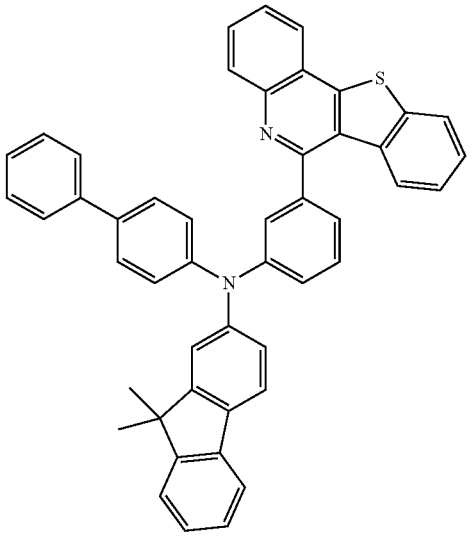

97
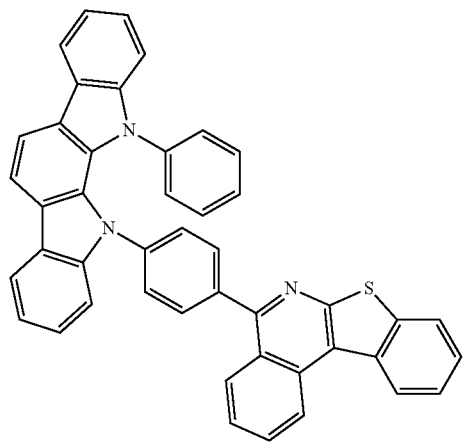
98
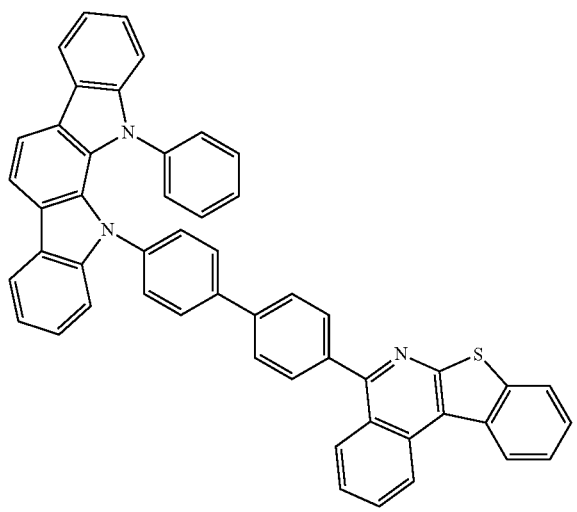
99
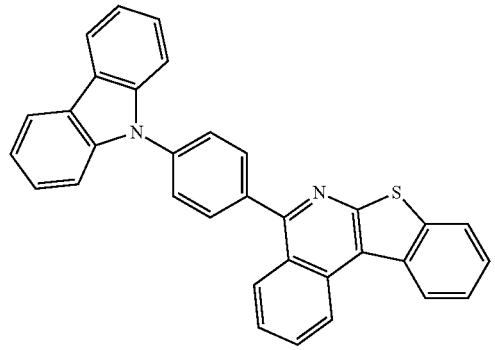
100
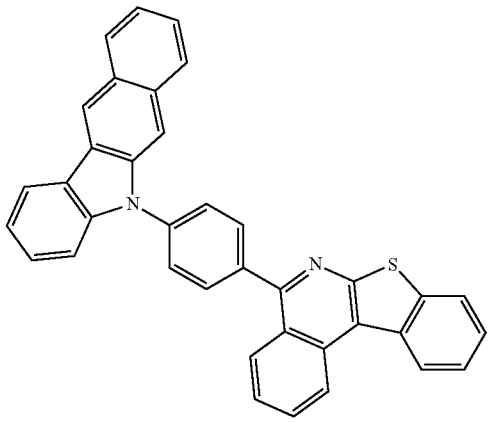
101
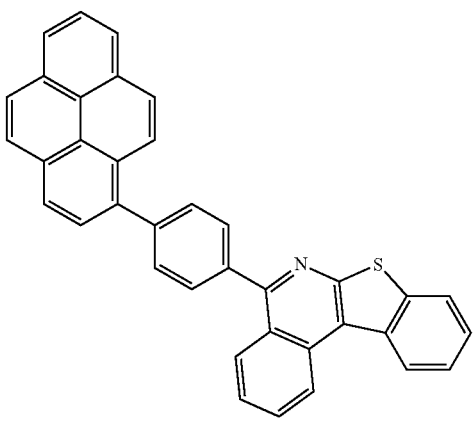
102
103

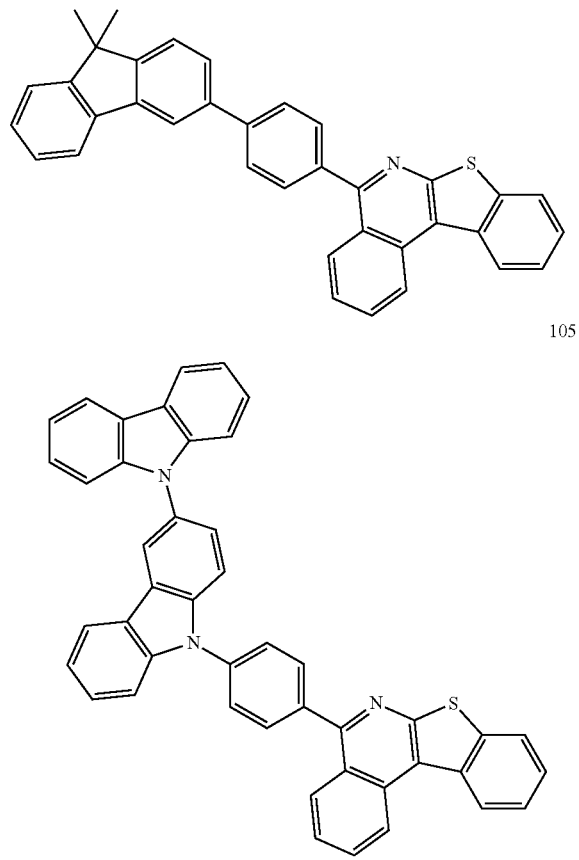

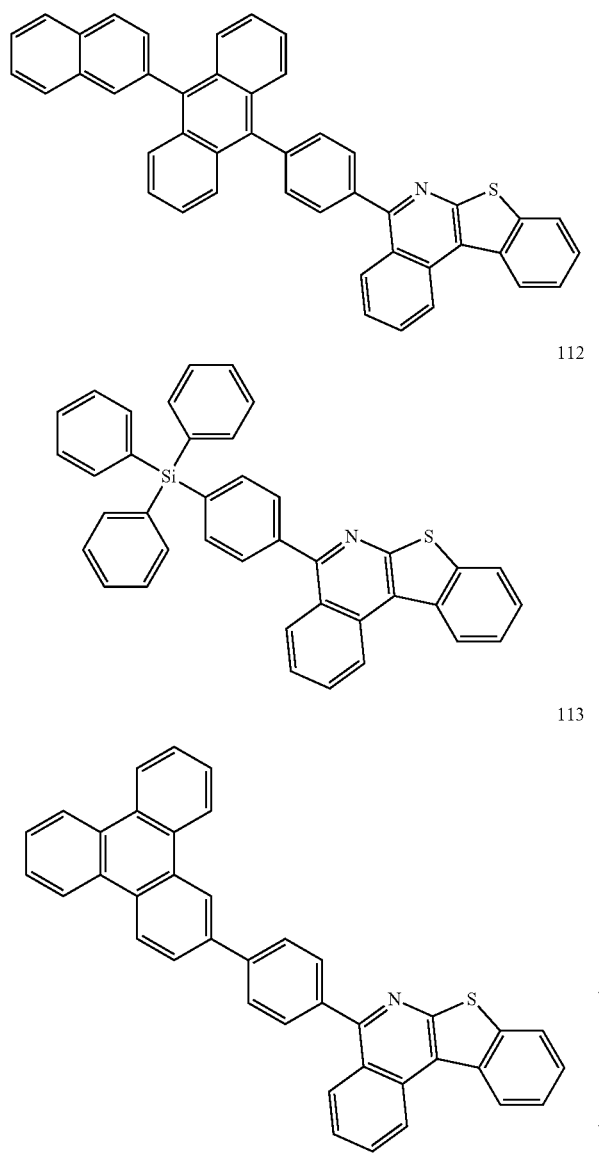
111
112
113
114
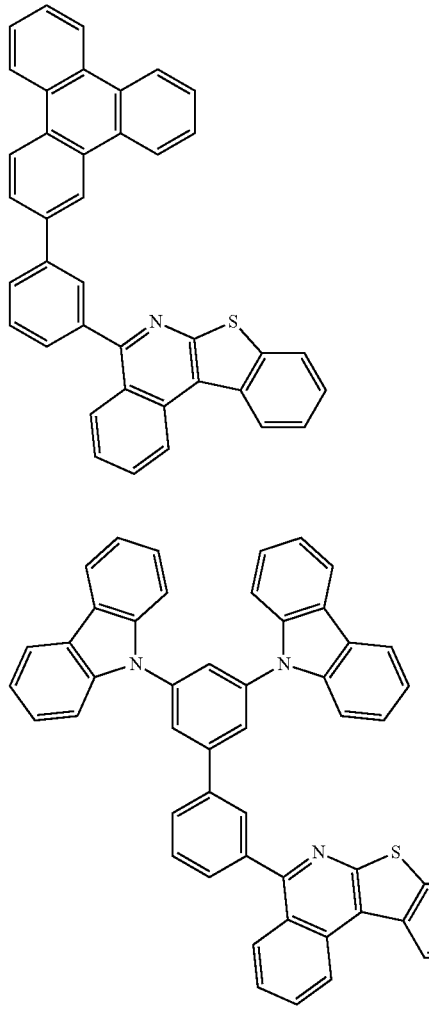
115
116
117

118
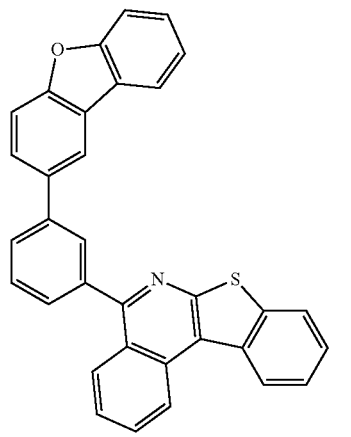
119
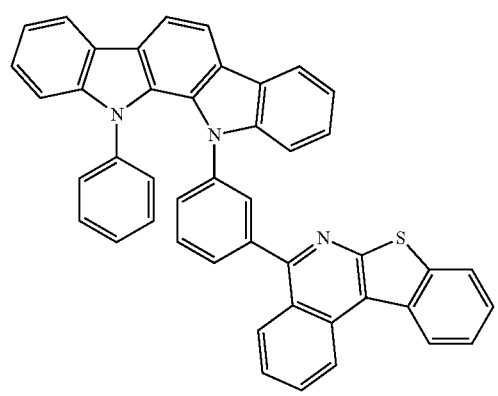
120
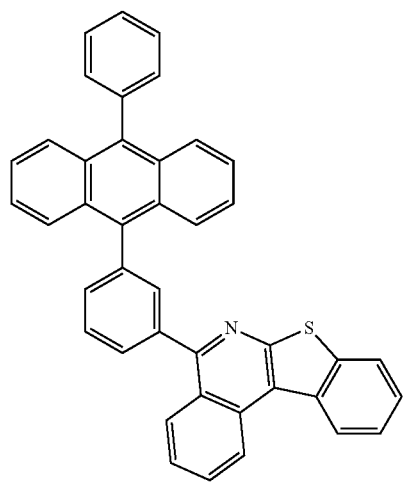
121
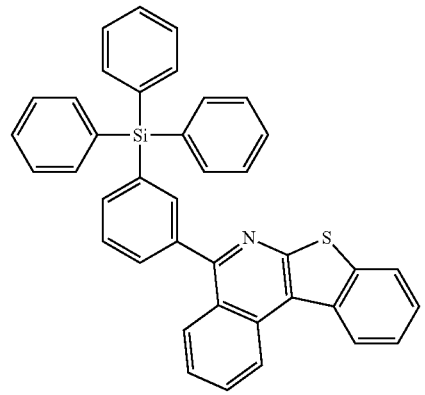
122
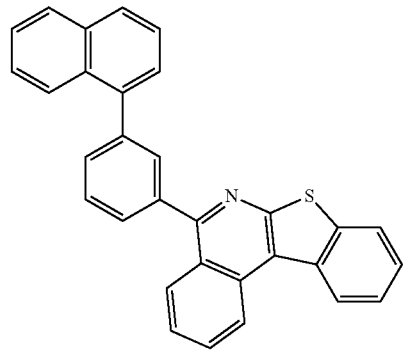
123
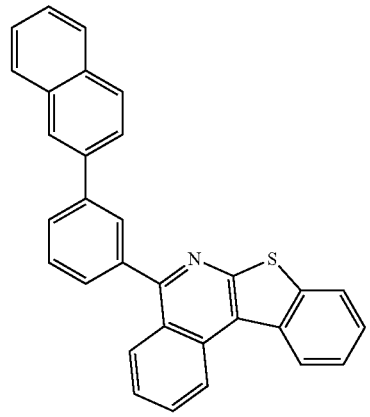
124
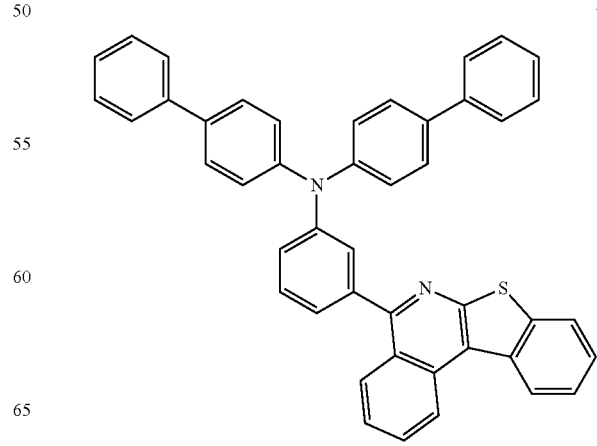

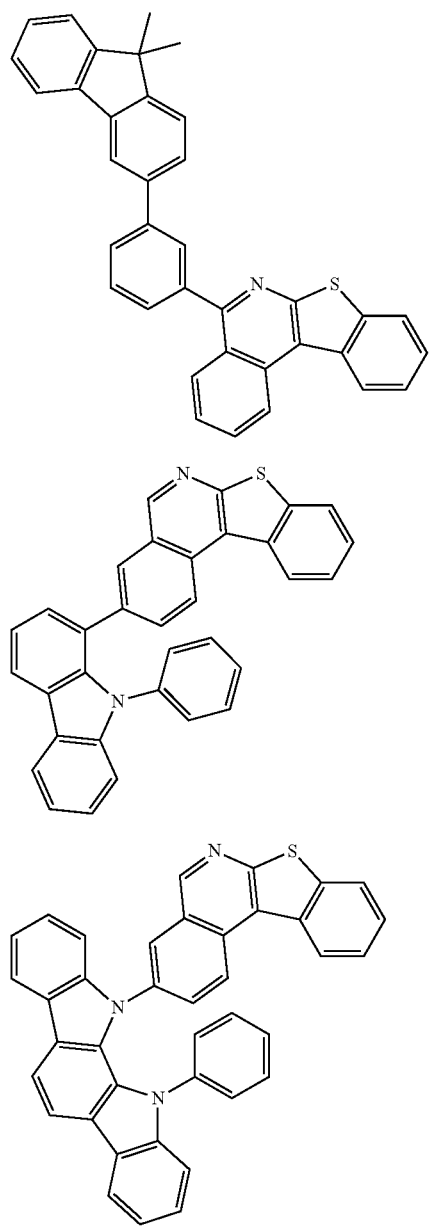
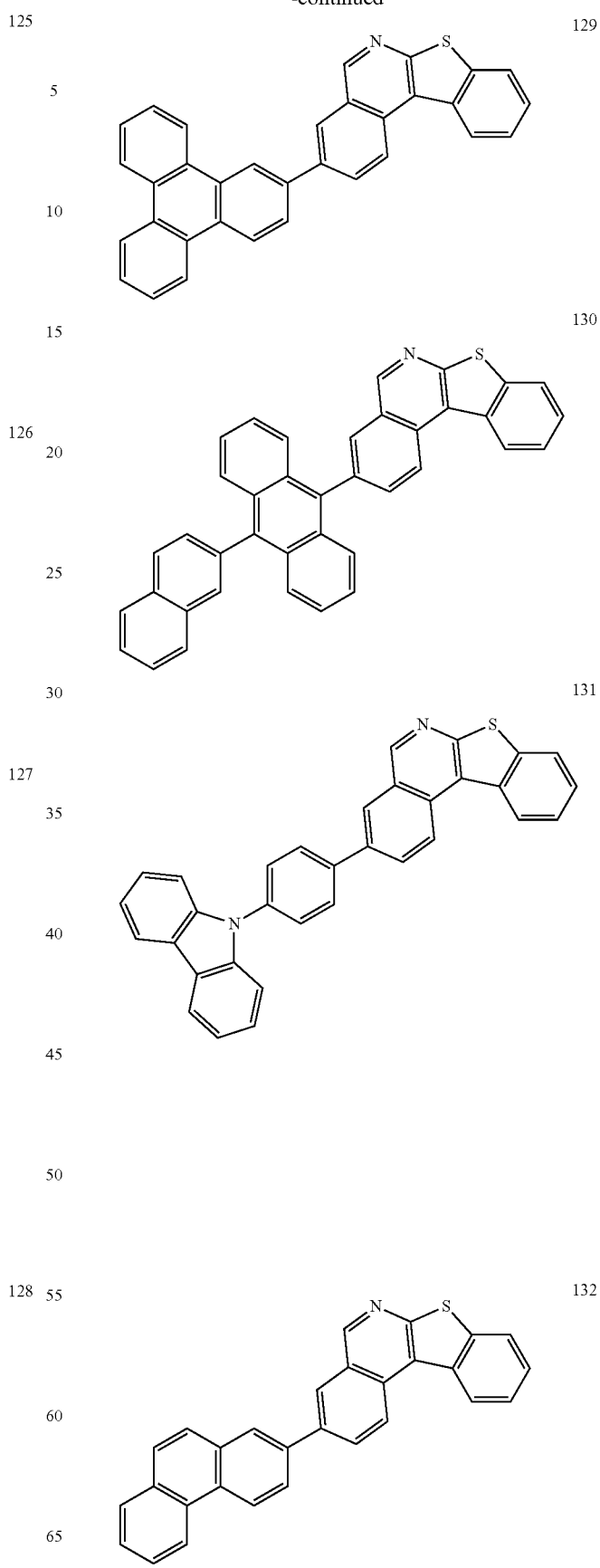

133
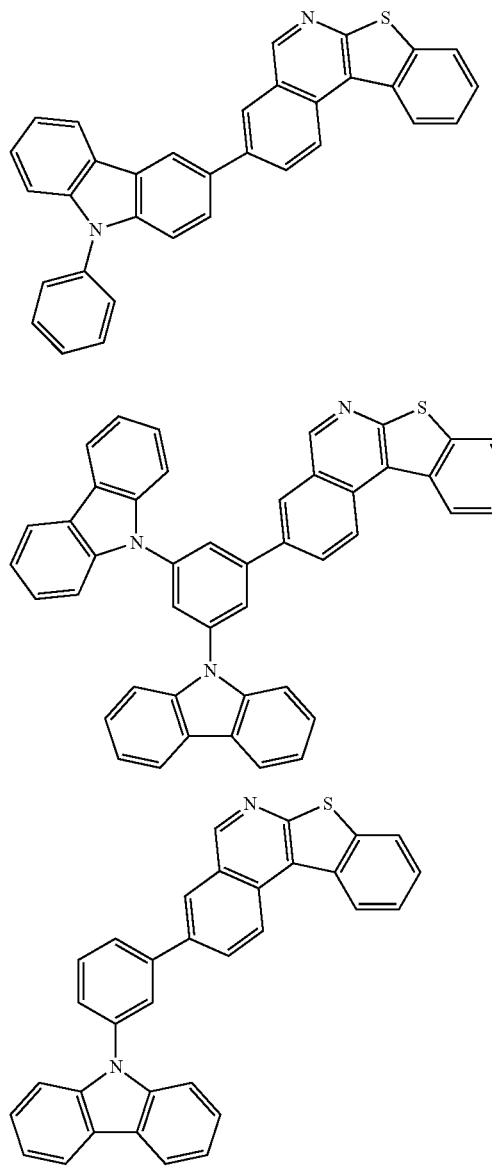
134
135
136
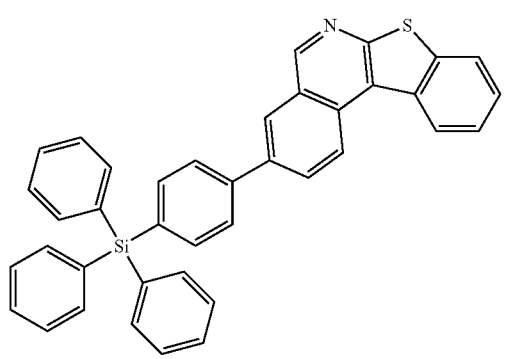
137
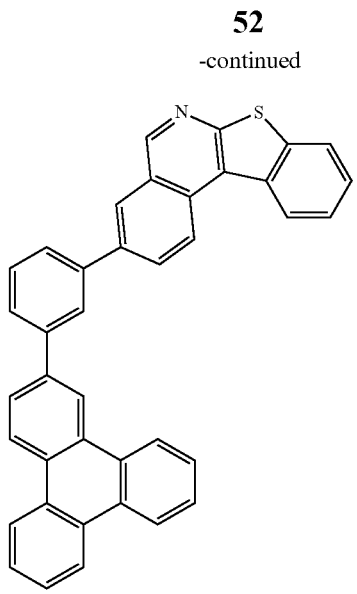
138
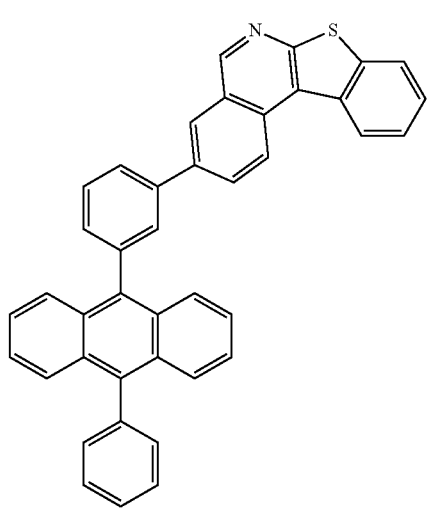
139
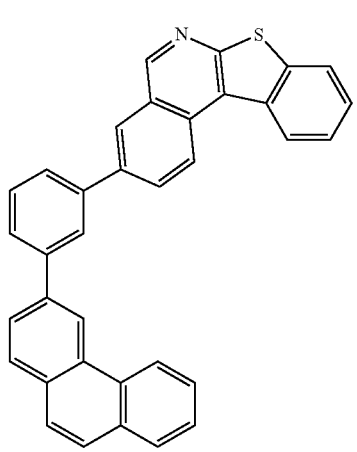

140
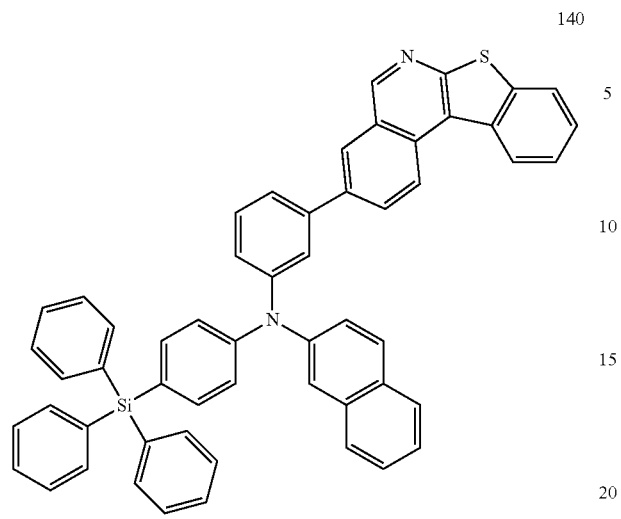
141
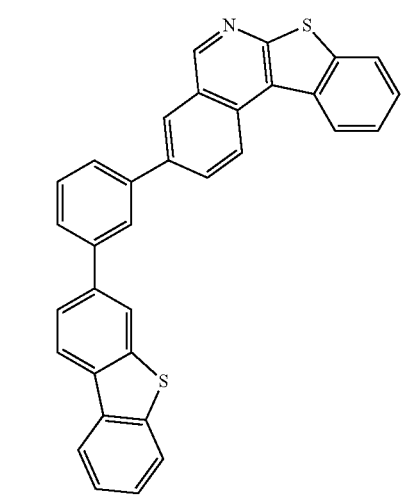
142
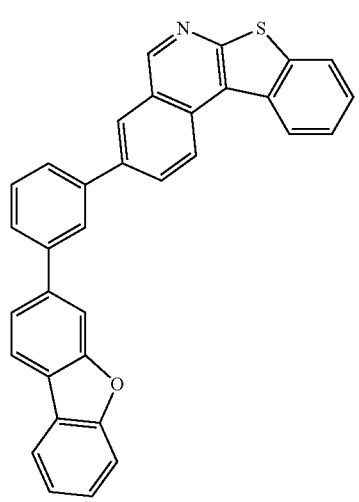
143
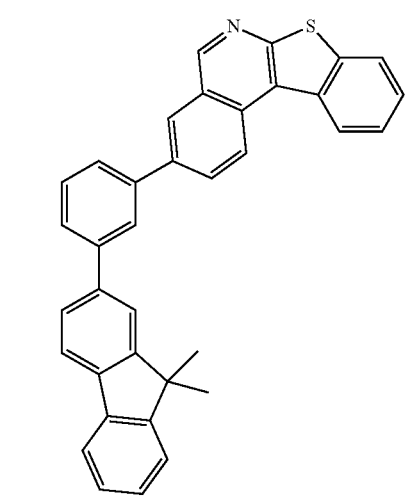
144
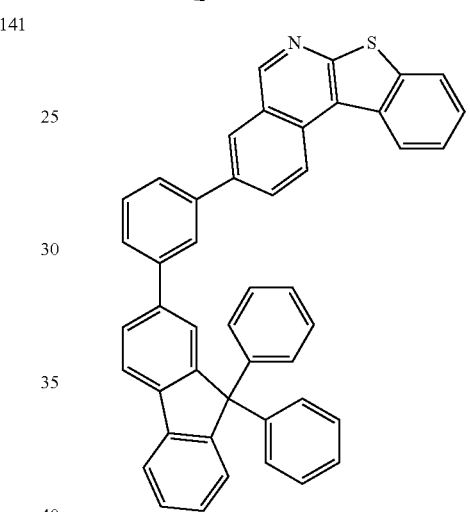
145
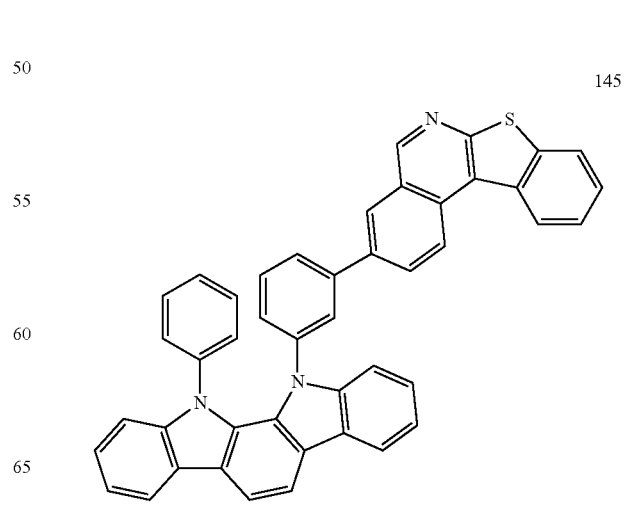

146
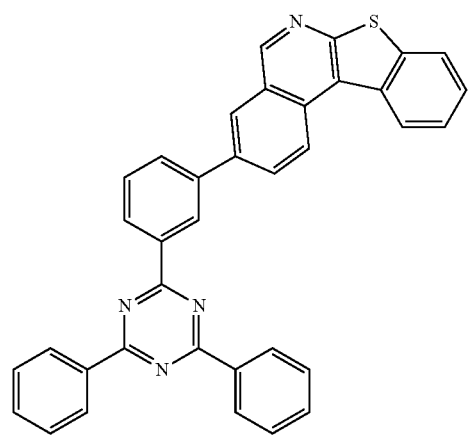
147
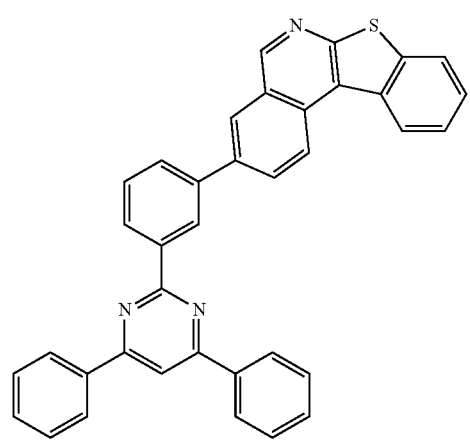
148
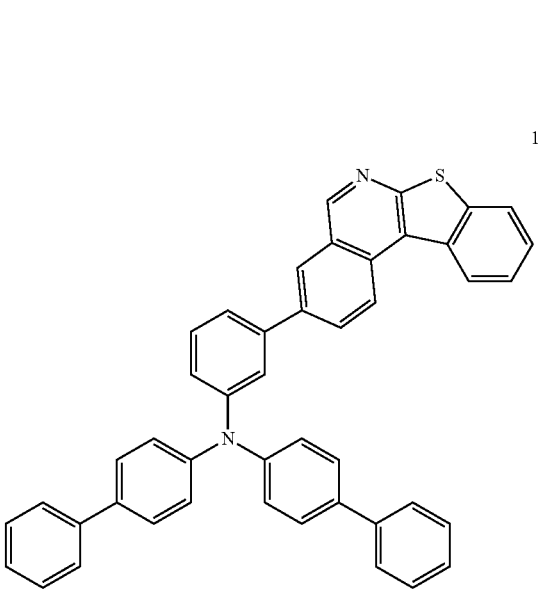
149
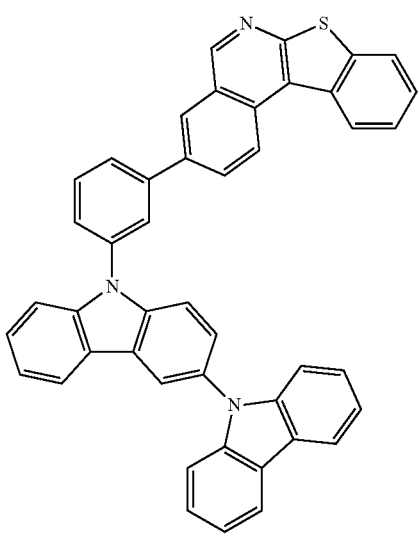
150
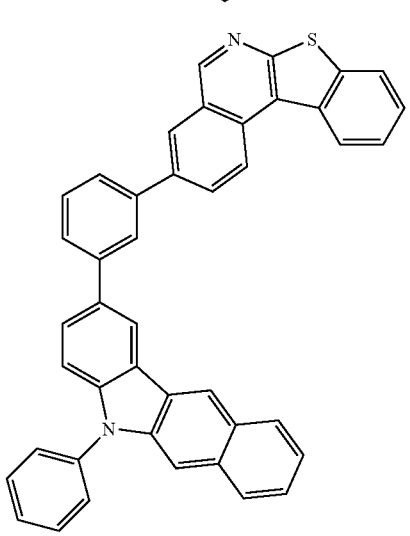
151
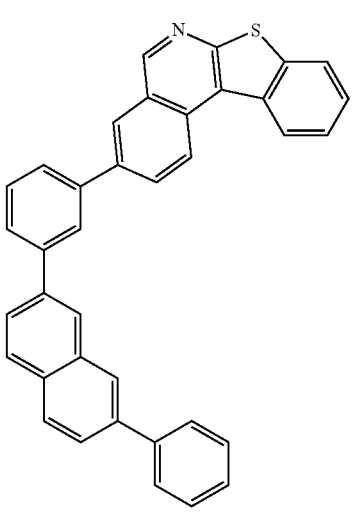

152
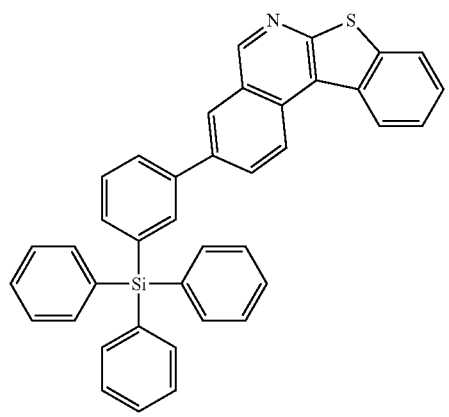
153
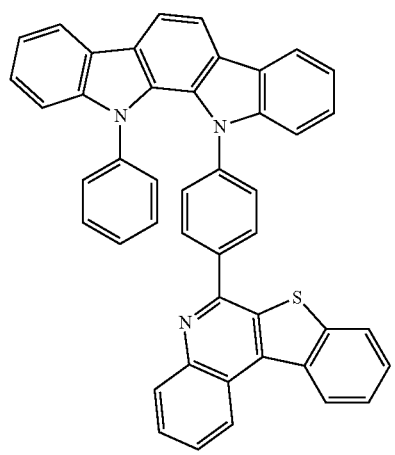
154
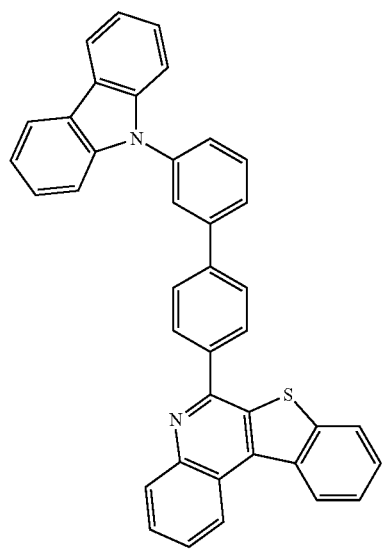
155
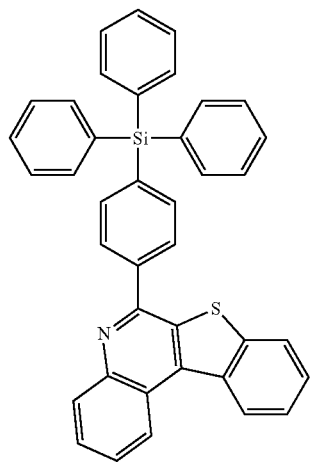
156
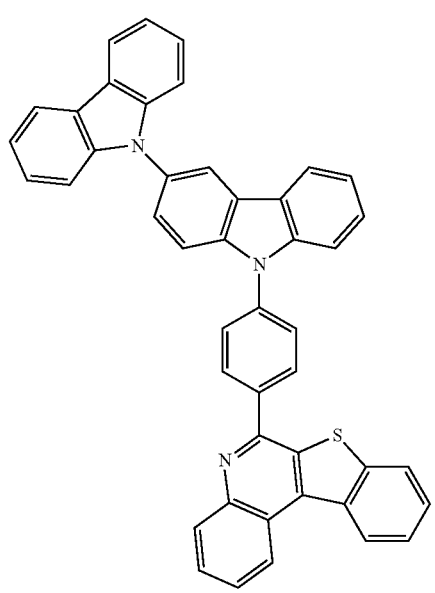
157
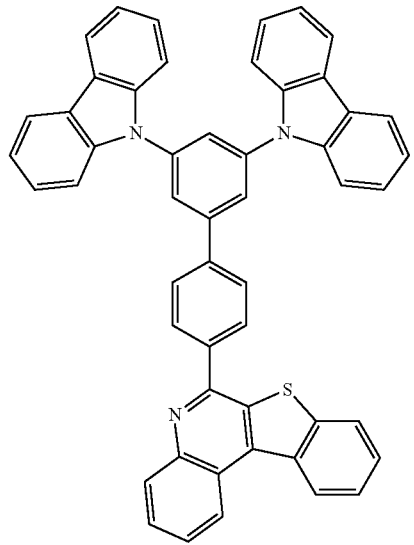

158
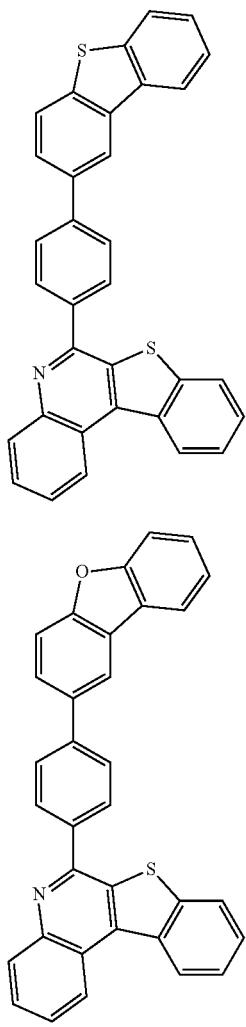
159
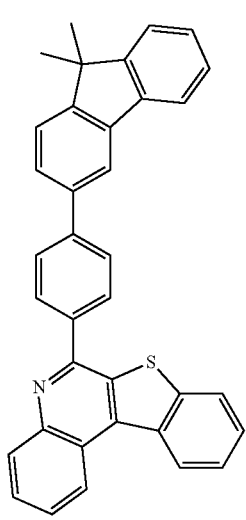
161
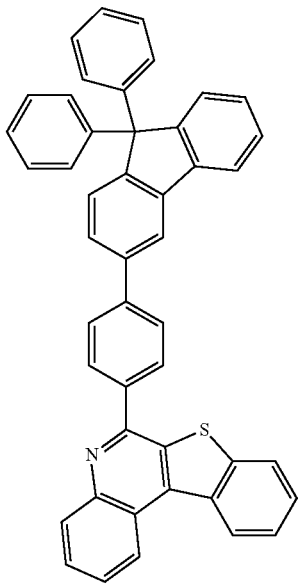
162
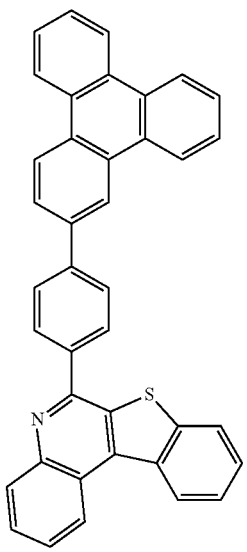

163
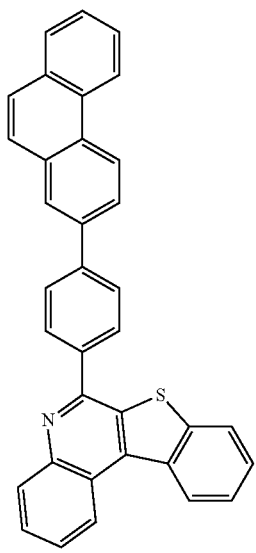
164
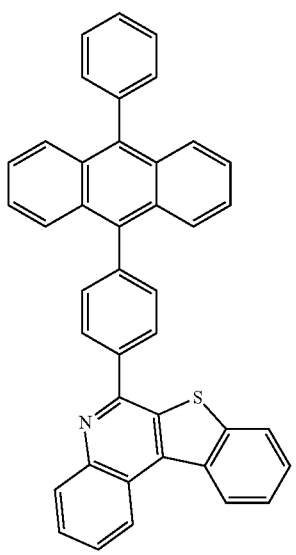
165
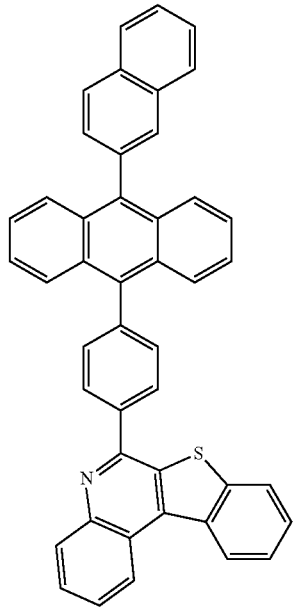
166
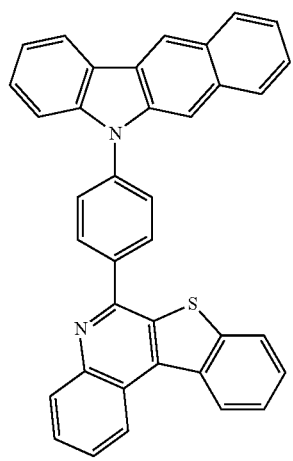
167
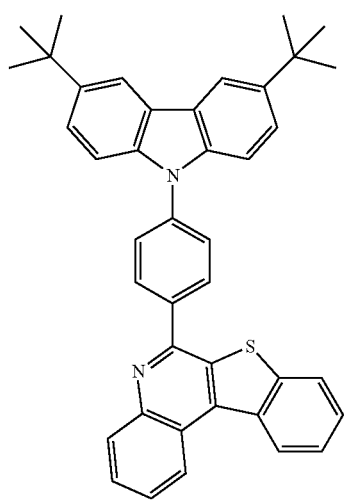

168
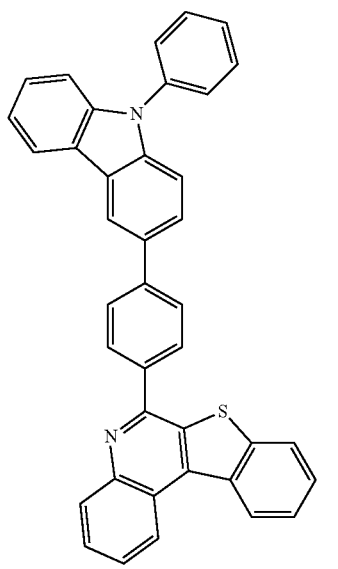
169
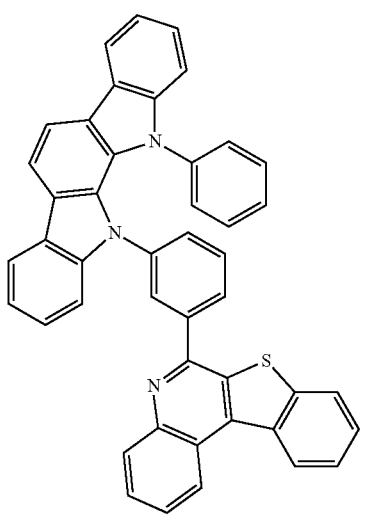
170
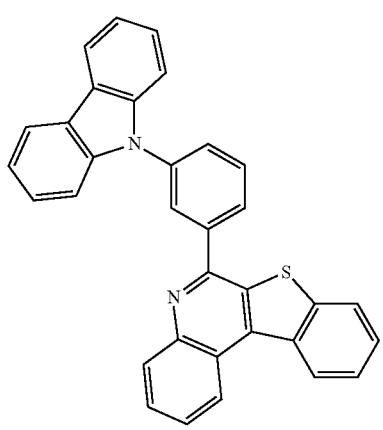
171
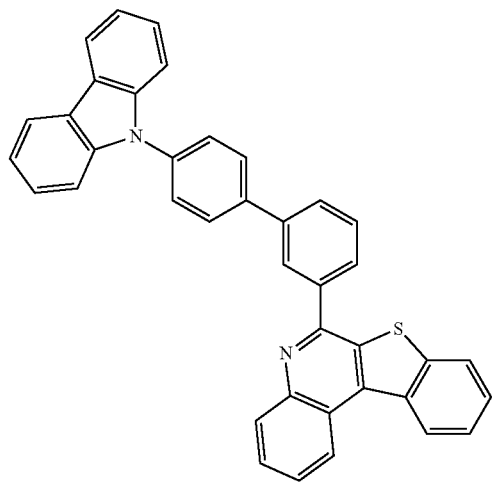
172
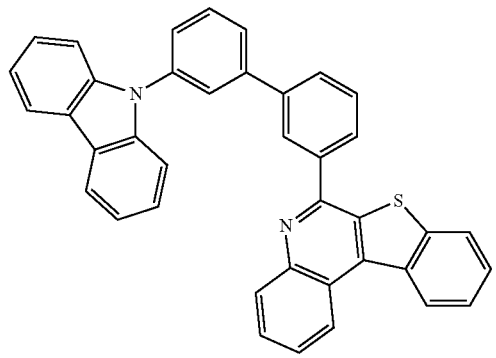
173
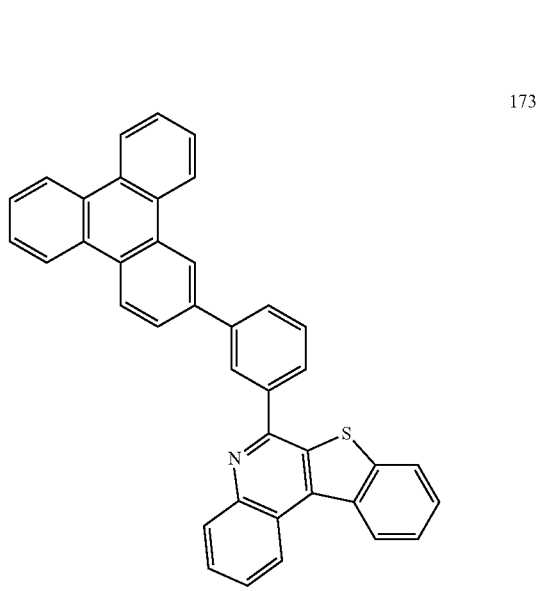

174
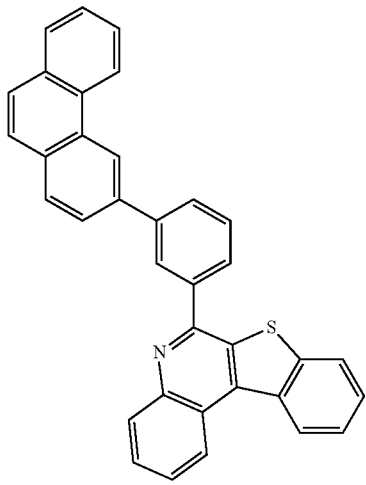
175
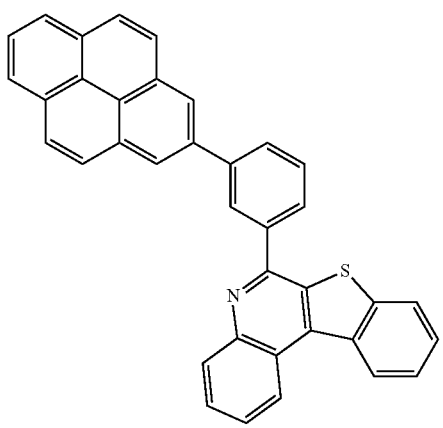
176
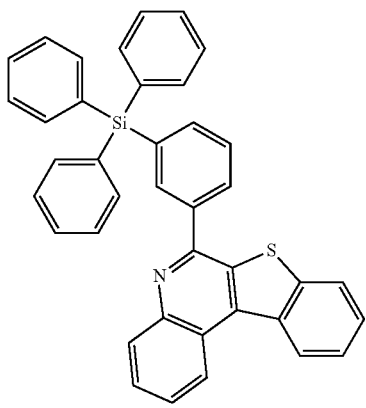
177
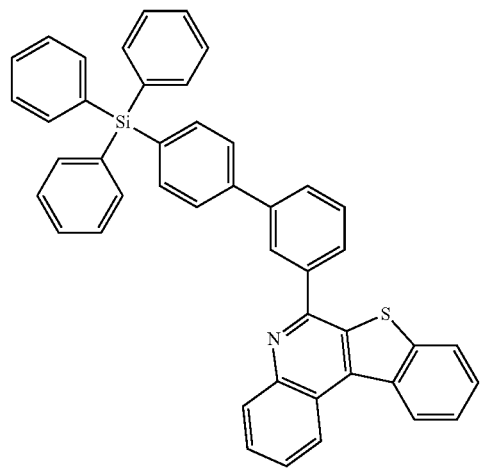
178
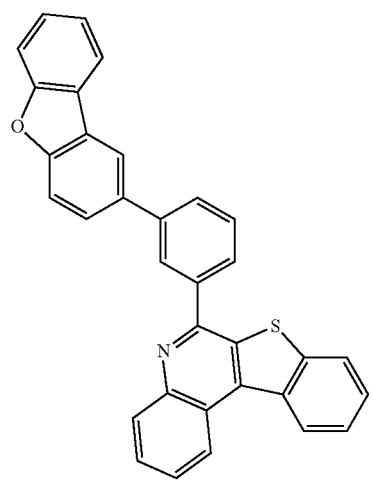
179

180
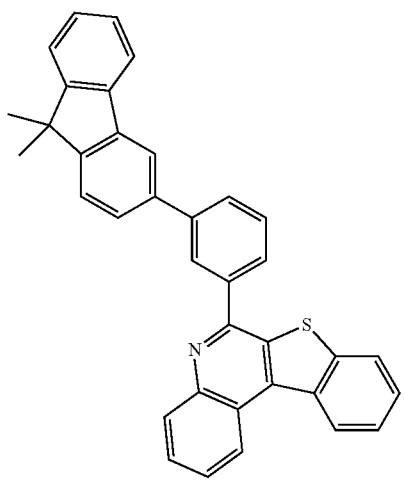
181
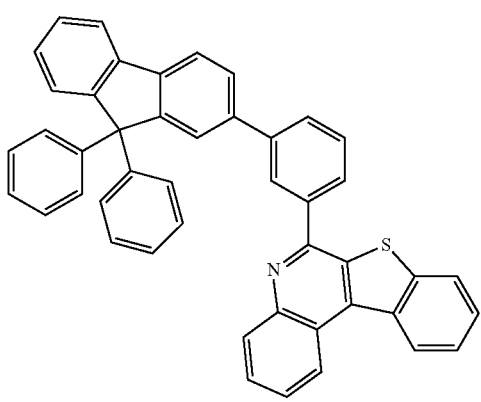
182
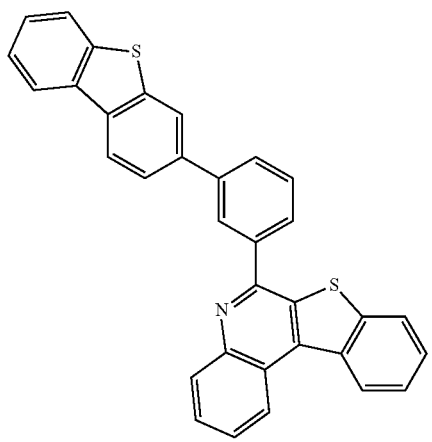
183
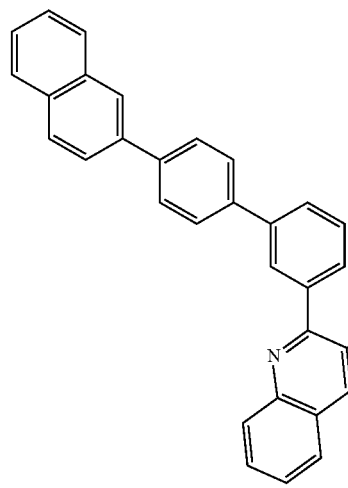
184
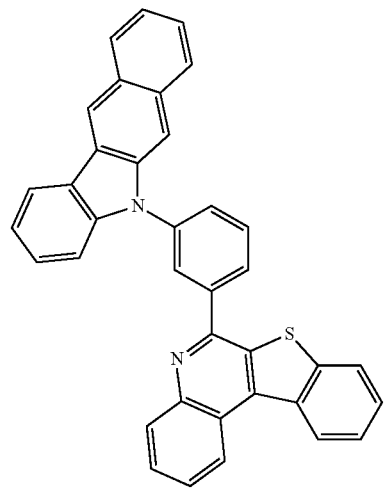
185
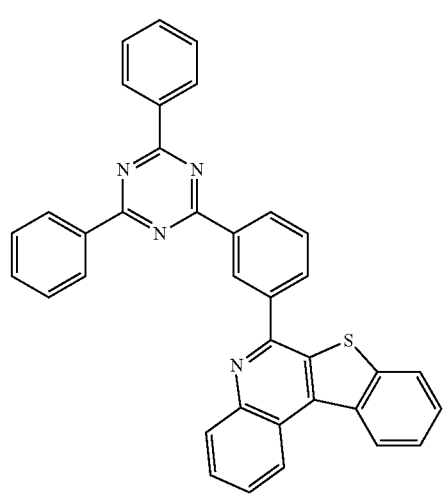

186
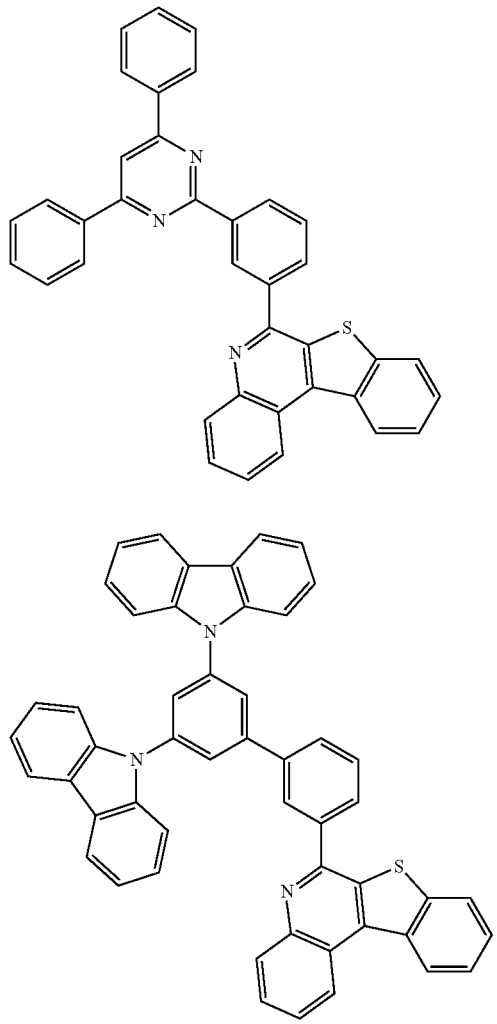
187
188
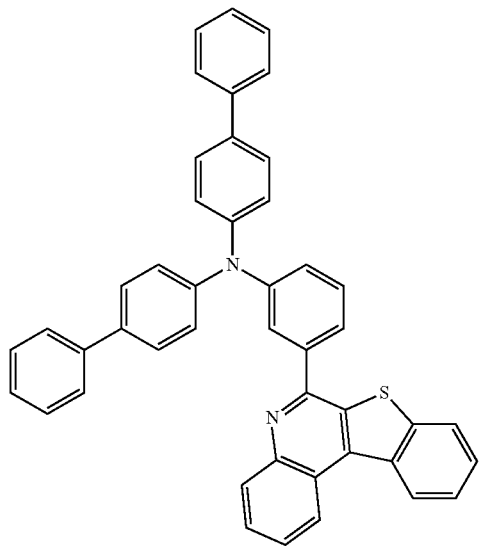
189
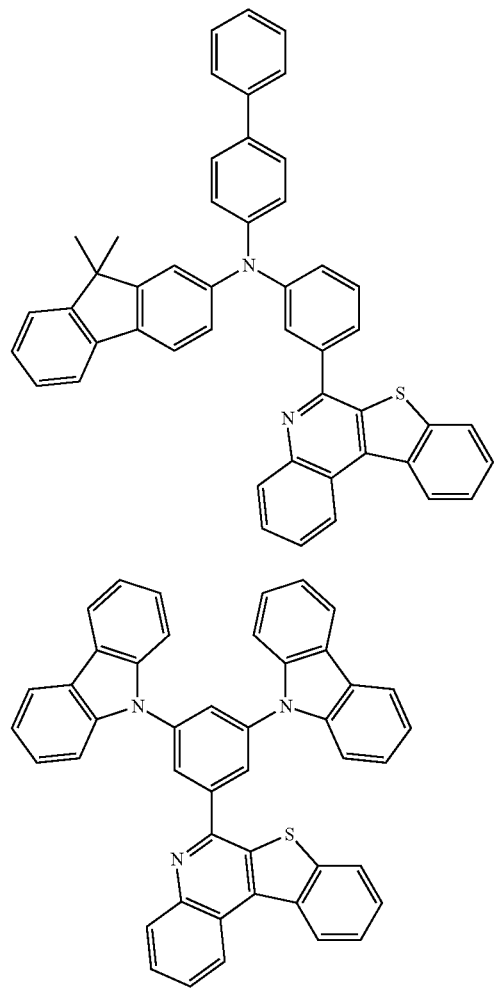
190
191
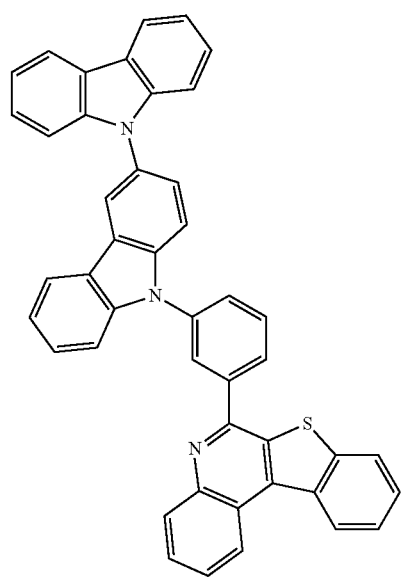

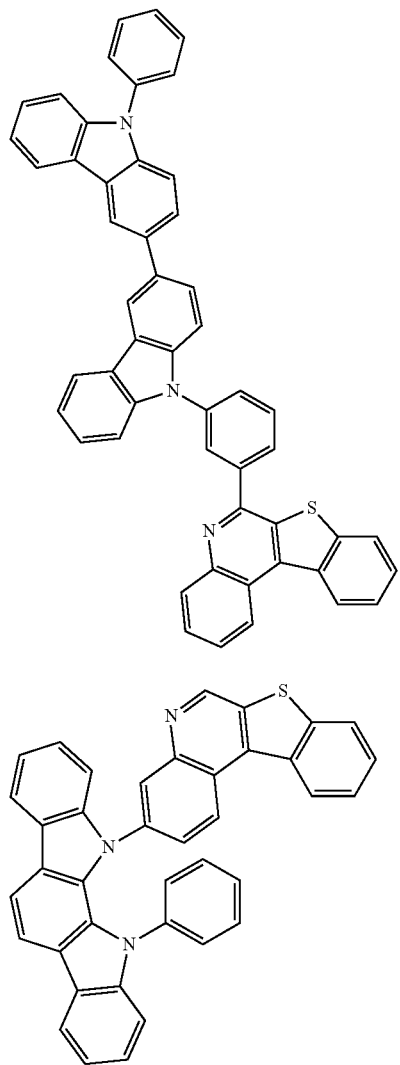
192
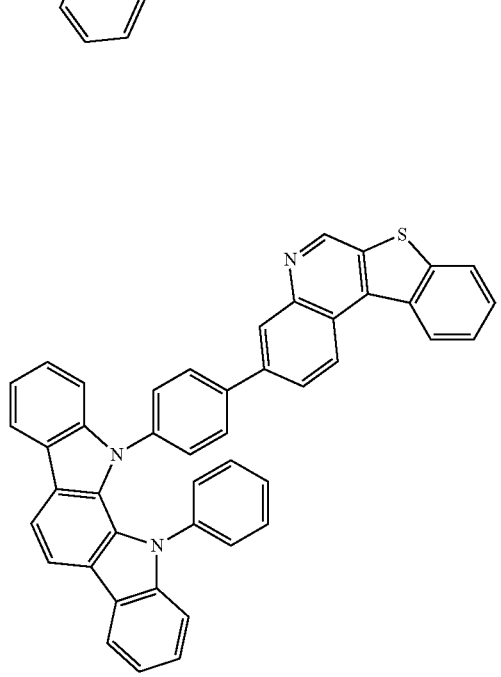
193
194
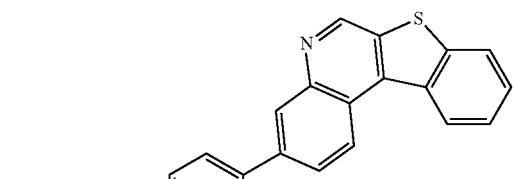
195
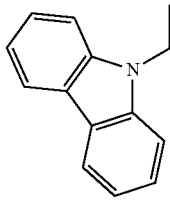
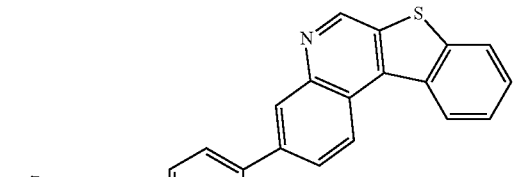
196
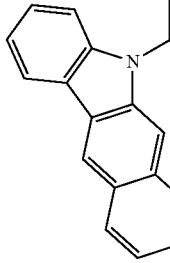
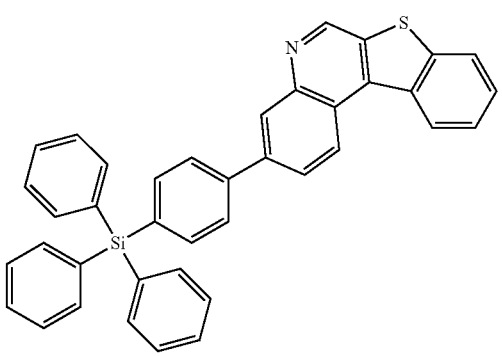
197

-continued
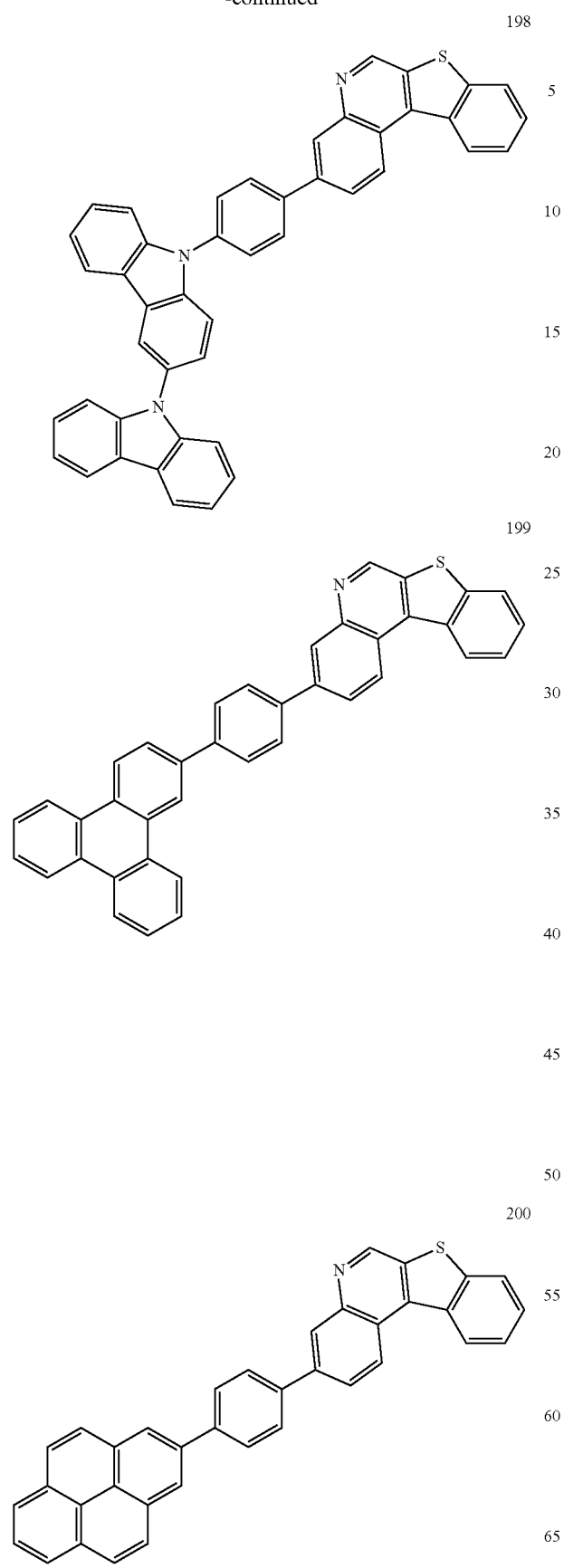
-continued
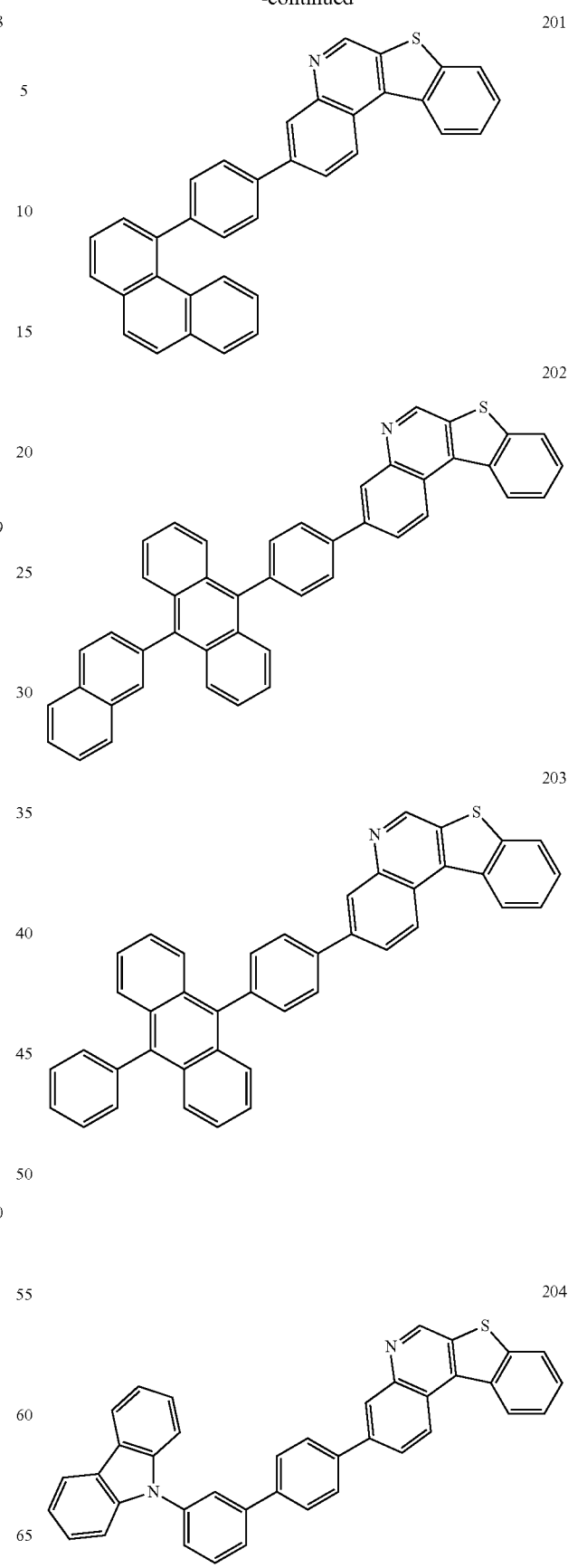

205
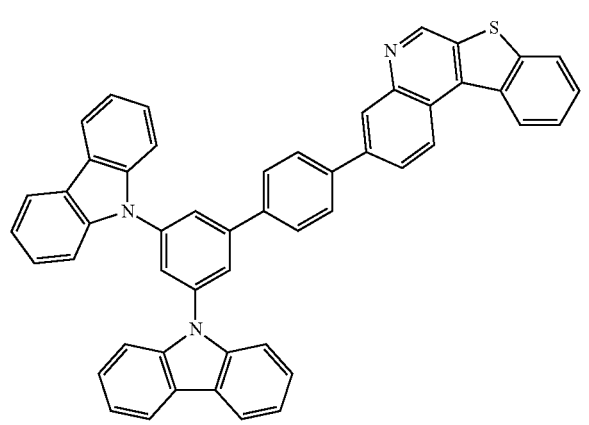
206
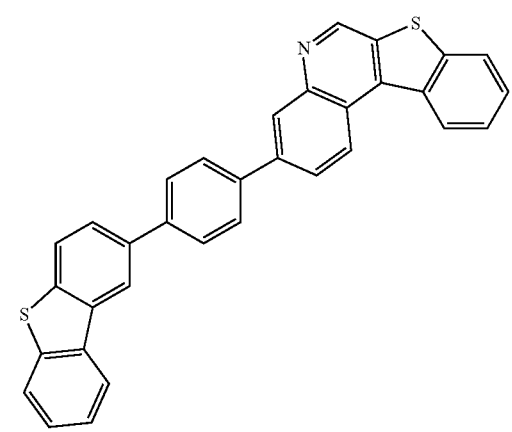
207
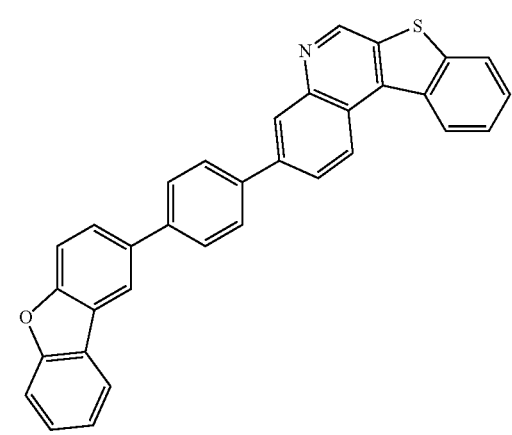
208
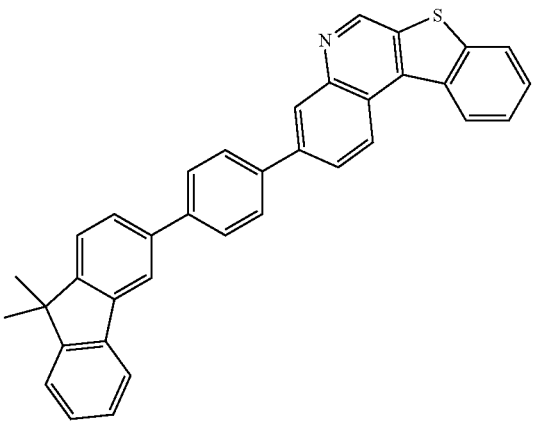
209
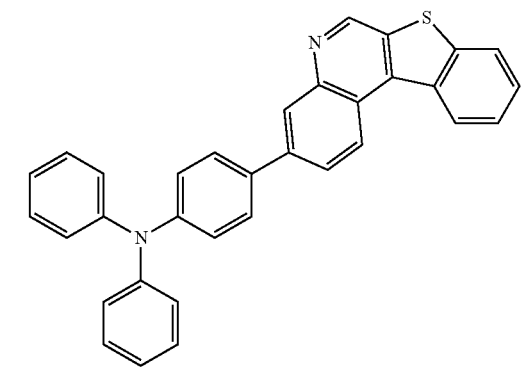
210
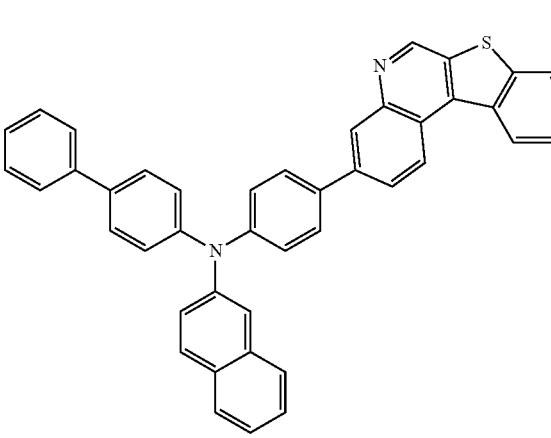

211
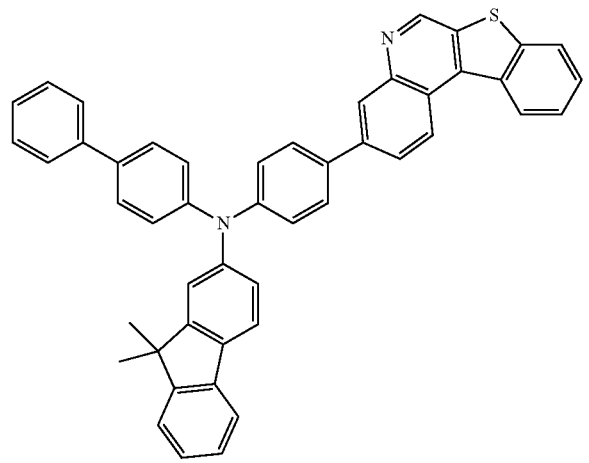
212
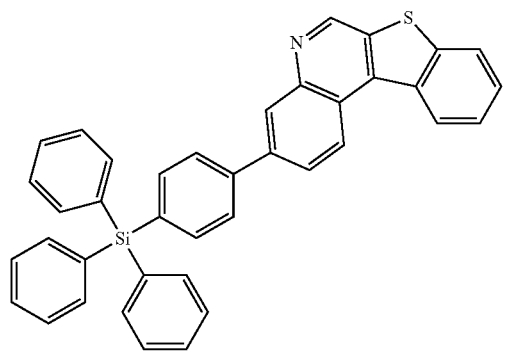
213
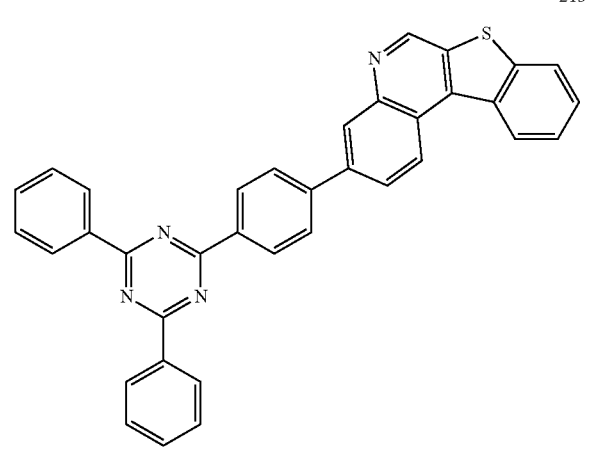
214
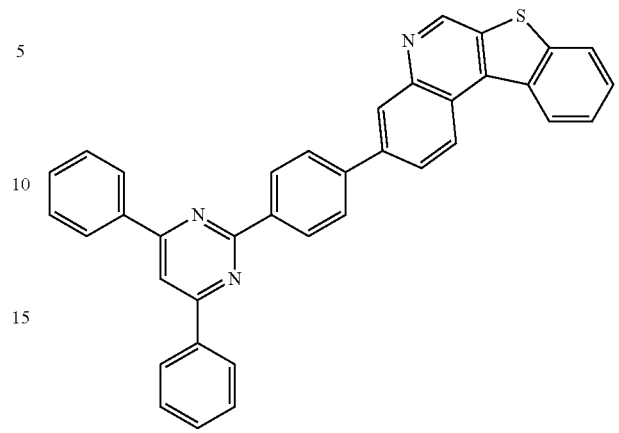
215
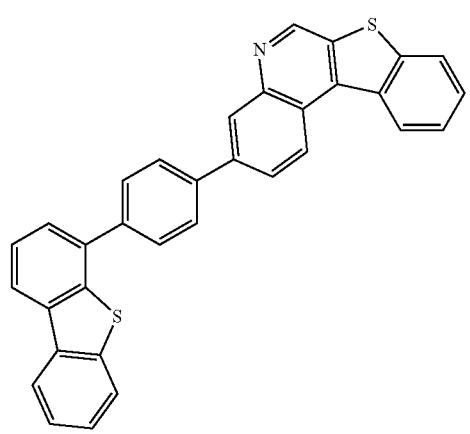
216
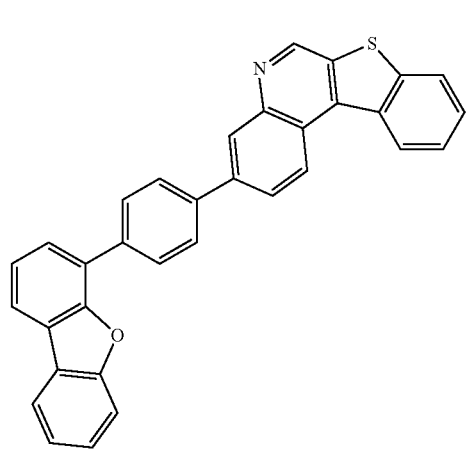

217
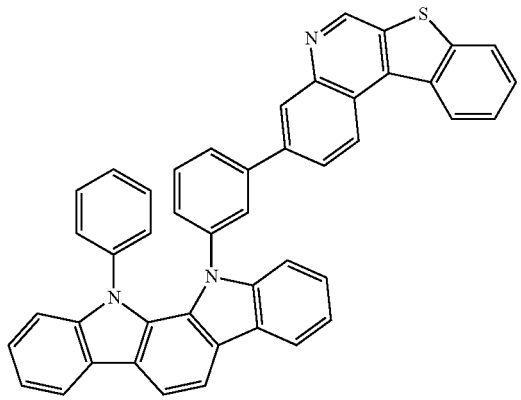
218
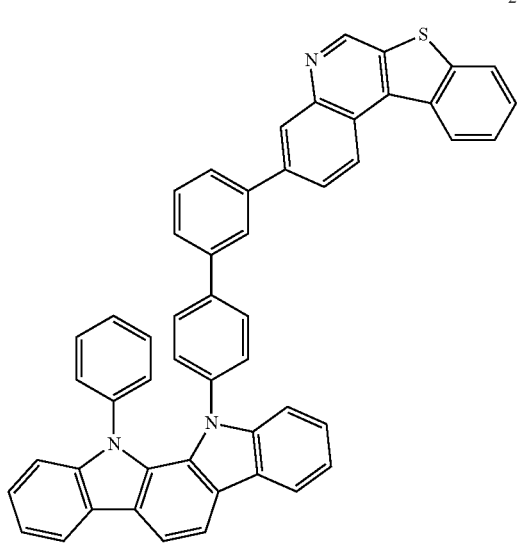
219
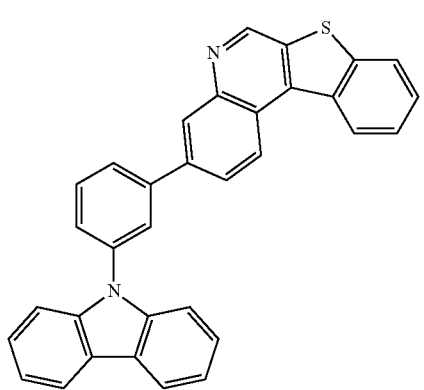
220
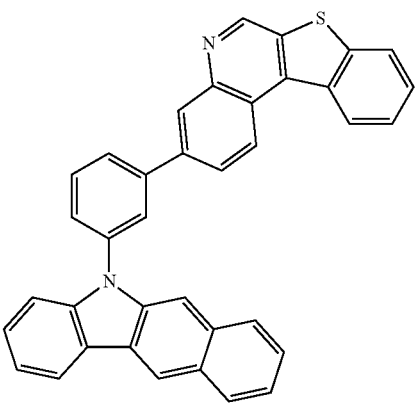
221
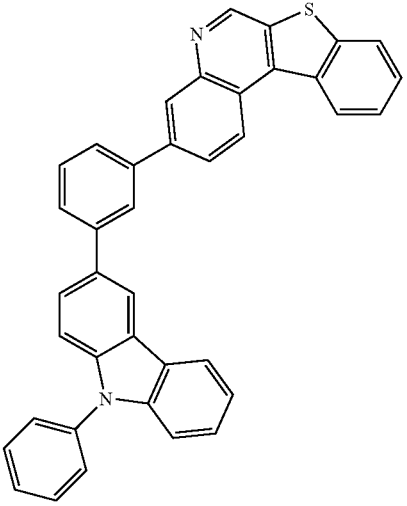
222
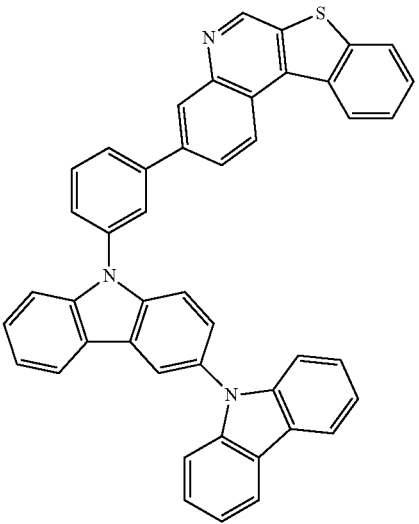

-continued
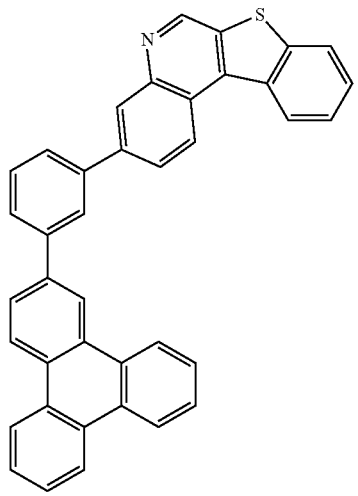
223
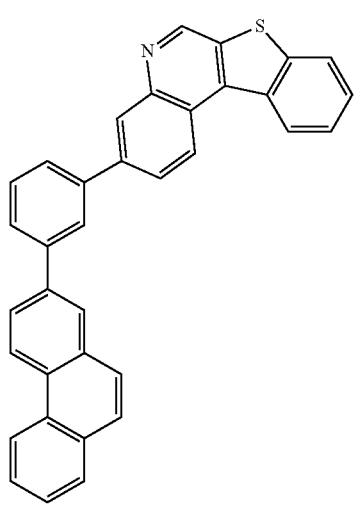
224
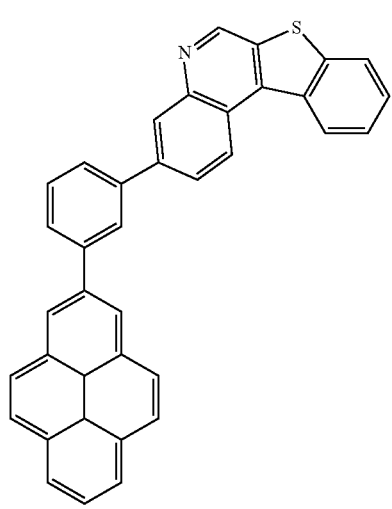
225
-continued
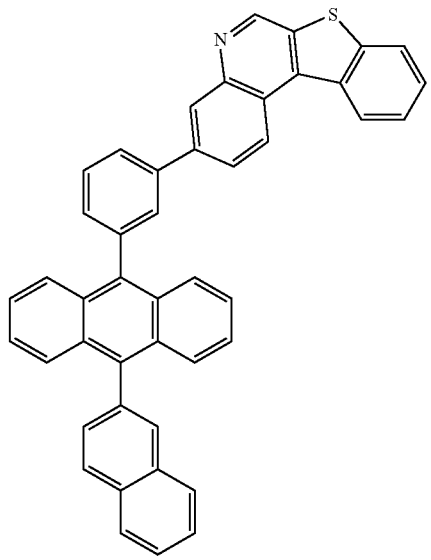
226
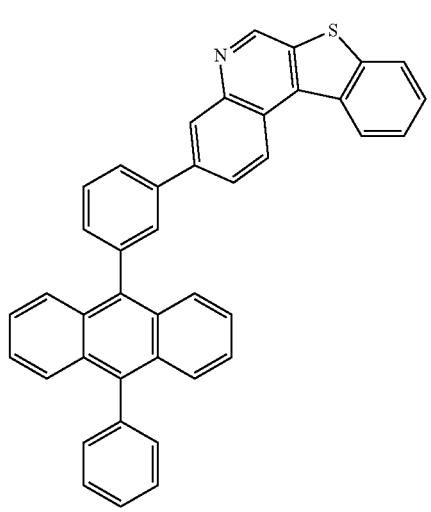
227
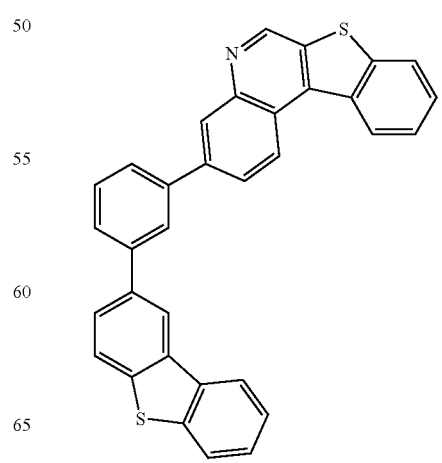
228

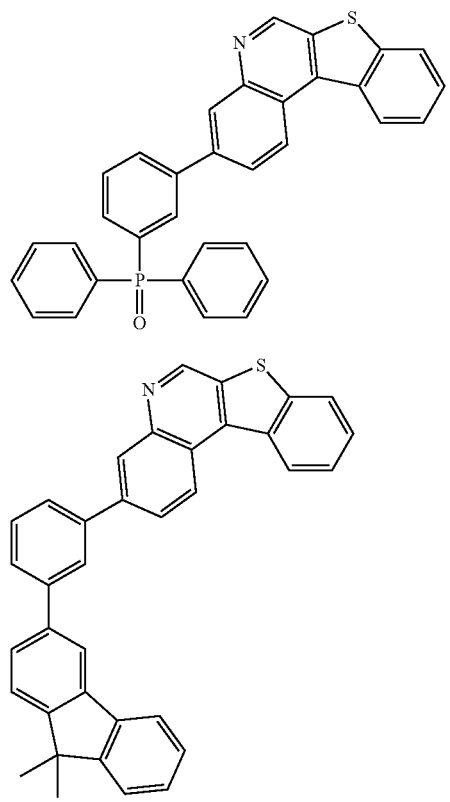
229
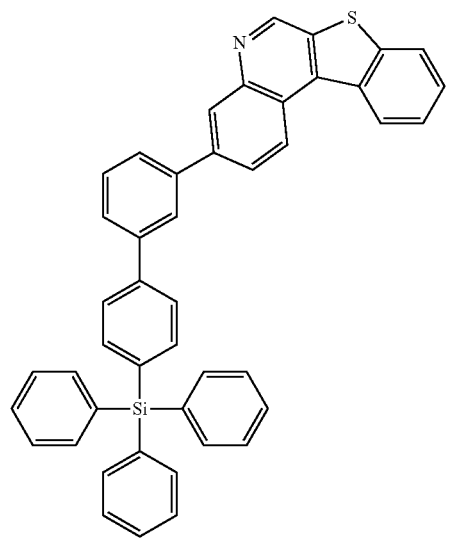
230
231
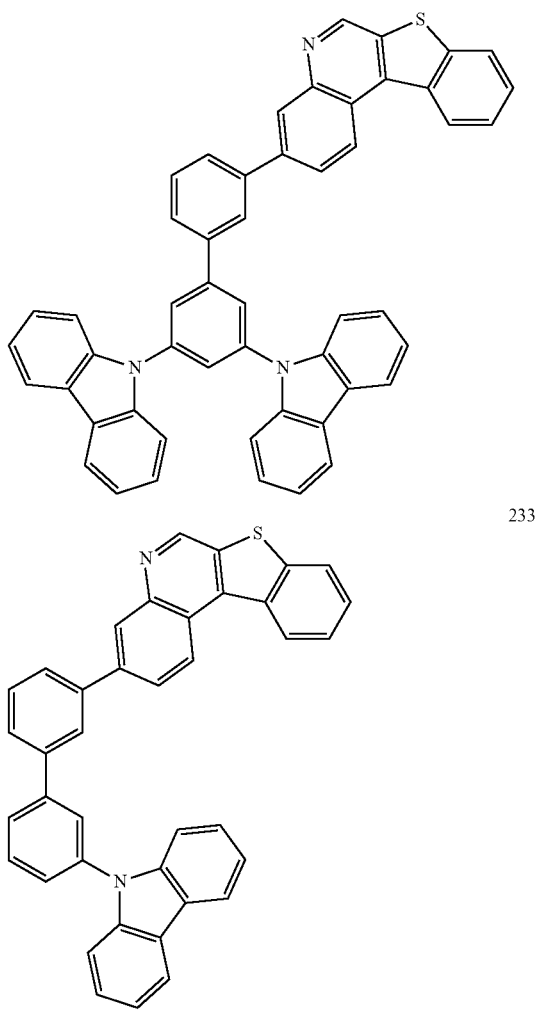
232
233
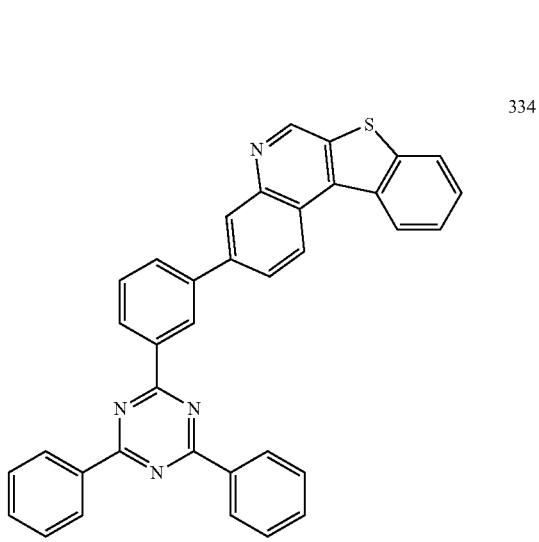
334

235 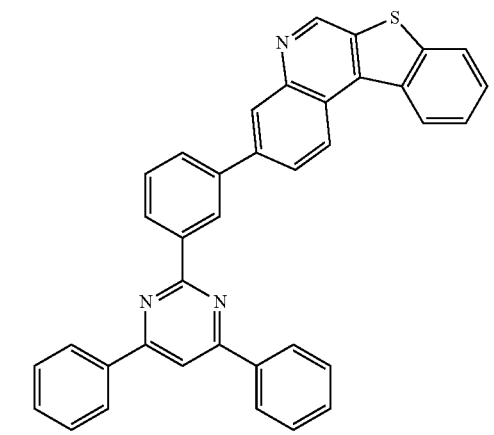
236 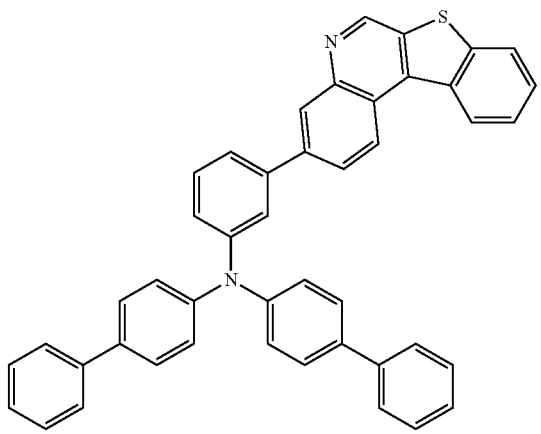
237 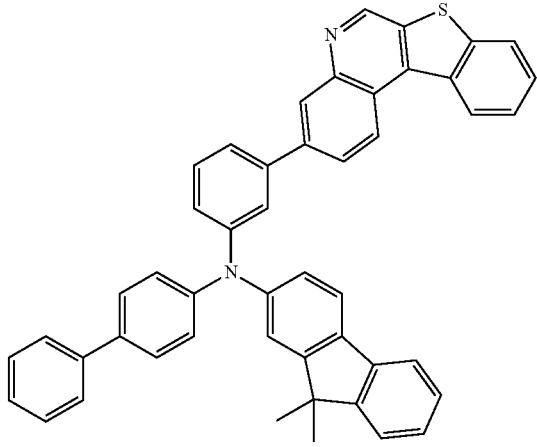
238 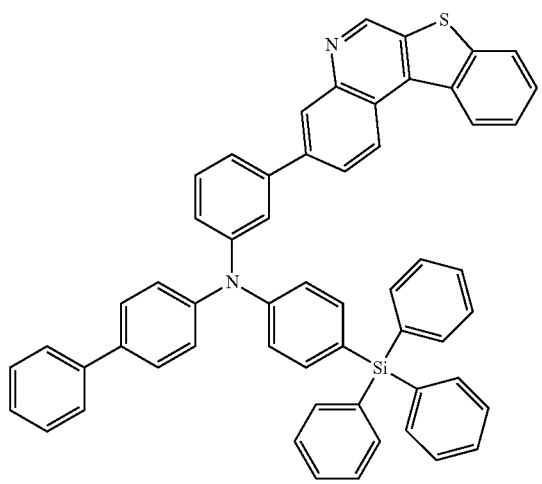
239 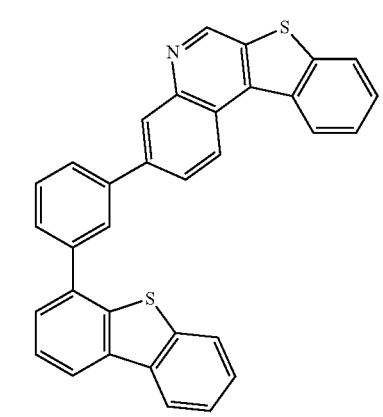
240 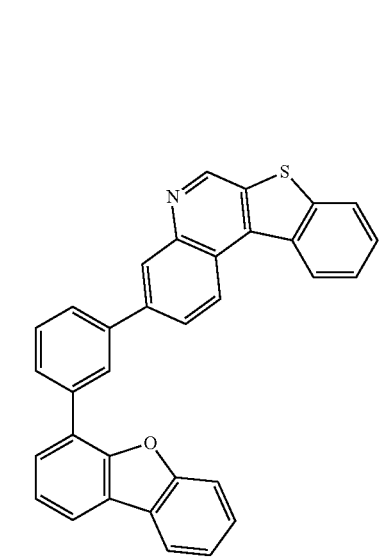

87
-continued
241
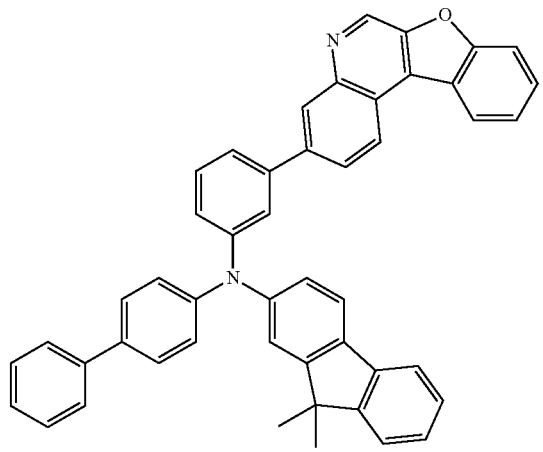
242
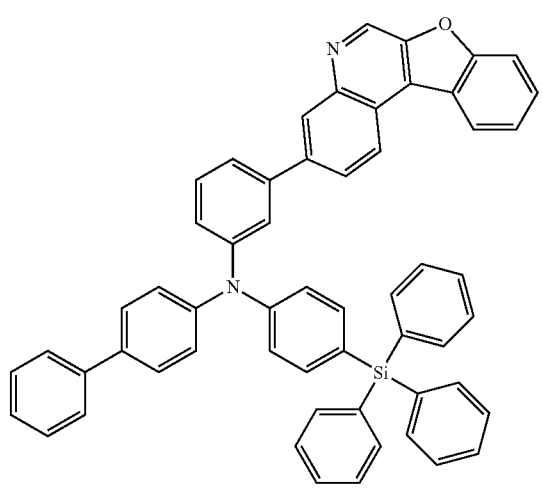
243
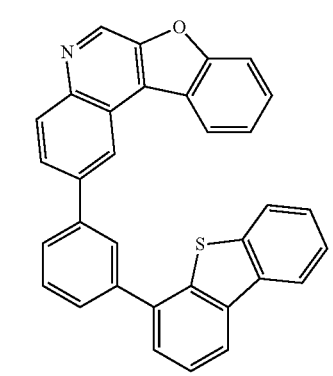
88
-continued
244
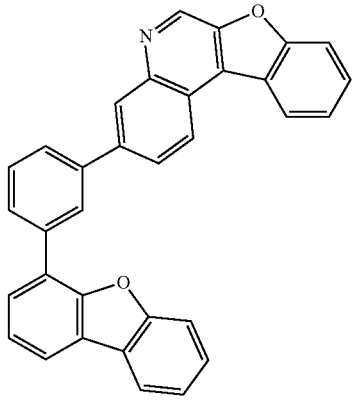
245
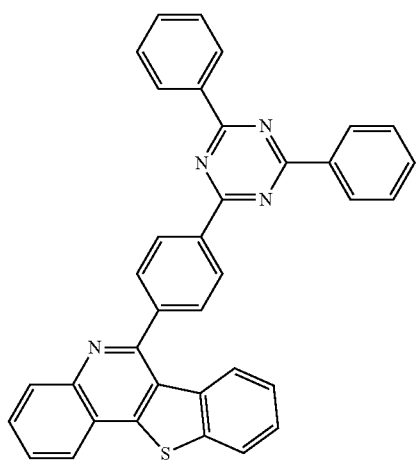
246
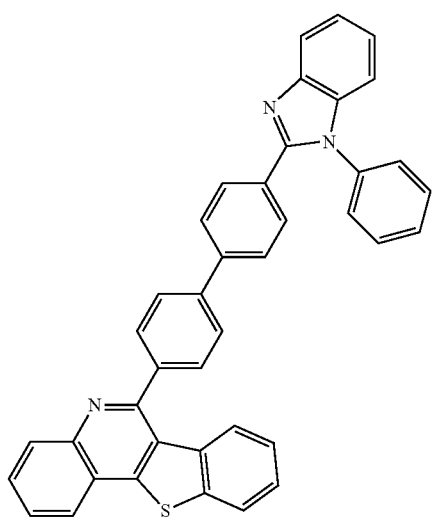

247
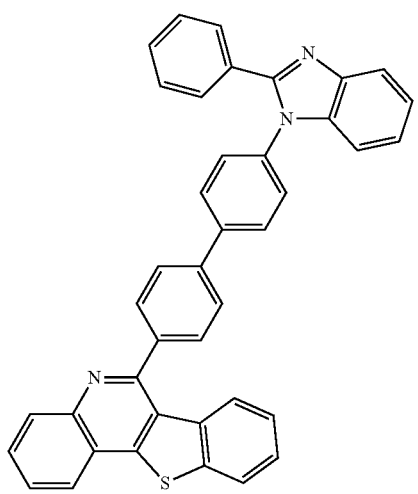
248
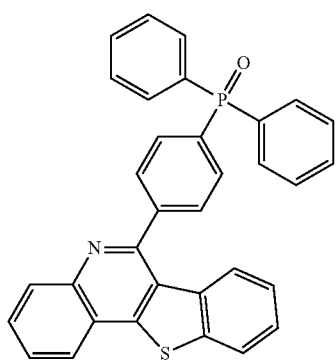
249
250
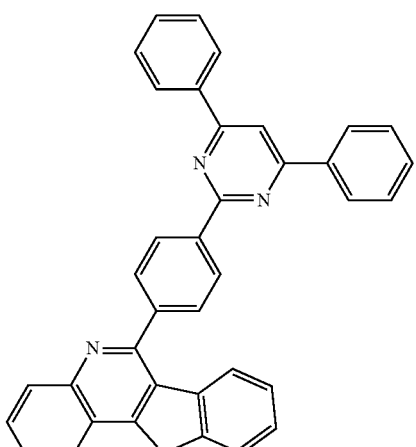
251
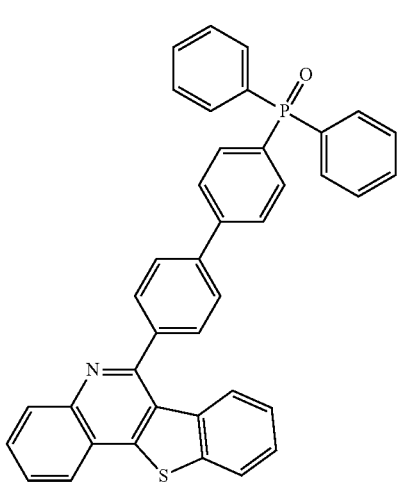
252

253
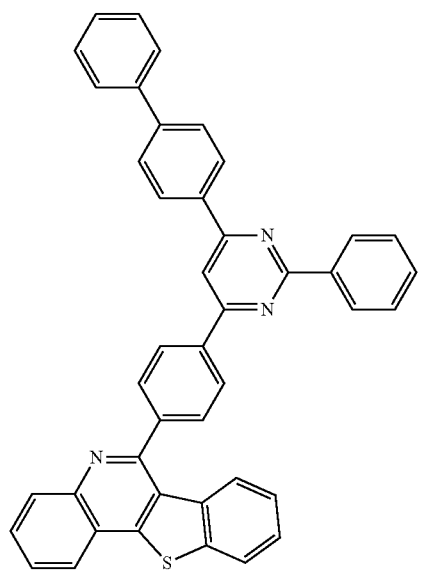
254
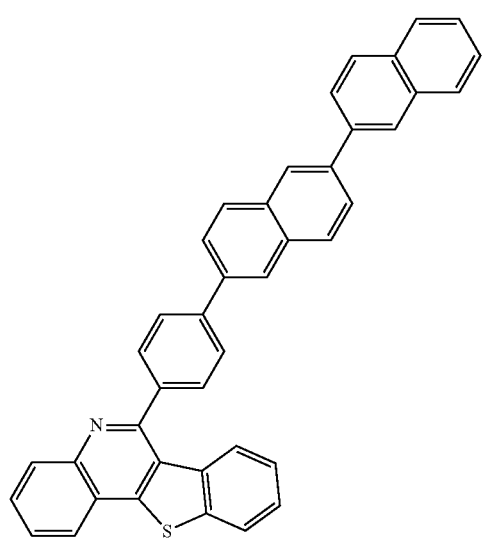
255
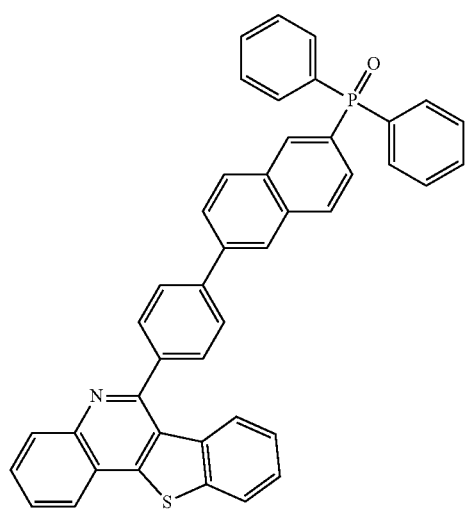
256
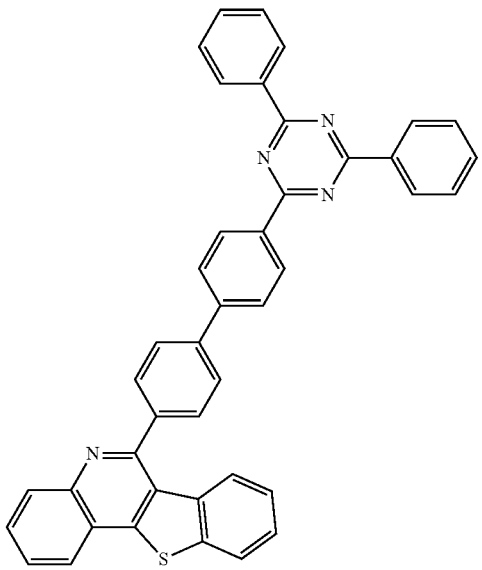
257
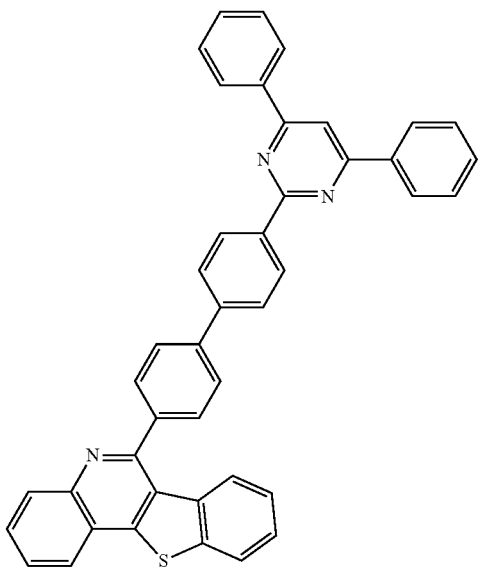
258
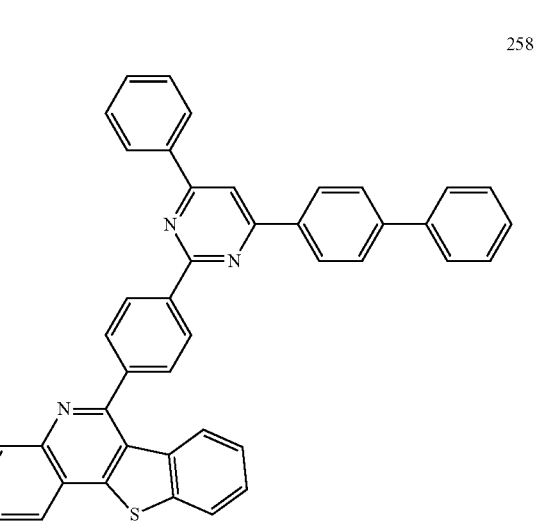

259
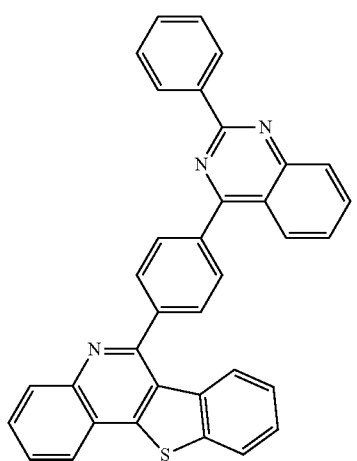
260
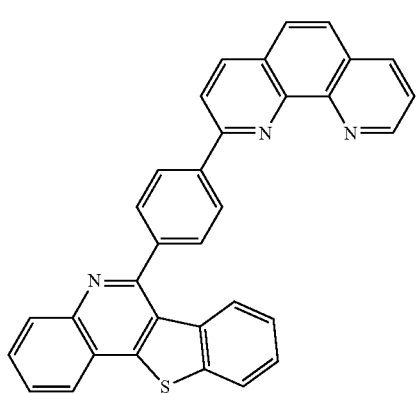
261
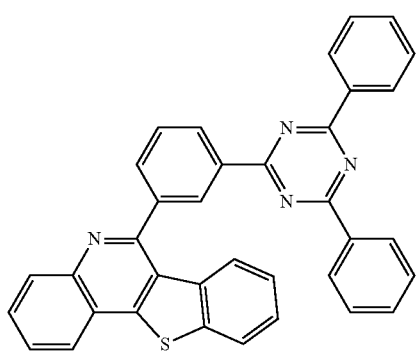
262
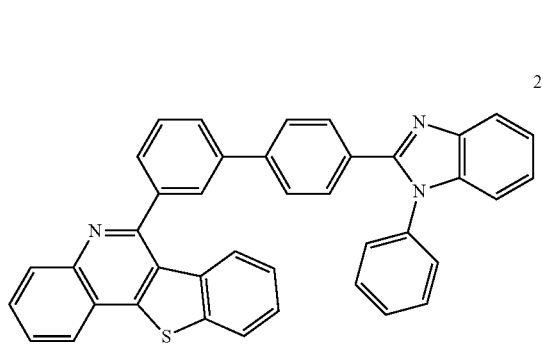
263
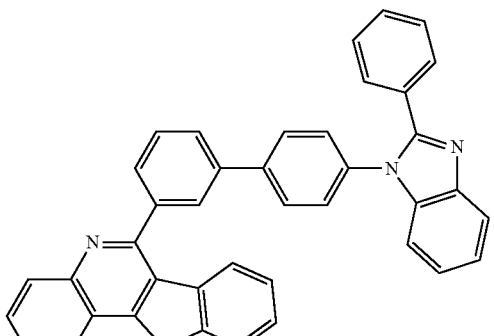
264
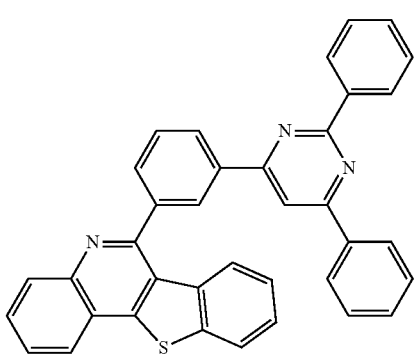
265
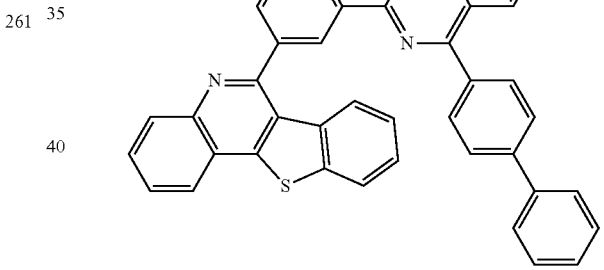
266
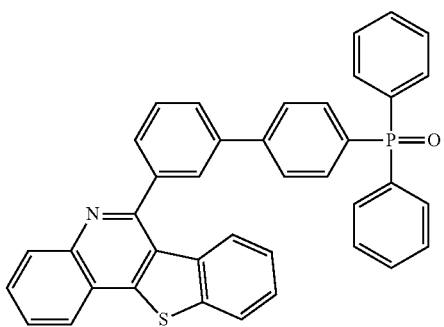

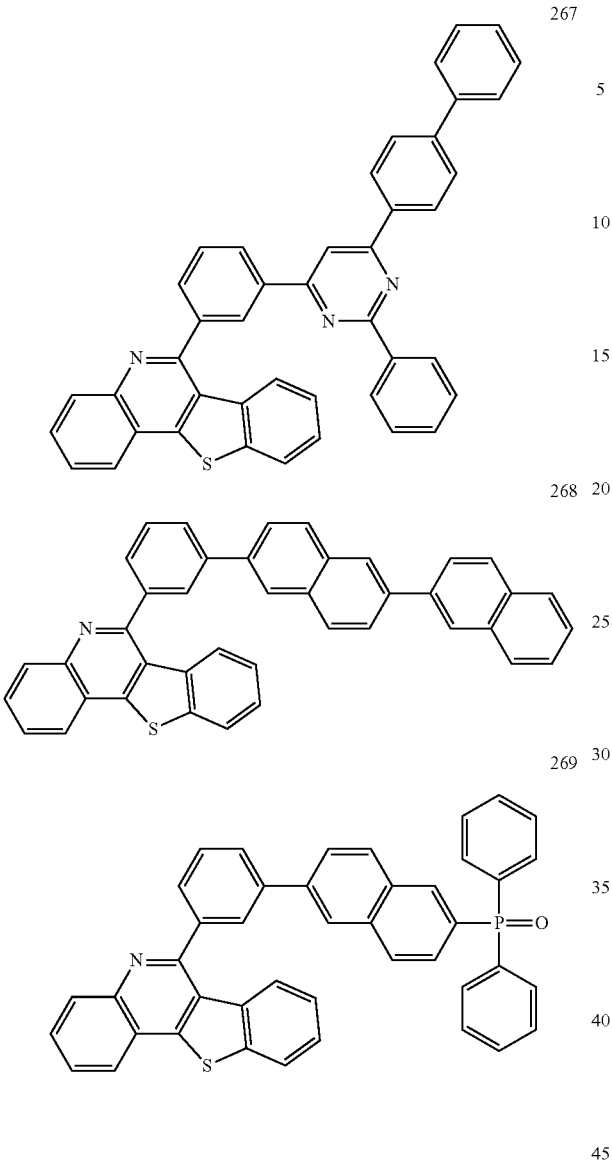
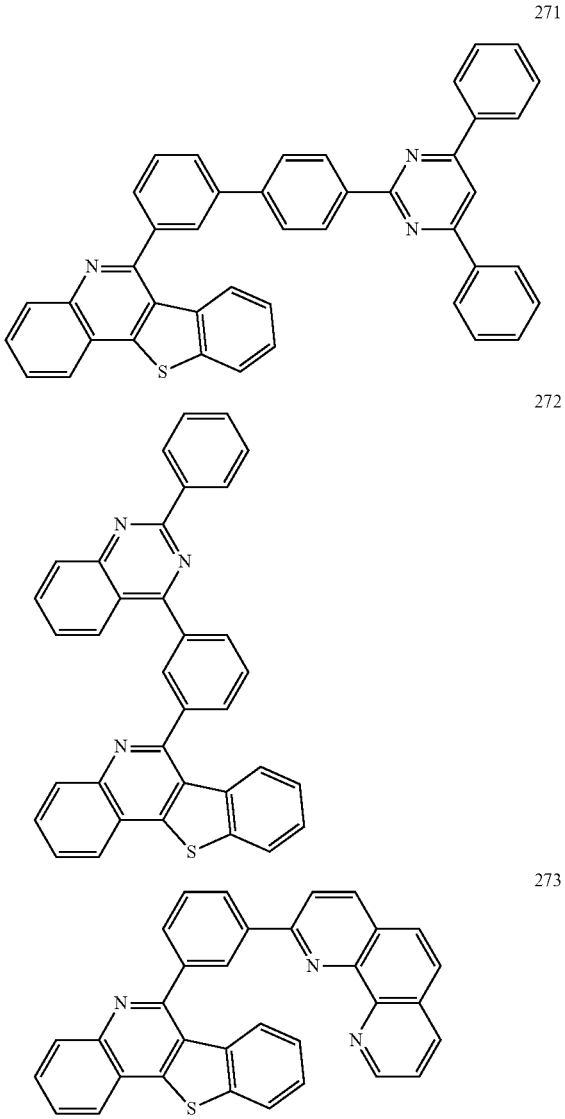
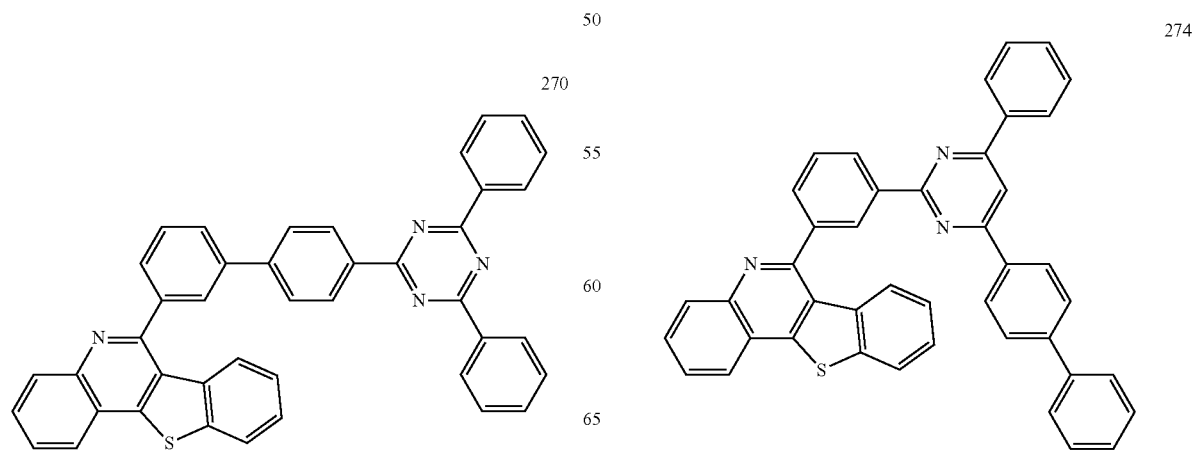

275
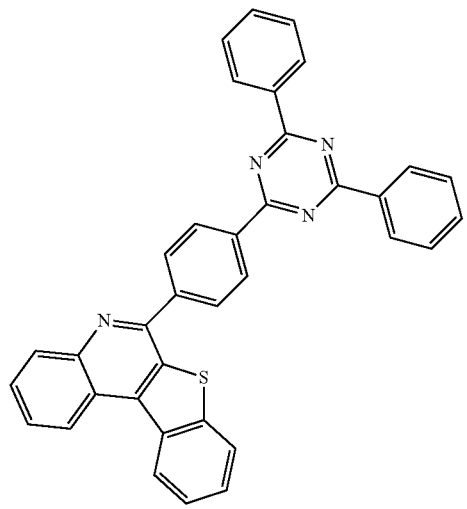
276
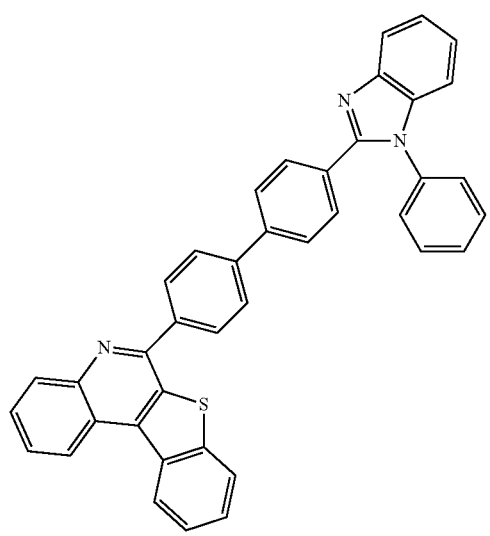
278
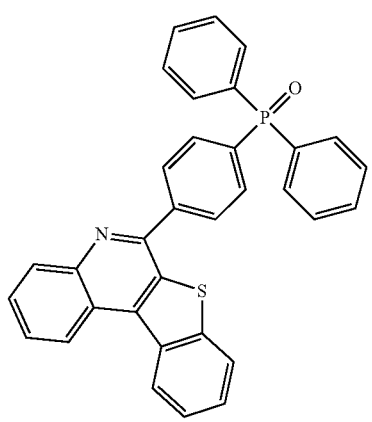
279
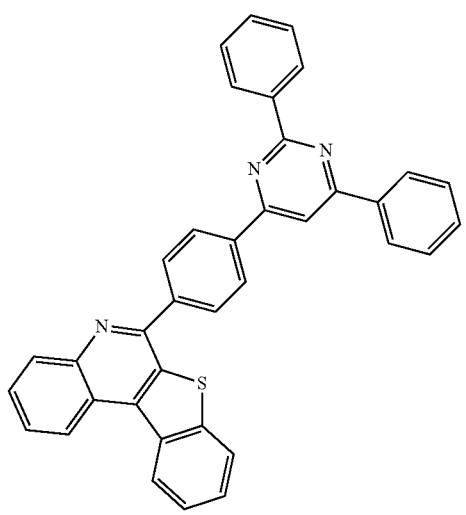
280
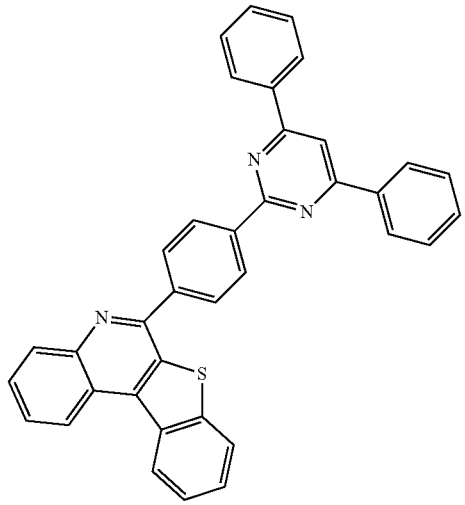
277

99
-continued
100
-continued
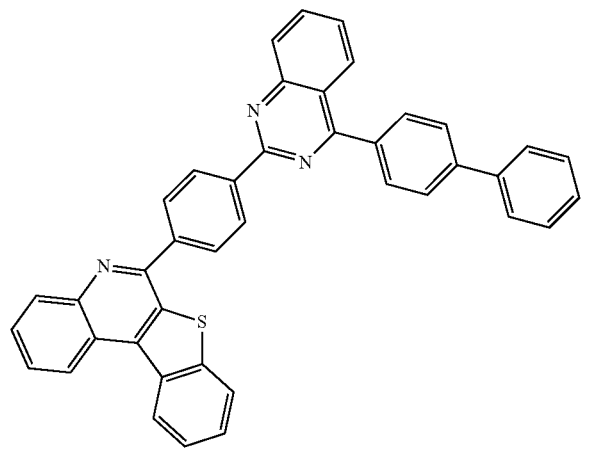
281
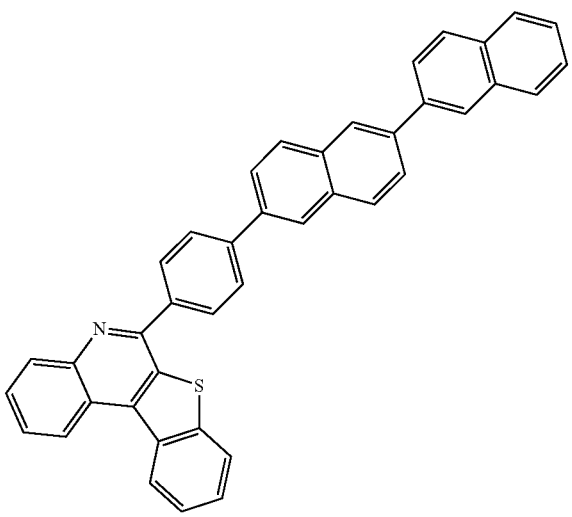
284
282
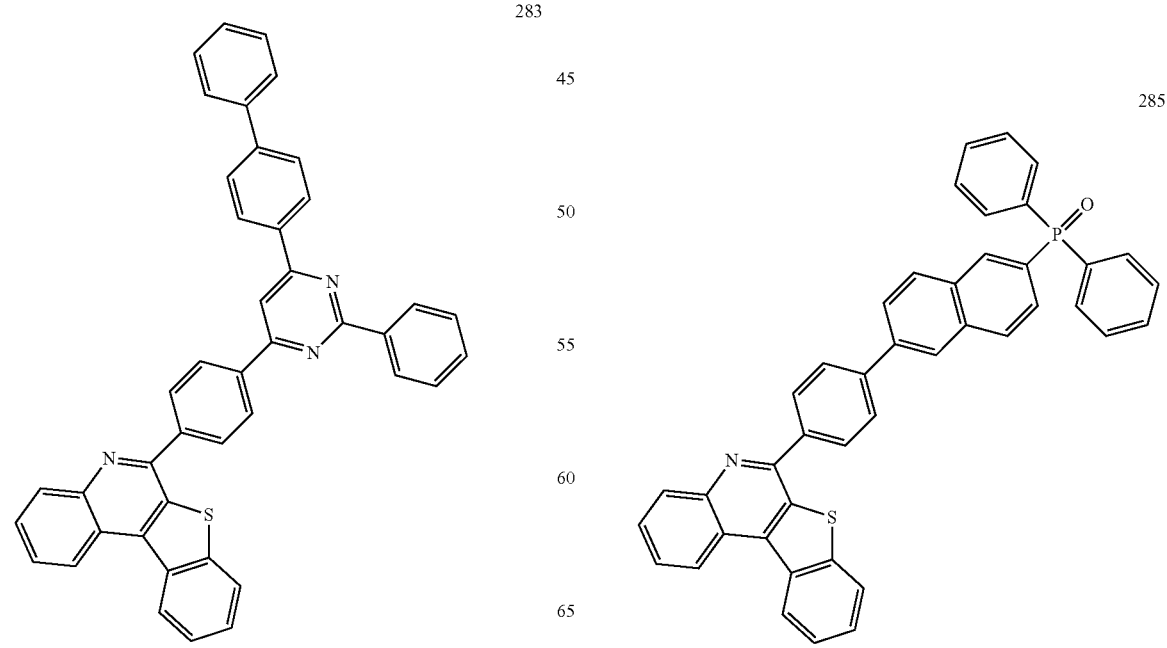
283
285

286
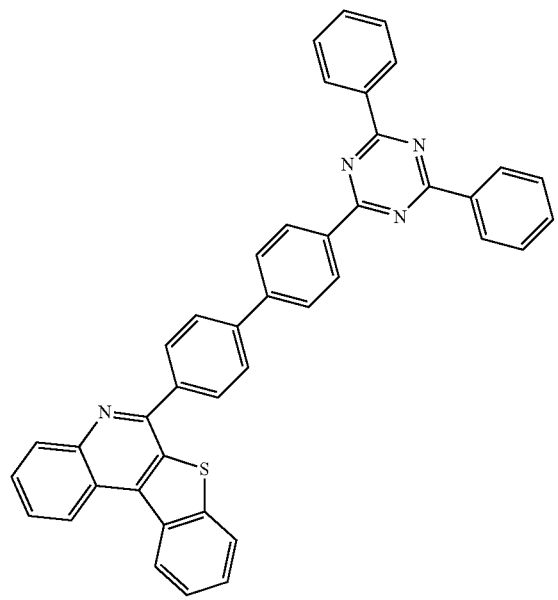
287
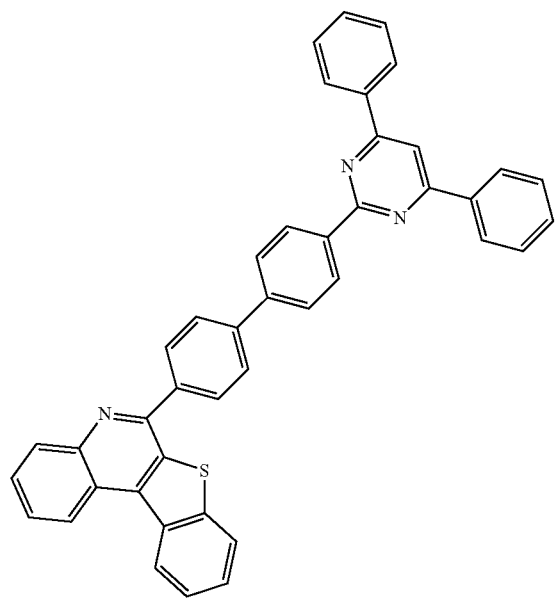
288
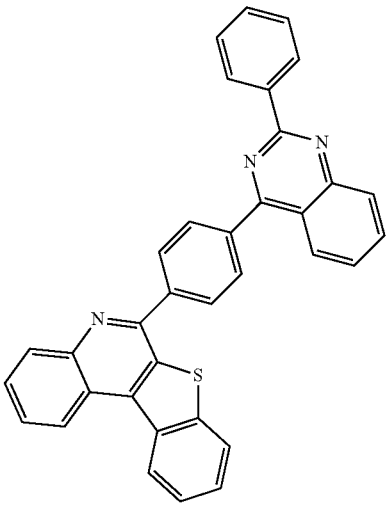
289
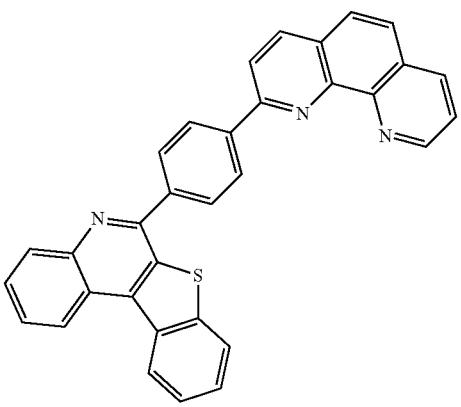
290
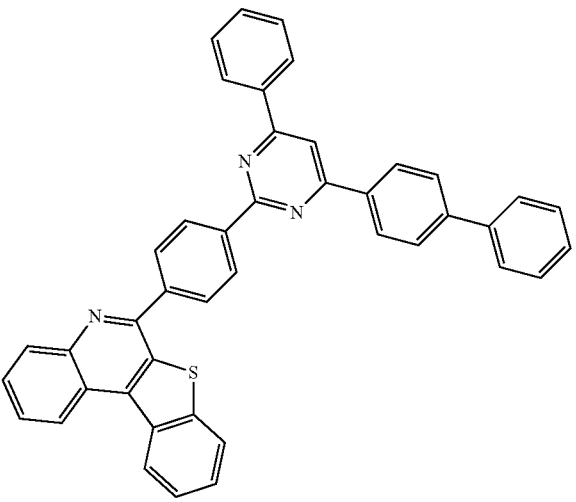

291
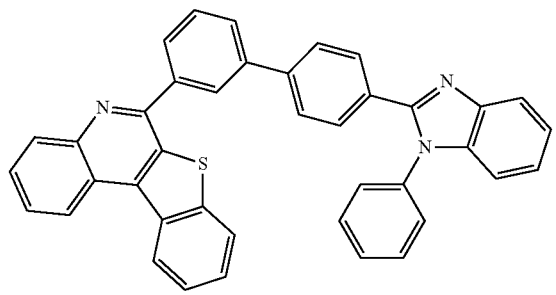
292
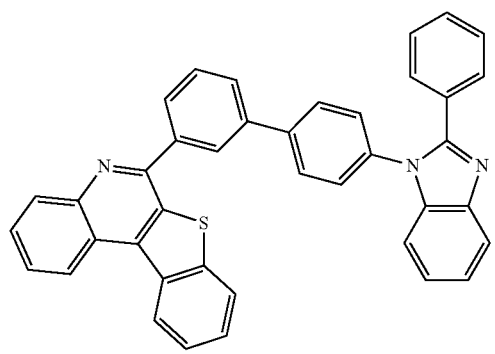
293
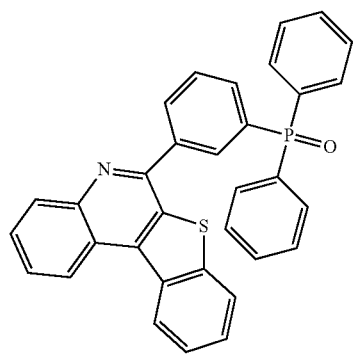
294
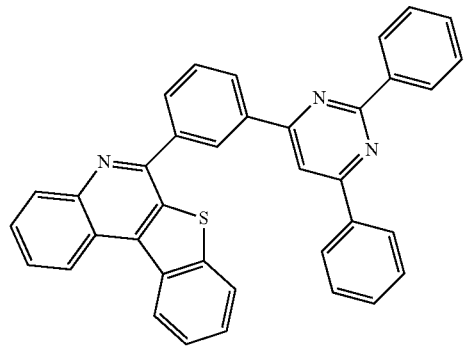
295
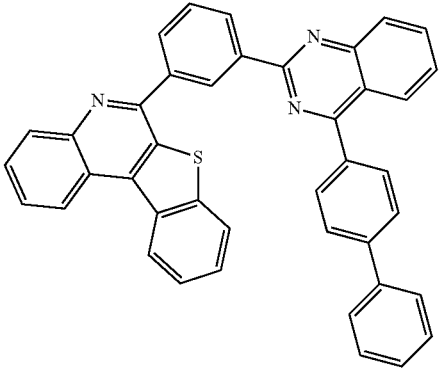
296
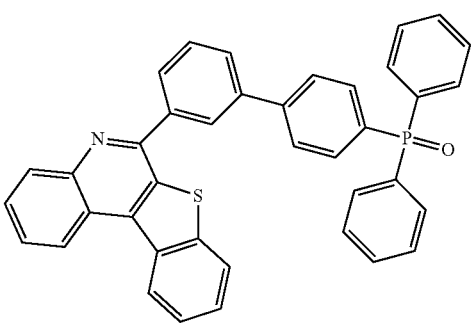
297
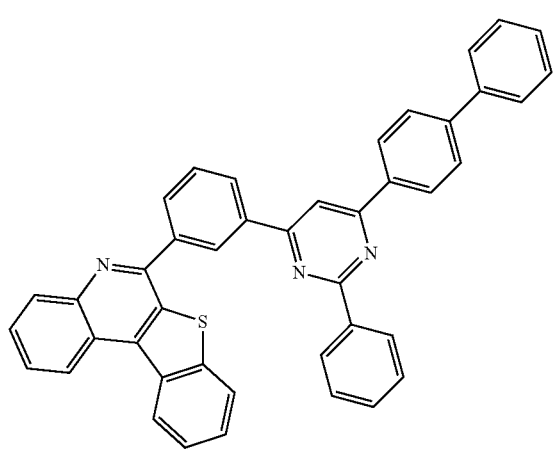
298
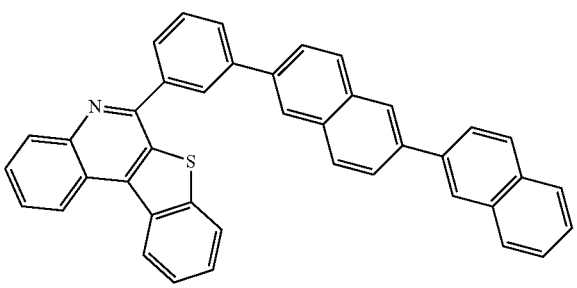

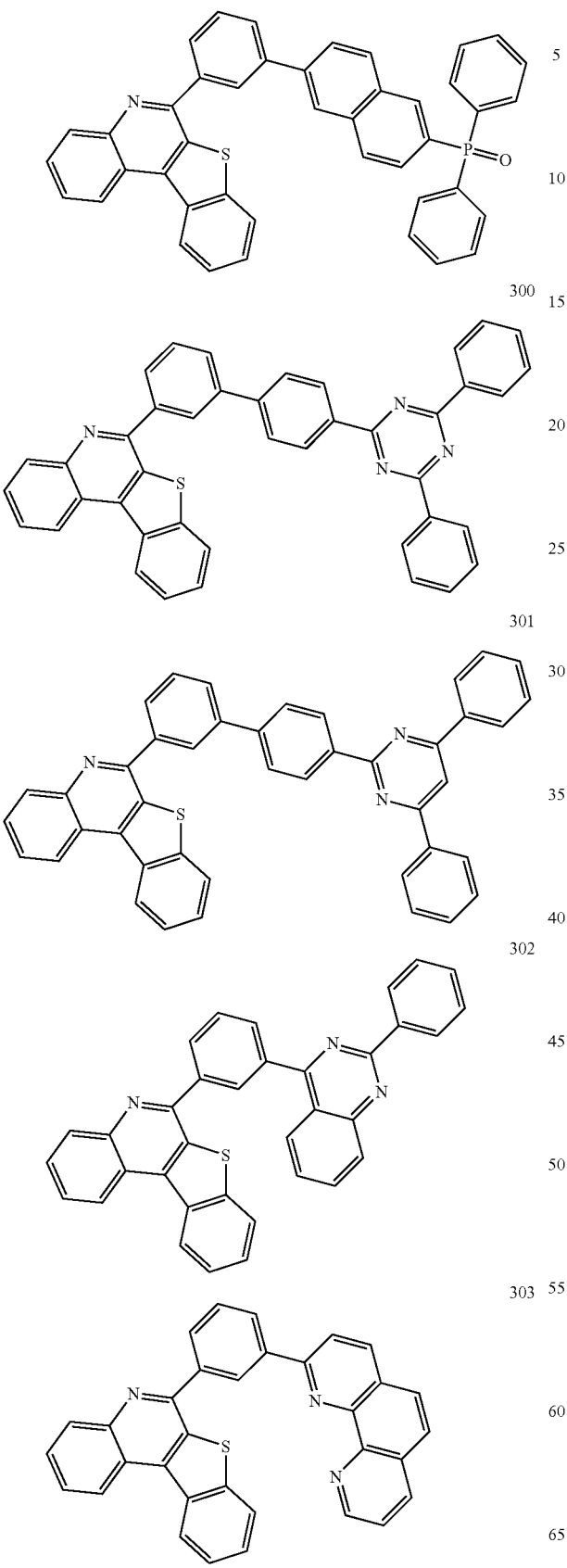
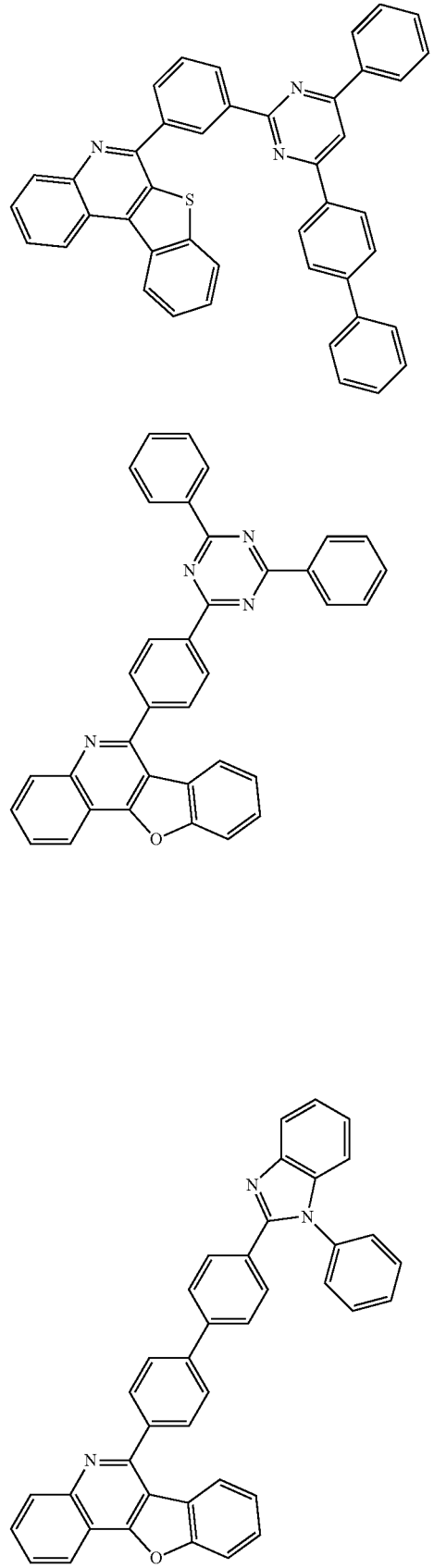

307
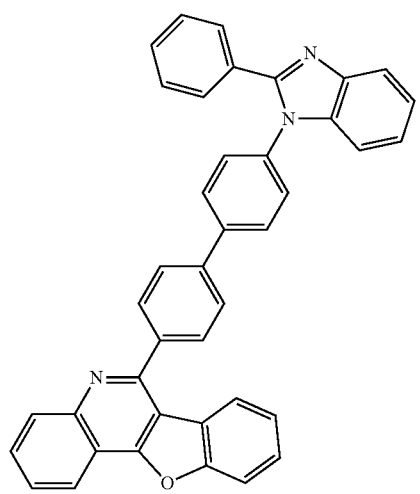
308
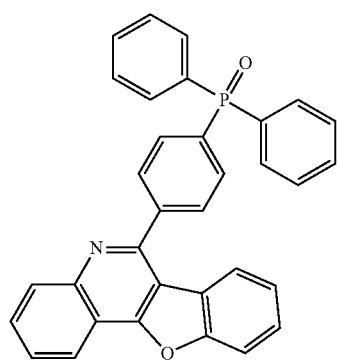
309
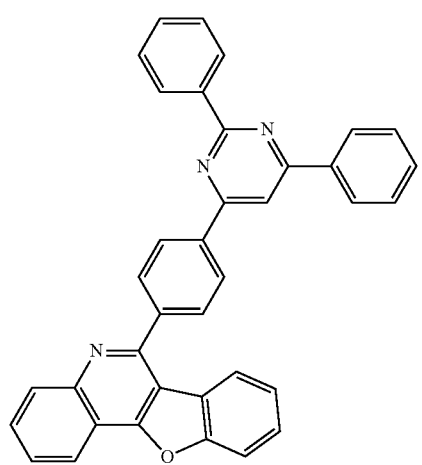
310
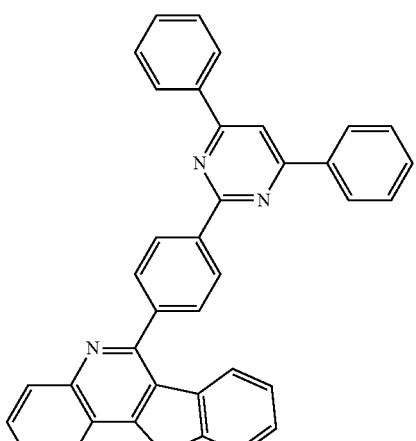
311
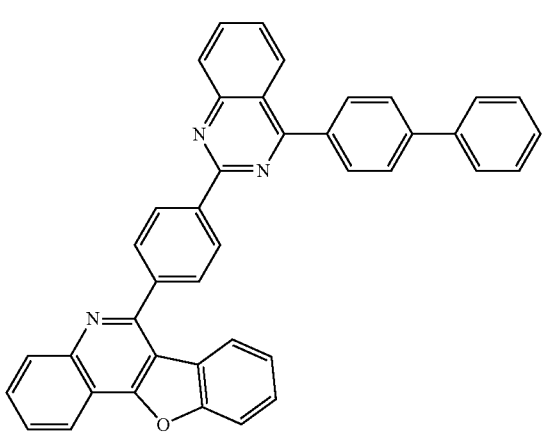
312
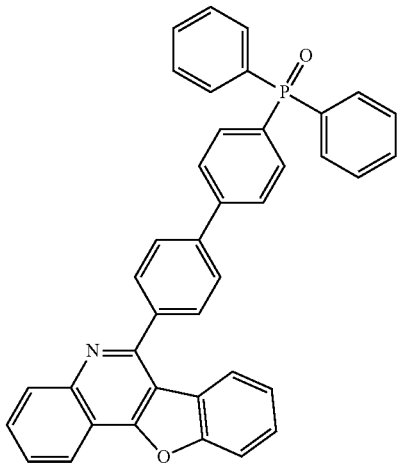

313
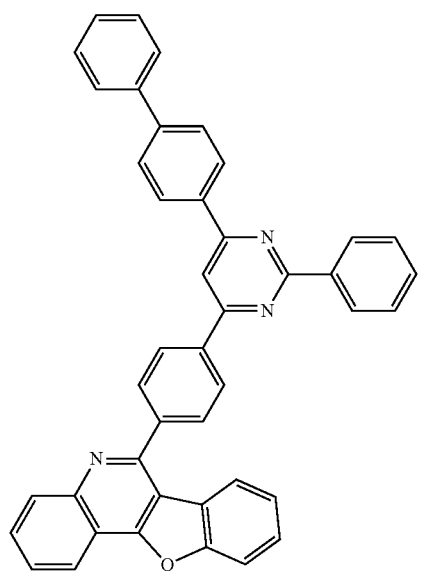
314
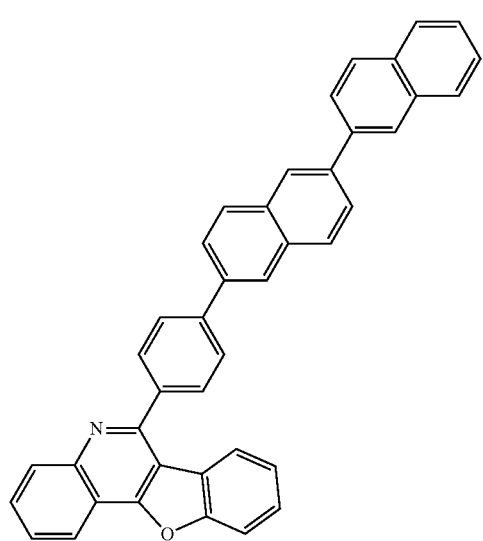
315
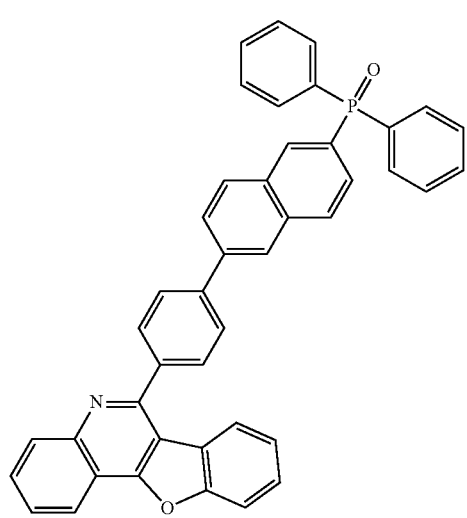
316
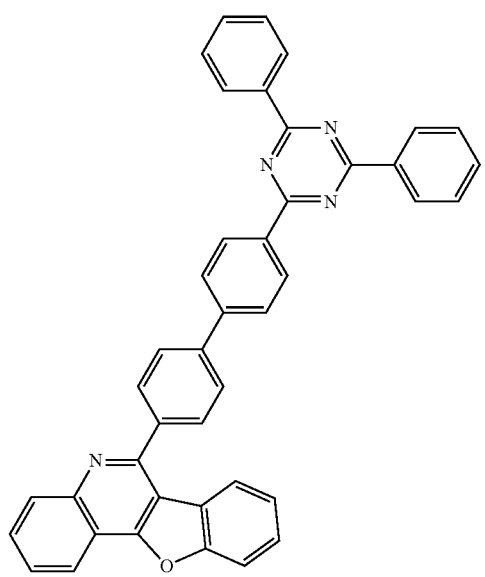
317
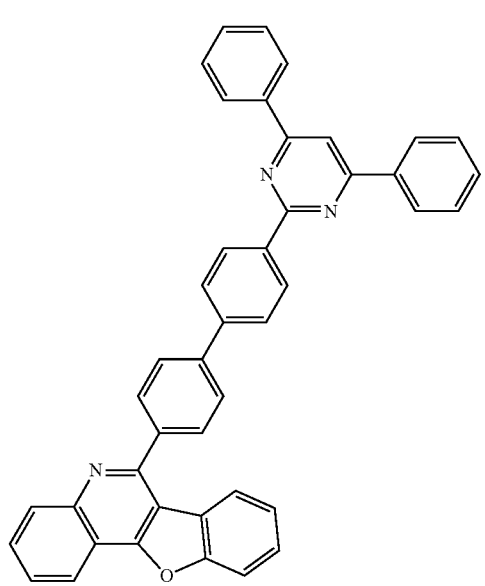
318
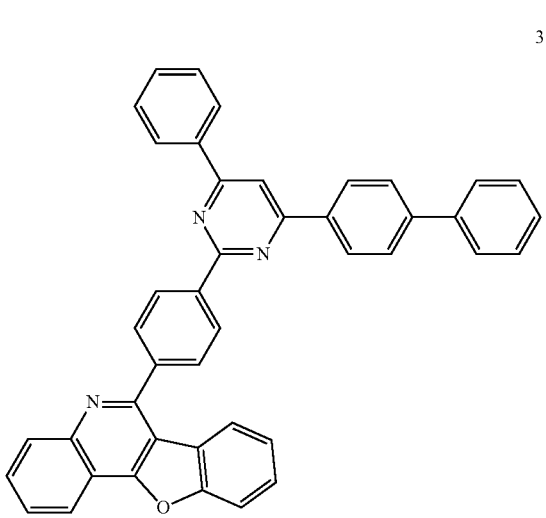

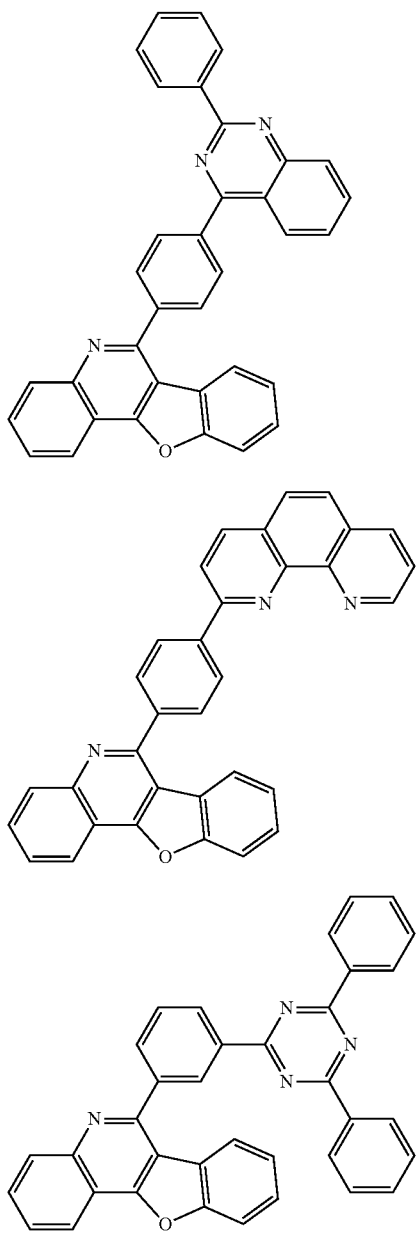
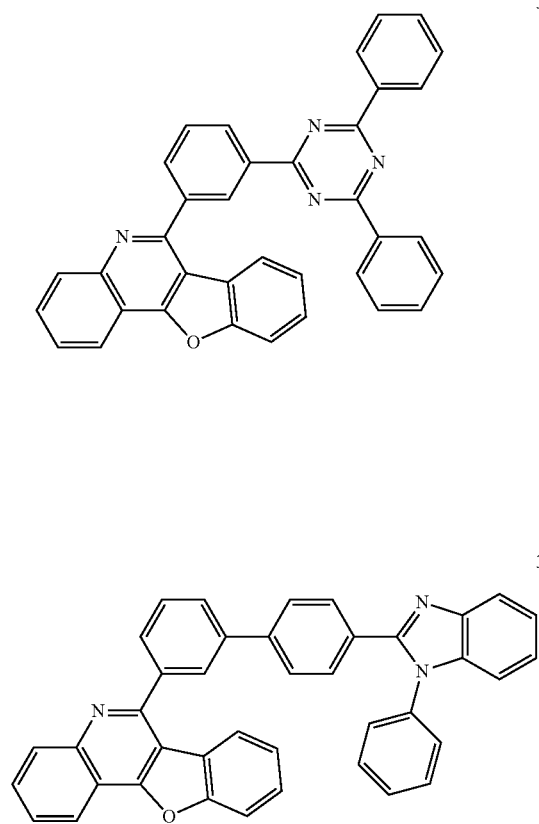
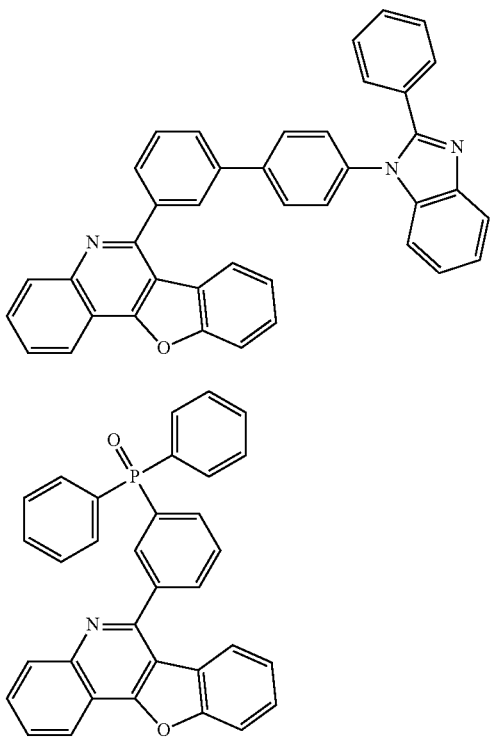
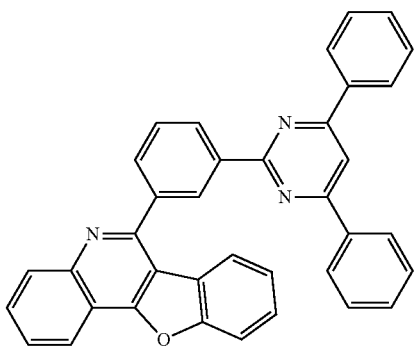

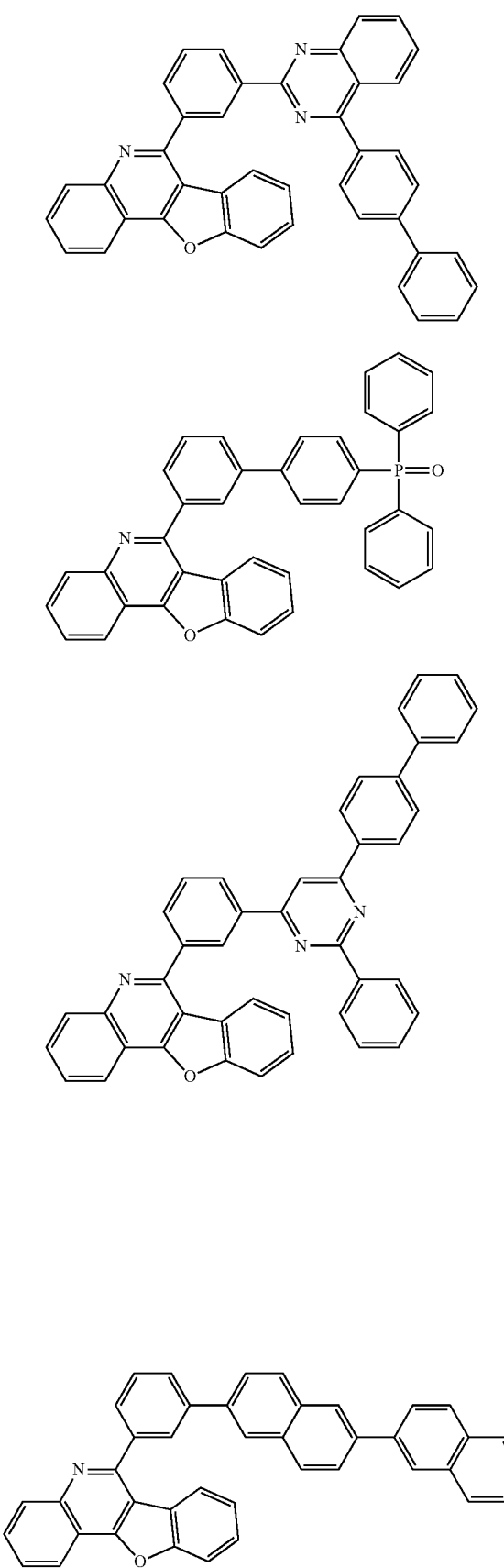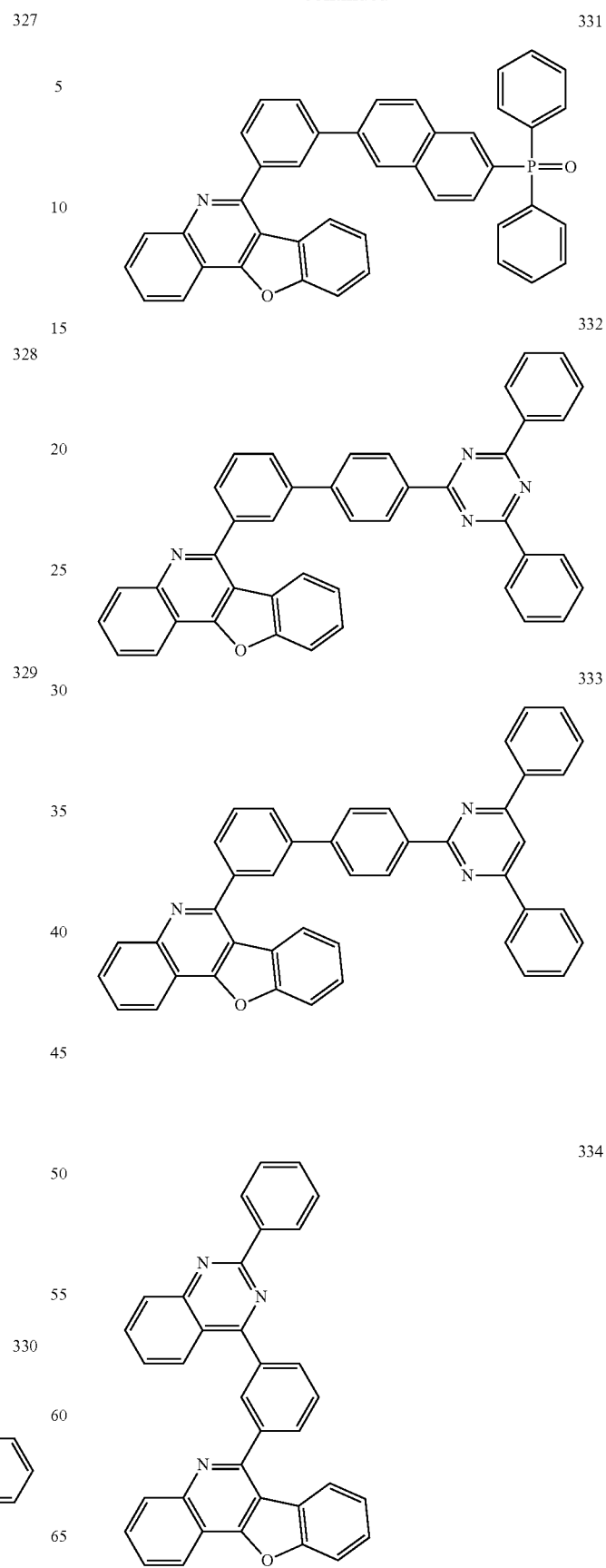

115
-continued
335
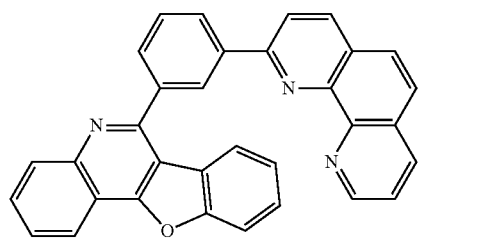
336
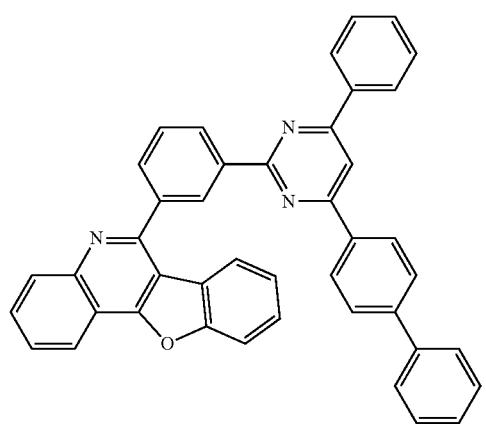
337
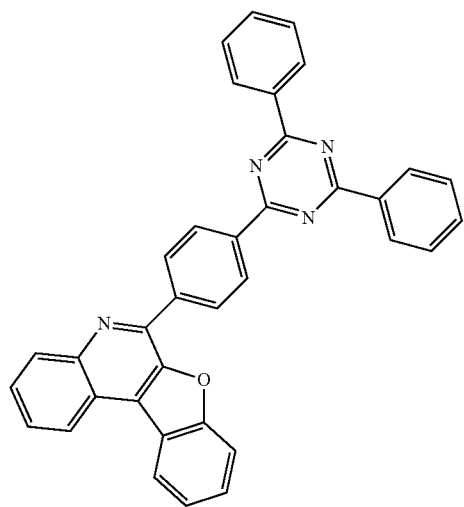
116
-continued
338
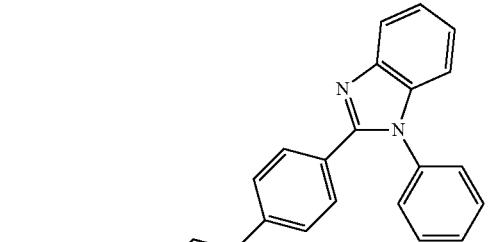
339
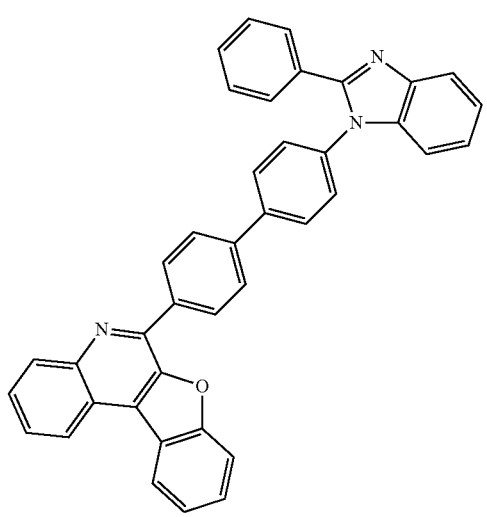
340
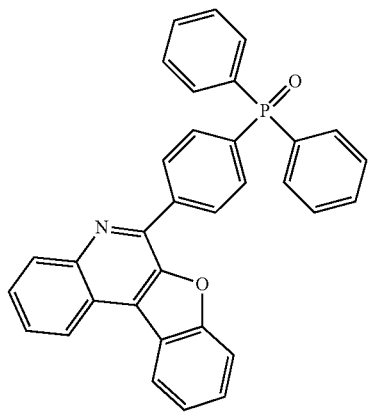

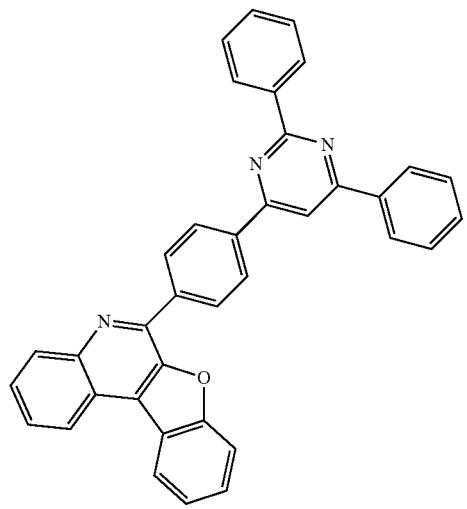
341
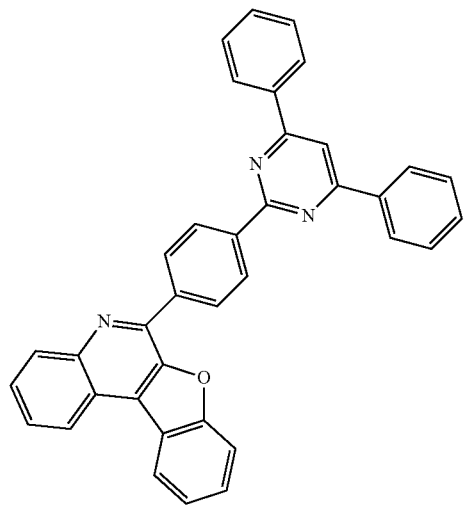
342
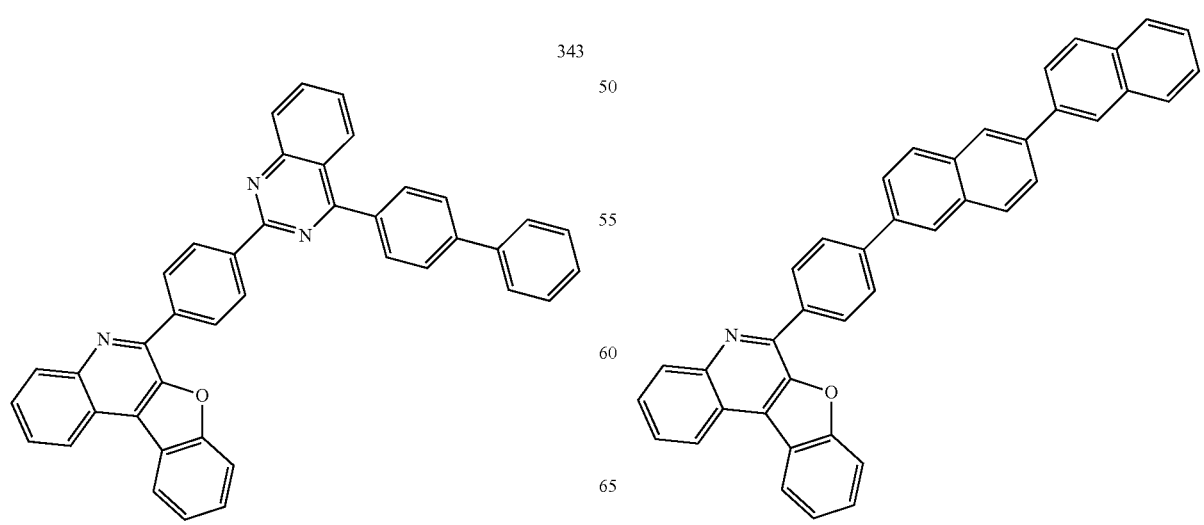
343
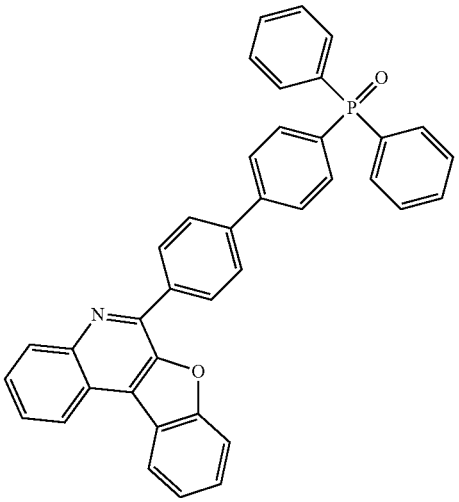
344
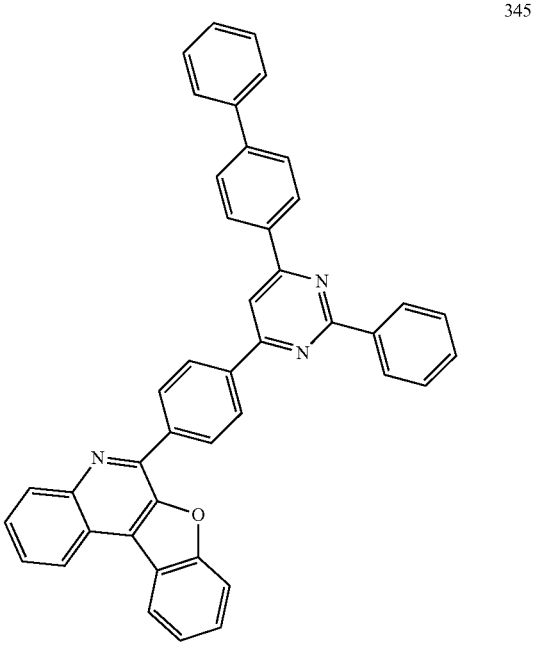
345
346

347
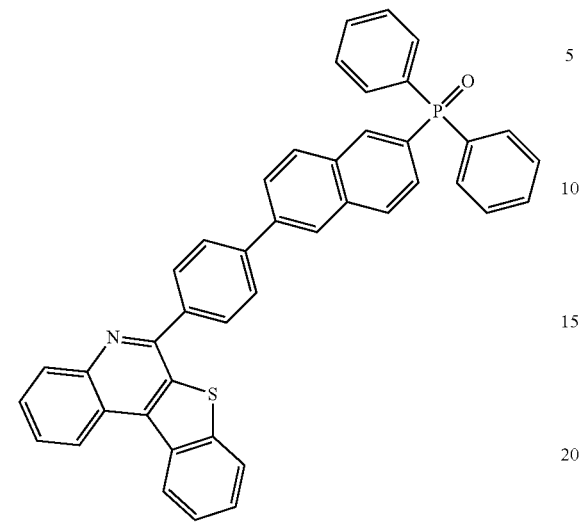
348
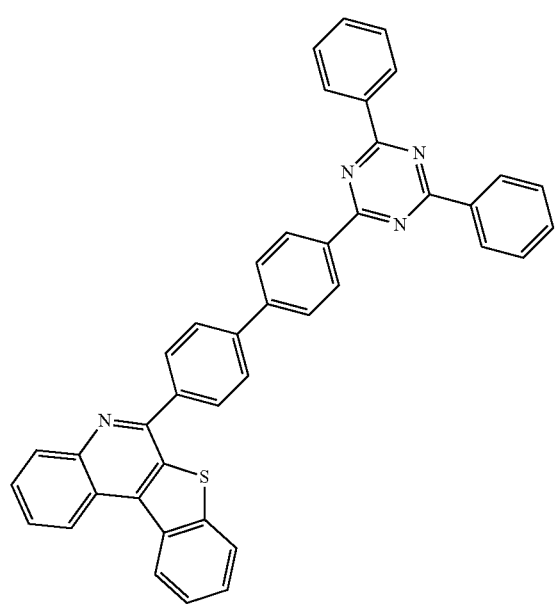
349
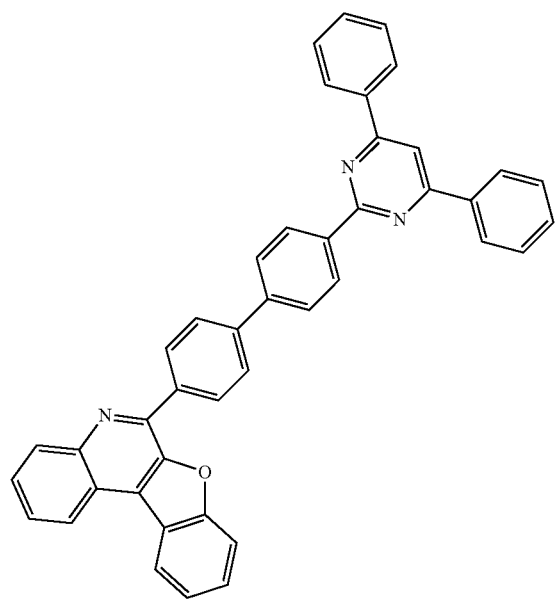
350
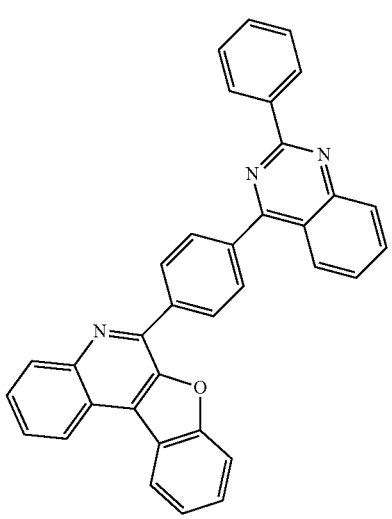
351
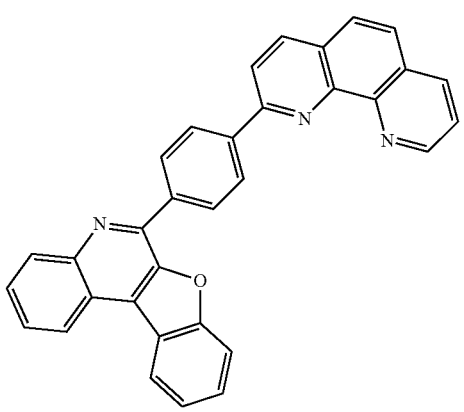

-continued
352
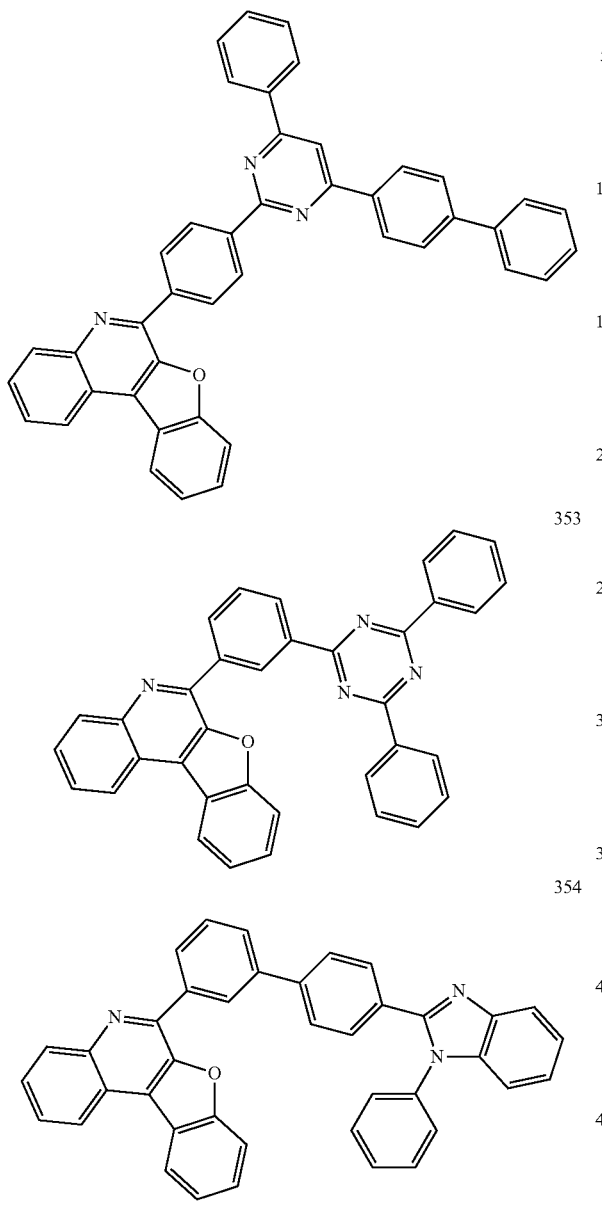
353
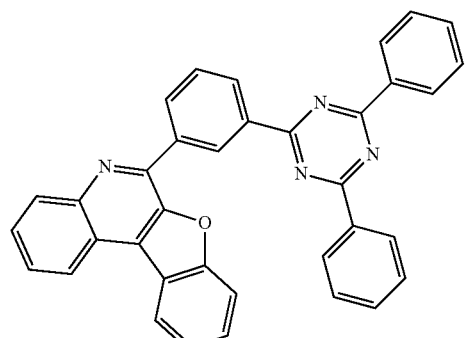
354
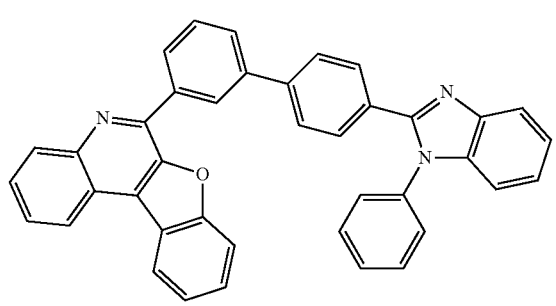
355
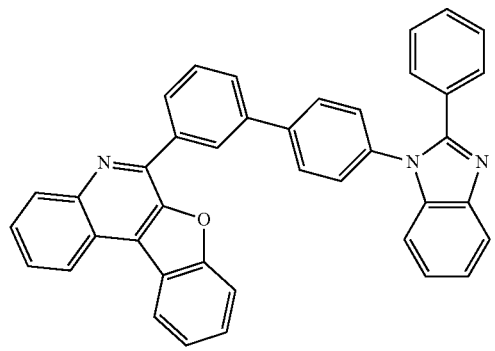
-continued
356
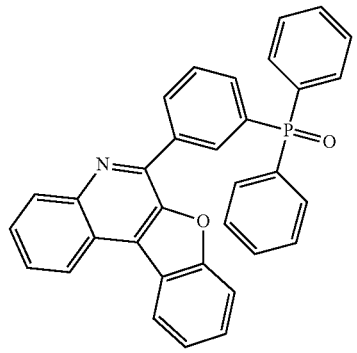
357
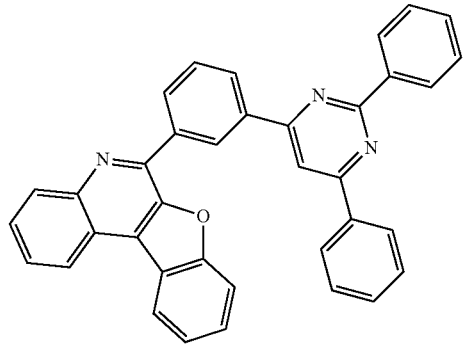
358
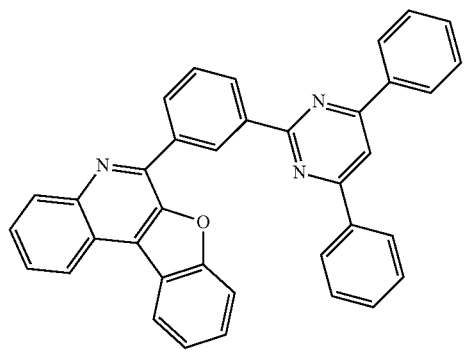
359
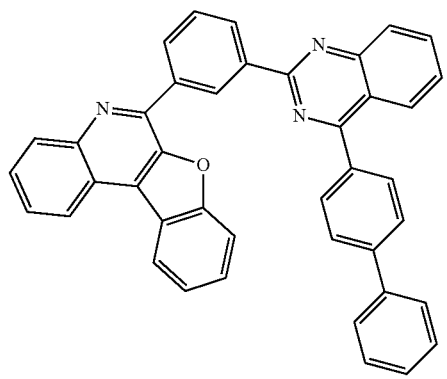

123
-continued
124
-continued
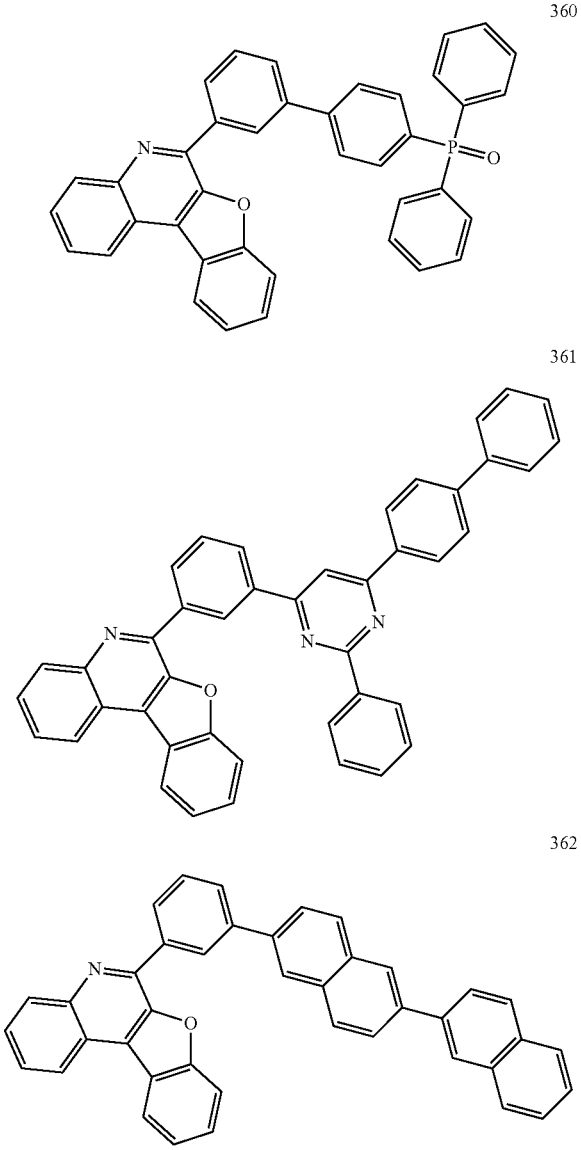
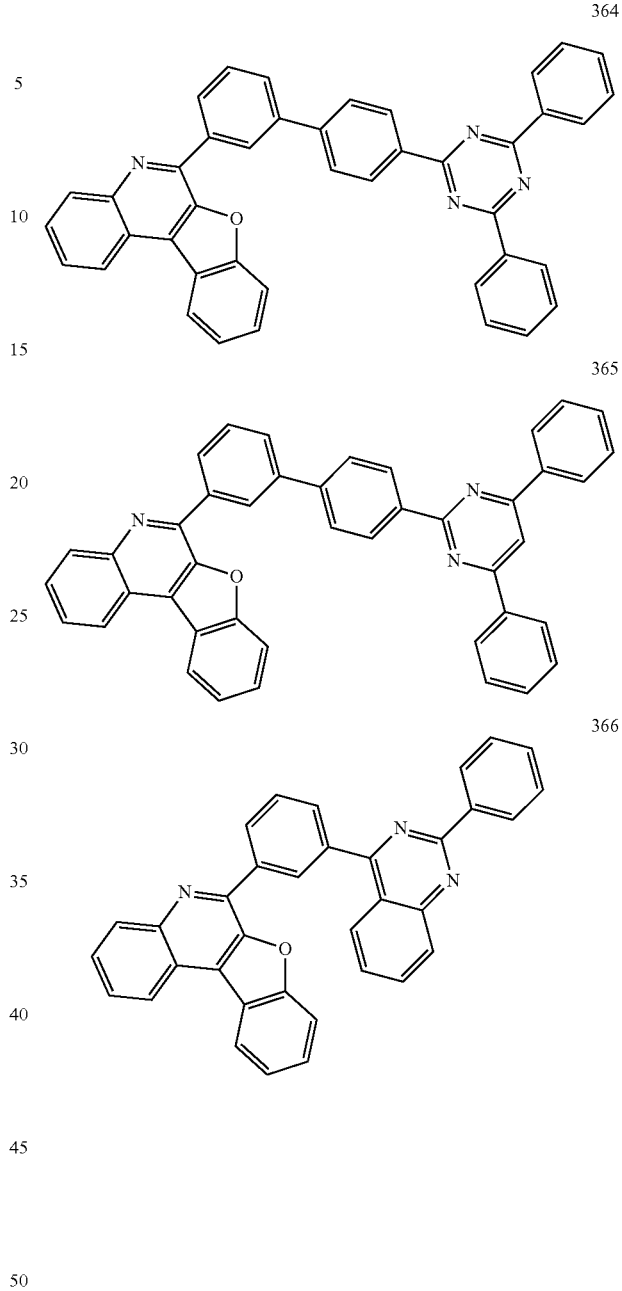
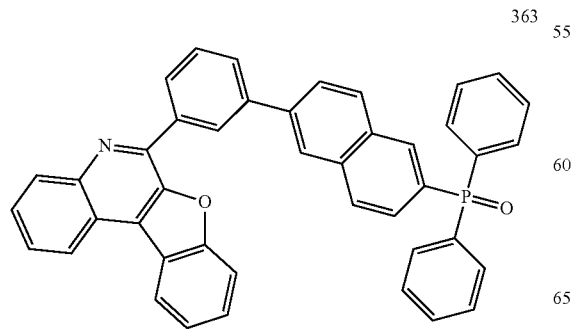
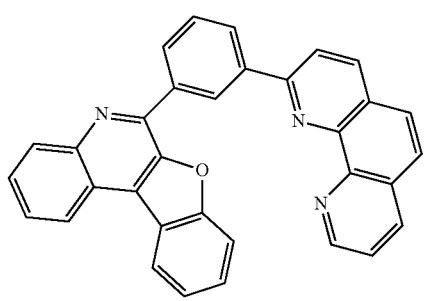

-continued
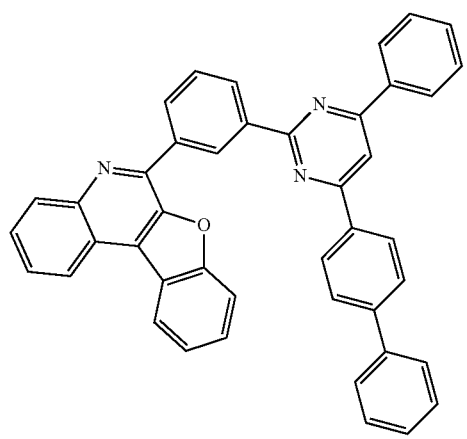
368
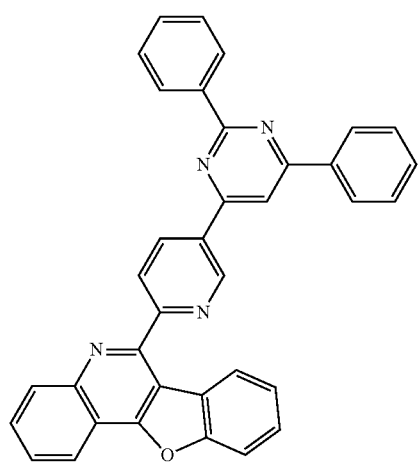
369
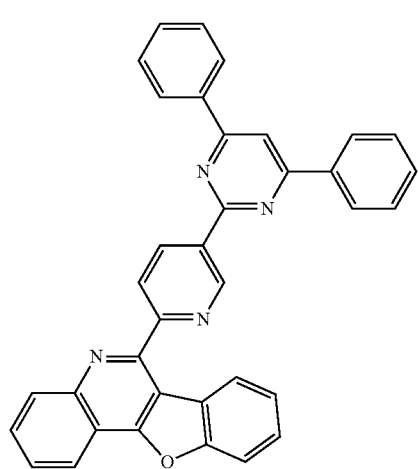
370
-continued
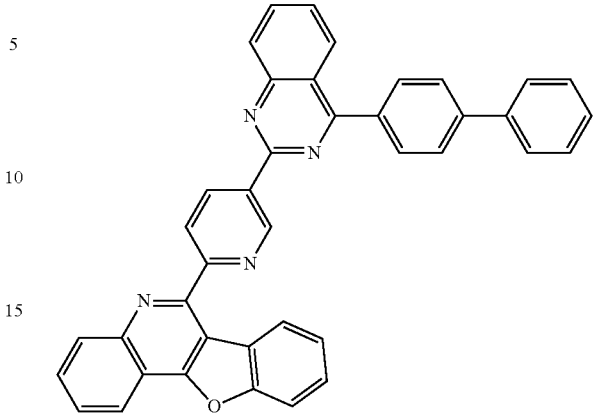
371
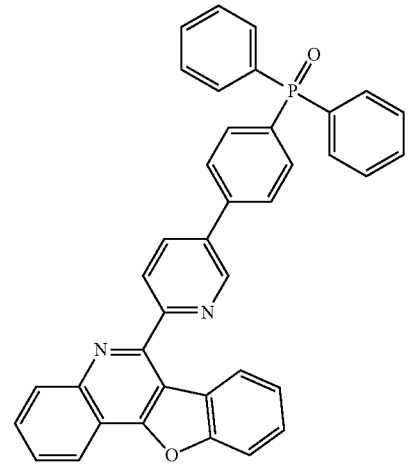
372
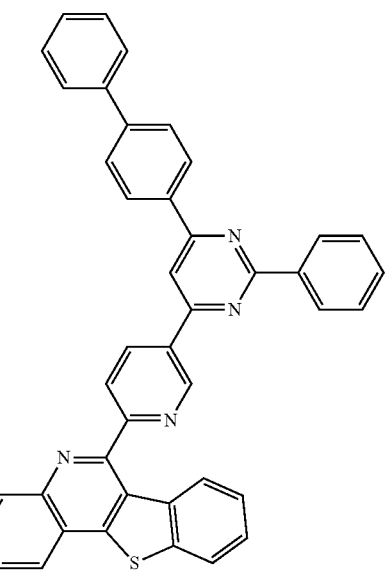
373

127
-continued
128
-continued
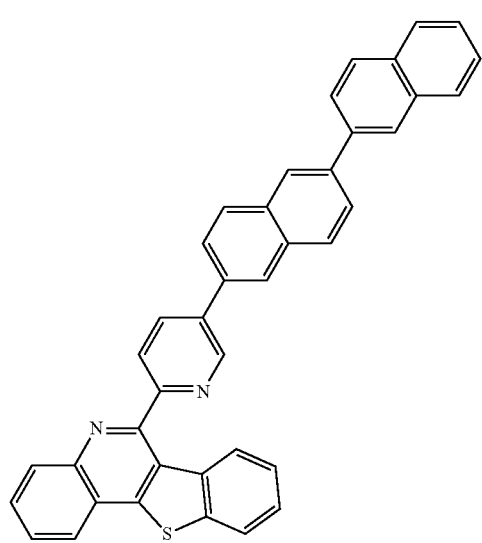
374
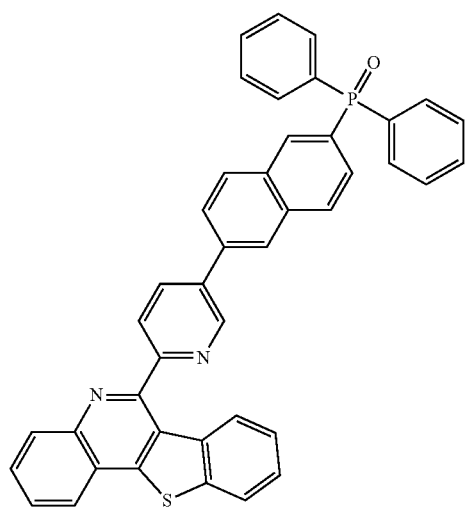
375
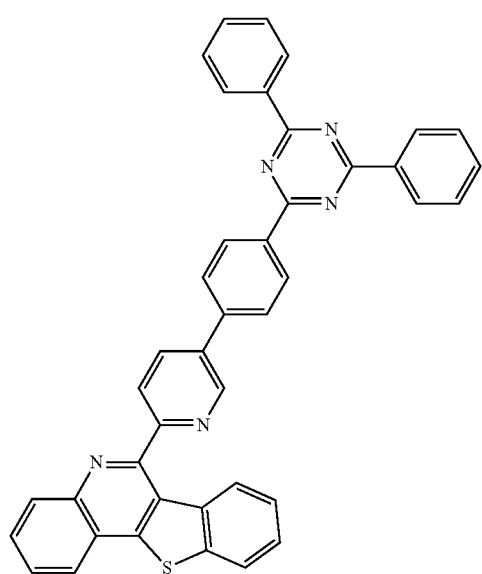
376
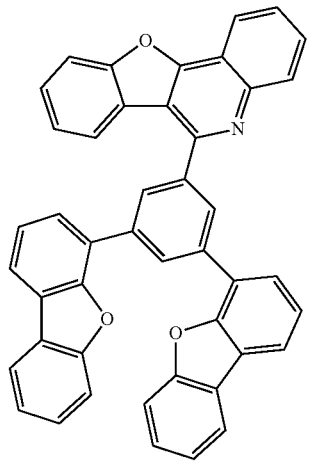
377
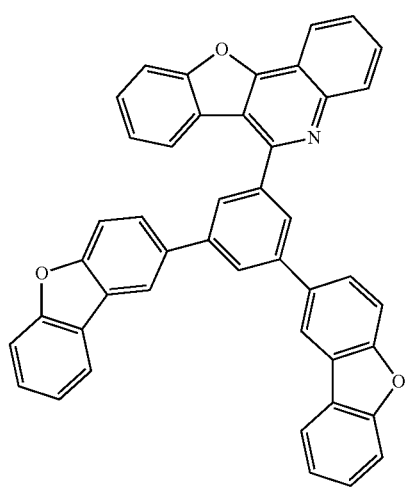
378
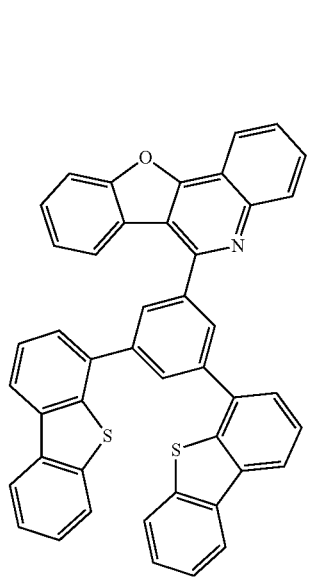
379

380
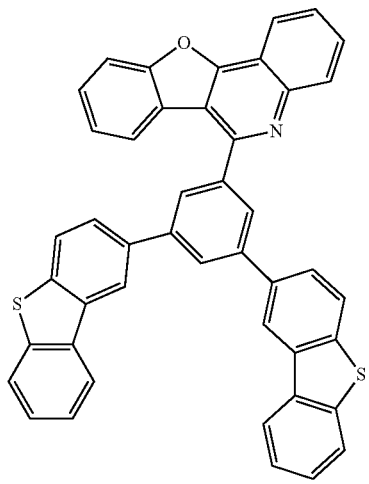
381
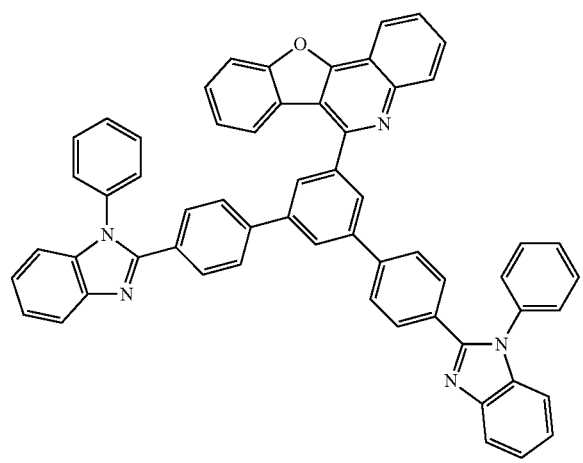
382
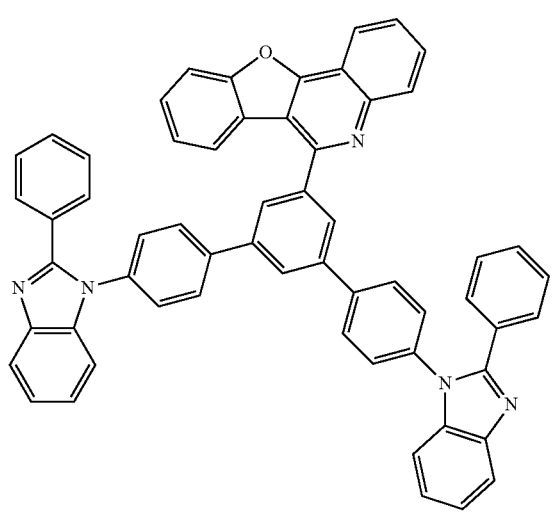
383
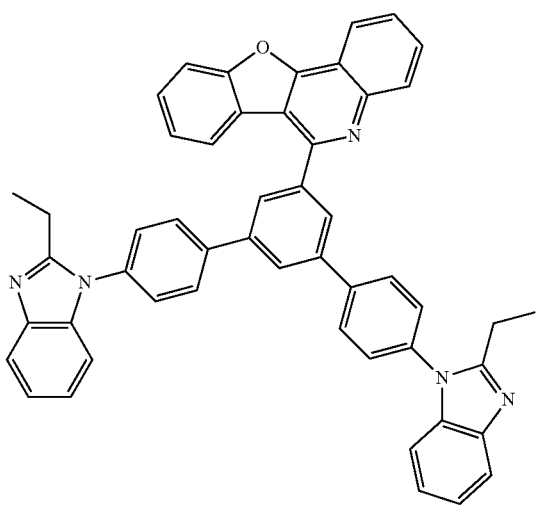
384
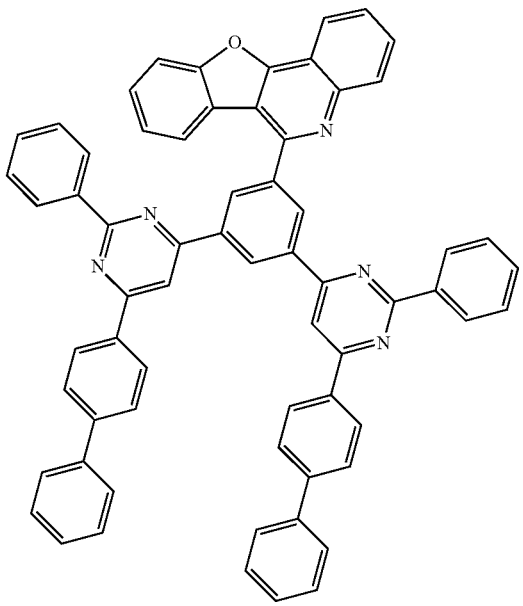
385
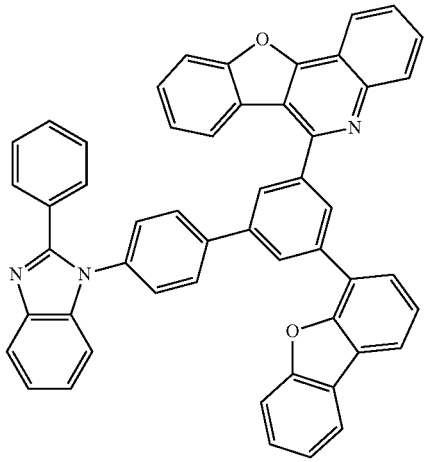

386
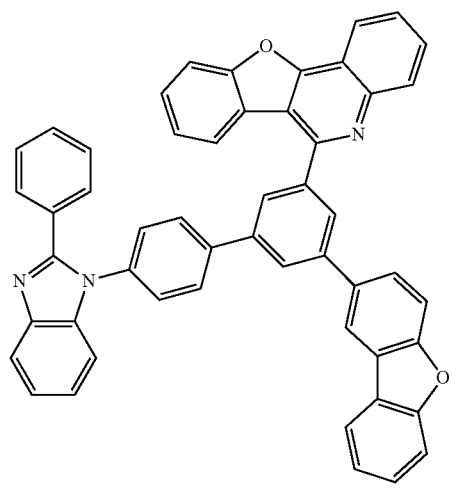
387
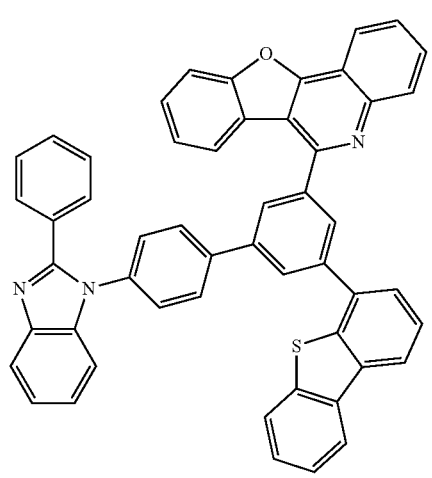
388
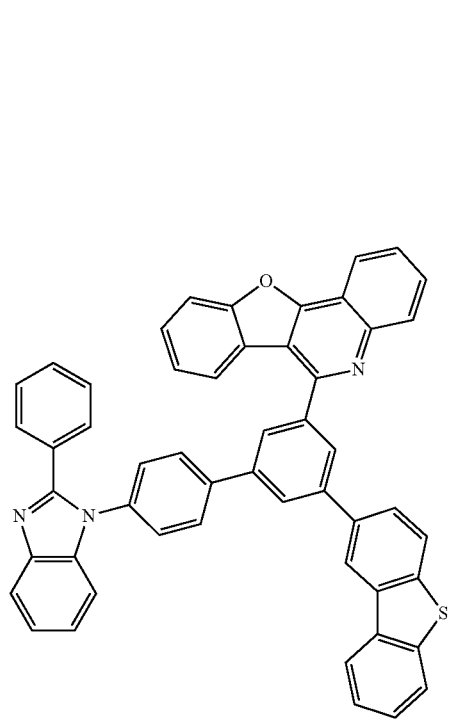
389
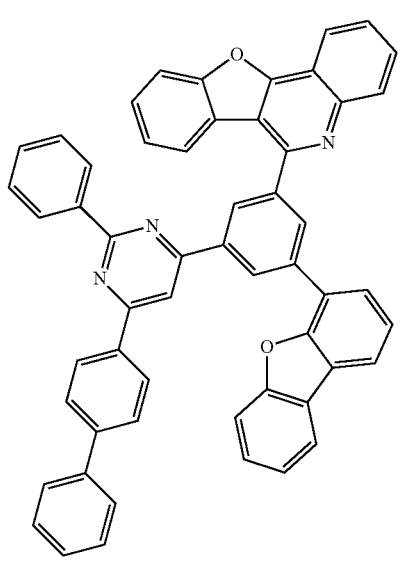
390
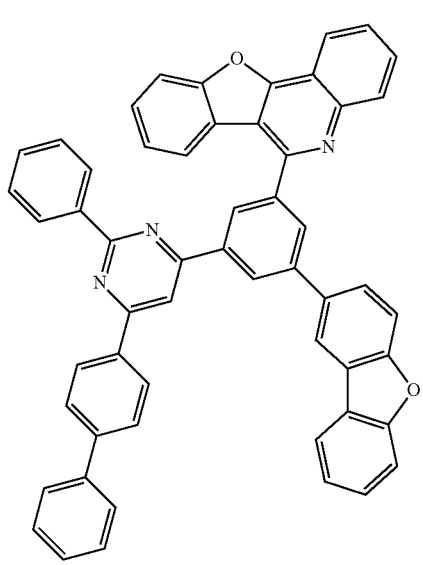
391
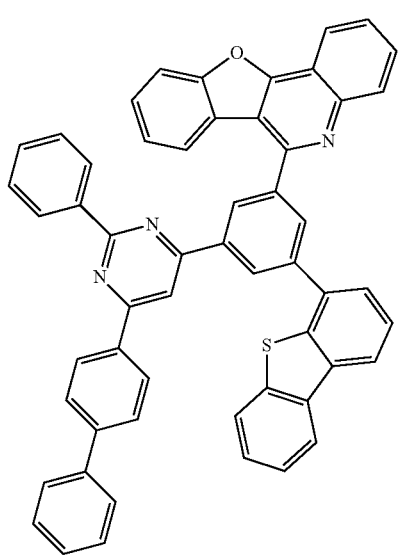

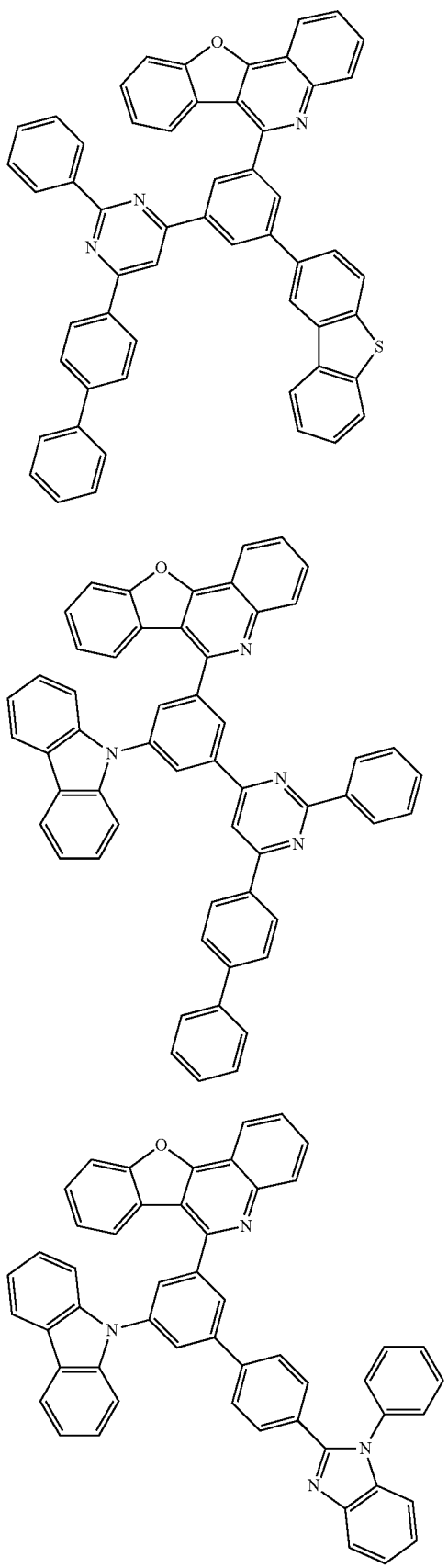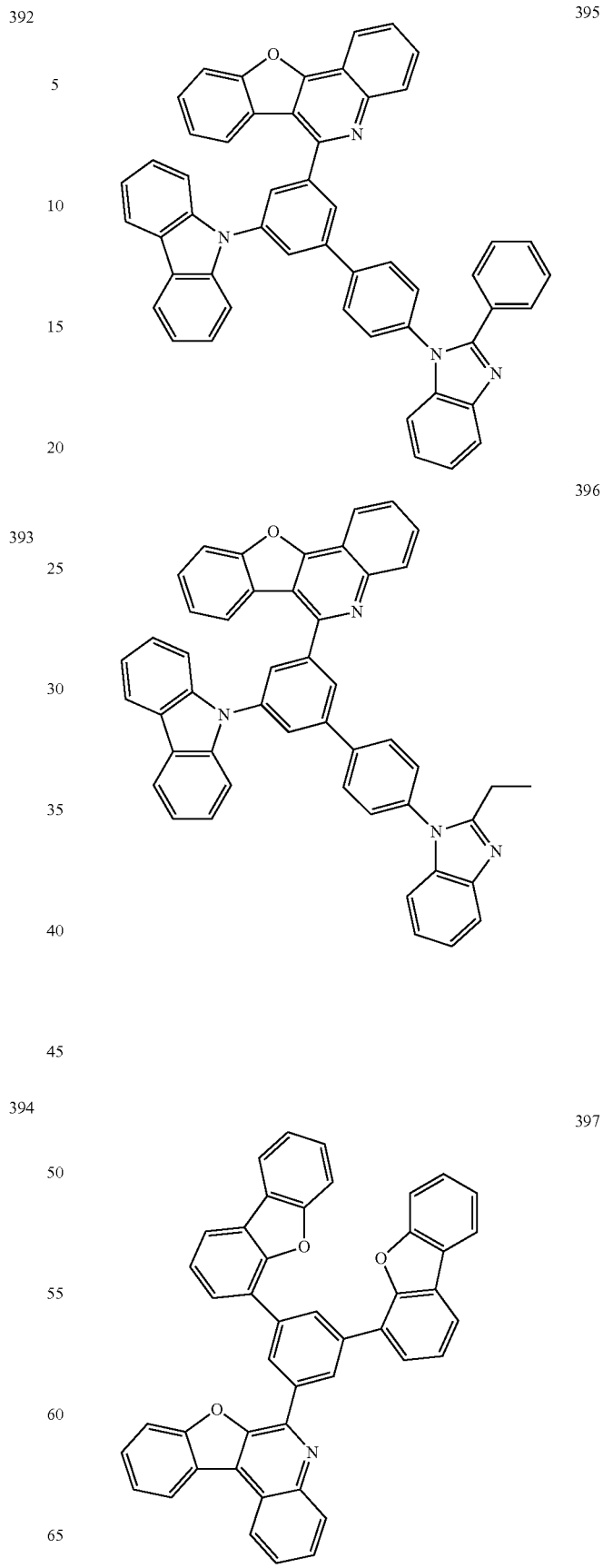

398
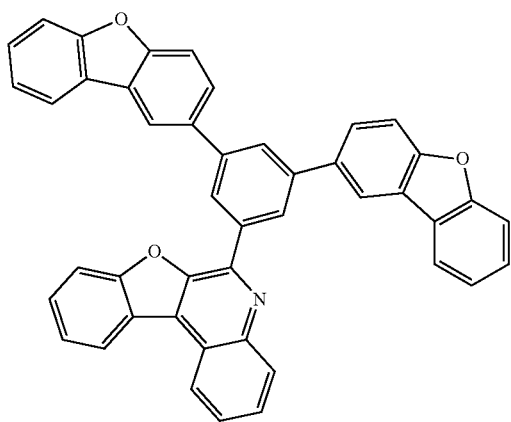
399
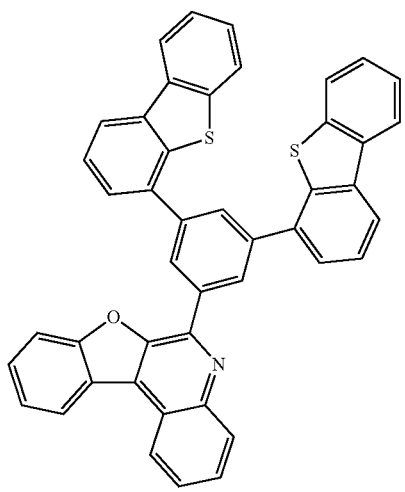
400
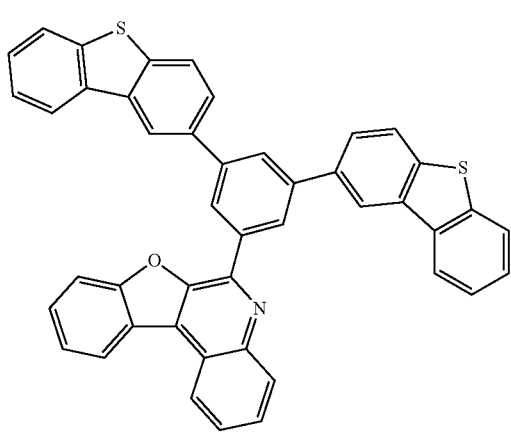
401
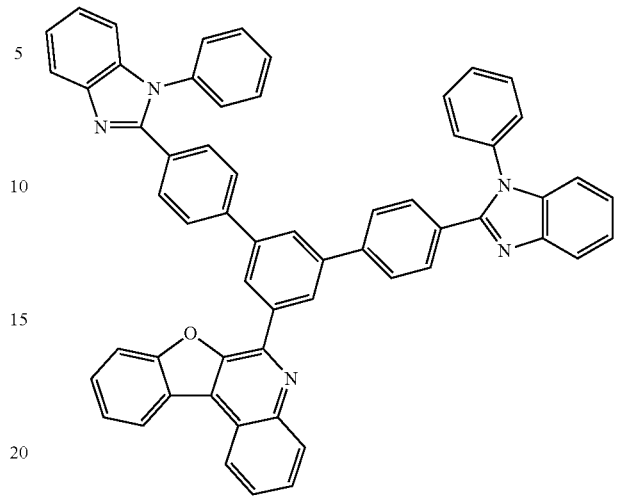
402
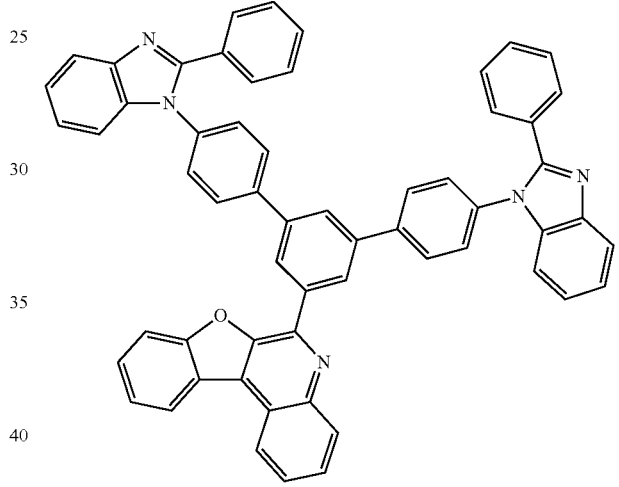
403
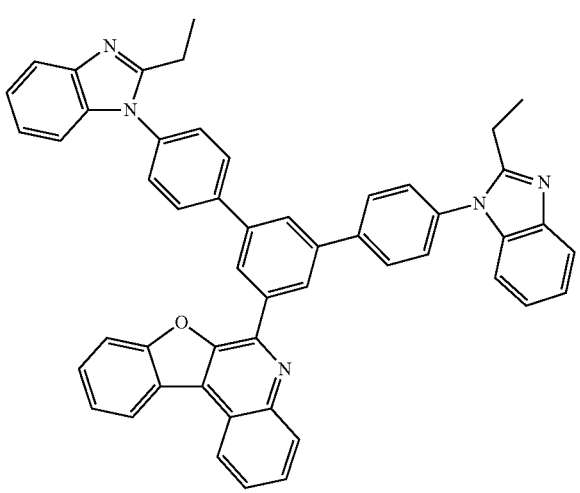

404
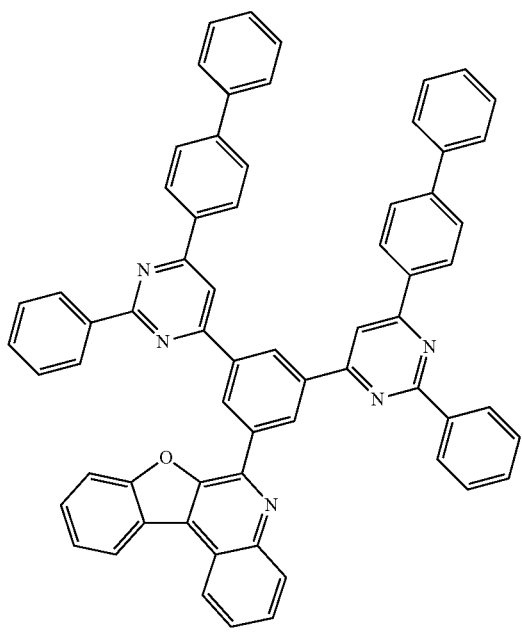
406
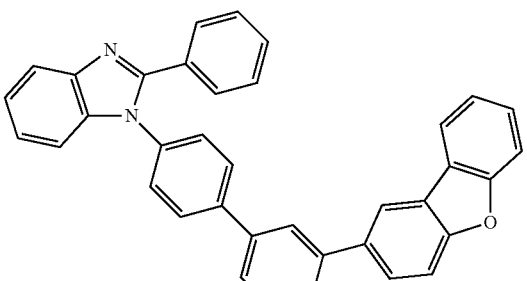
407
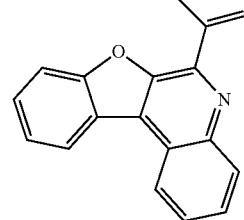
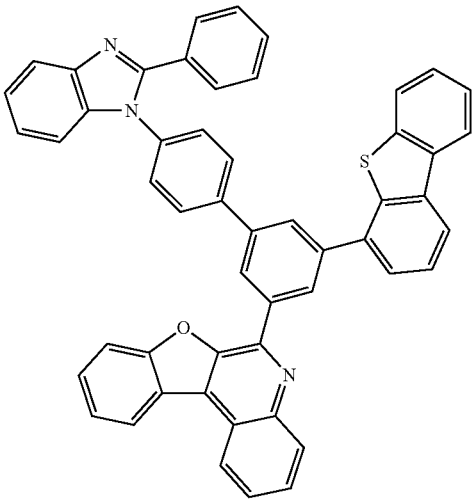
405
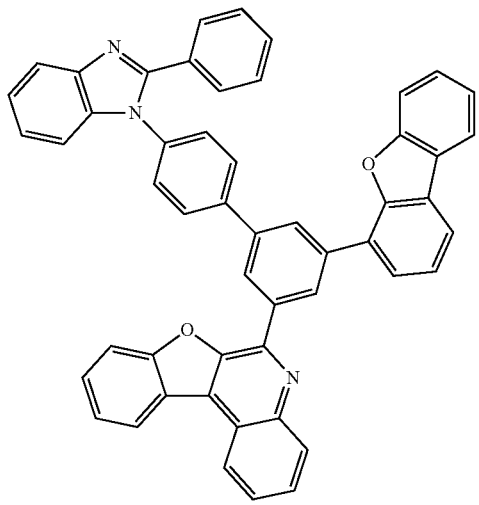
408
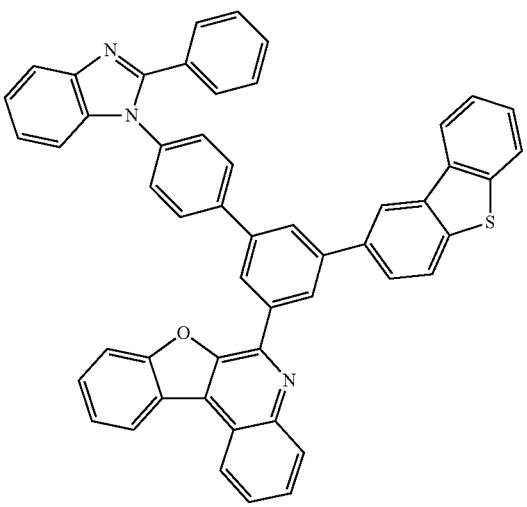

139
-continued
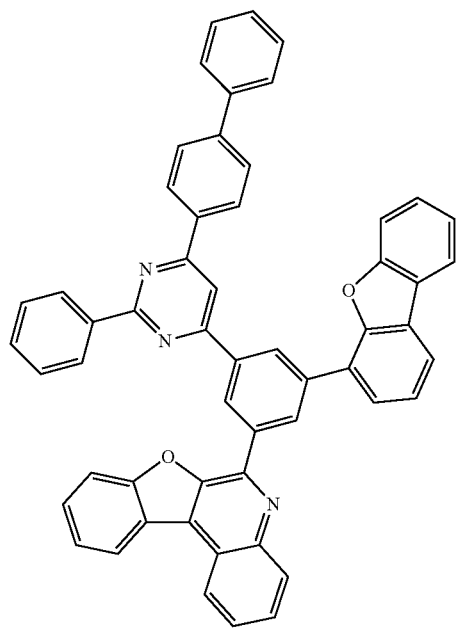
409
140
-continued
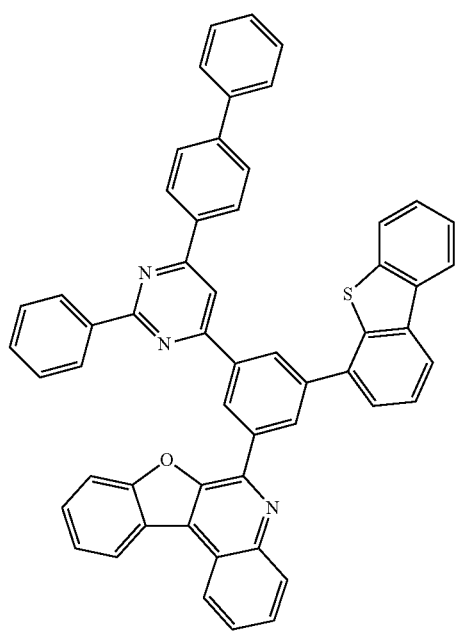
411
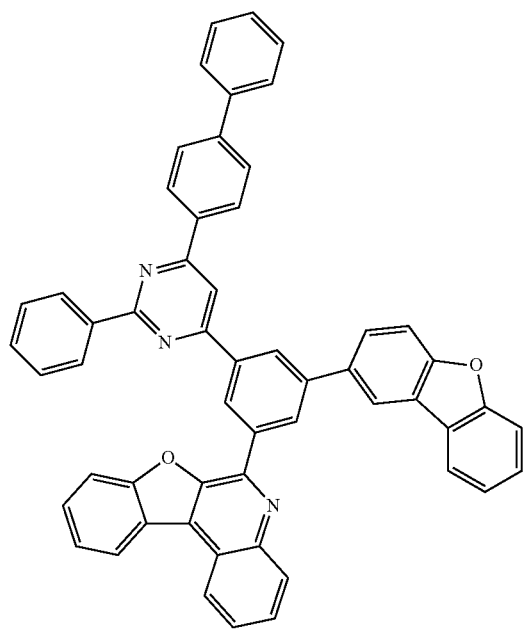
410
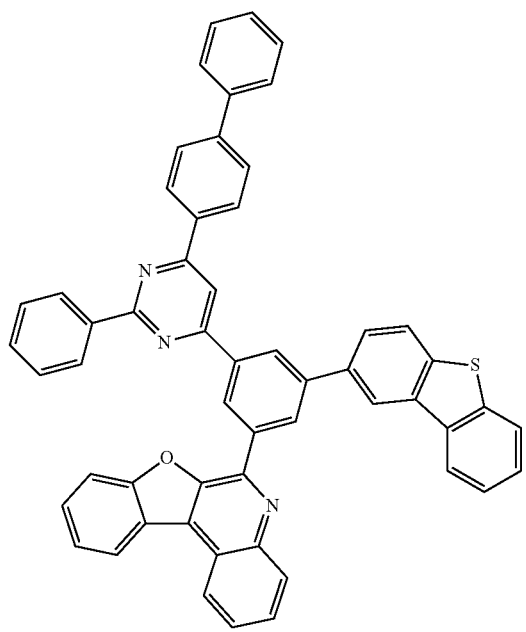
412

-continued
413
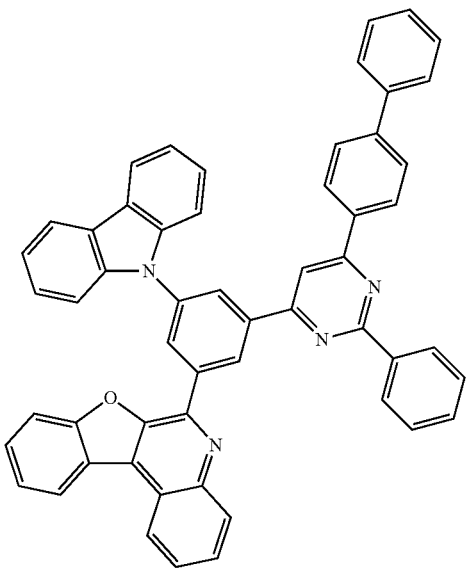
414
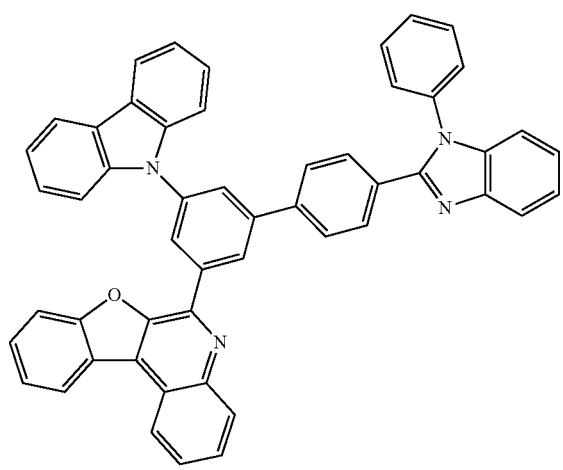
415
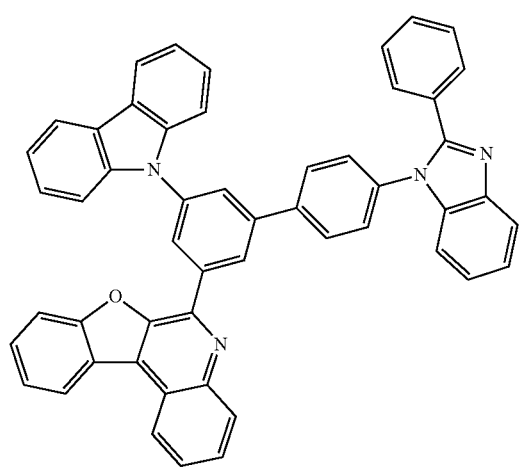
-continued
416
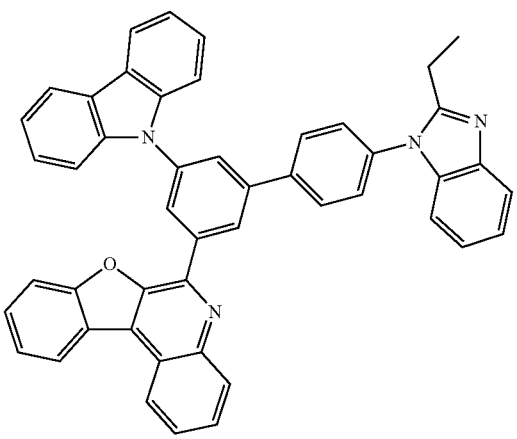
417
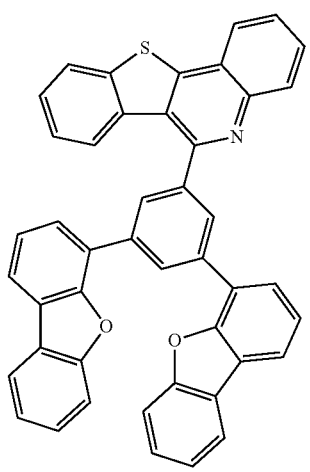
418
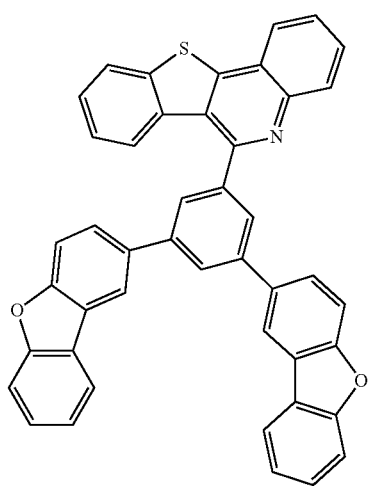

419
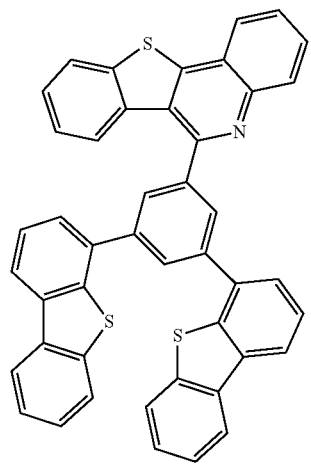
420
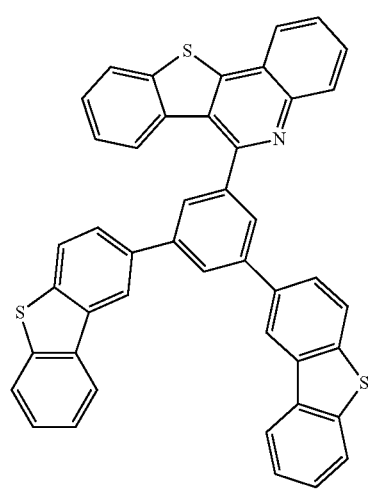
421
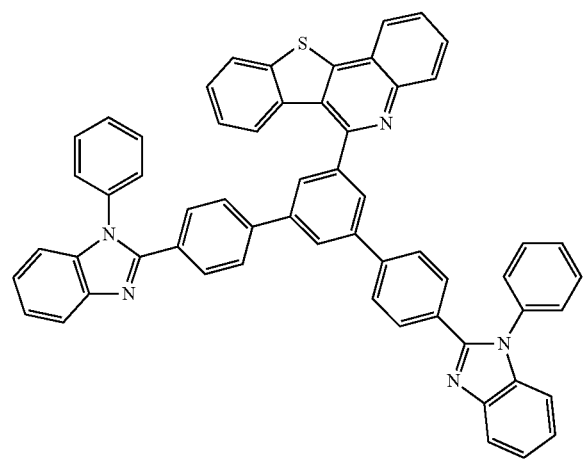
422
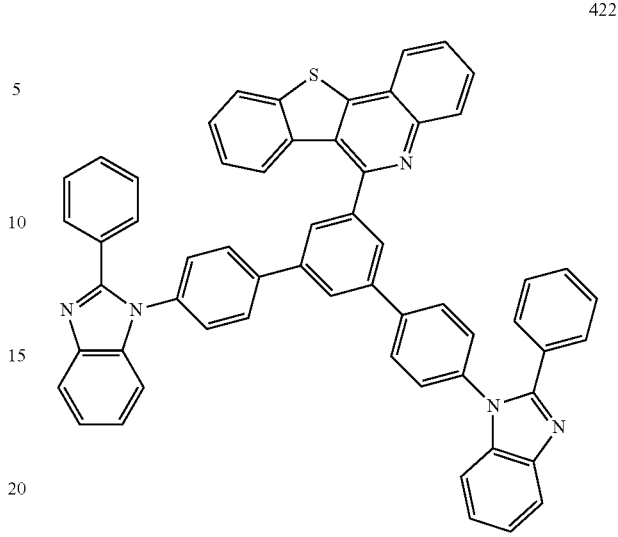
423
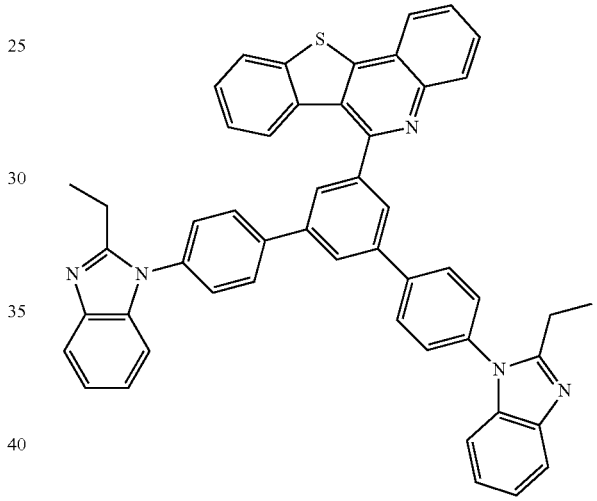
424
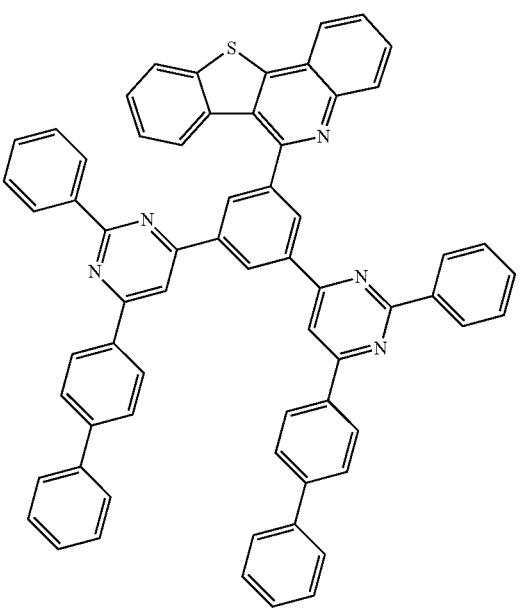

425
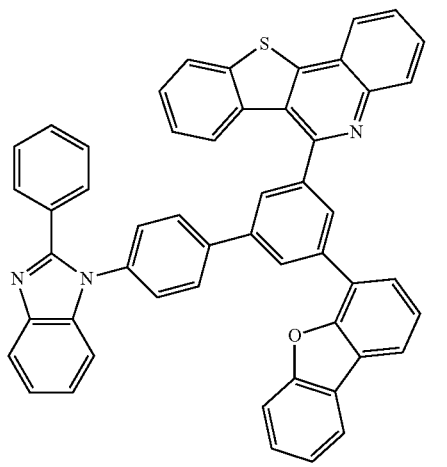
426
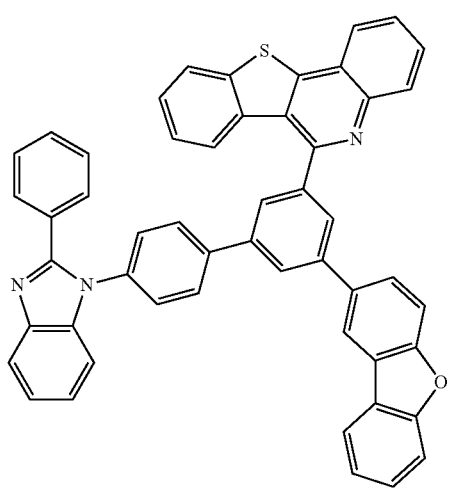
427
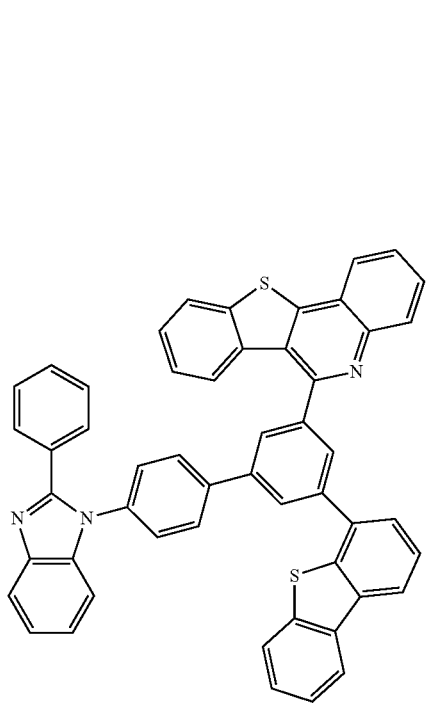
428
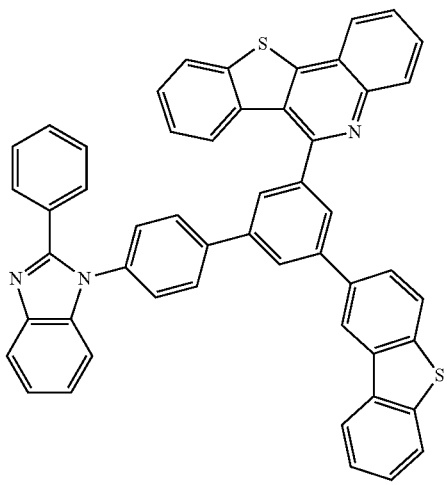
429
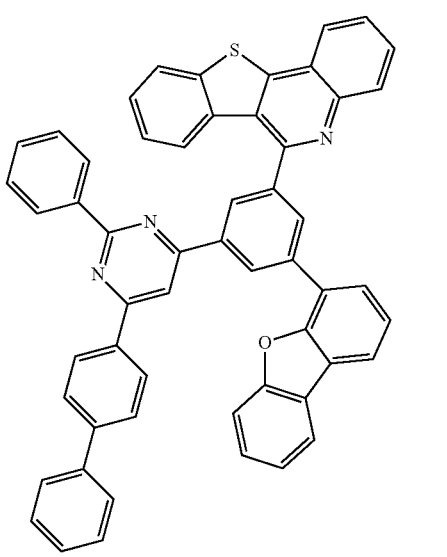
430
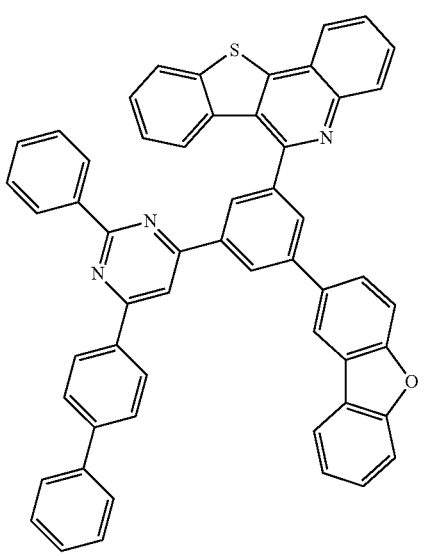

147
-continued
431
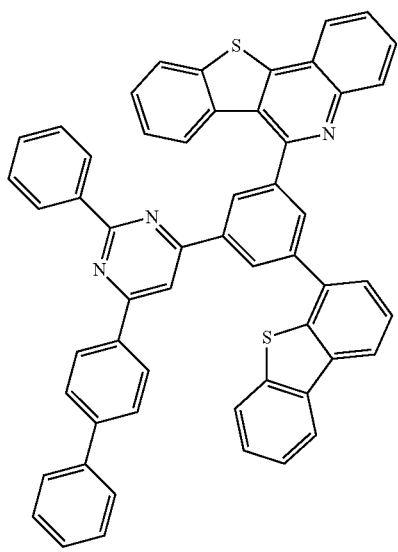
432
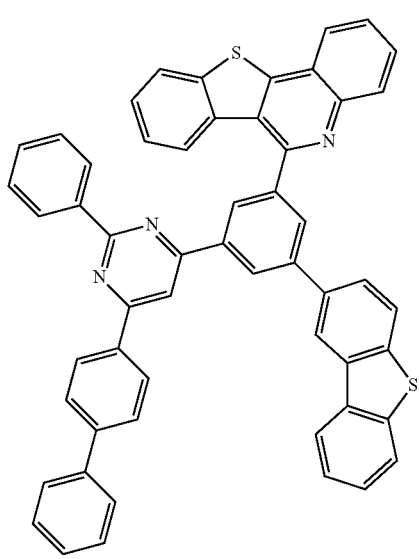
148
-continued
433
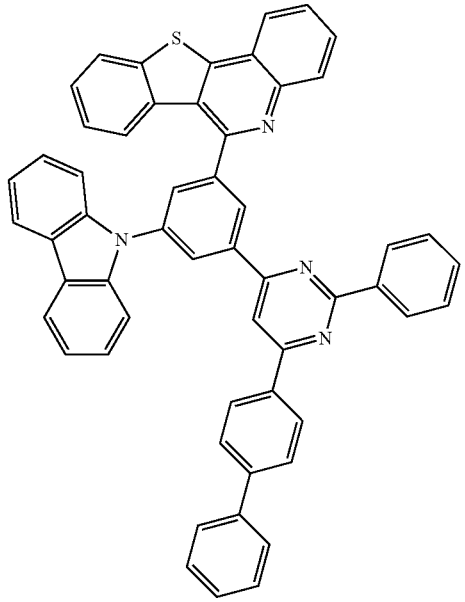
434
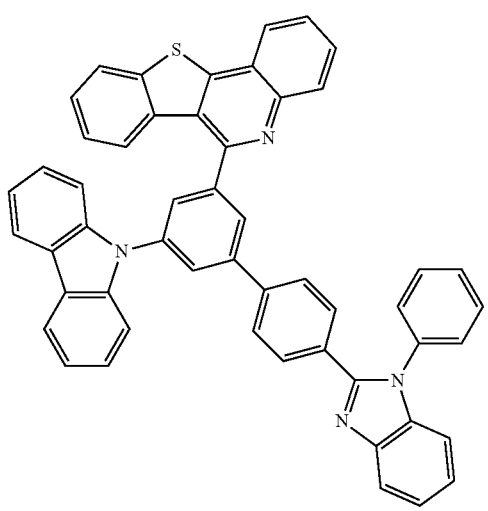
435
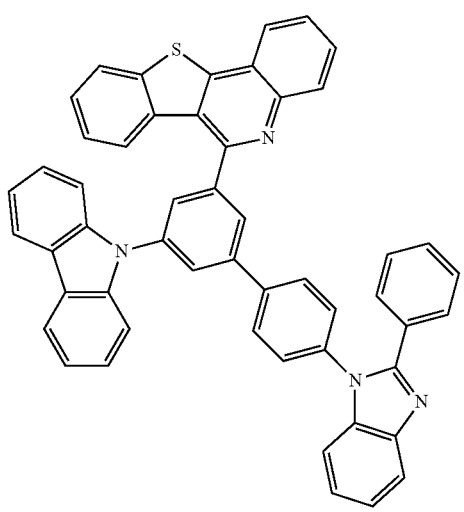

436
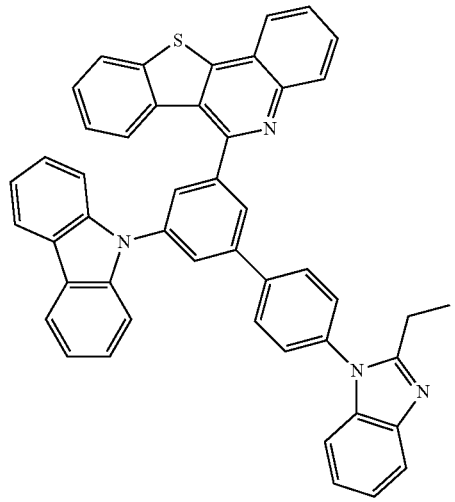
437
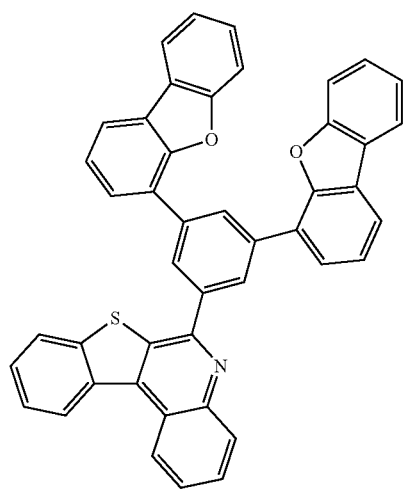
438
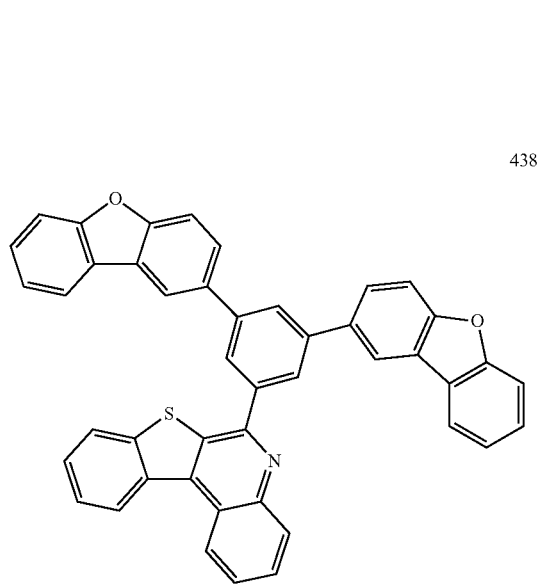
439
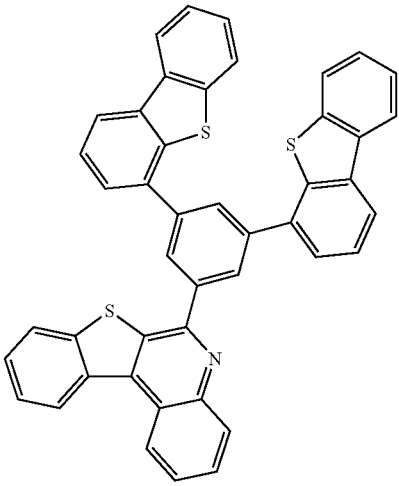
440
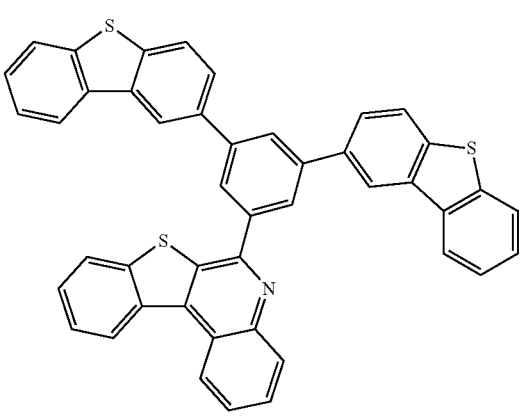
441
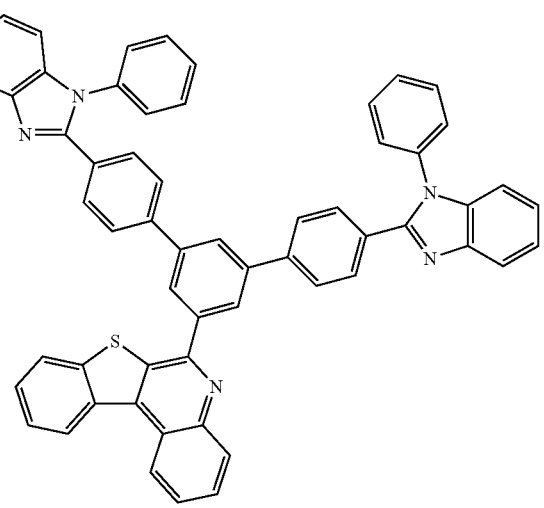

442
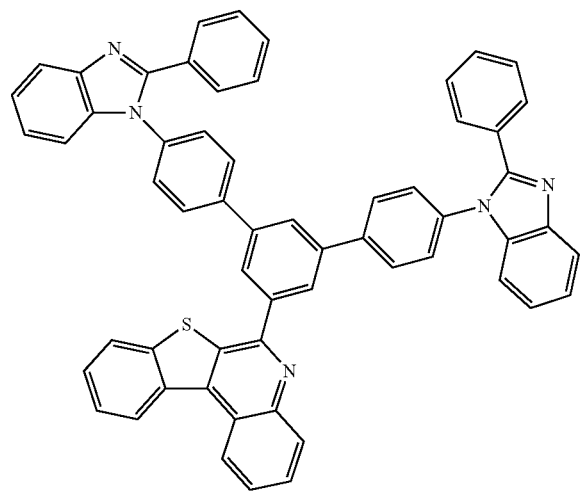
443
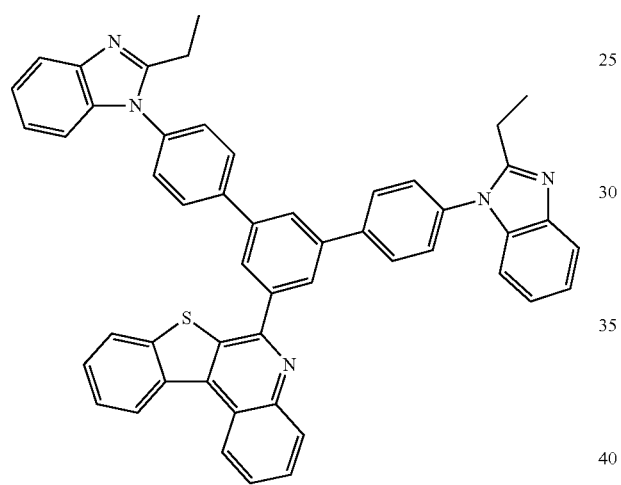
444
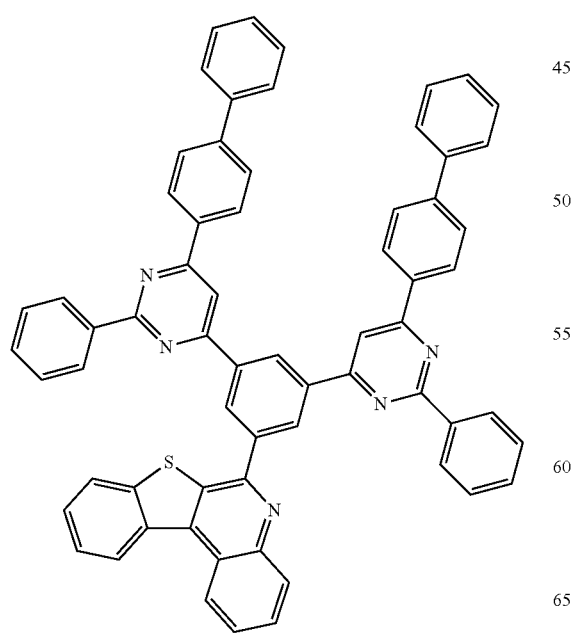
445
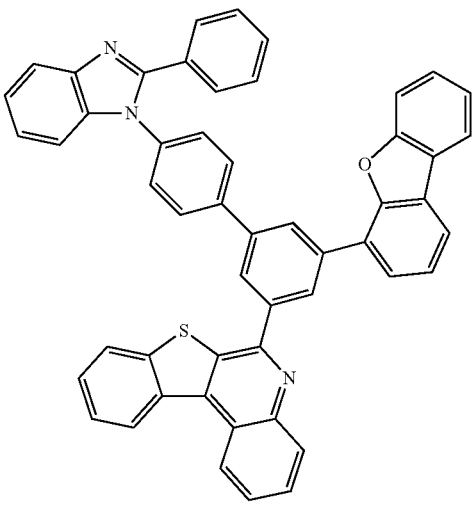
446
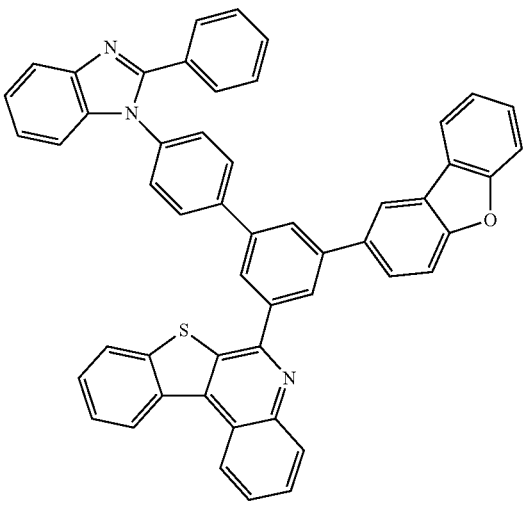
447
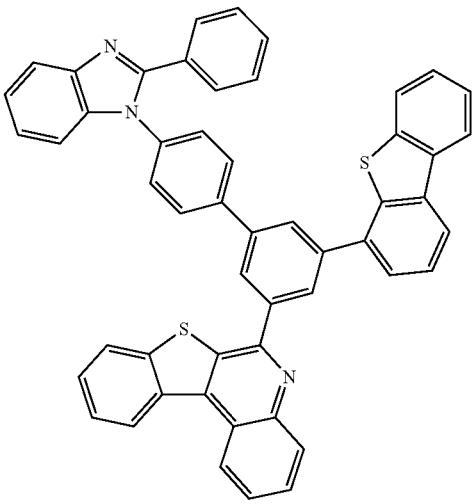

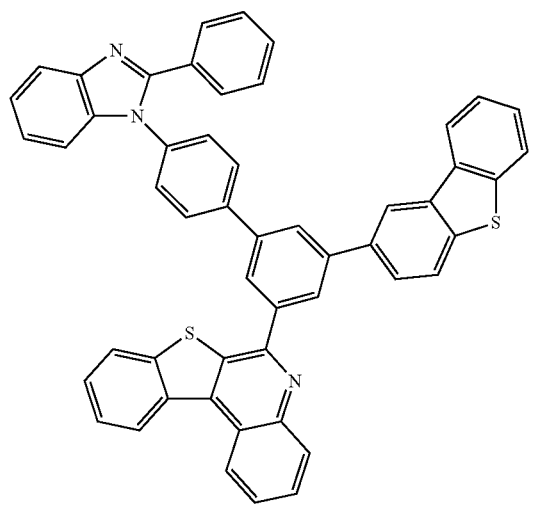
448
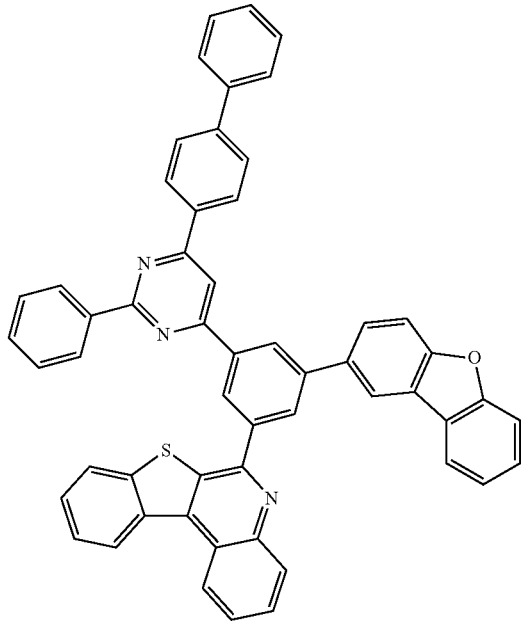
450
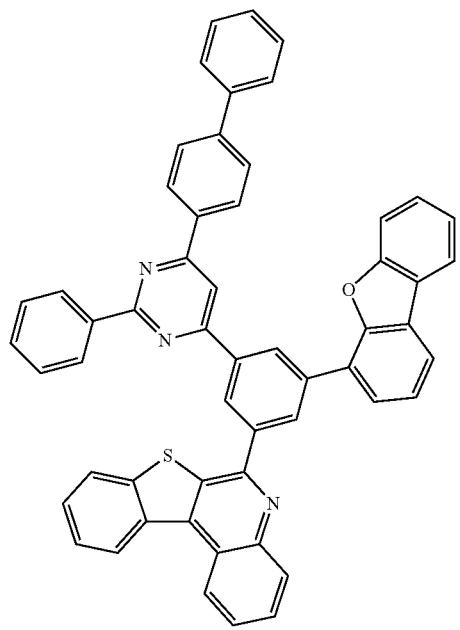
449
451

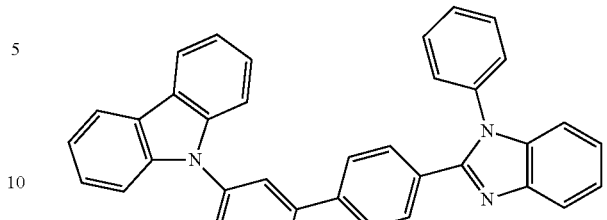

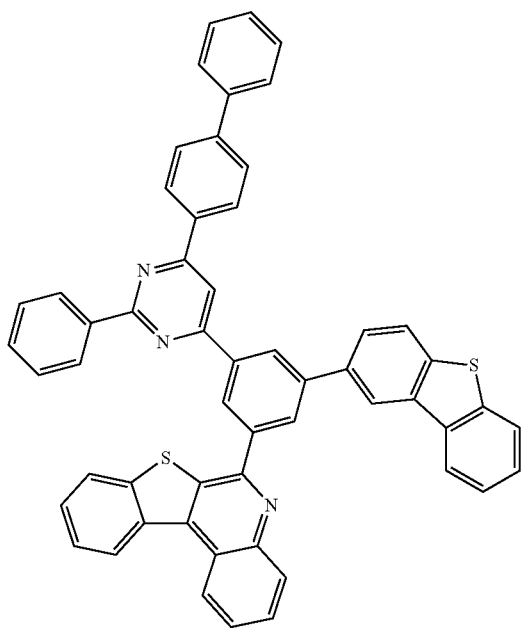

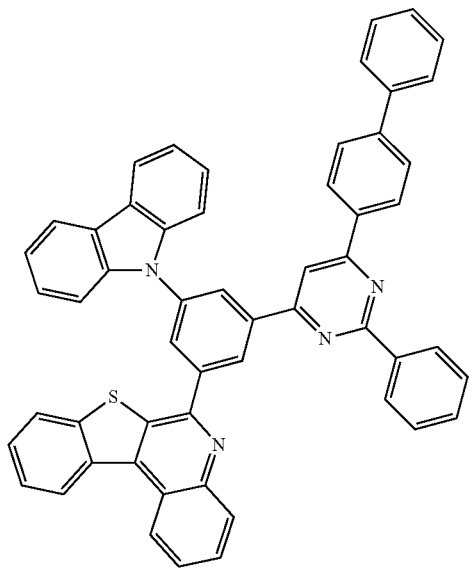

The above-described compounds may be prepared based on the Preparation Examples to be described below. Representative examples will be described in the Preparation Examples to be described below, but if necessary, a substituent may be added or excluded, and the position of the substituent may be changed. Further, a starting material, a reactant, reaction conditions, and the like may be changed based on the technology known in the art. A person with ordinary skill in the art may change the kind or position of substituents at the other positions, if necessary, by using the technology known in the art.

For example, in the compound of Formula 4, a core structure may be prepared as in the following Formulae 1 and 2. In the following Formulae 1 and 2, the case where Y of Formula 4 is S is exemplified, but the case where Y is oxygen (O) may also be available.

The substituent may be bonded by a method known in the art, and the position of the substituent or the number of substituents may be changed according to the technology known in the art.

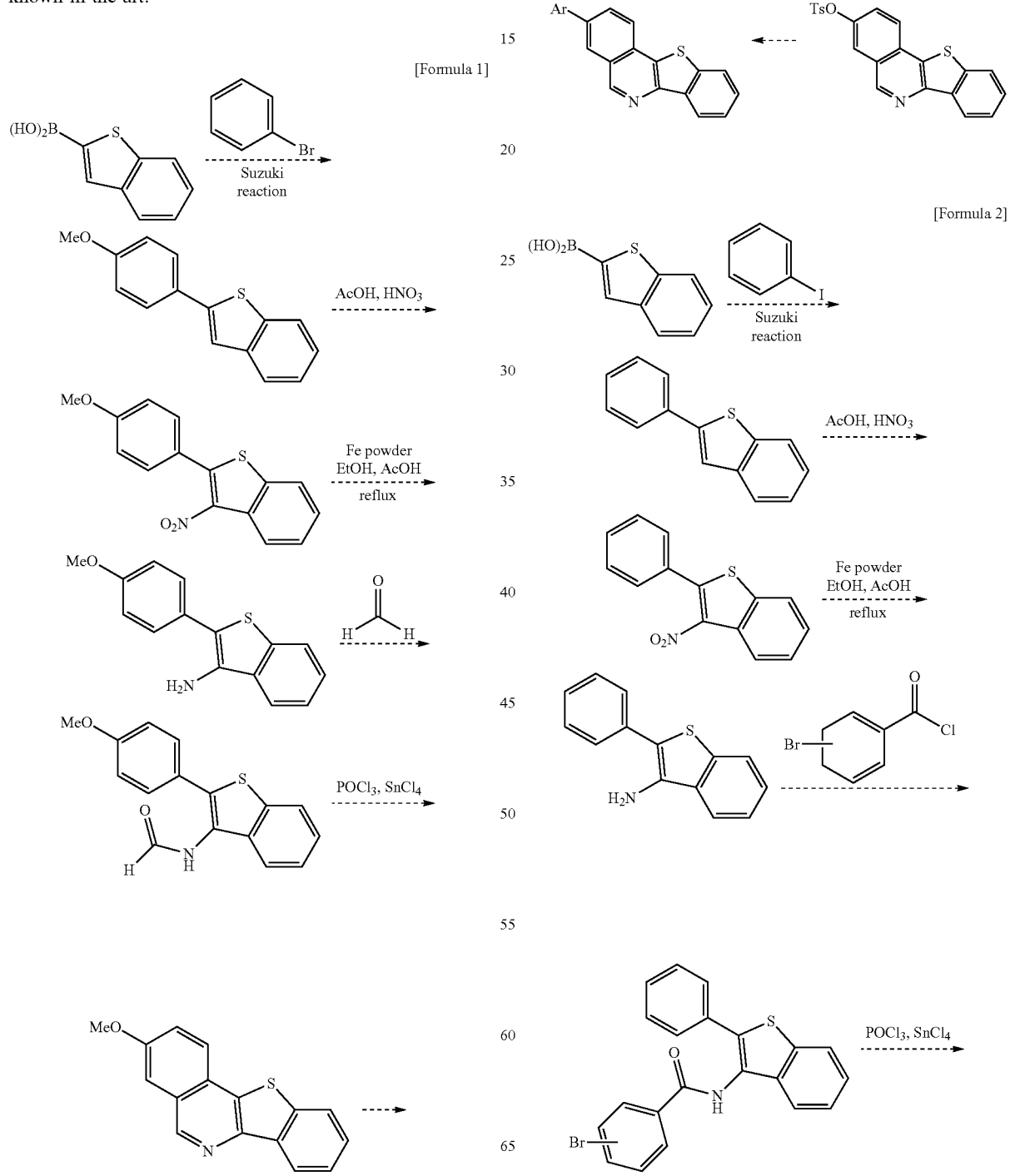

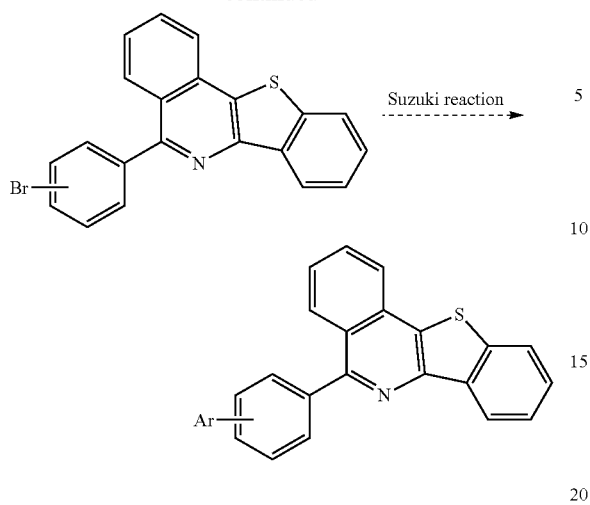

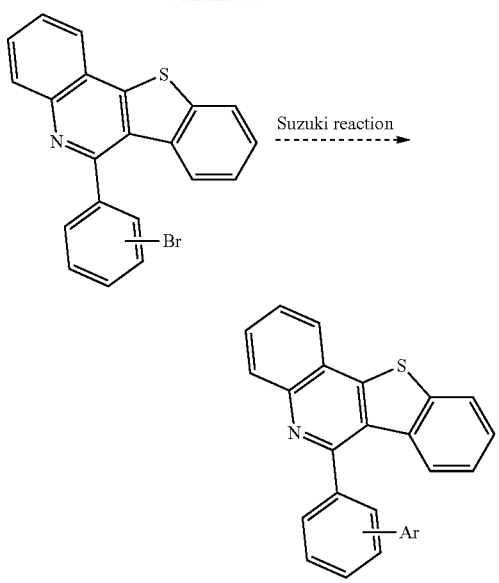

Formula 1 is an example of the reaction in which a substituent is bonded to the $R_2$ position in the core structure of Formula 4. Specifically, the last compound of Formula 1 is a case where $R_2$ in Formula 4 is a phenyl substituted with Ar. Ar is the same as the definition of Z described above.

Formula 2 is an example of the reaction in which a substituent is bonded to the R3 position in the core structure of Formula 4. Specifically, the last compound of Formula 2 is a case where $R_3$ in Formula 4 is a phenyl substituted with Ar. Ar is the same as the definition of Z described above.

For example, in the compound of Formula 5, a core structure may be prepared as in the following Formula 3. The substituent may be bonded by a method known in the art, and the position of the substituent or the number of substituents may be changed according to the technology known in the art.

Formula 3 is an example of the reaction in which a substituent is bonded to the $R_3$ position in the core structure of Formula 5. Specifically, the last compound of Formula 3 is a case where $R_3$ in Formula 5 is a phenyl substituted with Ar. Ar is the same as the definition of Z described above.

For example, in the compound of Formula 6, a core structure may be prepared as in the following Formula 4. The substituent may be bonded by a method known in the art, and the position of the substituent or the number of substituents may be changed according to the technology known in the art.

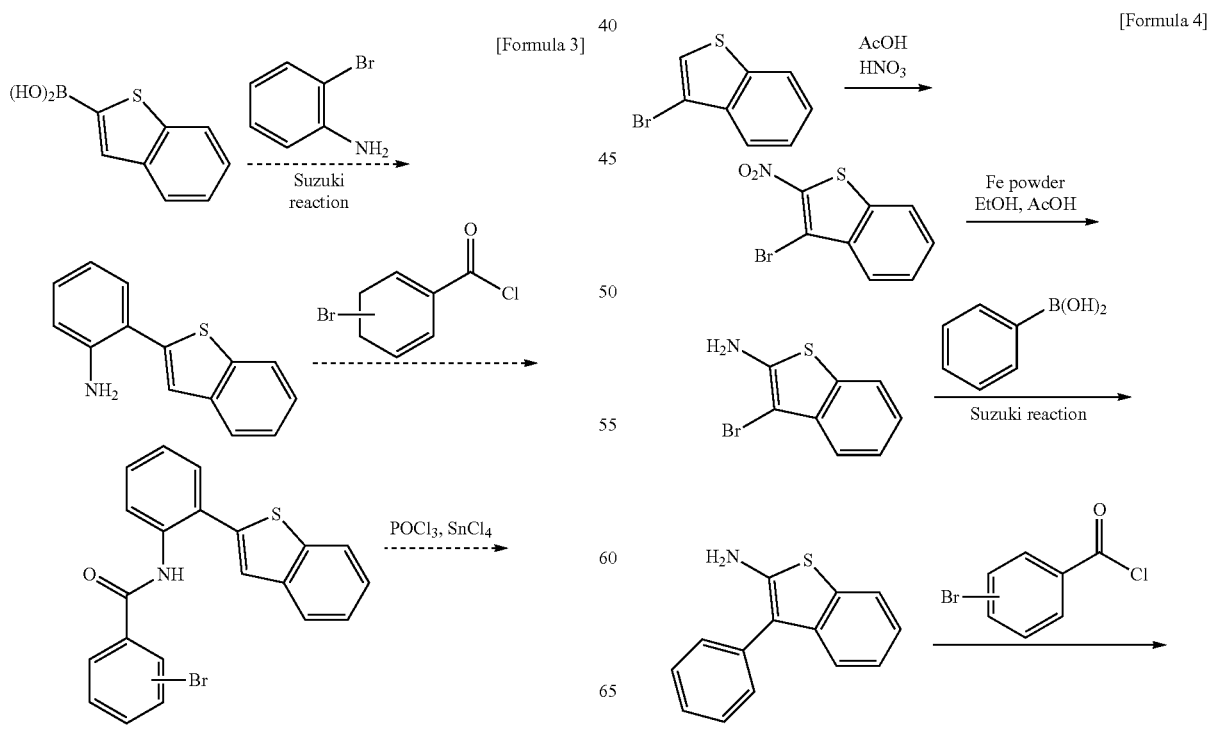

-continued

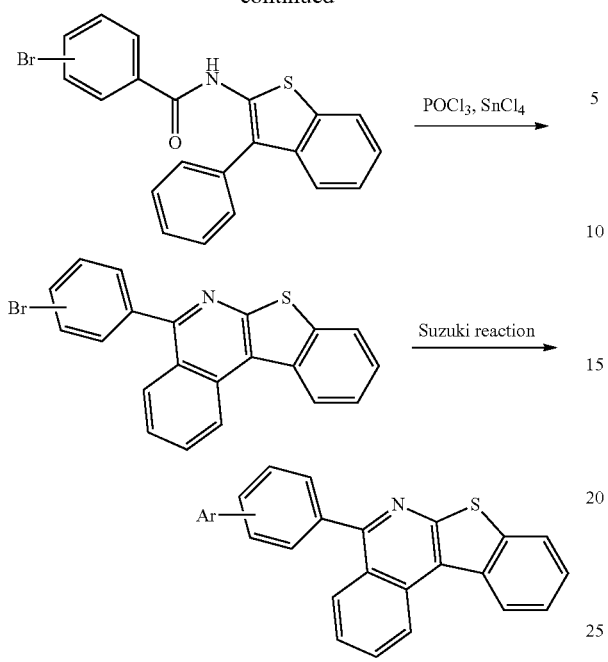

Formula 4 is an example of the reaction in which a substituent is bonded to the R3 position in the core structure of Formula 6. Specifically, the last compound of Formula 4 is a case where $R_3$ in Formula 6 is a phenyl substituted with Ar. Ar is the same as the definition of Z described above.

For example, in the compound of Formula 7, a core structure may be prepared as in the following Formula 5. The substituent may be bonded by a method known in the art, and the position of the substituent or the number of substituents may be changed according to the technology known in the art.

[Formula 5]

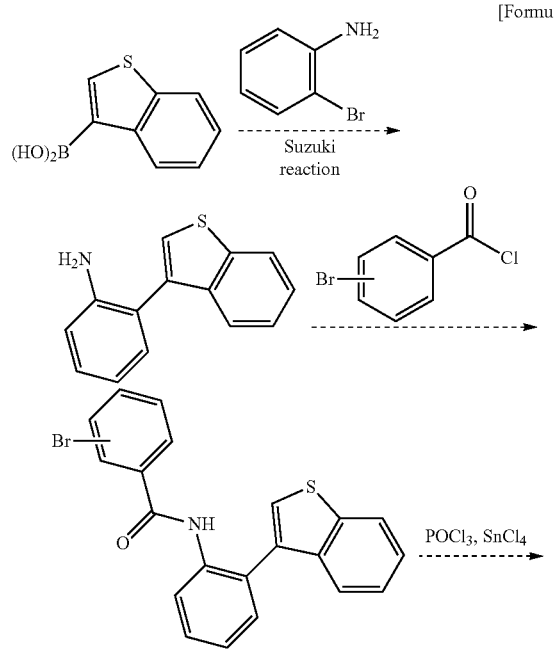

-continued

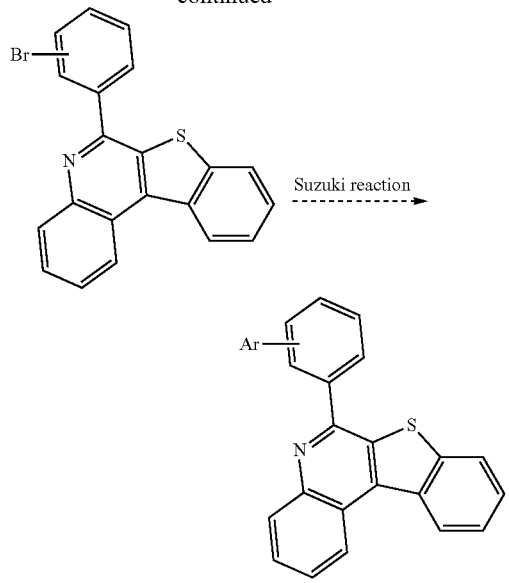

Formula 5 is an example of the reaction in which a substituent is bonded to the R3 position in the core structure of Formula 7. Specifically, the last compound of Formula 3 is a case where $R_3$ in Formula 7 is a phenyl substituted with Ar. Ar is the same as the definition of Z described above.

Another exemplary embodiment of the present application provides an organic light emitting device including the above-described compound of Formula 1. Specifically, the organic light emitting device according to the present application includes a positive electrode, a negative electrode, and one or more organic material layers provided between the positive electrode and the negative electrode, and one or more of the organic material layers include the compound of Formula 1.

FIGS. 1 to 3 illustrate the stacking sequence of the electrodes and the organic material layers of the organic light emitting device according to exemplary embodiments of the present application. However, the scope of the present application is not intended to be limited by these drawings, and the structure of the organic light emitting device known in the art may also be applied to the present application.

According to FIG. 1, an organic light emitting device in which a positive electrode 200, an organic material layer 300, and a negative electrode 400 are sequentially stacked on a substrate 100 is illustrated. However, the organic light emitting device is not limited only to such a structure, and as in FIG. 2, an organic light emitting device in which a negative electrode, an organic material layer, and a positive electrode are sequentially stacked on a substrate may also be implemented.

FIG. 3 exemplifies a case where the organic material layer is a multilayer. The organic light emitting device according to FIG. 3 includes a hole injection layer 301, a hole transport layer 302, a light emitting layer 303, a hole blocking layer 304, an electron transport layer 305, and an electron injection layer 306. However, the scope of the present application is not limited by the stacking structure as described above, and if necessary, the other layers except for the light emitting layer may be omitted, and another necessary functional layer may be further added.

The organic light emitting device according to the present application may be manufactured by the materials and methods known in the art, except that one or more layers of the organic material layers include the compound of Formula 1.

The compound of Formula 1 may alone constitute one or more layers of the organic material layers of the organic light emitting device. However, the compound of Formula 1 may be mixed with another material, if necessary, to constitute an organic material layer.

The compound of Formula 1 may be used as a hole injection material, a hole transport material, a light emitting material, an electron transport material, an electron injection material, and the like in the organic light emitting device.

For example, the compound according to an exemplary embodiment of the present application may be used as a material for an electron injection layer, an electron transport layer, or a layer which injects and transports electrons simultaneously in the organic light emitting device.

In addition, the compound according to an exemplary embodiment of the present application may be used as a material for a light emitting layer of an organic light emitting device. Specifically, the compound may also be used alone as a light emitting material, and as a host material or a dopant material of the light emitting layer.

Furthermore, the compound according to an exemplary embodiment of the present application may be used as a phosphorescent host material of an organic light emitting device. In this case, the compound according to an exemplary embodiment of the present application is included along with a phosphorescent dopant.

Further, the compound according to an exemplary embodiment of the present application may be used as a material for a hole blocking layer of an organic light emitting device.

In the organic light emitting device according to the present application, materials other than the compound of Formula 1 will be exemplified below, but these materials are provided only for exemplification and are not for limiting the scope of the present application, and may be replaced with materials publicly known in the art.

As a material for the positive electrode, materials having a relatively large work function may be used, and a transparent conductive oxide, a metal or a conductive polymer, and the like may be used.

As a material for the negative electrode, materials having a relatively small work function may be used, and a metal, a metal oxide, or a conductive polymer, and the like may be used.

As a hole injection material, a publicly-known hole injection material may also be used, and it is possible to use, for example, a phthalocyanine compound, such as copper phthalocyanine, disclosed in U.S. Pat. No. 4,356,429 or starburst-type amine derivatives described in the document [Advanced Material, 6, p. 677 (1994)], for example, TCTA, m-MTDATA, m-MTDAPB, polyaniline/dodecylbenzenesulfonic acid (Pani/DBSA) or poly(3,4-ethylenedioxythiophene)/poly(4-styrenesulfonate) (PEDOT/PSS), which is a soluble conductive polymer, polyaniline/camphor sulfonic acid (Pani/CSA) or polyaniline/poly(4-styrene-sulfonate) (PANI/PSS), and the like.

As the hole transport material, a pyrazoline derivative, an arylamine-based derivative, a stilbene derivative, a triphenyldiamine derivative, and the like may be used, and a low-molecular weight or polymer material may also be used.

As the electron transport material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and the like, and a low-molecular weight material and a polymer material may also be used.

As the electron injection material, for example, LiF is typically used in the art, but the present application is not limited thereto.

As the light emitting material, a red, green, or blue light emitting material may be used, and if necessary, two or more light emitting materials may be mixed and used. Further, as the light emitting material, a fluorescent material may also be used, but a phosphorescent material may also be used. As the light emitting material, it is also possible to use alone a material which emits light by combining holes and electrons each injected from the positive electrode and the negative electrode, but materials in which a host material and a dopant material work together to emit light may also be used.

When the compound according to the present application is used as a phosphorescent host material, those known in the art may be used as a phosphorescent dopant material to be used together.

For example, phosphorescent dopant materials represented by LL'MX, LL'L"M, LMXX', L$_2$MX, and L$_3$M may be used, but the scope of the present application is not limited by these examples.

Here, L, L', L", X, and X' are bidendate ligands different from each other, and M is a metal forming an octahedral complex.

M may be iridium, platinum, osmium, and the like.

L is an anionic, bidendate ligand coordinated on M by sp$^2$ carbon and a heteroatom, and X may perform a function of trapping electrons or holes. Non-limiting examples of L include 2-(1-naphthyl)benzoxazole, (2-phenylbezoxazole), (2-phenylbenzothiazole), (2-phenylbenzoquinoline), (thienylpyrizine), phenylpyridine, benzothienylpyrizine, 3-methoxy-2-phenylpyridine, thienylpyrizine, tolylpyridine, and the like. Non-limiting examples of X include acetylacetonate (acac), hexafluoroacetylacetonate, salicylidene, picolinate, 8-hydroxyquinolinate, and the like.

More specific examples thereof will be shown below, but the present application is not limited only to these examples.

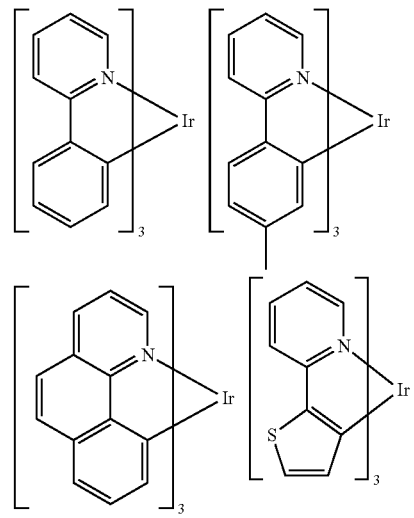

-continued
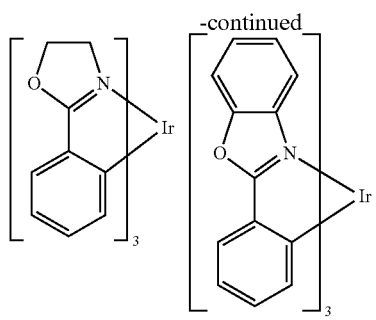
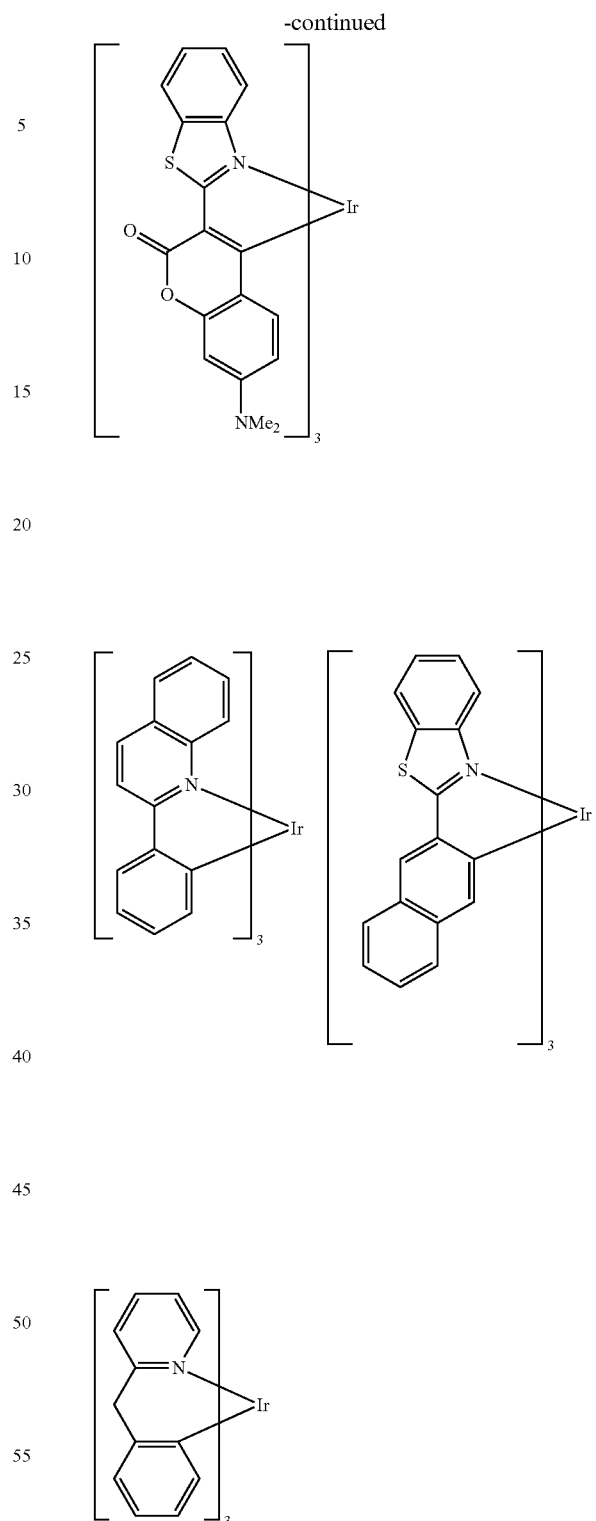
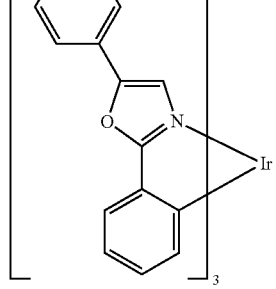
MODE FOR INVENTION
Hereinafter, the present application will be described in more detail through the Examples, but these are provided only for exemplifying the present application, and are not for limiting the scope of the present application.

EXAMPLES

<Preparation Example 1> Preparation of Compound 1

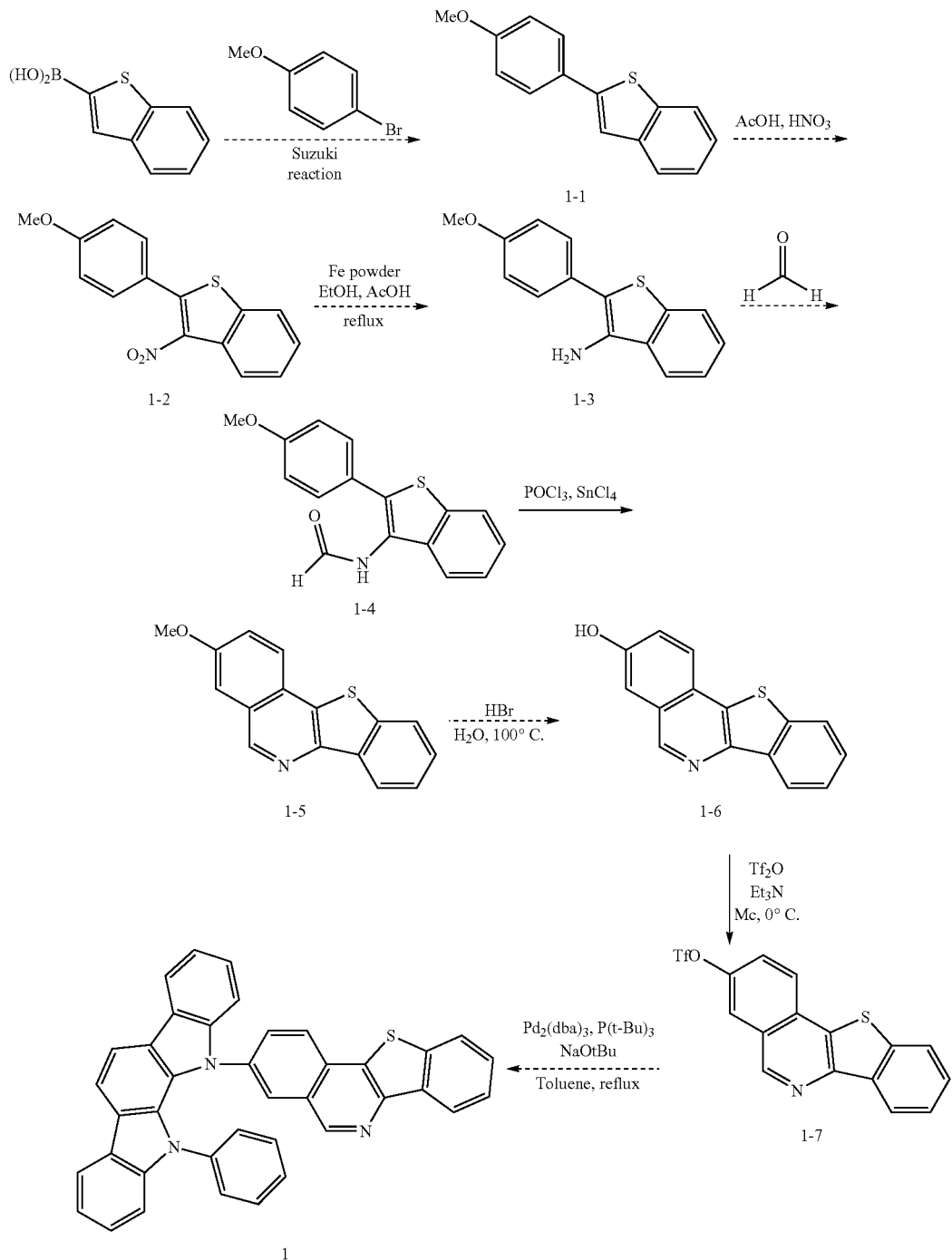

Preparation of Compound 1-1

30 g (168.5 mmol) of benzo[b]thiophen-2-ylboronic acid, 37.8 g (202.26 mmol) of 1-bromo-4-methoxybenzene, 9.7 g (8.4 mmol) of Pd(PPh$_3$)$_4$, and 35.7 g (336.9 mmol) of Na$_2$CO$_3$ were put into a vessel along with 300 mL of toluene, 120 mL of ethanol (EtOH), and 120 mL of H$_2$O, and the resulting mixture was refluxed at 120° C. for 1 hour. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was washed with ethyl acetate (EA) and hexane to obtain 18.0 g (51%) of Target Compound 1-1.

Preparation of Compound 1-2

8 g (38.0 mmol) of Compound 1-1 and 400 mL of acetic acid (AcOH) were put into a vessel, the resulting mixture was stirred at room temperature for 10 minutes, and then 400 mL of acetic acid and 20 mL of $HNO_3$ were mixed and slowly added thereto. After 1 hour, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was purified by column chromatography using dichloromethane and hexane as an eluting solvent to obtain 5.8 g (53%) of Target Compound 1-2.

Preparation of Compound 1-3

6 g (21.0 mmol) of Compound 1-2, 300 mL of ethanol, and 3.6 g (65.1 mmol) of iron (Fe) power were put into a vessel and the resulting mixture was stirred at room temperature for 10 minutes. 30 mL of acetic acid was slowly added dropwise thereto, and then the resulting mixture was refluxed at 60° C. for 1 hour. After completion of the reaction, the reaction product was cooled to room temperature, and then a solid produced by adding $H_2O$ thereto was filtered and then washed with $H_2O$ and hexane to obtain 5.3 g (99%) of Target Compound 1-3.

Preparation of Compound 1-4

3.9 mL of HCOH and 9.77 mL of acetic acid were put into a vessel, stirred at 60° C. for 2 hours, and then cooled to room temperature. Thereafter, 360 mL of ethyl ether and 12 g (46.9 mmol) of Compound 1-3 were added thereto, and the resulting mixture was stirred at room temperature. After 1 hour, a solid produced was filtered and washed with ethyl ether to obtain 6.5 g (49%) of Target Compound 1-4.

Preparation of Compound 1-5

6.5 g (22.94 mmol) of Compound 1-4, 0.43 mL (4.59 mmol) of $POCl_3$, and 30 mL of nitrobenzene were put into a vessel, the resulting mixture was refluxed for 1 hour and cooled to room temperature, and then 3.76 mL (32.12 mmol) of $SnCl_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was washed with methanol and then purified to obtain 2.74 g (45%) of Target Compound 1-5.

Preparation of Compound 1-6

4.0 g (15.08 mmol) of Compound 1-5 and 3.65 g (45.22 mmol) of HBr were refluxed along with 50 mL of $H_2O$ for 1 hour, and the resulting mixture was cooled to room temperature and then extracted with distilled water and methylene chloride (MC). After the organic layer was dried over anhydrous $MgSO_4$, the solvent was removed by a rotary evaporator, and then the resulting product was washed with methanol and then purified to obtain 3.49 g (92%) of Target Compound 1-6.

Preparation of Compound 1-7

5.0 g (19.89 mmol) of Compound 1-6 and 2.0 g (19.89 mmol) of triethylamine were put into a vessel, the resulting mixture was stirred at room temperature for about 1 hour, and then 4.18 g (19.89 mmol) of $Tf_2O$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was washed with methanol and then purified to obtain 6.71 g (88%) of Target Compound 1-7.

Preparation of Compound 1

5.0 g (13.04 mmol) of Compound 1-7, 4.77 g (14.35 mmol) of 11-phenyl-11,12-dihydroindolo[2,3-a]carbazole, 0.60 g (0.65 mmol) of $Pd_2(dba)_3$, 0.75 g (1.30 mmol) of XantPhos, and 5.28 g (26.08 mmol) of NaOtBu were refluxed along with 80 mL of toluene at 130° C. for 3 hours. After completion of the reaction, the reaction product was cooled to room temperature, and then extracted with distilled water and ethyl acetate (EA). After the organic layer was dried over anhydrous $MgSO_4$, the solvent was removed by a rotary evaporator, and then the resulting mixture was completely dissolved in toluene, and the resulting solution was filtered with silica gel. Thereafter, the product was filtered with hot toluene and purified to obtain 5.9 g (80%) of Compound 1.

<Preparation Example 2> Preparation of Compound 17

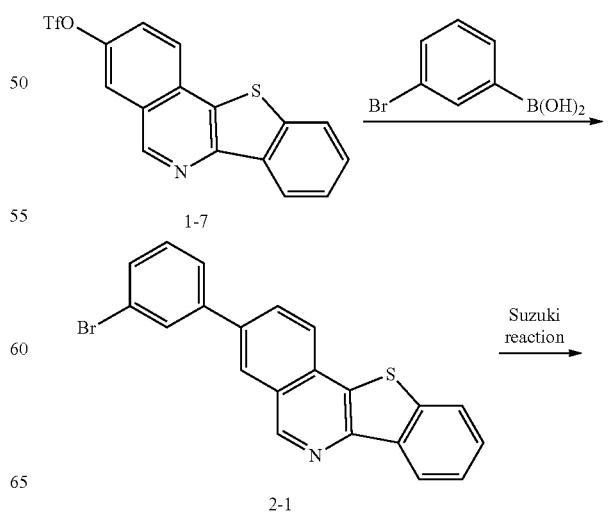

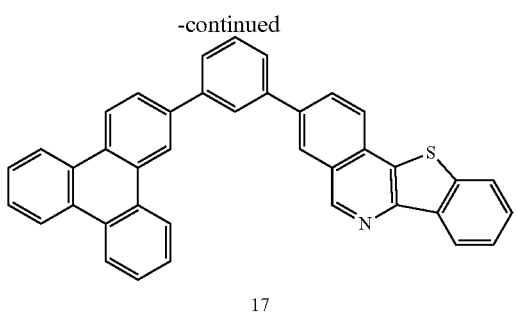

17

Preparation of Compound 2-1

10 g (26.09 mmol) of Compound 1-7, 6.29 g (31.31 mmol) of (3-bromophenyl)boronic acid, 1.5 g (1.3 mmol) of Pd(PPh$_3$)$_4$, and 5.53 g (52.18 mmol) of Na$_2$CO$_3$ were refluxed along with 200 mL of toluene, 40 mL of ethanol, and 40 mL of H$_2$O at 120° C. for 6 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was washed with ethyl acetate (EA) and hexane to obtain 6.82 g (67%) of Target Compound 3-1.

Preparation of Compound 17

5.0 g (12.81 mmol) of Compound 2-1, 4.18 g (15.37 mmol) of triphenylen-2-ylboronic acid, 0.74 g (0.64 mmol) of Pd(PPh$_3$)$_4$, and 2.71 g (25.62 mmol) of Na$_2$CO$_3$ were refluxed along with 100 mL of toluene, 20 mL of ethanol, and 20 mL of H$_2$O at 120° C. for 4 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was washed with ethyl acetate (EA) and hexane to obtain 6.06 g (88%) of Target Compound 17.

<Preparation Example 3> Preparation of Compound 29

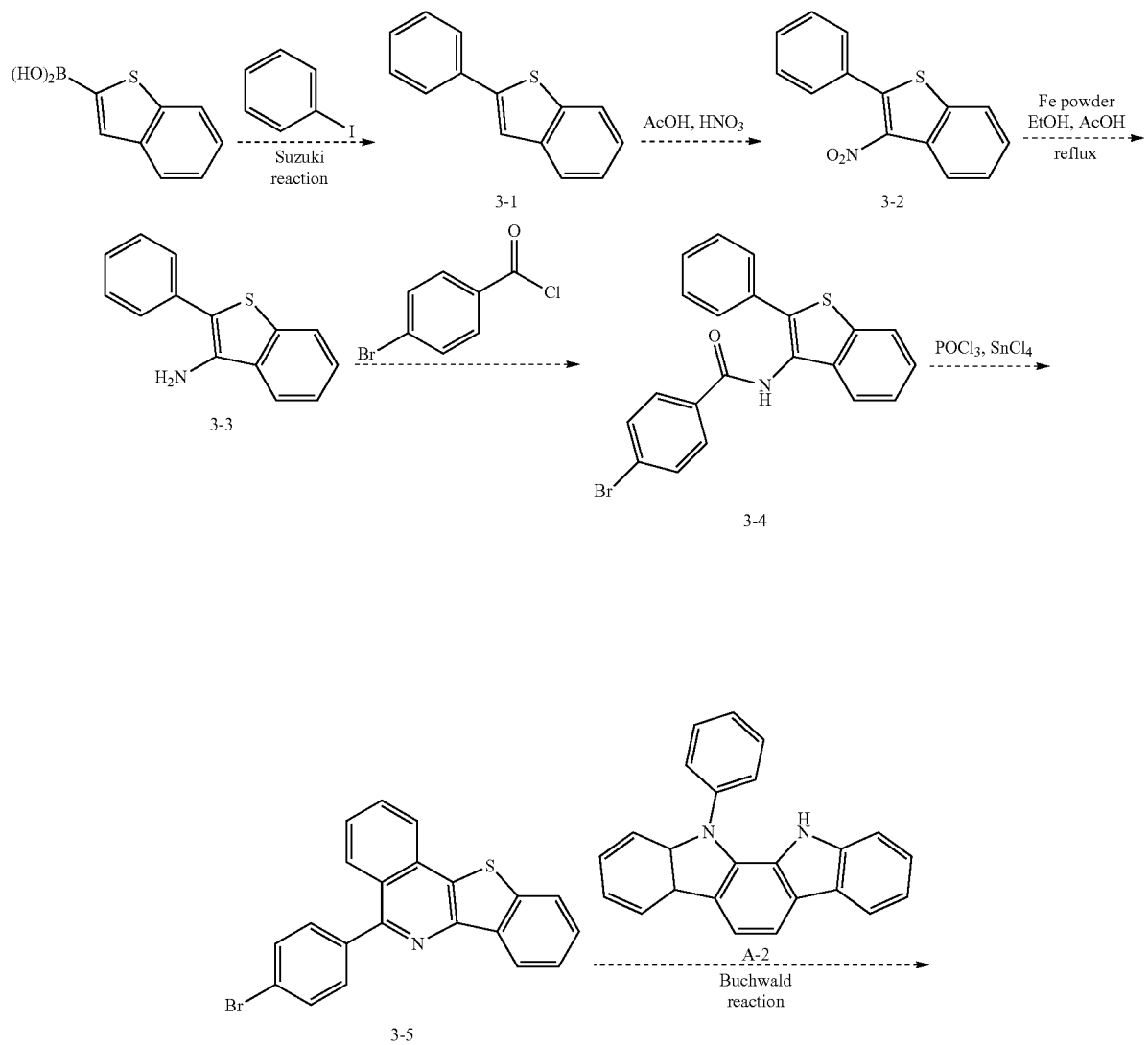

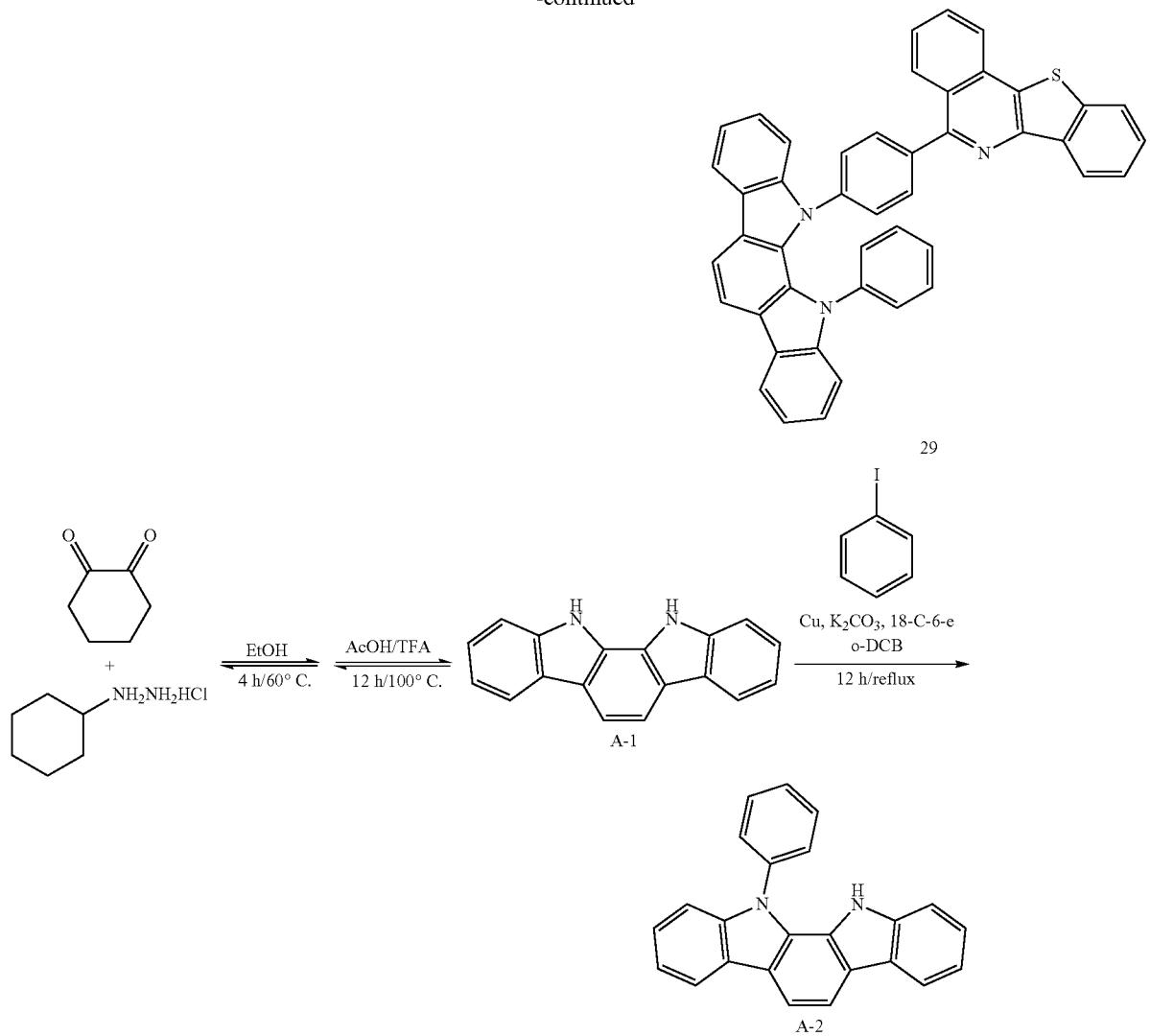

Preparation of Compound A-1

1.4 mL (0.0374 mol) of sulfuric acid was slowly added dropwise to a mixture of 30.0 g (0.374 mol) of 1,2-dicyclohexanone and 77.37 g (0.749 mol) of phenylhydrazine hydrochloride in 1,000 ml of ethanol in a one-neck round bottom flask under nitrogen, and then the resulting mixture was stirred at 60° C. for 4 hours. The solution cooled to room temperature was filtered to obtain a yellow brown solid (69 g, 93%). 46.5 mL (0.6 mol) of trifluoroacetic acid was put into a mixture of 68.9 g (0.25 mol) of the solid and 700 ml of acetic acid in a one-neck round bottom flask, and the resulting mixture was stirred at 100° C. for 12 hours. The solution cooled to room temperature was washed with acetic acid and hexane and filtered to obtain ivory-colored solid A-1 (27.3 g, 42%).

Preparation of Compound A-2

A mixture of 2.1 g (0.0082 mol) of Compound A-1, 2.5 g (0.013 mol) of iodobenzene, 0.312 g (0.0049 mol) of Cu, 0.433 g (0.0016 mol) of 18-crown-6-ether, and 3.397 g (0.0246 mol) of $K_2CO_3$ in 20 ml of o-dichlorobenzene (o-DCB) was stirred under reflux under nitrogen for 16 hours in a two neck round bottom flask. The solution cooled to room temperature was extracted with methylene chloride/$H_2O$ and concentrated, and separated by column chromatography ($SiO_2$, hexane:ethyl acetate=10:1) to obtain white solid Compound A-2 (1.76 g, 64%).

Preparation of Compound 3-1

30 g (168.5 mmol) of benzo[b]thiophen-2-ylboronic acid, 41.2 g (202.26 mmol) of iodobenzene, 19.0 g (16.9 mmol) of $Pd(PPh_3)_4$, and 35.7 g (336.9 mmol) of $Na_2CO_3$ were refluxed along with 300 mL of toluene, 120 mL of ethanol (EtOH) and 120 mL of $H_2O$ at 120° C. for 1 hour. After completion of the reaction, the reaction product was cooled to room temperature, and then extracted with distilled water and ethyl acetate (EA). After the organic layer was dried over anhydrous $MgSO_4$, the solvent was removed by a rotary evaporator, and then the resulting product was washed with ethyl acetate (EA) and hexane to obtain 18.0 g (51%) of Target Compound 3-1.

Preparation of Compound 3-2

10 g (47.55 mmol) of Compound 3-1 and 400 mL of acetic acid were put into a vessel, the resulting mixture was stirred at room temperature for 10 minutes, and then 400 mL of acetic acid and 20 mL of $HNO_3$ were mixed and slowly added thereto. After 1 hour, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was purified by column chromatography using dichloromethane and hexane as an eluting solvent to obtain 5.9 g (50%) of Target Compound 3-2.

Preparation of Compound 3-3

6 g (23.5 mmol) of Compound 3-2, 300 mL of ethanol, and 4.06 g (72.8 mmol) of iron (Fe) power were put into a vessel and the resulting mixture was stirred at room temperature for 10 minutes. 30 mL of acetic acid was slowly added dropwise thereto, and then the resulting mixture was refluxed for 1 hour. After completion of the reaction, the reaction product was cooled to room temperature, and then a solid produced by adding $H_2O$ thereto was filtered and then washed with $H_2O$ and hexane to obtain 5.5 g (99%) of Target Compound 3-3.

Preparation of Compound 3-4

2.93 mL (22.19 mmol) of 4-bromo benzoylchloride was completely dissolved in 30 mL of methylene chloride (MC), and then 3.12 mL (22.19 mmol) of triethylamine (TEA) was added thereto, and after the resulting mixture was stirred at room temperature for 15 minutes and then maintained at 0° C., 2.93 mL (22.19 mmol) of Compound 3-3 was slowly added thereto. After about 1 hour, a white solid was produced and filtered, and then the resulting product was washed with hexane and dried to obtain 8.0 g (87%) of Target Compound 3-4.

Preparation of Compound 3-5

6.5 g (22.94 mmol) of Compound 3-4, 0.43 mL (4.59 mmol) of $POCl_3$, and 30 mL of nitrobenzene were put into a vessel, the resulting mixture was refluxed for 1 hour and cooled to room temperature, and then 3.76 mL (32.12 mmol) of $SnCl_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was purified by column chromatography using dichloromethane and hexane as an eluting solvent to obtain 2.74 g (45%) of Target Compound 3-5.

Preparation of Compound 29

8 g (20.5 mmol) of Compound 3-5, 6.1 g (18.44 mmol) of Compound A-2, 0.38 g (0.41 mmol) of $Pd_2(dba)_3$, 0.47 g (0.82 mmol) of XantPhos, and 8.3 g (41.0 mmol) of NaOtBu were refluxed along with 80 mL of toluene at 130° C. for 3 hours. After completion of the reaction, the reaction product was cooled to room temperature, and then extracted with distilled water and ethyl acetate (EA). After the organic layer was dried over anhydrous $MgSO_4$, the solvent was removed by a rotary evaporator, and then the resulting mixture was completely dissolved in toluene, and the resulting solution was filtered with silica gel. Thereafter, the product was filtered with hot toluene and purified to obtain 8.8 g (67%) of Compound 29.

<Preparation Example 4> Preparation of Compound 42

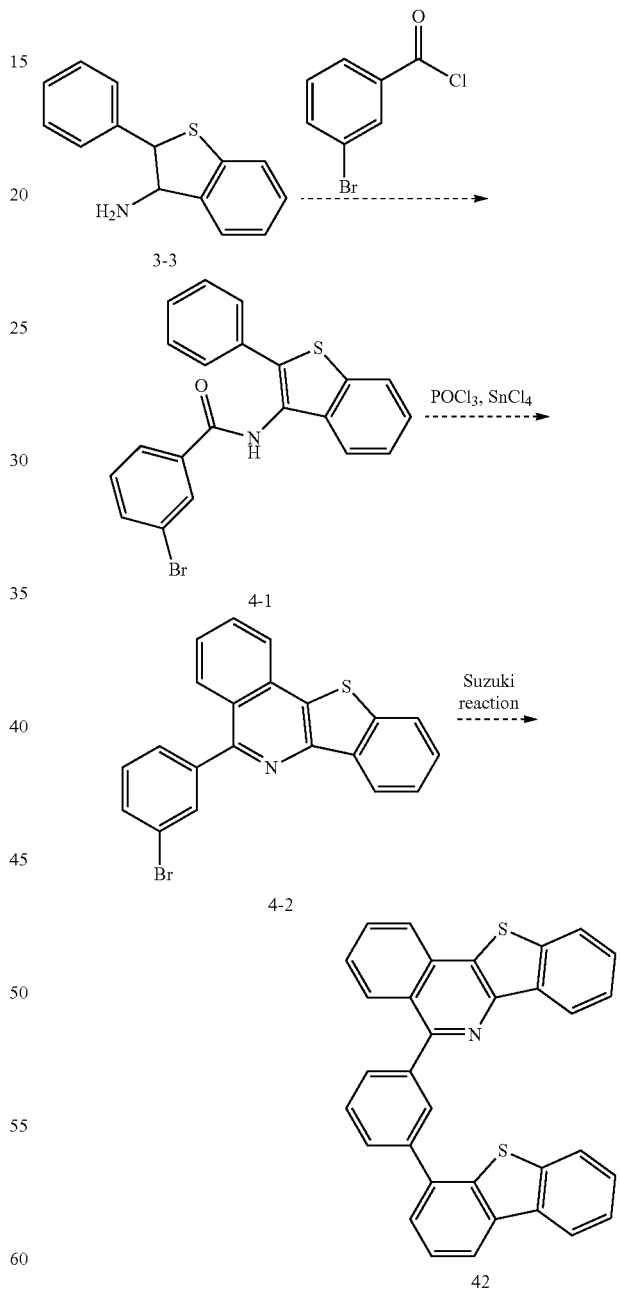

Preparation of Compound 4-1

2.93 mL (22.19 mmol) of 3-bromo benzoylchloride was completely dissolved in 30 mL of methylene chloride (MC), and then 3.12 mL (22.19 mmol) of triethylamine (TEA) was added thereto, and after the resulting mixture was stirred at room temperature for 15 minutes and then maintained at 0° C., 2.93 mL (22.19 mmol) of Compound 3-3 was slowly added thereto. After about 1 hour, a white solid was produced and filtered, and then the resulting product was washed with hexane and dried to obtain 8.0 g (87%) of Target Compound 4-1.

Preparation of Compound 4-2

8.0 g (19.59 mmol) of Compound 4-1, 1.8 mL (19.59 mmol) of POCl$_3$, and 80 mL of nitrobenzene were put into a vessel, the resulting mixture was refluxed for 1 hour and cooled to room temperature, and then 4.5 mL (54.85 mmol) of SnCl$_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous MgSO$_4$, the solvent was removed by a rotary evaporator, and then the resulting product was washed with methanol and then purified to obtain 5.03 g (66%) of Target Compound 4-2.

Preparation of Compound 42

5 g (12.81 mmol) of Compound 4-2, 3.5 g (15.37 mmol) of dibenzo[b,d]thiophen-4-ylboronic acid, 0.74 g (0.64 mmol) of Pd(PPh$_3$)$_4$, and 3.5 g (25.62 mmol) of K$_2$CO$_3$ were refluxed along with 50 mL of toluene, 5 mL of ethanol, and 5 mL of H$_2$O at 120° C. for 5 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was purified by column chromatography using dichloromethane and hexane as an eluting solvent to obtain 5.56 g (88%) of Compound 42.

<Preparation Example 5> Preparation of Compound 48

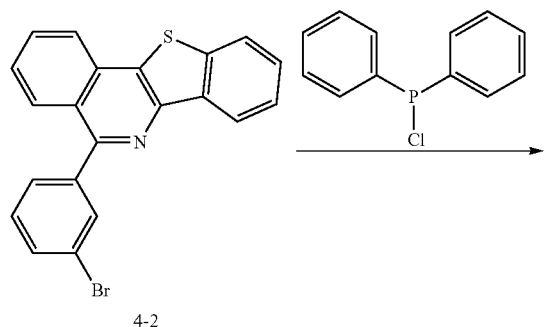

4-2

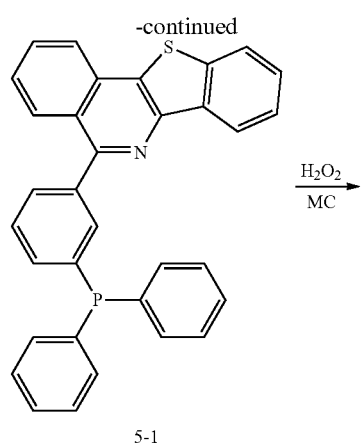

5-1

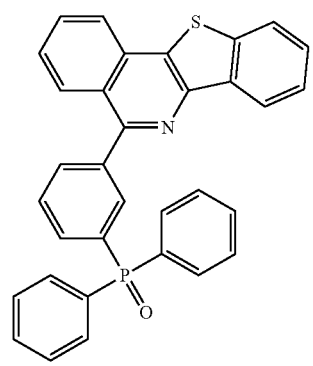

48

Preparation of Compound 5-1

Compound 4-2 (10 g, 25.62 mmol) was dissolved in 100 ml of THF, and then the resulting solution was cooled to −78° C. n-Butyllithium (2.5 M in hexane) (13.3 ml, 33.31 mmol) was slowly added dropwise thereto, and then the resulting mixture was stirred for 1 hour. Chlorodiphenylphosphine (5.65 ml, 25.62 mol) was added dropwise to the solution, and the resulting solution was stirred at room temperature for 12 hours. The reaction mixture was extracted with MC/H$_2$O, and then distilled under reduced pressure. After the organic layer was dried over anhydrous MgSO$_4$, the solvent was removed by a rotary evaporator, and then the resulting product was purified by column chromatography using dichloromethane and hexane as an eluting solvent to obtain 4.19 g (33%) of Compound 5-1.

Preparation of Compound 48

5 g (10.09 mmol) of Compound 5-1 was completely dissolved in 50 mL of methylene chloride (MC), and then the resulting mixture was stirred along with a 10 ml of H$_2$O$_2$ aqueous solution (30 wt. %) at room temperature for 1 hour. The reaction mixture was extracted with MC/H$_2$O, and then distilled under reduced pressure. After the organic layer was dried over anhydrous MgSO$_4$, the solvent was removed by a rotary evaporator, and then the resulting product was purified by column chromatography using dichloromethane and hexane as an eluting solvent to obtain 1.14 g (22%) of Compound 48.

<Preparation Example 6> Preparation of Compound 74

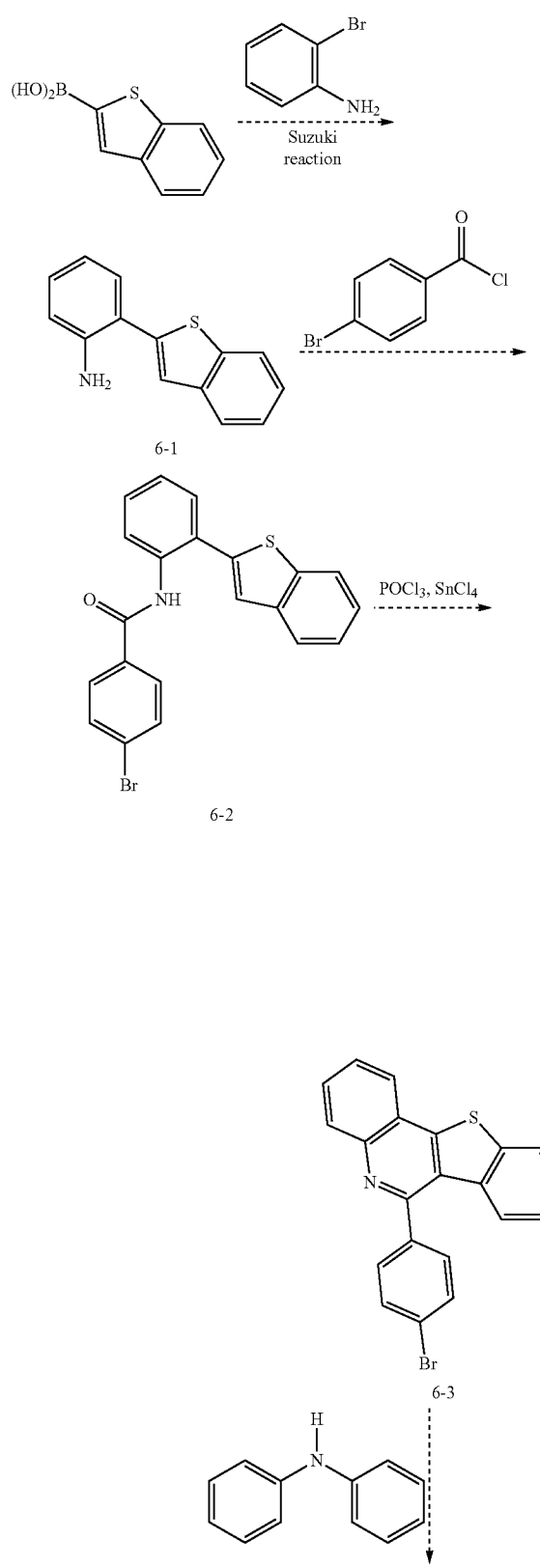

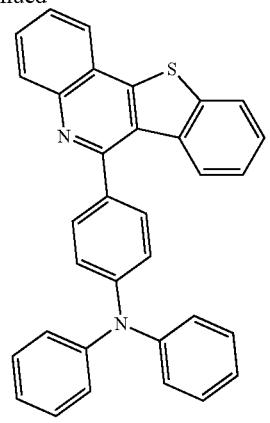

74

Preparation of Compound 6-1

20 g (112.34 mmol) of benzo[b]thiophen-2-ylboronic acid, 20.4 g (101.11 mmol) of 2-bromoaniline, 6.5 g (5.12 mmol) of Pd(PPh$_3$)$_4$, and 31.05 g (224.68 mmol) of K$_2$CO$_3$ were refluxed along with 200 mL of toluene, 40 mL of ethanol, and 40 mL of H$_2$O at 120° C. for 16 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was purified by column chromatography using dichloromethane and hexane as an eluting solvent to obtain 16.9 g (67%) of Compound 6-1.

Preparation of Compound 6-2

10 g (44.38 mmol) of Compound 6-1 was completely dissolved in methylene chloride (MC), and then the resulting solution was stirred along with 6.2 mL (44.38 mmol) of triethylamine (TEA) at room temperature for 15 minutes. Thereafter, the solution was maintained at 0° C., and then 9.7 g (44.38 mmol) of 4-bromo benzoylchloride was slowly added thereto. After about 1 hour, a white solid was produced and filtered, and then the resulting product was washed with EA and hexane to obtain 17.2 g (95%) of Target Compound 6-2.

Preparation of Compound 6-3

15 g (36.74 mmol) of Compound 6-2, 3.4 mL (36.74 mmol) of POCl$_3$, and 150 mL of nitrobenzene were put into a vessel, the resulting mixture was refluxed for 1 hour and cooled to room temperature, and then 12.04 mL (102.87 mmol) of SnCl$_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous MgSO$_4$, the solvent was removed by a rotary evaporator, and then the resulting product was washed with methanol (MeOH) and hexane to obtain 6.17 g (43%) of Target Compound 6-3.

Preparation of Compound 74

5 g (12.81 mmol) of Compound 6-3, 2.38 g (14.09 mmol) of diphenylamine, 0.74 g (0.64 mmol) of Pd(PPh$_3$)$_4$, and 3.5 g (25.62 mmol) of K$_2$CO$_3$ were refluxed along with 50 mL of toluene, 5 mL of ethanol, and 5 mL of H$_2$O at 120° C. for 6 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was purified by column chromatography using dichloromethane and hexane as an eluting solvent to obtain 4.72 g (77%) of Compound 74.

<Preparation Example 7> Preparation of Compound 85

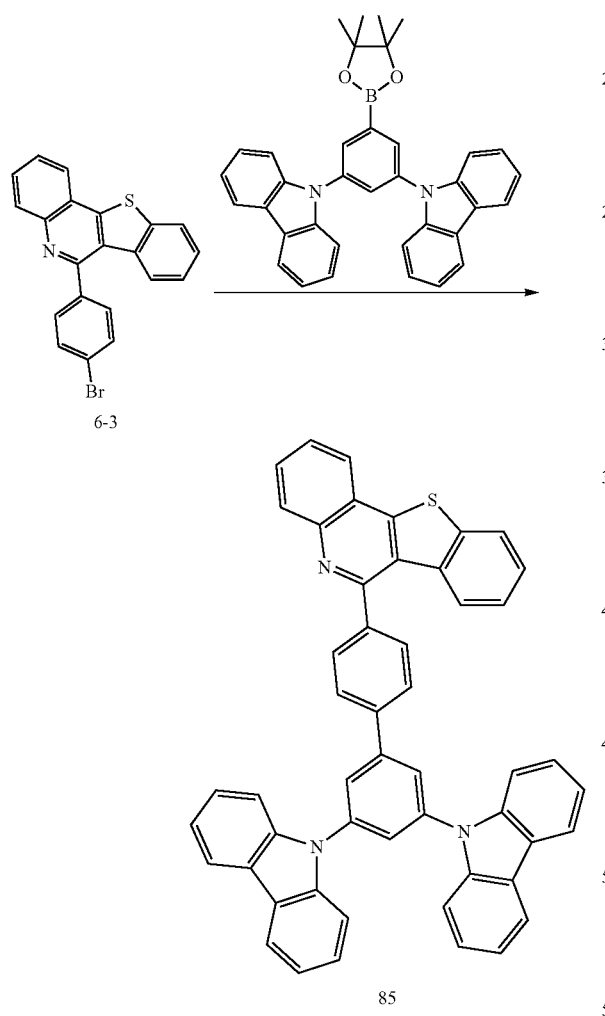

fied by column chromatography using dichloromethane and hexane as an eluting solvent to obtain 6.4 g (69%) of Compound 85.

<Preparation Example 8> Preparation of Compound 86

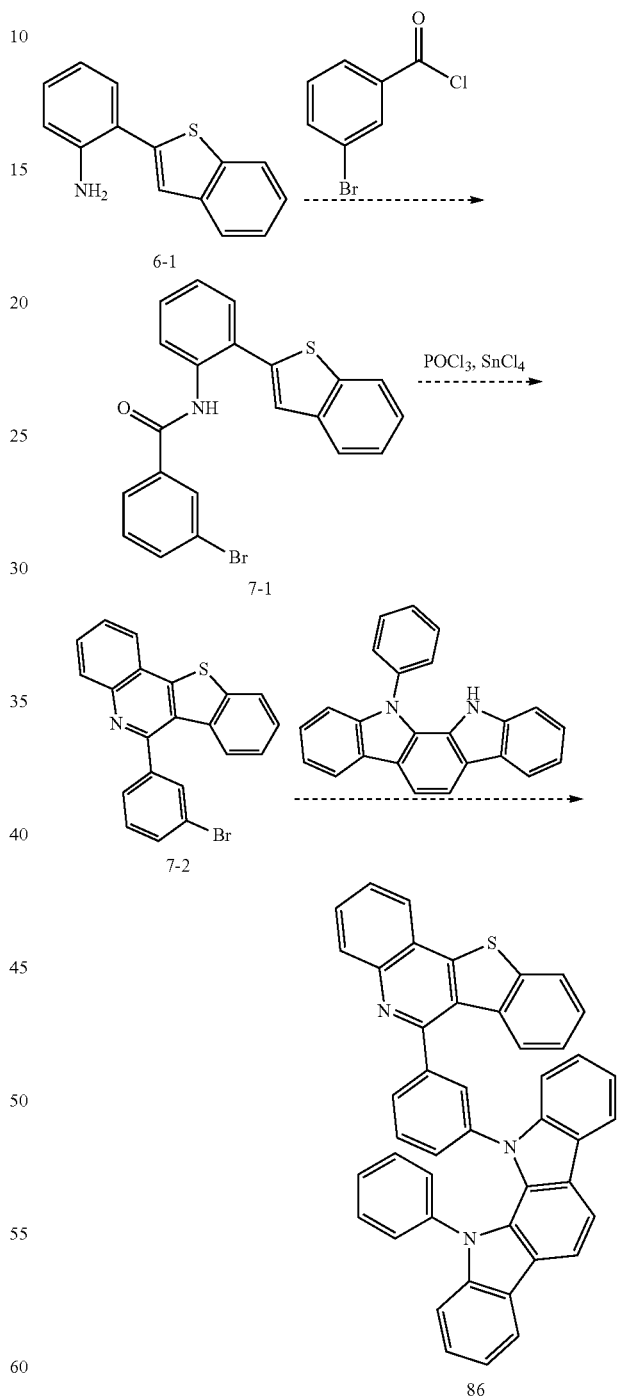

5 g (12.81 mmol) of Compound 6-3, 6.37 g (14.09 mmol) of (3,5-di(9H-carbazol-9-yl)phenyl)boronic acid, 0.74 g (0.64 mmol) of Pd(PPh$_3$)$_4$, and 3.5 g (25.62 mmol) of K$_2$CO$_3$ were refluxed along with 50 mL of toluene, 5 mL of ethanol, and 5 mL of H$_2$O at 120° C. for 6 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was puri- Preparation of Compound 7-1

10 g (44.38 mmol) of Compound 6-1 was completely dissolved in methylene chloride (MC), and then the resulting solution was stirred along with 6.2 mL (44.38 mmol) of triethylamine (TEA) at room temperature for 15 minutes. Thereafter, the solution was maintained at 0° C., and then 9.7 g (44.38 mmol) of 3-bromo benzoylchloride was slowly added thereto. After about 1 hour, a white solid was produced and filtered, and then the resulting product was washed with ethyl acetate (EA) and hexane to obtain 17.2 g (95%) of Target Compound 7-1.

Preparation of Compound 7-2

15 g (36.74 mmol) of Compound 7-1, 3.4 mL (36.74 mmol) of $POCl_3$, and 150 mL of nitrobenzene were put into a vessel, the resulting mixture was refluxed for 1 hour and cooled to room temperature, and then 12.04 mL (102.87 mmol) of $SnCl_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was washed with methanol (MeOH) and hexane to obtain 7.89 g (55%) of Target Compound 7-2.

Preparation of Compound 86

8 g (20.5 mmol) of Compound 7-2, 6.1 g (18.44 mmol) of 11-phenyl-11,12-dihydroindolo[2,3-a]carbazole, 0.38 g (0.41 mmol) of $Pd_2(dba)_3$, 0.47 g (0.82 mmol) of XantPhos, and 8.3 g (41.0 mmol) of NaOtBu were refluxed along with 80 mL of toluene at 130° C. for 3 hours. After completion of the reaction, the reaction product was cooled to room temperature, and then extracted with distilled water and ethyl acetate (EA). After the organic layer was dried over anhydrous $MgSO_4$, the solvent was removed by a rotary evaporator, and then the resulting mixture was completely dissolved in toluene, and the resulting solution was filtered with silica gel. Thereafter, the product was filtered with hot toluene and purified to obtain 7.3 g (56%) of Compound 86.

<Preparation Example 9> Preparation of Compound 87

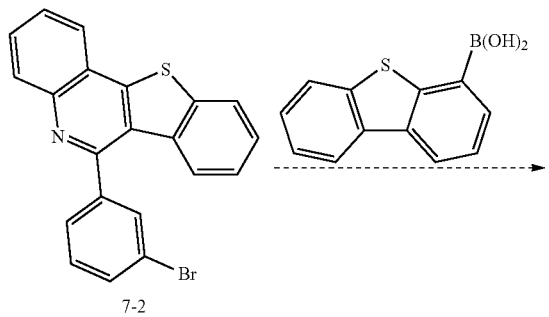

7-2

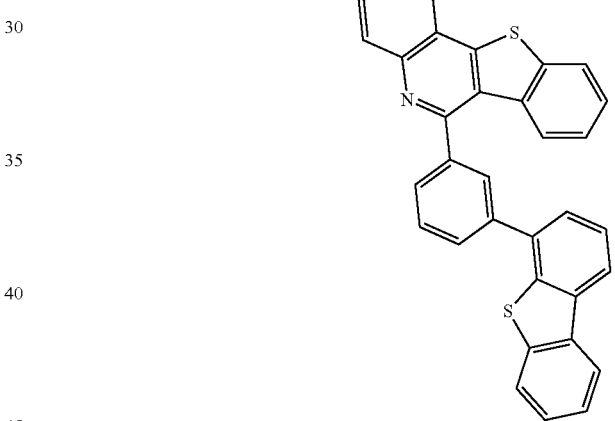

87

5 g (12.81 mmol) of Compound 7-2, 3.5 g (15.37 mmol) of dibenzo[b,d]thiophen-4-ylboronic acid, 0.74 g (0.64 mmol) of $Pd(PPh_3)_4$, and 3.5 g (25.62 mmol) of $K_2CO_3$ were refluxed along with 50 mL of toluene, 5 mL of ethanol, and 5 mL of $H_2O$ at 120° C. for 5 hours. After completion of the reaction, the reaction product was cooled to room temperature, and then extracted with distilled water and ethyl acetate (EA). After the organic layer was dried over anhydrous $MgSO_4$, the solvent was removed by a rotary evaporator, and then the resulting product was purified by column chromatography using dichloromethane and hexane as an eluting solvent to obtain 4.80 g (76%) of Compound 87.

<Preparation Example 10> Preparation of Compound 88

<Preparation Example 11> Preparation of Compound 90

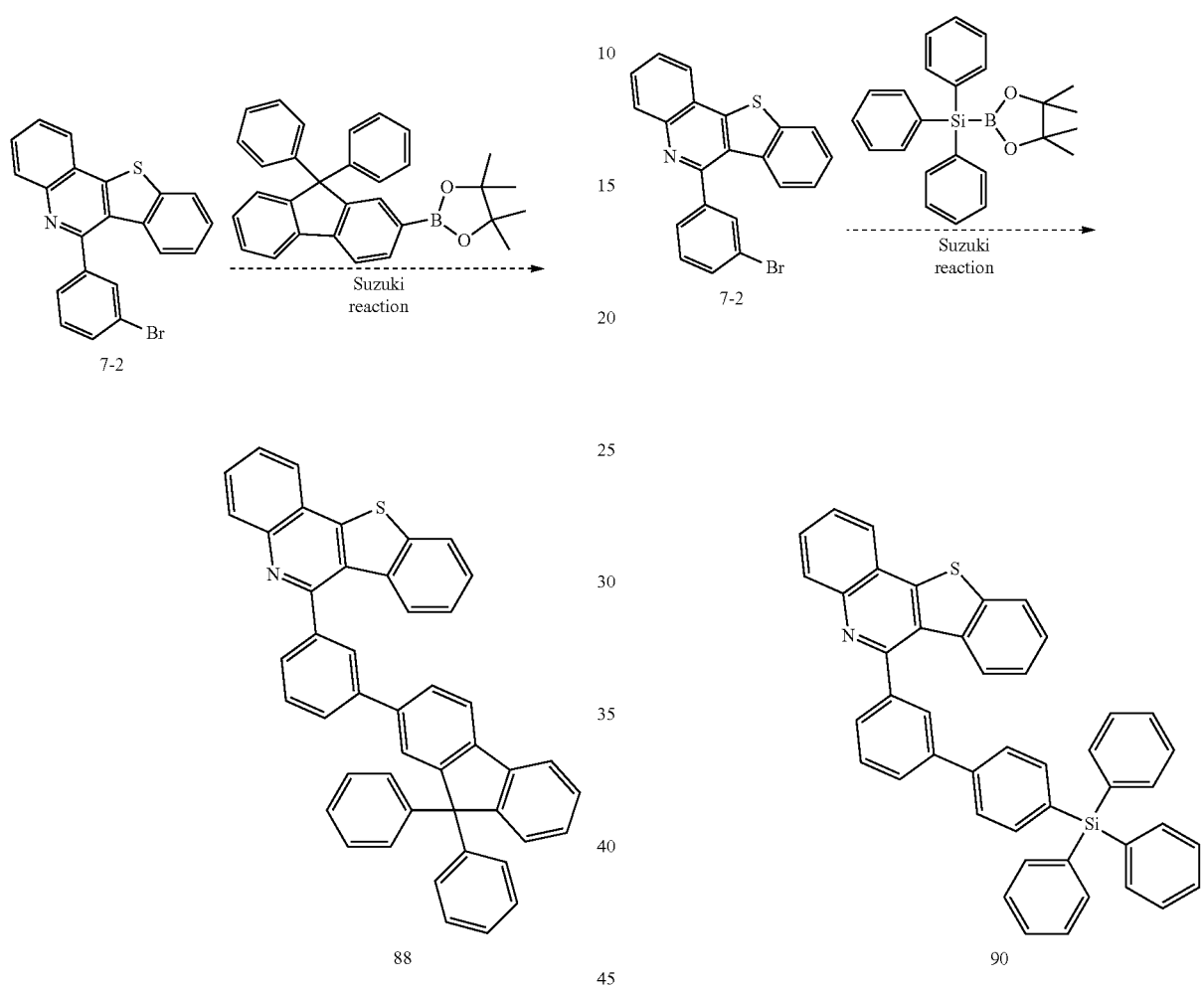

5 g (12.81 mmol) of Compound 7-2, 5.7 g (12.81 mmol) of 2-(9,9-diphenyl-9H-fluoren-2-yl)-4,4,5,5-tetramethyl-1,3,2-dioxaborolane, 0.74 g (0.64 mmol) of Pd(PPh$_3$)$_4$, and 3.5 g (25.62 mmol) of K$_2$CO$_3$ were refluxed along with 100 mL of toluene, 20 ml of toluene, and 20 mL of H$_2$O at 120° C. for 24 hours. After completion of the reaction, the reaction product was cooled to room temperature, and then extracted with distilled water and MC. After the organic layer was dried over anhydrous MgSO$_4$, the solvent was removed by a rotary evaporator, and then the resulting product was purified by column chromatography using dichloromethane and hexane as an eluting solvent to obtain 6.0 g (74%) of Compound 88.

5 g (12.81 mmol) of Compound 7-2, 5.9 g (12.81 mmol) of triphenyl(4,4,5,5-tetramethyl-1,3,2-dioxaborolan-2-yl)silane, 0.74 g (0.64 mmol) of Pd(PPh$_3$)$_4$, and 3.5 g (25.62 mmol) of K$_2$CO$_3$ were refluxed along with 100 mL of toluene, 20 mL of ethanol, and 20 mL of H$_2$O at 120° C. for 24 hours. After completion of the reaction, the reaction product was cooled to room temperature, and then extracted with distilled water and MC. After the organic layer was dried over anhydrous MgSO$_4$, the solvent was removed by a rotary evaporator, and then the resulting product was purified by column chromatography using dichloromethane and hexane as an eluting solvent to obtain 6.5 g (78%) of Compound 90.

<Preparation Example 12> Preparation of Compound 91

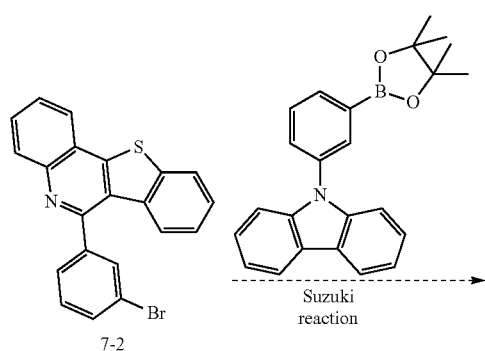

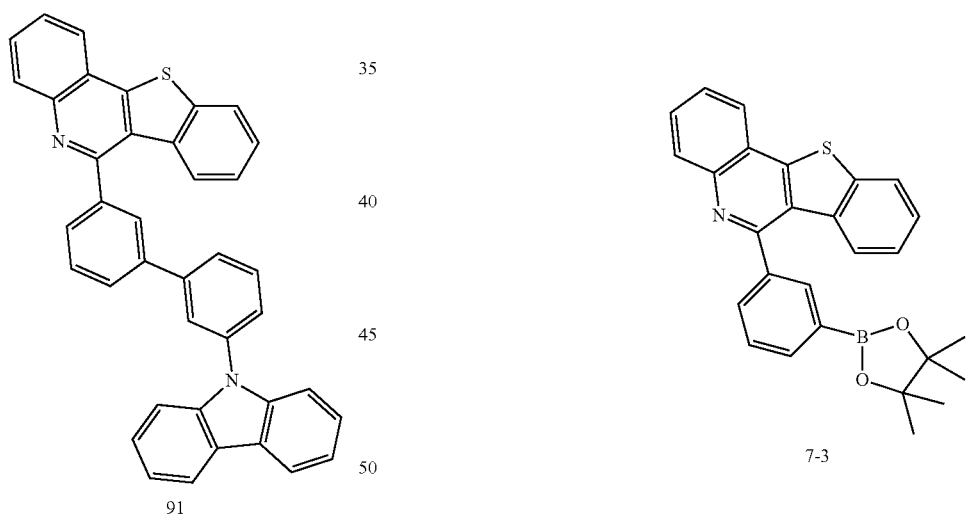

5 g (12.81 mmol) of Compound 7-2, 5.6 g (12.81 mmol) of 9-(3-(4,4,5,5-tetramethyl-1,3,2-dioxaborolan-2-yl)phenyl)-9H-carbazole, 0.74 g (0.64 mmol) of Pd(PPh₃)₄, and 3.5 g (25.62 mmol) of K₂CO₃ were refluxed along with 100 mL of toluene, 20 mL of ethanol, and 20 mL of H₂O at 120° C. for 24 hours. After completion of the reaction, the reaction product was cooled to room temperature, and then extracted with distilled water and MC. After the organic layer was dried over anhydrous MgSO₄, the solvent was removed by a rotary evaporator, and then the resulting product was purified by column chromatography using dichloromethane and hexane as an eluting solvent to obtain 5.0 g (70%) of Compound 91.

<Preparation Example 13> Preparation of Compound 92

Preparation of Compound 7-3

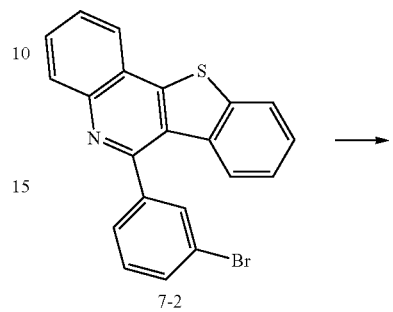

10 g (25.6 mmol) of Compound 7-2, 13.0 g (51.2 mmol) of bis(pinacolato)diboron, 0.93 g (1.3 mmol) of PdCl₂(dppf), and 7.5 g (51.2 mmol) of KOAc were refluxed along with 200 mL of DMF at 130° C. for 4 hours. After completion of the reaction, the reaction product was cooled to room temperature, and then extracted with distilled water and MC. After the organic layer was dried over anhydrous MgSO₄, the solvent was removed by a rotary evaporator, and then the resulting product was purified by column chromatography using dichloromethane and hexane as an eluting solvent to obtain 7.5 g (67%) of Compound 7-3.

Preparation of Compound 92
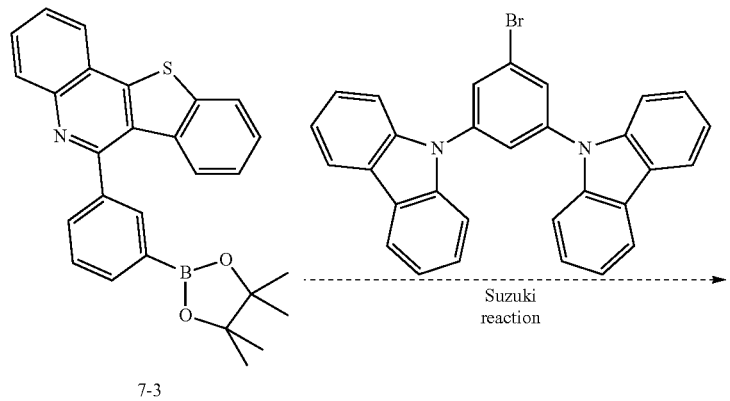
7-3
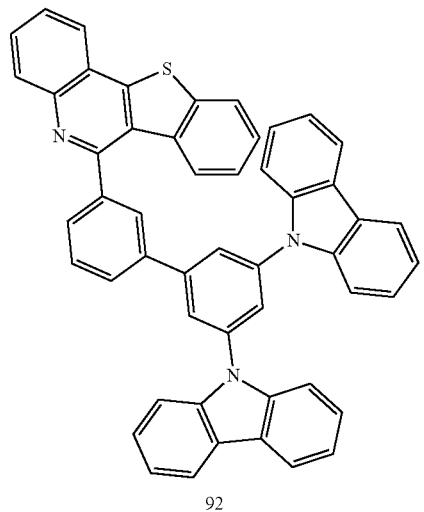
92

7.5 g (17.1 mmol) of Compound 7-3, 8.35 g (17.1 mmol) of 9,9'-(5-bromo-1,3-phenylene)bis(9H-carbazole), 1.0 g (0.85 mmol) of Pd(PPh$_3$)$_4$, and 4.7 g (34.0 mmol) of K$_2$CO$_3$ were refluxed along with 200 mL of toluene, 40 mL of ethanol, and 40 mL of H$_2$O at 100° C. for 24 hours. After completion of the reaction, the reaction product was cooled to room temperature, and then extracted with distilled water and MC. After the organic layer was dried over anhydrous MgSO$_4$, the solvent was removed by a rotary evaporator, and then the resulting product was purified by column chromatography using dichloromethane and hexane as an eluting solvent to obtain 9.0 g (73%) of Compound 92.

<Preparation Example 14> Preparation of Compound 93

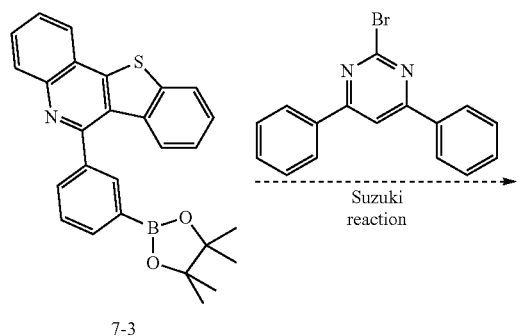

7-3

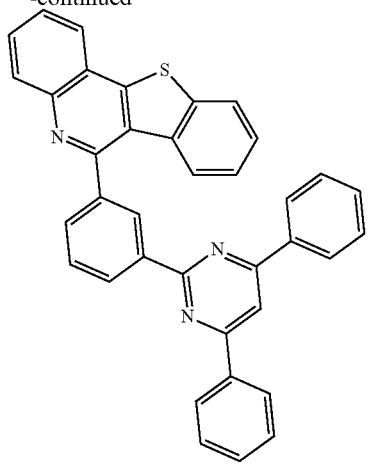

93

6.15 g (14.1 mmol) of Compound 7-3, 5.3 g (16.9 mmol) of 2-bromo-4,6-diphenylpyrimidine, 0.81 g (0.70 mmol) of Pd(PPh$_3$)$_4$, and 3.9 g (28.1 mmol) of K$_2$CO$_3$ were refluxed along with 100 mL of toluene, 20 mL of ethanol, and 20 mL of H$_2$O at 120° C. for 24 hours. After completion of the reaction, the reaction product was cooled to room temperature, and then extracted with distilled water and MC. After the organic layer was dried over anhydrous MgSO$_4$, the solvent was removed by a rotary evaporator, and then the resulting product was purified by column chromatography using dichloromethane and hexane as an eluting solvent to obtain 7.3 g (96%) of Compound 93.

<Preparation Example 15> Preparation of Compound 110

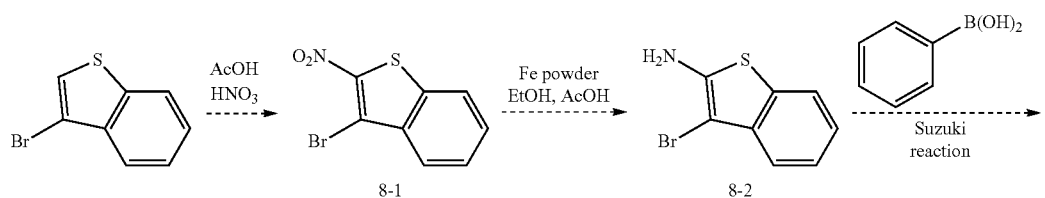

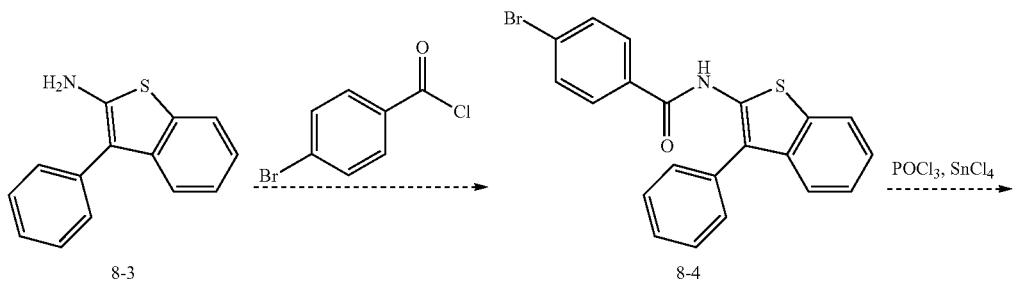

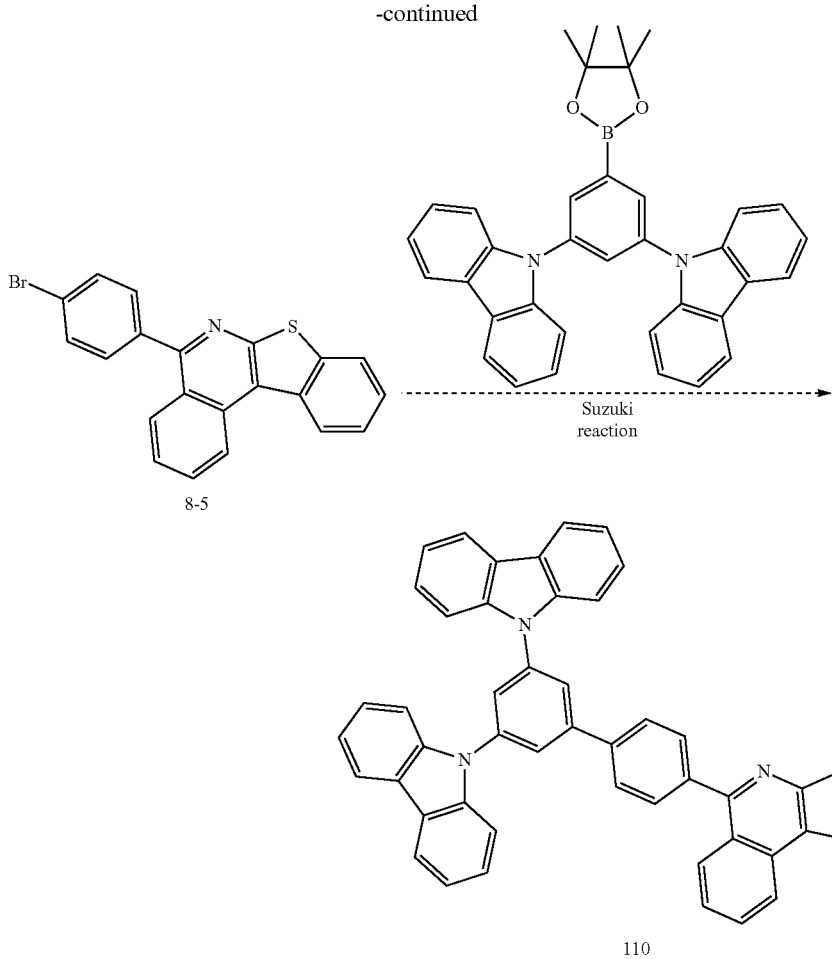

Preparation of Compound 8-1

10 g (46.93 mmol) of the compound 3-bromobenzo[b]thiophene and 400 mL of acetic acid were put into a vessel, the resulting mixture was stirred at room temperature for 10 minutes, and then 400 mL of acetic acid and 20 mL of $HNO_3$ were mixed and slowly added thereto. After 1 hour, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was purified by column chromatography using dichloromethane and hexane as an eluting solvent to obtain 9.34 g (77%) of Target Compound 8-1.

Preparation of Compound 8-2

9 g (34.87 mmol) of Compound 8-1, 300 mL of ethanol, and 6.03 g (108.1 mmol) of iron (Fe) power were put into a vessel and the resulting mixture was stirred at room temperature for 10 minutes. 30 mL of acetic acid was slowly added dropwise thereto, and then the resulting mixture was refluxed at 60° C. for 1 hour. After completion of the reaction, the reaction product was cooled to room temperature, and then a solid produced by adding $H_2O$ thereto was filtered and then washed with $H_2O$ and hexane to obtain 7.9 g (99%) of Target Compound 8-2.

Preparation of Compound 8-3

10 g (43.84 mmol) of Compound 8-2, 5.87 g (48.22 mmol) of phenyl boronic acid, 4.27 g (3.69 mmol) of $Pd(PPh_3)_4$, and 9.29 g (87.66 mmol) of $Na_2CO_3$ were refluxed along with 100 mL of toluene, 20 mL of ethanol, and 20 mL of $H_2O$ at 120° C. for 1 hour. After completion of the reaction, the reaction product was cooled to room temperature, and then extracted with distilled water and ethyl acetate (EA). After the organic layer was dried over anhydrous $MgSO_4$, the solvent was removed by a rotary evaporator, and then the resulting product was washed with ethyl acetate (EA) and hexane to obtain 9.08 g (92%) of Target Compound 8-3.

Preparation of Compound 8-4

9 g (39.94 mmol) of Compound 8-3 was completely dissolved in methylene chloride (MC), and then the resulting solution was stirred along with 5.6 mL (39.94 mmol) of TEA at room temperature for 15 minutes. Thereafter, the solution was maintained at 0° C., and then 8.77 g (39.94 mmol) of 4-bromo benzoylchloride was slowly added thereto. After about 1 hour, a white solid was produced and filtered, and then the resulting product was washed with ethyl acetate (EA) and hexane to obtain 15.0 g (92%) of Target Compound 8-4.

Preparation of Compound 8-5

15 g (36.74 mmol) of Compound 8-4, 3.4 mL (36.74 mmol) of $POCl_3$, and 150 mL of nitrobenzene were put into a vessel, the resulting mixture was refluxed for 1 hour and cooled to room temperature, and then 12.04 mL (102.87 mmol) of $SnCl_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was washed with methanol (MeOH) and hexane to obtain 11.1 g (77%) of Target Compound 8-5.

Preparation of Compound 110

5 g (12.81 mmol) of Compound 8-5, 6.37 g (14.09 mmol) of (3,5-di(9H-carbazol-9-yl)phenyl)boronic acid, 0.74 g (0.64 mmol) of $Pd(PPh_3)_4$, and 3.5 g (25.62 mmol) of $K_2CO_3$ were refluxed along with 50 mL of toluene, 5 mL of ethanol, and 5 mL of $H_2O$ at 120° C. for 6 hours. After completion of the reaction, the reaction product was cooled to room temperature, and then extracted with distilled water and ethyl acetate (EA). After the organic layer was dried over anhydrous $MgSO_4$, the solvent was removed by a rotary evaporator, and then the resulting product was purified by column chromatography using dichloromethane and hexane as an eluting solvent to obtain 7.1 g (77%) of Compound 110.

<Preparation Example 16> Preparation of Compound 119

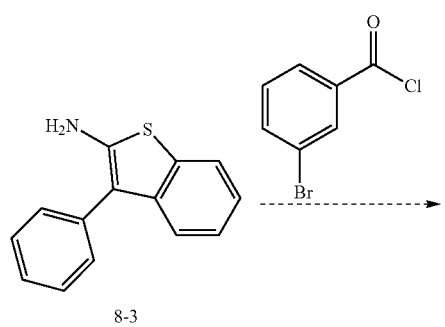

8-3

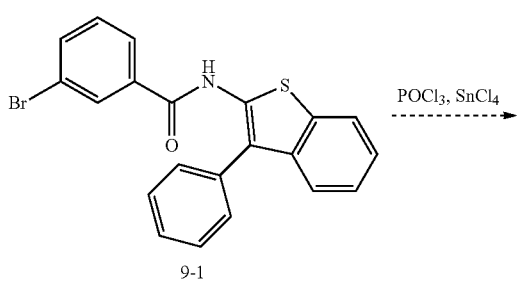

9-1

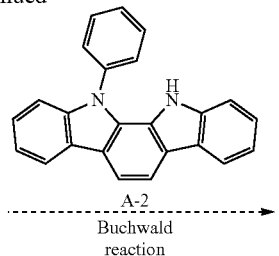

9-2

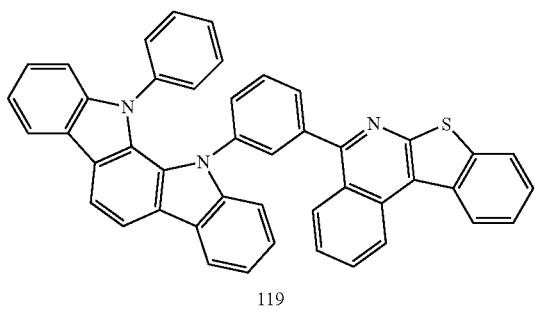

119

Preparation of Compound 9-1

10 g (44.38 mmol) of Compound 8-3 was completely dissolved in methylene chloride (MC), and then the resulting solution was stirred along with 6.2 mL (44.38 mmol) of TEA at room temperature for 15 minutes. Thereafter, the solution was maintained at 0° C., and then 9.7 g (44.38 mmol) of 3-bromo benzoylchloride was slowly added thereto. After about 1 hour, a white solid was produced and filtered, and then the resulting product was washed with ethyl acetate (EA) and hexane to obtain 17.7 g (98%) of Target Compound 9-1.

Preparation of Compound 9-2

15 g (36.74 mmol) of Compound 9-1, 3.4 mL (36.74 mmol) of $POCl_3$, and 150 mL of nitrobenzene were put into a vessel, the resulting mixture was refluxed for 1 hour and cooled to room temperature, and then 12.04 mL (102.87 mmol) of $SnCl_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous $MgSO_4$, the solvent was removed by a rotary evaporator, and then the resulting product was washed with methanol (MeOH) and hexane to obtain 9.18 g (64%) of Target Compound 9-2.

Preparation of Compound 119

8 g (20.5 mmol) of Compound 9-2, 6.1 g (18.44 mmol) of Compound A-2, 0.38 g (0.41 mmol) of $Pd_2(dba)_3$, 0.47 g (0.82 mmol) of XantPhos, and 8.3 g (41.0 mmol) of NaOtBu were refluxed along with 80 mL of toluene at 130° C. for 3 hours. After completion of the reaction, the reaction product was cooled to room temperature, and then extracted with distilled water and ethyl acetate (EA). After the organic layer was dried over anhydrous $MgSO_4$, the solvent was removed by a rotary evaporator, and then the resulting product was purified by column chromatography using dichloromethane and hexane as an eluting solvent to obtain 6.8 g (52%) of Target Compound 119.

<Preparation Example 17> Preparation of Compound 156

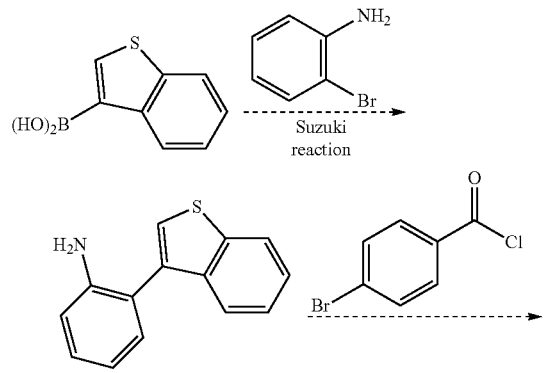

10-1

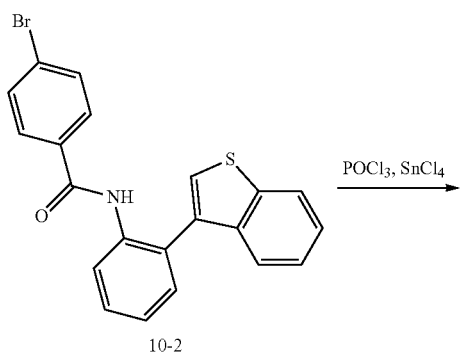

10-2

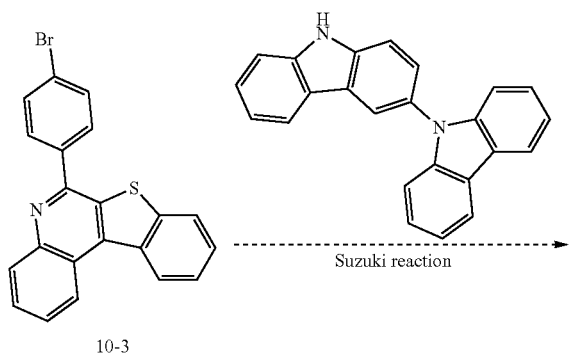

10-3

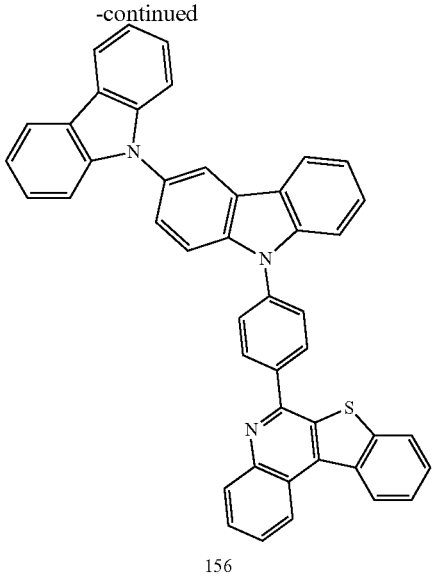

156

Preparation of Compound 10-1

20 g (112.34 mmol) of benzo[b]thiophen-3-ylboronic acid, 20.4 g (101.11 mmol) of 2-bromoanilline, 6.5 g (5.12 mmol) of Pd(PPh$_3$)$_4$, and 31.05 g (224.68 mmol) of K$_2$CO$_3$ were refluxed along with 200 mL of toluene, 40 mL of ethanol, and 40 mL of H$_2$O at 120° C. for 16 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was purified by column chromatography using dichloromethane and hexane as an eluting solvent to obtain 15.1 g (60%) of Compound 10-1.

Preparation of Compound 10-2

10 g (44.38 mmol) of Compound 10-1 was completely dissolved in methylene chloride (MC), and then the resulting solution was stirred along with 6.2 mL (44.38 mmol) of triethylamine (TEA) at room temperature for 15 minutes. Thereafter, the solution was maintained at 0° C., and then 9.7 g (44.38 mmol) of 4-bromo benzoylchloride was slowly added thereto. After about 1 hour, a white solid was produced and filtered, and then the resulting product was washed with ethyl acetate (EA) and hexane to obtain 15.9 g (88%) of Target Compound 10-2.

Preparation of Compound 10-3

15 g (36.74 mmol) of Compound 10-2, 3.4 mL (36.74 mmol) of POCl$_3$, and 150 mL of nitrobenzene were put into a vessel, the resulting mixture was refluxed for 1 hour and cooled to room temperature, and then 12.04 mL (102.87 mmol) of SnCl$_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous MgSO$_4$, the solvent was removed by a rotary evaporator, and then the resulting product was washed with methanol (MeOH) and hexane to obtain 9.47 g (66%) of Target Compound 10-3.

Preparation of Compound 156

5 g (12.81 mmol) of Compound 10-3, 5.1 g (15.37 mmol) of 9H-3,9'-bicarbazole, 0.74 g (0.64 mmol) of Pd(PPh$_3$)$_4$, and 3.5 g (25.62 mmol) of K$_2$CO$_3$ were refluxed along with 50 mL of toluene, 5 mL of ethanol, and 5 mL of H$_2$O at 120° C. for 5 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was purified by column chromatography using dichloromethane and hexane as an eluting solvent to obtain 6.3 g (77%) of Compound 156.

<Preparation Example 18> Preparation of Compound 185

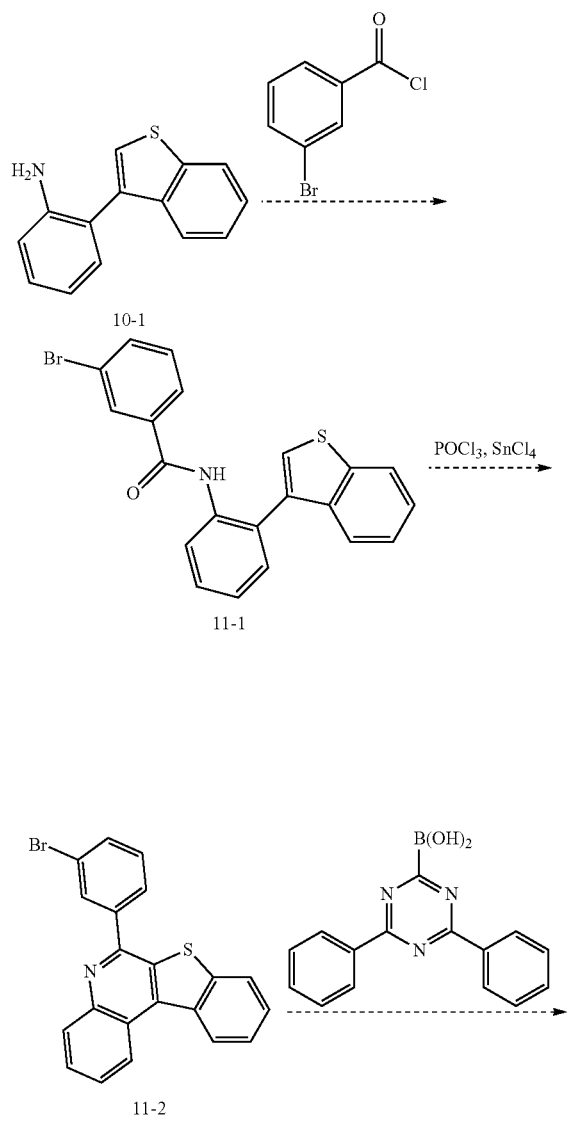

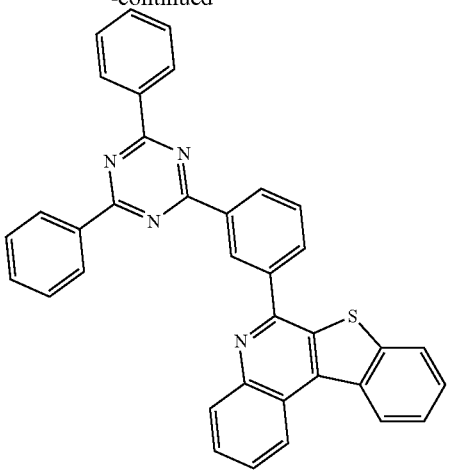

185

Preparation of Compound 11-1

10 g (44.38 mmol) of Compound 10-1 was completely dissolved in methylene chloride (MC), and then the resulting solution was stirred along with 6.2 mL (44.38 mmol) of triethylamine (TEA) at room temperature for 15 minutes. Thereafter, the solution was maintained at 0° C., and then 9.7 g (44.38 mmol) of 3-bromo benzoylchloride was slowly added thereto. After about 1 hour, a white solid was produced and filtered, and then the resulting product was washed with ethyl acetate (EA) and hexane to obtain 17.3 g (96%) of Target Compound 11-1.

Preparation of Compound 11-2

15 g (36.74 mmol) of Compound 11-1, 3.4 mL (36.74 mmol) of POCl$_3$, and 150 mL of nitrobenzene were put into a vessel, the resulting mixture was refluxed for 1 hour and cooled to room temperature, and then 12.04 mL (102.87 mmol) of SnCl$_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous MgSO$_4$, the solvent was removed by a rotary evaporator, and then the resulting product was washed with methanol (MeOH) and hexane to obtain 7.89 g (55%) of Target Compound 11-2.

Preparation of Compound 185

5 g (12.81 mmol) of Compound 11-2, 3.5 g (15.37 mmol) of (4,6-diphenyl-1,3,5-triazin-2-yl)boronic acid, 0.74 g (0.64 mmol) of Pd(PPh$_3$)$_4$, and 3.5 g (25.62 mmol) of K$_2$CO$_3$ were refluxed along with 50 mL of toluene, 5 mL of ethanol, and 5 mL of H$_2$O at 120° C. for 5 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was purified by column chromatography using dichloromethane and hexane as an eluting solvent to obtain 4.80 g (69%) of Compound 185.

<Preparation Example 19> Preparation of Compound 243

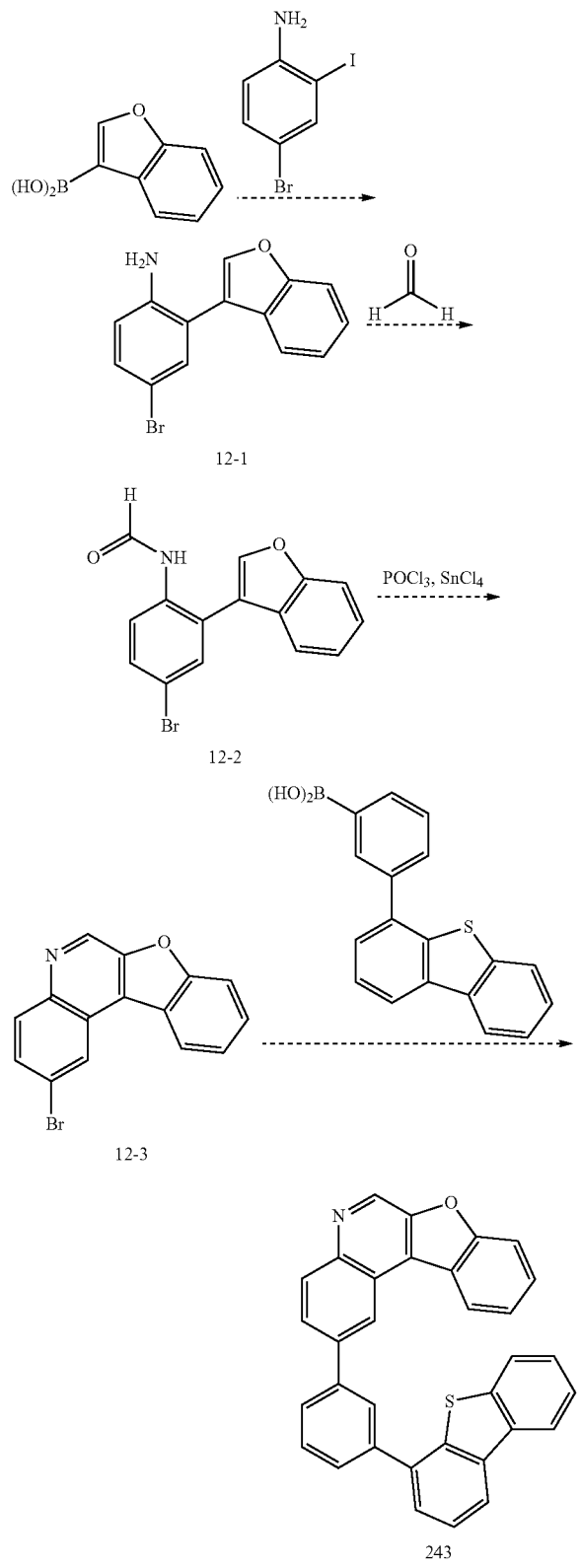

Preparation of Compound 12-1

20 g (123.49 mmol) of benzofuran-3-ylboronic acid, 36.4 g (123.49 mmol) of 4-bromo-2-iodoaniline, 14.2 g (12.35 mmol) of Pd(PPh$_3$)$_4$, and 51.2 g (370.47 mmol) of K$_2$CO$_3$ were refluxed along with 400 mL of toluene, 80 mL of ethanol, and 80 mL of H$_2$O at 120° C. for 24 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was purified by column chromatography using dichloromethane and hexane as an eluting solvent to obtain 28.8 g (81%) of Compound 12-1.

Preparation of Compound 12-2

3.9 mL of HCOH and 9.77 mL of acetic acid were put into a vessel, and the resulting mixture was stirred at 60° C. for 2 hours, and then cooled to room temperature. Thereafter, 360 mL of ethyl ether and 13.5 g (46.9 mmol) of Compound 12-1 were added thereto, and the resulting mixture was stirred at room temperature. After 1 hour, a solid produced was filtered and washed with ethyl ether to obtain 8.45 g (57%) of Target Compound 12-2.

Preparation of Compound 12-3

8.45 g (26.7 mmol) of Compound 12-2, 3.4 mL (36.74 mmol) of POCl$_3$, and 150 mL of nitrobenzene were put into a vessel, the resulting mixture was refluxed for 1 hour and cooled to room temperature, and then 12.04 mL (102.87 mmol) of SnCl$_4$ was slowly added dropwise thereto. After the resulting mixture was stirred under reflux for 2 hours, the reaction was completed, and then the resulting product was cooled to room temperature and extracted with distilled water and methylene chloride (MC). After the organic layer was dried over anhydrous MgSO$_4$, the solvent was removed by a rotary evaporator, and then the resulting product was washed with methanol (MeOH) and hexane to obtain 7.00 g (88%) of Target Compound 12-3.

Preparation of Compound 243

7 g (23.48 mmol) of Compound 12-3, 7.1 g (23.48 mmol) of (3-(dibenzo[b,d]thiophen-4-yl)phenyl)boronic acid, 2.7 g (2.35 mmol) of Pd(PPh$_3$)$_4$, and 9.73 g (70.44 mmol) of K$_2$CO$_3$ were refluxed along with 150 mL of toluene, 30 mL of ethanol, and 30 mL of H$_2$O at 120° C. for 7 hours. After completion of the reaction, the reaction product was cooled to room temperature, and then extracted with distilled water and ethyl acetate (EA). After the organic layer was dried over anhydrous MgSO$_4$, the solvent was removed by a rotary evaporator, and then the resulting product was purified by column chromatography using dichloromethane and hexane as an eluting solvent to obtain 8.75 g (78%) of Compound 243.

<Preparation Example 20> Preparation of Compound 245
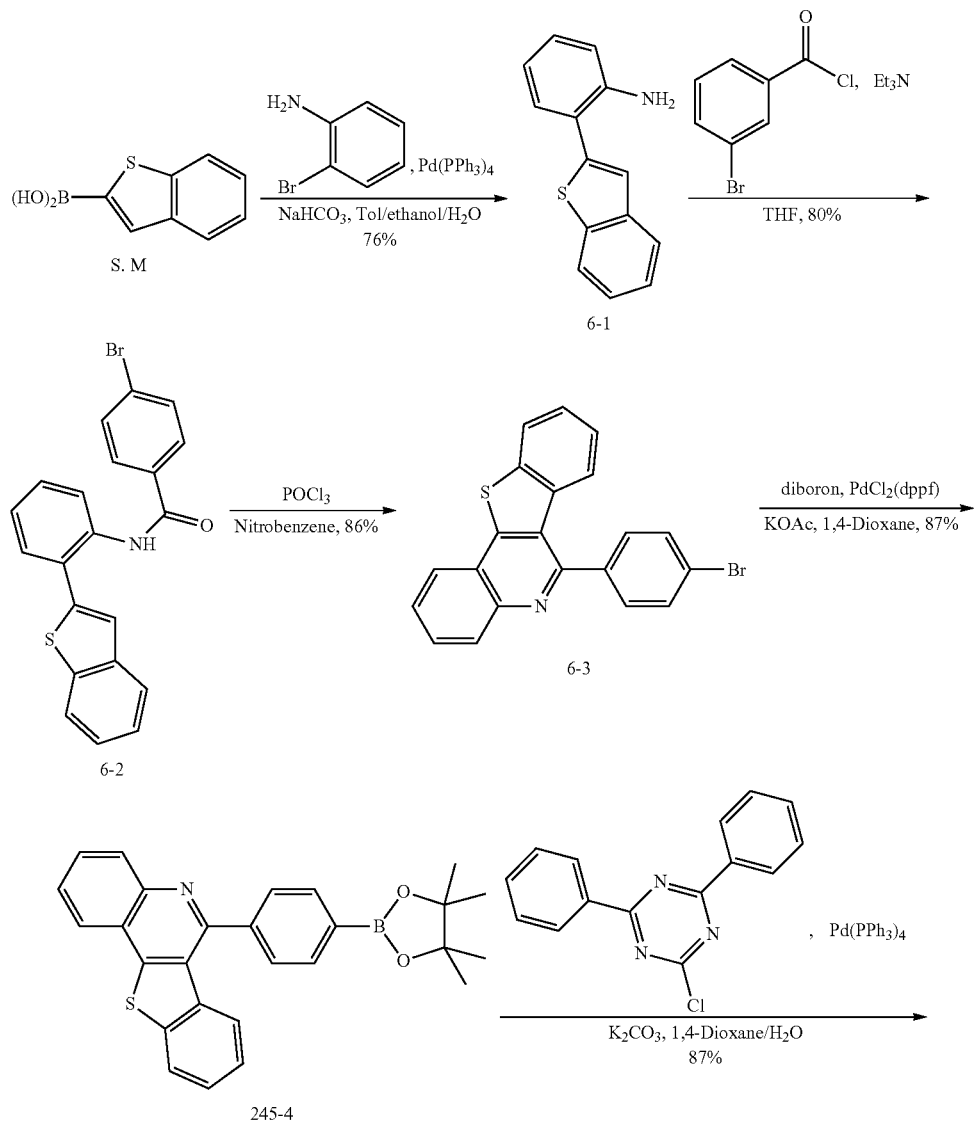
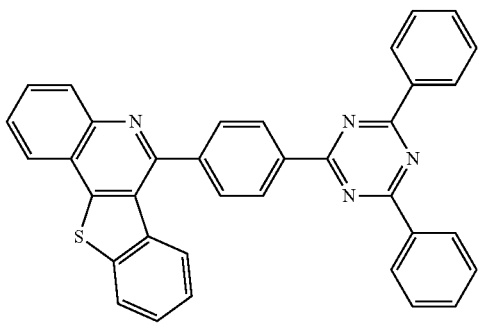

Preparation of Compound 6-1

A mixture of 2-bromoaniline (50 g, 290 mmol), tetrakis(triphenylphosphine)palladium(0) (16.75 g, 14.5 mmol), and sodiumbicarbonate (58.4 g, 696 mmol) in toluene/ethanol/water (1,000 ml/200 ml/200 ml) was refluxed at 100° C. for 1 hour in a one neck round bottom flask.

The temperature was lowered to 80° C., benzo[b]thiophen-2-ylboronic acid (62 g, 348 mmol) in a solid state was added thereto, and then the resulting mixture was stirred for 2 hours. The mixture was extracted with MC, and then the organic layer was dried over $MgSO_4$. After concentration, the mixture was separated by column chromatography ($SiO_2$, hexane:dichloromethane=1:1) (50 g, 76%).

Preparation of Compound 6-2

Triethyl amine (15.5 ml, 110 mmol) was added to a mixture of 6-1 (22.6 g, 100 mmol) and tetrahydrofuran (400 ml) in a one neck round bottom flask under nitrogen, and then the resulting mixture was stirred for 10 minutes. The temperature was lowered to 0° C., a mixture of 4-bromobenzoyl chloride (26.4 g, 120 mmol) in tetrahydrofuran (100 ml) was added thereto, and then the resulting mixture was stirred for 30 minutes. After the mixture was extracted with MC, the organic layer was concentrated, and then methanol was added thereto, and the resulting mixture was sonicated and then filtered (33 g, 81%).

Preparation of Compound 6-3

Phosphorus(V)oxychloride (7.2 ml, 77.8 mmol) was added to a mixture of 6-2 (31.8 g, 77.8 mmol) in nitrobenzene (320 ml) in a one neck round bottom flask filled with nitrogen, and then the resulting mixture was stirred at 150° C. for 2 hours. The reaction of the reactant was terminated with a saturated sodium bicarbonate aqueous solution at 0° C., and then the resulting product was extracted with dichloromethane. After concentration, nitrobenzene was removed, and then MeOH was added thereto, and the resulting mixture was stirred and then filtered (26.6 g, 87%).

Preparation of Compound 245-4

A mixture of 6-3 (26.6 g, 68.15 mmol), pinacol diboron (34.6 g, 136.3 mmol), $PdCl_2(dppf)$ (2.5 g, 3.4 mmol), and KOAc (20 g, 204 mmol) in 1,4-dioxane (70 ml) was refluxed at 120° C. for 3 hours in a one neck round bottom flask under nitrogen. The resulting product was extracted with dichloromethane, and then the organic layer was dried over magnesium sulfate. After concentration, the mixture was separated by column chromatography ($SiO_2$, hexane:dichloromethane=1:4).

Preparation of Compound 245

A mixture of 245-4 (6 g, 13.7 mmol), 2-chloro-4,6-diphenyl-1,3,5-triazine (4 g, 15.09 mmol), $Pd(PPh_3)_4$ (1.58 g, 1.37 mmol), and $K_2CO_3$ (3.78 g, 27.4 mmol) in 1,4-dioxane (120 ml)/$H_2O$ (30 ml) was stirred at 120° C. for 3 hours in a one neck round bottom flask. The reactant was filtered in a state of 110° C., and then the resulting product was washed with 1,4-dioxane and with $H_2O$ and MeOH (6.4 g, 87%).

<Preparation Example 21> Preparation of Compound 246

A preparation was performed in the same manner as in the preparation of Compound 245 in Preparation Example 20 to obtain Target Compound 246 (10.1 g, 76%), except that the compound 2-(4-bromophenyl)-1-phenyl-1H-benzo[d]imidazole was used instead of the compound 2-chloro-4,6-diphenyl-1,3,5-triazine.

<Preparation Example 22> Preparation of Compound 250

A preparation was performed in the same manner as in the preparation of Compound 245 in Preparation Example 20 to obtain Target Compound 250 (9.7 g, 78%), except that the compound 2-chloro-4,6-diphenylpyrimidine was used instead of the compound 2-chloro-4,6-diphenyl-1,3,5-triazine.

<Preparation Example 23> Preparation of Compound 248

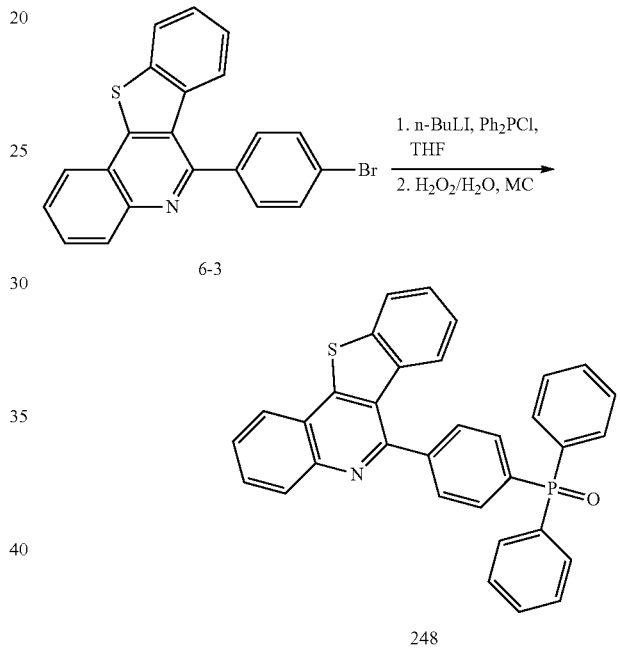

10 g (25.6 mmol) of Compound 6-3 was dissolved in 20 ml of anhydrous THF in a one neck round bottom flask under nitrogen, and then the resulting solution was cooled to −78° C. n-butyllithium (2.5 M in hexane) (10.2 ml, 25.6 mmol) was slowly added dropwise thereto, and then the resulting mixture was stirred for 1 hour. Chlorodiphenylphosphine (4.7 ml, 25.6 mmol) was added dropwise to the solution, and the resulting solution was stirred at room temperature for 12 hours. The reaction mixture was extracted with MC/$H_2O$, and then distilled under reduced pressure. The reaction mixture was dissolved in MC (200 ml), and then the resulting solution was stirred along with a 30% $H_2O_2$ aqueous solution (10 ml) at room temperature for 1 hour. The reaction mixture was extracted with MC/$H_2O$, and then the concentrated mixture was separated by column chromatography ($SiO_2$, MC:methanol=25:1) to obtain solid Compound 248 (7.2 g, 54%).

<Preparation Example 24> Preparation of Compound 253

A preparation was performed in the same manner as in the preparation of Compound 245 in Preparation Example 20 to obtain Target Compound 253 (11.5 g, 82%), except that the compound 4-([1,1'-biphenyl]-4-yl)-6-chloro-2-phenylpyrimidine was used instead of the compound 2-chloro-4,6-diphenyl-1,3,5-triazine.

<Preparation Example 25> Preparation of Compound 256

A preparation was performed in the same manner as in the preparation of Compound 245 in Preparation Example 20 to obtain Target Compound 256 (10.2 g, 72%), except that the compound 2-(4-bromophenyl)-4,6-diphenyl-1,3,5-triazine was used instead of the compound 2-chloro-4,6-diphenyl-1,3,5-triazine.

<Preparation Example 26> Preparation of Compound 259

A preparation was performed in the same manner as in the preparation of Compound 245 in Preparation Example 20 to obtain Target Compound 259 (7.3 g, 62%), except that the compound 4-bromo-2-phenylquinazoline was used instead of the compound 2-chloro-4,6-diphenyl-1,3,5-triazine.

<Preparation Example 27> Preparation of Compound 260

A preparation was performed in the same manner as in the preparation of Compound 245 in Preparation Example 20 to obtain Target Compound 260 (7.7 g, 69%), except that the compound 2-bromo-1,10-phenanthroline was used instead of the compound 2-chloro-4,6-diphenyl-1,3,5-triazine.

<Preparation Example 28> Preparation of Compound 261

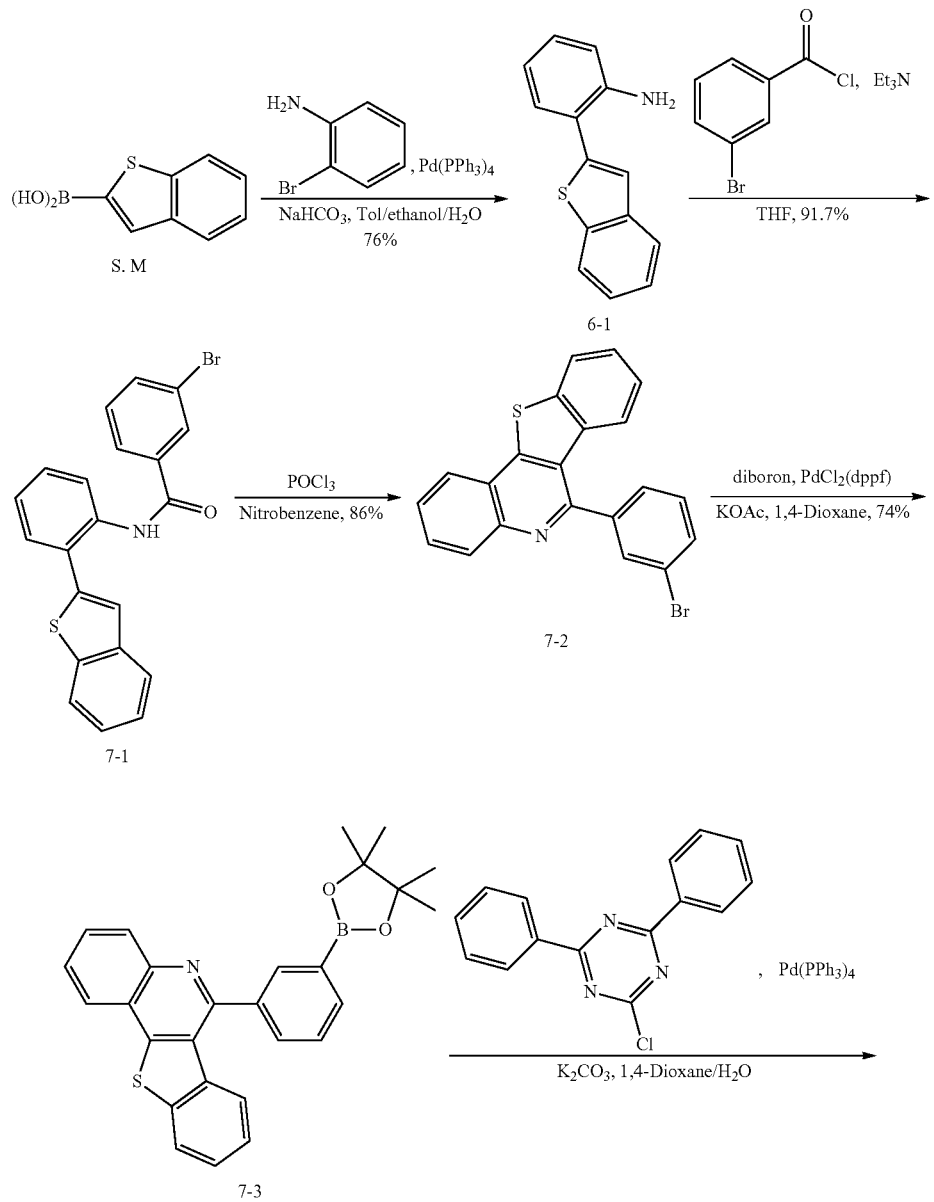

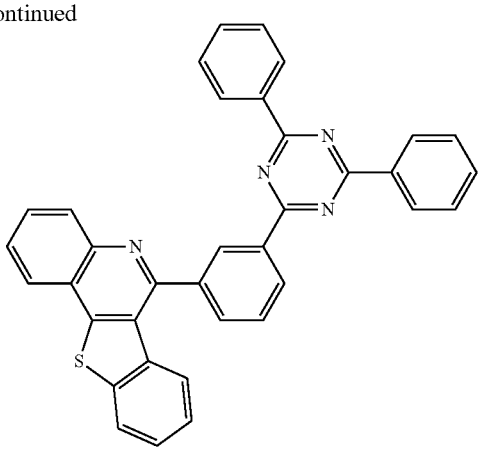

261

Preparation of Compound 7-1

Triethyl amine (26 ml, 186 mmol) was added to a mixture of 6-1 (35 g, 155 mmol) and tetrahydrofuran (600 ml) in a one neck round bottom flask under nitrogen, and then the resulting mixture was stirred for 10 minutes. The temperature was lowered to 0° C., a mixture of 3-bromobenzoyl chloride (40.8 g, 186 mmol) in tetrahydrofuran (150 ml) was added thereto, and then the resulting mixture was stirred for 30 minutes. After the mixture was extracted with MC, the organic layer was concentrated, and then methanol was added thereto, and the resulting mixture was sonicated and then filtered (58 g, 91.7%).

Preparation of Compound 7-2

Phosphorus(V)oxychloride (12 ml, 127 mmol) was added to a mixture of 7-1 (52 g, 127 mmol) in nitrobenzene (1,000 ml) in a one neck round bottom flask filled with nitrogen, and then the resulting mixture was stirred at 150° C. for 3 hours. The reaction of the reactant was terminated with a saturated sodium bicarbonate aqueous solution at 0° C., and then the resulting product was extracted with dichloromethane. After concentration, nitrobenzene was removed, and then MeOH was added thereto, and the resulting mixture was stirred and then filtered (43 g, 86%).

Preparation of Compound 7-3

A mixture of 7-2 (43 g, 110 mmol), pinacol diboron (56 g, 220 mmol), PdCl$_2$(dppf) (4 g, 5.5 mmol), and KOAc (32.3 g, 330 mmol) in 1,4-dioxane (400 ml) was refluxed at 120° C. for 3 hours in a one neck round bottom flask under nitrogen. The resulting product was extracted with dichloromethane, and then the organic layer was dried over magnesium sulfate. After concentration, silica gel filtration was performed, the mixture was stirred with MeOH and then filtered to obtain the title compound (36 g, 74%).

Preparation of Compound 261

A preparation was performed in the same manner as in the preparation of Compound 245 in Preparation Example 20 to obtain Target Compound 261 (9.4 g, 76%), except that Compound 7-3 was used instead of 245-4.

<Preparation Example 29> Preparation of Compound 274

A preparation was performed in the same manner as in the preparation of Compound 261 in Preparation Example 28 to obtain Target Compound 274 (11.1 g, 79%), except that the compound 4-([1,1'-biphenyl]-4-yl)-2-chloro-6-phenylpyrimidine was used instead of the compound 2-chloro-4,6-diphenyl-1,3,5-triazine.

<Preparation Example 30> Preparation of Compound 278

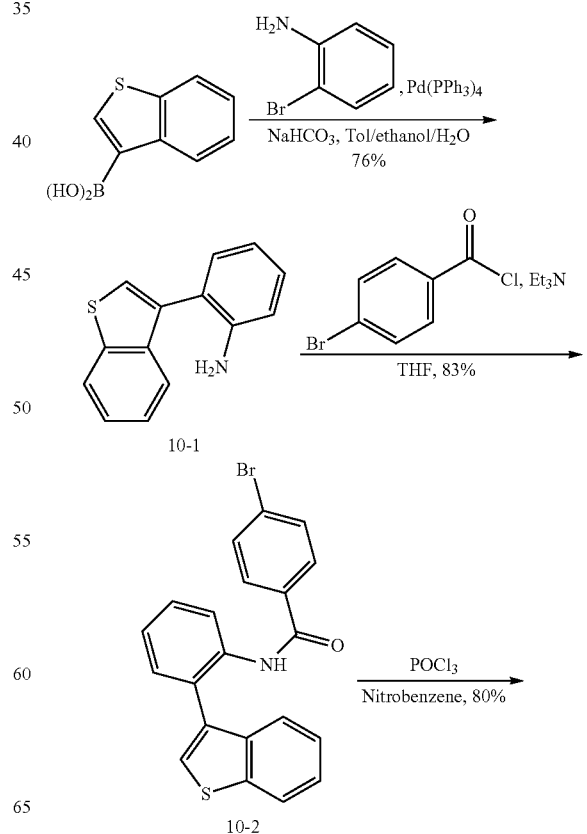

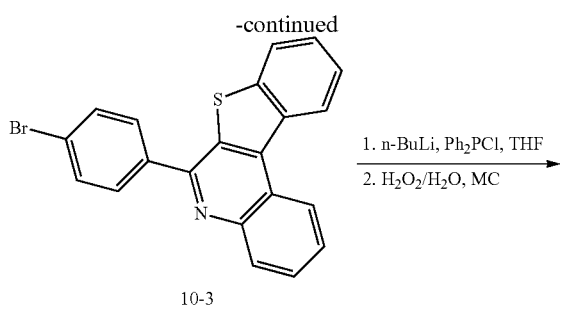

Preparation of Compound 10-1

A mixture of 2-bromoaniline (100 g, 580 mmol), tetrakis(triphenylphosphine)palladium(0) (33.5 g, 29 mmol), and sodiumbicarbonate (116.8 g, 1,392 mmol) in toluene/ethanol/water (2,000 ml/400 ml/400 ml) was refluxed at 100° C. for 1 hour in a one neck round bottom flask.

The temperature was lowered to 80° C., benzo[b]thiophen-3-ylboronic acid (124 g, 696 mmol) in a solid state was added thereto, and then the resulting mixture was stirred for 3 hours. The mixture was extracted with MC, and then the organic layer was dried over $MgSO_4$. After concentration, the mixture was separated by column chromatography ($SiO_2$, hexane:dichloromethane=1:1) (100 g, 76%).

Preparation of Compound 10-2

Triethyl amine (100 ml, 707 mmol) was added to a mixture of 10-1 (145 g, 643 mmol) and tetrahydrofuran (2,000 ml) in a one neck round bottom flask under nitrogen, and then the resulting mixture was stirred for 10 minutes. The temperature was lowered to 0° C., a mixture of 4-bromobenzoyl chloride (155.3 g, 707.9 mmol) in tetrahydrofuran (1,000 ml) was added thereto, and then the resulting mixture was stirred for 30 minutes. After the mixture was extracted with MC, the organic layer was concentrated, and then methanol was added thereto, and the resulting mixture was sonicated and then filtered (220 g, 83%).

Preparation of Compound 10-3

Phosphorus(V)oxychloride (55 ml, 592.6 mmol) was added to a mixture of 10-2 (220 g, 538.8 mmol) in nitrobenzene (2,000 ml) in a one neck round bottom flask filled with nitrogen, and then the resulting mixture was stirred at 150° C. for 3 hours. The reaction of the reactant was terminated with a saturated sodium bicarbonate aqueous solution at 0° C., and then the resulting product was extracted with dichloromethane. After concentration, nitrobenzene was removed, and then MeOH was added thereto, and the resulting mixture was stirred and then filtered (167 g, 80%).

Preparation of Compound 278

A preparation was performed in the same manner as in the preparation of Compound 248 in Preparation Example 23 to obtain Target Compound 278 (8.6 g, 69%), except that Compound 10-3 was used instead of 6-3.

<Preparation Example 31> Preparation of Compound 294

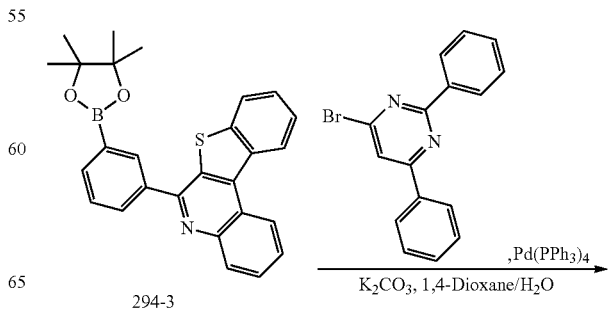

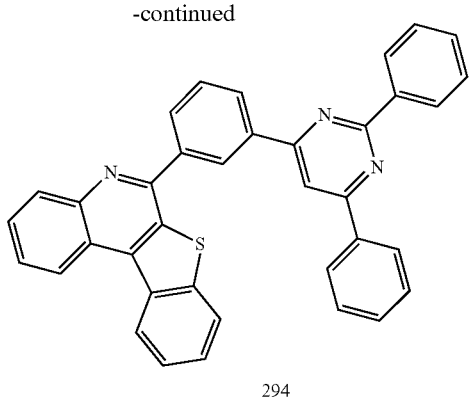

294

Preparation of Compound 11-1

Triethyl amine (26 ml, 186 mmol) was added to a mixture of 10-1 (35 g, 155 mmol) and tetrahydrofuran (600 ml) in a one neck round bottom flask under nitrogen, and then the resulting mixture was stirred for 10 minutes. The temperature was lowered to 0° C., a mixture of 4-bromobenzoyl chloride (40.8 g, 186 mmol) in tetrahydrofuran (100 ml) was added thereto, and then the resulting mixture was stirred for 30 minutes. After the mixture was extracted with MC, the organic layer was concentrated, and then methanol was added thereto, and the resulting mixture was sonicated and then filtered (58 g, 91%).

Preparation of Compound 11-2

Phosphorus(V)oxychloride (12 ml, 127 mmol) was added to a mixture of 11-1 (52 g, 127 mmol) in nitrobenzene (1,000 ml) in a one neck round bottom flask filled with nitrogen, and then the resulting mixture was stirred at 150° C. for 2 hours. The reaction of the reactant was terminated with a saturated sodium bicarbonate aqueous solution at 0° C., and then the resulting product was extracted with dichloromethane. After concentration, nitrobenzene was removed, and then MeOH was added thereto, and the resulting mixture was stirred and then filtered (43 g, 86%).

Preparation of Compound 294-3

A mixture of 11-2 (43 g, 110 mmol), pinacol diboron (56 g, 220 mmol), PdCl$_2$(dppf) (4 g, 5.5 mmol), and KOAc (32.3 g, 330 mmol) in 1,4-dioxane (400 ml) was refluxed at 120° C. for 3 hours in a one neck round bottom flask under nitrogen. The resulting product was extracted with dichloromethane, and then the organic layer was dried over magnesium sulfate. After concentration, silica gel filtration was performed, and after concentration, the mixture was stirred with MeOH and then filtered to obtain the title compound (36 g, 74%).

Preparation of Compound 294

A preparation was performed in the same manner as in the preparation of Compound 245 in Preparation Example 20 to obtain Target Compound 294 (9.8 g, 79%), except that Compound 294-3 and 4-bromo-2,6-diphenylpyrimidine were used instead of 245-4 and 2-chloro-4,6-diphenyl-1,3,5-triazine.

<Preparation Example 32> Preparation of Compound 309

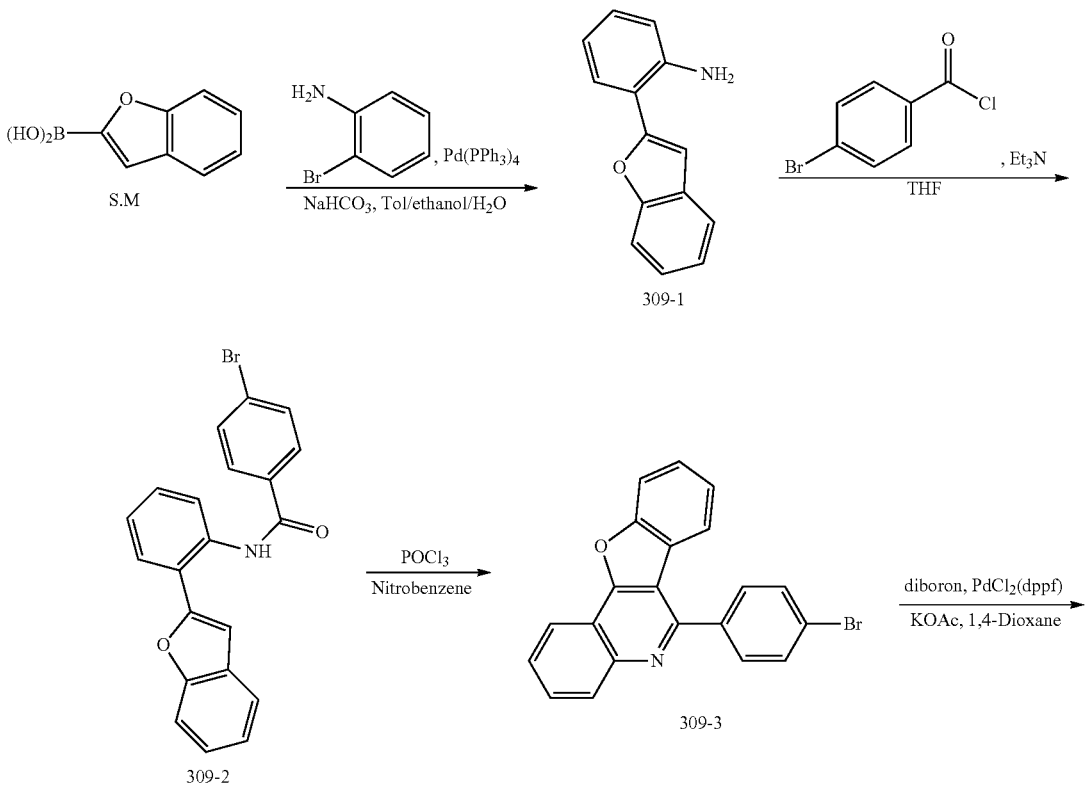

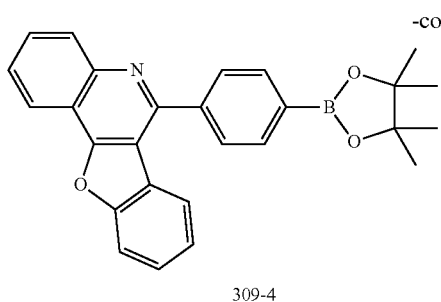

309-4

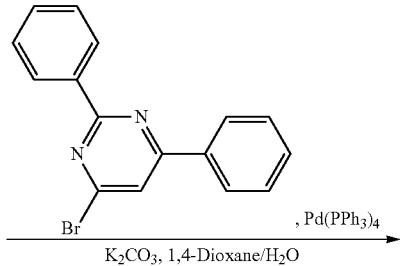

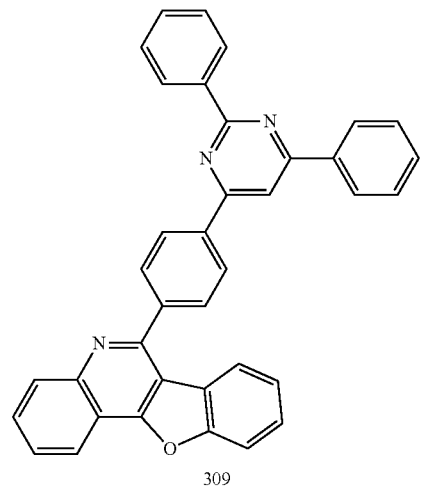

309

Preparation of Compound 309-4

A preparation was performed in the same manner as in the preparation of Compound 245-4 in Preparation Example 20 to obtain Target Compound 309-4, except that the compound benzofuran-2-ylboronic acid was used instead of benzo[b]thiophen-2-ylboronic acid.

Preparation of Compound 309

A preparation was performed in the same manner as in the preparation of Compound 245 in Preparation Example 20 to obtain Target Compound 309 (9.2 g, 73%), except that Compound 309-4 and 4-bromo-2,6-diphenylpyrimidine were used instead of 245-4 and 2-chloro-4,6-diphenyl-1,3,5-triazine.

<Preparation Example 33> Preparation of Compound 321

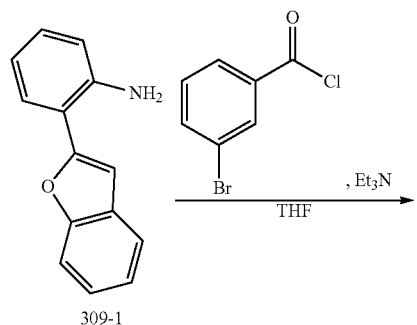

309-1

-continued

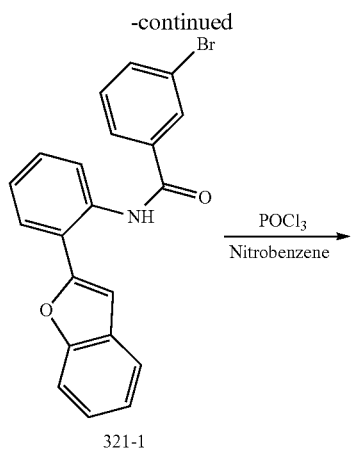

321-1

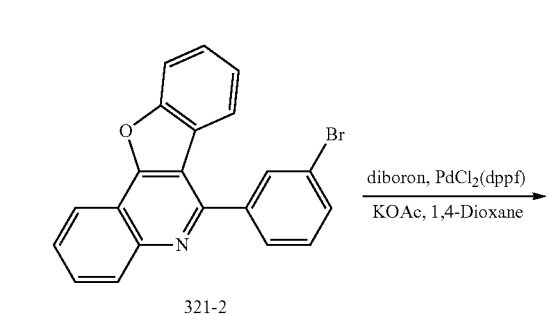

321-2

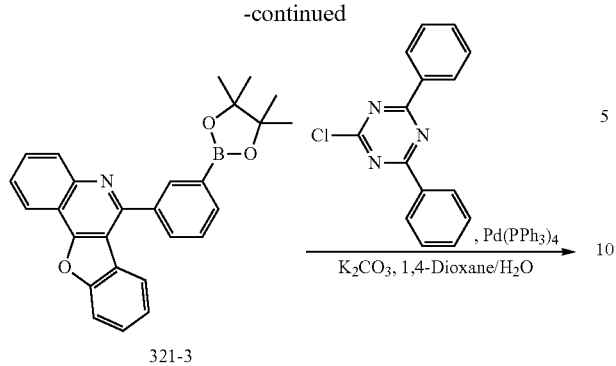

321-3

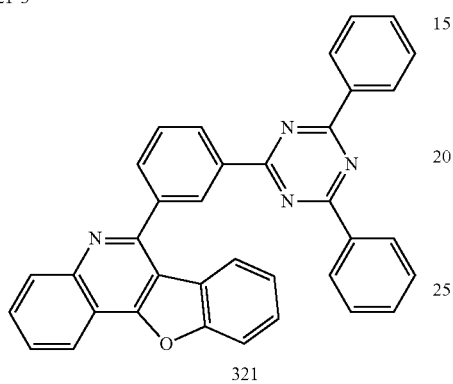

321

Preparation of Compound 321-3

A preparation was performed in the same manner as in the preparation of Compound 270-3 in Preparation Example 28 to obtain Target Compound 321-3, except that Compound 309-1 was used instead of 6-1.

Preparation of Compound 321

A preparation was performed in the same manner as in the preparation of Compound 245 in Preparation Example 20 to obtain Target Compound 321 (8.9 g, 71%), except that Compound 321-3 and 2-chloro-4,6-diphenyl-1,3,5-triazine were used instead of 245-4 and 2-chloro-4,6-diphenyl-1,3,5-triazine.

<Preparation Example 34> Preparation of Compound 343

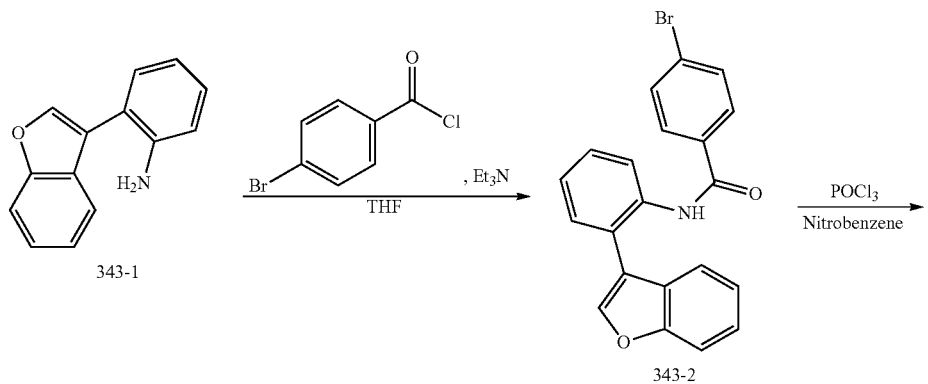

343-1        343-2

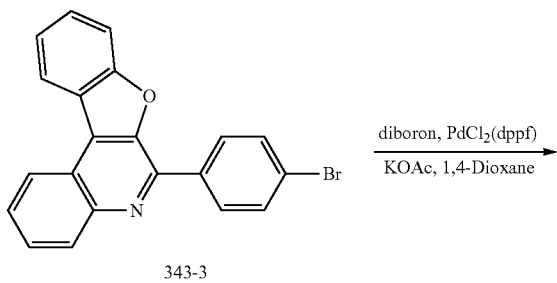

343-3

-continued

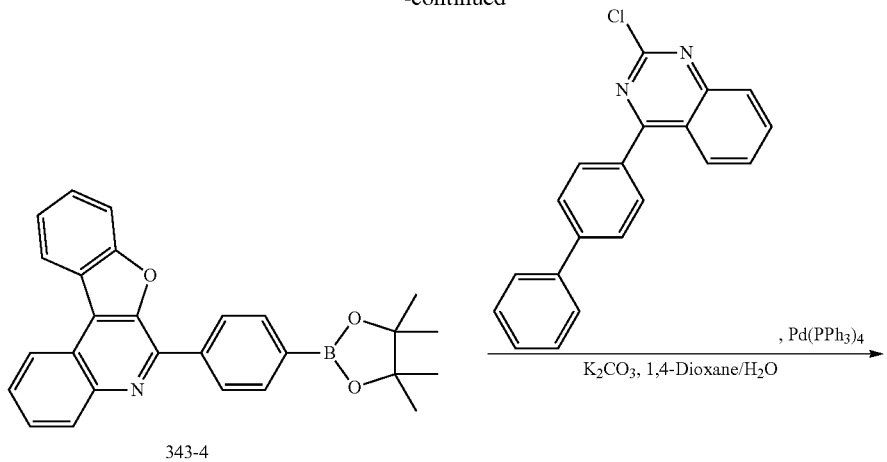

343-4

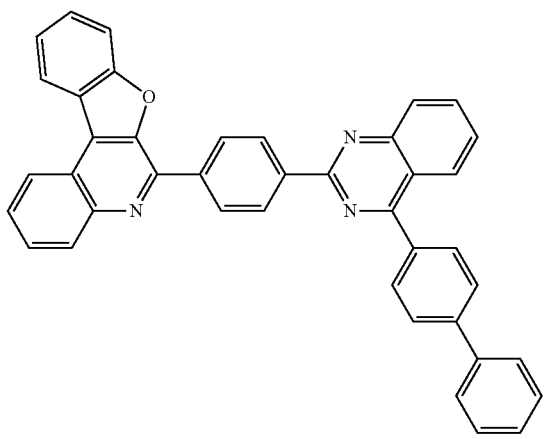

343

Preparation of Compound 343-3

A preparation was performed in the same manner as in the preparation of Compound 10-3 in Preparation Example 30 to obtain Target Compound 343-3, except that Compound 343-1 was used instead of 10-1.

Preparation of Compound 343-4

A mixture of 343-3 (21.5 g, 55 mmol), pinacol diboron (28 g, 110 mmol), PdCl$_2$(dppf) (2 g, 2.7 mmol), and KOAc (14 g, 165 mmol) in 1,4-dioxane (200 ml) was refluxed at 120° C. for 4 hours in a one neck round bottom flask under nitrogen. The resulting product was extracted with dichloromethane, and then the organic layer was dried over magnesium sulfate. After concentration, silica gel filtration was performed, and after concentration, the resulting product was stirred with MeOH and then filtered to obtain the title compound (18 g, 73%).

Preparation of Compound 343

A preparation was performed in the same manner as in the preparation of Compound 245 in Preparation Example 20 to obtain Target Compound 343 (9.3 g, 68%), except that Compound 343-4 and 4-([1,1'-biphenyl]-4-yl)-2-chloroquinazoline were used instead of 245-4 and 2-chloro-4,6-diphenyl-1,3,5-triazine.

<Preparation Example 35> Preparation of Compound 354
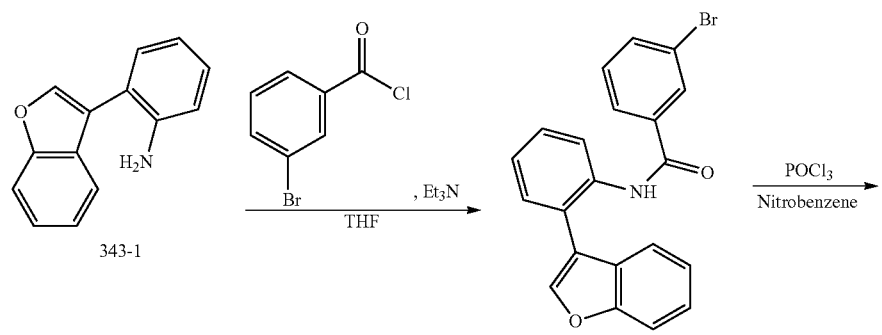
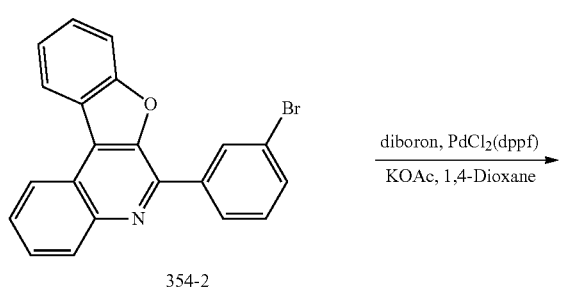
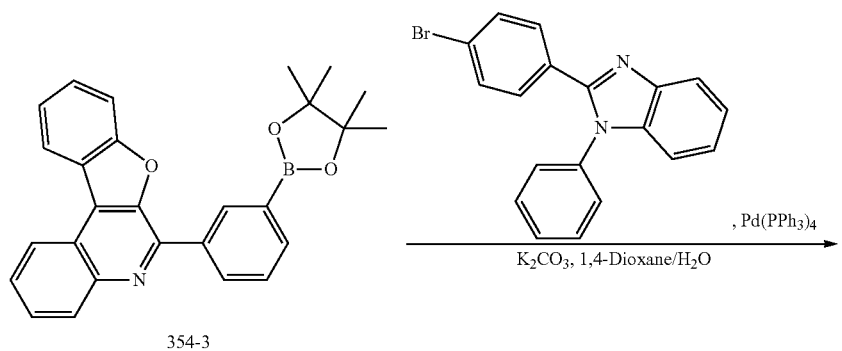
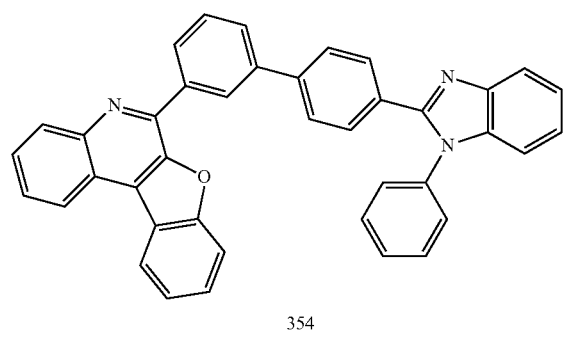

Preparation of Compound 354-3

A preparation was performed in the same manner as in the preparation of Compound 294-3 in Preparation Example 31 to obtain Target Compound 354-3, except that Compound 343-1 was used instead of 10-1.

Preparation of Compound 354

A preparation was performed in the same manner as in the preparation of Compound 245 in Preparation Example 20 to obtain Target Compound 354 (10.2 g, 76%), except that Compound 354-3 and 2-(4-bromophenyl)-1-phenyl-1H-benzo[d]imidazole were used instead of Compound 245-4 and 2-chloro-4,6-diphenyl-1,3,5-triazine.

<Preparation Example 36> Preparation of Compound 370

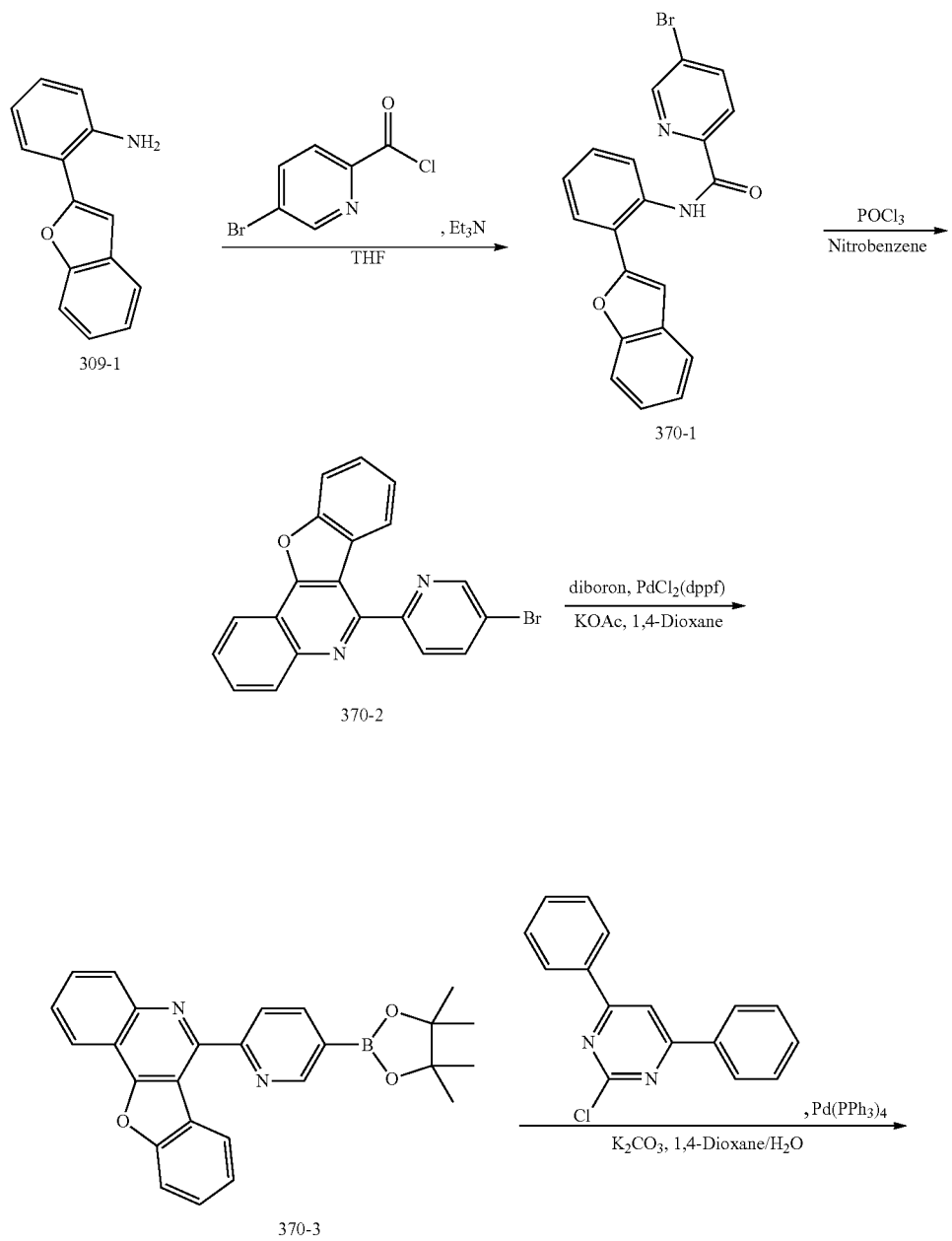

-continued

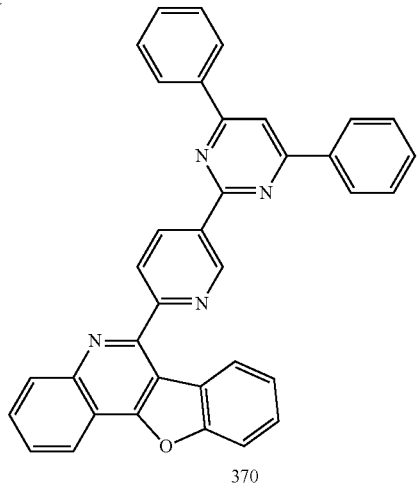

370

Preparation of Compound 370-3

A preparation was performed in the same manner as in the preparation of Compound 309-4 in Preparation Example 32 to obtain Target Compound 370-3, except that the compound 5-bromopicolinoyl chloride was used instead of 4-bromobenzoyl chloride.

Preparation of Compound 370

A preparation was performed in the same manner as in the preparation of Compound 245 in Preparation Example 20 to obtain Target Compound 370 (9.6 g, 77%), except that Compound 370-3 and 2-chloro-4,6-diphenylpyrimidine were used instead of 245-4 and 2-chloro-4,6-diphenyl-1,3,5-triazine.

<Preparation Example 37> Preparation of Compound 373

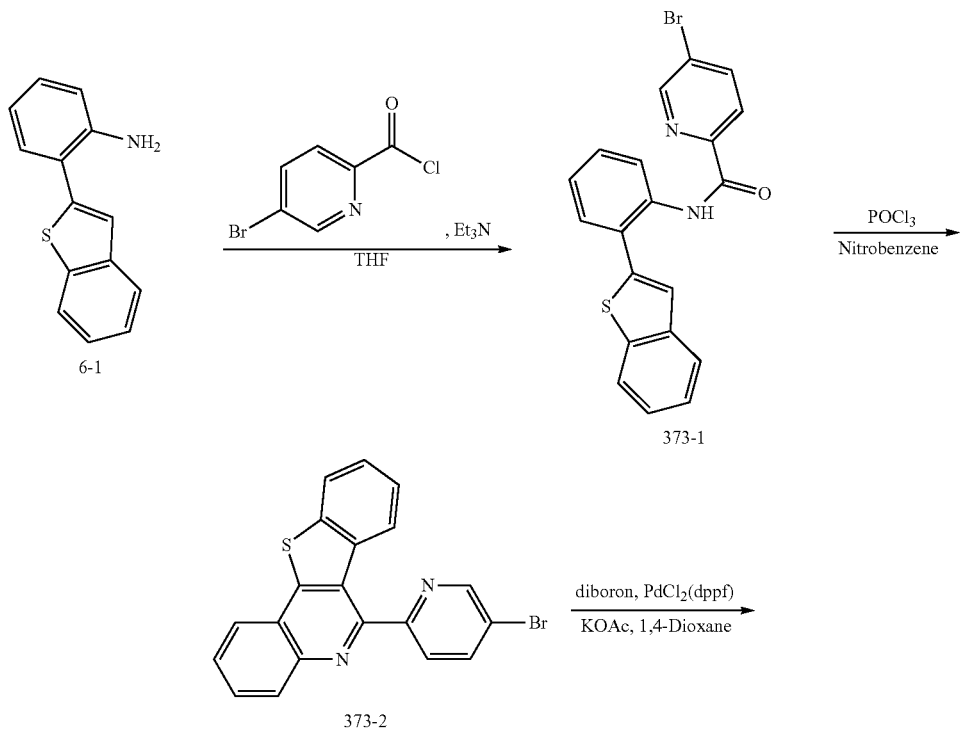

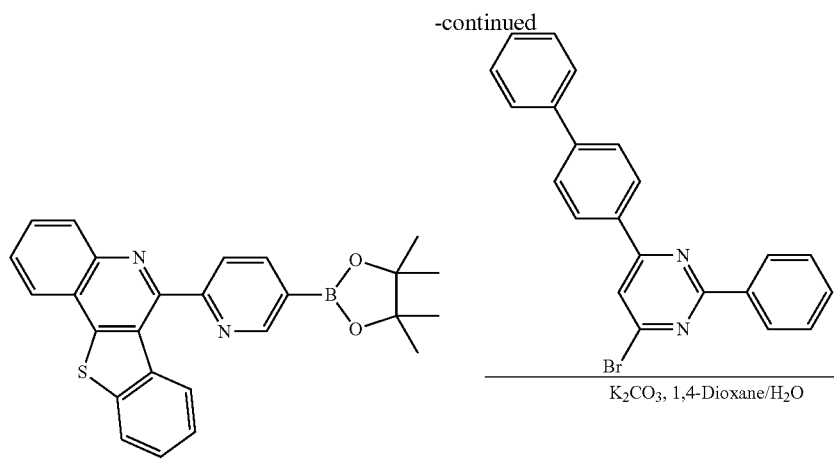

373-3

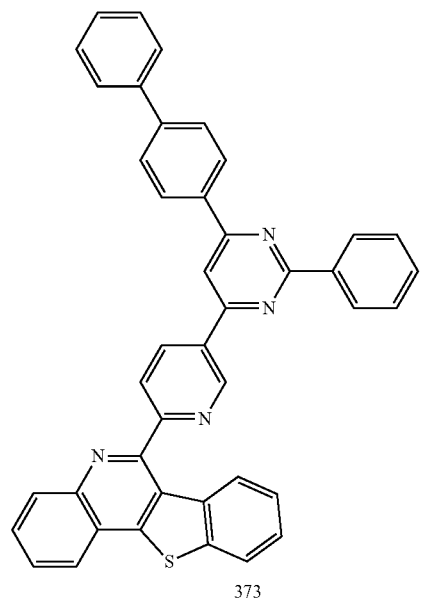

373

Preparation of Compound 373-3

A preparation was performed in the same manner as in the preparation of Compound 370-3 in Preparation Example 36 to obtain Target Compound 373-3, except that Compound 6-1 was used instead of 309-1.

Preparation of Compound 373

A preparation was performed in the same manner as in the preparation of Compound 245 in Preparation Example 20 to obtain Target Compound 370 (12.4 g, 87%), except that Compound 373-3 and 2-chloro-4,6-diphenylpyrimidine were used instead of 245-4 and 2-chloro-4,6-diphenyl-1,3,5-triazine.

<Preparation Example 38> Preparation of Compound 419

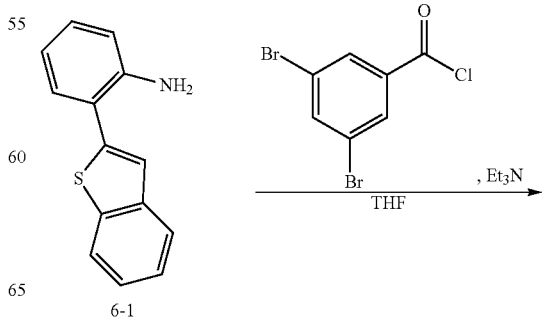

6-1

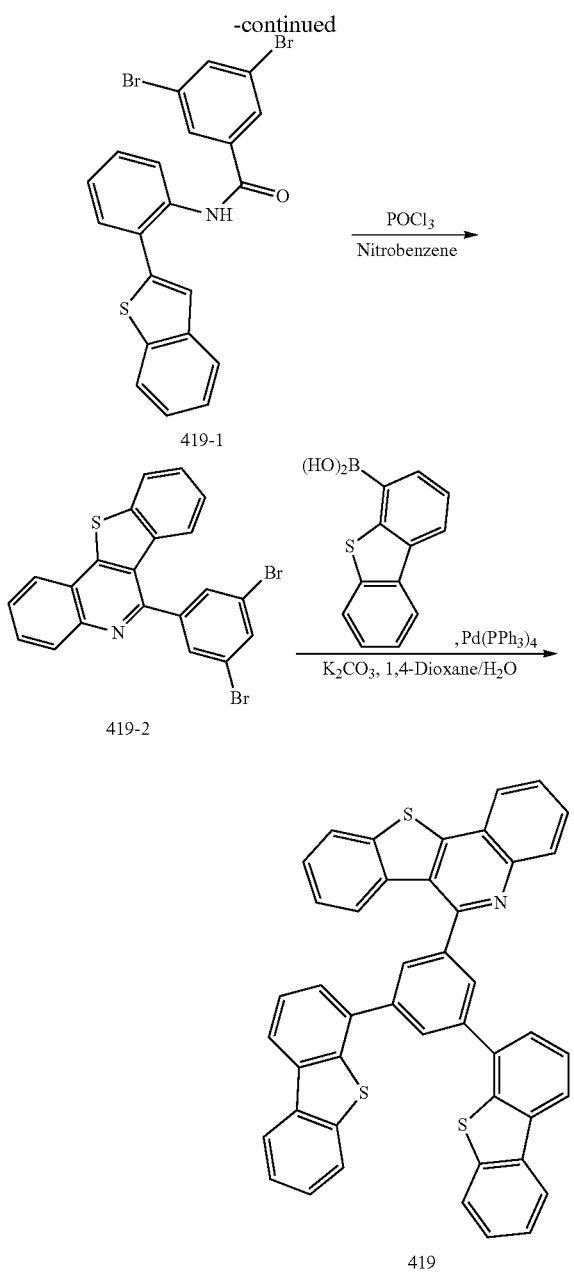

Preparation of Compound 419-1

Triethyl amine (34 ml, 244 mmol) was added to a mixture of 6-1 (50 g, 221.9 mmol) and tetrahydrofuran (800 ml) in a one neck round bottom flask under nitrogen, and then the resulting mixture was stirred for 10 minutes. The temperature was lowered to 0° C., a mixture of 3,5-dibromobenzoyl chloride (100 g, 332.8 mmol) in tetrahydrofuran (200 ml) was added thereto, and then the resulting mixture was stirred for 30 minutes. After the mixture was extracted with MC, the organic layer was concentrated, and then methanol was added thereto, and the resulting mixture was sonicated and then filtered (107 g, 99%).

Preparation of Compound 419-2

Phosphorus(V)oxychloride (20 ml, 216 mmol) was added to a mixture of 419-1 (96 g, 197 mmol) in nitrobenzene (2,000 ml) in a one neck round bottom flask filled with nitrogen, and then the resulting mixture was stirred at 150° C. for 3 hours. The reaction of the reactant was terminated with a saturated sodium bicarbonate aqueous solution at 0° C., and then the dichloromethane was slightly added thereto and then an excessive amount of methanol was added thereto to solidify the product, and then the product was filtered (60 g, 65%).

Preparation of Compound 419

A mixture of 419-2 (7 g, 14.91 mmol), dibenzo[b,d]thiophen-4-ylboronic acid (12.12 g, 37.29 mmol), Pd(PPh$_3$)$_4$ (1.72 g, 1.49 mmol), and K$_2$CO$_3$ (8.2 g, 59.64 mmol) in 1,4-dioxane (100 ml)/H$_2$O (20 ml) was stirred at 120° C. for 30 hours in a one neck round bottom flask. The reactant was filtered in a state of 110° C., and then the resulting product was washed with 1,4-dioxane at 110° C. (7.5 g, 74%).

<Preparation Example 39> Preparation of Compound 426

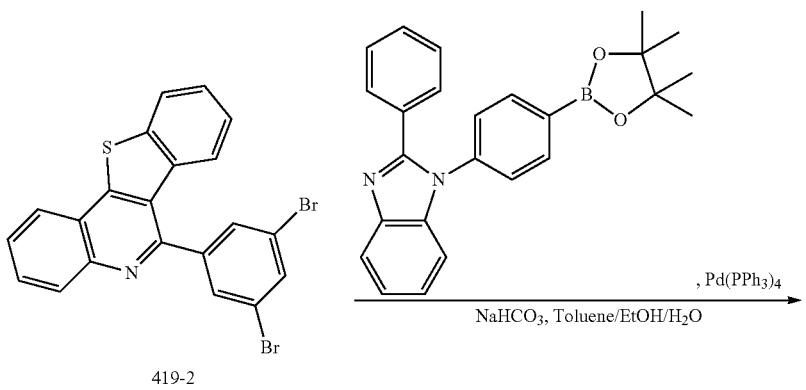

-continued
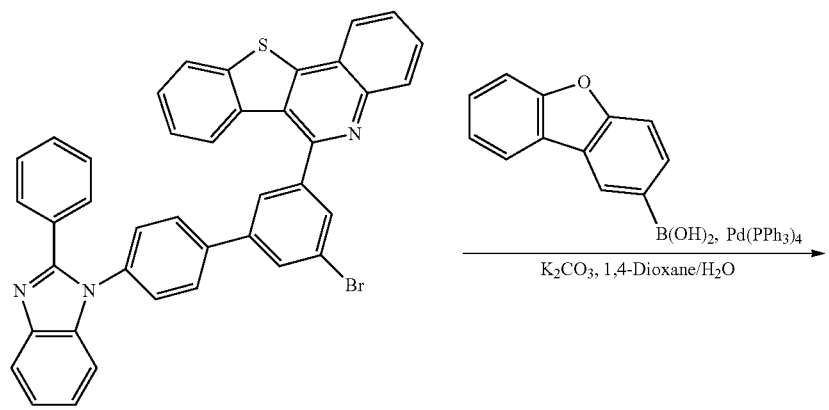
426-1
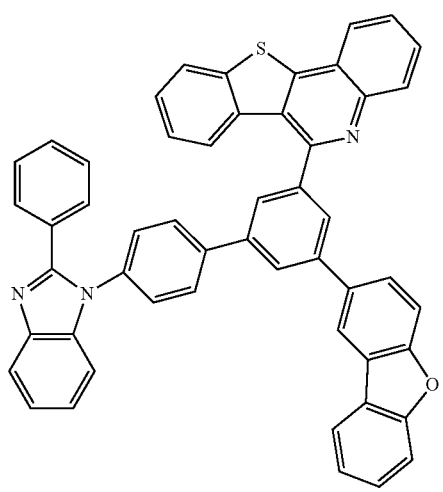
426

Preparation of Compound 426-1

A mixture of 419-2 (60 g, 127.8 mmol), 2-phenyl-1-(4-(4,4,5,5-tetramethyl-1,3,2-dioxaborolan-2-yl)phenyl)-1H-benzo[d]imidazole (55.7 g, 140.6 mmol), Pd(PPh₃)₄ (14.6 g, 12.7 mmol), and NaHCO₃ (21.4 g, 255.6 mmol) in toluene (1,000 ml)/EtOH (200 ml)/H₂O (200 ml) was stirred at 110° C. for 3 hours in a one neck round bottom flask. The reactant was extracted with MC, and then concentrated and separated by column chromatography (SiO₂, ethylacetate:dichloromethane=1:20) (47 g, 55%).

Preparation of Compound 426

A mixture of 426-1 (10.7 g, 15.16 mmol), dibenzo[b,d]furan-2-ylboronic acid (3.5 g, 16.67 mmol), Pd(PPh₃)₄ (1.7 g, 1.5 mmol), and K₂CO₃ (4.19 g, 30.32 mmol) in 1,4-dioxane (100 ml)/H₂O (20 ml) was stirred at 110° C. for 6 hours in a one neck round bottom flask. The reactant was extracted with MC, and then concentrated and separated by column chromatography (SiO₂, ethylacetate:dichloromethane=1:20) (8.3 g, 73%).

<Preparation Example 40> Preparation of Compound 437

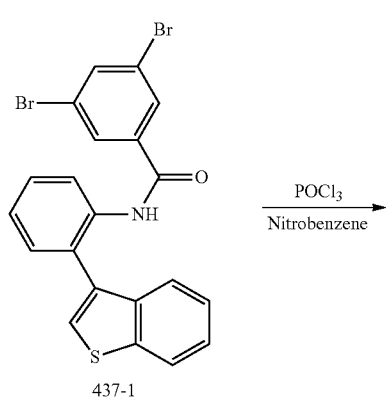

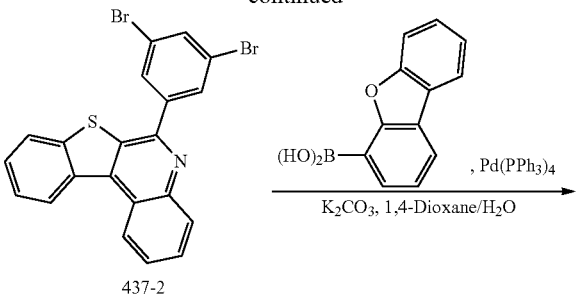

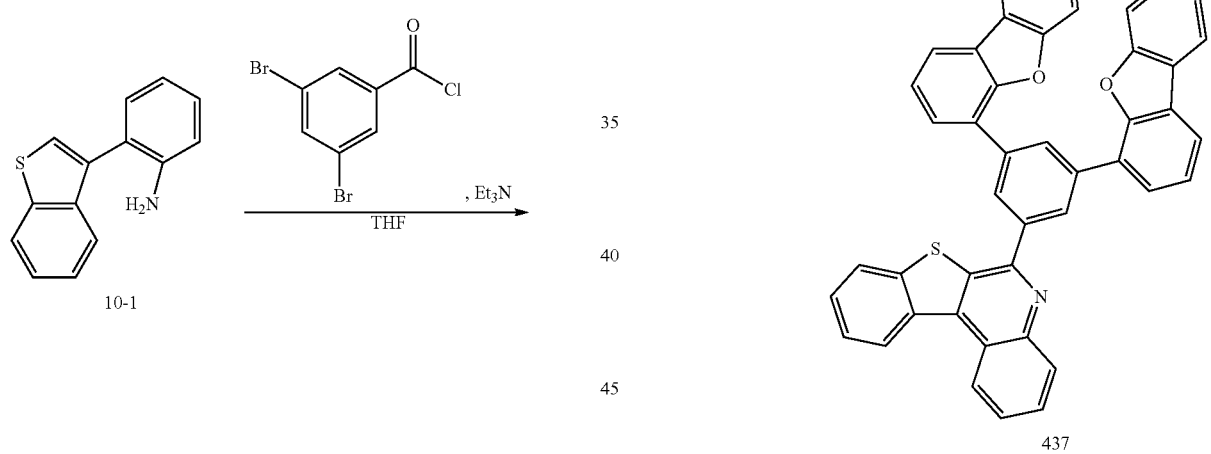

Preparation of Compound 437-2

A preparation was performed in the same manner as in the preparation of Compound 419-2 in Preparation Example 38 to obtain Target Compound 437-2, except that Compound 10-1 was used instead of 6-1.

Preparation of Compound 437

A preparation was performed in the same manner as in the preparation of Compound 419 in Preparation Example 38 to obtain Target Compound 437 (10.5 g, 76%), except that Compound 437-2 and dibenzo[b,d]furan-4-ylboronic acid were used instead of 419-2 and dibenzo[b,d]furan-2-ylboronic acid.

<Preparation Example 41> Preparation of Compound 454
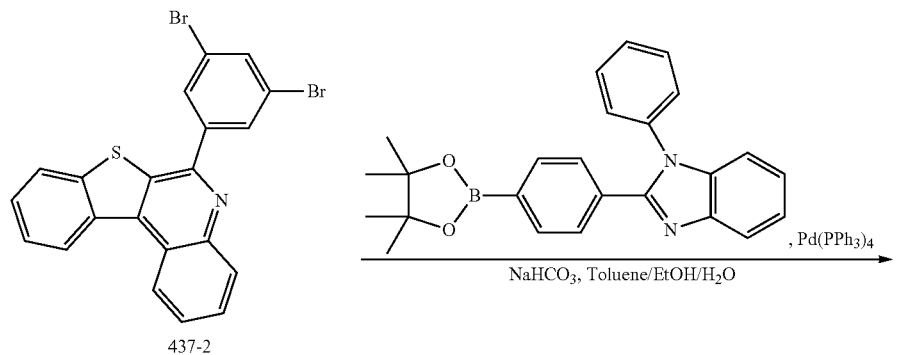
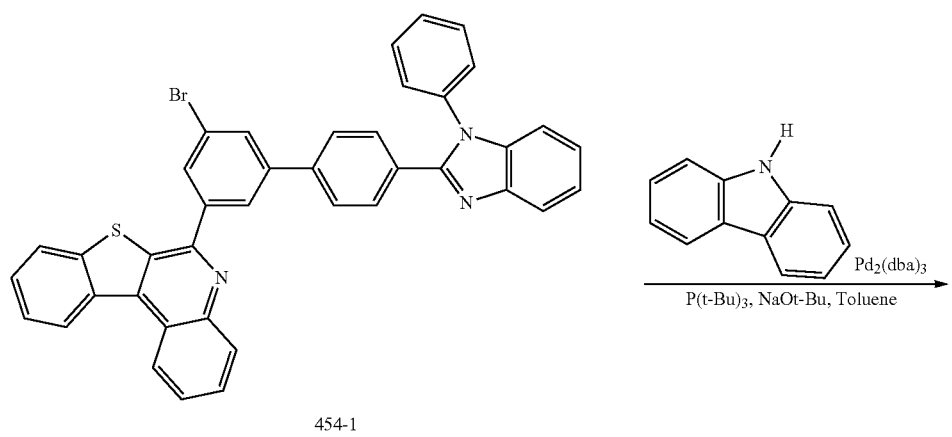
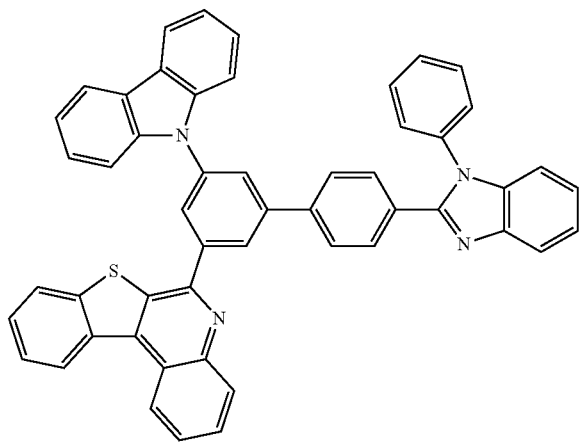

Preparation of Compound 454-1

A preparation was performed in the same manner as in the preparation of Compound 426-1 in Preparation Example 39 to obtain Target Compound 454-1, except that Compound 437-2 and 1-phenyl-2-(4-(4,4,5,5-tetramethyl-1,3,2-dioxaborolan-2-yl)phenyl)-1H-benzo[d]imidazole were used instead of 419-2 and 2-phenyl-1-(4-(4,4,5,5-tetramethyl-1,3,2-dioxaborolan-2-yl)phenyl)-1H-benzo[d]imidazole.

Preparation of Compound 454

A mixture of 454-1 (11.9 g, 18 mmol), 9H-carbazole (3.62 g, 21.6 mmol), Pd$_2$(dba)$_3$ (1.6 g, 1.8 mmol), P(t-Bu)$_3$ (6 ml, 5.4 mmol), and NaOt-Bu (3.45 g, 36 mmol) in toluene (100 ml) was stirred at 110° C. for 8 hours in a one neck round bottom flask. The reactant was extracted with MC, and then concentrated and separated by column chromatography (SiO$_2$, ethylacetate:dichloromethane=1:20) (11.5 g, 85%).

<Preparation Example 42> Preparation of Compound 379

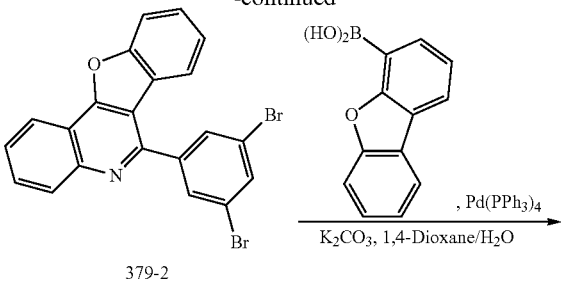

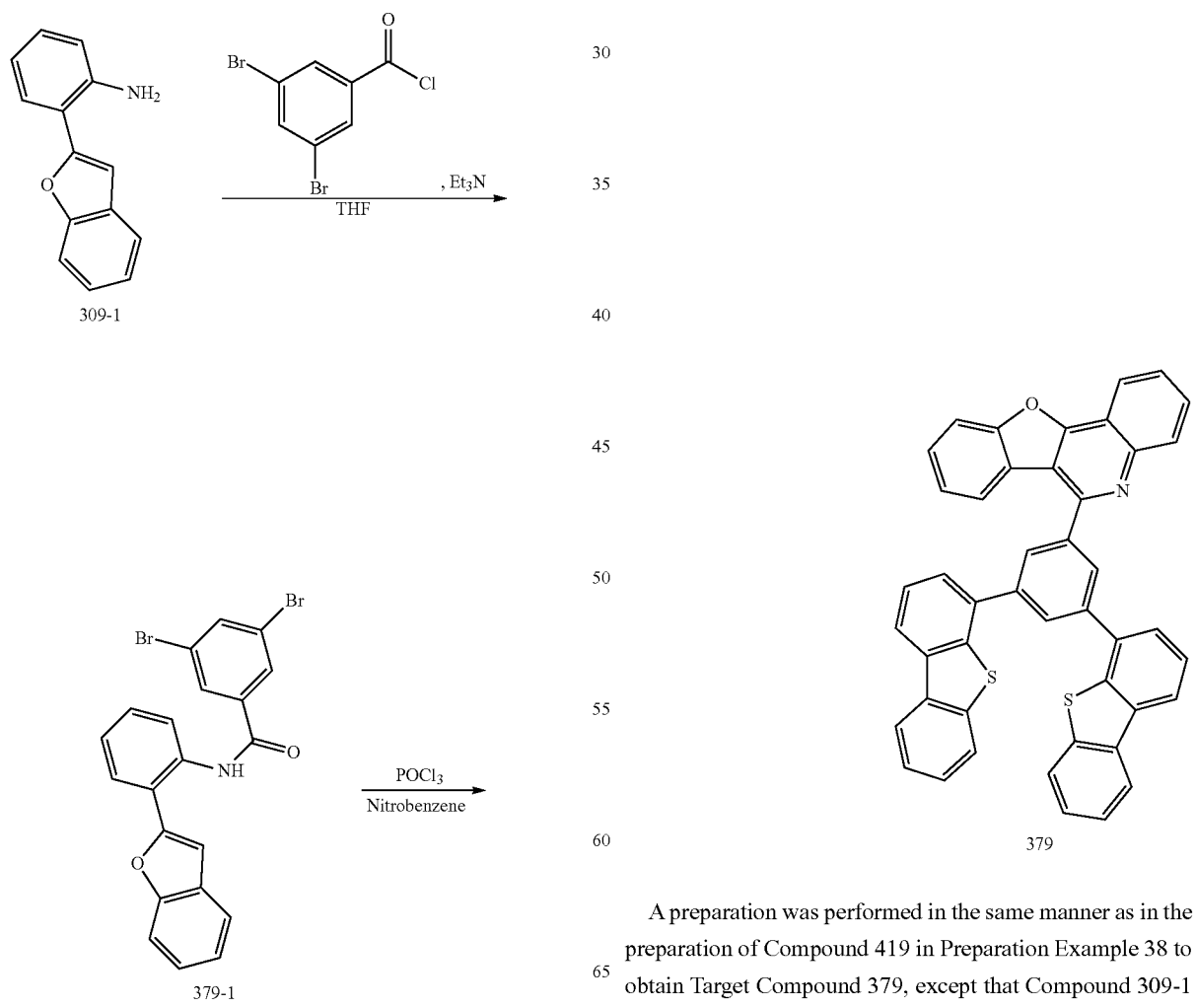

A preparation was performed in the same manner as in the preparation of Compound 419 in Preparation Example 38 to obtain Target Compound 379, except that Compound 309-1 was used instead of 6-1.

<Preparation Example 43> Preparation of Compound 386
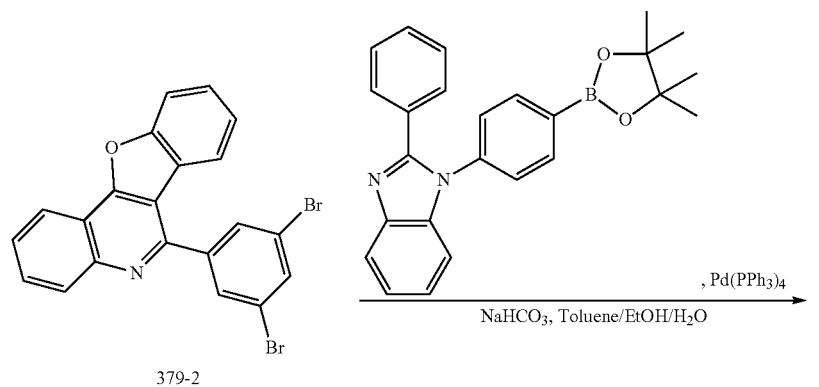
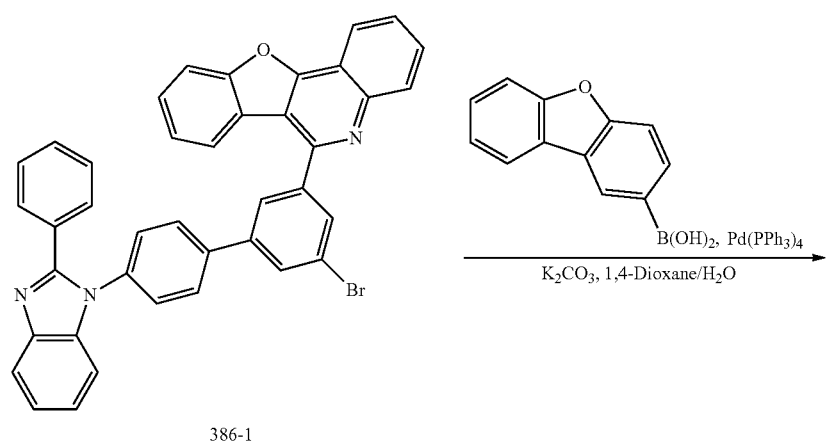
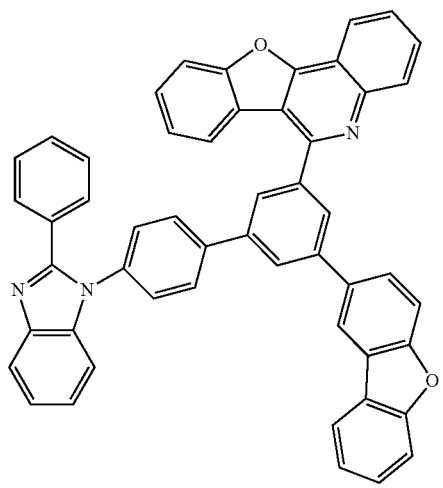

A preparation was performed in the same manner as in the preparation of Compound 426 in Preparation Example 39 to obtain Target Compound 386, except that Compound 379-2 was used instead of 419-2.

<Preparation Example 44> Preparation of Compound 397

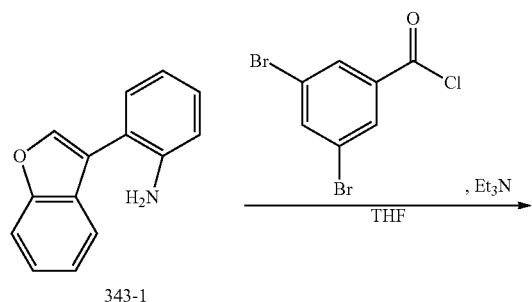

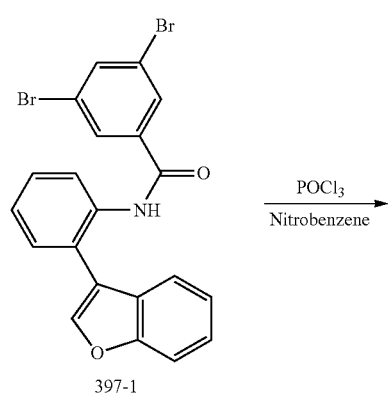

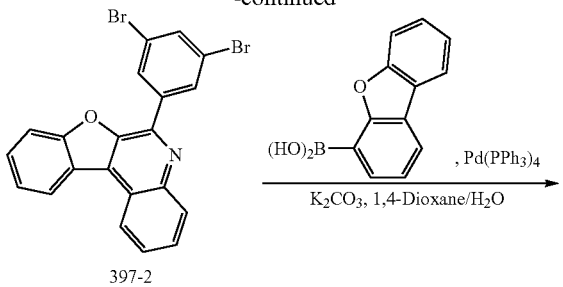

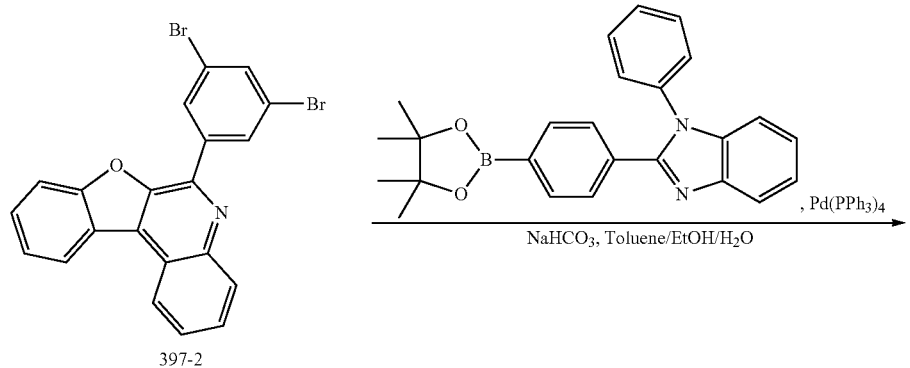

A preparation was performed in the same manner as in the preparation of Compound 437 in Preparation Example 40 to obtain Target Compound 397, except that Compound 343-1 was used instead of 10-1.

<Preparation Example 45> Preparation of Compound 414

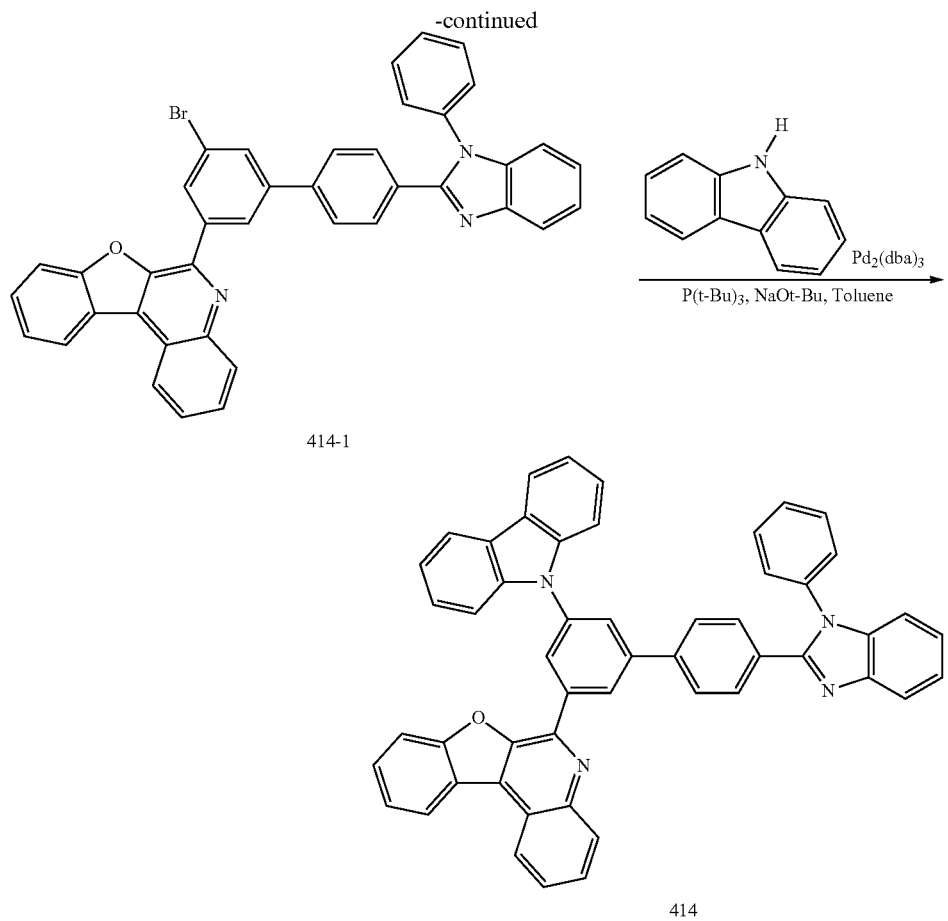

414-1

414

A preparation was performed in the same manner as in the preparation of Compound 454 in Preparation Example 41 to obtain Target Compound 414, except that Compound 397-2 was used instead of 437-2.

Compounds were prepared in the same manner as in the Preparation Examples, and the synthesis confirmation results thereof are shown in Tables 1 to 3.

TABLE 1

| Compound | $^1$H NMR (CDCl$_3$, 200 Mz) | MS/FAB found | MS/FAB calculated |
|---|---|---|---|
| 1 | δ = 7.16 (2H, m), 7.35~7.62 (11H, m), 7.93~8.12 (7H, m), 8.55 (2H, m), 9.32 (1H, s) | 565.69 | 565.16 |
| 16 | δ = 7.38~7.46 (17H, m), 7.65~7.69 (3H, m), 7.87~7.93 (3H, m), 8.05~8.08 (3H, m), 9.30 (1H, s) | 569.80 | 569.16 |
| 23 | δ = 7.42~7.62 (12H, m), 7.93~8.13 (12H, m), 8.30 (1H, d), 9.30 (1H, s) | 709.88 | 709.16 |
| 25 | δ = 7.25 (2H, d), 7.37~7.63 (6H, m), 7.88~8.09 (7H, m), 8.21 (4H, m), 8.69 (2H, d) | 613.78 | 613.19 |
| 29 | δ = 6.99~7.03 (4H, m), 7.17~7.23 (3H, m), 7.32~7.73 (11H, m), 7.84~7.88 (1H, t), 7.98~8.00 (1H, d), 8.17~8.23 (5H, m), 8.40~8.42 (1H, m), 8.64~8.66 (1H, d) | 641.79 | 641.19 |
| 42 | δ = 7.46~7.48 (2H, m), 7.57~7.67 (5H, m), 7.74~7.86 (3H, m), 7.92~7.97 (3H, m), 8.16~8.19 (4H, m), 8.39~8.41 (1H, d), 8.61~8.62 (1H, d) | 493.64 | 493.10 |
| 48 | δ = 7.42~7.55 (10H, m), 7.74~7.77 (5H, m), 7.87~7.97 (4H, m), 8.05 (1H, d), 8.48~8.52 (2H, m) | 511.58 | 511.12 |
| 51 | δ = 7.16 (2H, m), 7.35 (2H, m), 7.49~7.62 (11H, m), 7.89~7.94 (4H, m), 8.12 (1H, d), 8.21~8.28 (3H, m), 8.39~8.55 (3H, m) | 641.79 | 641.19 |
| 59 | δ = 7.49~7.73 (8H, m), 7.89~7.94 (4H, m), 8.25~8.45 (5H, m), 8.55 (1H, d) | 493.64 | 493.10 |
| 69 | δ = 7.16~7.20 (4H, m), 7.35 (2H, m), 7.49~7.61 (9H, m), 7.73 (1H, d), 7.89~7.94 (5H, m), 8.17~8.28 (6H, m), 8.39~8.55 (4H, m) | 717.89 | 717.22 |

TABLE 1-continued

| Compound | ¹H NMR (CDCl₃, 200 Mz) | MS/FAB found | MS/FAB calculated |
|---|---|---|---|
| 74 | δ = 7.00~7.24 (6H, m), 7.24 (4H, m), 7.37 (2H, d), 7.49~7.56 (2H, m), 7.70~7.94 (4H, m), 8.12~8.45 (4H, m) | 478.61 | 478.15 |
| 85 | δ = 7.16~7.20 (4H, m), 7.35 (2H, m), 7.49~7.60 (7H, m), 7.70 (1H, t), 7.85~7.94 (7H, m), 8.17~8.20 (5H, m), 8.45~8.69 (5H, m) | 717.89 | 717.22 |
| 86 | δ = 7.16 (2H, m), 7.35 (2H, m), 7.49~7.62 (11H, m), 7.85~7.94 (5H, m), 8.12~8.20 (3H, m), 8.45~8.60 (4H, m) | 641.79 | 641.19 |
| 87 | δ = 7.29~7.32 (1H, t), 7.44~7.55 (6H, m), 7.66~7.70 (1H, t), 7.76~7.82 (4H, m), 7.98~8.02 (3H, m), 8.14~8.21 (3H, m), 8.29~8.31 (1H, d) | 493.64 | 493.10 |
| 88 | δ = 7.19~7.21 (10H, m), 7.26~7.41 (10H, m), 7.60~7.67 (3H, m), 7.71~7.85 (4H, m), 7.93~7.98 (3H, m), 8.06~8.10 (2H, m), 8.38~8.40 (1H, d), 8.57 (1H, s) | 627.80 | 627.20 |
| 90 | δ = 7.18~7.25 (1H, t), 7.34~7.48 (11H, m), 7.57~7.69 (13H, m), 7.77~7.82 (2H, m), 7.93~7.99 (2H<, m), 8.18~8.22 (2H, d), 8.28~8.31 (1H, d) | 645.89 | 645.19 |
| 91 | δ = 7.18~7.43 (8H, m), 7.53~7.55 (1H, d), 7.63~7.94 (10H, m), 8.13~8.18 (3H, m), 8.26~8.28 (1H, d) | 552.69 | 552.17 |
| 92 | δ = 7.18~7.45 (12H, m), 7.58~7.81 (12H, m), 7.93~7.94 (2H, m), 8.01~8.04 (3H, m), 8.13~8.18 (5H, m), 8.26~8.28 (1H d) | 717.89 | 717.22 |
| 93 | δ = 7.16~7.20 (2H, m), 7.35~7.41 (2H, m), 7.50~7.52 (6H, m), 7.70~7.82 (4H, m), 7.96~8.04 (2H, m), 8.22~8.35 (6H, m), 8.99~9.00 (1H, d), 9.04 (1H, s) | 541.67 | 541.16 |
| 110 | δ = 7.16~7.20 (4H, m), 7.35 (2H, m), 7.50~7.60 (9H, m), 7.85~7.94 (7H, m), 8.17~8.19 (4H, m), 8.45~8.69 (5H, m) | 717.89 | 717.22 |
| 112 | δ = 7.38~7.56 (19H, m), 7.65 (2H, m), 7.88~7.97 (3H, m), 8.26 (2H, m), 8.45 (1H, d) | 569.80 | 569.16 |
| 119 | δ = 7.16 (2H, m), 7.35 (2H, m), 7.49~7.68 (12H, m), 7.88~7.94 (5H, m), 8.12~8.19 (2H, m), 8.45~8.55 (4H, m) | 641.79 | 641.19 |
| 130 | δ = 7.37~7.38 (5H, m), 7.49~7.69 (6H, m), 7.93~8.09 (6H, m), 8.21 (4H, m), 8.45 (1H, d), 9.30 (1H, s) | 537.68 | 537.16 |
| 134 | δ = 7.16~7.20 (3H, m), 7.35 (2H, m), 7.49~7.60 (7H, m), 7.69 (1H, d), 7.93~7.94 (3H, m), 8.07~8.08 (2H, m), 8.17~8.19 (4H, m), 8.45~8.55 (3H, m), 9.30 (1H, s) | 641.79 | 641.19 |
| 140 | δ = 7.11~7.18 (3H, m), 7.27~7.28 (3H, m), 7.38~7.56 (24H, m), 7.69~7.78 (3H, m), 7.93 (1H, m), 8.07~8.08 (2H, m), 8.45 (1H, d), 9.30 (1H, s) | 787.07 | 786.25 |
| 152 | δ = 7.38~7.61 (21H, m), 7.88~7.93 (2H, m), 8.07~8.08 (2H, m), 8.45 (1H, d), 9.30 (1H, s) | 569.80 | 569.16 |
| 154 | δ = 7.16~7.35 (2H, m), 7.49~7.70 (8H, m), 7.85~7.94 (6H, m), 8.19~8.21 (3H, m), 8.45~8.55 (2H, m), 8.69 (2H, m) | 552.69 | 552.17 |
| 156 | δ = 7.16~7.20 (3H, m), 7.35~7.38 (3H, m), 7.50~7.56 (4H, m), 7.67~7.72 (3H, m), 7.92~7.94 (7H, m), 8.19~8.20 (2H, m), 8.30 (2H, m), 8.45 (1H, d), 8.55 (2H, m) | 641.79 | 641.19 |
| 160 | δ = 1.69 (6H, s), 7.28~7.38 (2H, m), 7.49~7.56 (3H, m), 7.68~7.74 (3H, m), 7.85!7.93 (6H, m), 8.18~8.20 (2H, m), 8.45 (1H, d), 8.69 (2H, m) | 503.66 | 503.17 |
| 172 | δ = 7.16~7.20 (2H, m), 7.35 (1H, t), 7.50~7.73 (10H, m), 7.85~7.94 (4H, m), 8.19~8.21 (3H, m), 8.33 (2H, m), 8.45~8.55 (2H, m) | 552.69 | 552.17 |
| 176 | δ = 7.38~7.70 (20H, m), 7.85~7.94 (3H, m), 8.20~8.33 (3H, m), 8.45 (1H, d) | 569.80 | 569.16 |
| 181 | δ = 7.10~7.26 (11H, m), 7.38 (1H, t), 7.50~7.61 (4H, m), 7.73~7.94 (8H, m), 8.09 (1H, d), 8.20 (1H, d), 8.33 (2H, m), 8.45 (1H, d) | 627.80 | 627.20 |
| 185 | δ = 7.49~7.56 (8H, m), 7.70~7.73 (2H, m), 7.85~7.94 (3H, m), 8.20 (1H, d), 8.33~8.45 (8H, m) | 542.66 | 542.16 |
| 189 | δ = 1.69 (6H, s), 7.16~7.18 (2H, m), 7.37~7.56 (14H, m), 7.70~7.75 (4H, m), 7.85~7.94 (6H, m), 8.20 (1H, d), 8.45 (1H, d) | 670.87 | 670.24 |
| 198 | δ = 7.16~7.20 (3H, m), 7.35~7.38 (3H, m), 7.50~7.58 (4H, m), 7.67~7.72 (2H, m), 7.89~7.94 (8H, m), 8.19~8.25 (2H, m), 8.39~8.55 (4H, m), 8.83 (1H, s) | 641.79 | 641.19 |
| 213 | δ = 7.25 (2H, d), 7.49~7.56 (8H, m), 7.89~7.96 (4H, m), 8.25~8.45 (7H, m), 8.83 (1H, s) | 542.66 | 542.16 |
| 215 | δ = 7.25 (4H, s), 7.49~7.56 (4H, s), 7.70 (1H, t), 7.89~7.93 (3H, m), 8.25~8.55 (6H, m), 8.83 (1H, s) | 493.64 | 493.10 |
| 217 | δ = 7.16 (2H, m), 7.35 (2H, m), 7.47~7.62 (11H, m), 7.89~7.94 (4H, m), 8.12~8.25 (3H, m), 8.39~8.55 (4H, m), 8.83 (1H, s) | 641.79 | 641.19 |
| 222 | δ = 7.16~7.20 (3H, m), 7.40~7.72 (12H, m), 7.89~7.94 (4H, m), 8.12~8.25 (3H, m), 8.39~8.55 (4H, m), 8.83 (1H, s) | 641.79 | 641.19 |

TABLE 1-continued

| Compound | ¹H NMR (CDCl₃, 200 Mz) | MS/FAB found | MS/FAB calculated |
|---|---|---|---|
| 229 | δ = 7.49~7.51 (8H, m), 7.74~7.77 (6H, m), 7.87~7.93 (3H, m), 8.13 (1H, s), 8.25 (1H, s), 8.39~8.45 (2H, m), 8.83 (1H, s) | 511.58 | 511.12 |
| 231 | δ = 7.38~7.73 (22H, m), 7.87~7.94 (5H, m), 8.25 (1H, s), 8.39~8.45 (2H, m), 8.83 (1H, s) | 645.89 | 645.19 |
| 243 | δ = 7.31~7.70 (9H, m), 7.88~7.98 (4H, m), 8.07 (1H, d), 8.32~8.33 (2H, m), 8.45 (1H, d), 8.55 (1H, d), 8.82 (1H, s) | 447.58 | 447.12 |

TABLE 2

| Compound | ¹H NMR (CDCl₃, 200 Mz) |
|---|---|
| 245 | δ = 8.81 (2H, d), 8.45 (1H, m), 8.28 (4H, d), 8.06 (1H, d), 7.98 (2H, d), 7.88 (2H, d), 7.78 (1H, t), 7.60~7.41 (9H, m) |
| 246 | δ = 8.81 (2H, d), 8.56 (1H, m), 8.45 (1H, m), 8.06 (1H, d), 7.98 (2H, m), 7.88~7.78 (5H, m), 7.60~7.45 (9H, m), 7.25~7.22 (4H, m) |
| 250 | δ = 8.81 (2H, d), 8.45 (1H, m), 8.23 (1H, s), 8.06 (1H, d), 7.98 (2H, m), 7.88~7.78 (7H, m), 7.60~7.41 (9H, m) |
| 252 | δ = 8.81 (2H, d), 8.45 (1H, m), 8.06 (1H, d), 7.98 (2H, m), 7.88~7.77 (1H, m), 7.60~7.45 (9H, m) |
| 253 | δ = 8.81 (2H, d), 8.45 (1H, m), 8.33~8.23 (7H, m), 8.06 (1H, d), 7.98 (2H, m), 7.85~7.78 (3H, m), 7.60~7.41 (11H, m) |
| 256 | δ = 8.81 (2H, d), 8.45 (1H, m), 8.28 (4H, d), 8.06 (1H, d), 7.98 (2H, d), 7.88~7.78 (5H, m), 7.60~7.41 (9H, m), 7.25 (2H, d) |
| 259 | δ = 8.81 (2H, d), 8.45 (1H, m), 8.33~8.28 (4H, m), 8.16 (1H, d), 8.06 (1H, d), 7.98 (2H, d), 7.84~7.78 (3H, m), 7.60~7.41 (7H, m) |
| 260 | δ = 8.84~8.83 (5H, m), 8.45~8.38 (2H, m), 8.10~7.98 (5H, m), 7.81~7.78 (2H, m), 7.60~7.52 (4H, m), 7.35 (1H, d) |
| 270 | δ = 8.45 (1H, m), 8.28~8.21 (6H, m), 8.06 (1H, d), 7.98 (2H, d), 7.85~7.78 (3H, m), 7.60~7.41 (11H, m), 7.25 (1H, d) |
| 274 | δ = 8.45 (1H, m), 8.30~8.23 (6H, m), 8.06 (1H, d), 7.85~7.78 (5H, m), 7.60~7.41 (12H, m) |
| 278 | δ = 8.45 (1H, m), 8.30 (2H, d), 8.06 (1H, d), 7.98 (2H, d), 7.86~7.77 (7H, m), 7.60~7.45 (9H, m) |
| 294 | δ = 8.45 (1H, m), 8.28~8.21 (5H, m), 8.06~7.98 (3H, m), 7.81~7.78 (4H, m), 7.60~7.41 (10H, m) |
| 309 | δ = 8.81 (2H, d), 8.33~8.23 (5H, m), 8.06 (1H, d), 7.98 (1H, d), 7.89 (1H, d), 7.79~7.78 (3H, m), 7.66~7.41 (10H, m) |
| 321 | δ = 8.30~8.21 (7H, m), 8.06 (1H, d), 7.98 (1H, d), 7.89 (1H, d), 7.78 (1H, t), 7.66~7.41 (11H, m) |
| 343 | δ = 8.81 (2H, d), 8.30 (2H, d), 8.16 (1H, d), 8.06 (1H, d), 7.98 (1H, d), 7.89~7.78 (8H, m), 7.66~7.41 (10H, m) |
| 354 | δ = 8.56 (1H, m), 8.26~8.21 (2H, m), 8.06 (1H, d), 7.98 (1H, d), 7.89~7.78 (4H, m), 7.60~7.22 (16H, m) |
| 370 | δ = 8.99 (1H, d), 8.80 (1H, s), 8.59 (1H, s), 8.06 (1H, d), 7.98 (1H, d), 7.89~7.78 (7H, m), 7.66~7.32 (10H, m) |
| 373 | δ = 8.99 (1H, d), 8.80 (1H, s), 8.45 (1H, m), 8.30~8.28 (5H, m), 8.06 (1H, d), 7.98 (2H, d), 7.88~7.78 (4H, m), 7.60~7.41 (11H, m) |
| 379 | δ = 8.45~8.41 (4H, m), 8.20~8.17 (4H, m), 8.06~7.89 (5H, m), 7.78~7.50 (10H, m), 7.38~7.32 (2H, m |
| 386 | δ = 8.56 (1H, m), 8.28 (2H, d), 8.17 (2H, s), 8.06 (1H, d), 7.98 (1H, d), 7.89~7.22 (24H, m) |
| 397 | δ = 8.17 (2H, m), 8.06 (1H, d), 7.98 (1H, d), 7.89~7.66 (13H, m), 7.38~7.32 (8H, m) |
| 414 | δ = 8.56~8.55 (3H, m), 8.39 (1H, s), 8.12~8.06 (3H, m), 7.98~7.85 (6H, m), 7.66~7.25 (19H, m) |
| 419 | δ = 8.45~8.41 (5H, m), 8.20~8.17 (3H, m), 8.06~7.98 (5H, m), 7.78 (1H, t), 7.72 (1H, s), 7.60~7.50 (9H, m) |
| 426 | δ = 8.56 (1H, m), 8.45 (1H, m), 8.28 (2H, d), 8.17 (2H, s), 8.06~7.98 (3H, m), 7.89~7.32 (21H, m), 7.23~7.22 (2H, m) |
| 437 | δ = 8.45 (1H, m), 8.17 (2H, s), 7.98~7.50 (16H, m), 7.38~7.32 (6H, m) |
| 454 | δ = 8.56~8.55 (3H, m), 8.45 (1H, m), 8.39 (1H, s), 8.12~7.94 (6H, m), 7.85~7.78 (3H, m), 7.63~7.45 (11H, m), 7.33~7.22 (7H, m) |

TABLE 3

| Compound | FD-Mass | Compound | FD-Mass |
|---|---|---|---|
| 245 | m/z = 542.65 (C36H22N4S = 542.16) | 246 | m/z = 579.71 (C40H25N3S = 579.18) |
| 247 | m/z = 579.71 (C40H25N3S = 579.18) | 248 | m/z = 511.57 (C33H22NOPS = 511.12) |
| 249 | m/z = 541.66 (C37H23N3S = 541.16) | 250 | m/z = 541.66 (C37H23N3S = 541.16) |

TABLE 3-continued

| Compound | FD-Mass | Compound | FD-Mass |
|---|---|---|---|
| 251 | m/z = 591.72 (C41H25N3S = 591.18) | 252 | m/z = 587.67 (C39H26NOPS = 587.15) |
| 253 | m/z = 617.76 (C43H27N3S = 617.19) | 254 | m/z = 563.71 (C41H25NS = 563.17) |
| 255 | m/z = 637.73 (C43H28NOPS = 637.16) | 256 | m/z = 618.75 (C42H26N4S = 618.19) |
| 257 | m/z = 617.76 (C43H27N3S = 617.19) | 258 | m/z = 617.76 (C43H27N3S = 617.19) |
| 259 | m/z = 515.63 (C35H21N3S = 515.15) | 260 | m/z = 489.59 (C33H19N3S = 489.13) |
| 261 | m/z = 542.65 (C36H22N4S = 542.16) | 262 | m/z = 579.71 (C40H25N3S = 579.18) |
| 263 | m/z = 511.57 (C33H22NOPS = 511.12) | 264 | m/z = 541.66 (C37H23N3S = 541.16) |
| 265 | m/z = 591.72 (C41H25N3S = 591.18) | 266 | m/z = 587.67 (C39H26NOPS = 587.15) |
| 267 | m/z = 617.76 (C43H27N3S = 617.19) | 268 | m/z = 563.71 (C41H25NS = 563.17) |
| 269 | m/z = 637.73 (C43H28NOPS = 637.16) | 270 | m/z = 618.75 (C42H26N4S = 618.19) |
| 271 | m/z = 617.76 (C43H27N3S = 617.19) | 272 | m/z = 617.76 (C43H27N3S = 617.19) |
| 273 | m/z = 515.63 (C35H21N3S = 515.15) | 274 | m/z = 489.59 (C33H19N3S = 489.13) |
| 275 | m/z = 542.65 (C36H22N4S = 542.16) | 276 | m/z = 579.71 (C40H25N3S = 579.18) |
| 277 | m/z = 579.71 (C40H25N3S = 579.18) | 278 | m/z = 511.57 (C33H22NOPS = 511.12) |
| 279 | m/z = 541.66 (C37H23N3S = 541.16) | 280 | m/z = 541.66 (C37H23N3S = 541.16) |
| 281 | m/z = 591.72 (C41H25N3S = 591.18) | 282 | m/z = 587.67 (C39H26NOPS = 587.15) |
| 283 | m/z = 617.76 (C43H27N3S = 617.19) | 284 | m/z = 563.71 (C41H25NS = 563.17) |
| 285 | m/z = 637.73 (C43H28NOPS = 637.16) | 286 | m/z = 618.75 (C42H26N4S = 618.19) |
| 287 | m/z = 617.76 (C43H27N3S = 617.19) | 288 | m/z = 617.76 (C43H27N3S = 617.19) |
| 289 | m/z = 515.63 (C35H21N3S = 515.15) | 290 | m/z = 542.65 (C36H22N4S = 542.16) |
| 291 | m/z = 579.71 (C40H25N3S = 579.18) | 292 | m/z = 579.71 (C40H25N3S = 579.18) |
| 293 | m/z = 511.57 (C33H22NOPS = 511.12) | 294 | m/z = 541.66 (C37H23N3S = 541.16) |
| 295 | m/z = 591.72 (C41H25N3S = 591.18) | 296 | m/z = 587.67 (C39H26NOPS = 587.15) |
| 297 | m/z = 617.76 (C43H27N3S = 617.19) | 298 | m/z = 563.71 (C41H25NS = 563.17) |
| 299 | m/z = 637.73 (C43H28NOPS = 637.16) | 300 | m/z = 618.75 (C42H26N4S = 618.19) |
| 301 | m/z = 617.76 (C43H27N3S = 617.19) | 302 | m/z = 617.76 (C43H27N3S = 617.19) |
| 303 | m/z = 515.63 (C35H21N3S = 515.15) | 304 | m/z = 489.59 (C33H19N3S = 489.13) |
| 305 | m/z = 526.59 (C36H22N4O = 526.18) | 306 | m/z = 563.65 (C40H25N3O = 563.20) |
| 307 | m/z = 563.65 (C40H25N3O = 563.20) | 308 | m/z = 495.51 (C33H22NO2P = 495.14) |
| 309 | m/z = 525.60 (C37H23N3O = 525.18) | 310 | m/z = 525.60 (C37H23N3O = 525.18) |
| 311 | m/z = 575.66 (C41H25N3O = 575.20) | 312 | m/z = 571.60 (C39H26NO2P = 571.17) |
| 313 | m/z = 601.69 (C43H27N3O = 601.22) | 314 | m/z = 547.64 (C41H25NO = 547.19) |
| 315 | m/z = 621.66 (C43H28NO2P = 621.19) | 316 | m/z = 602.68 (C42H26N4O = 602.21) |
| 317 | m/z = 601.69 (C43H27N3O = 601.22) | 318 | m/z = 601.69 (C43H27N3O = 601.21) |
| 319 | m/z = 499.56 (C35H21N3OP = 499.17) | 320 | m/z = 473.52 (C33H19N3O = 473.15) |
| 321 | m/z = 526.59 (C36H22N4O = 526.18) | 322 | m/z = 563.65 (C40H25N3O = 563.20) |
| 323 | m/z = 563.65 (C40H25N3O = 563.20) | 324 | m/z = 495.51 (C33H22NO2P = 495.14) |
| 325 | m/z = 525.60 (C37H23N3O = 525.18) | 326 | m/z = 525.60 (C37H23N3O = 525.18) |
| 327 | m/z = 575.66 (C41H25N3O = 575.20) | 328 | m/z = 571.60 (C39H26NO2P = 571.17) |
| 329 | m/z = 601.69 (C43H27N3O = 601.22) | 330 | m/z = 547.64 (C41H25NO = 547.19) |
| 331 | m/z = 621.66 (C43H28NO2P = 621.19) | 332 | m/z = 602.68 (C42H26N4O = 602.21) |
| 333 | m/z = 601.69 (C43H27N3O = 601.22) | 334 | m/z = 601.69 (C43H27N3O = 601.21) |
| 335 | m/z = 499.56 (C35H21N3OP = 499.17) | 336 | m/z = 473.52 (C33H19N3O = 473.15) |
| 337 | m/z = 526.59 (C36H22N4O = 526.18) | 338 | m/z = 563.65 (C40H25N3O = 563.20) |
| 339 | m/z = 563.65 (C40H25N3O = 563.20) | 340 | m/z = 495.51 (C33H22NO2P = 495.14) |
| 341 | m/z = 525.60 (C37H23N3O = 525.18) | 342 | m/z = 525.60 (C37H23N3O = 525.18) |
| 343 | m/z = 575.66 (C41H25N3O = 575.20) | 344 | m/z = 571.60 (C39H26NO2P = 571.17) |
| 345 | m/z = 601.69 (C43H27N3O = 601.22) | 346 | m/z = 547.64 (C41H25NO = 547.19) |
| 347 | m/z = 621.66 (C43H28NO2P = 621.19) | 348 | m/z = 602.68 (C42H26N4O = 602.21) |
| 349 | m/z = 601.69 (C43H27N3O = 601.22) | 350 | m/z = 601.69 (C43H27N3O = 601.21) |
| 351 | m/z = 499.56 (C35H21N3OP = 499.17) | 352 | m/z = 473.52 (C33H19N3O = 473.15) |
| 353 | m/z = 526.59 (C36H22N4O = 526.18) | 354 | m/z = 563.65 (C40H25N3O = 563.20) |
| 355 | m/z = 563.65 (C40H25N3O = 563.20) | 356 | m/z = 495.51 (C33H22NO2P = 495.14) |
| 357 | m/z = 525.60 (C37H23N3O = 525.18) | 358 | m/z = 525.60 (C37H23N3O = 525.18) |
| 359 | m/z = 575.66 (C41H25N3O = 575.20) | 360 | m/z = 571.60 (C39H26NO2P = 571.17) |
| 361 | m/z = 601.69 (C43H27N3O = 601.22) | 362 | m/z = 547.64 (C41H25NO = 547.19) |
| 363 | m/z = 621.66 (C43H28NO2P = 621.19) | 364 | m/z = 602.68 (C42H26N4O = 602.21) |
| 365 | m/z = 601.69 (C43H27N3O = 601.22) | 366 | m/z = 601.69 (C43H27N3O = 601.21) |
| 367 | m/z = 499.56 (C35H21N3OP = 499.17) | 368 | m/z = 473.52 (C33H19N3O = 473.15) |
| 369 | m/z = 526.59 (C36H22N4O = 526.18) | 370 | m/z = 526.59 (C36H22N4O = 526.18) |
| 371 | m/z = 576.64 (C40H24N4O = 576.20) | 372 | m/z = 572.59 (C38H25N2O2P = 572.17) |
| 373 | m/z = 618.75 (C42H26N4S = 618.19) | 374 | m/z = 564.70 (C40H24N2S = 564.17) |
| 375 | m/z = 638.72 (C42H27N2OPS = 638.16) | 376 | m/z = 619.74 (C41H25N5S = 619.18) |
| 377 | m/z = 627.68 (C45H25NO3 = 627.18) | 378 | m/z = 627.68 (C45H25NO3 = 627.18) |
| 379 | m/z = 659.82 (C45H25NOS2 = 659.14) | 380 | m/z = 660.14 (C45H25NOS2 = 659.14) |
| 381 | m/z = 831.96 (C59H37N5O = 831.30) | 382 | m/z = 831.96 (C59H37N5O = 831.30) |
| 383 | m/z = 735.87 (C51H37N5O = 735.30) | 384 | m/z = 908.05 (C65H41N5O = 907.33) |
| 385 | m/z = 729.82 (C52H31N3O2 = 729.24) | 386 | m/z = 729.82 (C52H31N3O2 = 729.24) |
| 387 | m/z = 745.89 (C52H31N3OS = 745.22) | 388 | m/z = 745.89 (C52H31N3OS = 745.22) |
| 389 | m/z = 767.87 (C55H33N3O2 = 767.26) | 390 | m/z = 767.87 (C55H33N3O2 = 767.26) |
| 391 | m/z = 783.94 (C55H33N3OS = 783.23) | 392 | m/z = 783.94 (C55H33N3OS = 783.23) |
| 393 | m/z = 766.88 (C55H34N4O = 766.27) | 394 | m/z = 728.84 (C52H32N4O = 728.26) |
| 395 | m/z = 728.84 (C52H32N4O = 728.26) | 396 | m/z = 680.79 (C48H32N4O = 680.26) |
| 397 | m/z = 627.68 (C45H25N3O = 627.18) | 398 | m/z = 627.68 (C45H25N3O = 627.18) |
| 399 | m/z = 659.82 (C45H25NOS2 = 659.82) | 400 | m/z = 659.82 (C45H25NOS2 = 659.82) |
| 401 | m/z = 831.96 (C59H37N5O = 831.30) | 402 | m/z = 831.96 (C59H37N5O = 831.30) |
| 403 | m/z = 735.87 (C51H37N5O = 730.30) | 404 | m/z = 908.05 (C65H41N5O = 907.33) |

TABLE 3-continued

| Compound | FD-Mass | Compound | FD-Mass |
|---|---|---|---|
| 405 | m/z = 729.82 (C52H31N3O2 = 729.24) | 406 | m/z = 729.82 (C52H31N3O2 = 729.24) |
| 407 | m/z = 745.89 (C52H31N3OS = 745.22) | 408 | m/z = 745.89 (C52H31N3OS = 745.22) |
| 409 | m/z = 767.87 (C55H33N3O2 = 767.26) | 410 | m/z = 767.87 (C55H33N3O2 = 767.26) |
| 411 | m/z = 783.94 (C55H33N3OS = 783.23) | 412 | m/z = 783.94 (C55H33N3OS = 783.23) |
| 413 | m/z = 766.88 (C55H34N4O = 766.27) | 414 | m/z = 728.84 (C52H32N4O = 728.26) |
| 415 | m/z = 728.84 (C52H32N4O = 728.26) | 416 | m/z = 680.79 (C48H32N4O = 680.26) |
| 417 | m/z = 643.75 (C45H25NO2S = 643.16) | 418 | m/z = 643.75 (C45H25NO2S = 643.16) |
| 419 | m/z = 675.88 (C45H25NS3 = 675.11) | 420 | m/z = 675.88 (C45H25NS3 = 675.11) |
| 421 | m/z = 848.02 (C59H37N5S = 847.28) | 422 | m/z = 848.02 (C59H37N5S = 847.28) |
| 423 | m/z = 751.94 (C51H37N5S = 751.28) | 424 | m/z = 924.31 (C65H41N5S = 12) |
| 425 | m/z = 745.89 (C52H31N3OS = 745.22) | 426 | m/z = 745.89 (C52H31N3OS = 745.22) |
| 427 | m/z = 761.95 (C52H31N3S2 = 761.20) | 428 | m/z = 761.95 (C52H31N3S2 = 761.20) |
| 429 | m/z = 783.94 (C55H33N3OS = 783.23) | 430 | m/z = 783.94 (C55H33N3OS = 783.23) |
| 431 | m/z = 800.00 (C55H33N3S2 = 799.21) | 432 | m/z = 800.00 (C55H33N3S2 = 799.21) |
| 433 | m/z = 782.95 (C55H34N4S = 782.25) | 434 | m/z = 744.90 (C52H32N4S = 744.23) |
| 435 | m/z = 744.90 (C52H32N4S = 744.23) | 436 | m/z = 696.86 (C48H32N4S = 696.23) |
| 437 | m/z = 643.75 (C45H25NOS = 643.16) | 438 | m/z = 643.75 (C45H25NOS = 643.16) |
| 439 | m/z = 675.88 (C45H25NS3 = 675.11) | 440 | m/z = 675.88 (C45H25NS3 = 675.11) |
| 441 | m/z = 848.02 (C59H37N5S = 847.28) | 442 | m/z = 848.02 (C59H37N5S = 847.28) |
| 443 | m/z = 751.94 (C51H37N5S = 751.28) | 444 | m/z = 924.12 (C65H41N5S = 923.31) |
| 445 | m/z = 745.89 (C52H31N3OS = 745.22) | 446 | m/z = 745.89 (C52H31N3OS = 745.22) |
| 447 | m/z = 761.95 (C52H31N3S2 = 761.20) | 448 | m/z = 761.95 (C52H31N3S2 = 761.20) |
| 449 | m/z = 783.94 (C55H33N3OS = 783.23) | 450 | m/z = 783.94 (C55H33N3OS = 783.23) |
| 451 | m/z = 800.00 (C55H33N3S2 = 799.21) | 452 | m/z = 800.00 (C55H33N3S2 = 799.21) |
| 453 | m/z = 782.95 (C55H34N4S = 782.25) | 454 | m/z = 744.90 (C52H32N4S = 744.23) |
| 455 | m/z = 744.90 (C52H32N4S = 744.23) | 456 | m/z = 696.86 (C48H32N4S = 696.23) |

<Experimental Example 1> Measurement of CV, UV, and PL of Compound

The CV was measured by employing NPB (HOMO=−5.5 eV) as a reference material and using a cyclic voltammetry (CV) measurement device (manufacturer: Princeton Applied Research, Model Name: Parstat2273).

The UV was measured by using a UV-visible light spectrophotometer (manufacturer: Perkin Elmer, Model Name: LS35), and was analyzed by using tetrahydrofuran (THF) at normal temperature.

The PL was measured by using a spectrometer (equipment: Perkin Elmer, Model Name: LS55), and was analyzed by using tetrahydrofuran (THF) at normal temperature.

FIG. 4 illustrates a measurement graph of UV and PL of Compound 29.

FIGS. 5 and 6 illustrate $E_{ox}$ values derived from the result of measuring CV of Compound 29.

FIG. 7 illustrates a measurement graph of UV and PL of Compound 42.

FIGS. 8 and 9 illustrate $E_{ox}$ values derived from the result of measuring CV of Compound 42.

FIG. 10 illustrates a measurement graph of UV and PL of Compound 87.

FIGS. 11 and 12 illustrate $E_{ox}$ values derived from the result of measuring CV of Compound 87.

FIG. 13 illustrates a measurement graph of UV and PL of Compound 88.

FIGS. 14 and 15 illustrate $E_{ox}$ values derived from the result of measuring CV of Compound 88.

FIG. 16 illustrates a measurement graph of UV and PL of Compound 90.

FIGS. 17 and 18 illustrate $E_{ox}$ values derived from the result of measuring CV of Compound 90.

FIG. 19 illustrates a measurement graph of UV and PL of Compound 91.

FIGS. 20 and 21 illustrate $E_{ox}$ values derived from the result of measuring CV of Compound 91.

FIG. 22 illustrates a measurement graph of UV and PL of Compound 92.

FIGS. 23 and 24 illustrate $E_{ox}$ values derived from the result of measuring CV of Compound 92.

FIG. 25 illustrates a measurement graph of UV and PL of Compound 93.

FIGS. 26 and 27 illustrate $E_{ox}$ values derived from the result of measuring CV of Compound 93.

FIG. 28 illustrates $E_{ox}$ values derived from the result of measuring CV of Compound 73.

FIG. 29 illustrates a measurement graph of UVPL of Compound 73.

FIG. 30 illustrates a measurement graph of LTPL of Compound 85.

FIG. 31 illustrates a measurement graph of UVPL of Compound 85.

FIG. 32 illustrates a measurement graph of LTPL of Compound 86.

FIG. 33 illustrates a measurement graph of UVPL of Compound 86.

FIG. 34 illustrates a measurement graph of LTPL of Compound 87.

FIG. 35 illustrates a measurement graph of UVPL of Compound 87.

FIG. 36 illustrates a measurement graph of LTPL of Compound 88.

FIG. 37 illustrates a measurement graph of UVPL of Compound 88.

FIG. 38 illustrates a measurement graph of LTPL of Compound 90.

FIG. 39 illustrates a measurement graph of UVPL of Compound 90.

FIG. 40 illustrates a measurement graph of LTPL of Compound 91.

FIG. 41 illustrates a measurement graph of UVPL of Compound 91.

FIG. 42 illustrates a measurement graph of LTPL of Compound 92.

FIG. 43 illustrates a measurement graph of UVPL of Compound 92.

FIG. 44 illustrates a measurement graph of LTPL of Compound 93.

FIG. 45 illustrates a measurement graph of UVPL of Compound 93.
FIG. 46 illustrates a measurement graph of LTPL of Compound 245.
FIG. 47 illustrates a measurement graph of UVPL of Compound 245.
FIG. 48 illustrates a measurement graph of LTPL of Compound 246.
FIG. 49 illustrates a measurement graph of UVPL of Compound 246.
FIG. 50 illustrates a measurement graph of LTPL of Compound 250.
FIG. 51 illustrates a measurement graph of UVPL of Compound 250.
FIG. 52 illustrates a measurement graph of LTPL of Compound 253.
FIG. 53 illustrates a measurement graph of UVPL of Compound 253.
FIG. 54 illustrates a measurement graph of LTPL of Compound 259.
FIG. 55 illustrates a measurement graph of UVPL of Compound 259.
FIG. 56 illustrates a measurement graph of LTPL of Compound 260.
FIG. 57 illustrates a measurement graph of UVPL of Compound 260.
FIG. 58 illustrates a measurement graph of LTPL of Compound 409.
FIG. 59 illustrates a measurement graph of UVPL of Compound 409.
FIG. 60 illustrates a measurement graph of LTPL of Compound 420.
FIG. 61 illustrates a measurement graph of UVPL of Compound 420.
FIG. 62 illustrates a measurement graph of LTPL of Compound 425.
FIG. 63 illustrates a measurement graph of UVPL of Compound 425.
FIG. 64 illustrates a measurement graph of LTPL of Compound 427.
FIG. 65 illustrates a measurement graph of UVPL of Compound 427.
FIG. 66 illustrates a measurement graph of LTPL of Compound 434.
FIG. 67 illustrates a measurement graph of UVPL of Compound 434.

In the graphs of FIGS. 5, 6, 8, 9, 11, 12, 14, 15, 17, 18, 20, 21, 23, 24, and 26 to 28, the y-axis indicates current (unit: A) and the x-axis indicates potential (unit: V).

In the graphs of FIGS. 4, 7, 10, 13, 16, 19, 22, and 25, the left graph (blue) indicates UV absorption, and the right graph (red) indicates PL light emitting values. In the graphs of FIGS. 4, 7, 10, 13, 16, 19, 22, 25, and 29 to 67, each of the y-axis and the x-axis indicates intensity and wavelength (unit: nm).

Further, the highest occupied molecular orbit (HOMO), the lowest unoccupied molecular orbital (LUMO), and the band gap of the compound may be confirmed by the following Equations.

$$\text{Homo} = -5.5 - (E_{ox}(\text{compound to be measured}) - E_{ox}(NPB))\text{eV}$$

$$\text{Band gap (Homo-Lumo)} = 1240/\text{UV absorption edge} \quad \text{<Equation>}$$

<Experimental Example 2> Manufacture of OLED Device

Comparative Example 1

Trichloroethylene, acetone, ethanol, and distilled water were sequentially used to ulutrasonically wash a transparent electrode ITO thin film obtained from glass for OLED (manufactured by Samsung-Corning Co., Ltd.) for each of 5 minutes, and then the ITO thin film was placed in isopropanol, stored, and then used.

Next, an ITO substrate was disposed in a substrate folder of a vacuum deposition equipment, and the following 4,4',4"-tris(N,N-(2-naphthyl)-phenylamino)triphenyl amine (2-TNATA) was placed in a cell in the vacuum deposition equipment.

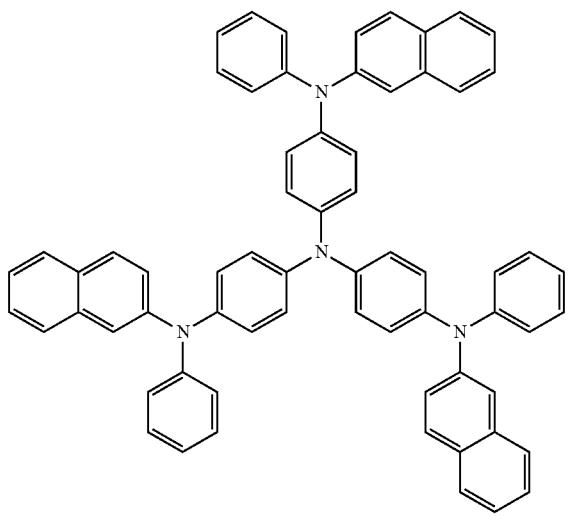

2-TNATA

Subsequently, air in the chamber was evacuated until the degree of vacuum in the chamber reached $10^{-6}$ torr, and then a hole injection layer having a thickness of 600 Å was deposited on the ITO substrate by applying current to the cell to evaporate 2-TNATA.

A hole transport layer having a thickness of 300 Å was deposited on the hole inejection layer by placing the following N,N'-bis(α-naphthyl)-N,N'-diphenyl-4,4'-diamine (NPB) in another cell in the vacuum deposition equipment and applying current to the cell to evaporate NPB.

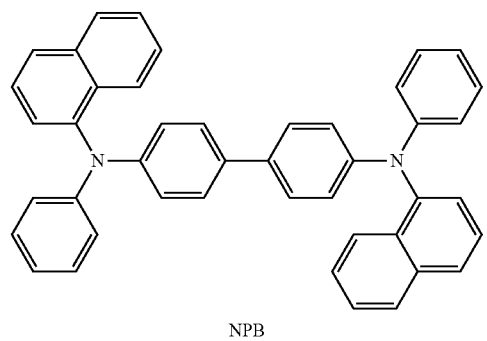 [SMILES: c1ccc(N(c2ccc(-c3ccc(N(c4ccccc4)c4cccc5ccccc45)cc3)cc2)c2cccc3ccccc23)cc1 ; "NPB"]

NPB

The hole injection layer and the hole transport layer were formed as described above, and then a blue light emitting material having the following structure as a light emitting layer was deposited thereon. Specifically, the blue light emitting host material H1 was vacuum deposited to have a thickness of 200 Å on one cell in the vacuum deposition equipment, and the blue light emitting dopant material D1 was vacuum deposited thereon in an amount of 5% with respect to the host material.

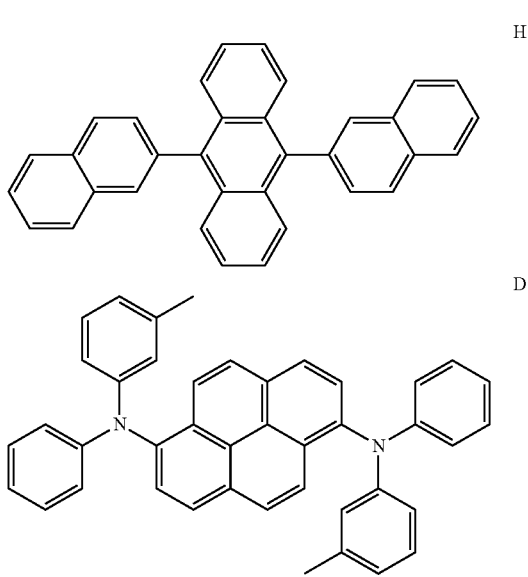

H1

D1

Subsequently, a compound having the following structural formula E1 as an electron transport layer was vacuum deposited to have a thickness of 300 Å.

E1

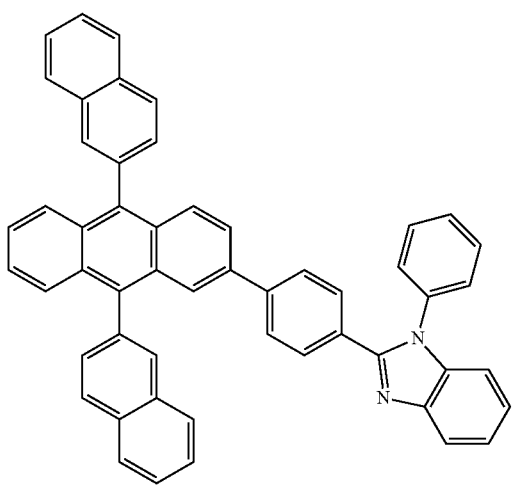

An OLED device was manufactured by depositing lithium fluoride (LiF) as an electron injection layer to have a thickness of 10 Å and allowing the Al negative electrode to have a thickness of 1,000 Å.

Meanwhile, all the organic compounds required for manufacturing an OLED device were subjected to vacuum sublimed purification under $10^{-6}$ to $10^{-8}$ torr for each material, and used for the manufacture of OLED.

Comparative Example 2

The device structure as in Comparative Example 1 was manufactured, and E2 material was used instead of E1 material.

E2

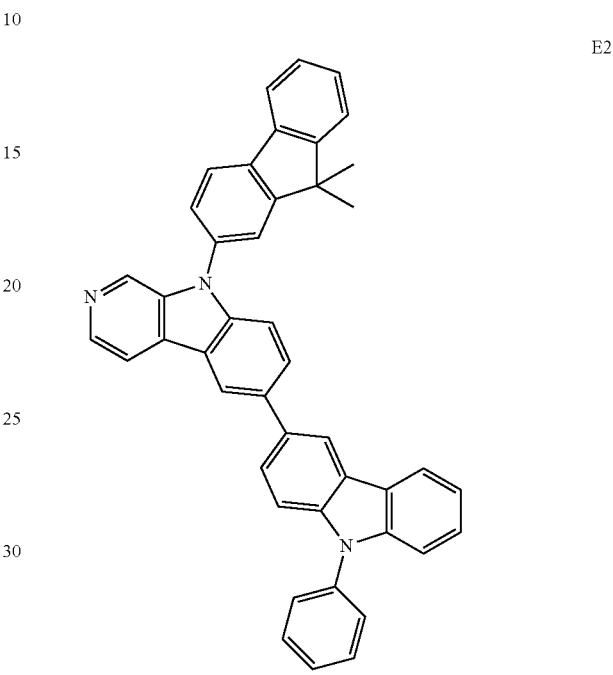

Comparative Example 3

An organic electroluminescence device was manufactured by the following method.

A glass substrate, in which ITO was thinly coated to have a thickness of 1,500 Å, was ultrasonically washed with distilled water. When the washing with distilled water is finished, the glass substrate was ultrasonically washed with a solvent such as acetone, methanol, and isopropyl alcohol, dried and then was subjected to UVO treatment for 5 minutes by using UV in a UV washing machine. Thereafter, the substrate was transferred to a plasma washing machine (PT), and then was subjected to plasma treatment for an ITO work function in a vacuum state and the removal of a residual film, and thus, was transferred to a thermal deposition equipment for organic deposition.

As the common layers, the hole injection layer 4,4',4"-tris[2-naphthyl(phenyl)amino]triphenylamine (2-TNATA) and the hole transport layer N,N'-di(1-naphthyl)-N,N'-diphenyl-(1,1'-biphenyl)-4,4'-diamine (NPB) were formed on the ITO transparent electrode (positive electrode) prepared as described above.

The light emitting layer was thermally vacuum deposited thereon as follows. The light emitting layer was deposited to have a thickness of 400 Å by using 4,4'-N,N'-dicarbazole-biphenyl (CBP) as a host and tris(2-phenylpyridine)iridium $(Ir(ppy)_3)$ as a green phosphorescent dopant to dope CBP with $Ir(ppy)_3$ in an amount of 7%. Thereafter, BCP as a hole blocking layer was deposited to have a thickness of 60 Å, and $Alq_3$ as an electron transport layer was deposited to have a thickness of 200 Å thereon. Finally, an organic electroluminescence device was manufactured by depositing lithium fluoride (LiF) to have a thickness of 10 Å on the electron transport layer to form an electron injection layer, and then depositing an aluminum (Al) negative electrode to have a thickness of 1,200 Å on the electron injection layer to form a negative electrode.

Meanwhile, all the organic compounds required for manufacturing an OLED device were subjected to vacuum sublimed purification under $10^{-6}$ to $10^{-8}$ torr for each material, and used for the manufacture of OLED.

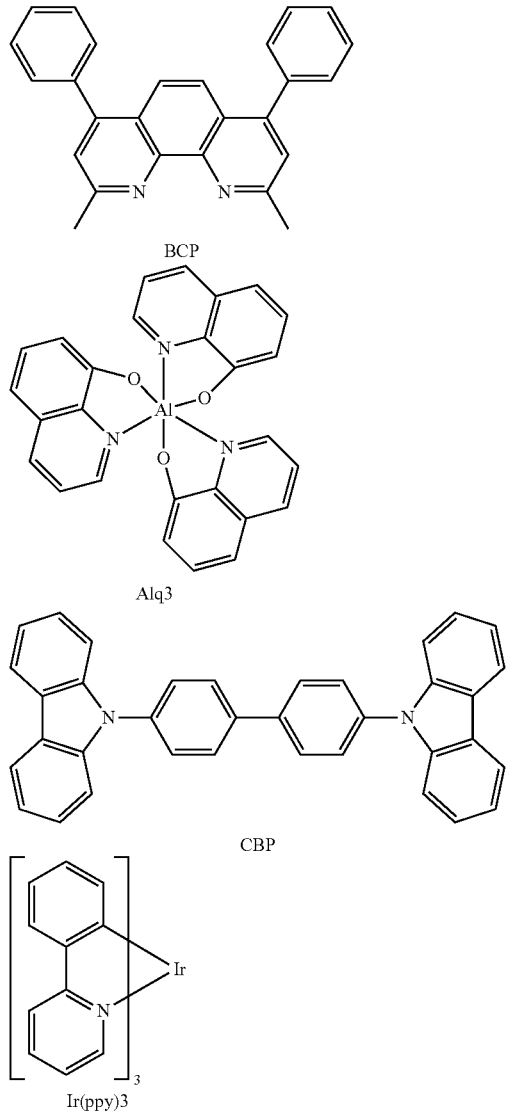

Examples 1 to 98

An organic electroluminescence device was manufactured in the same manner as in Comparative Examples 1 and 2, except that the compounds synthesized in Preparation Examples 20 to 45 were used instead of E1 and E2 used when the electron transport layers in Comparative Examples 1 and 2 were formed.

For each of the organic electroluminescence devices manufactured in Comparative Examples 1 and 2 and Examples 1 to 98, the driving voltage, the efficiency, the color coordinate, and the durability (service life) were measured at a light emitting brightness of 700 cd/m² and evaluated, and the results are shown in the following Table 4.

TABLE 4

| Experimental Example | Electron transport layer material | Driving voltage (V) | Efficiency (cd/A) | Color coordinate (x, y) | Service life ($T_{50}$) |
|---|---|---|---|---|---|
| Comparative Example 1 | E1 | 4.7 | 4.5 | (0.15, 0.18) | 330 |
| Comparative Example 2 | E2 | 5.5 | 3.2 | (0.15, 0.17) | 325 |
| Example 1 | Compound 245 | 4.4 | 4.7 | (0.15, 0.17) | 420 |
| Example 2 | Compound 246 | 4.4 | 4.8 | (0.15, 0.18) | 496 |
| Example 3 | Compound 247 | 4.5 | 4.7 | (0.15, 0.18) | 350 |
| Example 4 | Compound 248 | 4.6 | 4.9 | (0.15, 0.18) | 520 |
| Example 5 | Compound 250 | 4.5 | 4.7 | (0.15, 0.18) | 402 |
| Example 6 | Compound 253 | 4.2 | 4.8 | (0.15, 0.17) | 430 |
| Example 7 | Compound 254 | 4.7 | 4.5 | (0.15, 0.18) | 400 |
| Example 8 | Compound 256 | 4.0 | 4.7 | (0.15, 0.18) | 412 |
| Example 9 | Compound 259 | 4.1 | 4.6 | (0.15, 0.17) | 386 |
| Example 10 | Compound 260 | 4.6 | 4.6 | (0.15, 0.18) | 345 |
| Example 11 | Compound 261 | 4.7 | 5.0 | (0.15, 0.17) | 360 |
| Example 12 | Compound 262 | 4.6 | 4.9 | (0.15, 0.18) | 365 |
| Example 13 | Compound 263 | 4.0 | 5.5 | (0.15, 0.17) | 340 |
| Example 14 | Compound 274 | 4.5 | 4.8 | (0.15, 0.17) | 398 |
| Example 15 | Compound 275 | 4.3 | 4.6 | (0.15, 0.19) | 345 |
| Example 16 | Compound 278 | 4.6 | 5.0 | (0.15, 0.18) | 505 |
| Example 17 | Compound 279 | 4.5 | 4.6 | (0.15, 0.18) | 338 |
| Example 18 | Compound 280 | 4.3 | 4.9 | (0.15, 0.18) | 366 |
| Example 19 | Compound 281 | 4.7 | 5.0 | (0.15, 0.19) | 334 |
| Example 20 | Compound 283 | 4.2 | 4.8 | (0.15, 0.17) | 340 |
| Example 21 | Compound 284 | 4.7 | 4.6 | (0.15, 0.18) | 333 |
| Example 22 | Compound 287 | 4.7 | 4.6 | (0.15, 0.17) | 450 |
| Example 23 | Compound 292 | 4.0 | 4.7 | (0.15, 0.19) | 377 |
| Example 24 | Compound 293 | 4.3 | 4.6 | (0.15, 0.18) | 389 |
| Example 25 | Compound 294 | 4.4 | 4.8 | (0.15, 0.17) | 395 |
| Example 26 | Compound 295 | 4.3 | 4.6 | (0.15, 0.18) | 440 |
| Example 27 | Compound 299 | 4.2 | 4.6 | (0.15, 0.19) | 410 |
| Example 28 | Compound 302 | 4.6 | 4.9 | (0.15, 0.18) | 367 |
| Example 29 | Compound 304 | 4.3 | 4.7 | (0.15, 0.18) | 387 |
| Example 30 | Compound 307 | 4.5 | 4.9 | (0.15, 0.18) | 399 |
| Example 31 | Compound 308 | 4.2 | 4.6 | (0.15, 0.17) | 359 |
| Example 32 | Compound 309 | 4.6 | 4.7 | (0.15, 0.18) | 397 |
| Example 33 | Compound 310 | 4.7 | 4.9 | (0.15, 0.18) | 366 |
| Example 34 | Compound 313 | 4.7 | 4.6 | (0.15, 0.18) | 390 |
| Example 35 | Compound 315 | 4.5 | 4.6 | (0.15, 0.19) | 397 |
| Example 36 | Compound 316 | 4.2 | 4.6 | (0.15, 0.18) | 430 |
| Example 37 | Compound 317 | 4.6 | 4.8 | (0.15, 0.17) | 411 |
| Example 38 | Compound 318 | 4.6 | 4.6 | (0.15, 0.17) | 456 |
| Example 39 | Compound 321 | 4.5 | 4.7 | (0.15, 0.17) | 388 |
| Example 40 | Compound 323 | 4.7 | 4.8 | (0.15, 0.18) | 388 |
| Example 41 | Compound 324 | 4.7 | 4.9 | (0.15, 0.17) | 362 |
| Example 42 | Compound 327 | 4.4 | 4.6 | (0.15, 0.18) | 402 |
| Example 43 | Compound 329 | 4.6 | 4.8 | (0.15, 0.18) | 359 |
| Example 44 | Compound 333 | 4.5 | 4.9 | (0.15, 0.17) | 377 |
| Example 45 | Compound 334 | 4.6 | 4.6 | (0.15, 0.18) | 389 |
| Example 46 | Compound 340 | 4.3 | 4.8 | (0.15, 0.17) | 370 |
| Example 47 | Compound 343 | 4.4 | 4.8 | (0.15, 0.17) | 377 |
| Example 48 | Compound 345 | 4.2 | 4.7 | (0.15, 0.18) | 355 |
| Example 49 | Compound 347 | 4.6 | 4.9 | (0.15, 0.18) | 370 |
| Example 50 | Compound 354 | 4.6 | 4.9 | (0.15, 0.18) | 440 |
| Example 51 | Compound 356 | 4.6 | 4.8 | (0.15, 0.18) | 390 |
| Example 52 | Compound 360 | 4.7 | 4.6 | (0.15, 0.17) | 380 |
| Example 53 | Compound 361 | 4.7 | 4.8 | (0.15, 0.18) | 385 |
| Example 54 | Compound 363 | 4.5 | 4.8 | (0.15, 0.18) | 355 |
| Example 55 | Compound 364 | 4.2 | 4.6 | (0.15, 0.17) | 357 |
| Example 56 | Compound 370 | 4.0 | 4.7 | (0.15, 0.18) | 372 |
| Example 57 | Compound 373 | 4.1 | 4.8 | (0.15, 0.18) | 381 |
| Example 58 | Compound 378 | 4.7 | 4.6 | (0.15, 0.17) | 337 |
| Example 59 | Compound 382 | 4.7 | 4.7 | (0.15, 0.18) | 343 |
| Example 60 | Compound 385 | 4.3 | 4.9 | (0.15, 0.18) | 365 |
| Example 61 | Compound 391 | 4.5 | 4.9 | (0.15, 0.18) | 359 |
| Example 62 | Compound 393 | 4.2 | 4.9 | (0.15, 0.18) | 420 |
| Example 63 | Compound 398 | 4.6 | 4.6 | (0.15, 0.17) | 490 |
| Example 64 | Compound 400 | 4.5 | 4.6 | (0.15, 0.18) | 358 |
| Example 65 | Compound 401 | 4.4 | 4.7 | (0.15, 0.19) | 344 |

TABLE 4-continued

| Experimental Example | Electron transport layer material | Driving voltage (V) | Efficiency (cd/A) | Color coordinate (x, y) | Service life ($T_{50}$) |
|---|---|---|---|---|---|
| Example 66 | Compound 405 | 4.2 | 4.8 | (0.15, 0.17) | 406 |
| Example 67 | Compound 407 | 4.7 | 4.6 | (0.15, 0.17) | 366 |
| Example 68 | Compound 411 | 4.4 | 4.9 | (0.15, 0.18) | 389 |
| Example 69 | Compound 415 | 4.7 | 4.7 | (0.15, 0.18) | 419 |
| Example 70 | Compound 416 | 4.7 | 5.1 | (0.15, 0.19) | 477 |
| Example 71 | Compound 417 | 4.3 | 4.8 | (0.15, 0.18) | 378 |
| Example 72 | Compound 418 | 4.4 | 4.7 | (0.15, 0.19) | 369 |
| Example 73 | Compound 419 | 4.3 | 4.8 | (0.15, 0.18) | 398 |
| Example 74 | Compound 420 | 4.3 | 4.6 | (0.15, 0.17) | 345 |
| Example 75 | Compound 421 | 4.3 | 4.7 | (0.15, 0.17) | 372 |
| Example 76 | Compound 423 | 4.6 | 4.6 | (0.15, 0.18) | 335 |
| Example 77 | Compound 426 | 4.2 | 4.9 | (0.15, 0.17) | 467 |
| Example 78 | Compound 427 | 4.5 | 4.7 | (0.15, 0.18) | 354 |
| Example 79 | Compound 429 | 4.7 | 4.6 | (0.15, 0.18) | 341 |
| Example 80 | Compound 430 | 4.6 | 4.6 | (0.15, 0.17) | 339 |
| Example 81 | Compound 431 | 4.5 | 4.8 | (0.15, 0.18) | 390 |
| Example 82 | Compound 436 | 4.6 | 5.0 | (0.15, 0.18) | 339 |
| Example 83 | Compound 437 | 4.3 | 4.7 | (0.15, 0.18) | 376 |
| Example 84 | Compound 438 | 4.1 | 4.8 | (0.15, 0.17) | 402 |
| Example 85 | Compound 439 | 4.7 | 4.6 | (0.15, 0.17) | 347 |
| Example 86 | Compound 440 | 4.2 | 4.9 | (0.15, 0.17) | 398 |
| Example 87 | Compound 441 | 4.5 | 4.7 | (0.15, 0.18) | 368 |
| Example 88 | Compound 443 | 4.7 | 4.6 | (0.15, 0.19) | 346 |
| Example 89 | Compound 444 | 4.6 | 4.6 | (0.15, 0.17) | 354 |
| Example 90 | Compound 445 | 4.6 | 4.5 | (0.15, 0.17) | 336 |
| Example 91 | Compound 447 | 4.6 | 4.8 | (0.15, 0.18) | 376 |
| Example 92 | Compound 450 | 4.7 | 4.9 | (0.15, 0.18) | 379 |
| Example 93 | Compound 453 | 4.5 | 5.0 | (0.15, 0.18) | 487 |
| Example 94 | Compound 454 | 4.1 | 5.0 | (0.15, 0.17) | 477 |
| Example 95 | Compound 379 | 4.4 | 4.7 | (0.15, 0.18) | 401 |
| Example 96 | Compound 386 | 4.3 | 4.8 | (0.15, 0.17) | 455 |
| Example 97 | Compound 397 | 4.3 | 4.6 | (0.15, 0.17) | 362 |
| Example 98 | Compound 414 | 4.2 | 4.9 | (0.15, 0.18) | 452 |

It can be known that when the devices were manufactured by using the electron transport layer material used in Example 1 of the present invention, the service life of the device was increased and the driving voltage and efficiency thereof were improved compared to those of the devices manufactured by using E1 and E2 which are the electron transport layer materials used in Comparative Examples 1 and 2 as in Table 4.

Examples 99 to 118

An organic electroluminescence device was manufactured in the same manner as in Comparative Example 3, except that the compounds synthesized in Preparation Examples 1 to 19 were used instead of host CBP used during the formation of a light emitting layer in Comparative Example 3.

For each of the organic electroluminescence devices manufactured in Comparative Example 3 and Examples 99 to 118, electroluminescence (EL) characteristics were measured by M7000 manufactured by McScience Inc., and based on the measurement result thereof, $T_{90}$ was measured by a service life measurement equipment (M6000) manufactured by McScience Inc. when the reference brightness was 6,000 cd/m². The results are shown in the following Table 5.

TABLE 5

| Experimental Example | Compound | Driving voltage (V) | Efficiency (cd/A) | Color coordinate (x, y) | Service life ($T_{90}$) |
|---|---|---|---|---|---|
| Example 99 | 1 | 4.73 | 57.7 | (0.294, 0.654) | 59.3 |
| Example 100 | 17 | 4.71 | 58.8 | (0.293, 0.653) | 60.9 |
| Example 101 | 29 | 4.92 | 56.3 | (0.296, 0.654) | 57.4 |
| Example 102 | 42 | 4.69 | 57.2 | (0.297, 0.653) | 56.1 |
| Example 103 | 48 | 4.92 | 58.5 | (0.295, 0.654) | 58.2 |
| Example 104 | 74 | 4.68 | 56.2 | (0.296, 0.652) | 55.4 |
| Example 105 | 85 | 4.78 | 56.8 | (0.296, 0.655) | 58.7 |
| Example 106 | 86 | 4.87 | 56.2 | (0.292, 0.653) | 61.4 |
| Example 107 | 87 | 4.87 | 60.9 | (0.293, 0.654) | 55.7 |
| Example 108 | 88 | 4.82 | 59.2 | (0.294, 0.652) | 58.2 |
| Example 109 | 90 | 4.44 | 56.3 | (0.296, 0.652) | 60.9 |
| Example 110 | 91 | 4.39. | 57.2 | (0.296, 0.655) | 57.4 |
| Example 111 | 92 | 4.71 | 58.5 | (0.292, 0.653) | 56.1 |
| Example 112 | 93 | 4.92 | 57.2 | (0.295, 0.654) | 58.2 |
| Example 113 | 110 | 4.69 | 56.8 | (0.296, 0.652) | 58.7 |
| Example 114 | 119 | 4.87 | 56.2 | (0.296, 0.655) | 61.4 |
| Example 115 | 156 | 4.82 | 57.7 | (0.296, 0.655) | 56.1 |
| Example 116 | 185 | 4.78 | 58.8 | (0.292, 0.653) | 59.3 |
| Example 117 | 243 | 4.78 | 56.3 | (0.296, 0.655) | 59.7 |
| Comparative Example 118 | CBP | 5.24 | 48.1 | (0.295, 0.651) | 50.0 |

As can be seen from the results of Table 5, it can be known that the organic light emitting device in which the compound according to the present invention is applied to the light emitting layer has a lower driving voltage and a more improved light emitting efficiency than those of the organic light emitting device in Comparative Example 3, and the service life thereof is also significantly improved.

The invention claimed is:

1. A hetero-cyclic compound represented by the following Formula 1:

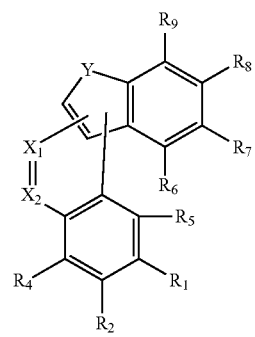

[Formula 1]

in Formula 1,

Y is S or O, $X_1$ and $X_2$ are the same as or different from each other, and are each independently N or $CR_{10}$, wherein at least one of $X_1$ and $X_2$ is N, $R_4$ to $R_9$ are hydrogen, one of $R_1$, $R_2$, and $R_{10}$ is -(L)m-(Z)n, the others are hydrogen, L is monocyclic or polycyclic substituted or unsubstituted $C_6$ to $C_{10}$ arylene; polycyclic substituted or unsubstituted $C_{15}$ to $C_{60}$ arylene; or monocyclic or polycyclic substituted or unsubstituted $C_2$ to $C_{60}$ heteroarylene, m is an integer of 0 to 3, n is an integer of 1 or 2, Z is represented by any one of the following structural formulae:

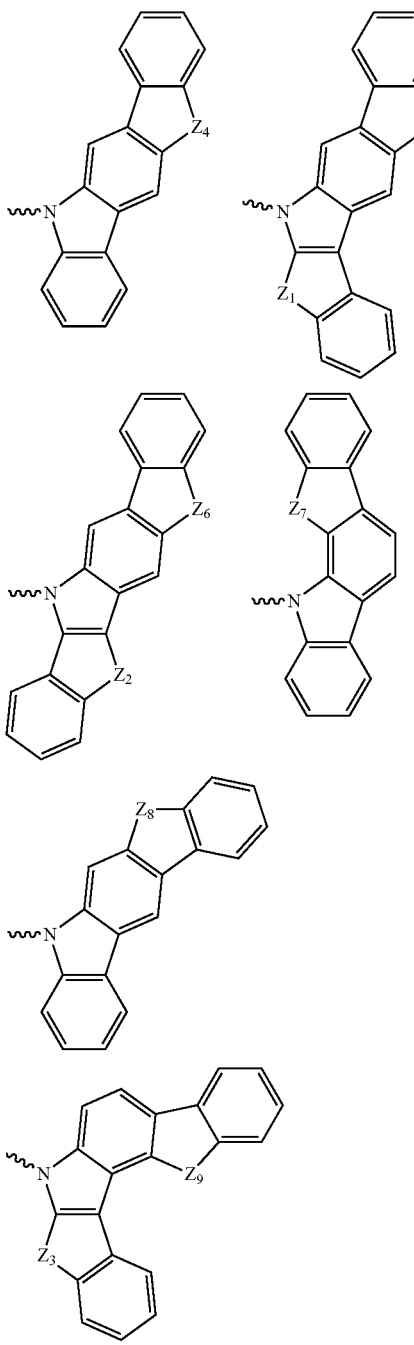

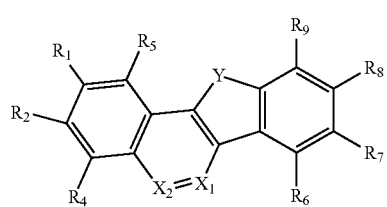

[Formula 2]

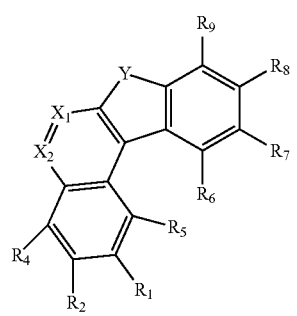

[Formula 3]

in Formulae 2 and 3, the definitions of Y, $X_1$, $X_2$, $R_1$, $R_2$, and $R_4$ to $R_9$ are the same as those defined in Formula 1.

3. The hetero-cyclic compound of claim 1, wherein Formula 1 is represented by any one of the following Formulae 4 to 7:

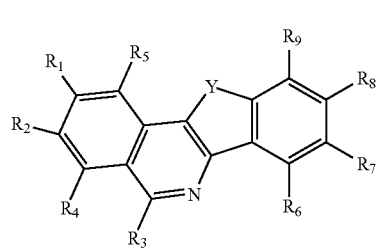

[Formula 4]

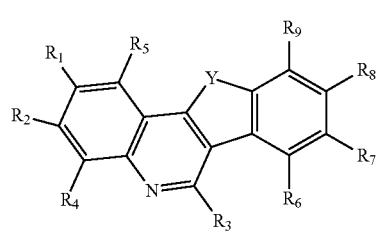

[Formula 5]

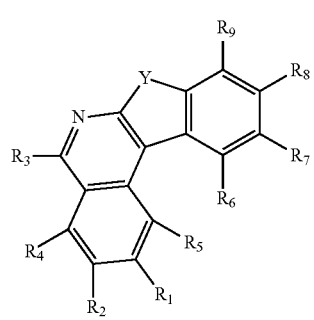

[Formula 6]

in the structural formulae, $Z_1$ to $Z_3$ are the same as or different from each other, and are each independently S or O, $Z_4$ to $Z_9$ are the same as or different from each other, and are each independently CR'R'', NR', S, or O, and R' and R'' are the same as or different from each other, and are each independently hydrogen; straight-chained or branched substituted or unsubstituted $C_1$ to $C_{60}$ alkyl; or monocyclic or polycyclic substituted or unsubstituted $C_6$ to $C_{60}$ aryl.

2. The hetero-cyclic compound of claim 1, wherein Formula 1 is represented by the following Formula 2 or 3:

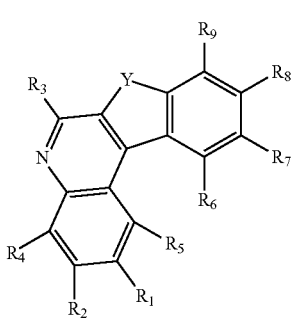

in Formulae 4 to 7,

Y, $R_1$, $R_2$, and $R_4$ to $R_9$ are the same as those defined in Formula 1, and $R_3$ is the same as the definition of $R_{10}$ of Formula 1.

4. A hetero-cyclic compound represented by any one of the following Formulae 8 to 11:

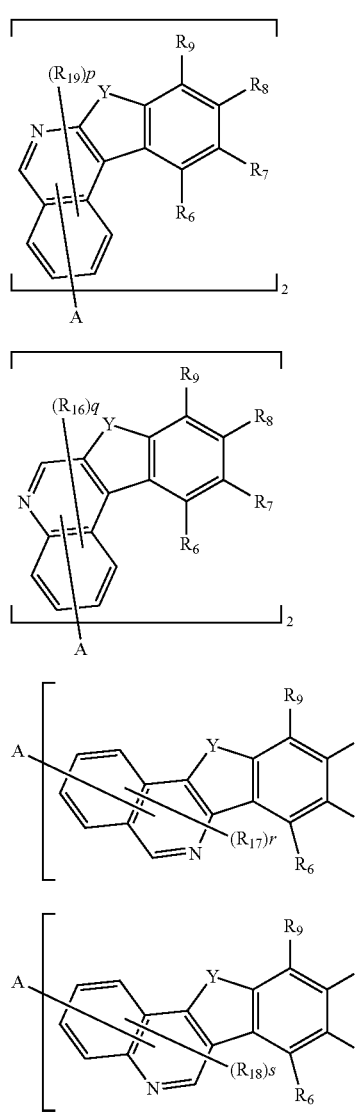

in Formulae 8 to 11,

A is selected from the group consisting of a direct bond; monocyclic or polycyclic substituted or unsubstituted $C_6$ to $C_{10}$ arylene; polycyclic substituted or unsubstituted $C_{15}$ to $C_{60}$ arylene; and monocyclic or polycyclic substituted or unsubstituted $C_2$ to $C_{60}$ heteroarylene, $R_{16}$ to $R_{19}$ are hydrogen, p, q, r, and s are an integer of 0 to 4, $R_6$ to $R_9$ are hydrogen, and Y is S or O.

5. The hetero-cyclic compound of claim 4, wherein A is selected from the group consisting of monocyclic or polycyclic substituted or unsubstituted $C_6$ to $C_{10}$ arylene; polycyclic substituted or unsubstituted $C_{15}$ to $C_{60}$ arylene; and monocyclic or polycyclic substituted or unsubstituted $C_2$ to $C_{60}$ heteroarylene.

6. A hetero-cyclic compound selected from the following compounds:

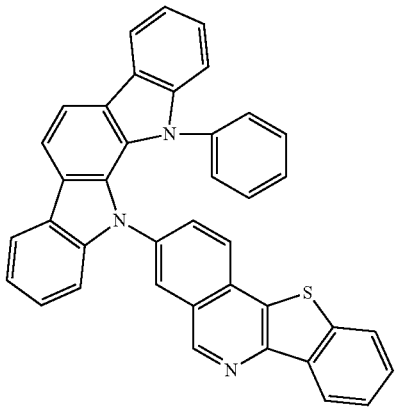

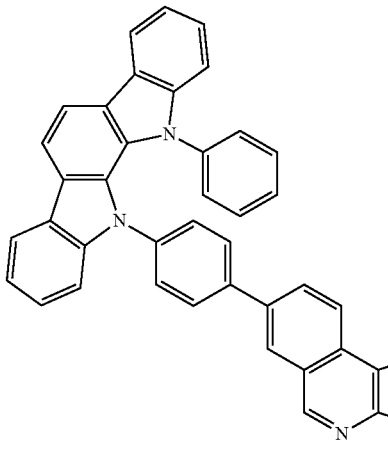

-continued
3
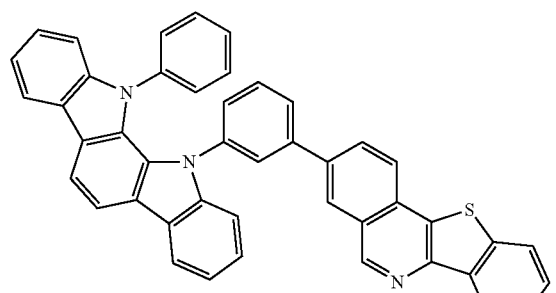
4
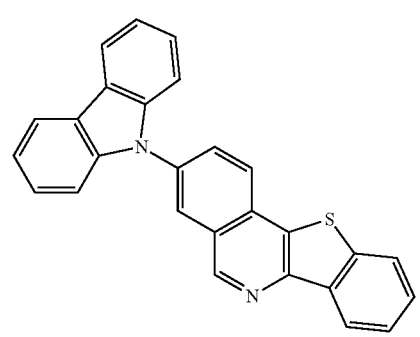
5
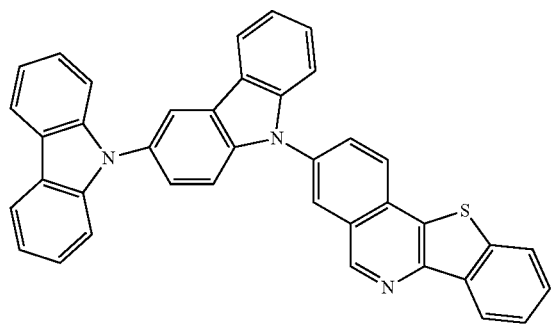
6
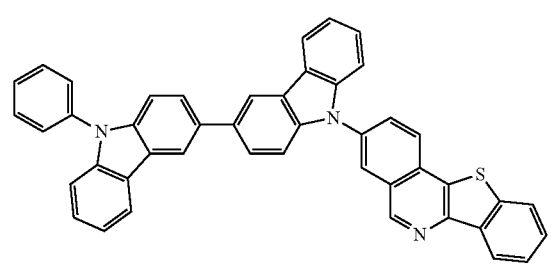
7
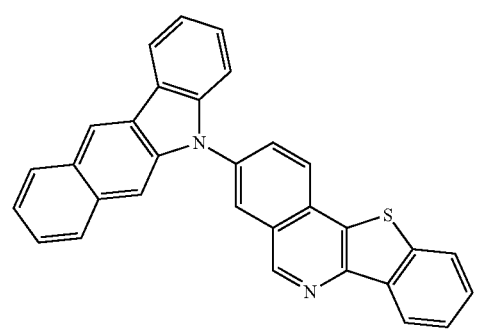
-continued
8
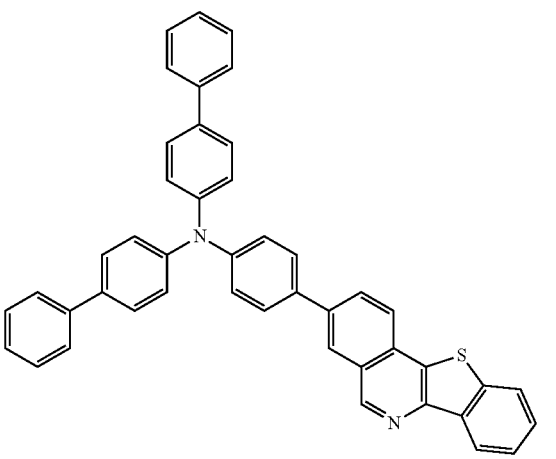
9
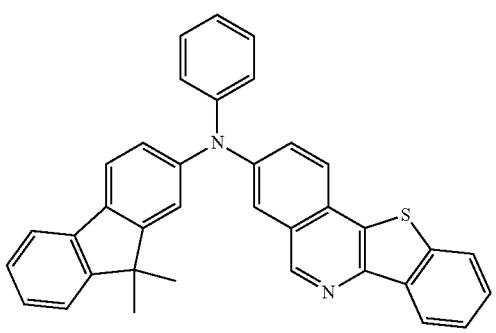
10
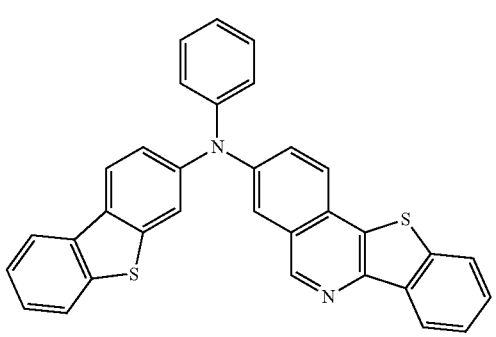
11
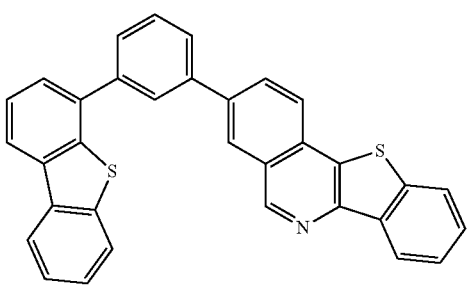

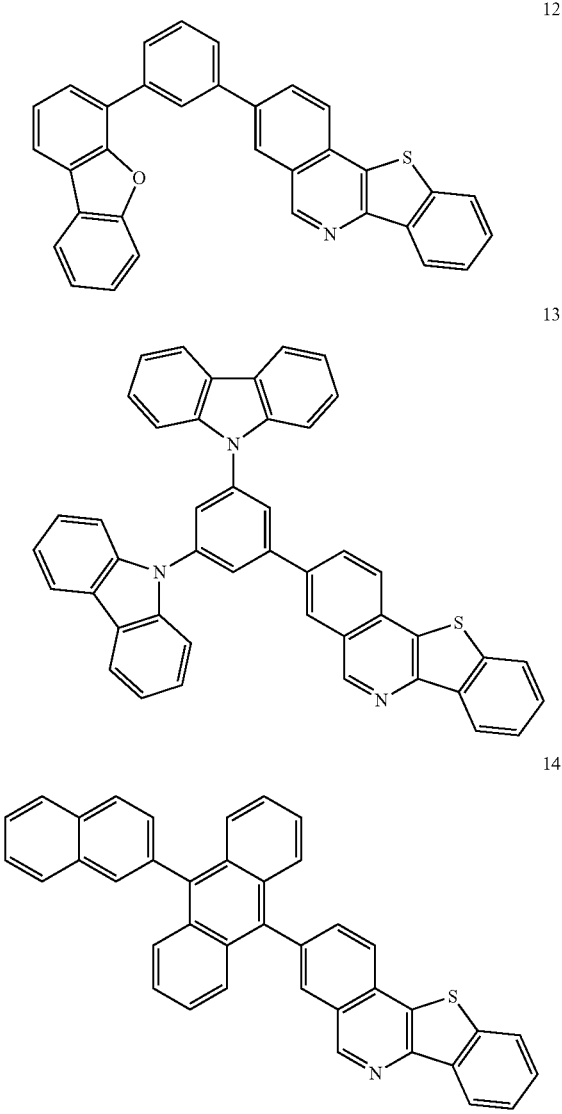
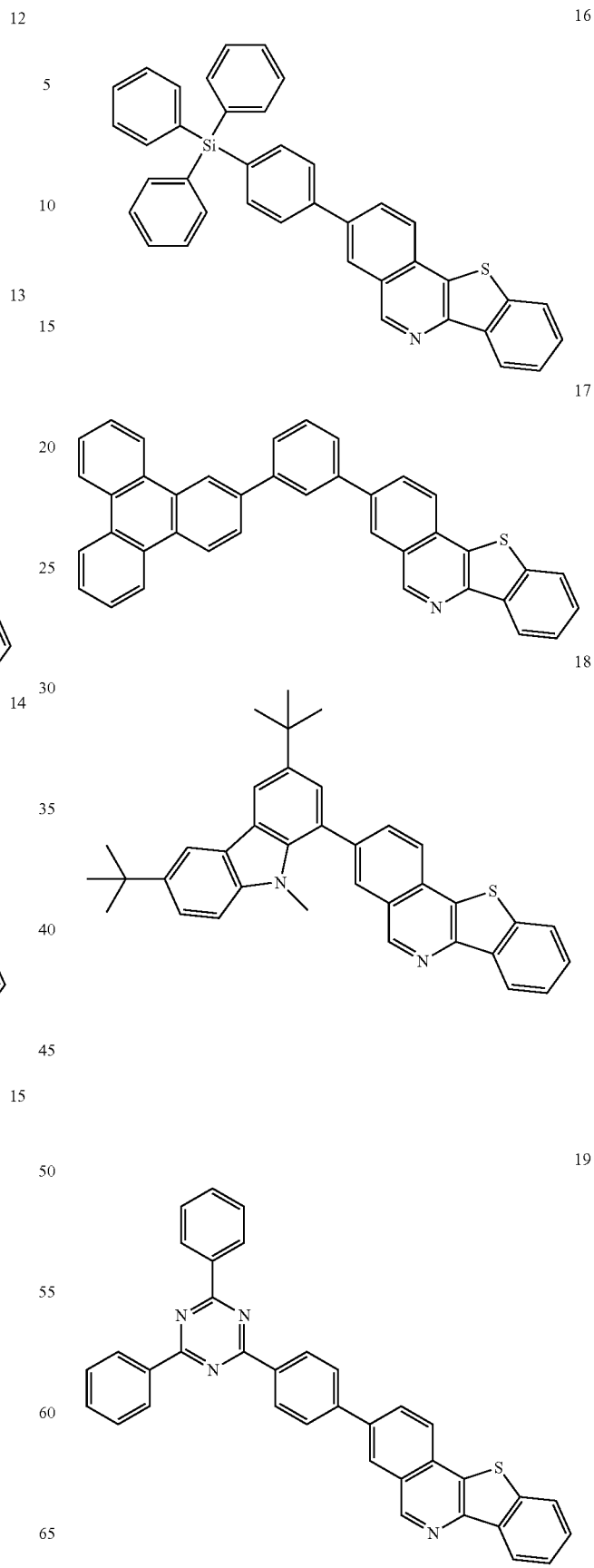

269
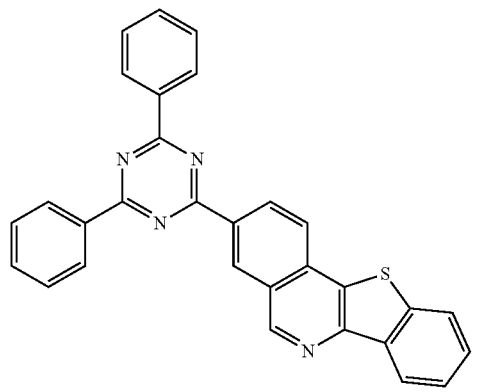
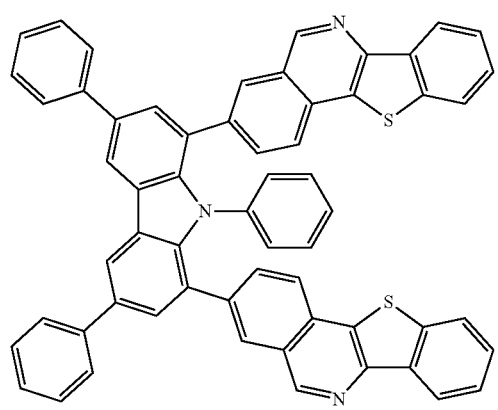
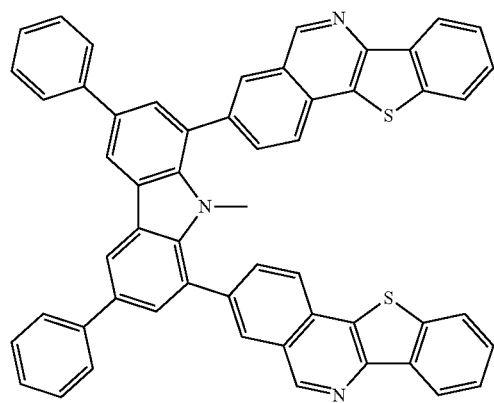
270
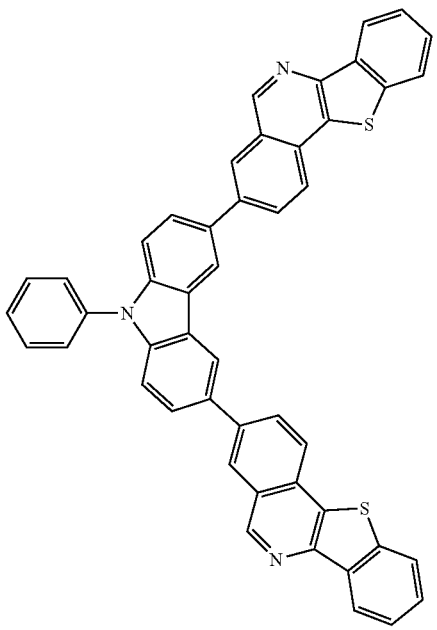
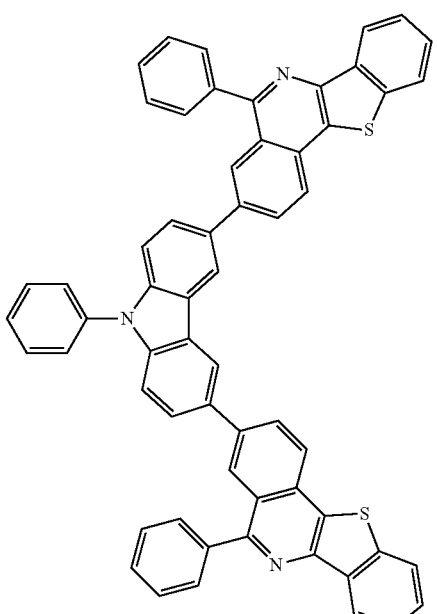
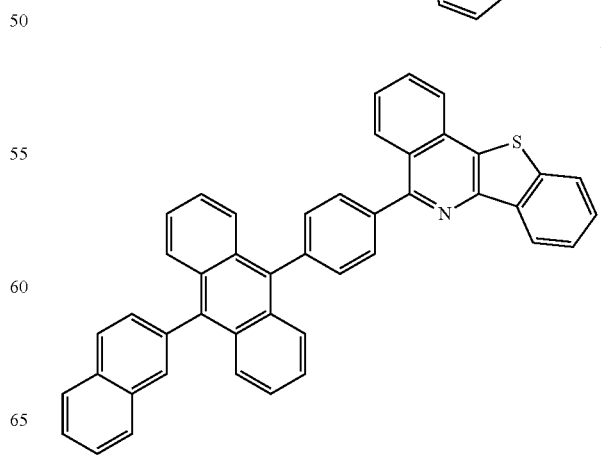

271
-continued
26
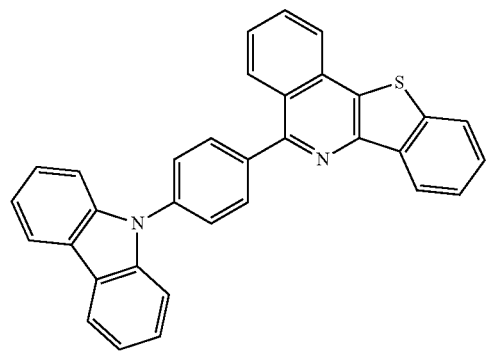
27
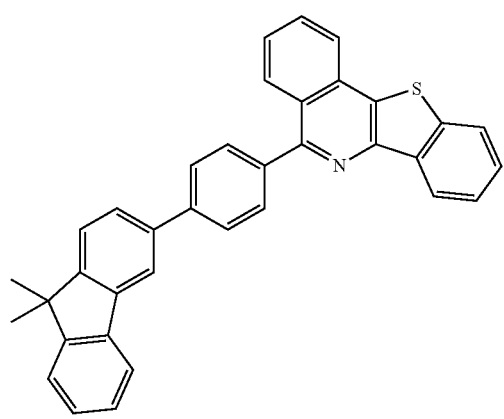
28
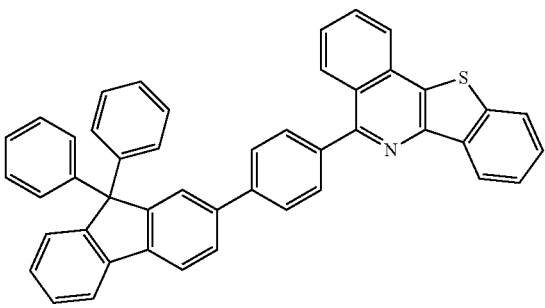
29
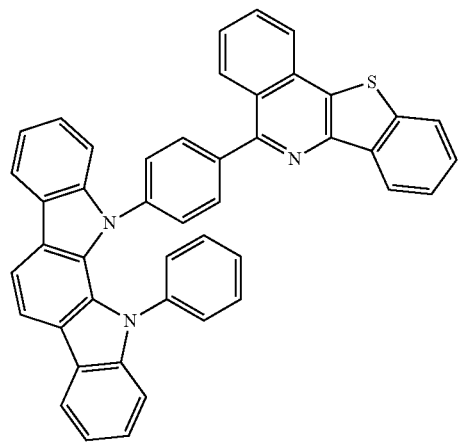
272
-continued
30
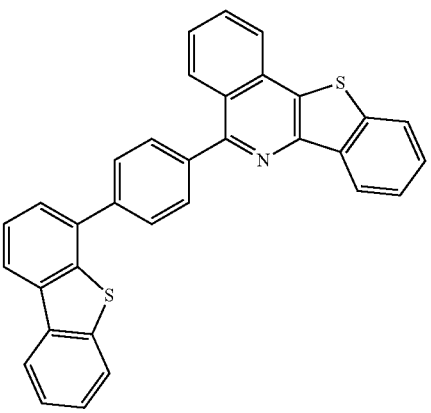
31
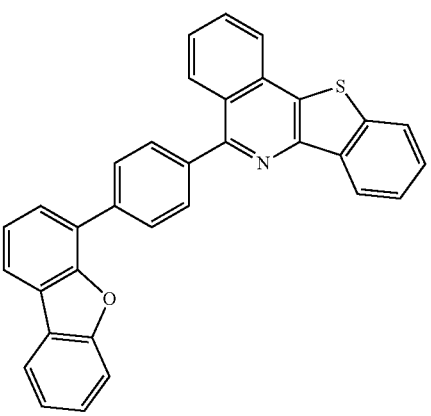
32
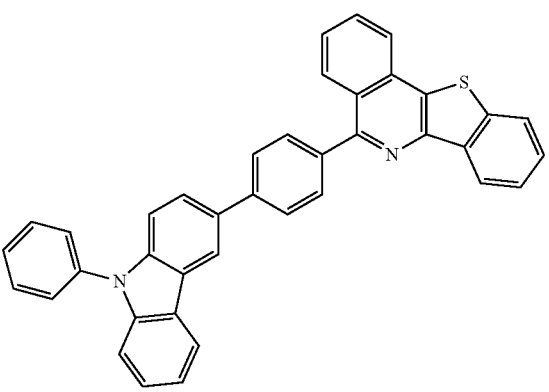
33
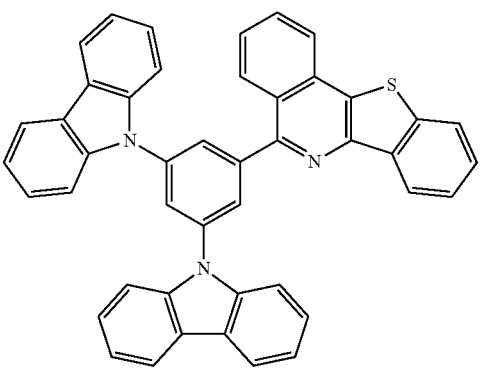

273
-continued
34
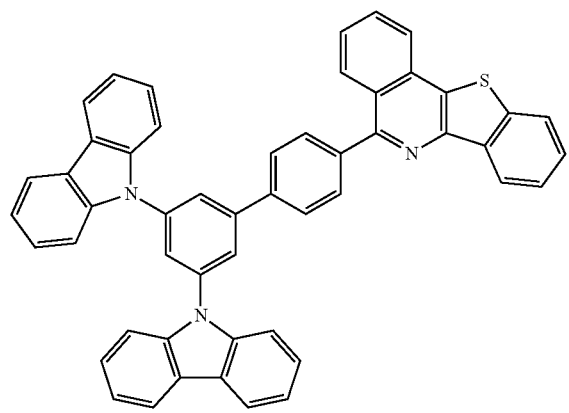
35
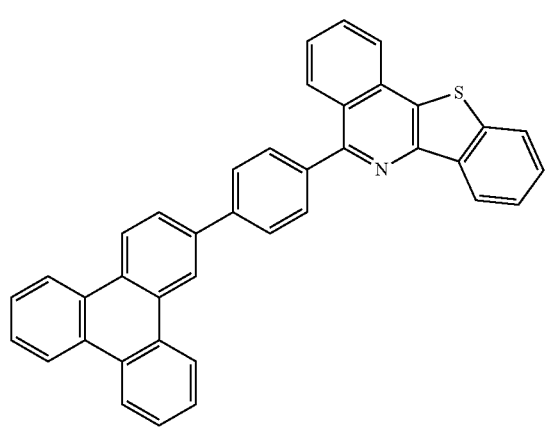
36
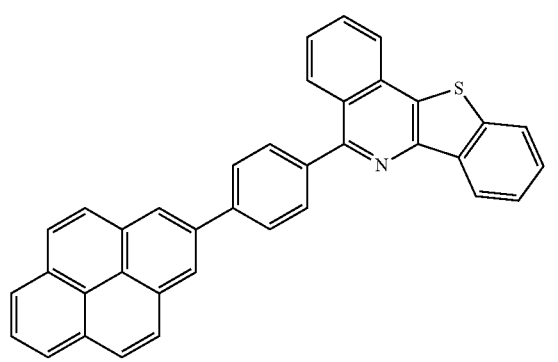
37
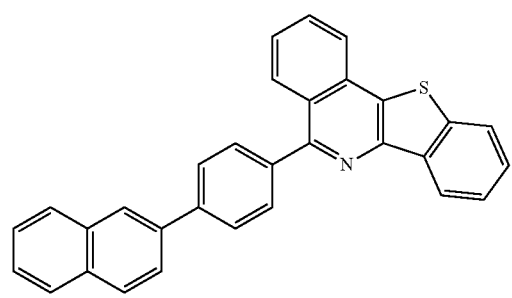
274
-continued
38
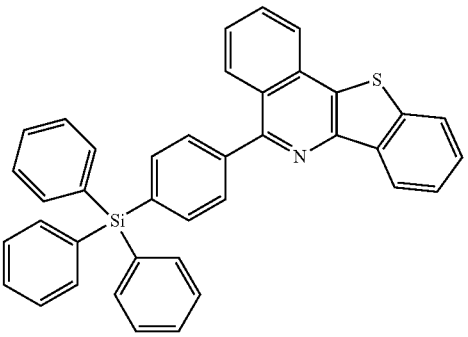
39
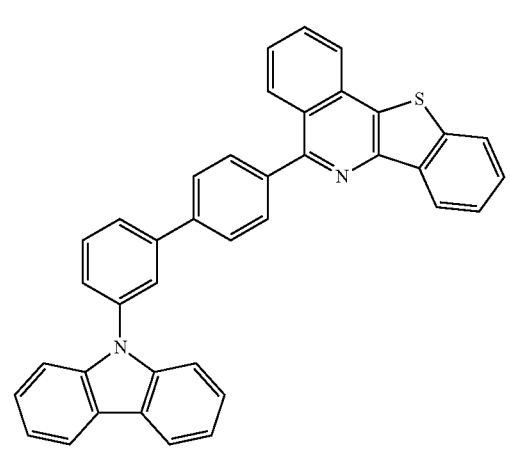
40
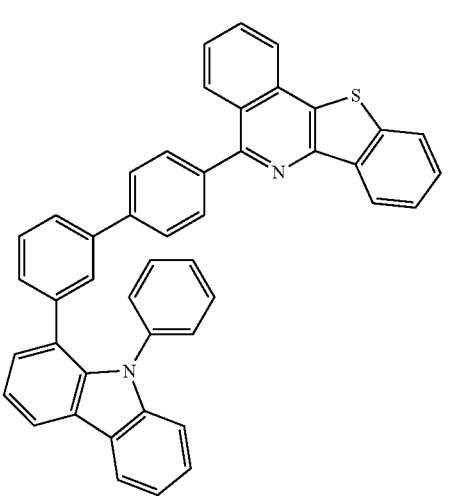

41
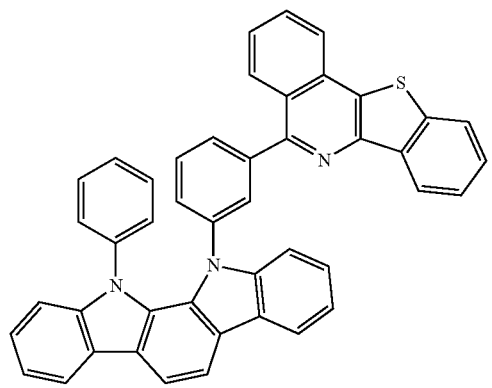
42
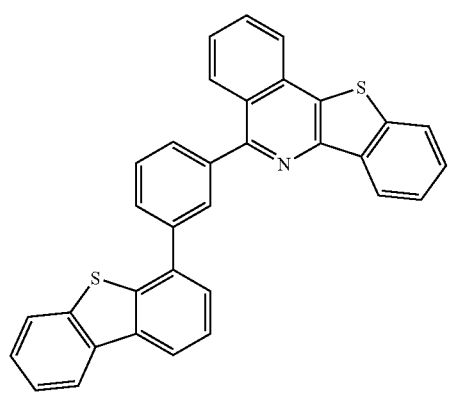
43
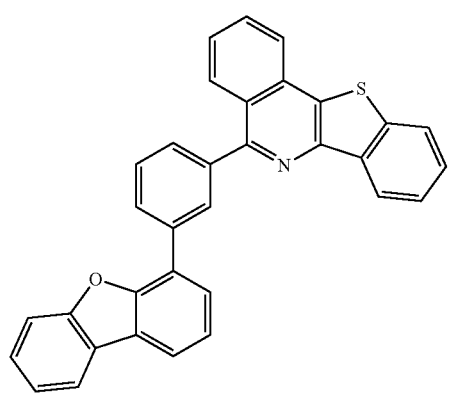
44
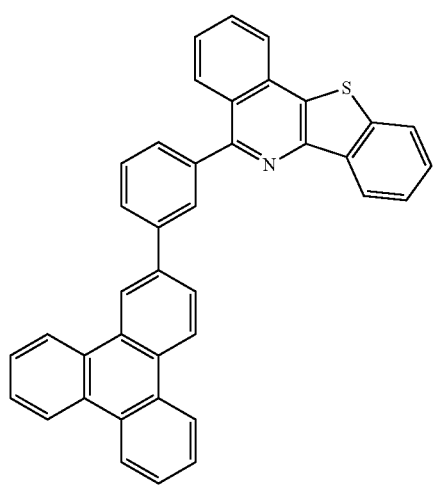
45
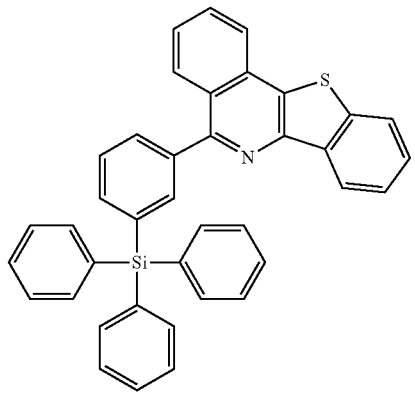
46
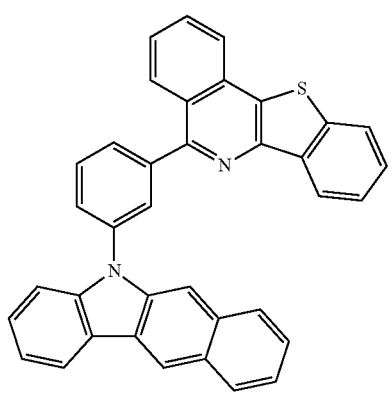
47
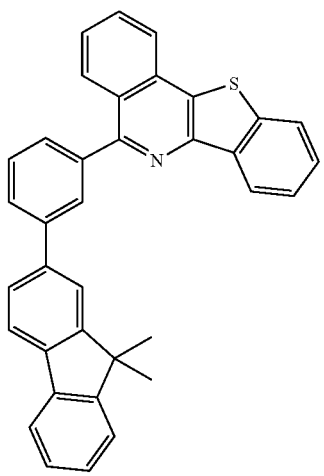
48
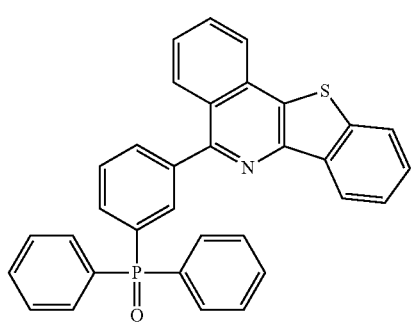

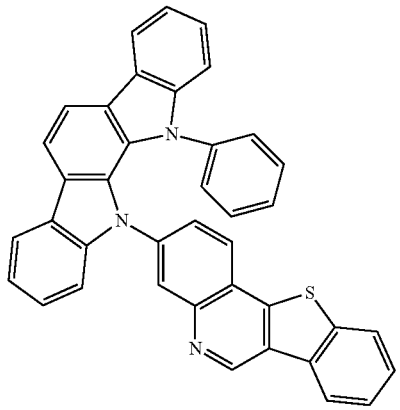
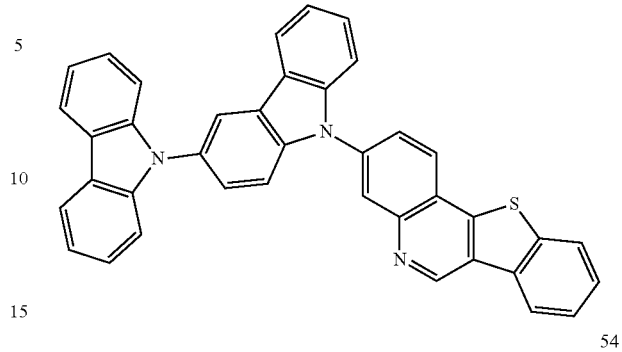
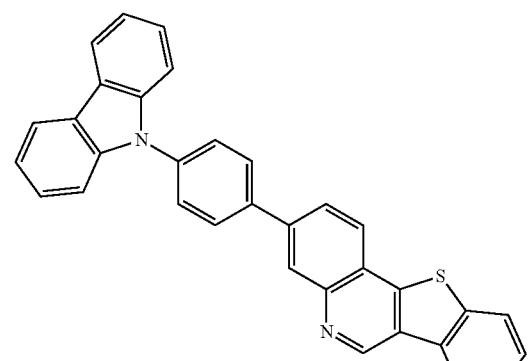
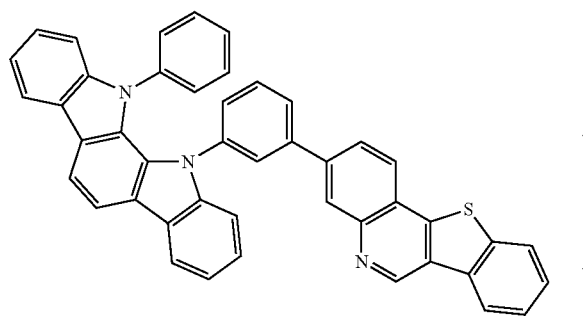
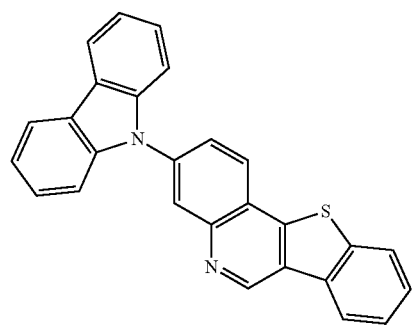
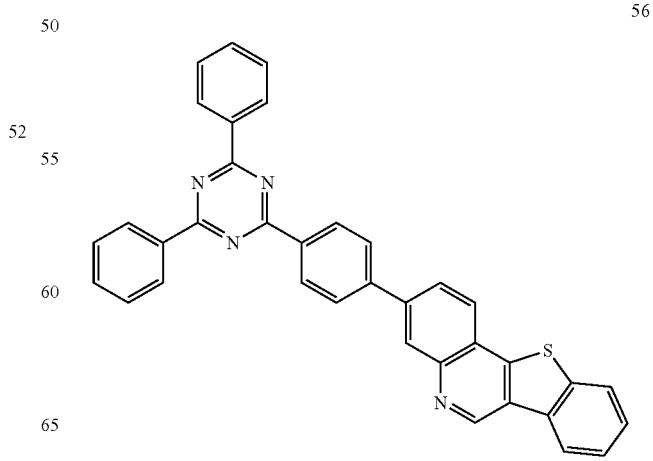

57
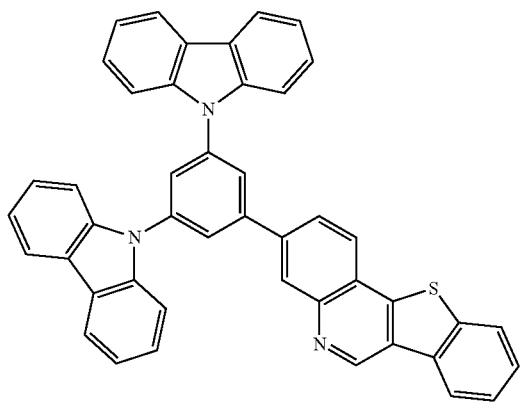
58
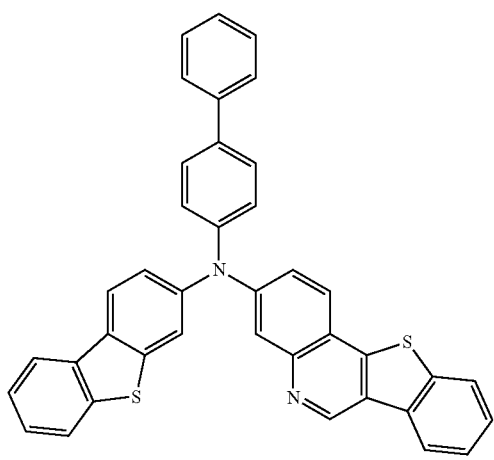
59
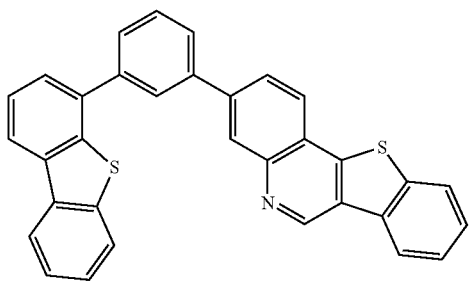
60
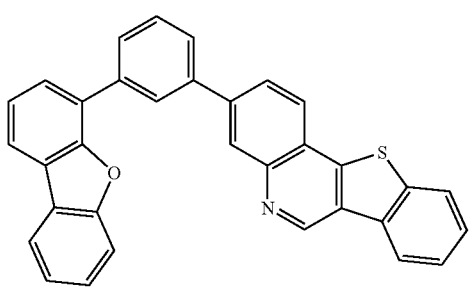
61
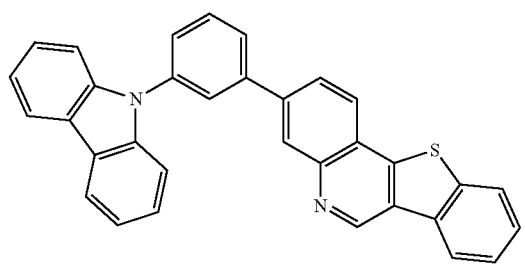
62
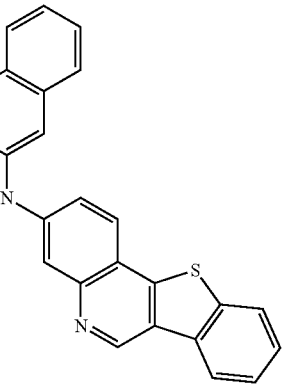
63
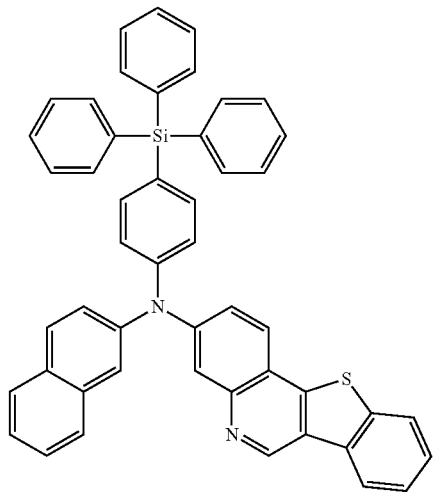
64
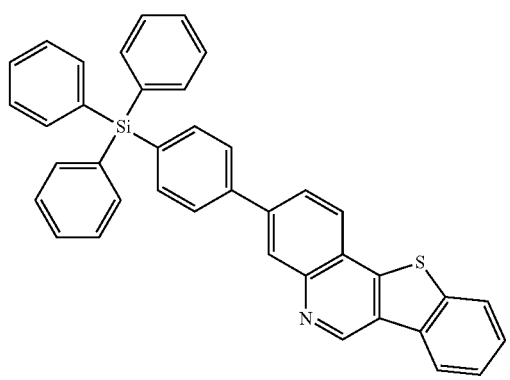

65
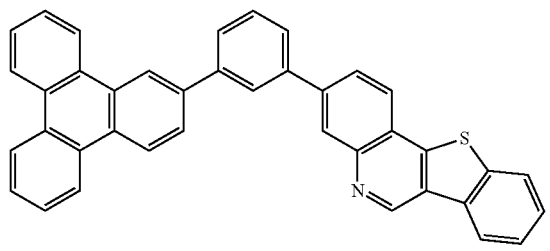
66
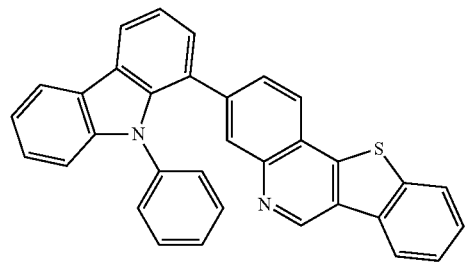
67
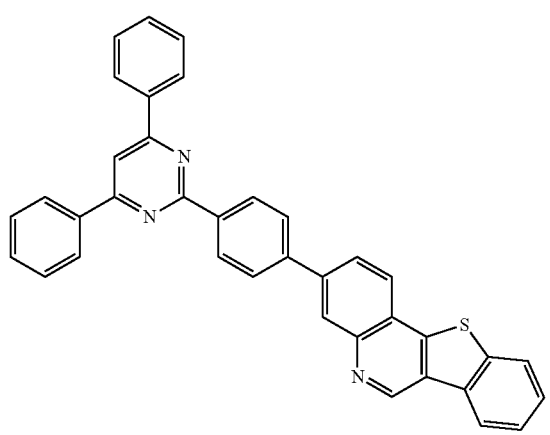
68
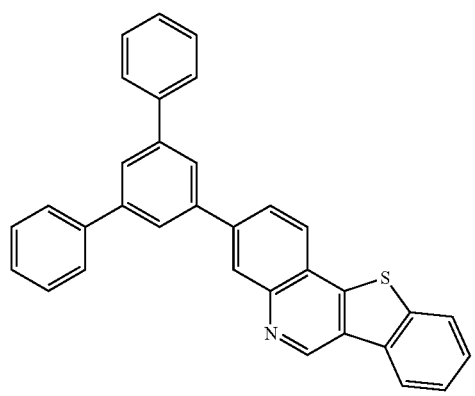
69
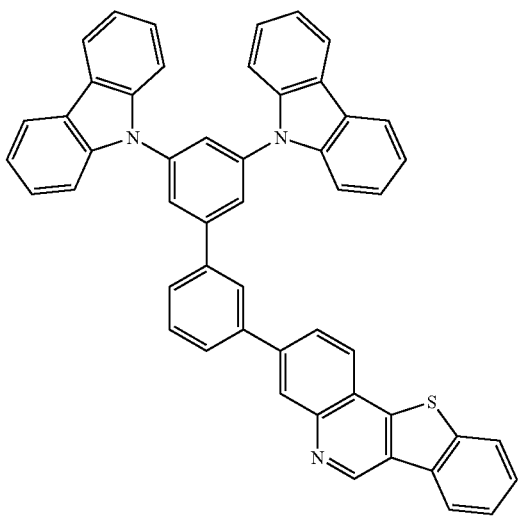
70
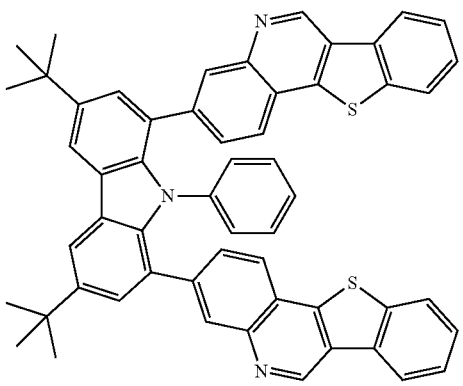
71
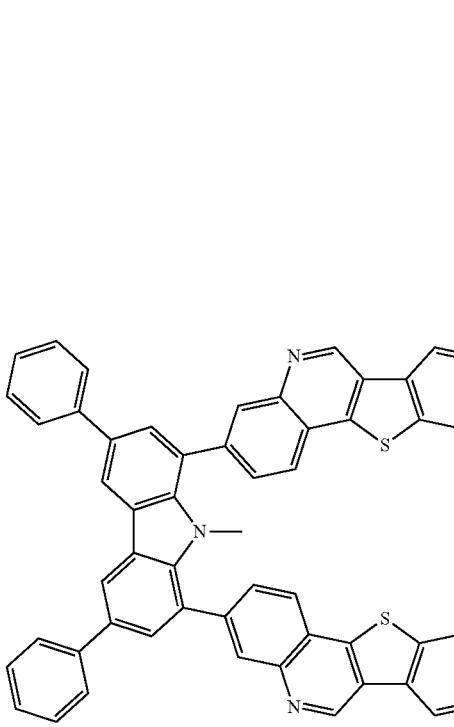

72
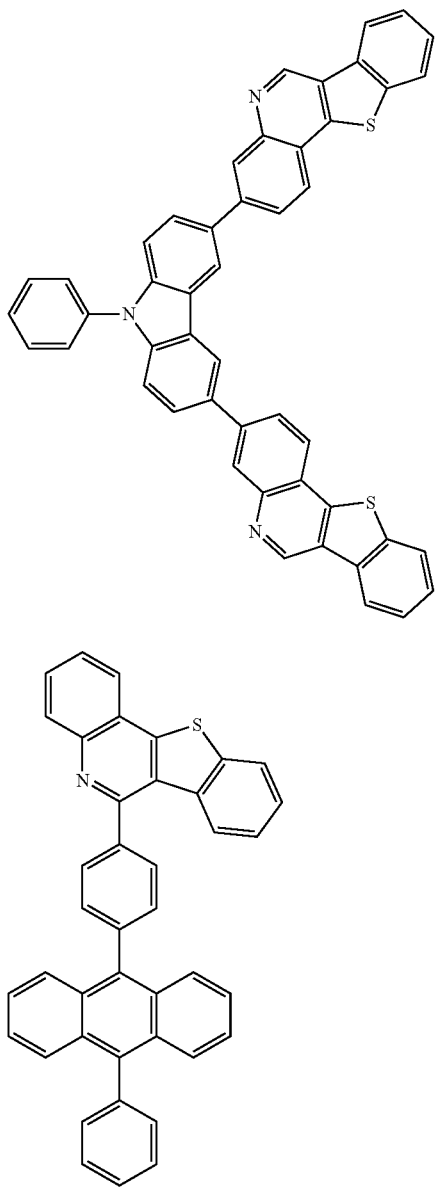
73
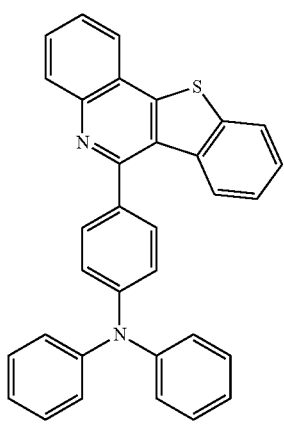
74
75
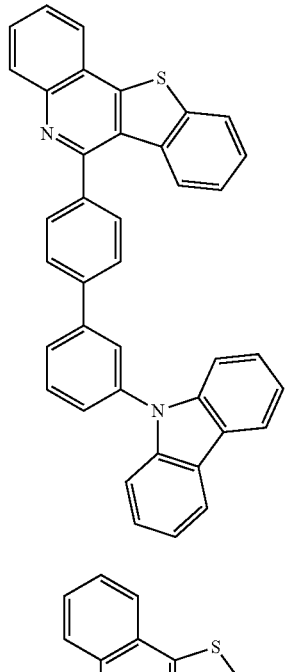
76
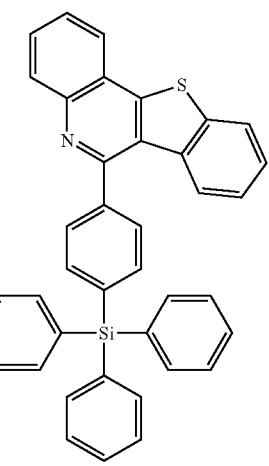
77
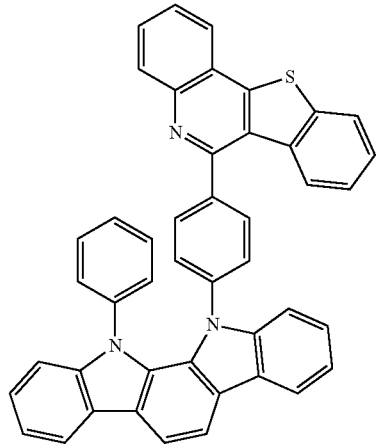

78
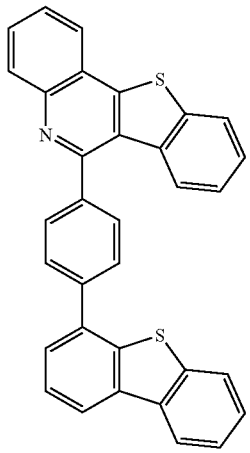
79
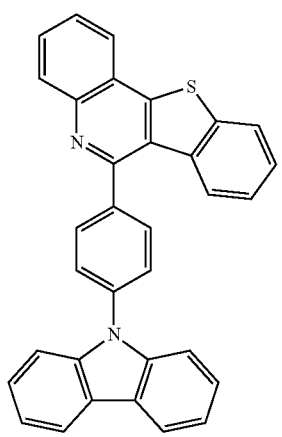
80
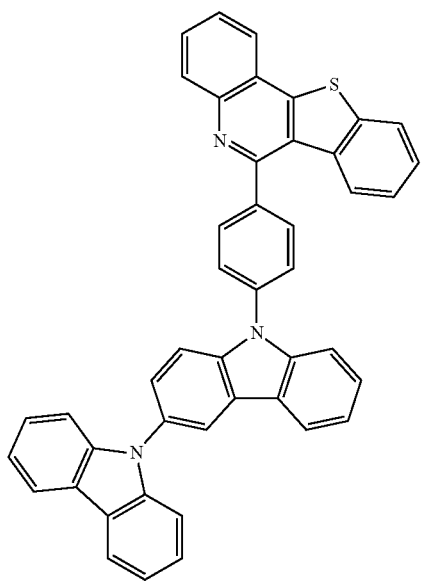
81
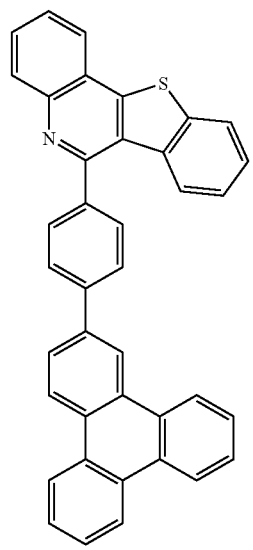
82
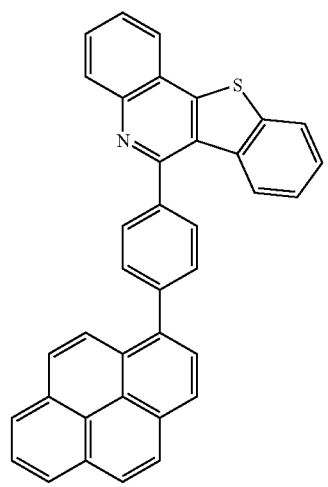
83
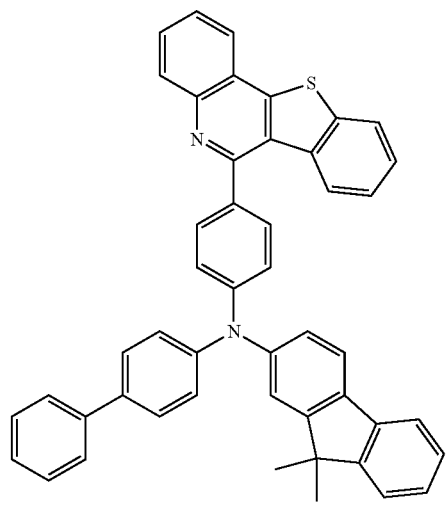

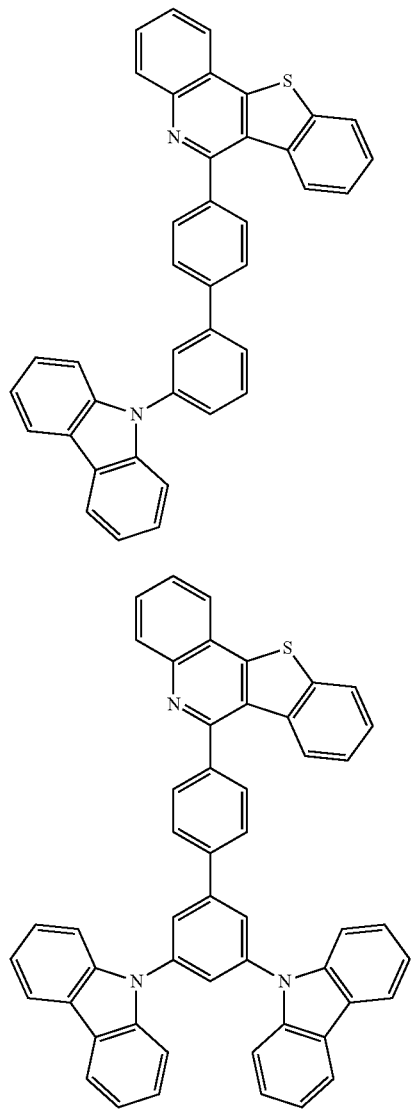
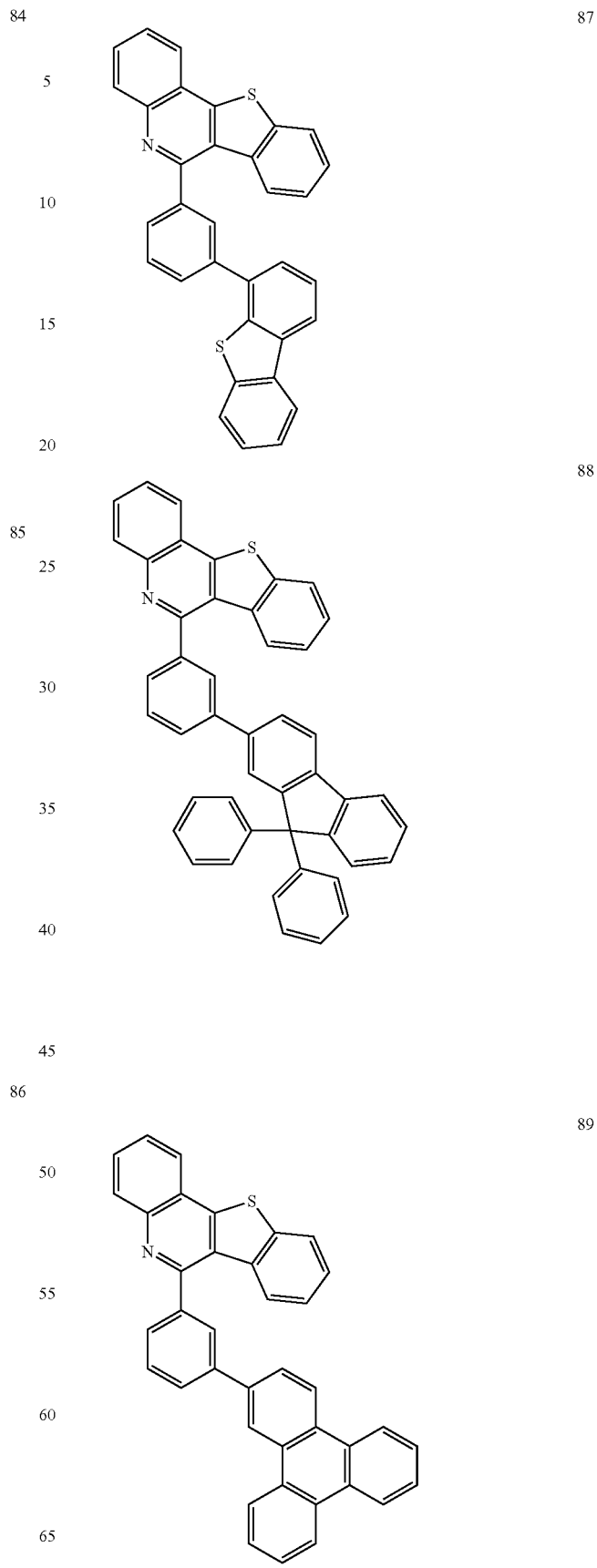

289
-continued
90
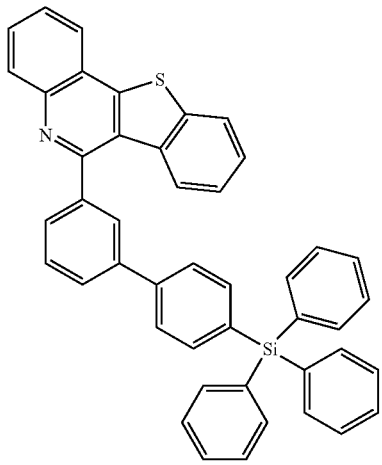
91
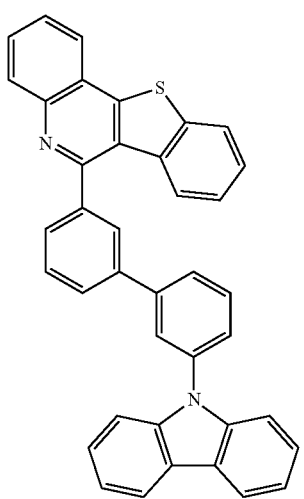
92
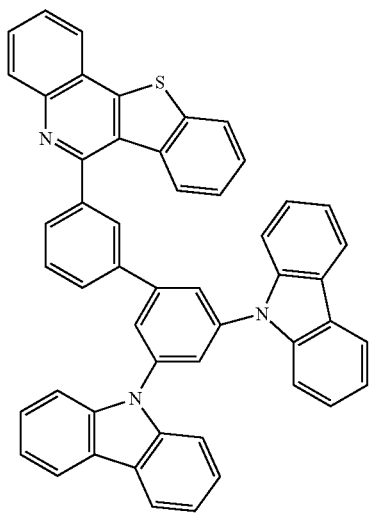
290
-continued
93
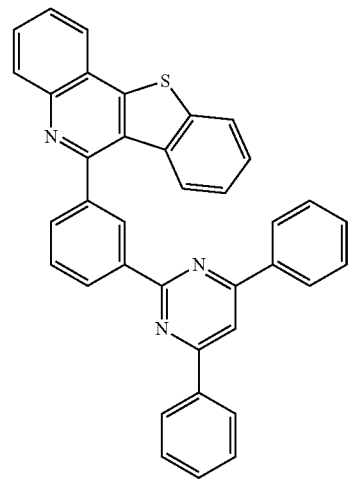
94
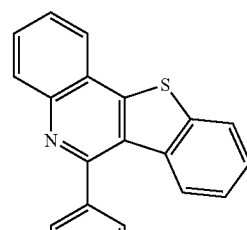
95

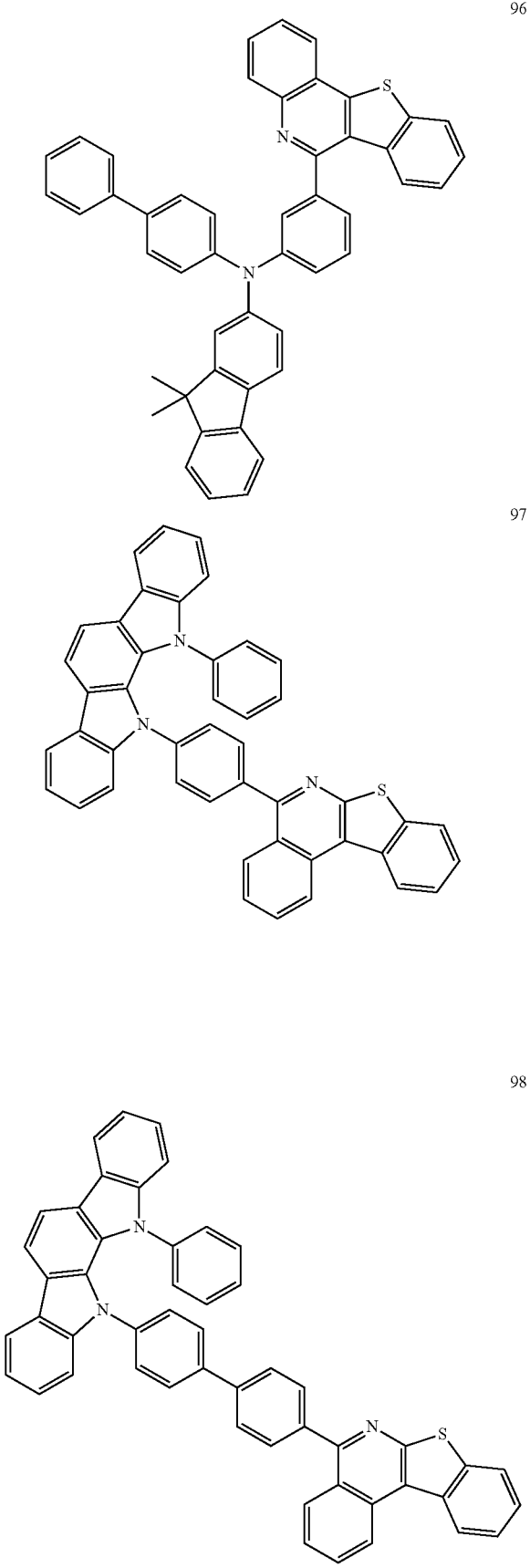

103
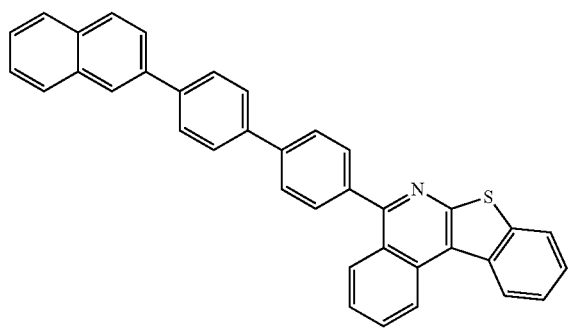
104
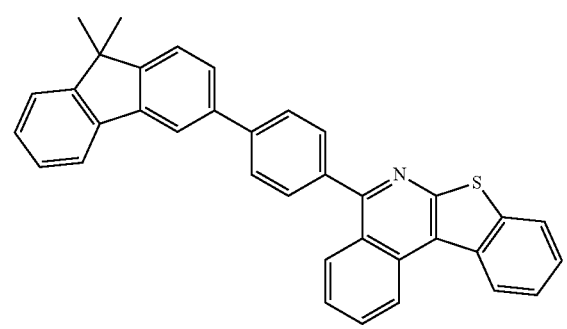
105
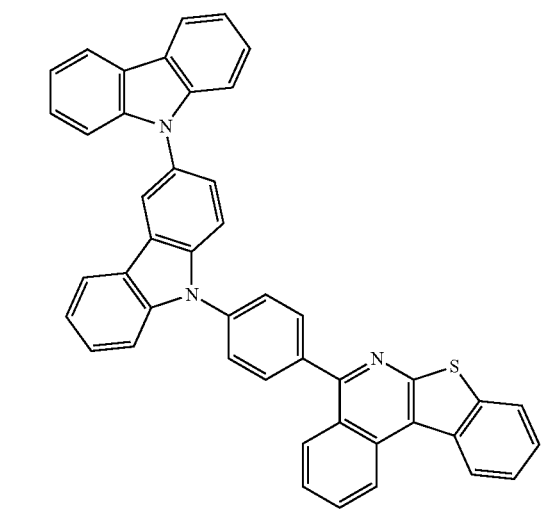
106
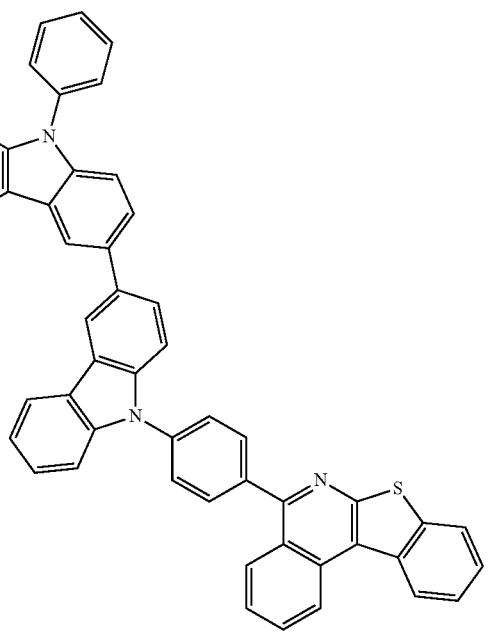
107
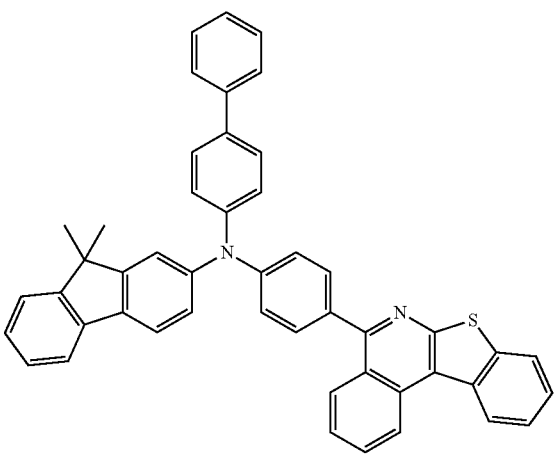
108

109
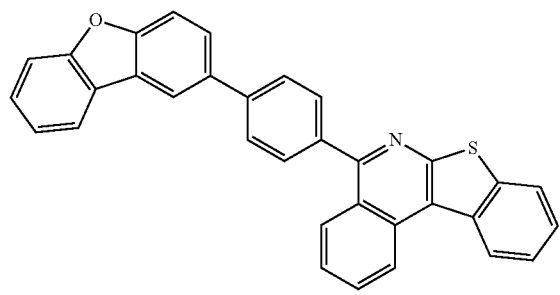
110
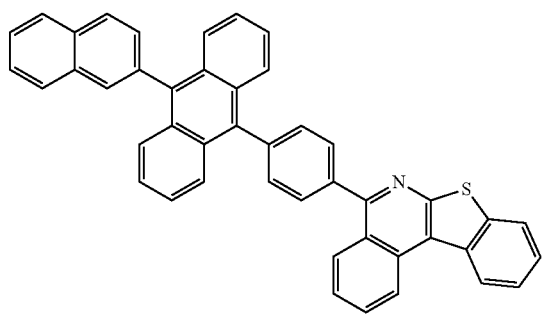
111
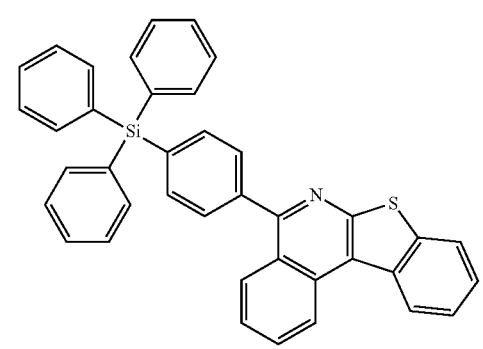
112
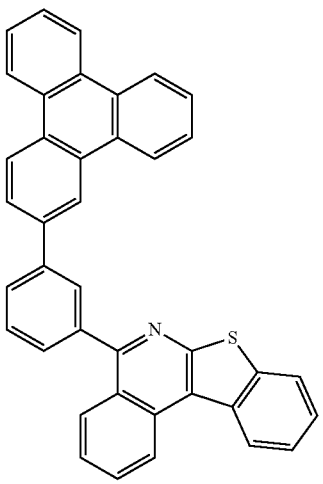
113
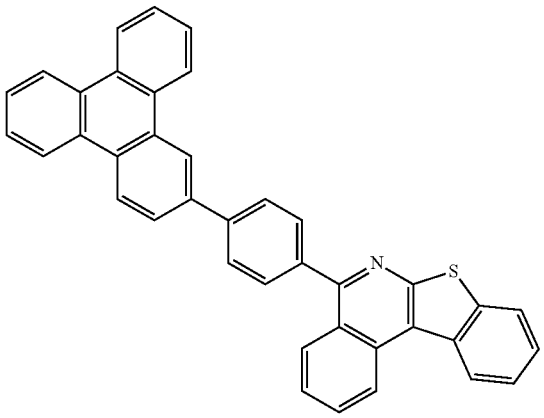
114
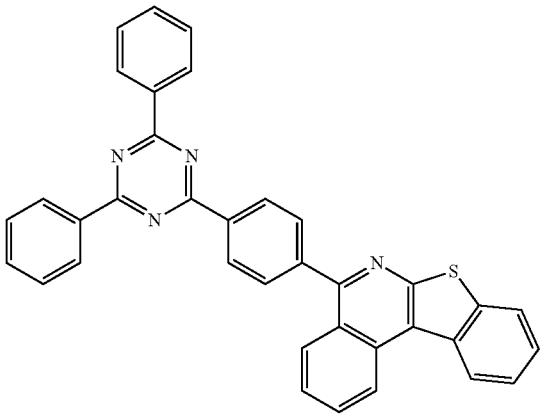
115

297
-continued
116
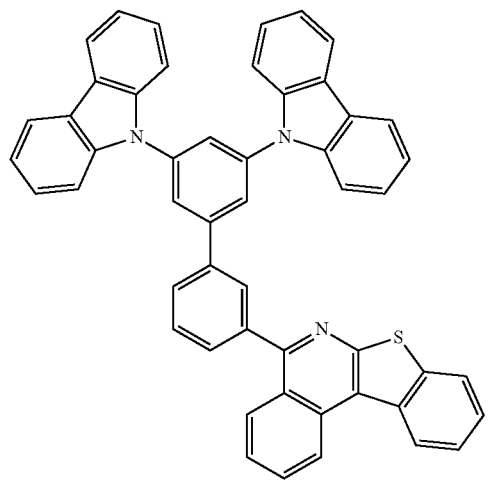
117
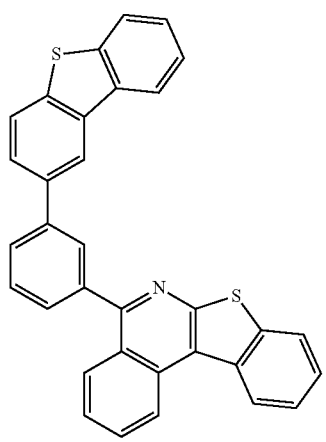
118
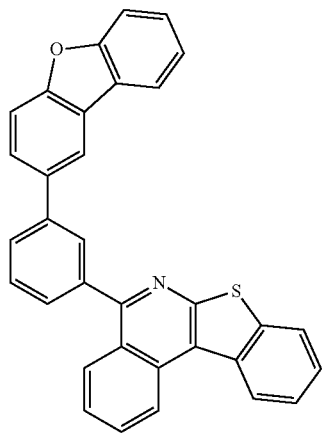
298
-continued
119
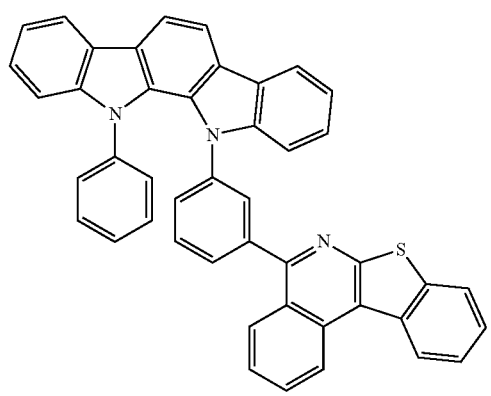
120
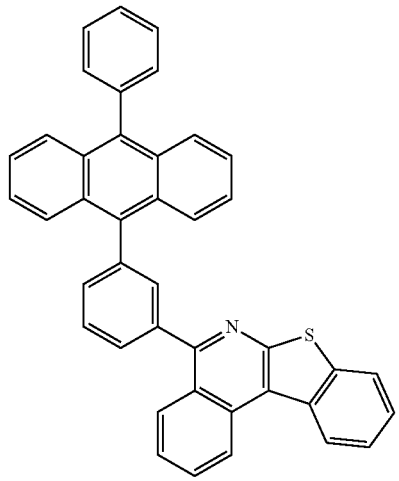
121
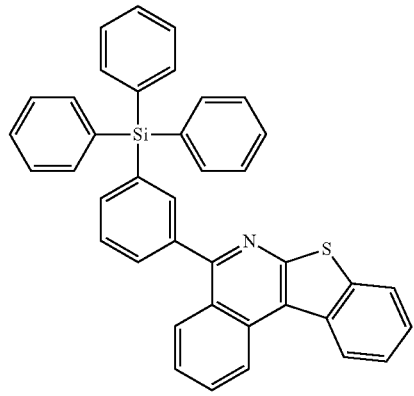
122
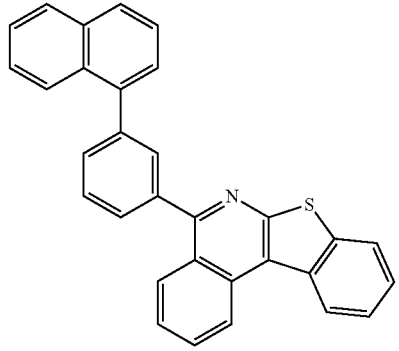

299
-continued
123
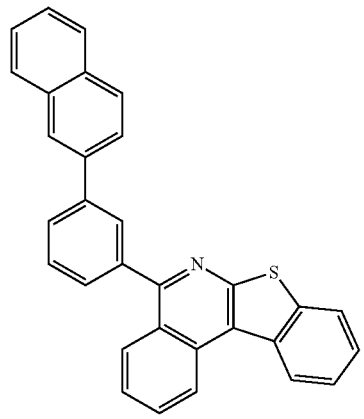
124
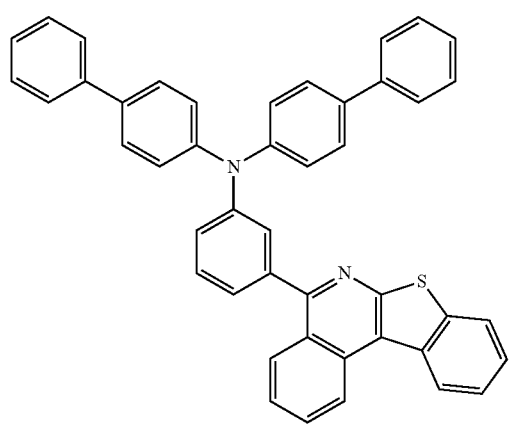
125
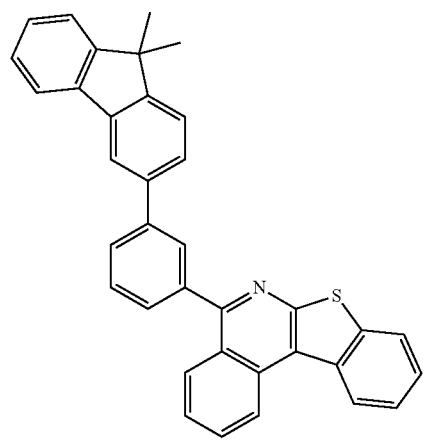
126
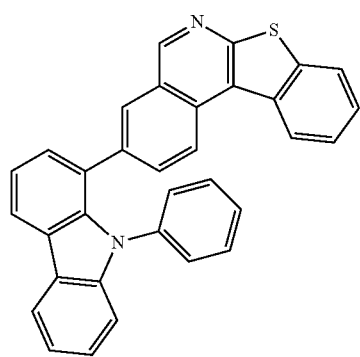
300
-continued
127
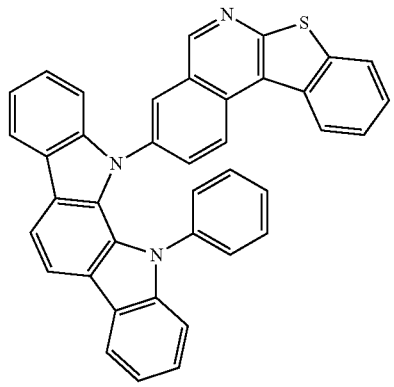
128
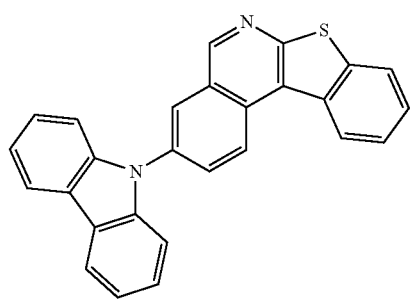
129
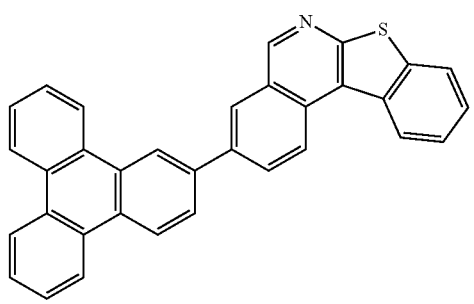
130
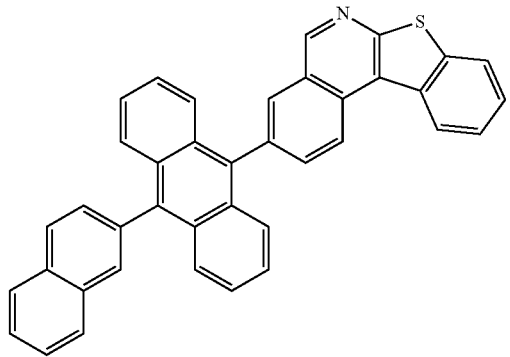

131
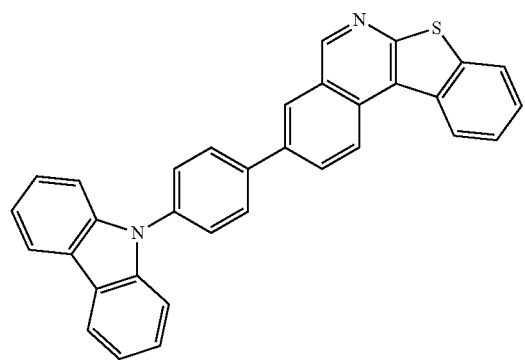
132
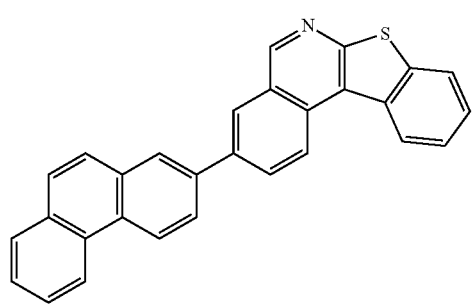
133
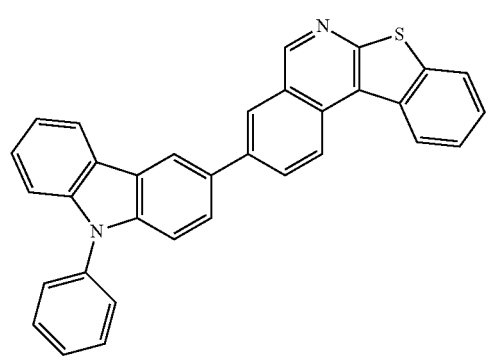
134
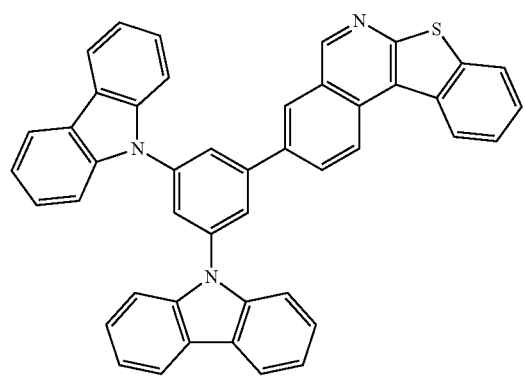
135
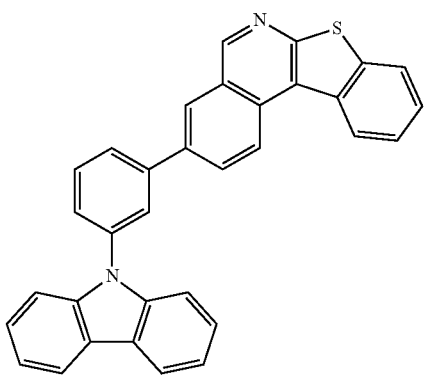
136
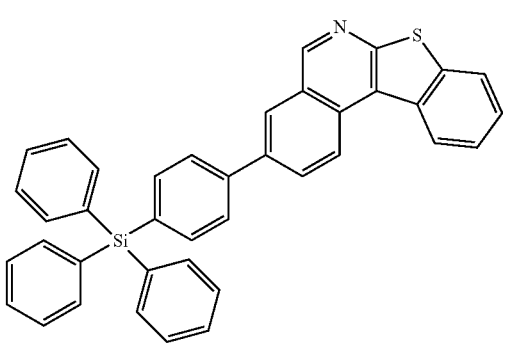
137
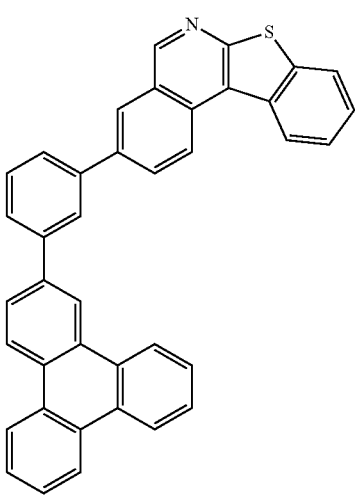

303
-continued
138
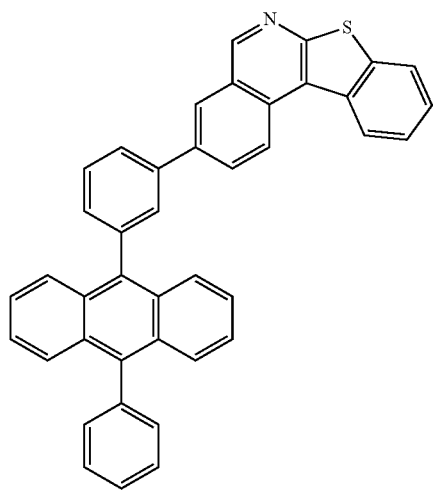
139
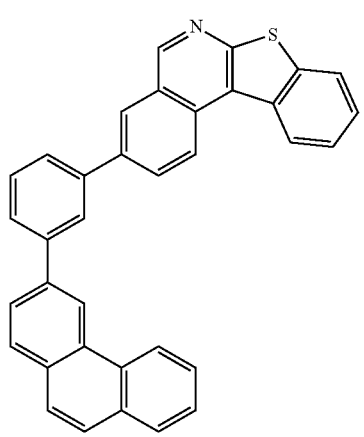
140
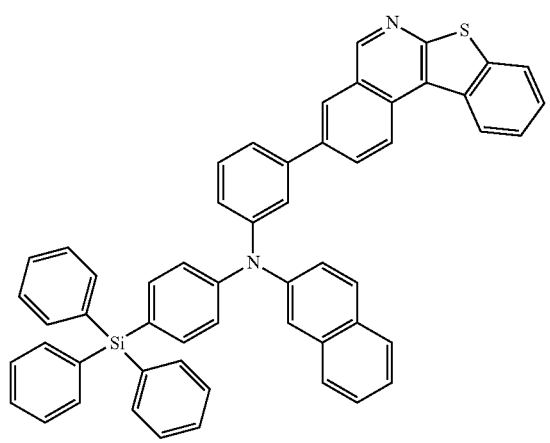
304
-continued
141
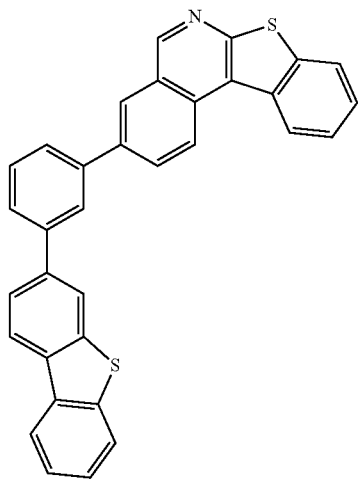
142
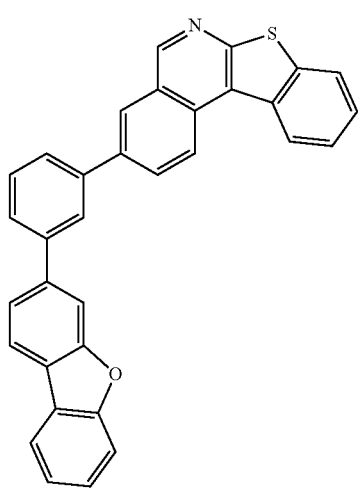
143
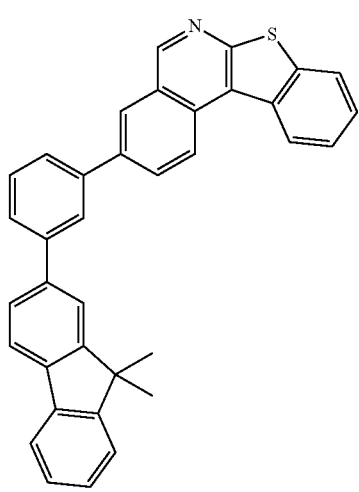

305
-continued
144
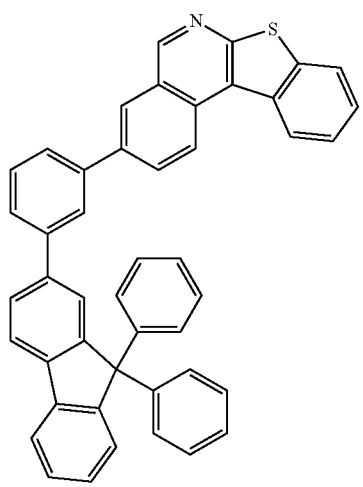
145
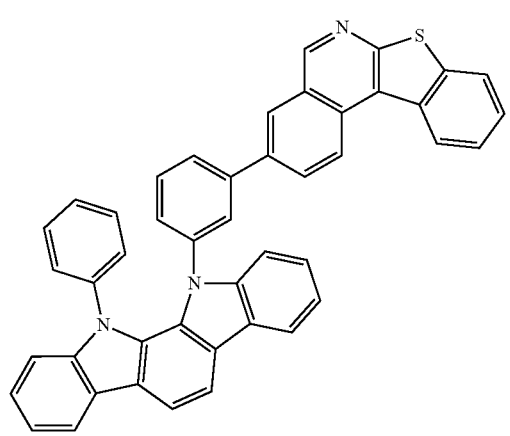
146
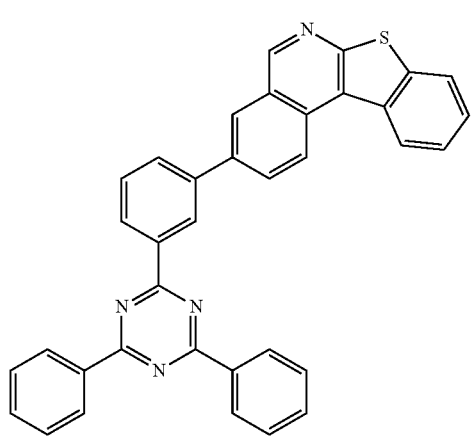
306
-continued
147
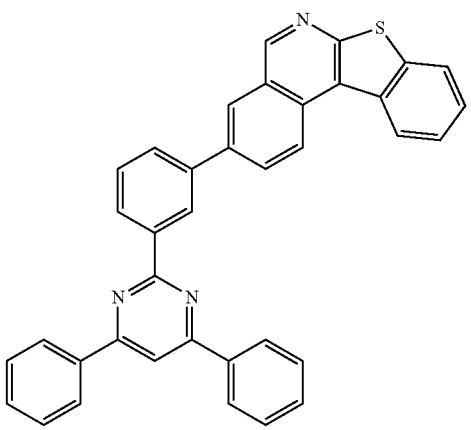
148
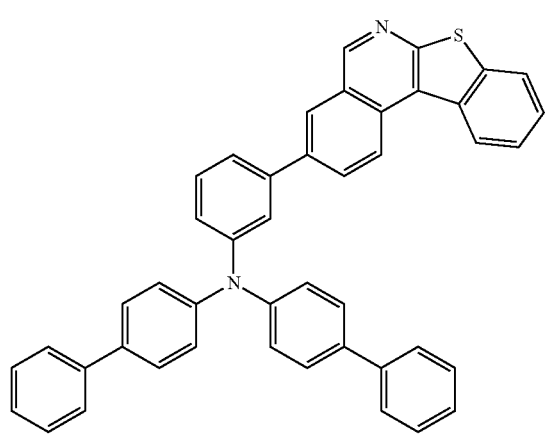
149
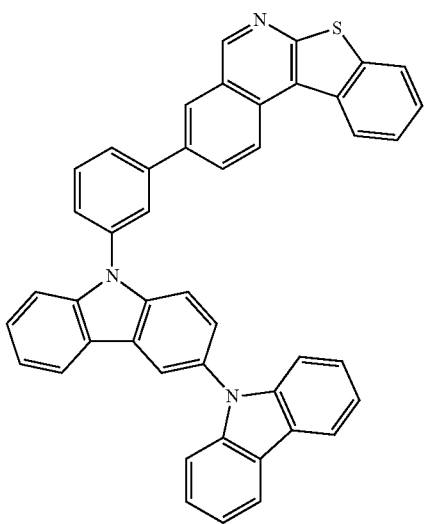

150
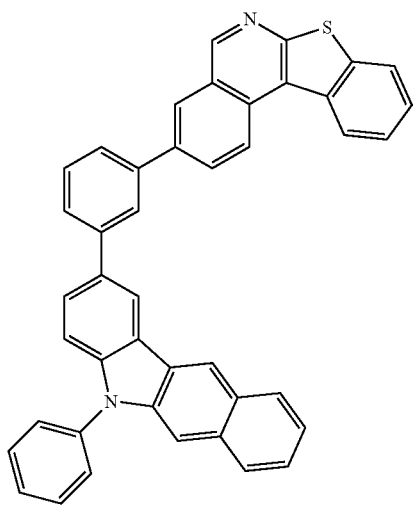
151
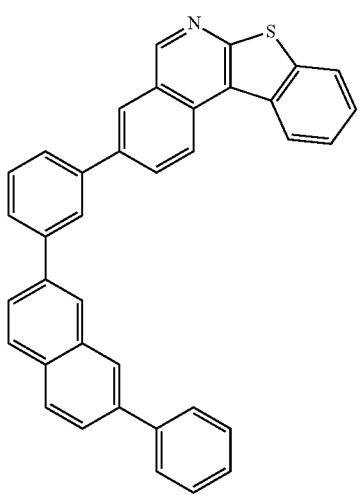
152
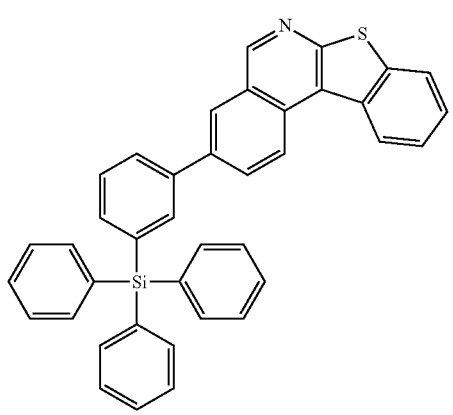
153
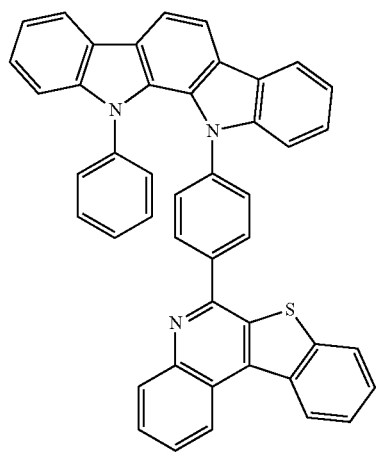
154
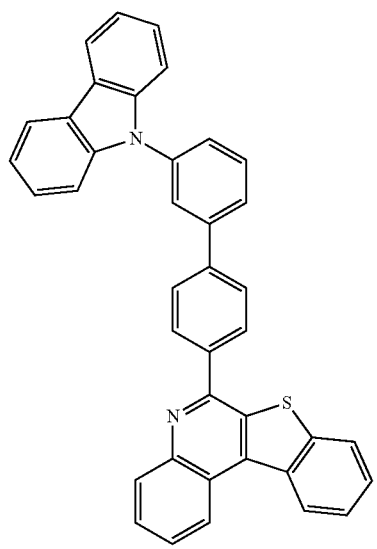
155
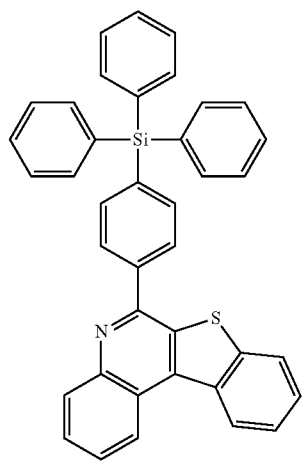

156
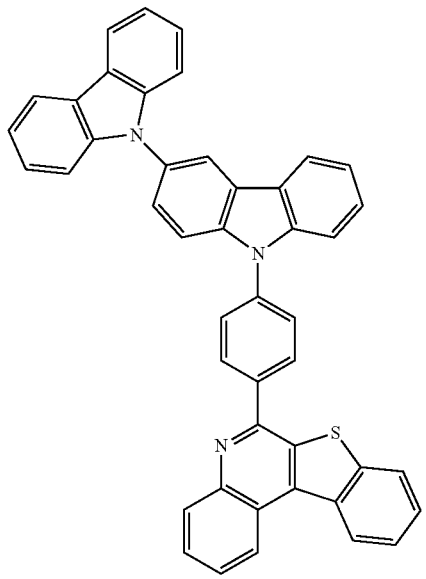
157
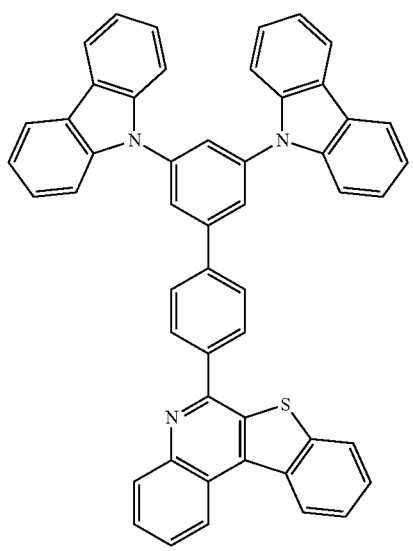
158
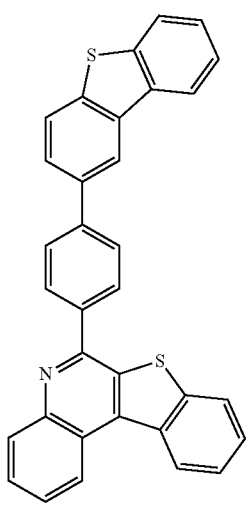
159
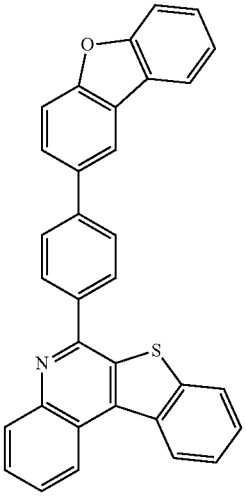
160
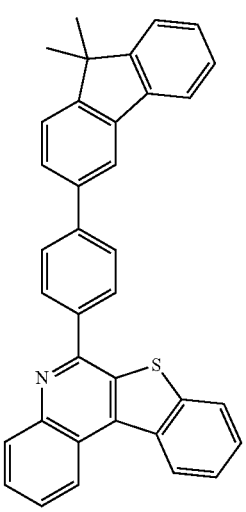
161
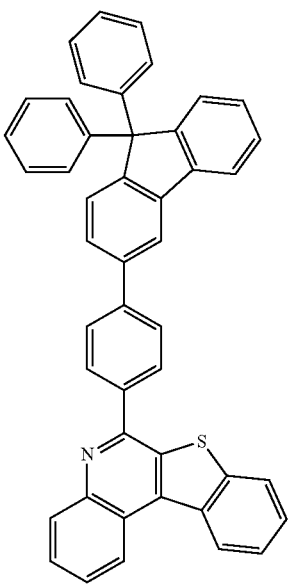

311
-continued
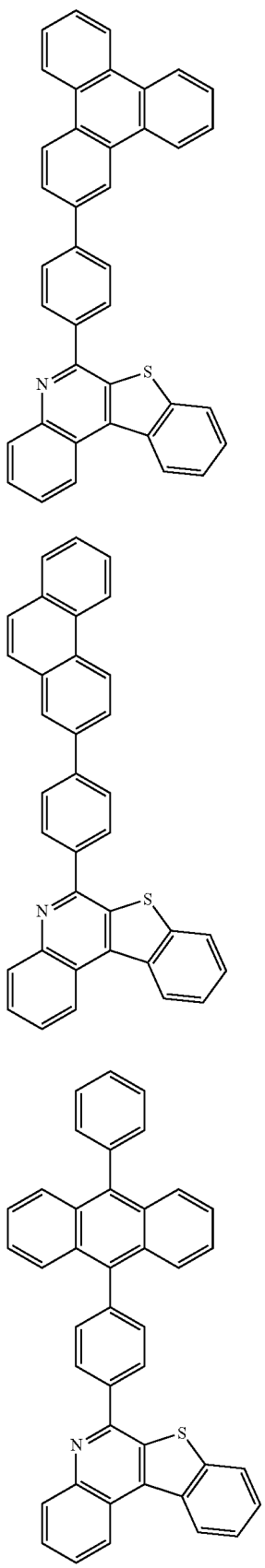
312
-continued
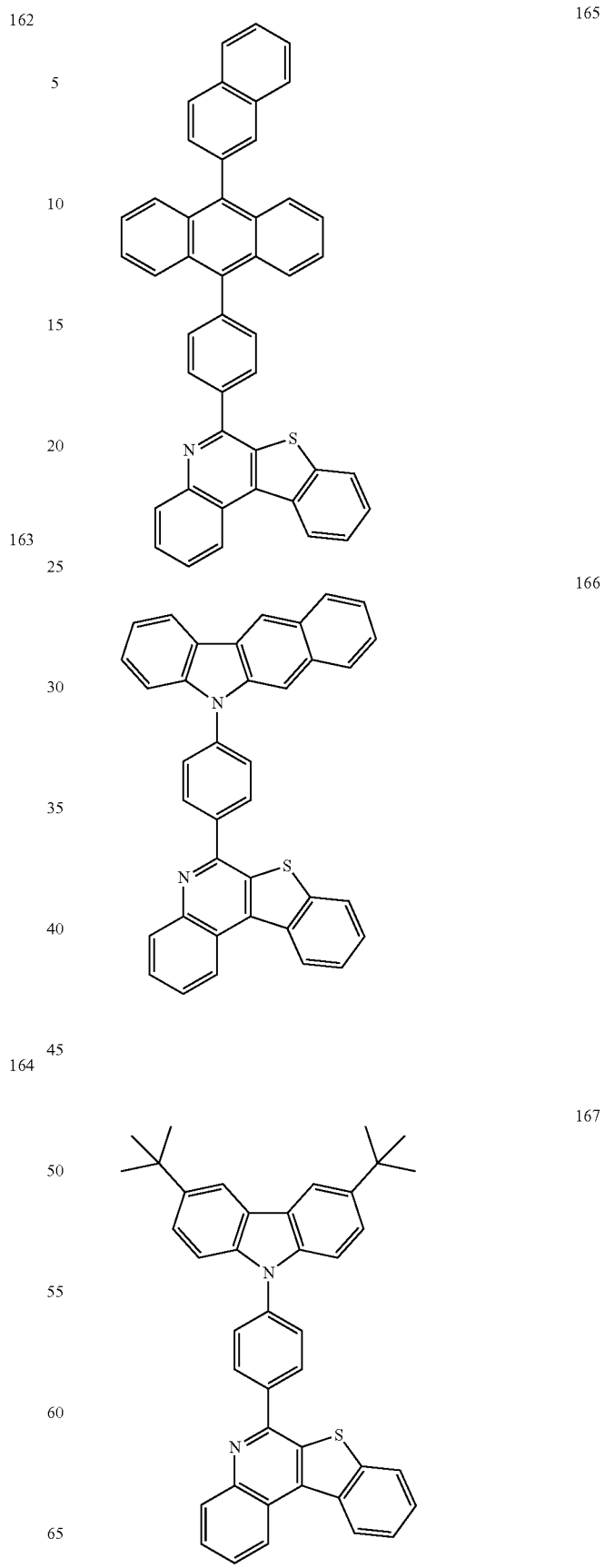

168
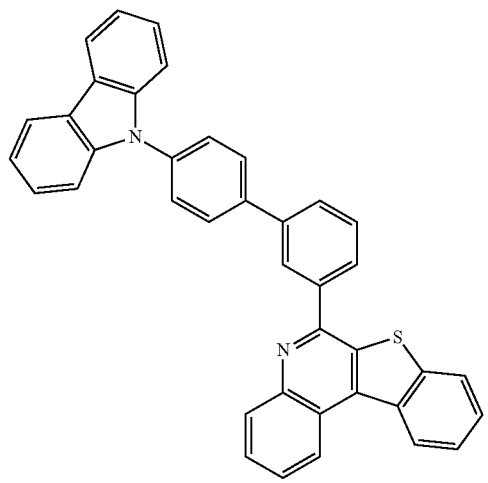
169
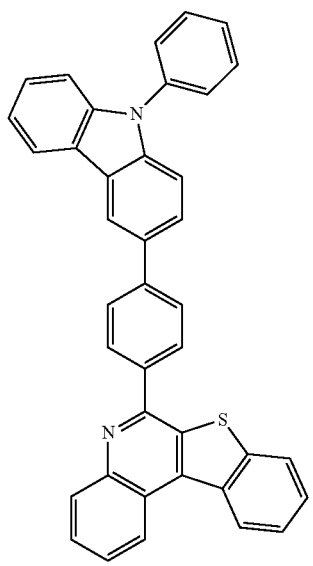
171
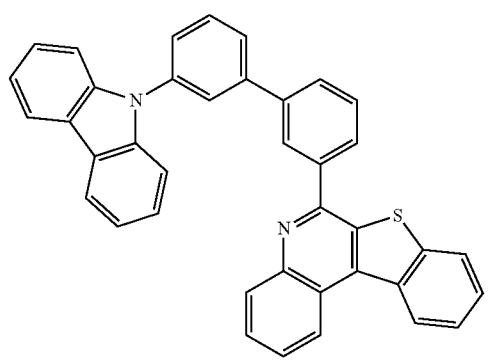
172
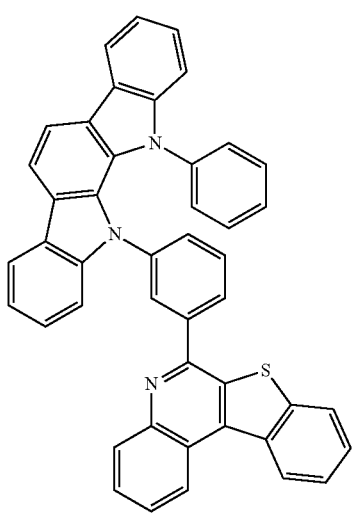
170
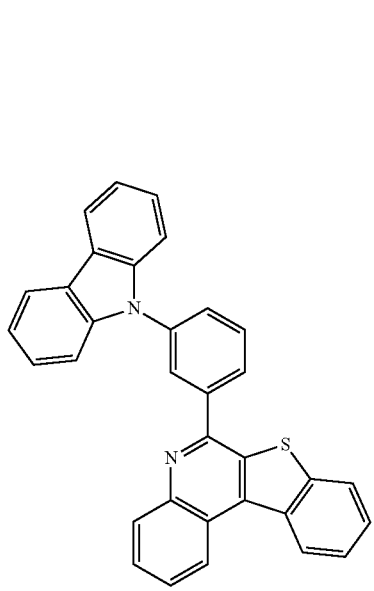
173
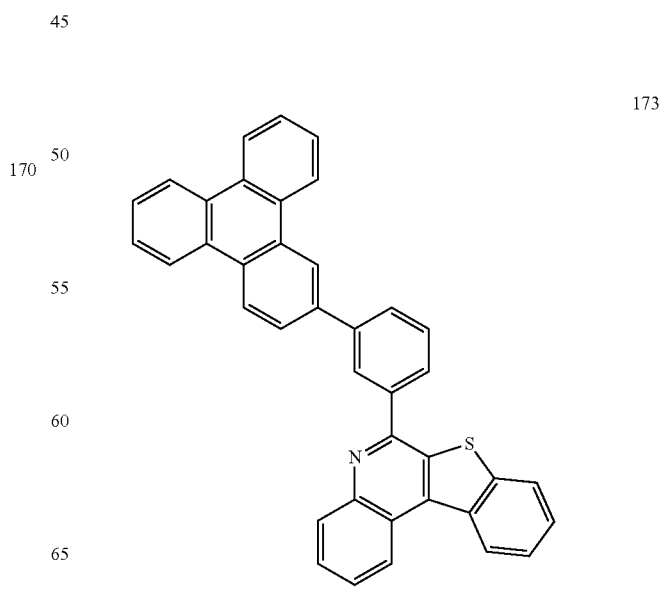

174
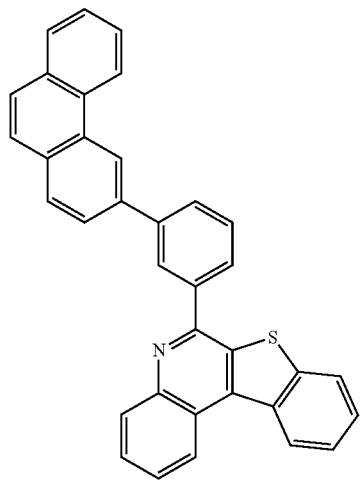
175
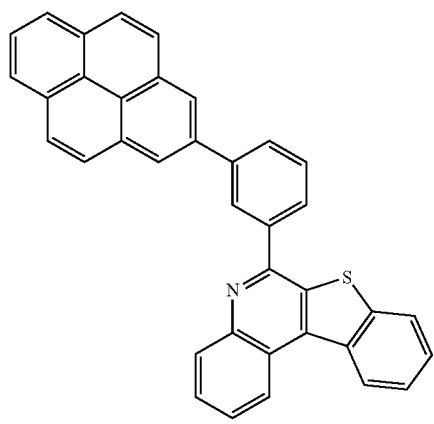
176
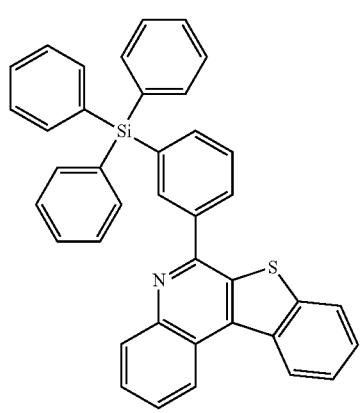
177
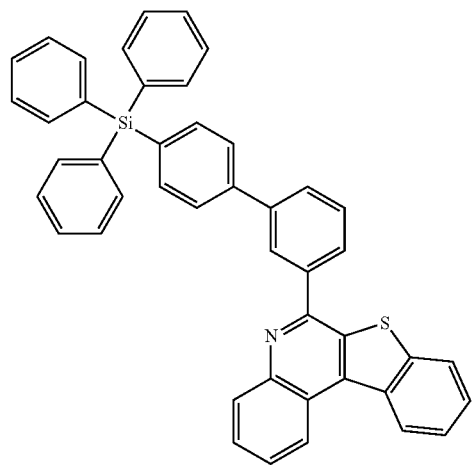
178
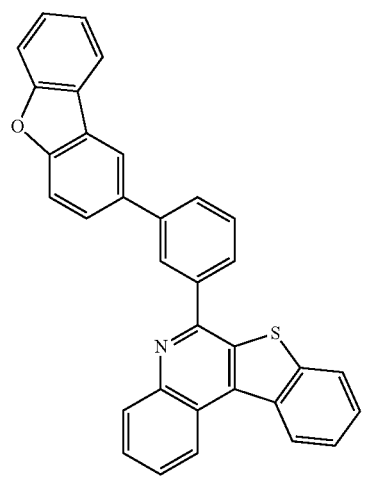
179

317
-continued
180
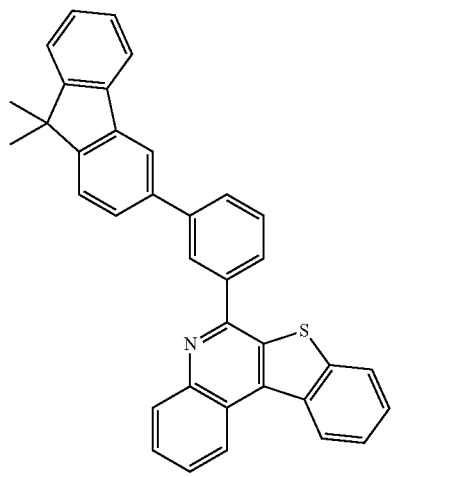
181
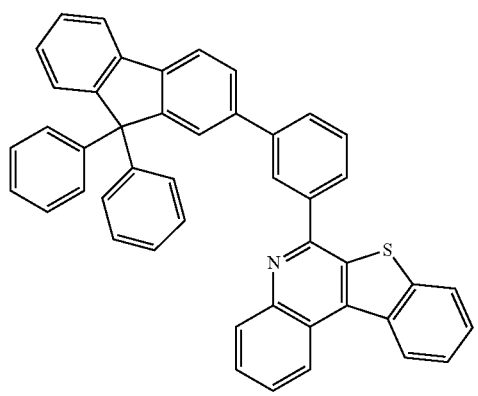
182
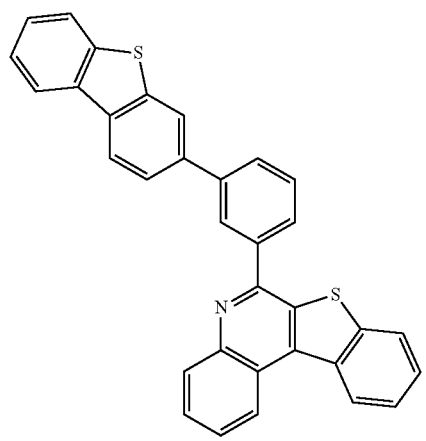
318
-continued
183
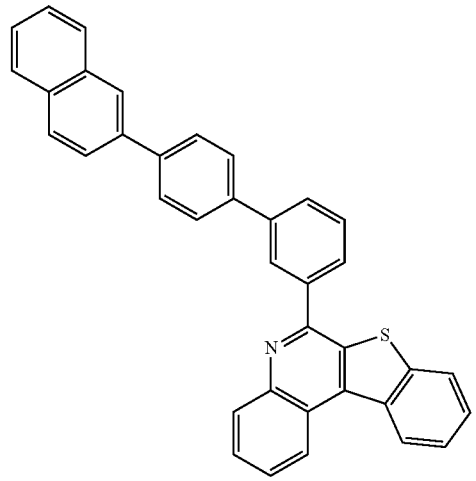
184
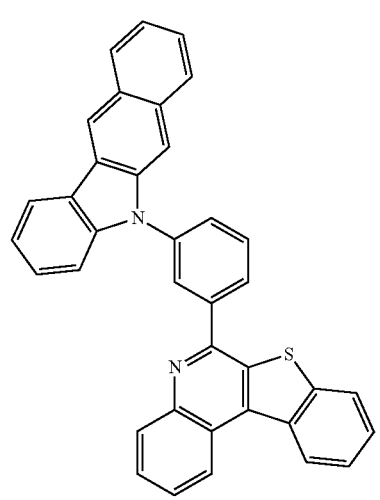
185
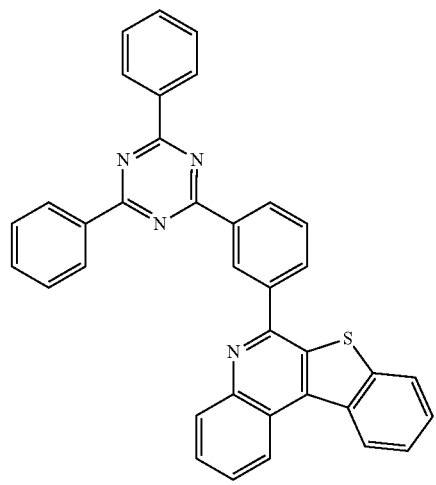

319
-continued
320
-continued
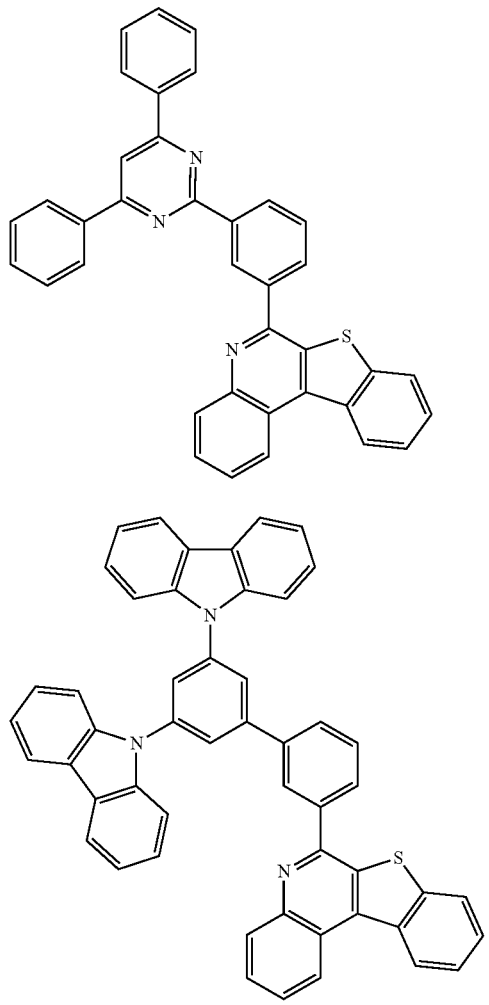
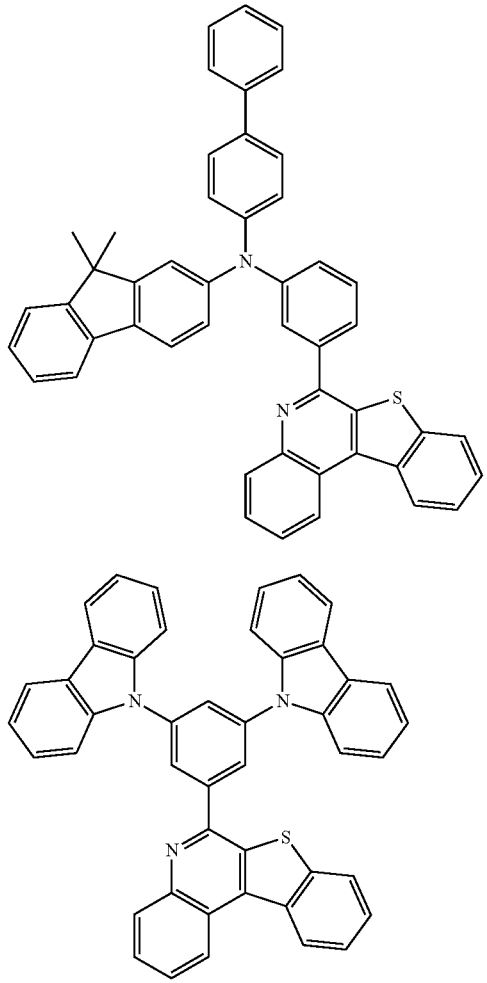
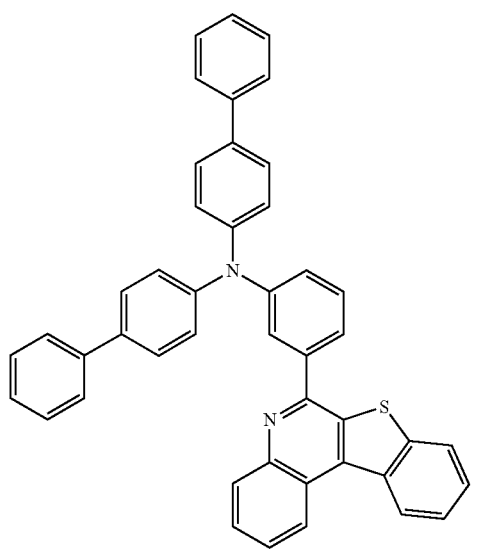
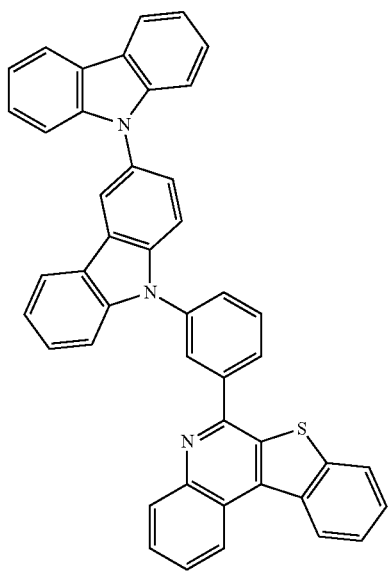

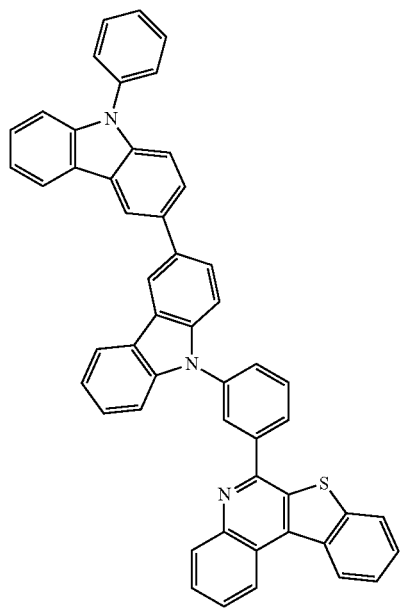
192
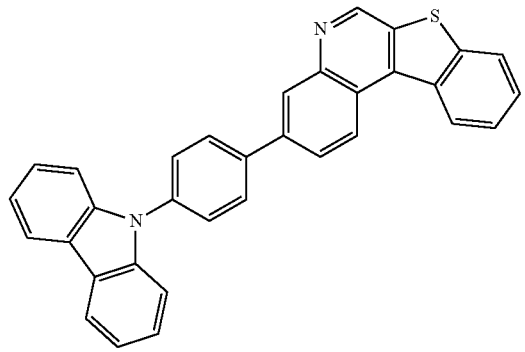
195
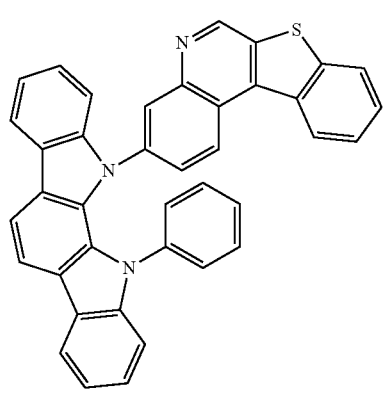
193
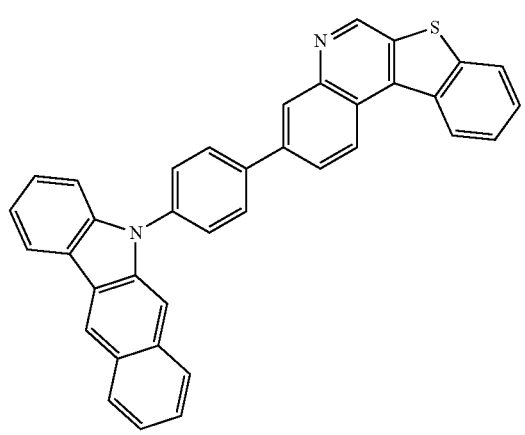
196
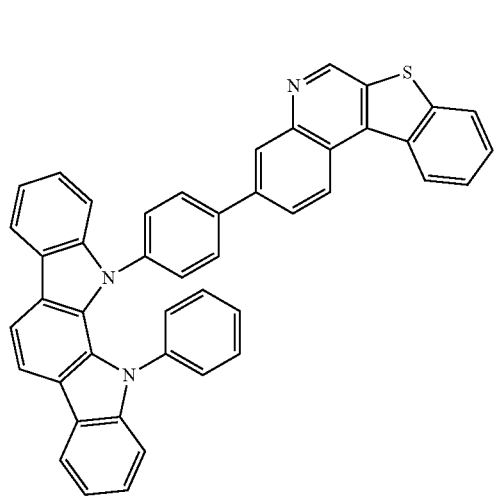
194
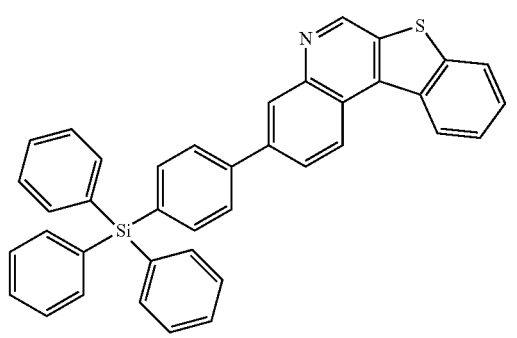
197

198
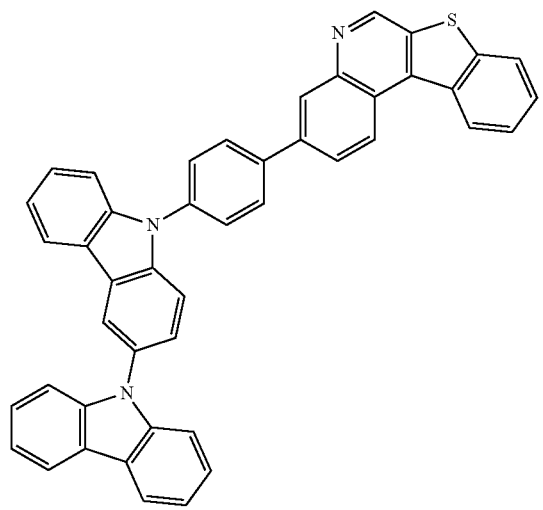
199
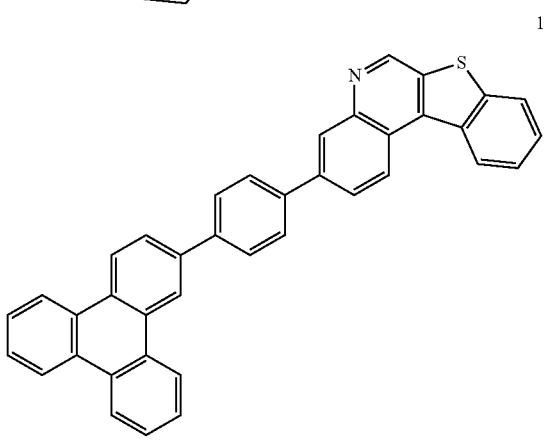
200
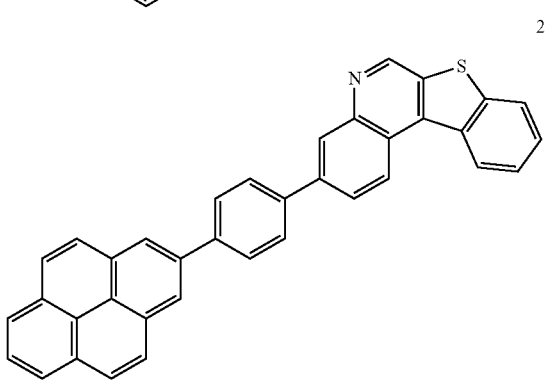
201
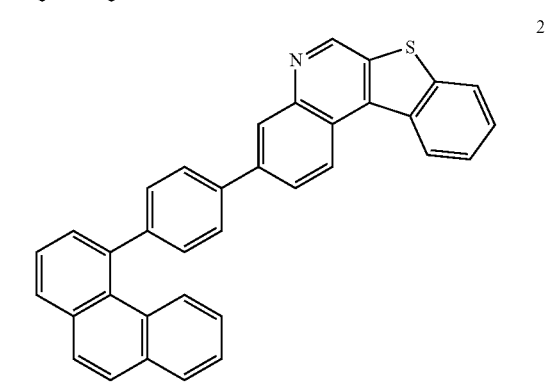
202
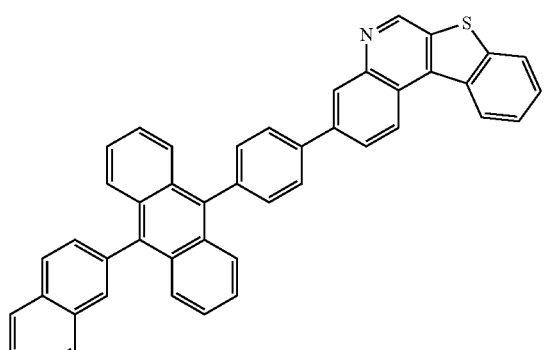
203
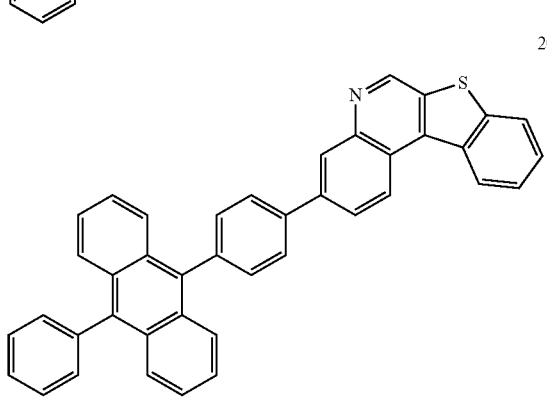
204
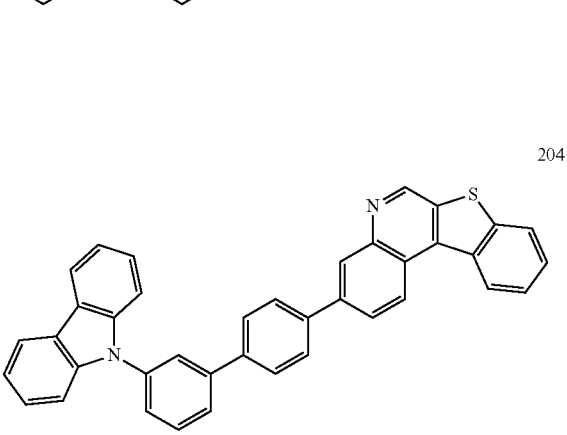
205
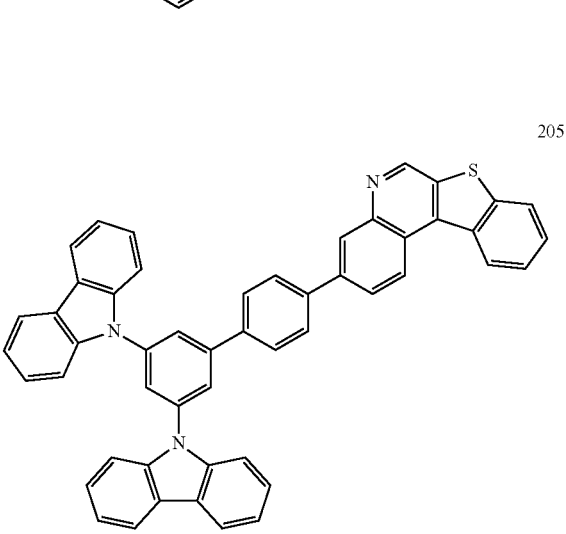

206
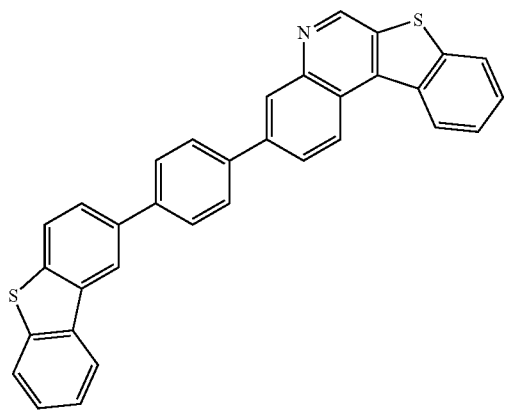
207
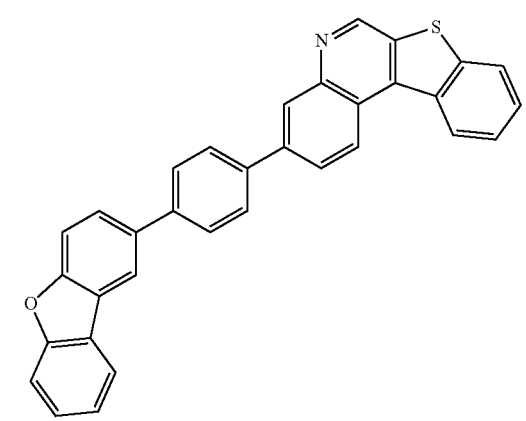
208
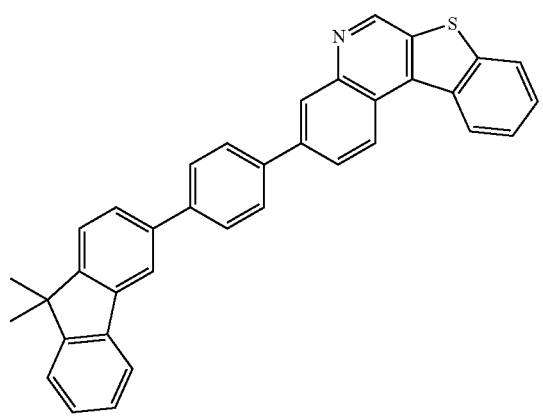
209
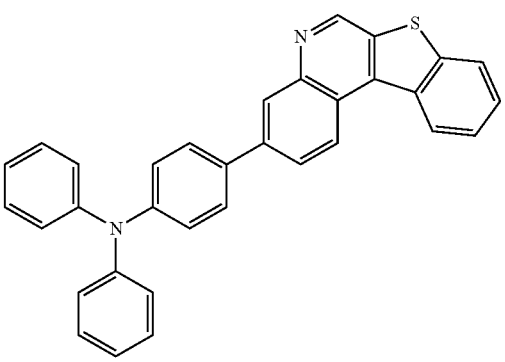
210
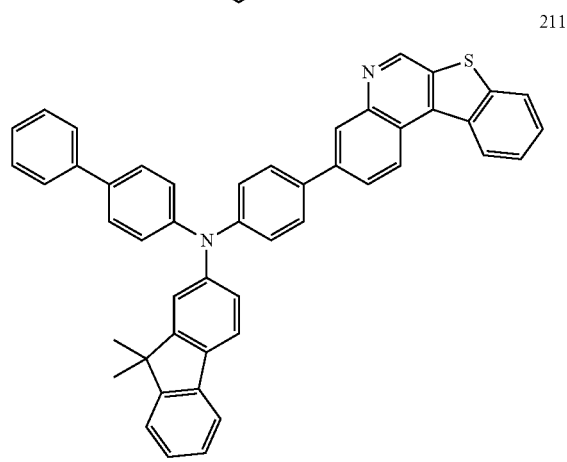
211
212
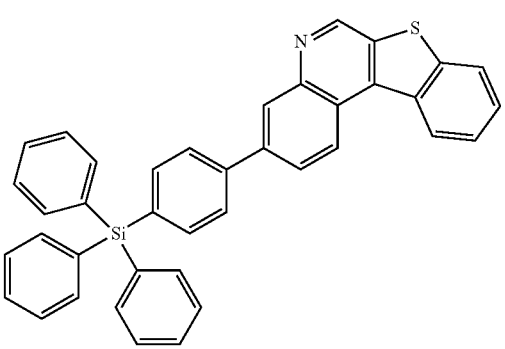

-continued
213
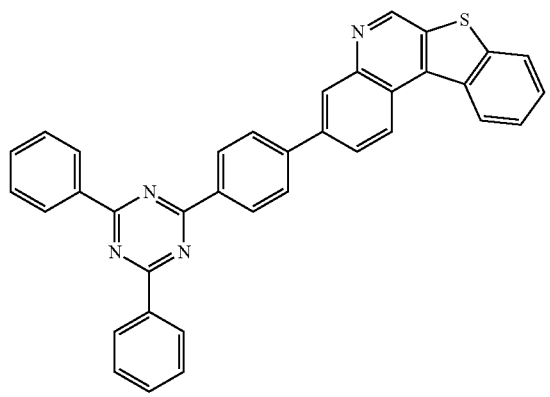
214
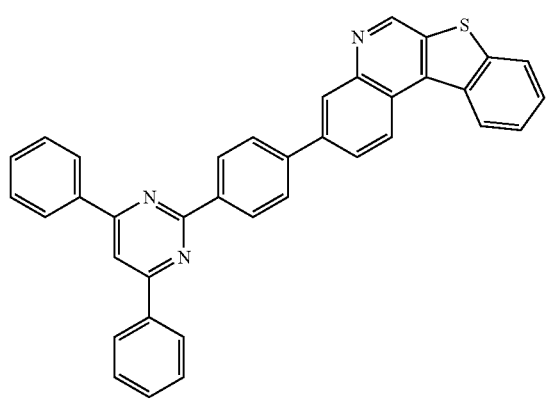
215
216
-continued
217
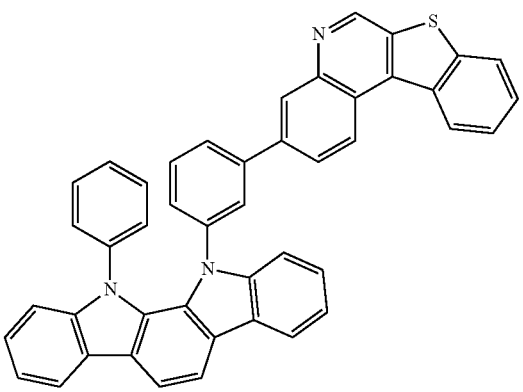
218
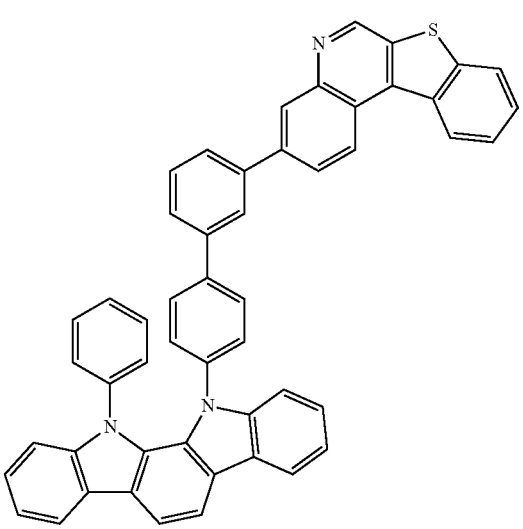
219
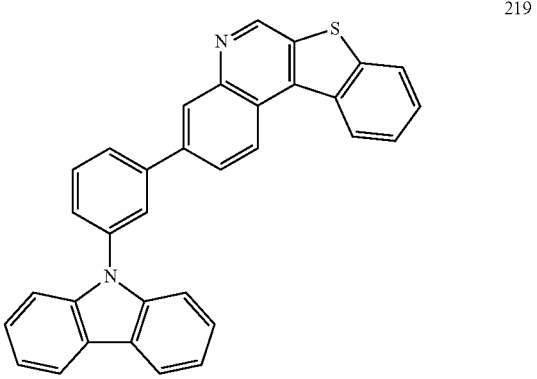

-continued
220 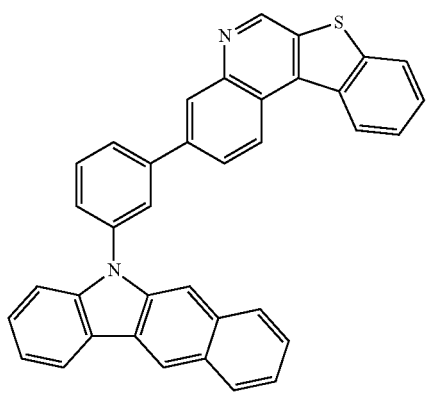
221 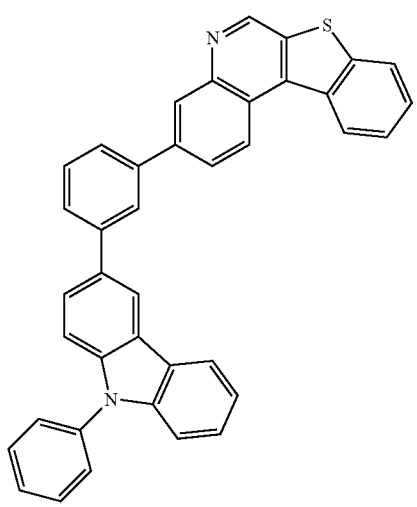
222 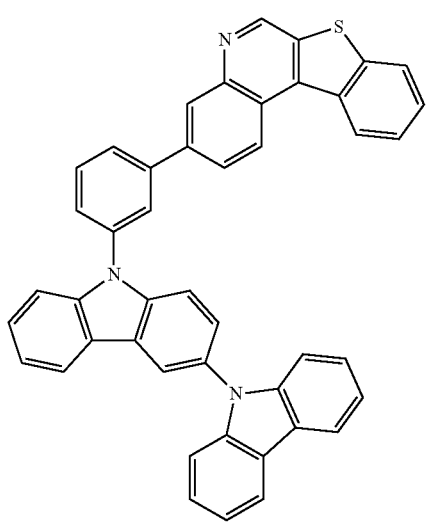
-continued
223 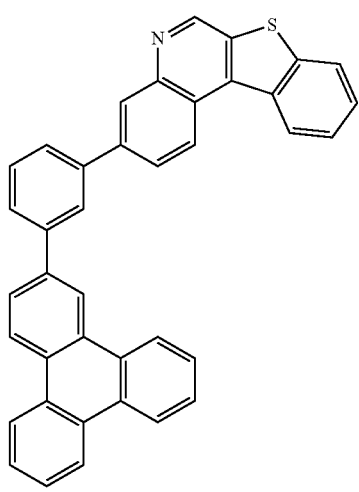
224 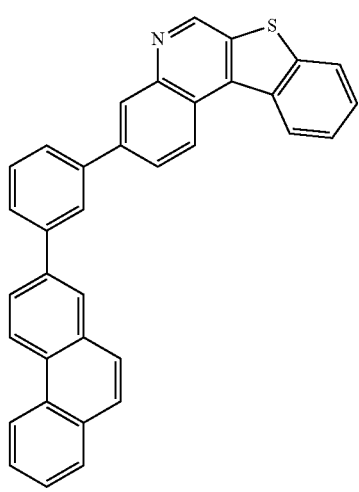
225 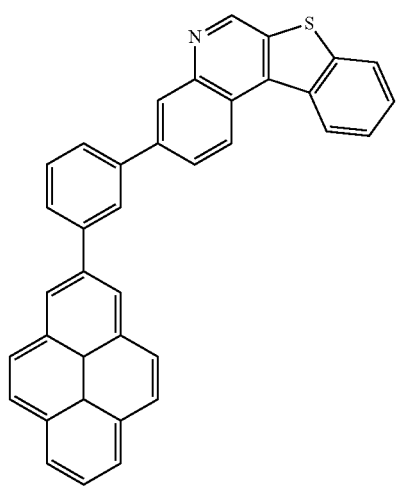

331
-continued
226
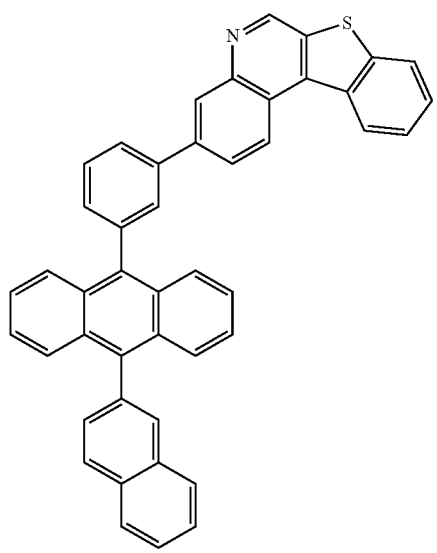
227
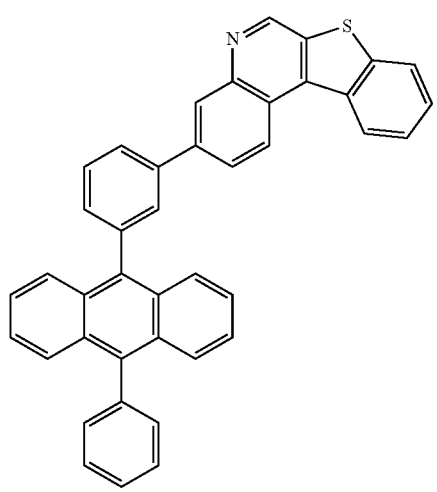
228
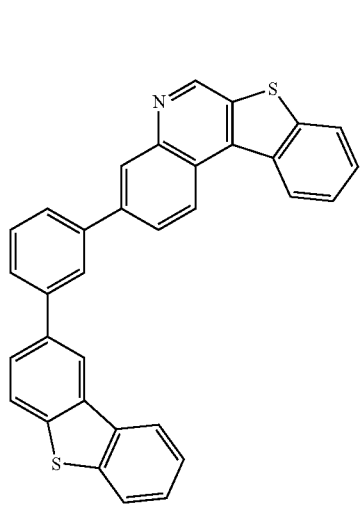
332
-continued
229
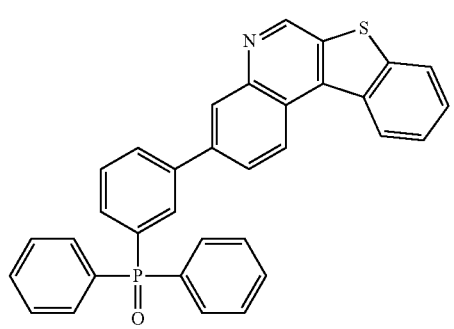
230
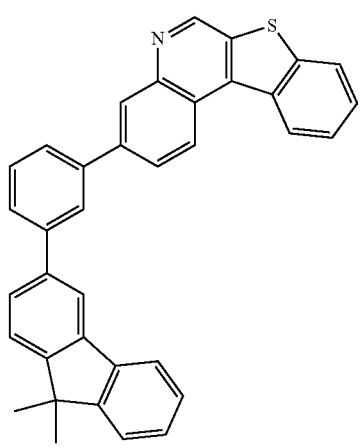
231
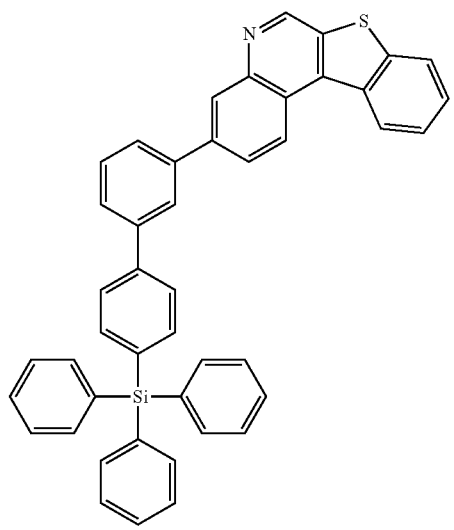

-continued
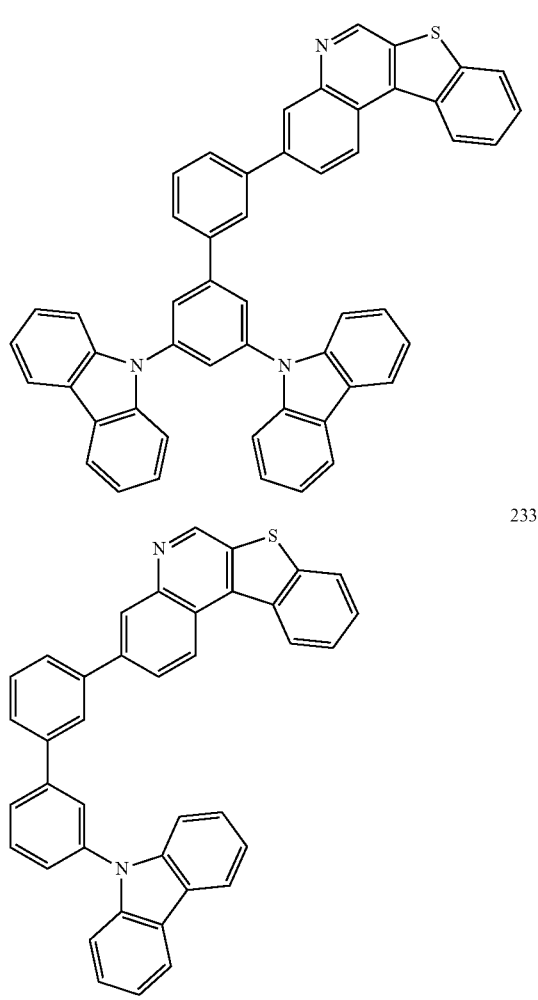
-continued
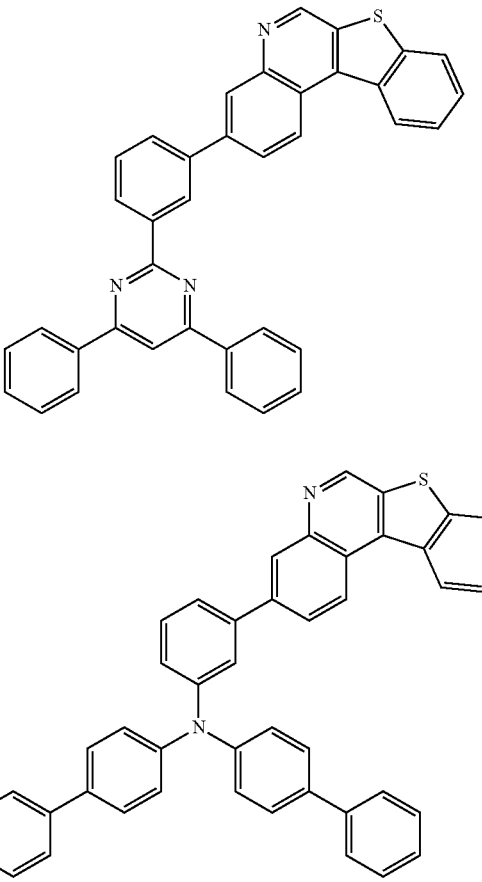
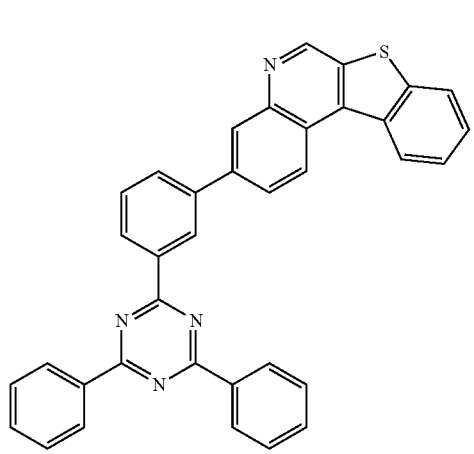
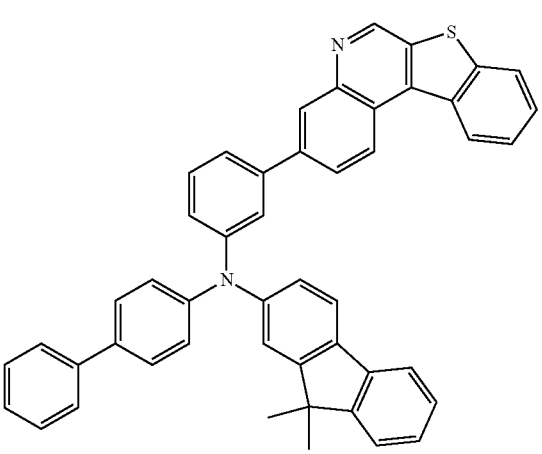

-continued
238
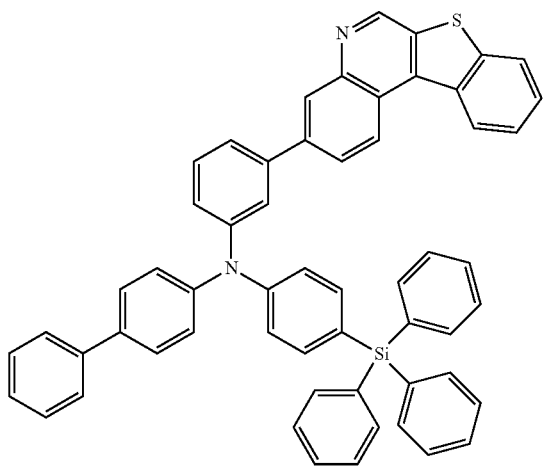
239
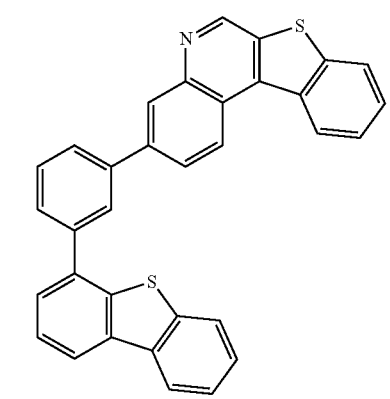
240
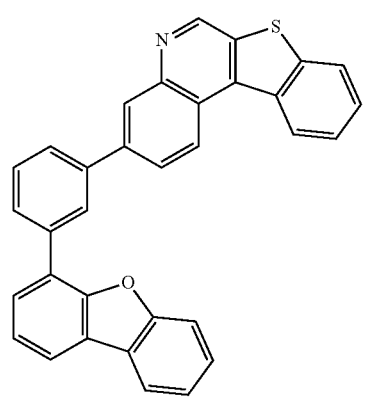
-continued
241
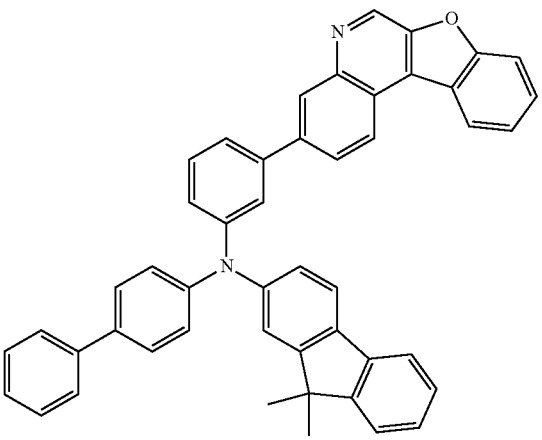
242
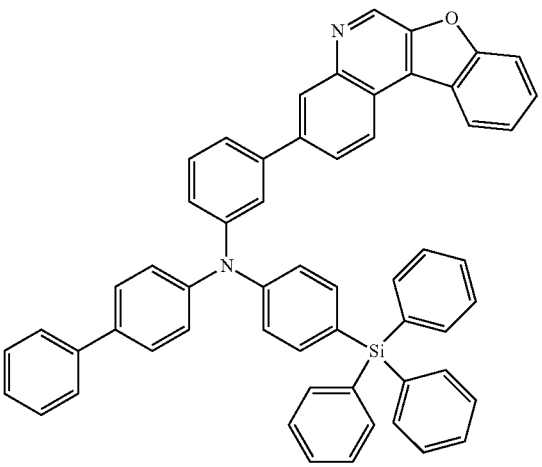
243
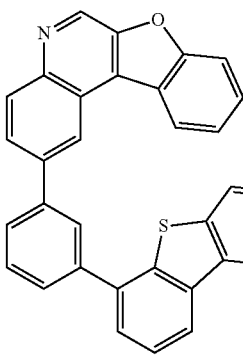

337
-continued
244
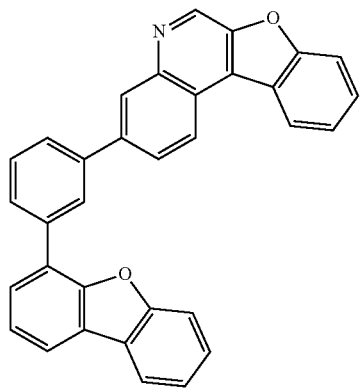
245
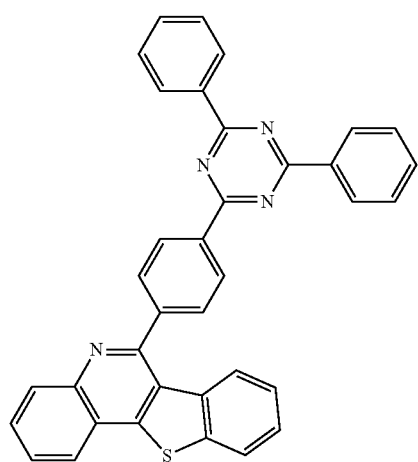
246
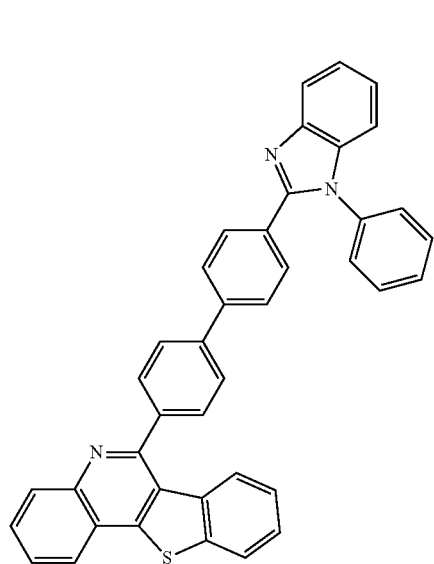
338
-continued
247
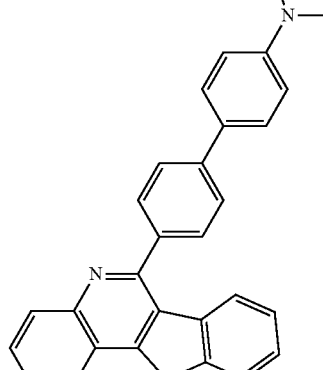
248
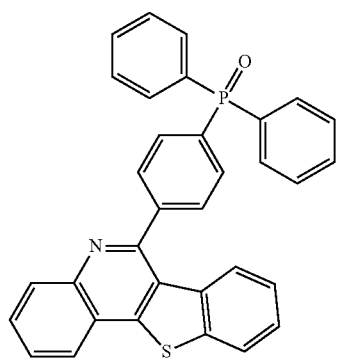
249
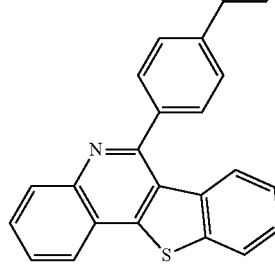

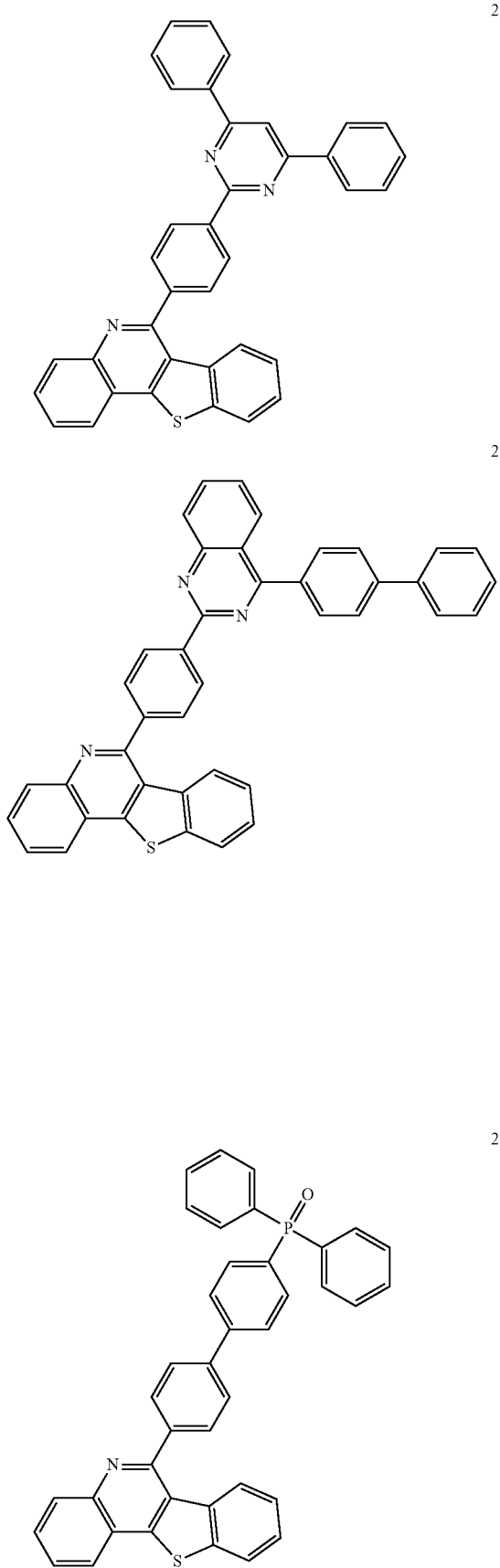

256
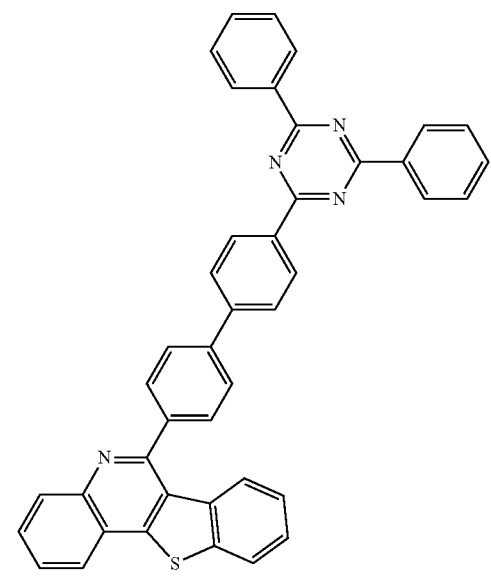
257
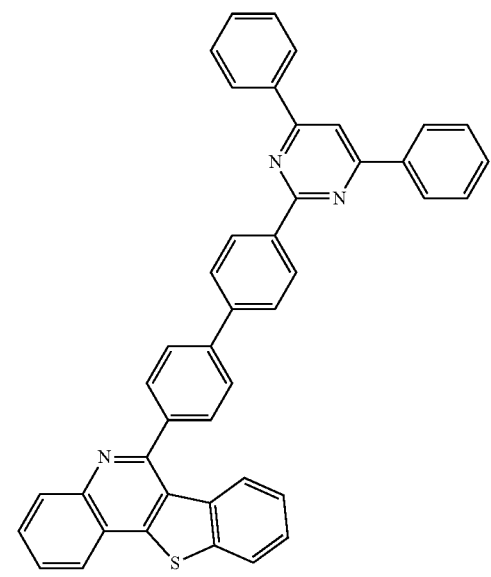
258
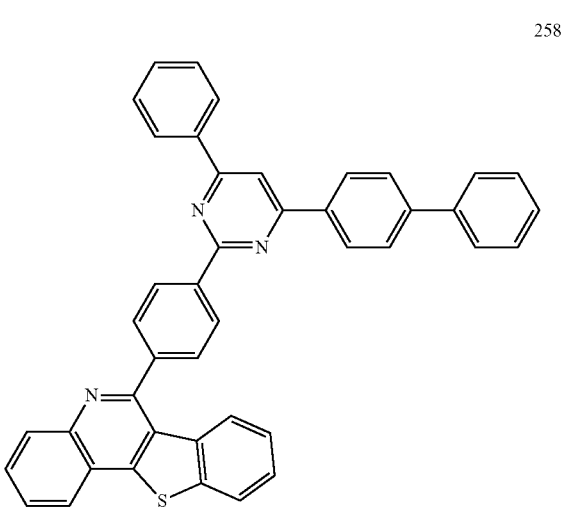
259
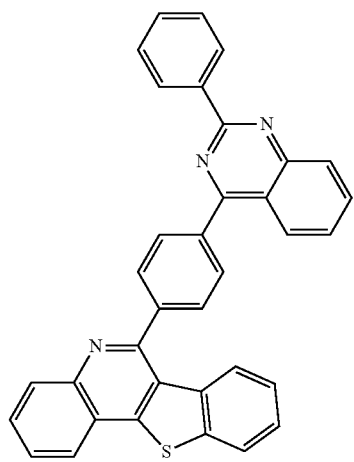
260
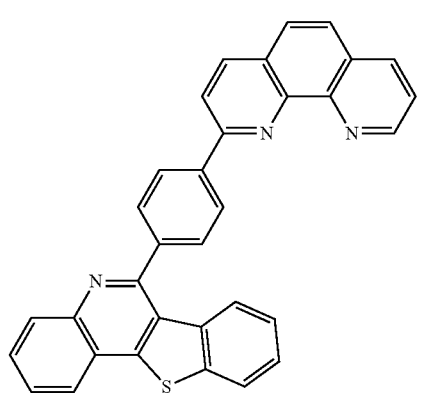
261
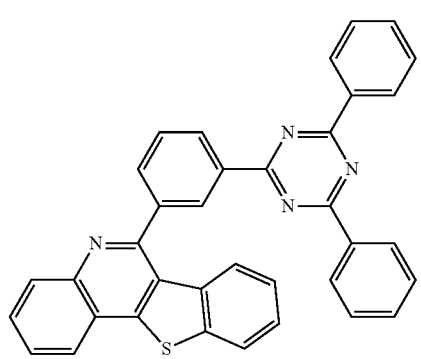
262
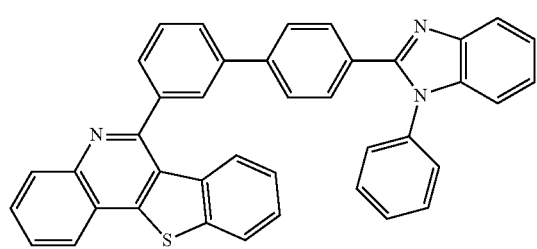

-continued
263
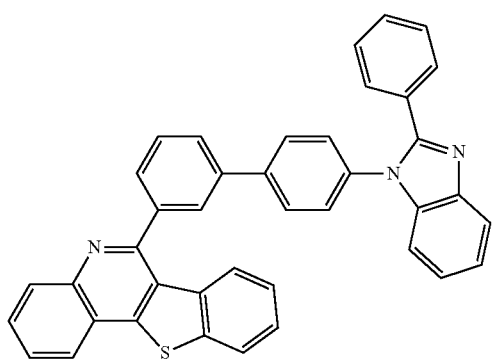
264
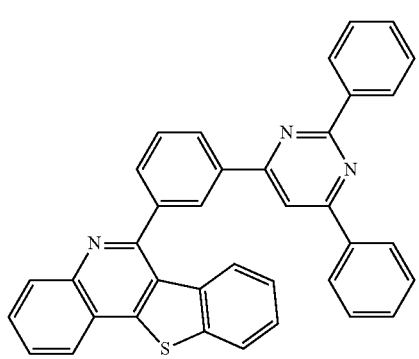
265
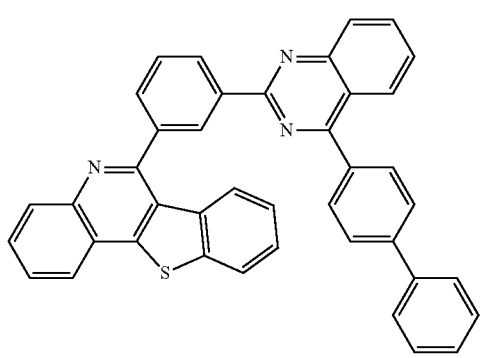
266
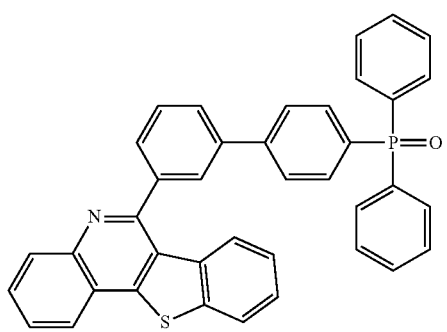
-continued
267
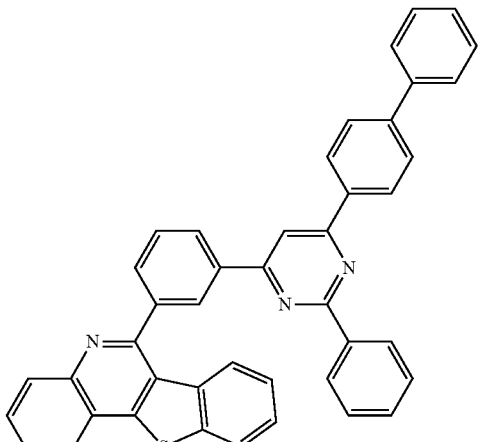
268
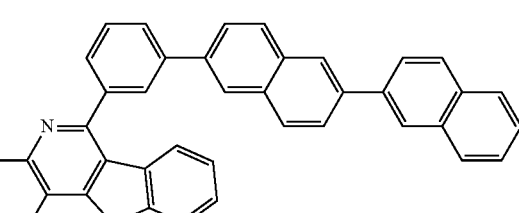
269
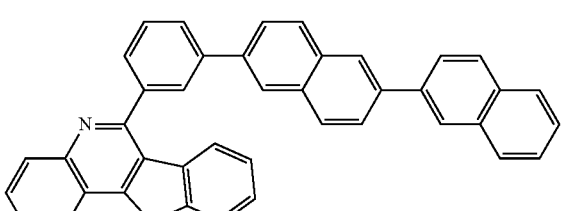
270
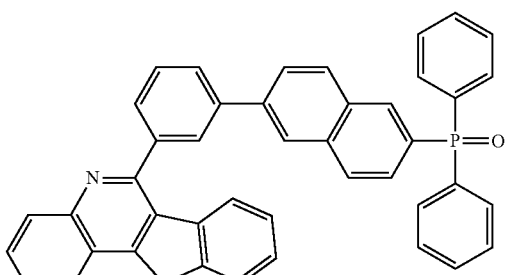

-continued
271
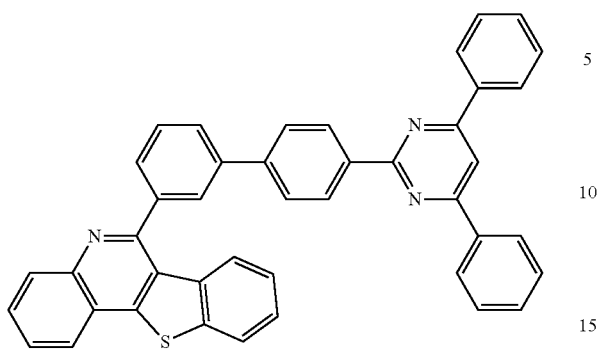
272
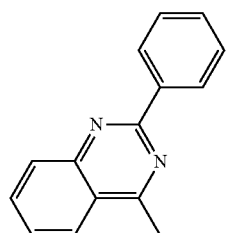
273
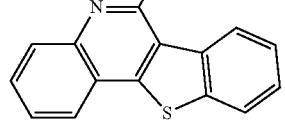
274
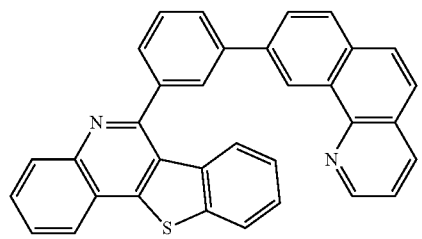
-continued
275
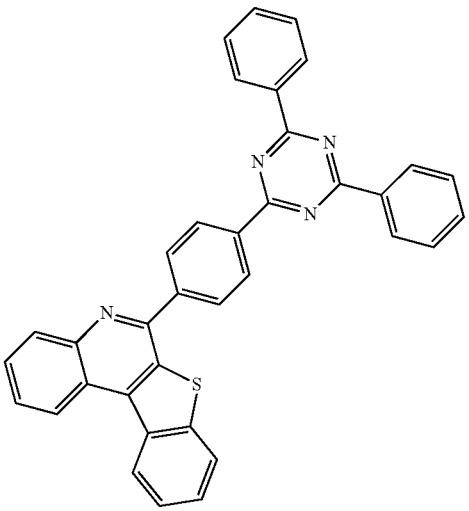
276
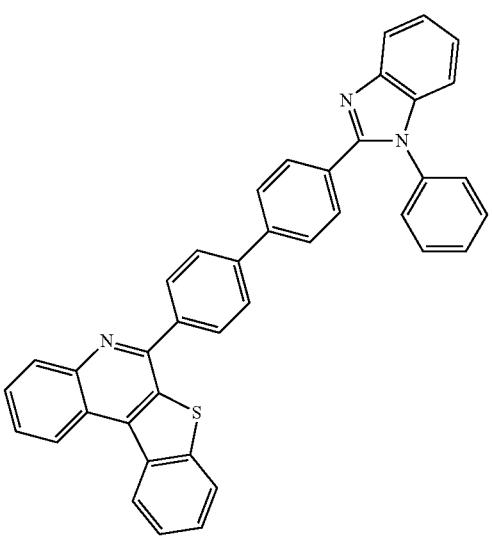
277
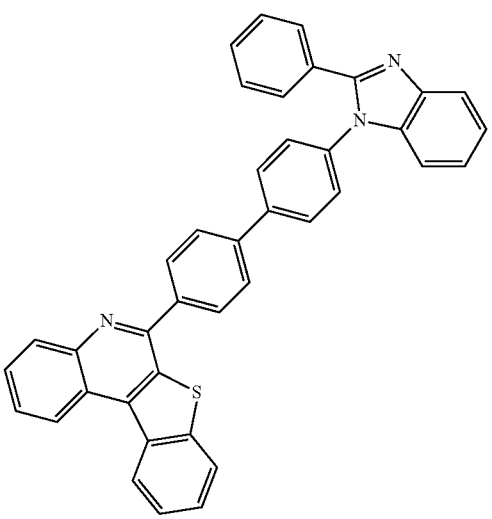

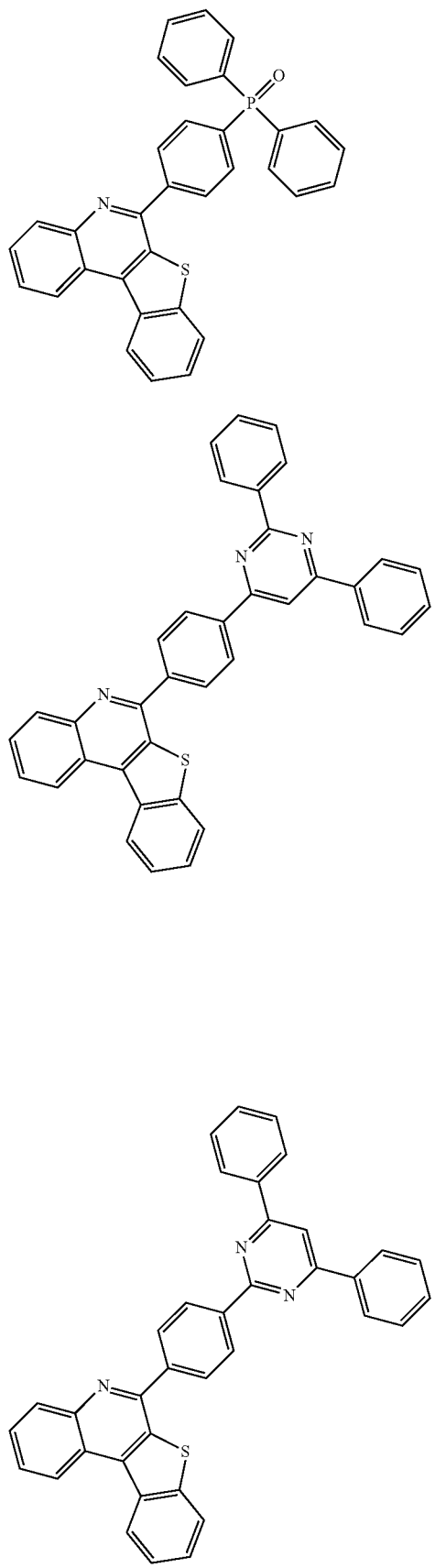
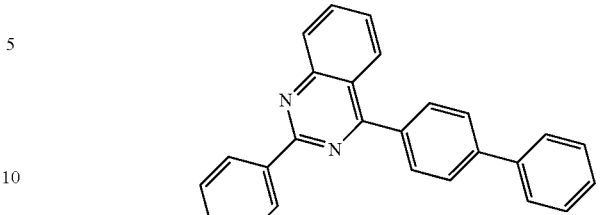
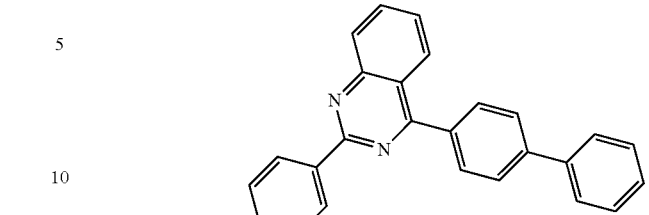
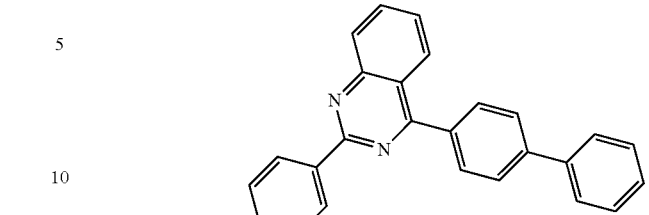

284
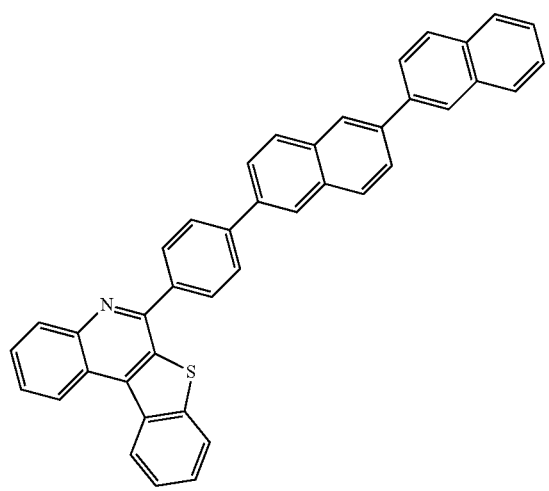
285
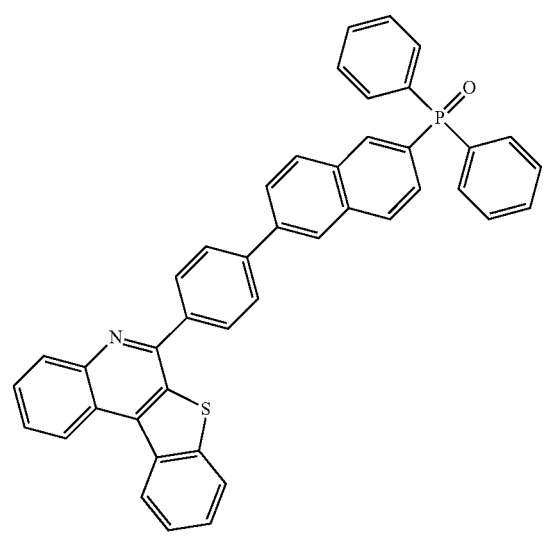
286
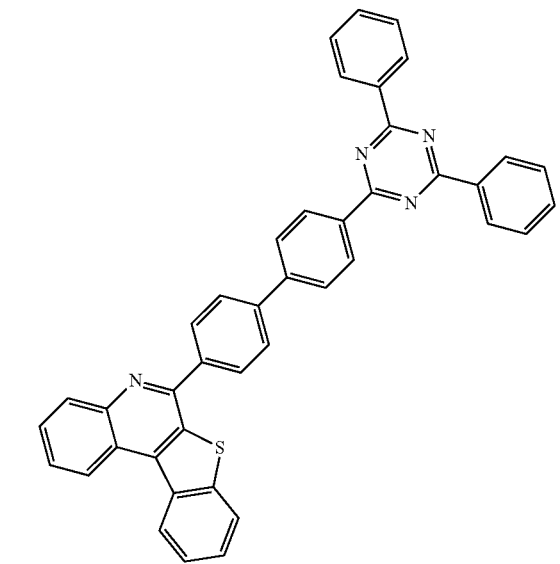
287
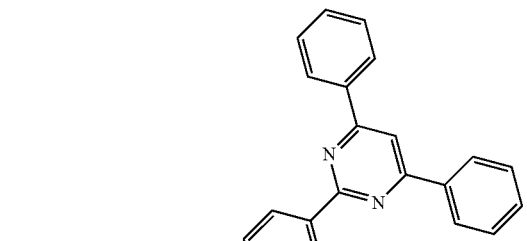
288
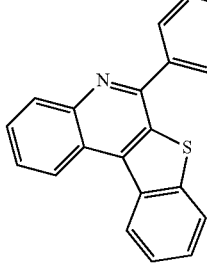
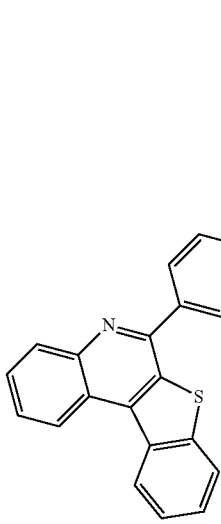
289
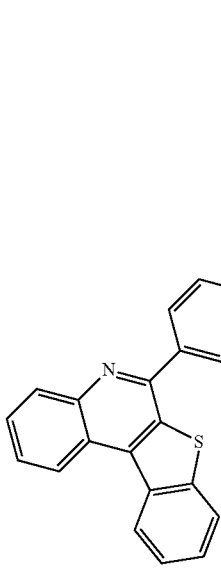

290
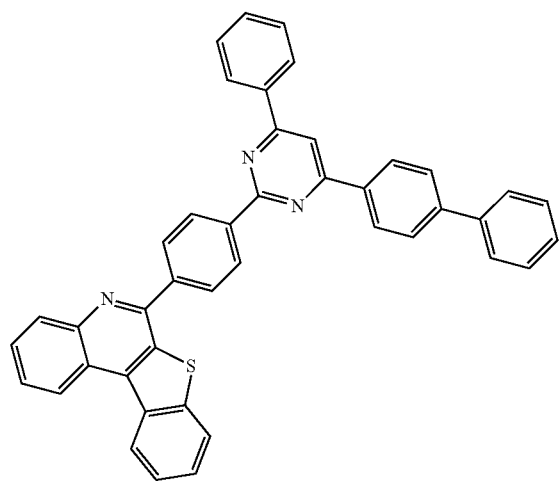
291
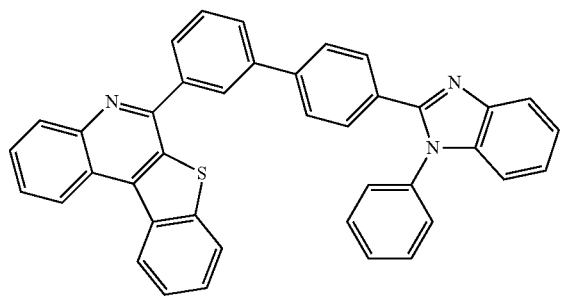
292
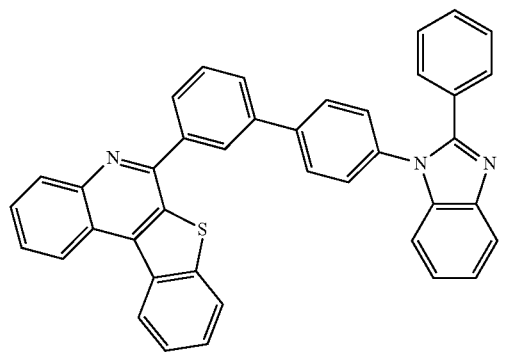
293
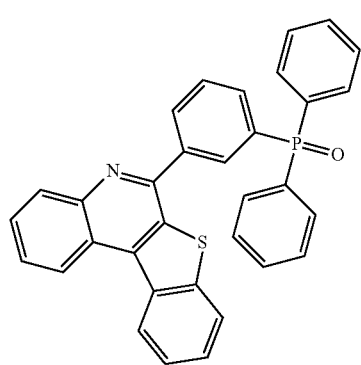
294
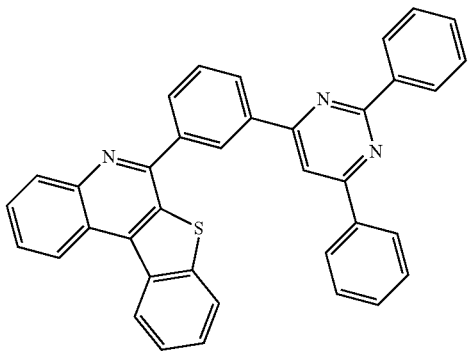
295
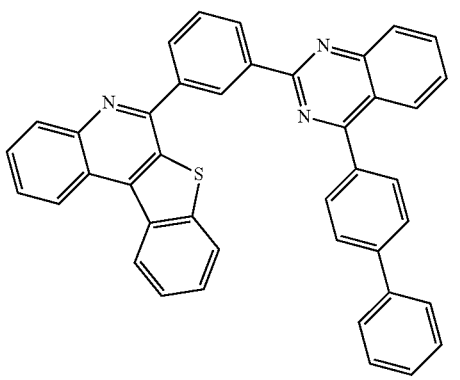
296
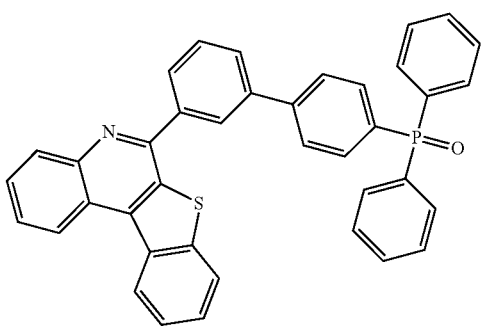
297
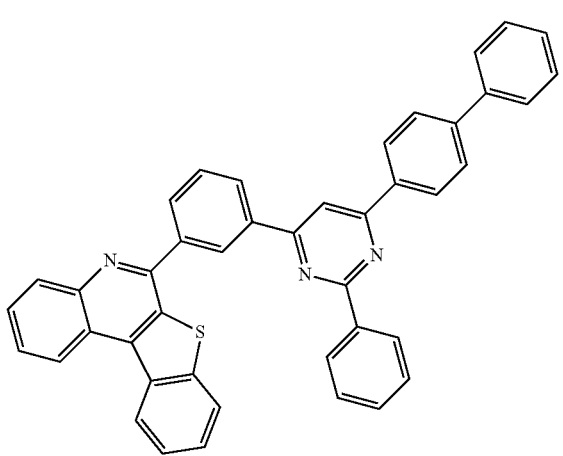

298
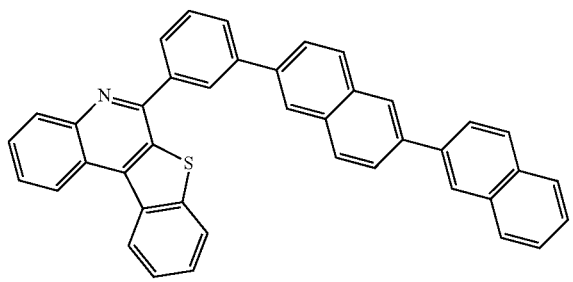
299
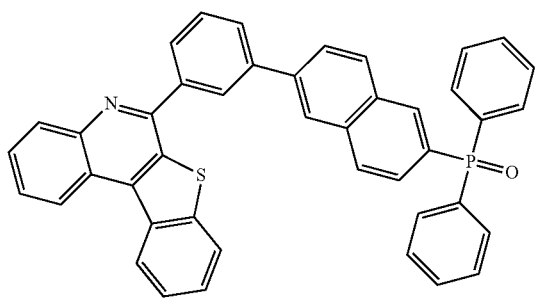
300
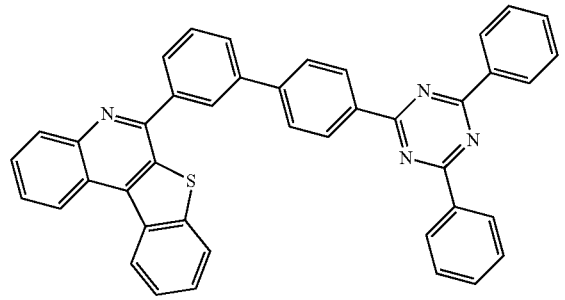
301
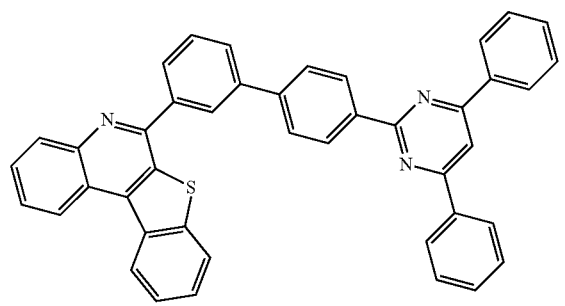
302
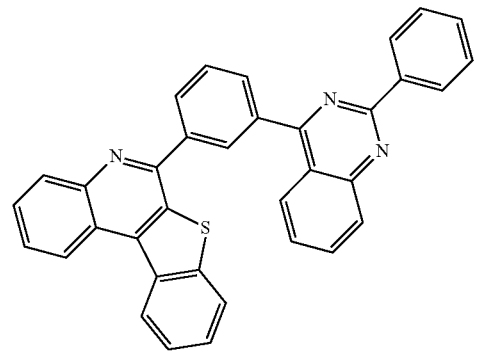
303
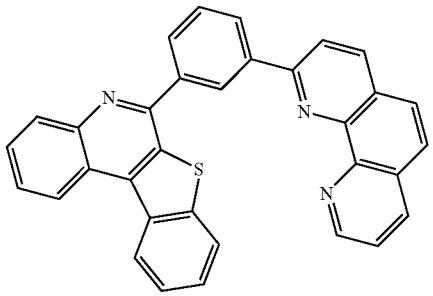
304
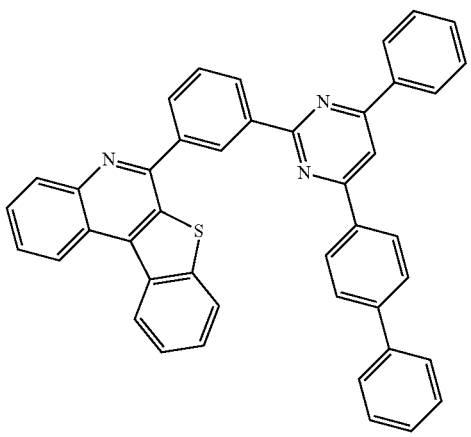
305
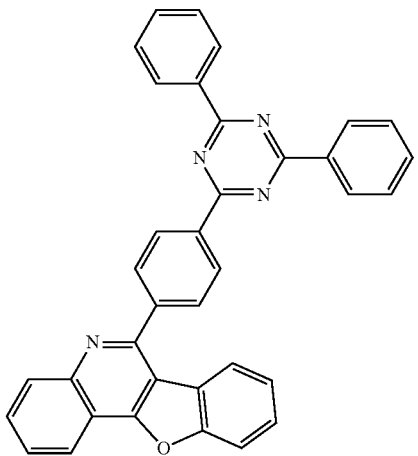

306
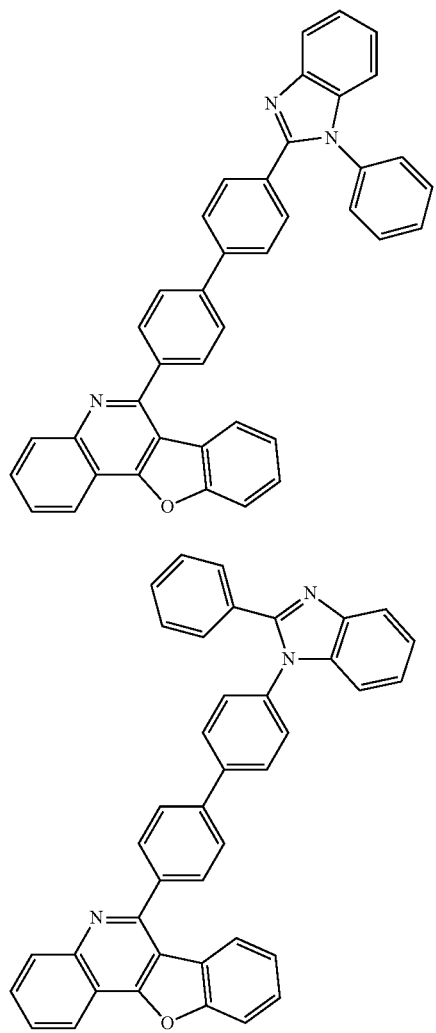
307
309
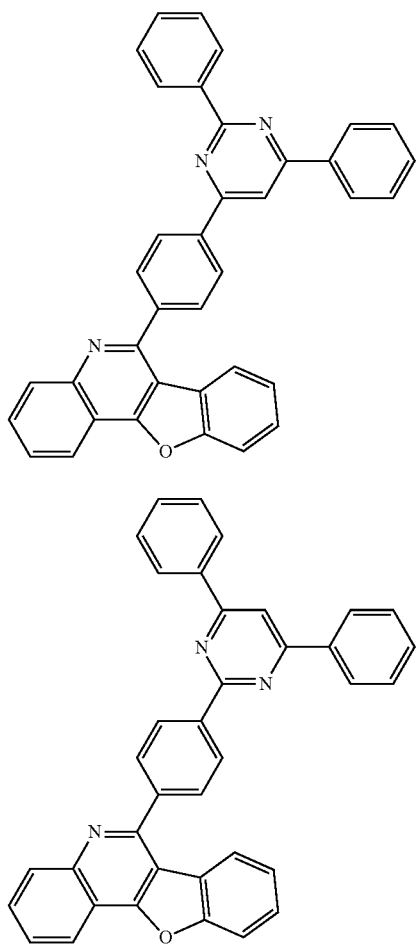
310
308
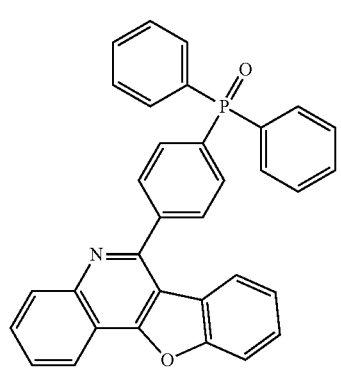
311
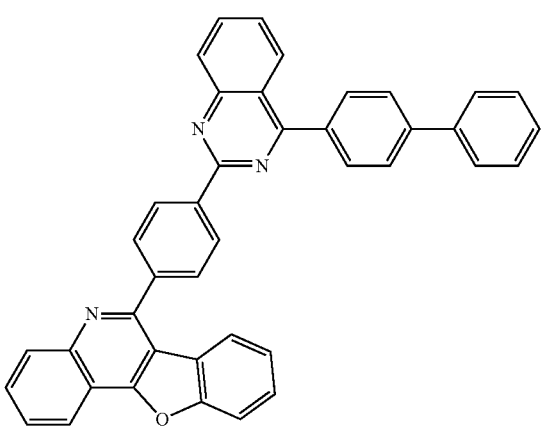

357
-continued
358
-continued
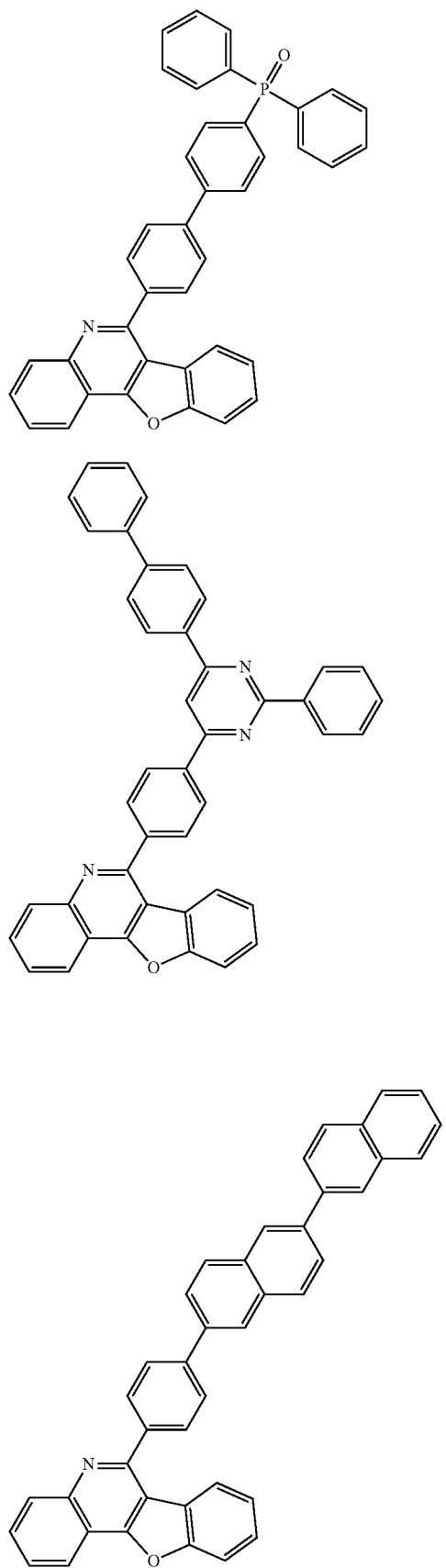
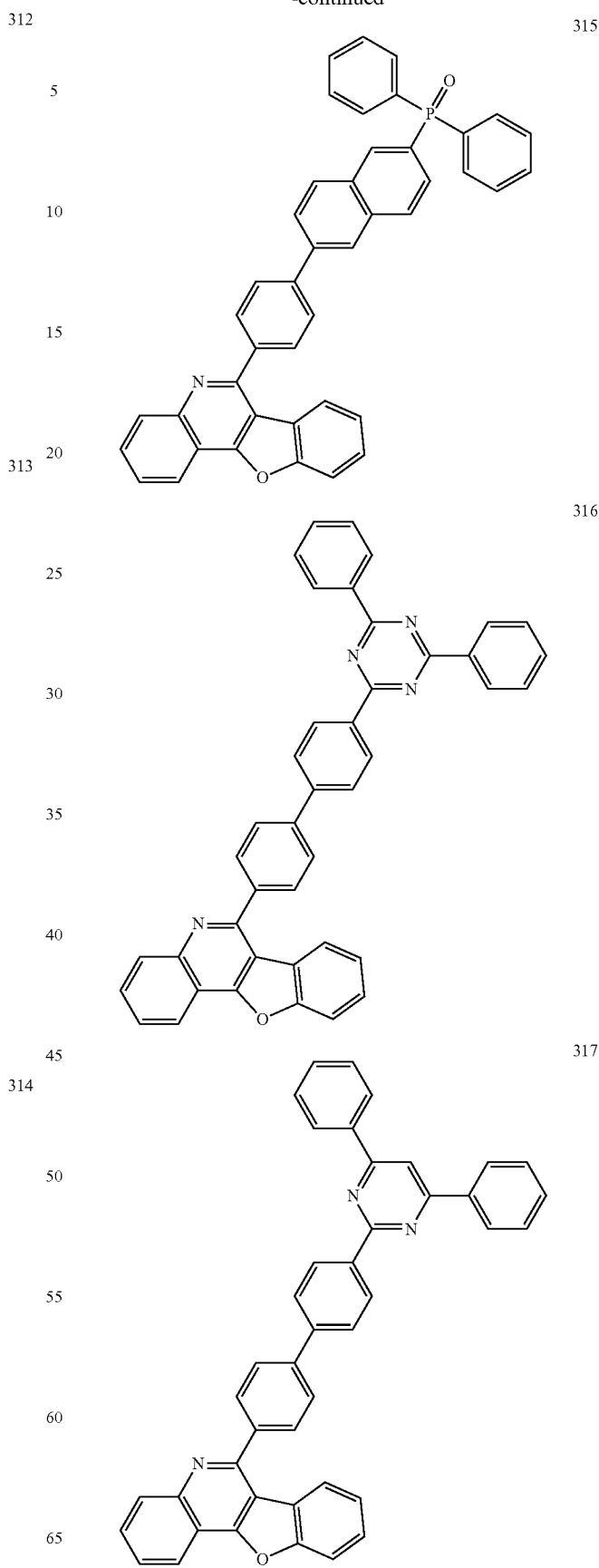

318
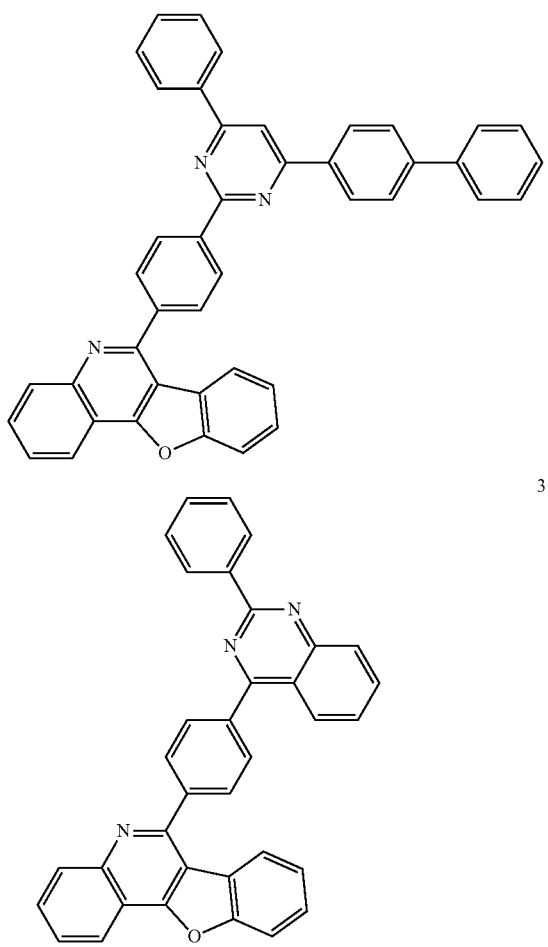
319
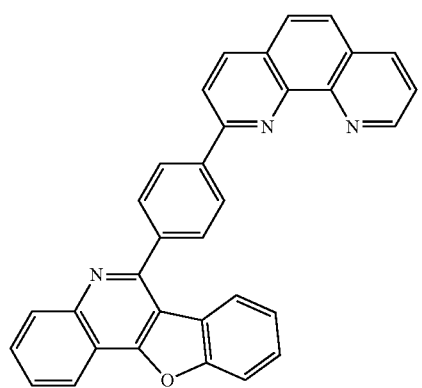
320
321
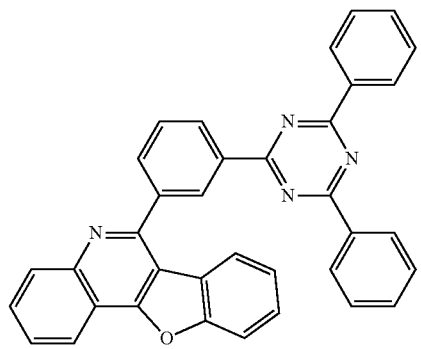
322
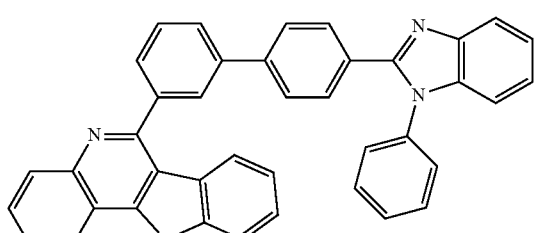
323
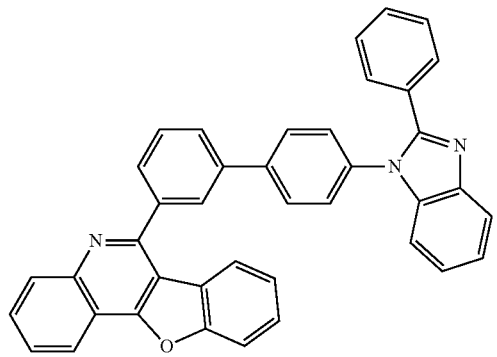
324
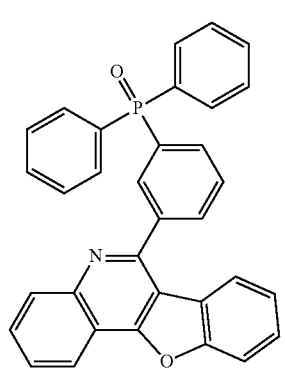

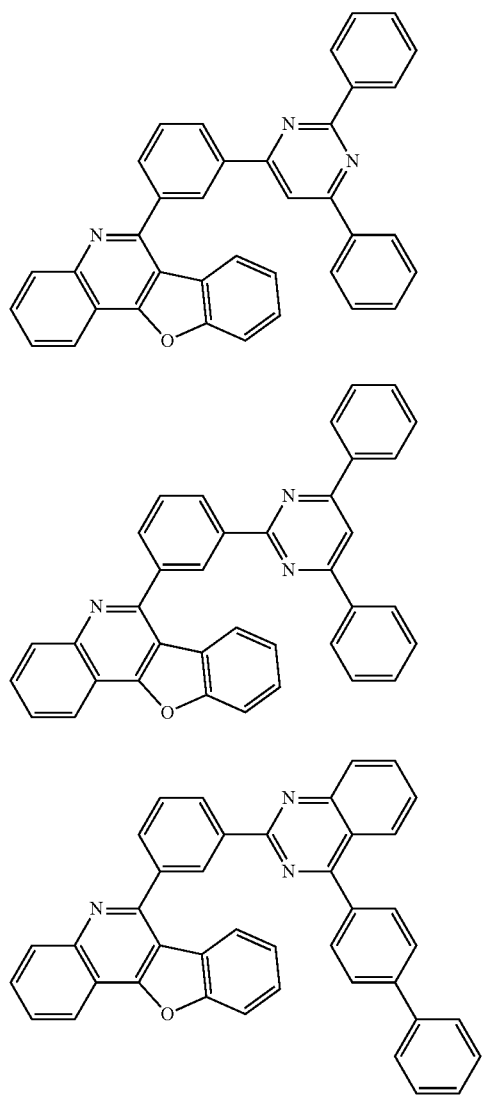
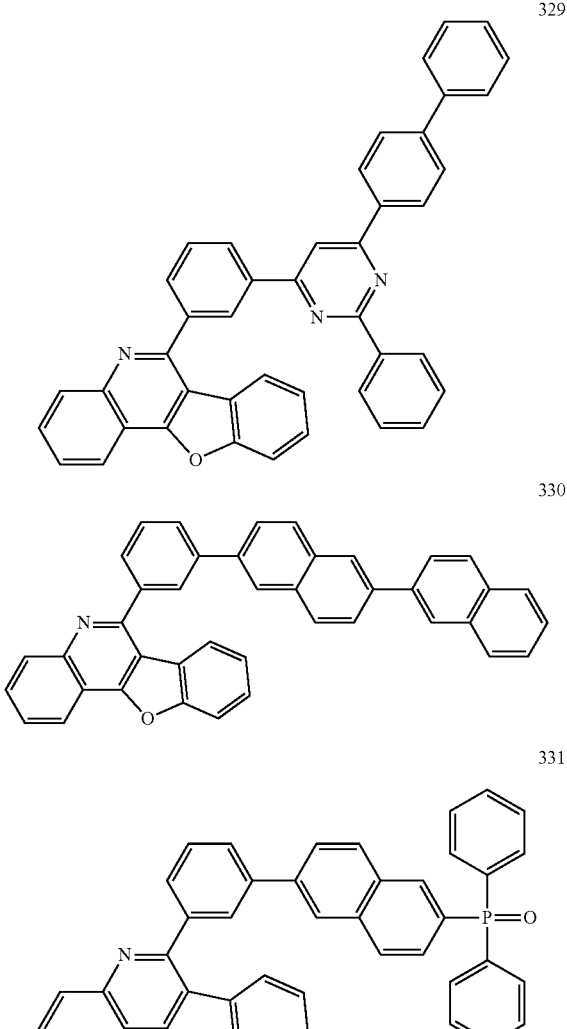
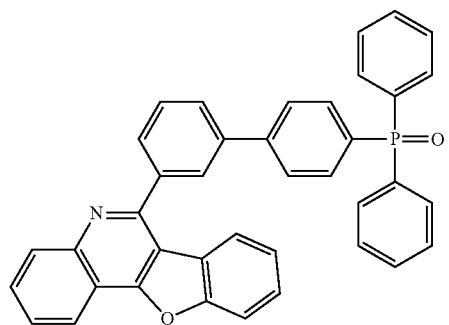

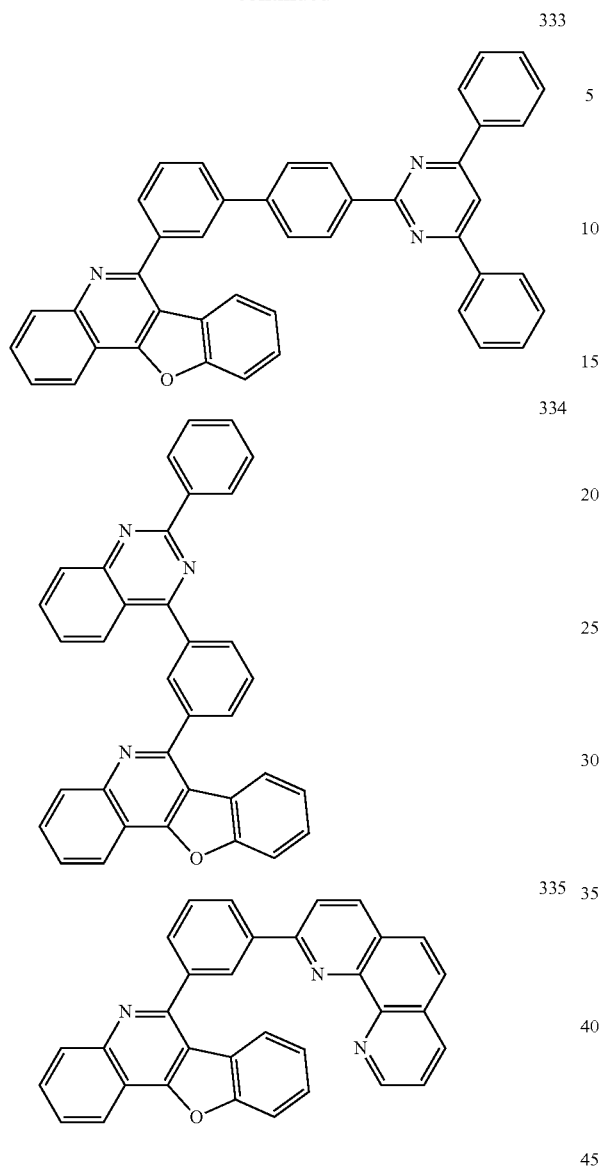
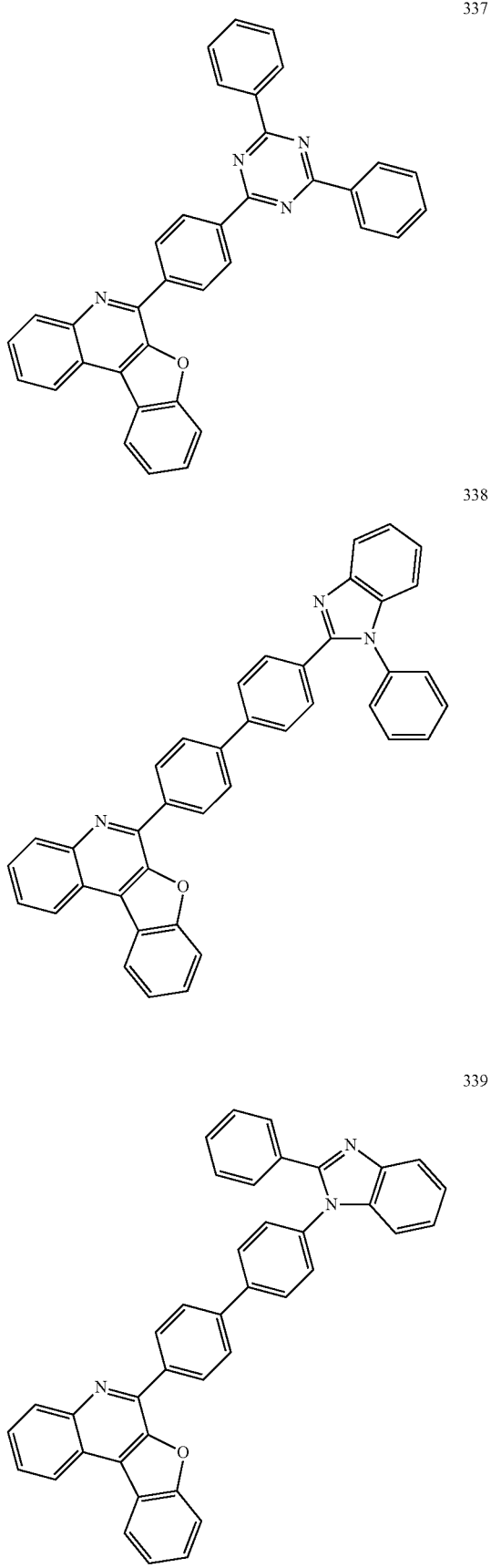

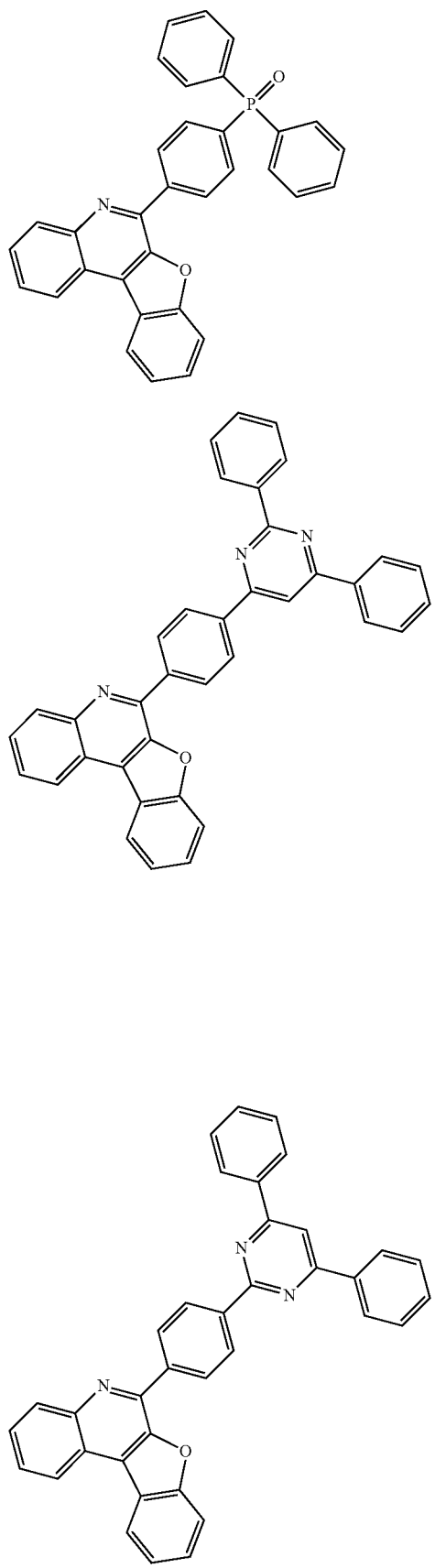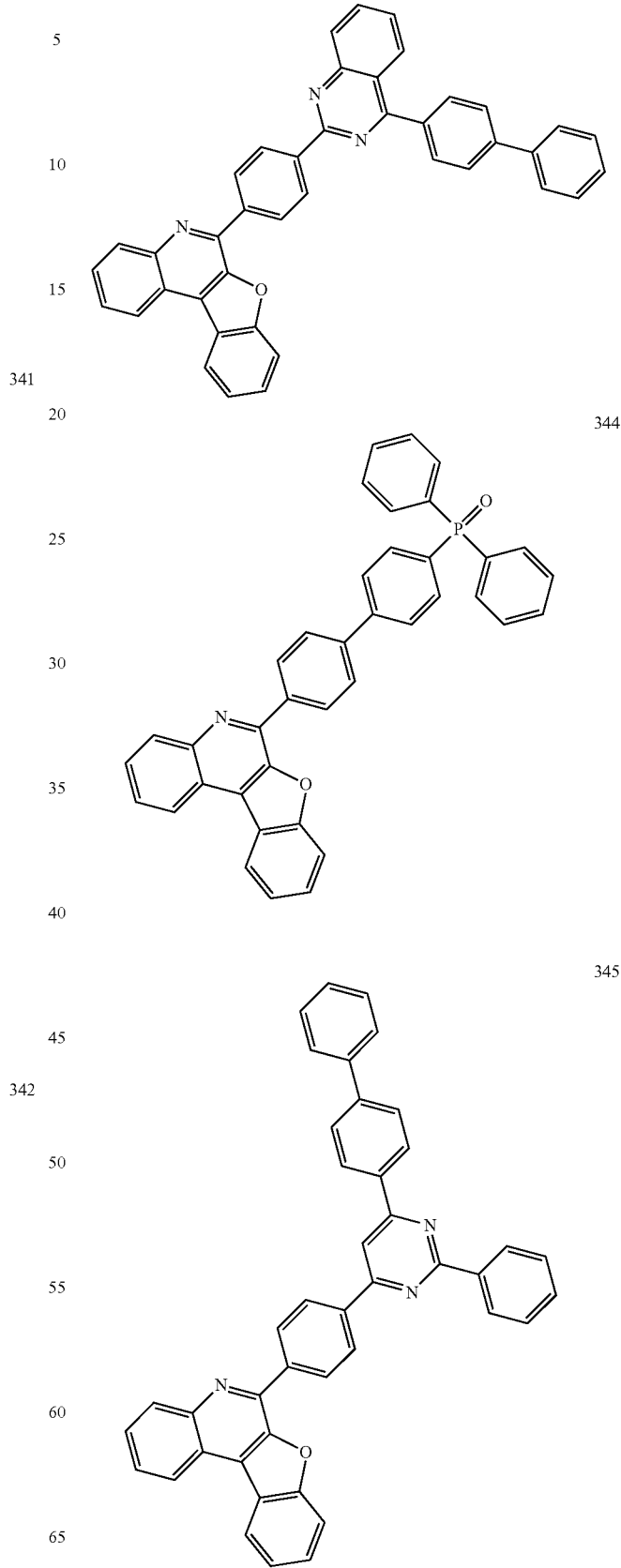

346
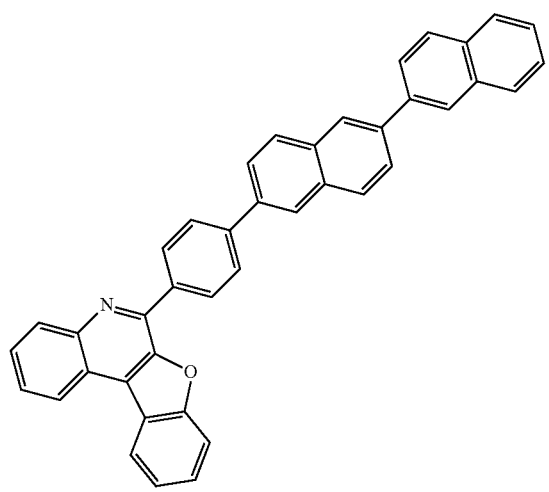
347
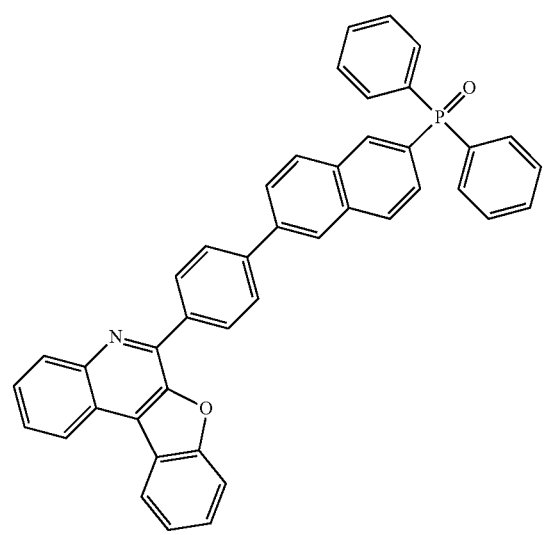
348
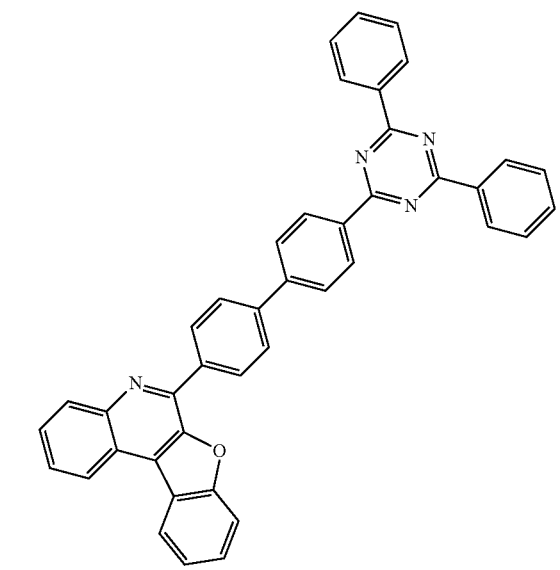
349
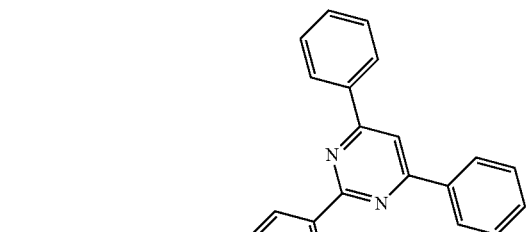
350
351
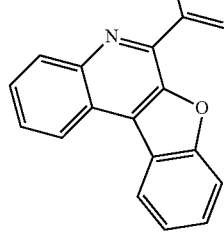

-continued
352
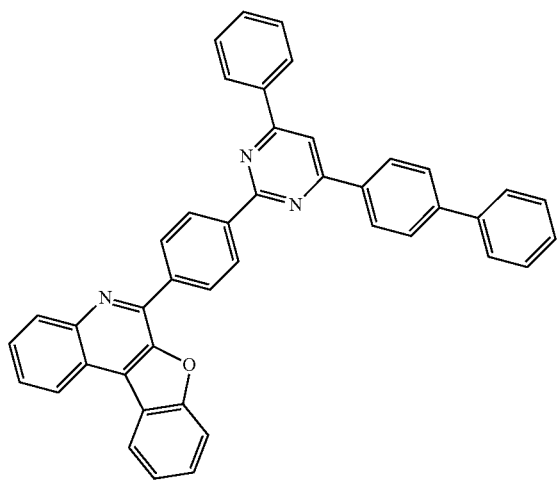
353
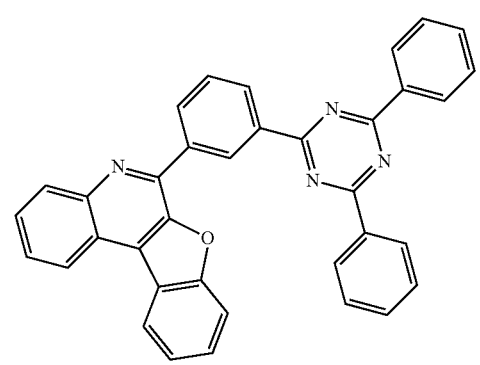
354
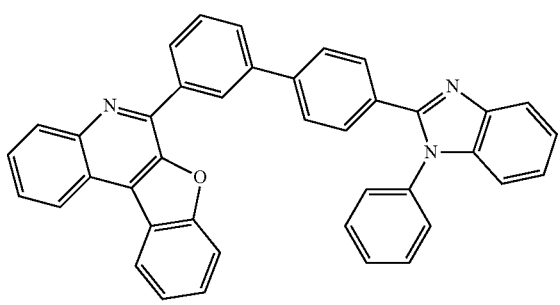
355
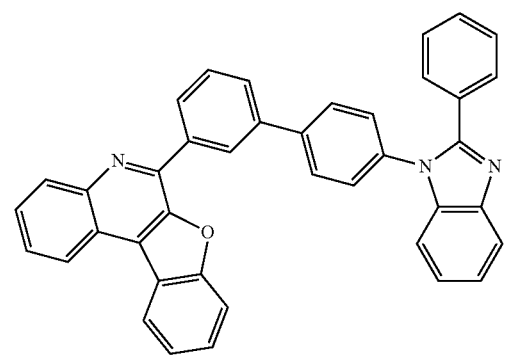
-continued
356
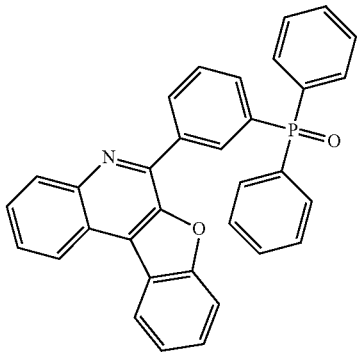
357
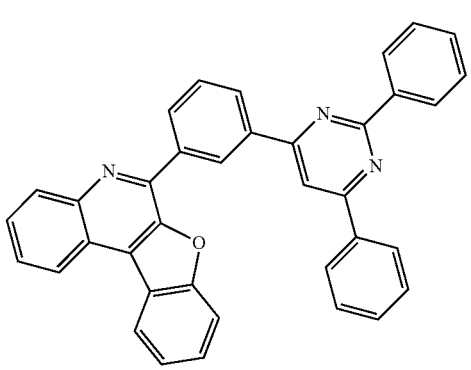
358
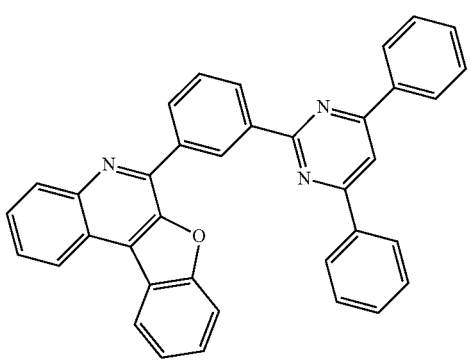
359
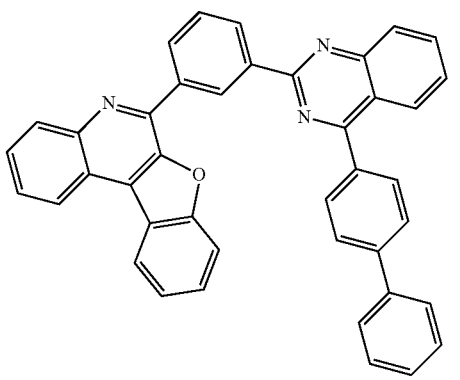

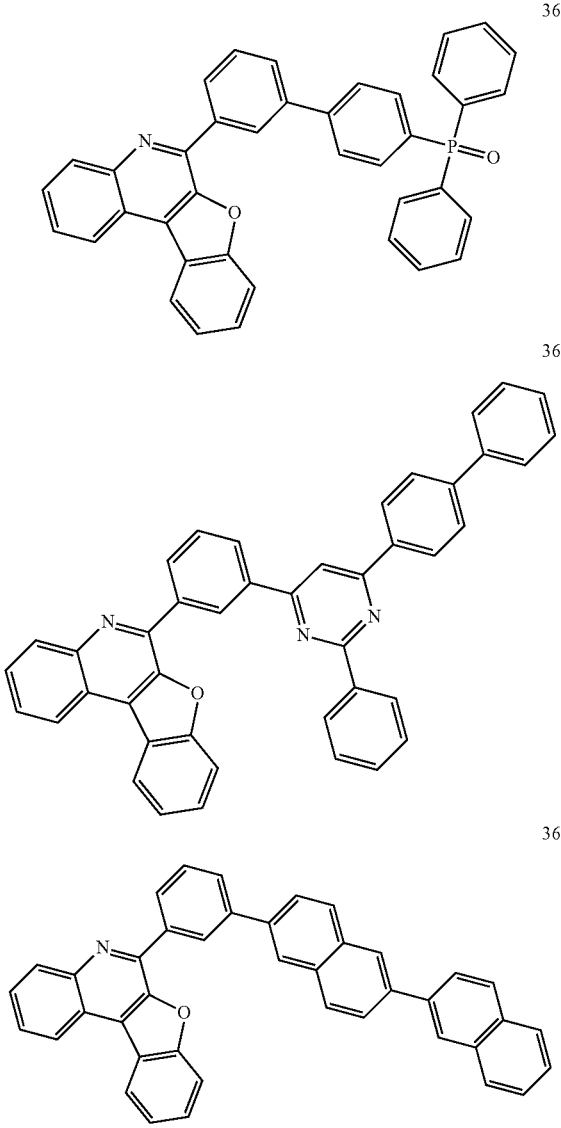
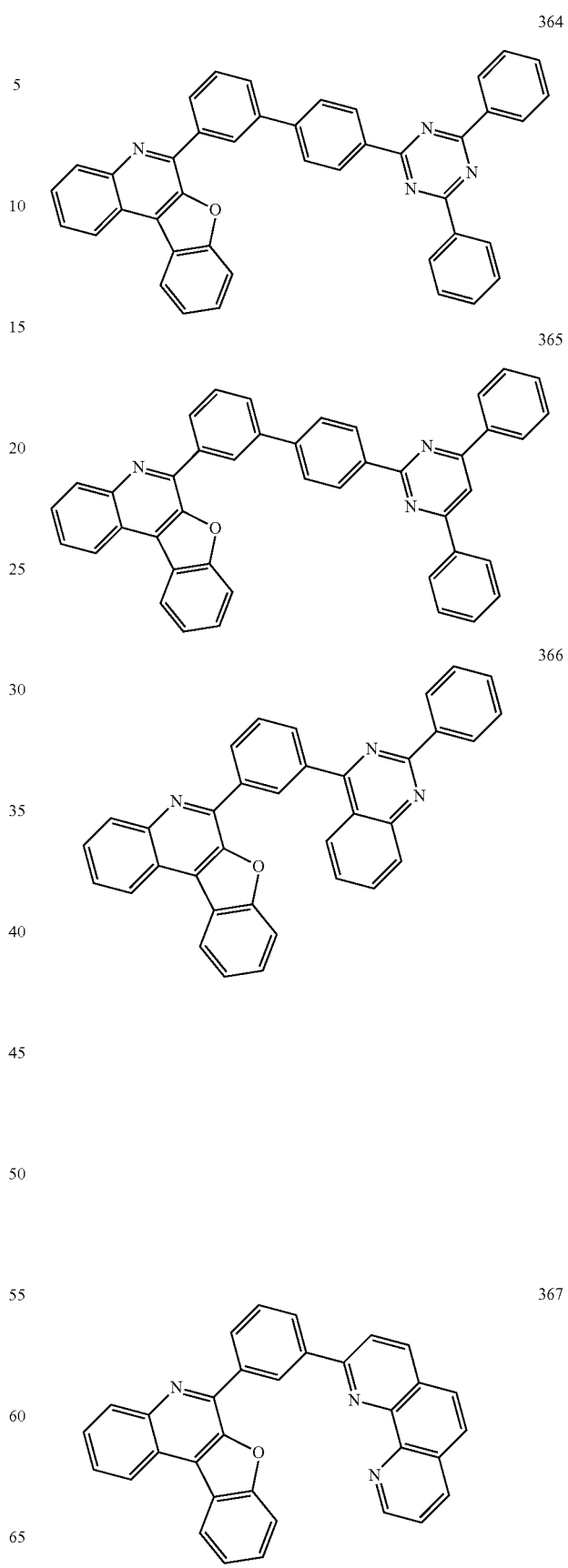

368
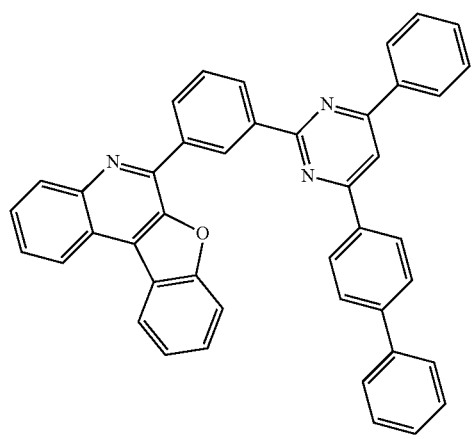
369
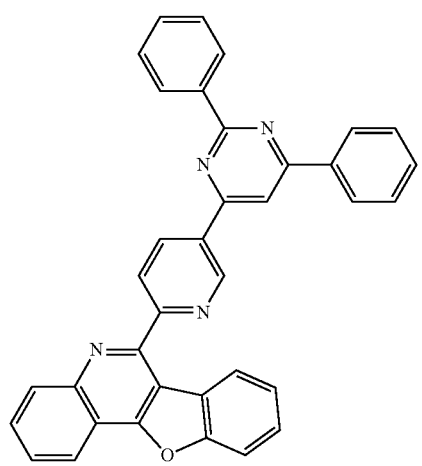
370
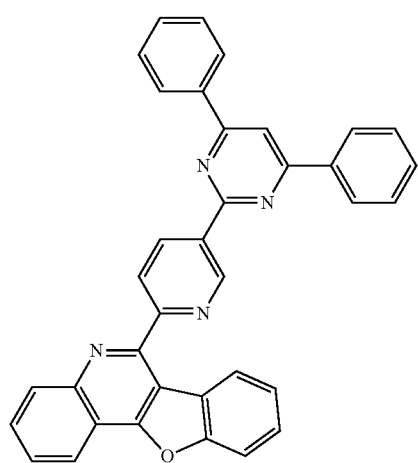
371
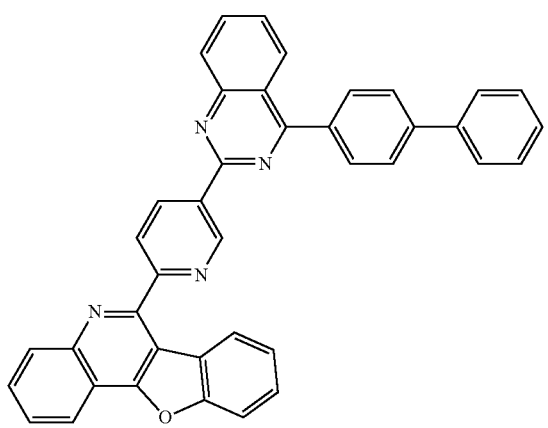
372
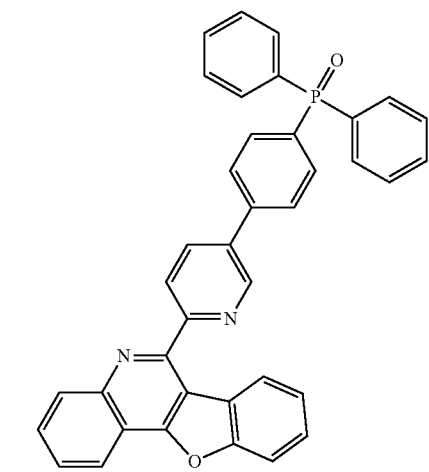
373
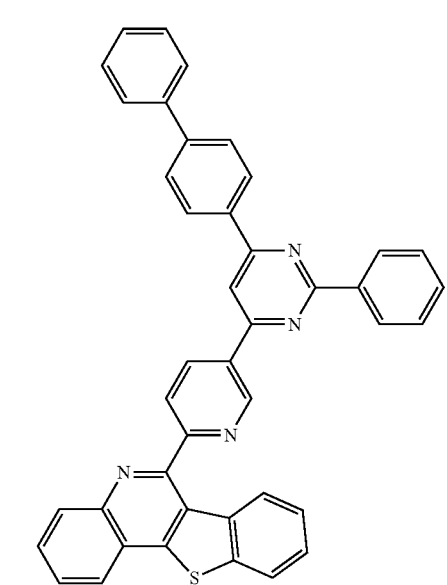

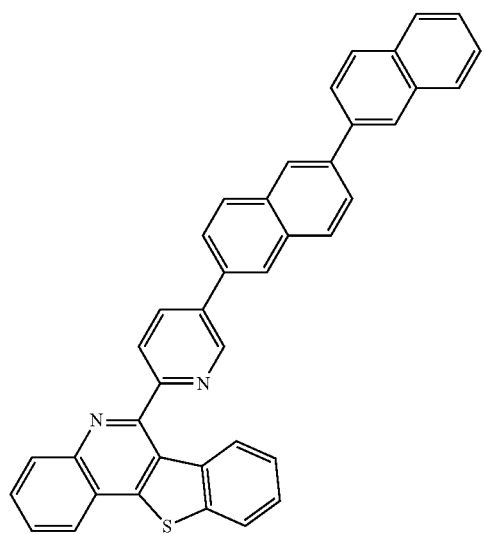
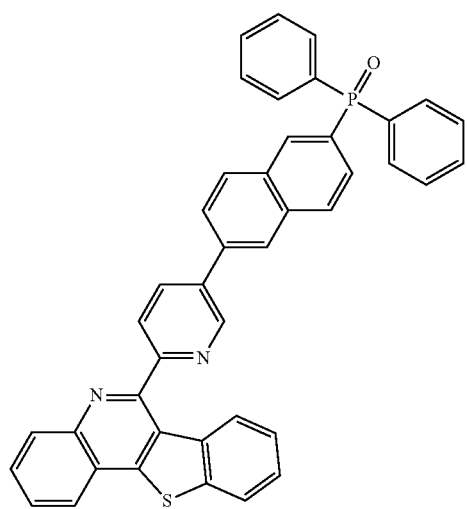
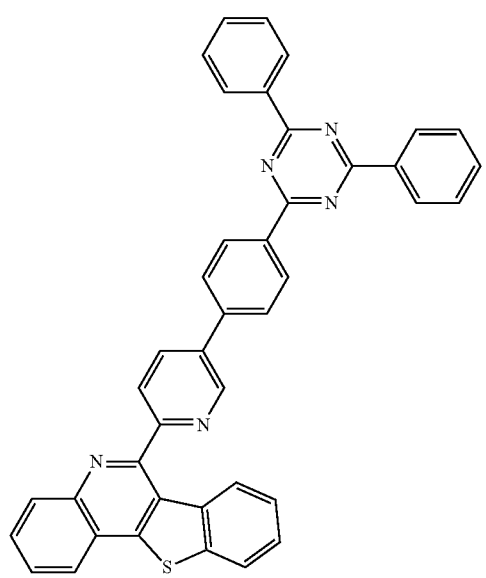
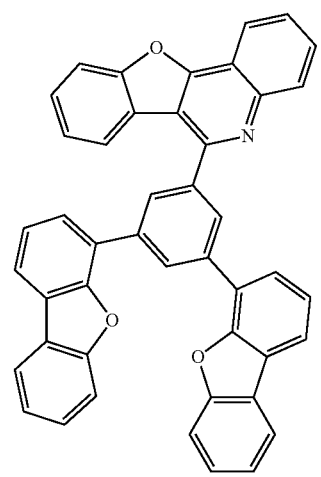
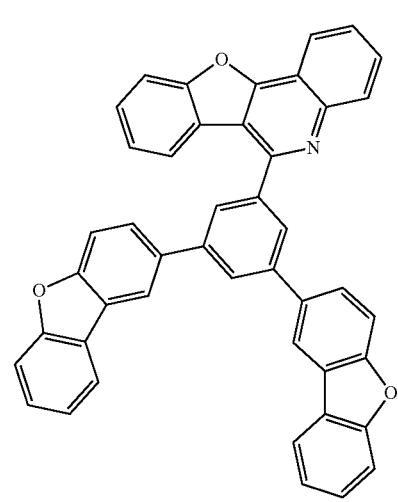
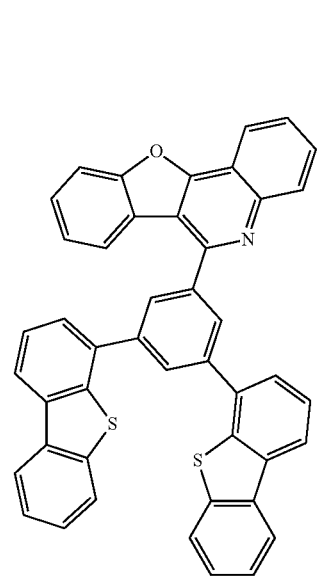

380
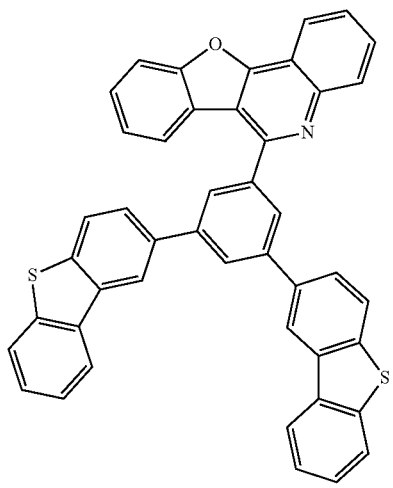
383
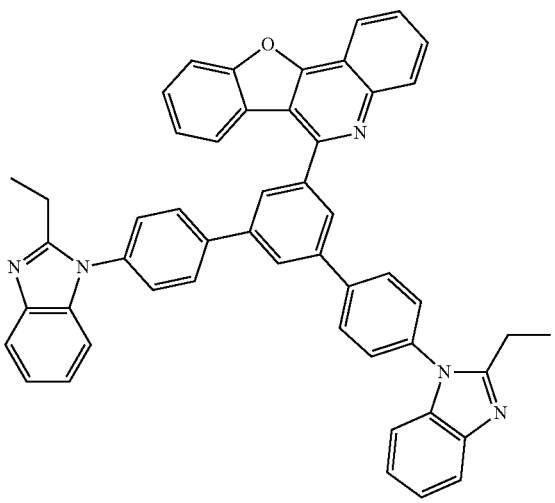
381
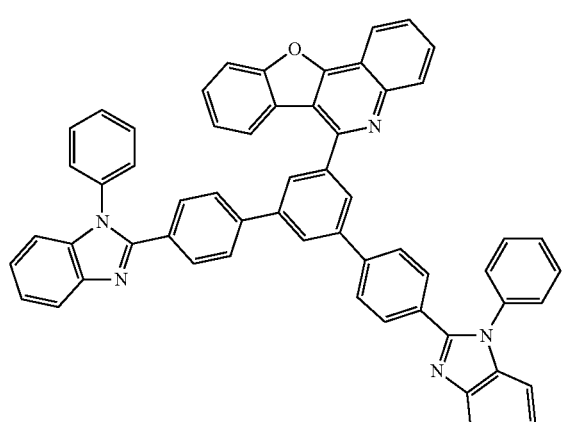
384
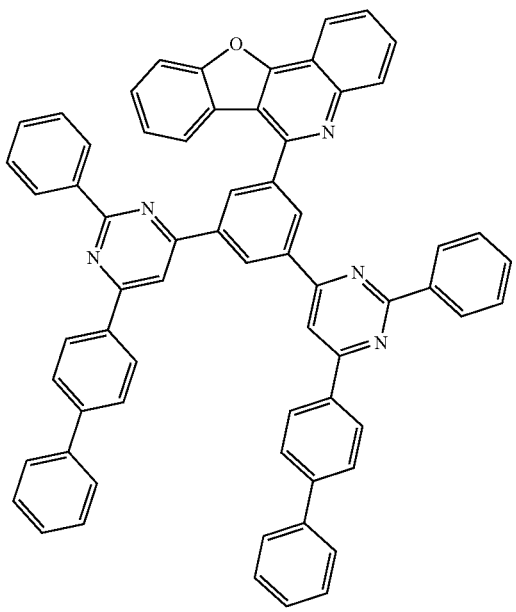
382
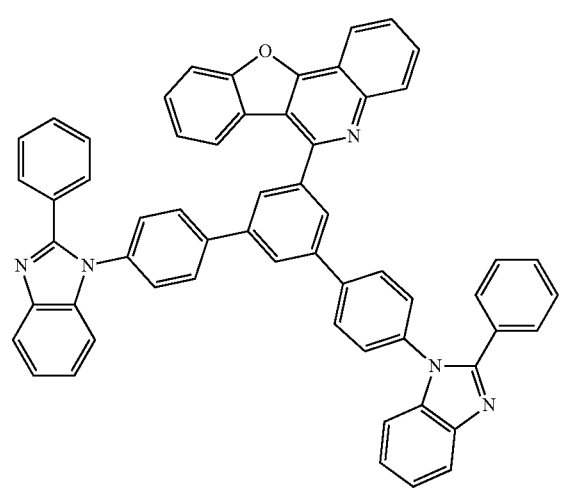
385
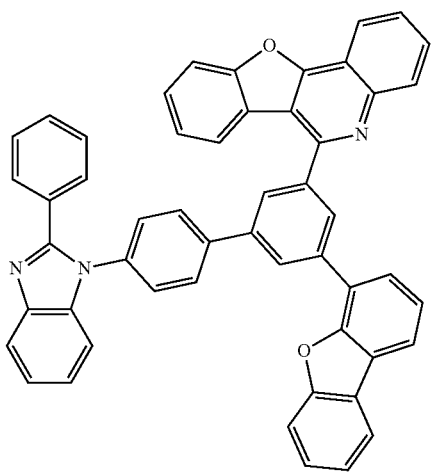

386
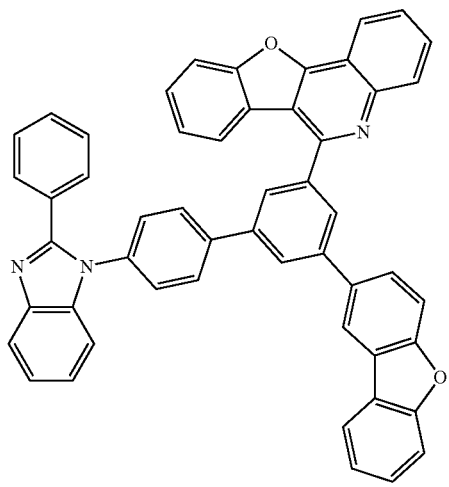
387
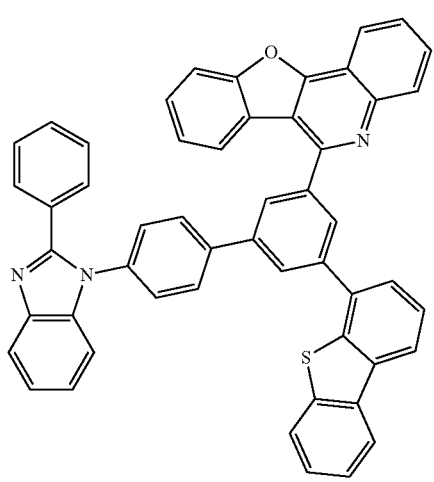
388
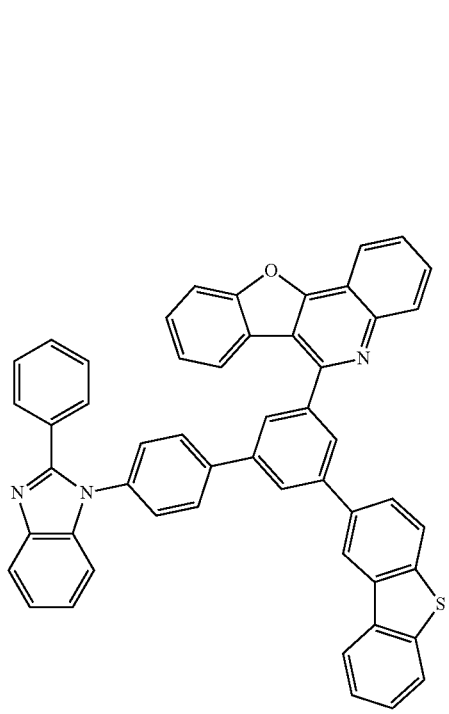
389
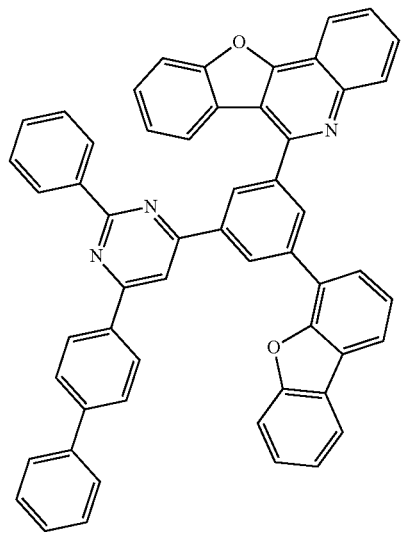
390
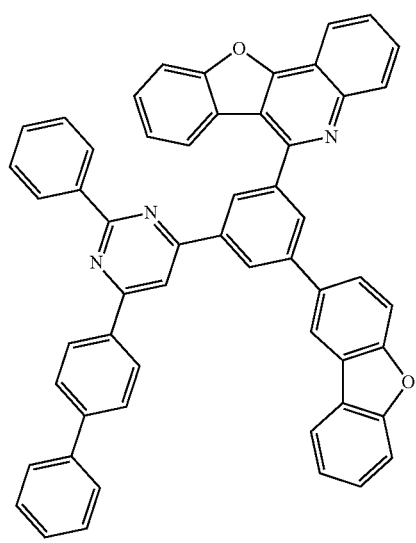
391
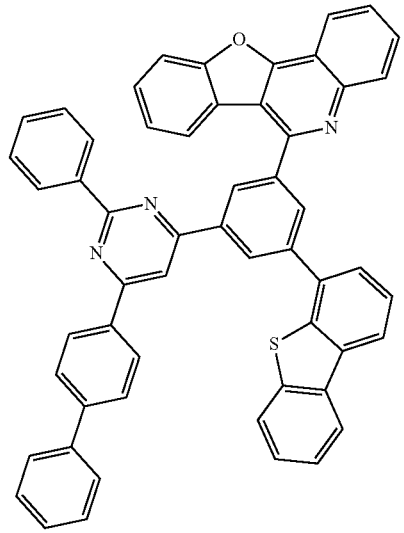

-continued
392
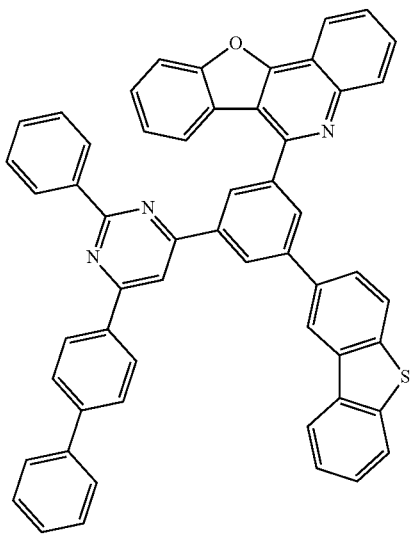
393
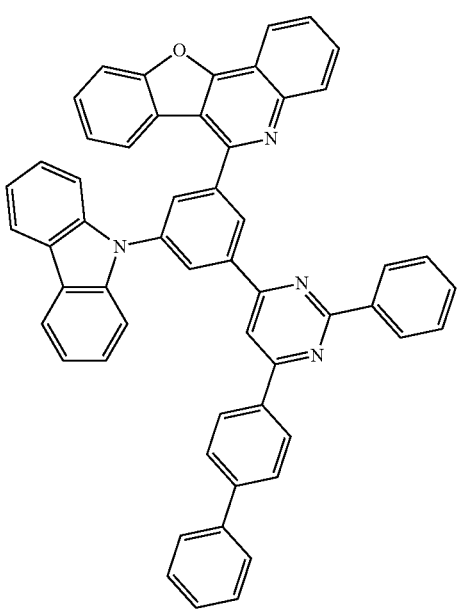
394
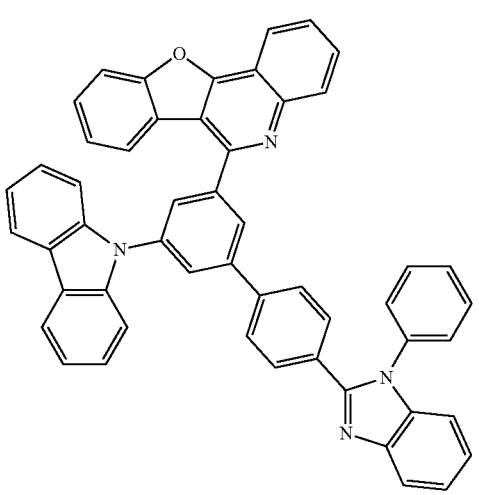
-continued
395
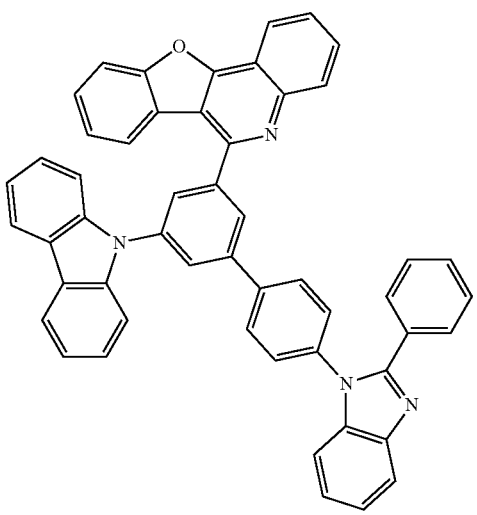
396
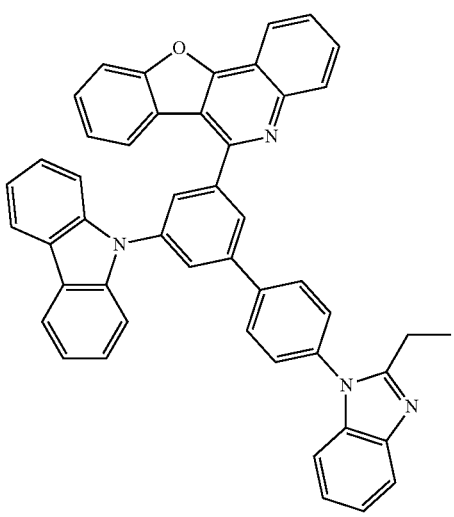
397
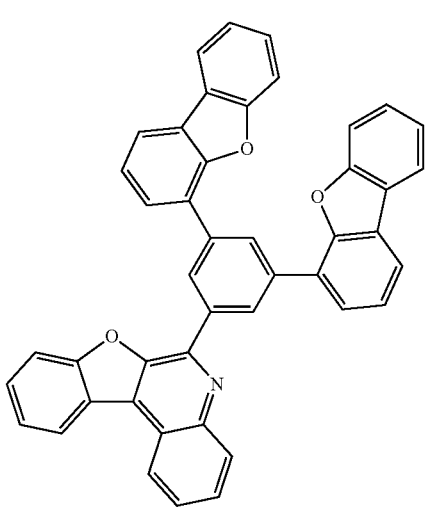

-continued
398
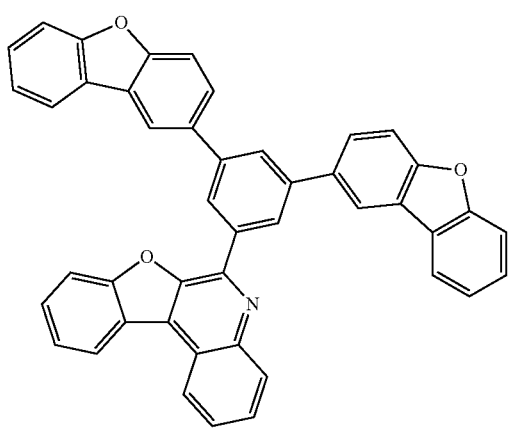
399
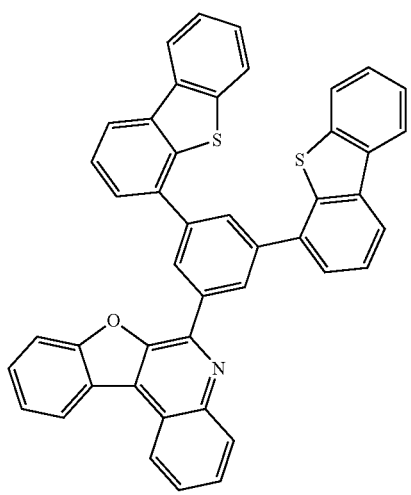
400
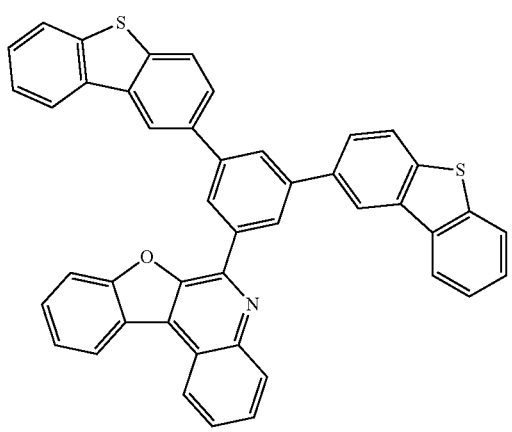
-continued
401
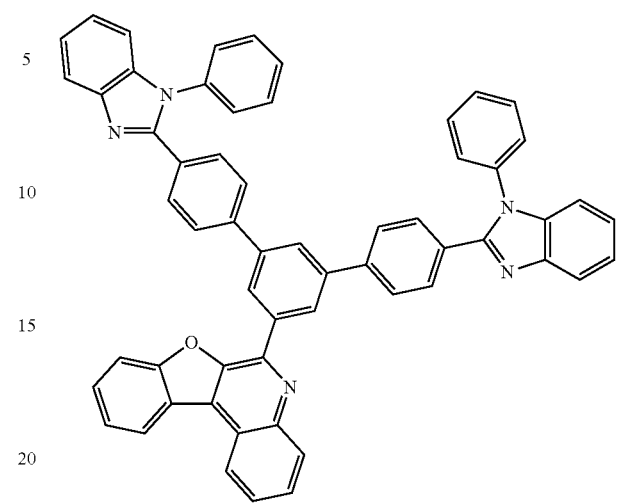
402
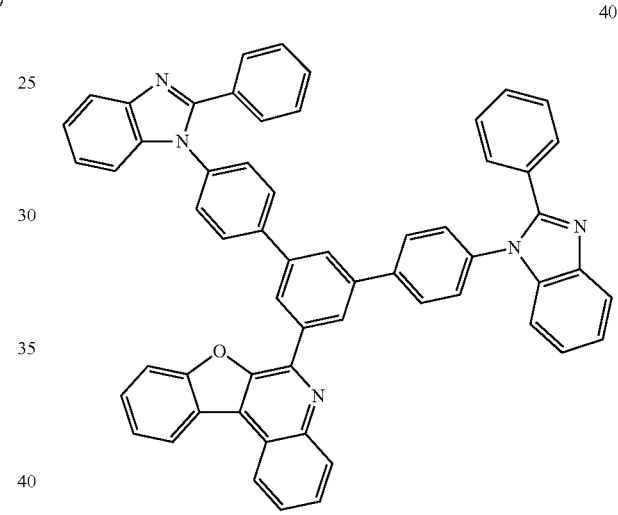
403
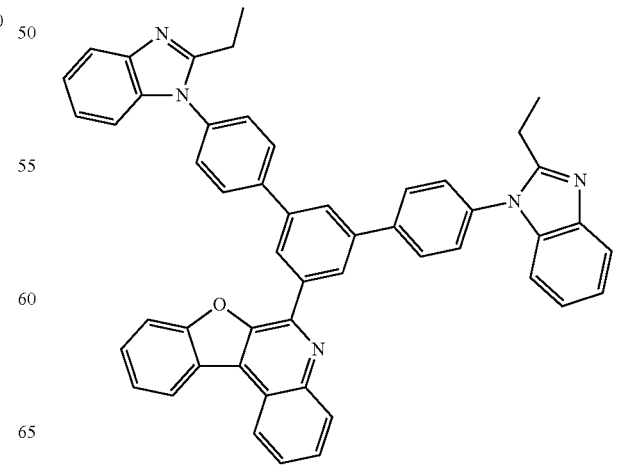

385
-continued
404
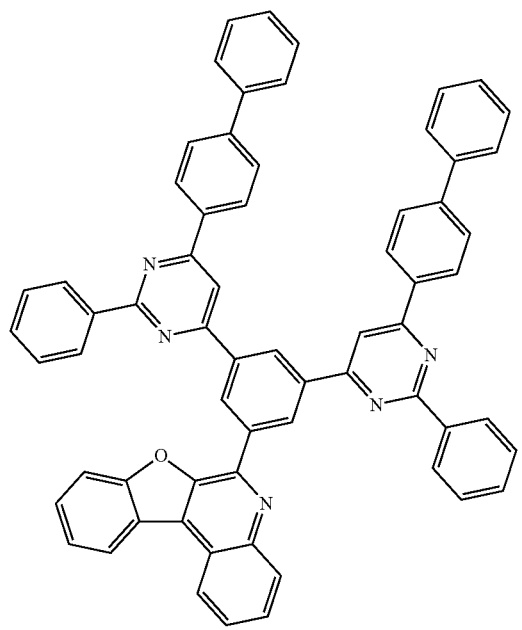
405
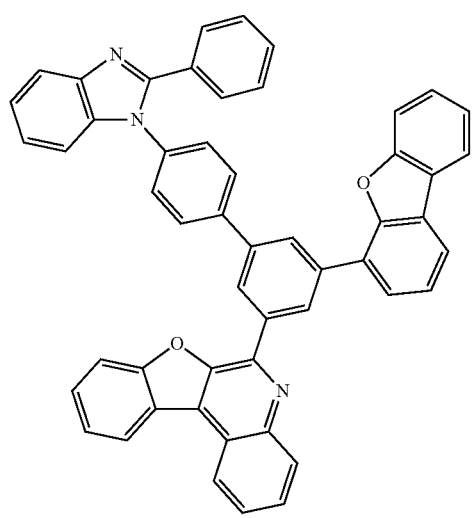
386
-continued
406
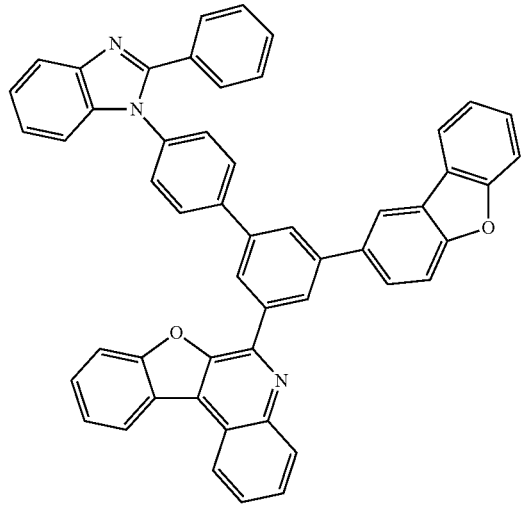
407
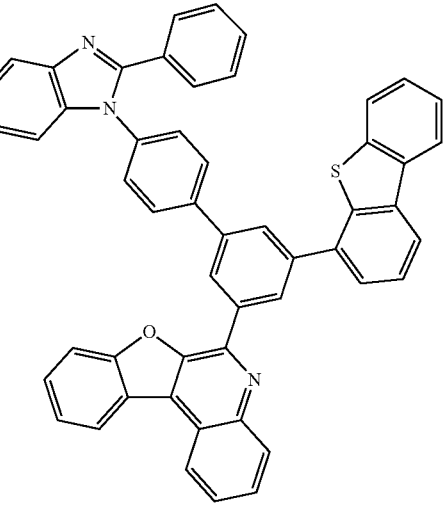
408

409
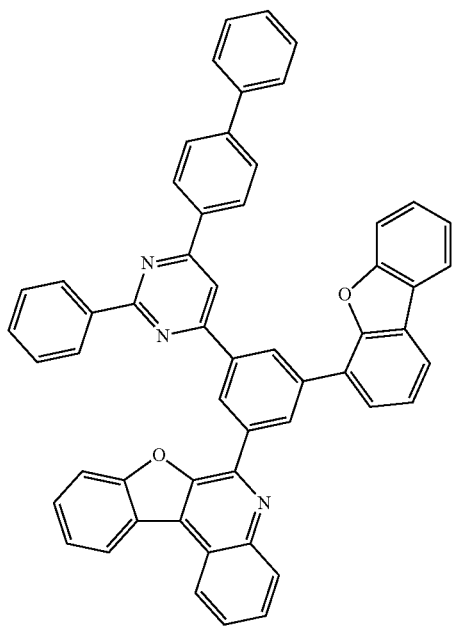
410
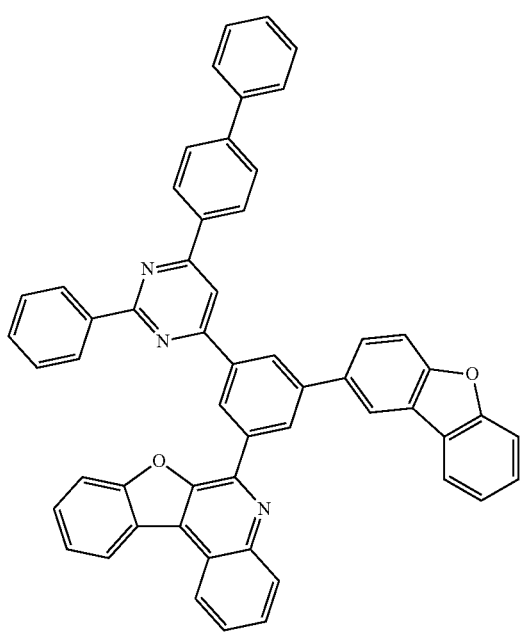
411
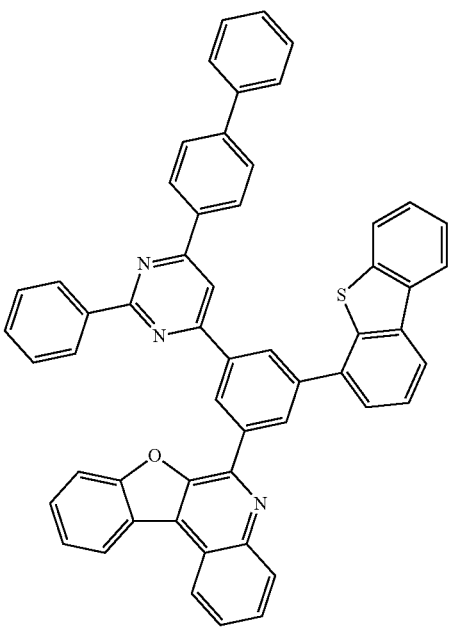
412
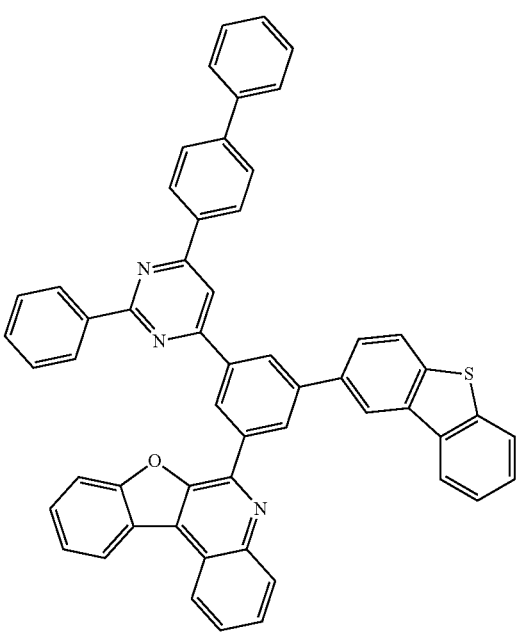

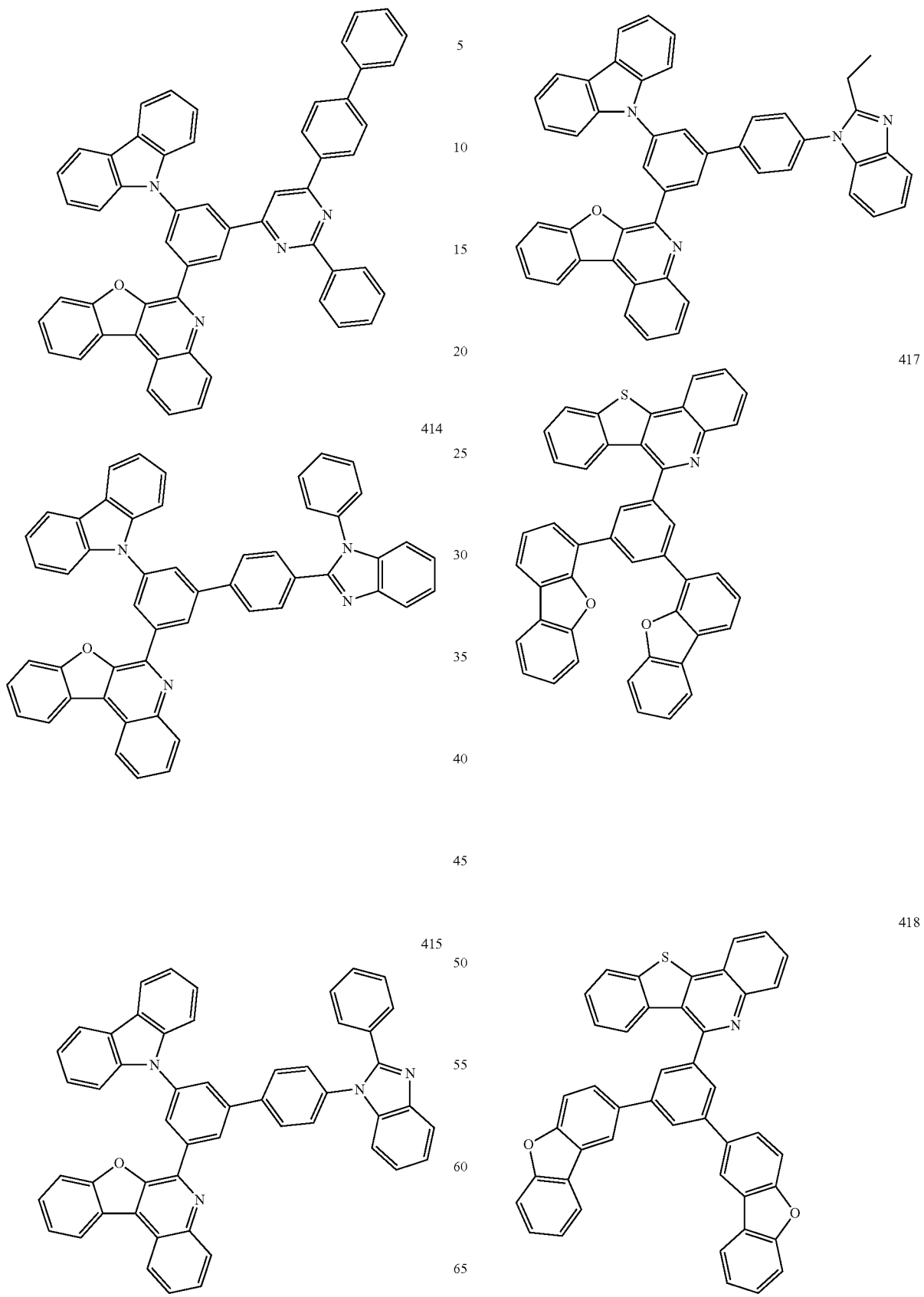

391
-continued
419
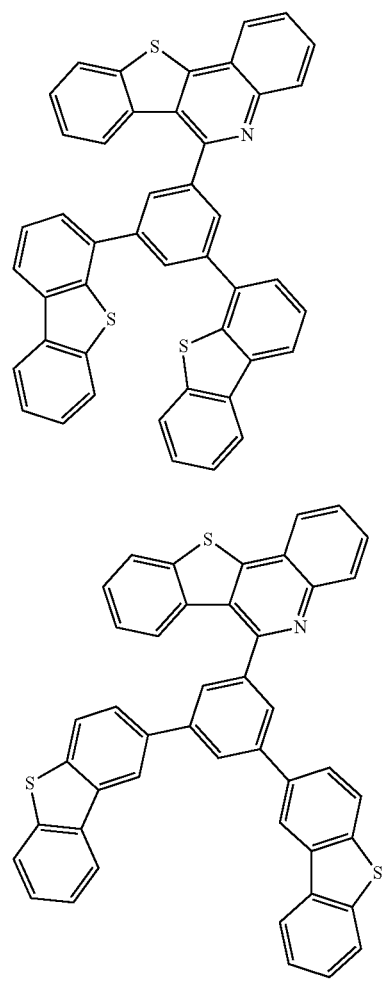
420
392
-continued
422
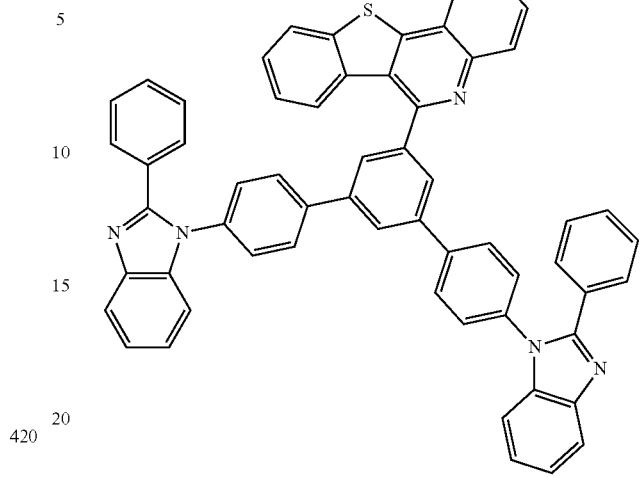
421
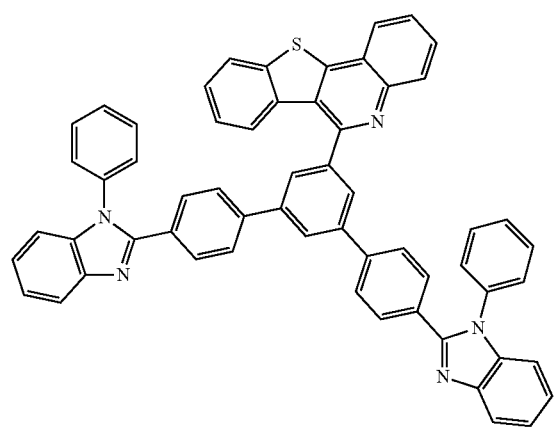
423
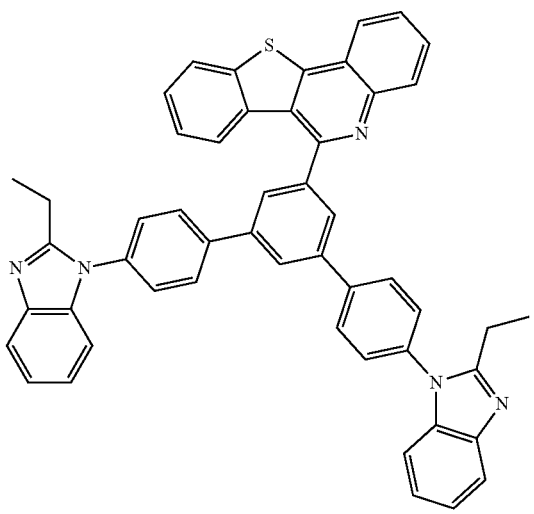

424
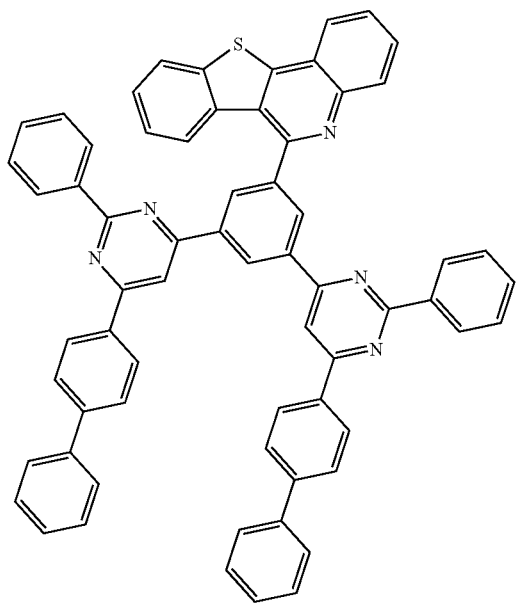
425
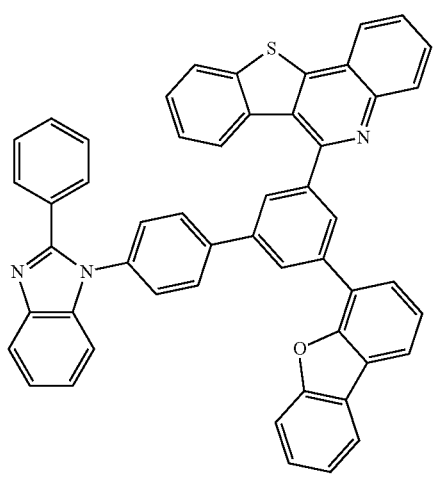
426
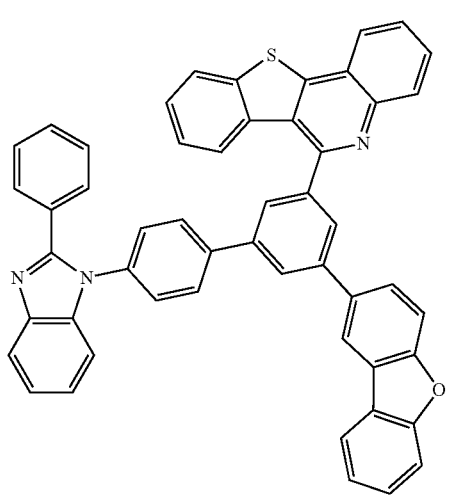
427
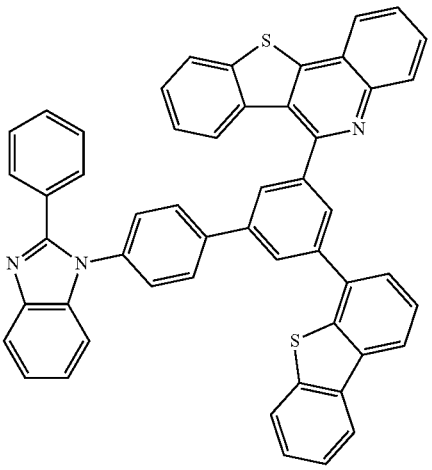
428
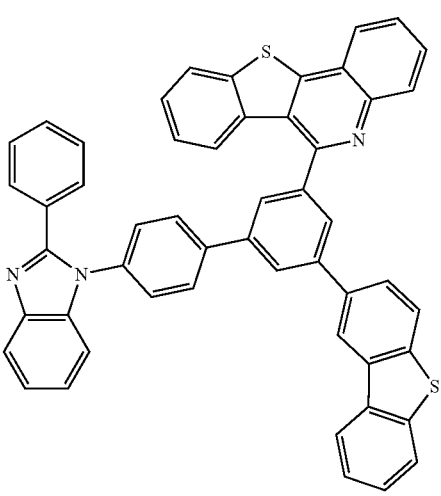
429
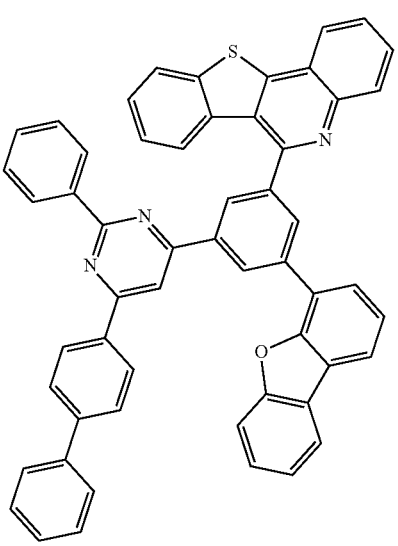

-continued
430
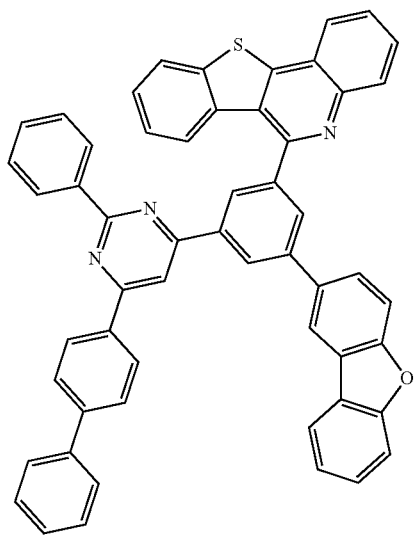
431
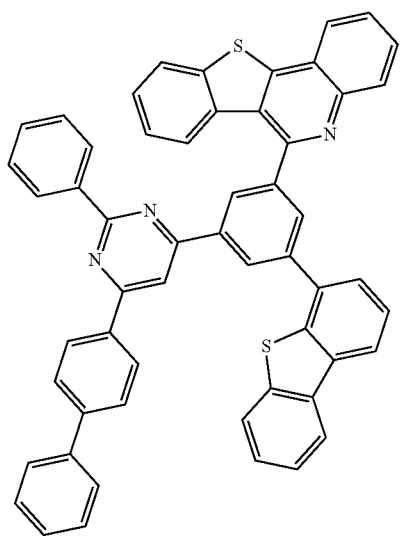
432
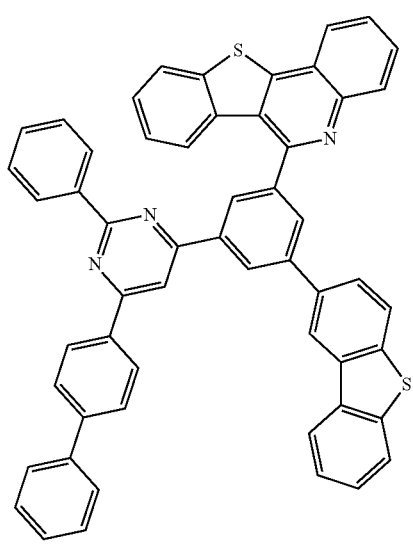
-continued
433
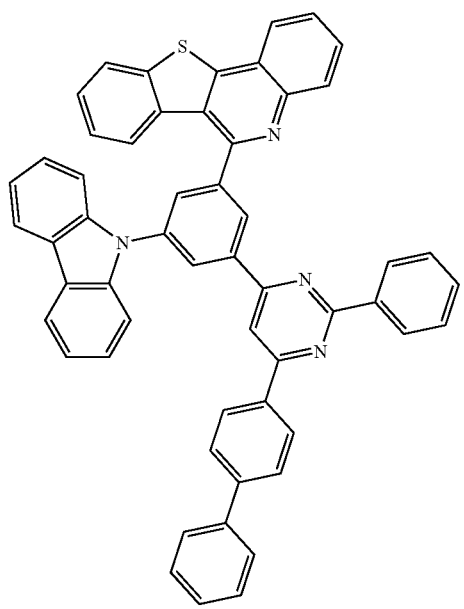
434
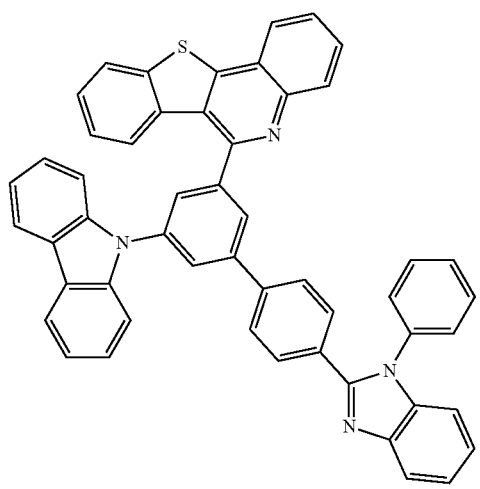
435
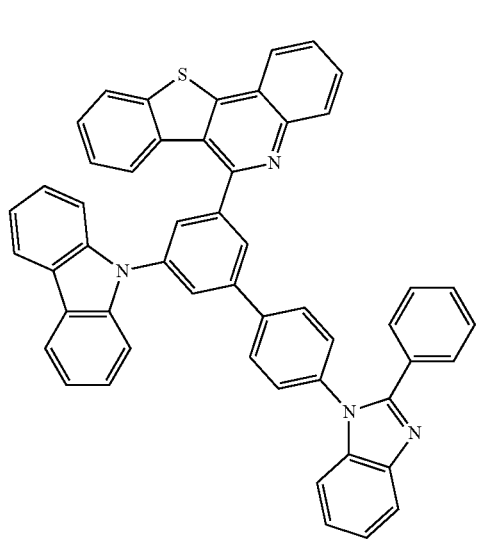

397
-continued
436
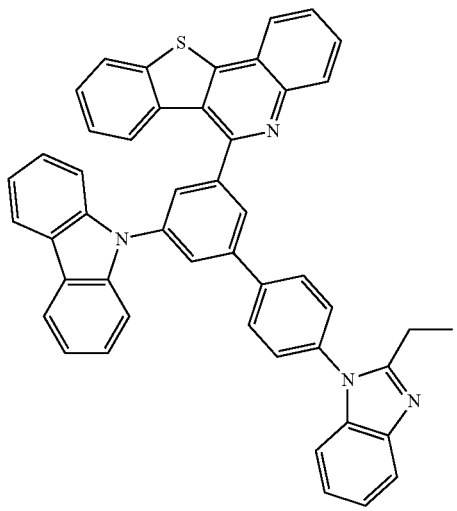
437
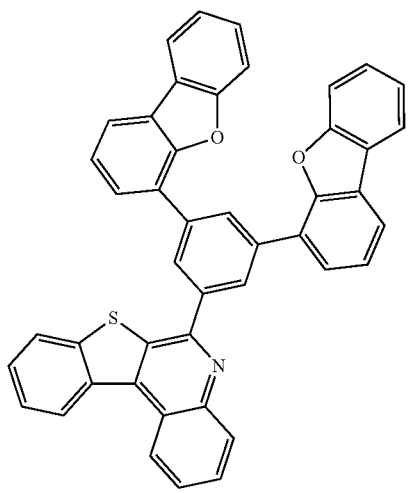
398
-continued
439
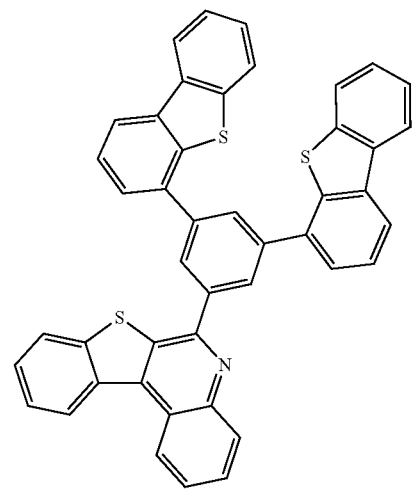
440
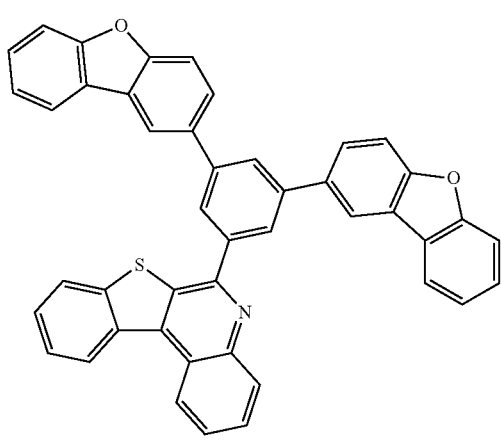
438
441
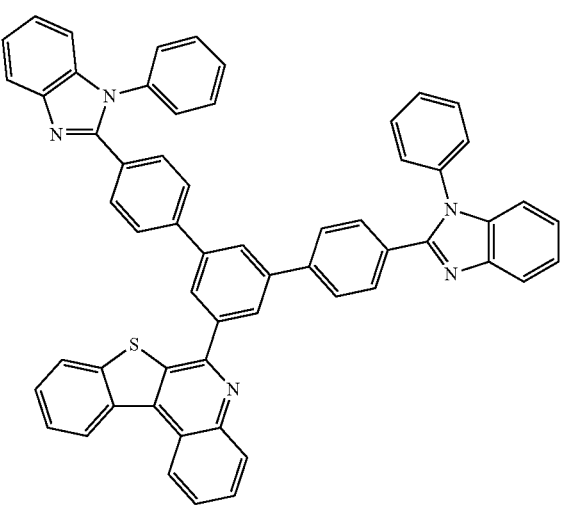

-continued
442
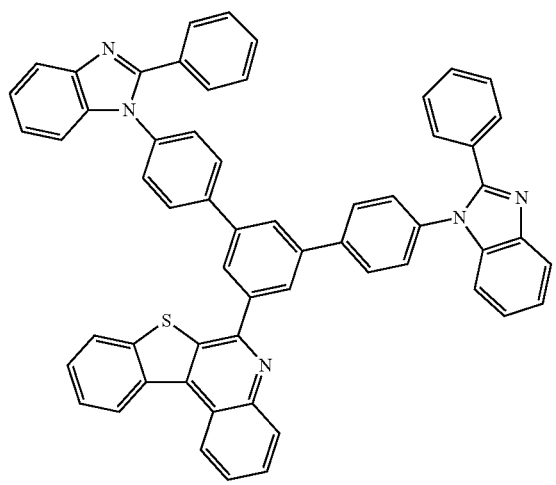
443
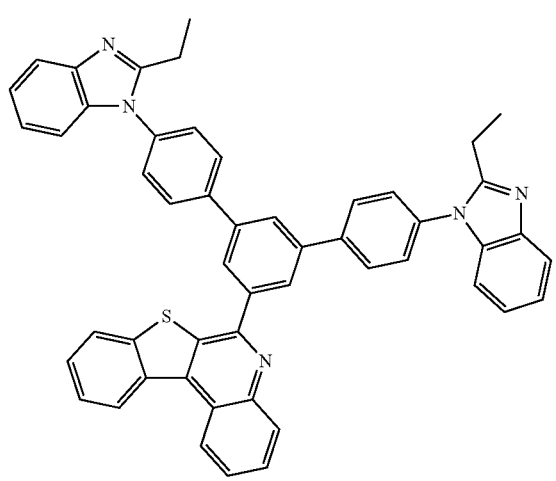
444
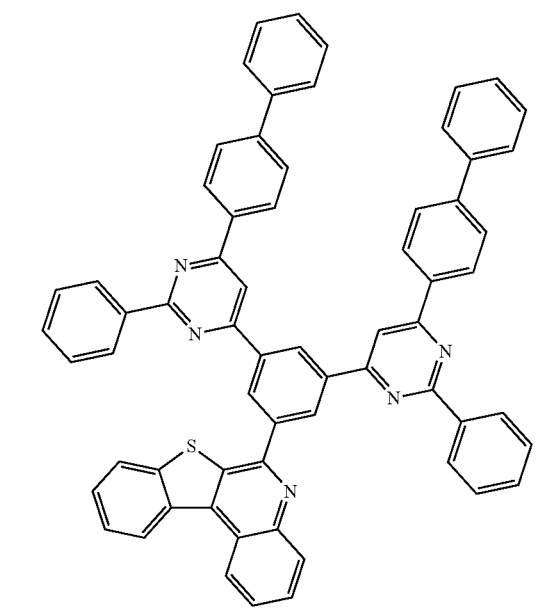
-continued
445
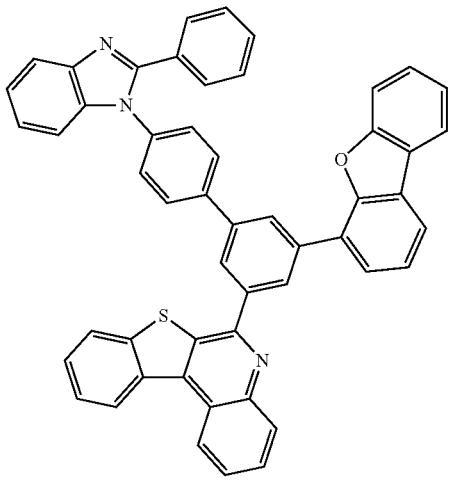
446
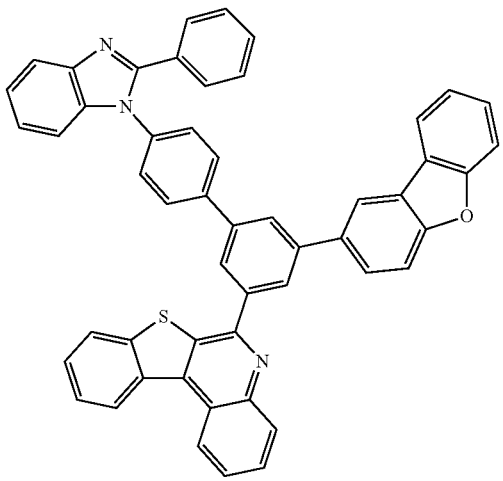
447
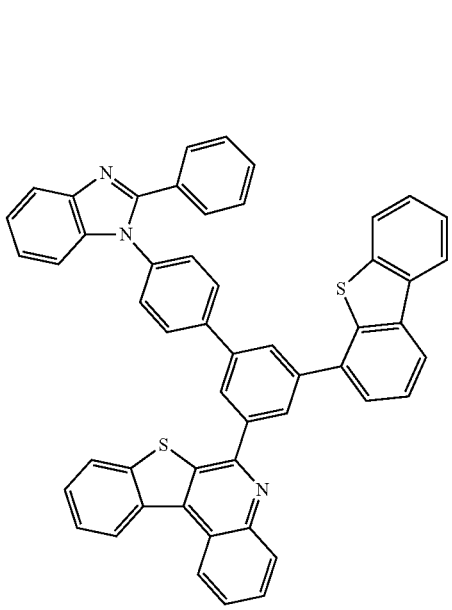

448
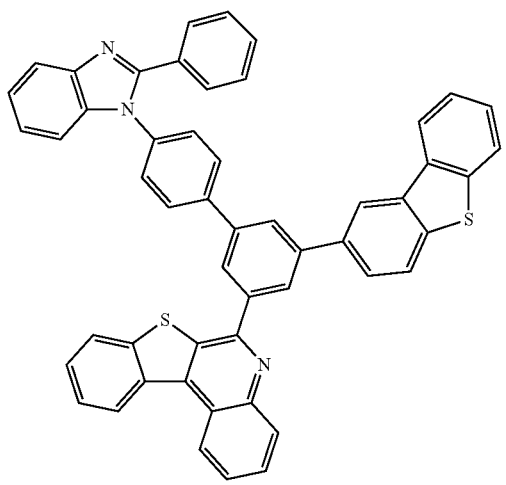
449
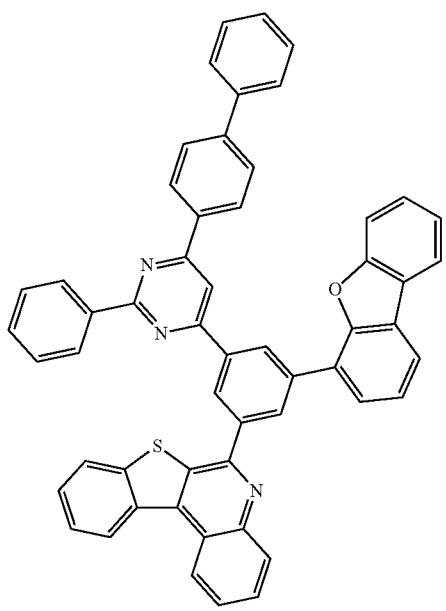
450
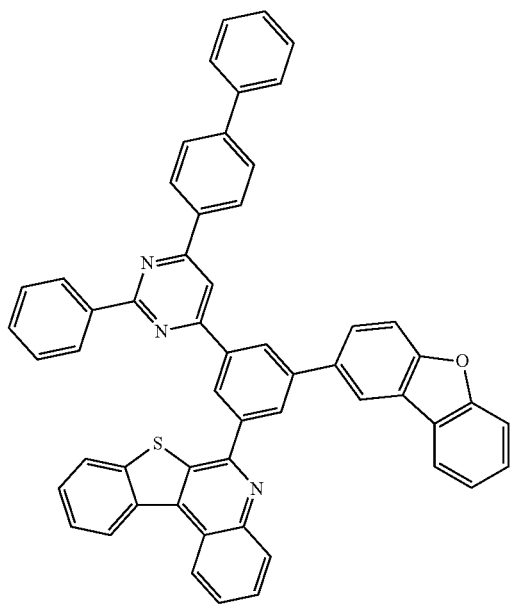
451
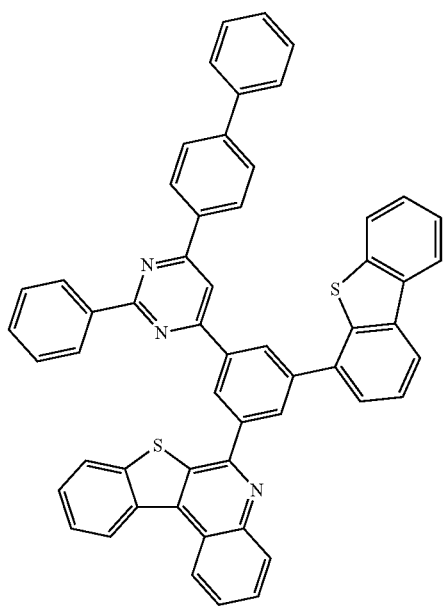

452

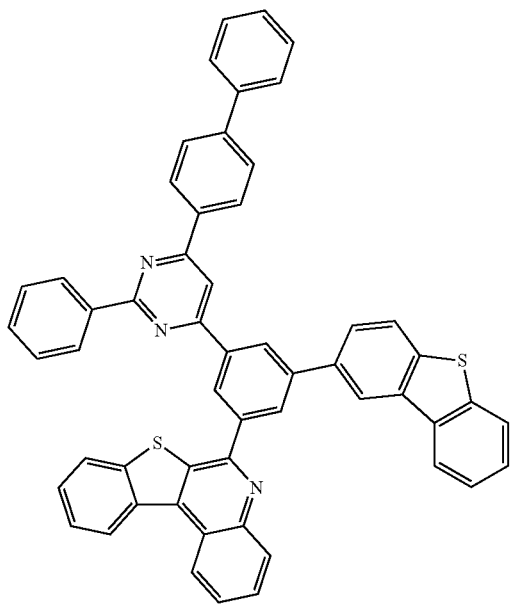

453

455

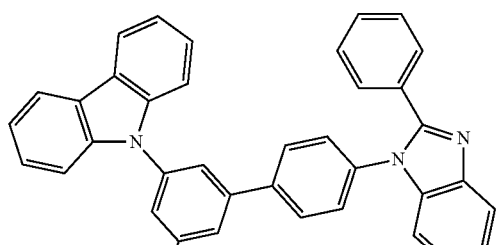

456

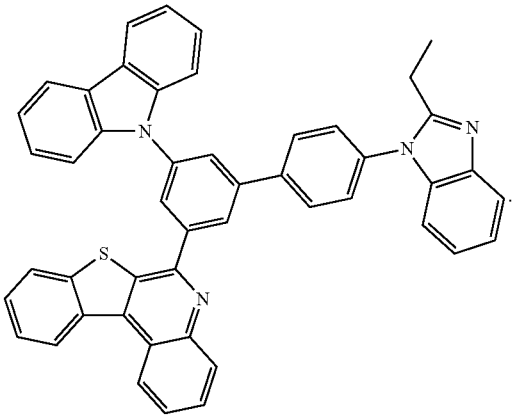

454

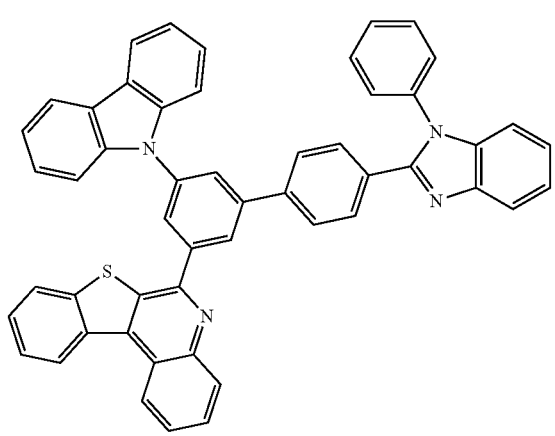

7. An organic light emitting device comprising:
   a positive electrode;
   a negative electrode; and
   one or more organic material layers provided between the positive electrode and the negative electrode, wherein one or more layers of the organic material layers comprise the hetero-cyclic compound of claim 1.

8. The organic light emitting device of claim 7, wherein the organic material layer comprises one or more layers selected from the group consisting of a hole injection layer, a hole transport layer, a light emitting layer, an electron transport layer, and an electron injection layer.

9. The organic light emitting device of claim 8, wherein the organic material layer comprising the hetero-cyclic compound is an electron transport layer.

10. The organic light emitting device of claim 8, wherein the organic material layer comprising the hetero-cyclic compound is a light emitting layer.

11. The organic light emitting device of claim 8, wherein the organic material layer comprising the hetero-cyclic compound is a hole blocking layer.

* * * * *